United States Patent
Angelini et al.

(10) Patent No.: US 11,485,781 B2
(45) Date of Patent: Nov. 1, 2022

(54) MULTIPLE SPECIFICITY BINDERS OF CXC CHEMOKINES

(71) Applicants: Massachusetts Institute of Technology, Cambridge, MA (US); The General Hospital Corporation, Boston, MA (US)

(72) Inventors: Alessandro Angelini, Lavagno (IT); Karl Dane Wittrup, Boston, MA (US); Andrew David Luster, Wellesley, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 68 days.

(21) Appl. No.: 16/638,992

(22) PCT Filed: Aug. 17, 2018

(86) PCT No.: PCT/US2018/046894
§ 371 (c)(1),
(2) Date: Feb. 13, 2020

(87) PCT Pub. No.: WO2019/036605
PCT Pub. Date: Feb. 21, 2019

(65) Prior Publication Data
US 2021/0246199 A1    Aug. 12, 2021

Related U.S. Application Data

(60) Provisional application No. 62/546,814, filed on Aug. 17, 2017.

(51) Int. Cl.
| | |
|---|---|
| *A61K 39/395* | (2006.01) |
| *C07K 16/24* | (2006.01) |
| *A61P 19/02* | (2006.01) |
| *C07K 14/765* | (2006.01) |
| *A61K 39/00* | (2006.01) |

(52) U.S. Cl.
CPC .............. *C07K 16/24* (2013.01); *A61P 19/02* (2018.01); *C07K 14/765* (2013.01); *A61K 2039/505* (2013.01); *C07K 2317/31* (2013.01); *C07K 2317/33* (2013.01); *C07K 2317/622* (2013.01); *C07K 2317/92* (2013.01); *C07K 2319/30* (2013.01)

(58) Field of Classification Search
None
See application file for complete search history.

(56) References Cited

U.S. PATENT DOCUMENTS

2012/0315267 A1* 12/2012 Clegg ..................... A61P 29/00
435/254.5

FOREIGN PATENT DOCUMENTS

| WO | 2008/130969 A2 | 10/2008 |
| WO | 2014/149733 A1 | 9/2014 |
| WO | 2019036605 A2 | 2/2019 |

OTHER PUBLICATIONS

Laing et al. Dev. Comp. Immunol. 28: 443-460, 2004.*
Edwards et al. (J. Mol. Biol. 334: 103-118, 2003).*
Torres et al. (Trends in Immunol. 29(2): 91-97, 2008).*
Khan et al. (J. Immunol. 192: 5398-5405, 2014).*
Poosarla et al. (Biotech. Bioengineer. 124(6): 1331-1342, 2017).*
(Paul, Fundamental Immunology, 3rd Edition, 1993, pp. 292-295).*
Rudikoff et al. (PNAS 79: 1979-1983, 1982).*
MacCallum, et al. (J. Mol. Biol. 262: 732-745, 1996).*
De Pacalis et al. (J. Immunol. 169: 3076-3084, 2002).*
Casset et al. (Biochem. Biophys. Res. Comm. 307: 198-205, 2003).*
Chen et al. (J. Mol. Biol. 293: 865-881, 1999).*
Wu et al. (J. Mol. Biol. 294: 151-162, 1999).*
Angelini, A. et al., "Directed evolution of broadly cross reactive chemokine-blocking antibodies efficacious in arthritis," Nature Communications, vol. 9, Article No. 1461: 18 pages (2018).
Evans L. et al., "The production, characterization and enhanced pharmacokinetics of scFv-albumin fusions expressed in *Saccharomyces cerevisiae*," Protein Expression and Purification, vol. 73(2):113-124 (2010).
Gong, J-H. et al., "Post-onset inhibition of murine arthritis using combined chemokine antagonist therapy," Rheumatology, vol. 43(1):39-42 (2004).
Parry C. M. et al., "A Broad Spectrum Secreted Chemokine Binding Protein Encoded by a herpesvirus" The Journal of Experimental Medicine, vol. 191(3):573-578 (2000).
Fagète, S. et al., "Specificity tuning of antibody fragments to neutralize two human chemokines with a single agent," MABS, vol. 1(3):288-296 (2009).
Szekanecz, Z. et al., "Chemokines and chemokine receptors in arthritis," Frontiers in Bioscience, vol. S2(1):153-167 (2010).
Wunder, A. et al., "Albumin-Based Drug Delivery as Novel Therapeutic Approach for Rheumatoid Arthritis," The Journal of Immunology, vol. 170(9): 4793-4801 (2003).
Sleep, "Albumin and its application in drug delivery" Expert Opinion on Drug Delivery, vol. 12 (5): 793-812 (May 2015).

* cited by examiner

*Primary Examiner* — Christine J Saoud
(74) *Attorney, Agent, or Firm* — McDonnell Boehnen Hulbert & Berghoff LLP

(57) ABSTRACT

The present disclosure provides for fusion proteins comprising multipsecific variable regions that bind more than one ELR+ CXC chemokine.

15 Claims, 12 Drawing Sheets

Specification includes a Sequence Listing.

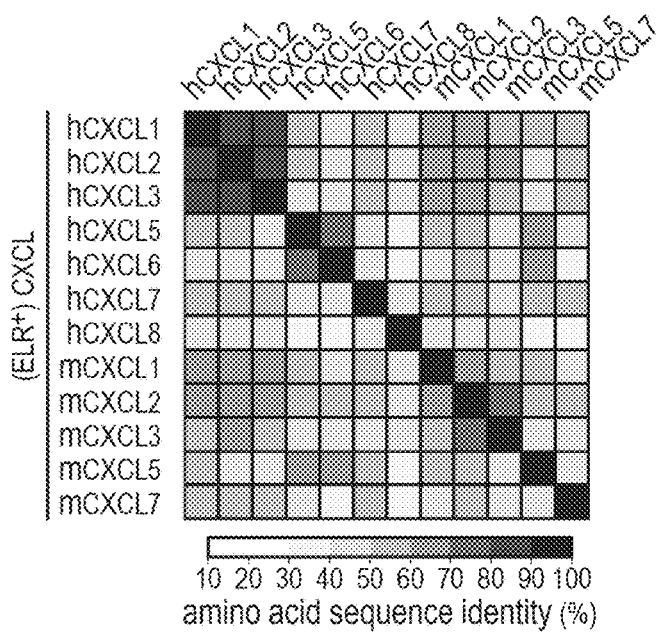 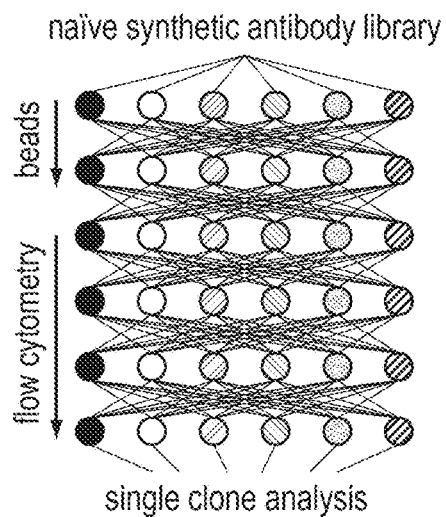
FIG. 2A                FIG. 2B
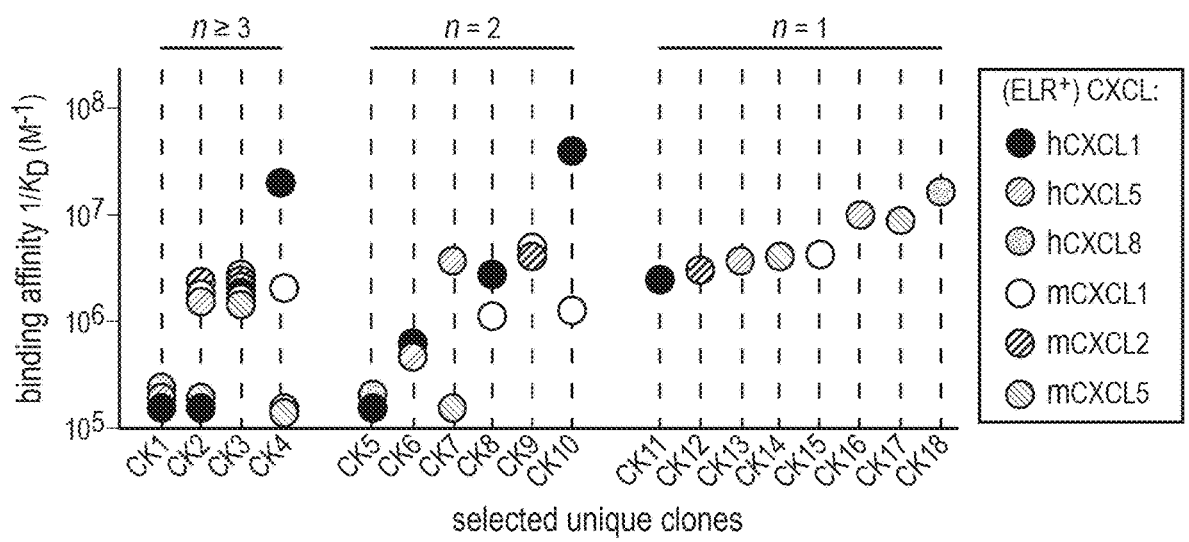
FIG. 2C

FIG. 3A
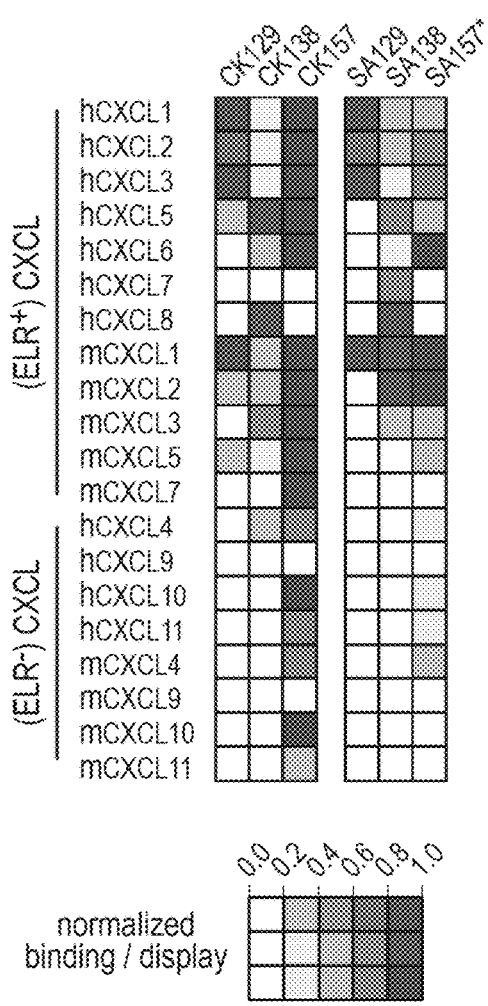
FIG. 3B
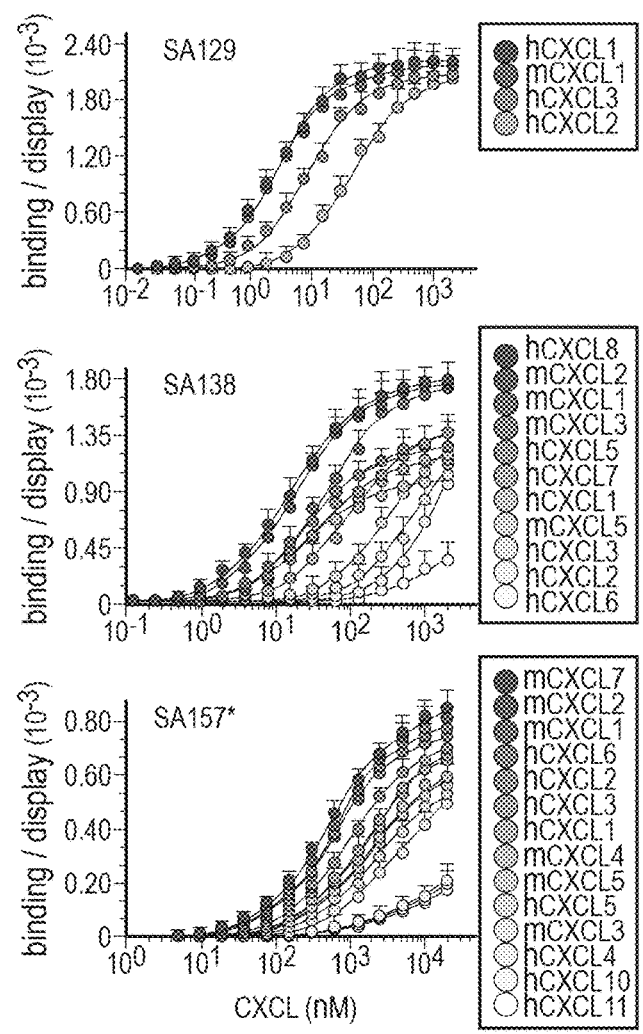
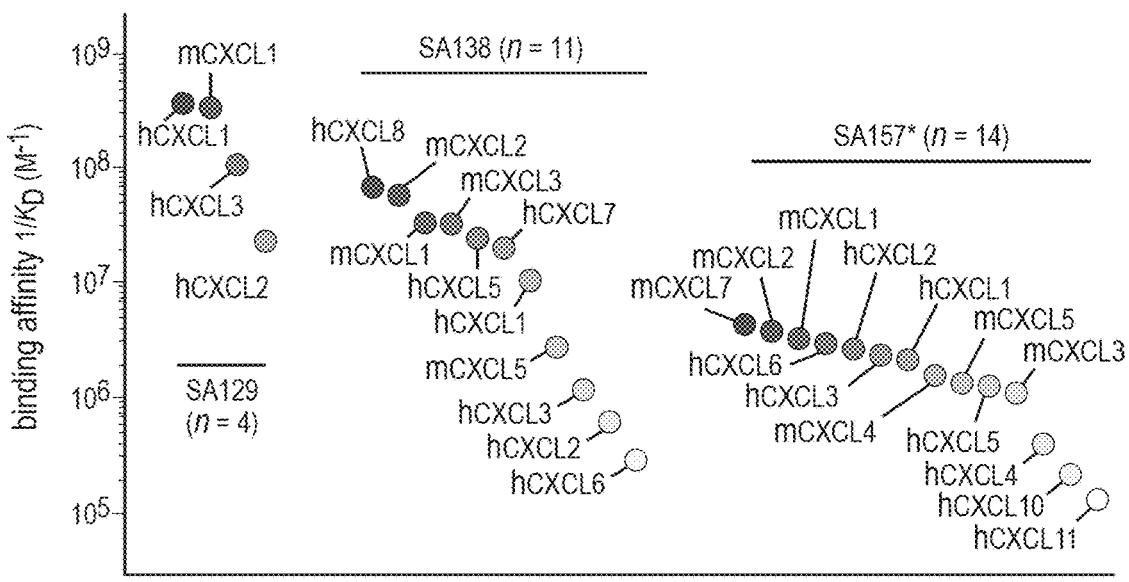
FIG. 3C

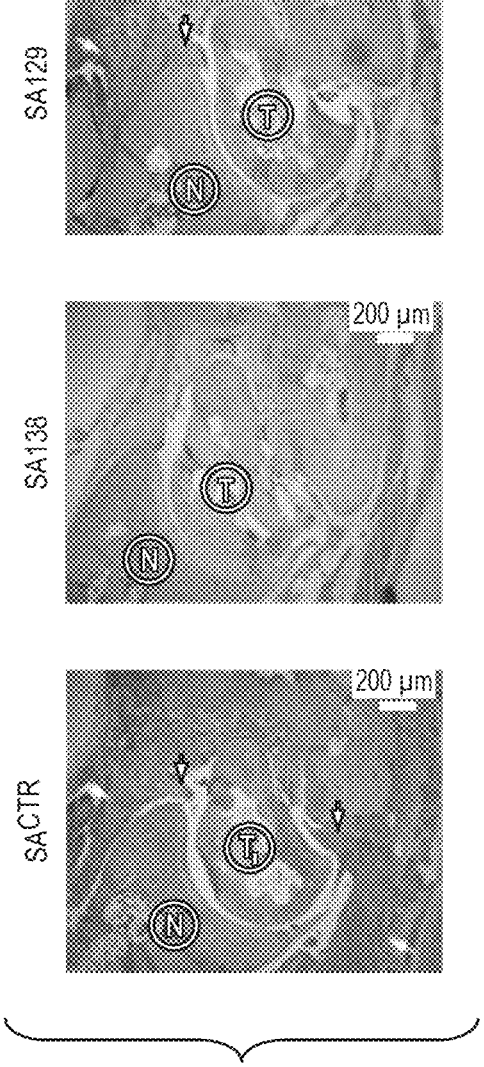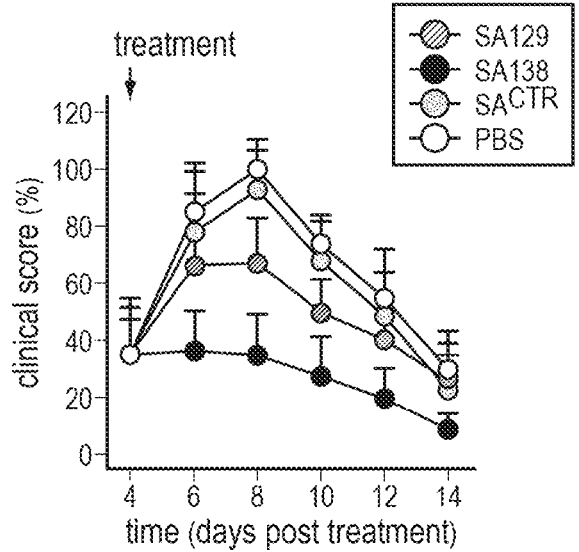
FIG. 7F
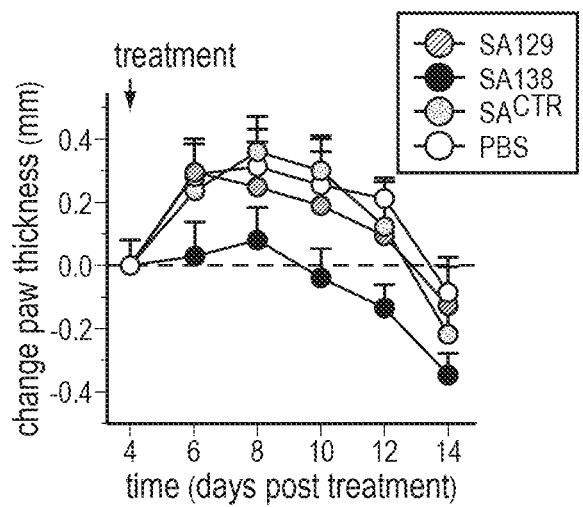
FIG. 7G
FIG. 7E

MULTIPLE SPECIFICITY BINDERS OF CXC CHEMOKINES

RELATED INFORMATION PARAGRAPH

This application is a 35 U.S.C. § 371 national stage filing of International Application No. PCT/US2018/046894, filed on Aug. 17, 2018, which claims the benefit of U.S. Provisional Application No. 62/546,814, filed on Aug. 17, 2017. The entire contents of the above-referenced patent applications are hereby incorporated by reference in their entirety.

REFERENCE TO SEQUENCE LISTING

The instant application contains a Sequence Listing which has been submitted electronically in ASCII format and is hereby incorporated by reference in its entirety. Said ASCII copy, created Jan. 30, 2020, is named "MITN-041US_Sequence-Listing.txt" and is 561669 bytes in size.

BACKGROUND

Chronic inflammatory diseases usually involve multiple ligands that act synergistically through promiscuous and diverse receptors (Cho, J. H & Feldman, M., *Nat Med.* 21, 730-738 (2015)). This complexity is well exemplified by the ELR+ CXC chemokine system, a large family of secreted proteins that play a prominent role in the development and progression of numerous inflammatory diseases, including rheumatoid arthritis (RA) (Cho, J. H & Feldman, M., *Nat Med.* 21, 730-738 (2015); Charo, I. F. & Ransohoff, R. M. *N. Engl. J. Med.* 354, 610-621 (2006); Viola, A. & Luster, A. D. *Annu. Rev. Pharmacol. Toxicol.* 48, 171-197 (2008)).

Despite their clinical and commercial success, monoclonal antibodies often fail to reduce the level of small antigens in circulation. For example, while small chemokines (~8-10 kDa) are rapidly eliminated through renal filtration ($t_{1/2}$<10 min) (Van Zee, K. J. et al. *J Immunol* 148, 1746-1752 (1992)), strategies targeting single or multiple chemokines using large monoclonal antibodies (150 kDa) that are long-lived in circulation ($t_{1/2}$ ~2 weeks) extends the systemic lifetimes of chemokines, thus increasing circulating chemokine levels. This buffering effect has been experimentally observed with numerous antibodies targeting small antigens (Mihara, M., Koishihara, Y., Fukui, H., Yasukawa, K. & Ohsugi, Y, *Immunology* 74, 55-59 (1991); Finkelman, F. D. et al. *J Immunol* 151, 1235-1244 (1993); May, L. T. et al. *J Immunol* 151, 3225-3236 (1993); Jayson, G. C. et al. *Eur J Cancer* 41, 555-563 (2005); Mostbock, S. *Curr Pharm Des* 15, 809-825 (2009); Letourneau, S. et al. *Proceedings of the National Academy of Sciences of the United States of America* 107, 2171-2176 (2010); O'Hear, C. & Foote, *J. Eur J Haematol* 84, 252-258 (2010)), including chemokines (Haringman, J. J. et al *Arthritis and rheumatism* 54, 2387-2392 (2006)), and is consistent with the affinity, binding kinetics and pharmacokinetic profiles of the circulating antibody-small antigen complexes in the absence of efficient clearance (O'Hear, C. E. & Foote, J. *Proceedings of the National Academy of Sciences of the United States of America* 102, 40-44 (2005)). Furthermore, functional full length antibodies that are able to recruit additional immune system cells via FcγR receptors are not ideal for the treatment of inflammatory diseases that exploit autoantibodies.

As chronic inflammatory diseases are complex and involve multiple ligands and receptors acting in concert, therapies targeting a single pathological molecule are often insufficient to achieve the desired clinical outcome. Accordingly, therapeutics that bind multiple targets are needed.

SUMMARY OF THE DISCLOSURE

The present disclosure is based on the discovery of engineered crossreactive therapeutic proteins that bind multiple homologus and orthologus targets, and are capable of preventing and reversing inflammation in an autoimmune model.

Accordingly, in some aspects the disclosure provides fusion proteins comprising a multispecific variable region operably coupled to a polymer, wherein the multispecific variable region binds to at least four ELR+ CXC chemokines. In some aspects, the fusion protein comprises a multispecific variable region that binds human or murine ELR+ CXC chemokines. In other aspects, the fusion protein comprises a multispecific variable region that binds human and murine ELR+ CXC chemokines. In some aspects, the disclosure provides a fusion protein comprising a multispecific variable region that binds at least four ELR+ CXC chemokines selected from the group consisting of: human CXCL1 (Groα), human CXCL2 (Groβ), human CXCL3 (Groγ), human CXCL5 (ENA-78), human CXCL6 (GCP-2), human CXCL7 (NAP-2), human CXCL8 (IL-8), murine CXCL1 (KC), murine CXCL2 (MIP-2), murine CXCL3 (DCIP-1), murine CXCL5 (LIX), and murine CXCL7 (NAP-2). In some aspects, the at least four ELR+ CXC chemokines are hCXCL1, hCXCL2, hCXCL3 and mCXCL1.

In some aspects, the disclosure provides a fusion protein comprising a multispecific variable region that binds at least five, at least six, at least seven, at least eight, at least nine, at least ten, at least eleven, or at least twelve ELR+ CXC chemokines selected from the group consisting of: human CXCL1 (Groα), human CXCL2 (Groβ), human CXCL3 (Groγ), human CXCL5 (ENA-78), human CXCL6 (GCP-2), human CXCL7 (NAP-2), human CXCL8 (IL-8), murine CXCL1 (KC), murine CXCL2 (MIP-2), murine CXCL3 (DCIP-1), murine CXCL5 (LIX), and murine CXCL7 (NAP-2). In some aspects, the at least six chemokines are human CXCL1, human CXCL5, human CXCL8, murine CXCL1, murine CXCL2 and murine CXCL5. In other aspects, the at least eleven chemokines are human CXCL8, murine CXCL2, murine CXCL1, murine CXCL3, murine CXCL7, human CXCL5, human CXCL1, murine CXCL5, human CXCL3, human CXCL2, and human CXCL6

In any of the foregoing aspects, the multispecific variable region is operably coupled to a polymer via a linker. In some aspects, the linker is a Gly-Ser linker.

In some aspects, the disclosure provides a fusion comprising a multispecific variable region operably coupled to a polymer, wherein the multispecific variable region is a scFv. In some aspects, the scFv is operably coupled to the C-terminus of the polymer. In some aspects, the scFv is operably coupled to the N-terminus of the polymer. In some aspects, the scFv is operably coupled to the polymer via a linker. In some aspects, the linker is a Gly-Ser linker.

In some aspects, the disclosure provides a fusion protein comprising a multispecific variable region described herein operably coupled to a polymer, wherein the polymer is a serum albumin moiety. In some aspects, the serum albumin moiety is mouse serum albumin. In other aspects, the serum albumin moiety is human serum albumin. In other aspects, the disclosure provides a fusion protein comprising a multispecific variable region operably coupled to a polymer, wherein the polymer is an Fc domain.

In any of the foregoing aspects, the disclosure provides a fusion protein wherein the multispecific variable region comprises a heavy chain variable region and a light chain variable region, wherein the heavy chain variable region comprises an amino acid sequence as set forth in SEQ ID NOs: 1, 11 or 21.

In any of the foregoing aspects, the disclosure provides a fusion protein wherein the multispecific variable region comprises a heavy chain variable region and a light chain variable region, wherein the light chain variable region comprises an amino acid sequence as set forth in SEQ ID NOs: 2, 12 or 22.

In any of the foregoing aspects, the disclosure provides a fusion protein wherein the multispecific variable region comprises a heavy chain variable region and a light chain variable region, wherein the heavy chain variable region comprises an amino acid sequence as set forth in SEQ ID NOs: 1, 11 or 21, and wherein the light chain variable region comprises an amino acid sequence as set forth in SEQ ID NOs: 2, 12 or 22.

In other aspects, the disclosure provides a fusion protein comprising a multispecific variable region operably coupled to a serum albumin moiety, wherein the multispecific variable region binds to at least four ELR+ CXC chemokines, and wherein the multispecific variable region comprises a heavy chain variable region and a light chain variable region comprising the amino acid sequences set forth in:
(a) SEQ ID NOs: 1 and 2, respectively;
(b) SEQ ID NOs: 11 and 12, respectively; or
(c) SEQ ID NOs: 21 and 22, respectively.

In another aspect, the disclosure provides a multispecific variable region operably coupled to a serum albumin moiety, wherein the multispecific variable region binds to at least four ELR+ CXC chemokines, and wherein the multispecific variable region comprises a heavy chain variable region and light chain variable region comprising amino acid sequences having 90% identity to the amino acid sequences set forth in:
(a) SEQ ID NOs: 1 and 2, respectively;
(b) SEQ ID NOs: 11 and 12, respectively; or
(c) SEQ ID NOs: 21 and 22, respectively.

In some aspects, the disclosure provides a fusion protein, comprising a multispecific variable region operably coupled to a serum albumin moiety, wherein the multispecific variable region binds to at least four ELR+ CXC chemokines, and wherein the multispecific variable region comprises heavy and light chain CDRs selected from the group consisting of:
(a) heavy chain CDR1, CDR2 and CDR3 sequences set forth in SEQ ID NOs: 5, 6 and 7, respectively, and light chain CDR1, CDR2 and CDR3 sequences set forth in SEQ ID NOs: 8, 9 and 10, respectively;
(b) heavy chain CDR1, CDR2 and CDR3 sequences set forth in SEQ ID NOs: 15, 16 and 17, respectively, and light chain CDR1, CDR2 and CDR3 sequences set forth in SEQ ID NOs: 18, 19 and 20, respectively; and
(c) heavy chain CDR1, CDR2 and CDR3 sequences set forth in SEQ ID NOs: 25, 26 and 27, respectively, and light chain CDR1, CDR2 and CDR3 sequences set forth in SEQ ID NOs: 28, 29 and 30, respectively.

In another aspect, the disclosure provides a fusion protein, comprising a multispecific variable region operably coupled to a serum albumin moiety, wherein the multispecific variable region binds to at least four ELR+ CXC chemokines, and wherein the multispecific variable region comprises heavy and light chain variable regions, wherein the heavy chain variable region comprises an amino acid sequence selected from the group consisting of SEQ ID NOs: 1, 11 and 21; and wherein the light chain variable region comprises an amino acid sequence selected from the group consisting of SEQ ID NOs: 2, 12 and 22.

In another aspect, the disclosure provides a fusion protein, comprising a multispecific variable region operably coupled to a serum albumin moiety, wherein the multispecific variable region binds to at least four ELR+ CXC chemokines, and wherein the multispecific variable region comprises heavy chain CDR1, CDR2 and CDR3 sequences set forth in SEQ ID NOs: 5, 6 and 7, respectively, and light chain CDR1, CDR2 and CDR3 sequences set forth in SEQ ID NOs: 8, 9 and 10, respectively. In another aspect, the disclosure provides a fusion protein, comprising a multispecific variable region operably coupled to a serum albumin moiety, wherein the multispecific variable region binds to at least human CXCL8, murine CXCL2, murine CXCL1, murine CXCL3, human CXCL7, human CXCL5, human CXCL1, murine CXCL5, human CXCL3, human CXCL2, and human CXCL6, and wherein the multispecific variable region comprises heavy chain CDR1, CDR2 and CDR3 sequences set forth in SEQ ID NOs: 5, 6 and 7, respectively, and light chain CDR1, CDR2 and CDR3 sequences set forth in SEQ ID NOs: 8, 9 and 10, respectively.

In yet another aspect, the disclosure provides a fusion protein, comprising a multispecific variable region operably coupled to a serum albumin moiety, wherein the multispecific variable region binds to at least four ELR+ CXC chemokines, and wherein the multispecific variable region comprises heavy chain CDR1, CDR2 and CDR3 sequences set forth in SEQ ID NOs: 25, 26 and 27, respectively, and light chain CDR1, CDR2 and CDR3 sequences set forth in SEQ ID NOs: 28, 29 and 30, respectively. In yet another aspect, the disclosure provides a fusion protein, comprising a multispecific variable region operably coupled to a serum albumin moiety, wherein the multispecific variable region binds to at least murine CXCL1, human CXCL1, human CXCL3, and human CXCL2, and wherein the multispecific variable region comprises heavy chain CDR1, CDR2 and CDR3 sequences set forth in SEQ ID NOs: 25, 26 and 27, respectively, and light chain CDR1, CDR2 and CDR3 sequences set forth in SEQ ID NOs: 28, 29 and 30, respectively.

In another aspect, the disclosure provides a fusion protein comprising an amino acid sequence selected from the group consisting of SEQ ID Nos: 95-105 and 160-170.

In another aspect, the disclosure provides a fusion protein comprising an amino acid sequence having at least 90% identity to an amino acid sequence selected from the group consisting of SEQ ID Nos: 95-105 and 160-170.

In any of the foregoing aspects, the fusion protein inhibits binding of ELR+ CXC chemokines to their cognate CXCR1 and CXCR2.

In another aspect, the disclosure provides an isolated monoclonal antibody, or binding fragment thereof, that binds to at least four ELR+ CXC chemokines. In some aspects, the isolated monoclonal antibody, or binding fragment thereof, binds human or murine ELR+ CXC chemokines. In some aspects, the isolated monoclonal antibody, or binding fragment thereof, binds human and murine ELR+ CXC chemokines. In some aspects, the disclosure provides an isolated monoclonal antibody, or binding fragment thereof, that binds to at least four ELR+ CXC chemokines selected from the group consisting of: human CXCL1 (Groα), human CXCL2 (Groβ), human CXCL3 (Groγ), human CXCL5 (ENA-78), human CXCL6 (GCP-2), human CXCL7 (NAP-2), human CXCL8 (IL-8), murine CXCL1 (KC), murine CXCL2 (MIP-2), murine CXCL3 (DCIP-1), murine CXCL5 (LIX), and murine CXCL7 (NAP-2). In some aspects, the at least four ELR+ CXC chemokines are hCXCL1, hCXCL2, hCXCL3 and mCXCL1

In some aspects, the disclosure provides an isolated monoclonal antibody, or binding fragment thereof that binds at least five, at least six, at least seven, at least eight, at least nine, at least ten, at least eleven, or at least twelve ELR+ CXC chemokines selected from the group consisting of: human CXCL1 (Groα), human CXCL2 (Groβ), human CXCL3 (Groγ), human CXCL5 (ENA-78), human CXCL6 (GCP-2), human CXCL7 (NAP-2), human CXCL8 (IL-8), murine CXCL1 (KC), murine CXCL2 (MIP-2), murine CXCL3 (DCIP-1), murine CXCL5 (LIX), and murine CXCL7 (NAP-2). In some aspects, the at least six chemokines are human CXCL1, human CXCL5, human CXCL8, murine CXCL1, murine CXCL2 and murine CXCL5. In other aspects, the at least eleven chemokines are human CXCL8, murine CXCL2, murine CXCL1, murine CXCL3, human CXCL7, human CXCL5, human CXCL1, murine CXCL5, human CXCL3, human CXCL2, and human CXCL6.

In any of the foregoing aspects, the binding fragment thereof is a single chain variable fragment (scFv).

In any of the foregoing aspects, the antibody or binding fragment thereof comprises a heavy chain variable region and a light chain variable region, wherein the heavy chain variable region comprises an amino acid sequence as set forth in SEQ ID NOs: 1, 11 or 21.

In any of the foregoing aspects, the antibody or binding fragment thereof, comprises a heavy chain variable region and a light chain variable region, wherein the light chain variable region comprises an amino acid sequence as set forth in SEQ ID NOs: 2, 12 or 22.

In any of the foregoing aspects, the antibody or binding fragment thereof, comprises a heavy chain variable region and a light chain variable region, wherein the heavy chain variable region comprises an amino acid sequence as set forth in SEQ ID NOs: 1, 11 or 21, and wherein the light chain variable region comprises an amino acid sequence as set forth in SEQ ID NOs: 2, 12 or 22.

In another aspect, the disclosure provides an isolated monoclonal antibody, or binding fragment thereof, that binds to at least four ELR+ CXC chemokines, comprising a heavy chain variable region and light chain variable region comprising the amino acid sequences set forth in:
 (a) SEQ ID NOs: 1 and 2, respectively;
 (b) SEQ ID NOs: 11 and 12, respectively; or
 (c) SEQ ID NOs: 21 and 22, respectively.

In other aspects, the disclosure provides an isolated monoclonal antibody, or binding fragment thereof, that binds at least four ELR+ CXC chemokines, comprising a heavy chain variable region and light chain variable region comprising amino acid sequences having 90% identity to the amino acid sequences set forth in:
 (a) SEQ ID NOs: 1 and 2, respectively;
 (b) SEQ ID NOs: 11 and 12, respectively; or
 (c) SEQ ID NOs: 21 and 22, respectively.

In another aspect, the disclosure provides an isolated monoclonal antibody, or binding fragment thereof, that binds at least four ELR+ CXC chemokines, comprising heavy and light chain CDRs selected from the group consisting of:
 (a) heavy chain CDR1, CDR2 and CDR3 sequences set forth in SEQ ID NOs: 5, 6 and 7, respectively, and light chain CDR1, CDR2 and CDR3 sequences set forth in SEQ ID NOs: 8, 9 and 10, respectively;
 (b) heavy chain CDR1, CDR2 and CDR3 sequences set forth in SEQ ID NOs: 15, 16 and 17, respectively, and light chain CDR1, CDR2 and CDR3 sequences set forth in SEQ ID NOs: 18, 19 and 20, respectively; and
 (c) heavy chain CDR1, CDR2 and CDR3 sequences set forth in SEQ ID NOs: 25, 26 and 27, respectively, and light chain CDR1, CDR2 and CDR3 sequences set forth in SEQ ID NOs: 28, 29 and 30, respectively.

In other aspects, the disclosure provides an isolated monoclonal antibody, or binding fragment thereof, that binds at least four ELR+ CXC chemokines, comprising heavy and light chain variable regions, wherein the heavy chain variable region comprises an amino acid sequence selected from the group consisting of SEQ ID NOs: 1, 11 or 21; and wherein the light chain variable region comprises an amino acid sequence selected from the group consisting of SEQ ID NOs: 2, 12 or 22.

In any of the foregoing aspects, the isolated monoclonal antibody, or binding fragment thereof, inhibits binding of ELR+ CXC chemokines to their cognate CXCR1 and CXCR2.

In another aspect, the disclosure provides methods of treating an autoimmune disorder in a subject in need thereof, the method comprising administering an effective amount of a fusion protein or isolated monoclonal antibody, or binding fragment thereof, described herein. In some aspects, the autoimmune disorder is rheumatoid arthritis.

In another aspect, the disclosure provides methods of blocking neutrophil infiltration in a subject with an autoimmune disorder, the method comprising administering an effective amount of a fusion protein or isolated monoclonal antibody, or binding fragment thereof, described herein. In some aspects, neutrophil infiltration of the synovial fluid of arthritic joints is blocked.

In another aspect, the disclosure provides methods of preventing establishment of an autoimmune disorder in a subject, the method comprising administering an effective amount of a fusion protein or isolated monoclonal antibody, or binding fragment thereof, described herein. In some aspects, the autoimmune disorder is rheumatoid arthritis.

In another aspect, the disclosure provides methods of reversing inflammatory arthritis in a subject in need thereof, the method comprising administering an effective amount of a fusion protein or isolated monoclonal antibody, or binding fragment thereof, described herein.

In another aspect, the disclosure provides a fusion protein or isolated monoclonal antibody, or binding fragment thereof, described herein, for use in treating an autoimmune disorder in a subject in need thereof, the method comprising administering an effective amount of. In some aspects, the autoimmune disorder is rheumatoid arthritis.

In another aspect, the disclosure provides a fusion protein or isolated monoclonal antibody, or binding fragment thereof, described herein, for use in blocking neutrophil infiltration in a subject with an autoimmune disorder. In some aspects, neutrophil infiltration of the synovial fluid of arthritic joints is blocked.

In another aspect, the disclosure provides a fusion protein or isolated monoclonal antibody, or binding fragment thereof, described herein, for use in preventing establishment of an autoimmune disorder in a subject. In some aspects, the autoimmune disorder is rheumatoid arthritis.

In another aspect, the disclosure provides a fusion protein or isolated monoclonal antibody, or binding fragment thereof, described herein, for use in reversing inflammatory arthritis in a subject in need thereof.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2A is a heat map displaying the sequence identity among multiple human and murine ELR+ CXC chemokines. h=human, m=murine.

FIG. 2B is a schematic representation of the iterative selection pathways applied to isolate promiscuous binders from a naïve library of synthetic antibodies displayed on the surface of yeast. Two cycles of magnetic bead screening followed by four cycles of flow cytometry sorting are shown.

FIG. 2C is a plot showing the binding affinities of eighteen unique yeast-displayed synthetic antibody protein binders (CK) selected from six diverse human and murine ELR+ CXC chemokines. Data are represented as inverted equilibrium binding constants ($1/K_D$; $M^{-1}$) and indicate the means of at least three independent experiments. h=human, m=murine.

FIG. 3A is a heat map indicating the normalized binding/display intensities of the engineered antibodies against twenty diverse human and murine CXC chemokines. Binding between soluble CXC chemokines and yeast-displayed CK129, CK138 and CK157 is shown on the left, and binding between soluble serum-albumin antibody fusions SA129, SA138 and SA157* are shown on the right. The intensity of color correlates with the strength of the interaction with weak and strong interactions shown in light and dark colors, respectively. h=human, m=murine.

FIG. 3B provides graphs showing the binding isotherms of yeast-displayed human and murine CXC chemokines to soluble SA129, SA138 and SA157* protein fusions. Equilibrium binding affinity ($K_D$) values were determined only for clones exhibiting signals at high concentration of soluble agents. h=human, m=murine.

FIG. 3C is a plot of the binding affinities of yeast-displayed human and murine CXC chemokines to soluble SA129, SA138 and SA157* protein fusions. The indicated values are displayed as filled circles and represent the means of at least three independent experiments presented as inverted of equilibrium binding constants ($1/K_D$; $M^{-1}$). h=human, m=murine.

FIG. 7E provides representative H&E staining of ankle tissue sections of mice treated with SA129 (top), SA138 (middle) and control SA$^{CTR}$ (bottom) on day 8. Scale bar represents 200 μm. White arrow indicates the infiltrated inflammatory cell in the joints and red arrow indicates pannus formation. T, taulus; N, navicular.

FIGS. 7F and 7G are plots providing the percent clinical score (FIG. 7F) and change in ankle thickness (mm) (FIG. 7G) of K/BxN serum-induced arthritic mice treated beginning on day 4 with serum albumin-antibody fusion proteins (therapeutic regimen). Arrows indicate day treatment began. All data are presented as mean (dots)±SE (bars).

DETAILED DESCRIPTION

Overview

Figure 1:
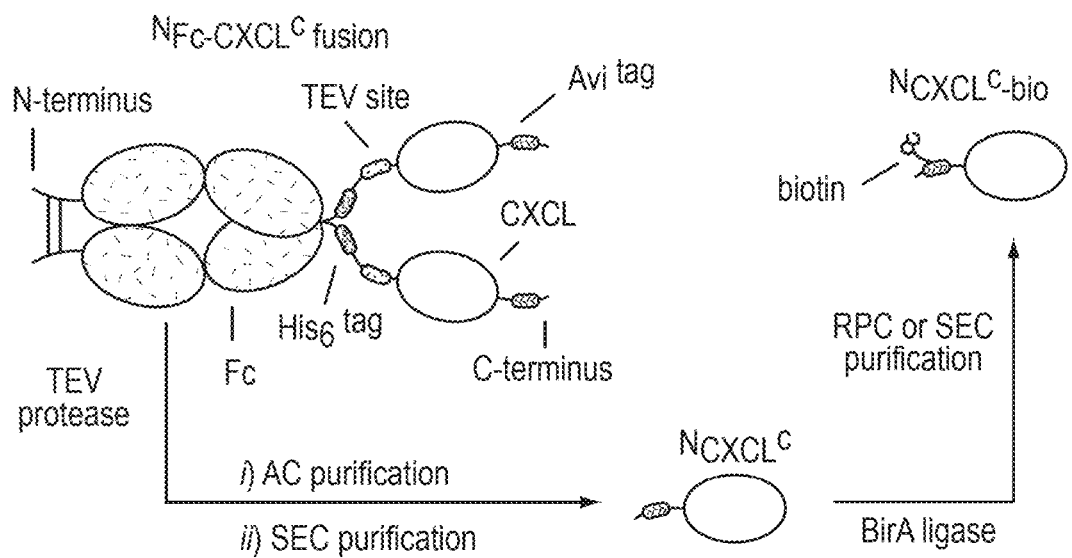
FIG. 1 is a schematic representation of the (i) Fc-ELR+ CXC chemokine fusion protein constructs (Fc-CXCL) and (ii) purification scheme applied to obtain pure, active, and biotinylated ELR+ CXC chemokines (CXCL-bio).

Various diseases are characterized by the development of immunological dysregulation in a patient. The presence of an impaired immune response in patients with autoimmune and related disorders has been particularly well-documented. Augmenting immune functions in patients may have beneficial effects for the alleviation of autoimmune and related diseases.

Described herein are fusion proteins, and isolated monoclonal antibodies, or antigen binding fragments thereof, that were designed to target soluble pro-inflammatory factors (e.g., ELR+ CXC chemokines).

ELR+ CXC chemokines (so-called because members of the chemokine family all possess an E-L-R amino acid motif immediately adjacent to their CXC motif) play an important role in a variety of pathogenic mechanisms, including the migration of neutrophils to sites of inflammation and angiogenesis. Neutrophils contribute to the pathogenesis of several acute and chronic inflammatory/autoimmune diseases.

In general, chemokines are grouped into four subfamilies: CXC, CC, (X)C, and CX3C. In the CXC chemokines, one amino acid separates the first two cysteines ("the CXC motif"). ELR+ CXC chemokines are ligands for CXCR1 and/or CXCR2 chemokine receptors, which are G-protein coupled seven transmembrane domain-type receptors that specifically bind ELR+ CXC chemokines. The seven human ELR+ CXC chemokines are human Gro-alpha (also known as CXCL1), human Gro-beta (also known as CXCL2), human Gro-gamma (also known as CXCL3), human ENA-78 (also known as CXCL5), human GCP-2 (also known as CXCL6), human NAP-2 (also known as CXCL7), and human IL-8 (also known as CXCL8). All ELR+ CXC chemokines bind the CXCR2 receptor; moreover, some ELR+ CXC chemokines bind both CXCR1 and CXCR2 receptors (i.e., CXCL6 and CXCL8), all of which contributes to redundancy in the activation pathways. The five murine ELR+ CXC chemokines are keratinocyte chemoattractant (KC) (also known as CXCL1), Macrophage Inflammatory Protein-2 (MIP-2) (also known as CXCL2), dendritic cell inflammatory protein-1 (DCIP-1) (also known as CXCL3), lipopolysaccharide-induced CXC chemokine (LIX) (also known as CXCL5), and neutrophil activating peptide-2 (NAP-2) (also known as CXCL7).

Crossreactive protein binders are challenging to obtain using traditional methodologies involving animal immunization and hybridoma development. Immune systems tend to remove self-reactive antibodies, making it difficult to generate in vivo antibodies against sequence- and structurally-related antigens derived from different species. In contrast, in vitro protein libraries associated with display technologies are unaffected by immune tolerance (Bradbury, A. R., et al. *Nature biotechnology* 29, 245-254 (2011)). Described herein are selection strategies for the isolation of protein binders with unprecedented crossreactivity towards a panel of structurally related, yet diverse in sequence, protein targets. Moreover, a serum albumin antibody fusion-based strategy was used to enable high drug dosing and optimal pharmacokinetic profiles, thus overcoming continuous receptor occupancy and buffering effect phenomena that have limited previous interventions.

Accordingly, in some aspects, the present disclosure provides fusion proteins comprising a multispecific variable region operably coupled to a polymer, wherein the multispecific variable region binds to at least four ELR+ CXC chemokines. In other aspects, the present disclosure provides methods for treating or preventing a disorder associated with an abnormal immune response (e.g., autoimmune disorder, e.g., rheumatoid arthritis), comprising administering a fusion protein described herein.

Definitions

Terms used in the claims and specification are defined as set forth below unless otherwise specified.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

The term "ameliorating" refers to any therapeutically beneficial result in the treatment of a disease state, e.g., autoimmune disorder, including prophylaxis, lessening in the severity or progression, remission, or cure thereof.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups {e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, larger "peptide insertions," can also be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide may have one or more mutations relative to the starting polypeptide, e.g., one or more amino acid residues which have been substituted with another amino acid residue or which has one or more amino acid residue insertions or deletions. A polypeptide can comprise an amino acid sequence which is not naturally occurring. Such variants necessarily have less than 100% sequence identity or similarity with the starting molecule. In some embodiments, the variant will have an amino acid sequence from about 75% to less than 100% amino acid sequence identity or similarity with the amino acid sequence of the starting polypeptide. In some embodiments, the variant has an amino acid sequence from about 80% to less than 100% amino acid sequence identity or similarity with the amino acid sequence of the starting polypeptide. In some embodiments, the variant has an amino acid sequence from about 85% to less than 100%, amino acid sequence identity or similarity with the amino acid sequence of the starting polypeptide. In some embodiments, the variant has an amino acid sequence from about 90% to less than 100% (e.g., 91%, 92%, 93%, 94%, 95%, 96%, 97%, 98%, 99%) amino acid sequence identity or similarity with the amino acid sequence of the starting polypeptide. In some embodiments, the variant has an amino acid sequence from about 95% to less than 100%, e.g., over the length of the variant molecule, amino acid sequence identity or similarity with the amino acid sequence of the starting polypeptide.

In some embodiments, there is one amino acid difference between a starting polypeptide sequence and the sequence derived therefrom. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity. In some embodiments, a polypeptide consists of, consists essentially of, or comprises an amino acid sequence selected from SEQ ID NOs: 1, 2, 5-12, 15-22, 25-30, 37-42, 63-82, 95-106, 127-146, 148, and 160-182. In some embodiments, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from SEQ ID NOs: 1, 2, 5-12, 15-22, 25-30, 37-42, 63-82, 95-106, 127-146, 148, and 160-182. In some embodiments, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from SEQ ID NOs: 1, 2, 5-12, 15-22, 25-30, 37-42, 63-82, 95-106, 127-146, 148, and 160-182. In some embodiments, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence selected from SEQ ID NOs: 1, 2, 5-12, 15-22, 25-30, 37-42, 63-82, 95-106, 127-146, 148, and 160-182.

In some embodiments, the polypeptides are encoded by a nucleotide sequence. Nucleotide sequences of the invention can be useful for a number of applications, including: cloning, gene therapy, protein expression and purification, mutation introduction, DNA vaccination of a host in need thereof, antibody generation for, e.g., passive immunization, PCR, primer and probe generation, and the like. In some embodiments, the nucleotide sequence described herein comprises, consists of, or consists essentially of, a nucleotide sequence selected from SEQ ID NOs: 3, 4, 13, 14, 23, 24, 31-36, 43-62, 83-94, 107-126, 147, 149, and 150-159. In some embodiments, a nucleotide sequence includes a nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence set forth in SEQ ID NOs: 3, 4, 13, 14, 23, 24, 31-36, 43-62, 83-94, 107-126, 147, 149, and 150-159. In some embodiments, a nucleotide sequence includes a contiguous nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous nucleotide sequence set forth in SEQ ID NOs: 3, 4, 13, 14, 23, 24, 31-36, 43-62, 83-94, 107-126, 147, 149, and 150-159. In some embodiments, a nucleotide sequence includes a nucleotide sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous nucleotides of a nucleotide sequence set forth in SEQ ID NOs: 3, 4, 13, 14, 23, 24, 31-36, 43-62, 83-94, 107-126, 147, 149, and 150-159.

It will also be understood by one of ordinary skill in the art that the polypeptides (e.g., fusion proteins) disclosed herein may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. Mutations may be introduced by standard techniques, such as site-directed mutagenesis and PCR-mediated mutagenesis.

The polypeptides disclosed herein may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In some embodiments, a string of amino acids can be replaced with a structurally similar string that differs in order and/or composition of side chain family members. Alternatively, in some embodiments, mutations may be introduced randomly along all or part of a coding sequence, such as by saturation mutagenesis, and the resultant mutants can be incorporated into binding polypeptides of the invention and screened for their ability to bind to the desired target.

As used herein, the term "antibody" refers to a whole antibody comprising two light chain polypeptides and two heavy chain polypeptides. Whole antibodies include different antibody isotypes including IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified or a recombinant antibody.

As used herein, the term "antibody fragment," "antigen-binding fragment," or similar terms refer to a fragment of an antibody that retains the ability to bind to a target antigen(s) (e.g., ELR+ CXC chemokine(s)) and promote, induce, and/ or increase the activity of the target antigen. Such fragments include, e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al. (2001) *J Immunol Methods* 248(1):47-66; Hudson and Kortt (1999) *J Immunol Methods* 231(1):177-189; Poljak (1994) *Structure* 2(12): 1121-1123; Rondon and Marasco (1997) *Annual Review of Microbiology* 51:257-283, the disclosures of each of which are incorporated herein by reference in their entirety.

As used herein, the term "antibody fragment" also includes, e.g., single domain antibodies such as camelized single domain antibodies. See, e.g., Muyldermans et al. (2001) *Trends Biochem Sci* 26:230-235; Nuttall et al. (2000) *Curr Pharm Biotech* 1:253-263; Reichmann et al. (1999) *J Immunol Meth* 231:25-38; PCT application publication nos. WO 94/04678 and WO 94/25591; and U.S. Pat. No. 6,005, 079, all of which are incorporated herein by reference in their entireties. In some embodiments, the disclosure provides single domain antibodies comprising two VH domains with modifications such that single domain antibodies are formed.

In some embodiment, an antigen-binding fragment includes the variable region of a heavy chain polypeptide and the variable region of a light chain polypeptide. In some embodiments, an antigen-binding fragment described herein comprises the CDRs of the light chain and heavy chain polypeptide of an antibody.

As used herein, the term "autoimmune and/or related diseases" refers to diseases, disorders, conditions, and/or syndromes arising from and/or directed against a patient's own cells, tissues, and/or organs, or a co-segregate or manifestation thereof, or resulting condition therefrom. Examples of autoimmune and related diseases include graft rejection (e.g. graft vs. host disease), allergy, inflammatory diseases, and also include, but are not limited to, Acute Disseminated Encephalomyelitis (ADEM), Acute necrotizing hemorrhagic leukoencephalitis, Addison's disease, Agammaglobulinemia, Allergic conjunctivitis, Allergic rhinitis, Allergic disorders of the gastrointestinal tract, Alopecia areata, Alzheimer's disease, Amyloidosis, Ankylosing spondylitis, Anti-GBM/Anti-TBM nephritis, Antiphospholipid syndrome (APS), Arteriosclerosis, Asthma, Autoimmune angioedema, Autoimmune aplastic anemia, Autoimmune-associated infertility, Autoimmune dysautonomia, Autoimmune encephalomyelitis, Autoimmune hemophilia, Autoimmune hepatitis, Autoimmune hyperlipidemia, Autoimmune immunodeficiency, Autoimmune inner ear disease (AIED), Autoimmune lymphoproliferative syndrome, Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Autoimmune uveoretinitis, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Eczema, Endometriosis, Eosinophilic esophagitis, Eosinophilic fasciitis, Erythema nodosum, Eustachian tube itching, Experimental allergic encephalomyelitis, Evans syndrome, Fibromyalgia, Fibrosing alveolitis, Giant cell arteritis (temporal arteritis), Giant cell myocarditis, Giant papillary conjunctivitis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Inflammatory Bowel Disease, Insulin resistance, Interstitial cystitis, Juvenile rheumatoid arthritis, Juvenile diabetes (Type 1 diabetes), Juvenile myositis, Kawasaki disease/syndrome, Lambert-Eaton syndrome, Leukocytoclastic vasculitis, Lichen planus, Lichen sclerosus, Ligneous conjunctivitis, Linear IgA disease (LAD), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Osteoarthritis, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatic, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sinusitis, Sjogren's syndrome, Sperm & testicular autoimmunity, Stiff person syndrome, Subacute bacterial endocarditis (SBE), Susac's syndrome, Sympathetic ophthalmia, Systemic lupus eythematosus (SLE), Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vernal conjunctivitis, Vernal keratoconjunctivitis, Vasculitis, Vesiculobullous dermatosis, Vitiligo, Wegener's granulomatosis (now termed Granulomatosis with Polyangiitis (GPA). Any one or more of the aforementioned or unmentioned autoimmune and/or related diseases may be the target disease for a method of treatment as disclosed herein.

As used herein, the term "bispecific" or "bifunctional antibody" refers to an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

Traditionally, the recombinant production of bispecific antibodies is based on the co-expression of two immunoglobulin heavy-chain/light-chain pairs, where the two heavy chain/light-chain pairs have different specificities (Milstein and Cuello (1983) *Nature* 305:537-539). Antibody variable domains with the desired binding specificities (antibody-antigen combining sites) can be fused to immunoglobulin constant domain sequences. The fusion of the heavy chain variable region is preferably with an immunoglobulin heavy-chain constant domain, including at least part of the hinge, CH2, and CH3 regions. For further details of illustrative currently known methods for generating bispecific antibodies see, e.g., Suresh et al. (1986) Methods in Enzymology 121:210; PCT Publication No. WO 96/27011; Brennan et al. (1985) Science 229:81; Shalaby et al., J Exp Med (1992) 175:217-225; Kostelny et al. (1992) J Immunol 148(5):1547-1553; Hollinger et al. (1993) Proc Natl Acad Sci USA 90:6444-6448; Gruber et al. (1994) J Immunol 152:5368; and Tutt et al. (1991) J Immunol 147:60. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) J Immunol 148(5):1547-1553. The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) Proc Natl Acad Sci USA 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) J Immunol 152:5368. Alternatively, the antibodies can be "linear antibodies" as described in, e.g., Zapata et al. (1995) Protein Eng. 8(10):1057-1062. Briefly, these antibodies comprise a pair of tandem Fd segments (VH-CH1-VH-CH1) which form a pair of antigen binding regions. Linear antibodies can be bispecific or monospecific. Antibodies with more than two valencies (e.g., trispecific antibodies) are contemplated and described in, e.g., Tutt et al. (1991) J Immunol 147:60.

As used herein, the term "chemokine" refers to a member of the family of small cytokines, or signaling proteins, that induce directed chemotaxis. Chemokines are grouped into four subfamilies: CXC, CC, (X)C, and CX3C. In some embodiments, the chemokine or chemokines of interest are CXC chemokines. In the CXC chemokines, one amino acid separates the first two cysteines ("the CXC motif").

As used herein, the term "cross-reacts" refers to the ability of an antibody or fusion protein of the disclosure to bind to chemokines from a different species. For example, an antibody or fusion protein of the present disclosure which binds human ELR+ CXC chemokines may also bind another species of ELR+ CXC chemokines. As used herein, cross-reactivity is measured by detecting a specific reactivity with purified antigen in binding assays (e.g., SPR, ELISA). Methods for determining cross-reactivity include standard binding assays as described herein, for example, by Biacore™ surface plasmon resonance (SPR) analysis using a Biacore™ 2000 SPR instrument (Biacore AB, Uppsala, Sweden), or flow cytometric techniques. In some embodiments, a fusion protein described herein comprises a multispecific variable region that binds human and murine ELR+ CXC chemokines.

As used herein, the term "ELR+ CXC chemokine" refers to a chemokine possessing an E-L-R amino acid motif immediately adjacent to a CXC motif. ELR+ CXC chemokines are ligands for CXCR1 and/or CXCR2 chemokine receptors, which are G-protein coupled seven transmembrane domain-type receptors that specifically binds ELR+ CXC chemokines. All ERL+ CXC chemokines bind the CXCR2 receptor, whereas some bind both CXCR1 and CXCR2 receptors. The ELR+ CXC chemokines are human Gro-alpha (also known as CXCL1), human Gro-beta (also known as CXCL2), human Gro-gamma (also known as CXCL3), human ENA-78 (also known as CXCL5), human GCP-2 (also known as CXCL6), human NAP-2 (also known as CXCL7), human IL-8 (also known as CXCL58). The five murine ELR+ CXC chemokines are keratinocyte chemoattractant (KC), Macrophage Inflammatory Protein-2 (MIP-2), dendritic cell inflammatory protein-1 (DCIP-1), neutrophil activating peptide-2 (NAP-2) and lipopolysaccharide-induced CXC chemokine (LIX). The table below provides the list of ELR+ CXC chemokines, their alternative names, including the murine equivalent, and what receptors they bind to.

| Chemokine | Alternative Names | Receptor(s) Binding |
|---|---|---|
| CXCL1 | GROα, MGSA, murine KC | CXCR2 |
| CXCL2 | GROβ, MIP-2a, murine MIP-2 | CXCR2 |

-continued

| Chemokine | Alternative Names | Receptor(s) Binding |
|---|---|---|
| CXCL3 | GROγ, MIP-2b, murine DCIP-1 | CXCR2 |
| CXCL5 | ENA-78, murine LIX | CXCR2 |
| CXCL6 | GCP-2 (no murine equivalent) | CXCR1, CXCR2 |
| CXCL7 | NAP-2 | CXCR2 |
| CXCL8 | IL-8 (no murine equivalent) | CXCR1, CXCR2 |

As used herein, the term "epitope" or "antigenic determinant" refers to a site on an antigen (e.g., ELR+ CXC chemokine) to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from a chemokine are tested for reactivity with the given antibody. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)).

Also, encompassed by the present disclosure are antibodies that bind to epitopes on chemokines (e.g., ELR+ CXC chemokines) which comprises all or a portion of an epitope recognized by the particular antibodies described herein (e.g., the same or an overlapping region or a region between or spanning the region).

Also encompassed by the present disclosure are antibodies that bind the same epitope and/or antibodies that compete for binding to chemokines (e.g., ELR+ CXC chemokines) with the antibodies described herein. Antibodies that recognize the same epitope or compete for binding can be identified using routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen. Numerous types of competitive binding assays are known, for example: solid phase direct or indirect radioimmunoassay (MA), solid phase direct or indirect enzyme immunoassay (ETA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label MA using I-125 label (see Morel et al., *Mol. Immunol.* 25(1):7 (1988)); solid phase direct biotin-avidin EIA (Cheung et al., *Virology* 176:546 (1990)); and direct labeled MA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

Other techniques include, for example, epitope mapping methods, such as, x-ray analyses of crystals of antigen: antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

As used herein, the term "Fc region" refers to the portion of a native immunoglobulin formed by the respective Fc domains (or Fc moieties) of its two heavy chains. As used herein, the term "Fc domain" refers to a portion of a single immunoglobulin (Ig) heavy chain wherein the Fc domain does not comprise an Fv domain. As such, an Fc domain can also be referred to as "Ig" or "IgG." In some embodiments, an Fc domain begins in the hinge region just upstream of the papain cleavage site and ends at the C-terminus of the antibody. Accordingly, a complete Fc domain comprises at least a hinge domain, a CH2 domain, and a CH3 domain. In some embodiments, an Fc domain comprises at least one of: a hinge (e.g., upper, middle, and/or lower hinge region) domain, a CH2 domain, a CH3 domain, a CH4 domain, or a variant, portion, or fragment thereof. In some embodiments, an Fc domain comprises a complete Fc domain (i.e., a hinge domain, a CH2 domain, and a CH3 domain). In some embodiments, an Fc domain comprises a hinge domain (or portion thereof) fused to a CH3 domain (or portion thereof). In some embodiments, an Fc domain comprises a CH2 domain (or portion thereof) fused to a CH3 domain (or portion thereof). In some embodiments, an Fc domain consists of a CH3 domain or portion thereof. In some embodiments, an Fc domain consists of a hinge domain (or portion thereof) and a CH3 domain (or portion thereof). In some embodiments, an Fc domain consists of a CH2 domain (or portion thereof) and a CH3 domain. In some embodiments, an Fc domain consists of a hinge domain (or portion thereof) and a CH2 domain (or portion thereof). In some embodiments, an Fc domain lacks at least a portion of a CH2 domain (e.g., all or part of a CH2 domain). An Fc domain herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. In some embodiments, the Fc domain is derived from an immunoglobulin of any species and/or any subtype, including, but not limited to, a human IgG1, IgG2, IgG3, IgG4, IgD, IgA, IgE, or IgM antibody. A human IgG1 constant region can be found at Uniprot P01857 and in Table 12 (i.e., SEQ ID NO: 172). The Fc domain of human IgG1 can be found in Table 12 (i.e., SEQ ID NO: 173). The Fc domain encompasses native Fc and Fc variant molecules. As with Fc variants and native Fc's, the term Fc domain includes molecules in monomeric or multimeric form, whether digested from whole antibody or produced by other means. The assignment of amino acid residue numbers to an Fc domain is in accordance with the definitions of Kabat. See, e.g., Sequences of Proteins of Immunological Interest (Table of Contents, Introduction and Constant Region Sequences sections), 5th edition, Bethesda, Md.:NIH vol. 1:647-723 (1991); Kabat et al., "Introduction" Sequences of Proteins of Immunological Interest, US Dept of Health and Human Services, NIH, 5th edition, Bethesda, Md. vol. l:xiii-xcvi (1991); Chothia & Lesk, J. Mol. Biol. 196:901-917 (1987); Chothia et al., Nature 342:878-883 (1989), each of which is herein incorporated by reference for all purposes.

As set forth herein, it will be understood by one of ordinary skill in the art that any Fc domain may be modified such that it varies in amino acid sequence from the native Fc domain of a naturally occurring immunoglobulin molecule. In some embodiments, the Fc domain has reduced effector function (e.g., FcγR binding).

In some embodiments, the Fc domains are derived from different immunoglobulin molecules. For example, an Fc domain may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

As used herein, the term "fusion protein" refers to a recombinant protein prepared by fusion of a multi specific variable region described herein, and a polymer (e.g., serum albumin).

As used herein, the term "gly-ser polypeptide linker" refers to a peptide that consists of glycine and serine residues. An exemplary gly-ser polypeptide linker comprises the amino acid sequence Ser(Gly4Ser)n (SEQ ID NO: 183). In some embodiments, n=1. In some embodiments, n=2. In some embodiments, n=3, i.e., Ser(Gly4Ser)3 (SEQ ID NO: 184). In some embodiments, n=4, i.e., Ser(Gly4Ser)4 (SEQ ID NO: 185). In some embodiments, n=5. In some embodiments, n=6. In some embodiments, n=7. In some embodiments, n=8. In some embodiments, n=9. In some embodiments, n=10. Another exemplary gly-ser polypeptide linker comprises the amino acid sequence (Gly4Ser)n (SEQ ID NO: 186). In some embodiments, n=1. In some embodiments, n=2. In some embodiments, n=3. In some embodiments, n=4. In some embodiments, n=5. In some embodiments, n=6. Another exemplary gly-ser polypeptide linker comprises the amino acid sequence (Gly3Ser)n (SEQ ID NO: 187). some embodiments, n=1. In some embodiments, n=2. In some embodiments, n=3. In some embodiments, n=4. In some embodiments, n=5. In some embodiments, n=6.

As used herein, "half-life" refers to the time taken for the serum or plasma concentration of a polypeptide to reduce by 50%, in vivo, for example due to degradation and/or clearance or sequestration by natural mechanisms. The fusion protein disclosed herein is stabilized in vivo and its half-life increased by, e.g., fusion to an Fc region, fusion to serum albumin (e.g., HSA or MSA), through PEGylation, or by binding to serum albumin molecules (e.g., human serum albumin) which resist degradation and/or clearance or sequestration. The half-life can be determined in any manner known per se, such as by pharmacokinetic analysis. Suitable techniques will be clear to the person skilled in the art, and may for example generally involve the steps of suitably administering a suitable dose of the amino acid sequence or compound to a subject; collecting blood samples or other samples from said subject at regular intervals; determining the level or concentration of the amino acid sequence or compound in said blood sample; and calculating, from (a plot of) the data thus obtained, the time until the level or concentration of the amino acid sequence or compound has been reduced by 50% compared to the initial level upon dosing. Further details are provided in, e.g., standard handbooks, such as Kenneth, A. et al., Chemical Stability of Pharmaceuticals: A Handbook for Pharmacists and in Peters et al., Pharmacokinetic Analysis: A Practical Approach (1996). Reference is also made to Gibaldi, M. et al., Pharmacokinetics, 2nd Rev. Edition, Marcel Dekker (1982).

As used herein, the term "human antibody" includes antibodies having variable and constant regions (if present) of human germline immunoglobulin sequences. Human antibodies of the disclosure can include amino acid residues not encoded by human germline immunoglobulin sequences (e.g., mutations introduced by random or site-specific mutagenesis in vitro or by somatic mutation in vivo) (see, Lonberg, N. et al. (1994) *Nature* 368(6474): 856-859); Lonberg, N. (1994) *Handbook of Experimental Pharmacology* 113:49-101; Lonberg, N. and Huszar, D. (1995) *Intern. Rev. Immunol.* Vol. 13: 65-93, and Harding, F. and Lonberg, N. (1995) *Ann. N.Y. Acad. Sci* 764:536-546). However, the term "human antibody" does not include antibodies in which CDR sequences derived from the germline of another mammalian species, such as a mouse, have been grafted onto human framework sequences (i.e., humanized antibodies).

As used herein, the term a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, "immune cell" is a cell of hematopoietic origin and that plays a role in the immune response. Immune cells include lymphocytes (e.g., B cells and T cells), natural killer cells, and myeloid cells (e.g., monocytes, macrophages, eosinophils, mast cells, basophils, and granulocytes).

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising a fusion protein described herein).

The term "in vivo" refers to processes that occur in a living organism.

As used herein, the term "isolated antibody" is intended to refer to an antibody which is substantially free of other antibodies having different antigenic specificities (e.g., an isolated antibody that binds to chemokines (e.g., ELR+ CXC chemokines) is substantially free of antibodies that specifically bind antigens other than chemokines (e.g., ELR+ CXC chemokines)). An isolated antibody that specifically binds to an epitope may, however, have cross-reactivity to other chemokines (e.g., ELR+ CXC chemokines) from different species. In addition, an isolated antibody is typically substantially free of other cellular material and/or chemicals.

As used herein, the term "isolated nucleic acid molecule" refers to nucleic acids encoding fusion proteins, antibodies or antibody portions (e.g., $V_H$, $V_L$, CDR3) that bind to chemokines (e.g., ELR+ CXC chemokines), is intended to refer to a nucleic acid molecule in which the nucleotide sequences encoding the fusion protein, antibody or antibody portion are free of other nucleotide sequences encoding fusion proteins, antibodies or antibody portions that bind antigens other than chemokines (e.g., ELR+ CXC chemokines), which other sequences may naturally flank the nucleic acid in human genomic DNA. For example, Table 12 shows nucleotide sequences comprising the heavy chain ($V_H$) and light chain ($V_L$) variable regions of multispecific monoclonal antibodies described herein.

As used herein, "isotype" refers to the antibody class (e.g., IgM or IgG1) that is encoded by heavy chain constant region genes. In some embodiments, an antibody of the disclosure is of the IgG1 isotype. In some embodiments, an antibody of the disclosure is of the IgG2 isotype. In some embodiments, an antibody of the disclosure is of the IgG3 isotype. In some embodiments, an antibody of the disclosure is of the IgG4 isotype.

As used herein, the term "isotype switching" refers to the phenomenon by which the class, or isotype, of an antibody changes from one Ig class to one of the other Ig classes.

As used herein, the term "kd" is intended to refer to the off rate constant for the dissociation of an antibody from the antibody/antigen complex.

As used herein, the term "ka" is intended to refer to the on rate constant for the association of an antibody with the antigen.

As used herein, the terms "linked," "fused", or "fusion", are used interchangeably. These terms refer to the joining together of two more elements or components or domains, by whatever means including chemical conjugation or recombinant means. Methods of chemical conjugation (e.g., using heterobifunctional crosslinking agents) are known in the art.

As used herein, "local administration" or "local delivery," refers to delivery that does not rely upon transport of the composition or agent to its intended target tissue or site via the vascular system. For example, the composition may be delivered by injection or implantation of the composition or agent or by injection or implantation of a device containing the composition or agent. Following local administration in the vicinity of a target tissue or site, the composition or agent, or one or more components thereof, may diffuse to the intended target tissue or site.

The term "mammal" or "subject" or "patient" as used herein includes both humans and non-humans and includes, but is not limited to, humans, non-human primates, canines, felines, murines, bovines, equines, and porcines.

The term "multispecific" as used herein refers to a polypeptide (e.g., fusion protein and/or variable region) capable of binding more than one target of interest (e.g., ELR+ CXC chemokine). In some embodiments, the terms "multispecific" and "crossreactive" are interchangeable. In some embodiments, the polypeptide binds at least two targets of interest (e.g., ELR+ CXC chemokines). In some embodiments, the polypeptide binds at least four targets of interest (e.g., ELR+ CXC chemokines). In some embodiments, the polypeptide binds at least five targets of interest (e.g., ELR+ CXC chemokines). In some embodiments, the polypeptide binds at least six targets of interest (e.g., ELR+ CXC chemokines). In some embodiments, the polypeptide binds at least seven targets of interest (e.g., ELR+ CXC chemokines). In some embodiments, the polypeptide binds at least eight targets of interest (e.g., ELR+ CXC chemokines). In some embodiments, the polypeptide binds at least nine targets of interest (e.g., ELR+ CXC chemokines). In some embodiments, the polypeptide binds at least ten targets of interest (e.g., ELR+ CXC chemokines). In some embodiments, the polypeptide binds at least eleven targets of interest (e.g., ELR+ CXC chemokines). In some embodiments, the polypeptide binds at least twelve targets of interest (e.g., ELR+ CXC chemokines).

"Nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., Biol. Chem. 260:2605-2608, 1985; and Cassol et al, 1992; Rossolini et al, Mol. Cell. Probes 8:91-98, 1994). For arginine and leucine, modifications at the second base can also be conservative. The term nucleic acid is used interchangeably with gene, cDNA, and mRNA encoded by a gene.

Polynucleotides used herein can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, the term "operably linked" or "operably coupled" refers to a juxtaposition wherein the components described are in a relationship permitting them to function in their intended manner.

As used herein, "parenteral administration," "administered parenterally," and other grammatically equivalent phrases, refer to modes of administration other than enteral and topical administration, usually by injection, and include, without limitation, intravenous, intranasal, intraocular, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

As used herein, the term "patient" includes human and other mammalian subjects that receive either prophylactic or therapeutic treatment.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

As generally used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

As used herein, the term "PK" is an acronym for "pharmacokinetic" and encompasses properties of a compound including, by way of example, absorption, distribution, metabolism, and elimination by a subject. As used herein, an "extended-PK group" refers to a polymer, protein, peptide, or moiety that increases the circulation half-life of a biologically active molecule when fused to or administered together with the multispecific variable region. Examples of an extended-PK group include PEG, human serum albumin (HSA) binders (as disclosed in U.S. Publication Nos. 2005/0287153 and 2007/0003549, PCT Publication Nos. WO 2009/083804 and WO 2009/133208, and SABA molecules as described in US2012/094909), serum albumin (e.g., HSA), Fc or Fc fragments and variants thereof, transferrin and variants thereof, and sugars (e.g., sialic acid). Other exemplary extended-PK groups are disclosed in Kontermann et al., Current Opinion in Biotechnology 2011; 22:868-876, which is herein incorporated by reference in its entirety.

"Polypeptide," "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, the term "preventing" when used in relation to a condition, refers to administration of a composition which reduces the frequency of, or delays the onset of, symptoms of a medical condition in a subject relative to a subject which does not receive the composition.

As used herein, the term "purified" or "isolated" as applied to any of the proteins (fusion proteins, antibodies or fragments) described herein refers to a polypeptide that has been separated or purified from components (e.g., proteins or other naturally-occurring biological or organic molecules) which naturally accompany it, e.g., other proteins, lipids, and nucleic acid in a prokaryote expressing the proteins. Typically, a polypeptide is purified when it constitutes at least 60 (e.g., at least 65, 70, 75, 80, 85, 90, 92, 95, 97, or 99) %, by weight, of the total protein in a sample.

As used herein, the term "recombinant host cell" (or simply "host cell") is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) Nature Biotech. 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

As used herein, the terms "specific binding," "selective binding," "selectively binds," and "specifically binds," refer to fusion protein or antibody binding to an epitope on a predetermined antigen. Typically, the fusion protein or antibody binds with an equilibrium dissociation constant ($K_d$) of approximately less than $10^{-6}$ M, such as approximately less than $10^{-7}$ M, $10^{-8}$ M, $10^{-9}$ M or $10^{-10}$ M or even lower when determined by surface plasmon resonance (SPR) technology in a BIACORE 2000 instrument using an ELR+ CXC chemokine of interest as the analyte and the fusion protein or antibody as the ligand and binds to the predetermined antigen with an affinity that is at least two-fold greater than its affinity for binding to a non-specific antigen (e.g., BSA, casein) other than the predetermined antigen or a closely-related antigen. The phrases "recognizing an antigen" and "specific for an antigen" are used interchangeably herein with the term "binds specifically to an antigen."

As used herein, the term "subject" includes any human or non-human animal. For example, the methods and compositions of the present disclosure can be used to treat a subject with an immune disorder. The term "non-human animal" includes all vertebrates, e.g., mammals and non-mammals, such as non-human primates, sheep, dog, cow, chickens, amphibians, reptiles, etc.

The term "sufficient amount" or "amount sufficient to" means an amount sufficient to produce a desired effect, e.g., an amount sufficient to reduce the size of a tumor.

The term "substantial homology" indicates that two nucleotide sequences or two amino acid sequences, when optimally aligned and compared, are identical, with appropriate insertions or deletions, in at least about 80% of the nucleotides or amino acids, usually at least about 90% to 95%, and more preferably at least about 98% to 99.5% of the nucleotides or amino acids. Alternatively, substantial homology exists when the segments will hybridize under selective hybridization conditions, to the complement of the strand.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present disclosure, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "T cell" refers to a type of white blood cell that can be distinguised from other white blood cells by the presence of a T cell receptor on the cell surface. There are several subsets of T cells, including, but not limited to, T helper cells (a.k.a. Tx cells or $CD4^+$ T cells) and subtypes, including $T_H1$, $T_H2$, $T_H3$, $T_H17$, $T_H9$, and $T_{FH}$ cells, cytotoxic T cells (a.k.a Tc cells, $CD8^+$ T cells, cytotoxic T lymphocytes, T-killer cells, killer T cells), memory T cells and subtypes, including central memory T cells ($T_{CM}$ cells), effector memory T cells ($T_{EM}$ and $T_{EMRA}$ cells), and resident memory T cells ($T_{RM}$ cells), regulatory T cells (a.k.a. $T_{reg}$ cells or suppressor T cells) and subtypes, including $CD4^+$ $FOXP3^+$ $T_{reg}$ cells, $CD4^+FOXP3^-$ $T_{reg}$ cells, Tr1 cells, Th3 cells, and $T_{reg}17$ cells, natural killer T cells (a.k.a. NKT cells), mucosal associated invariant T cells (MAITs), and gamma delta T cells (γδ T cells), including Vγ9/Vδ2 T cells. Any one or more of the aforementioned or unmentioned T cells may be the target cell type for a method as disclosed herein.

The term "therapeutically effective amount" is an amount that is effective to ameliorate a symptom of a disease. A therapeutically effective amount can be a "prophylactically effective amount" as prophylaxis can be considered therapy.

The terms "treat," "treating," and "treatment," as used herein, refer to therapeutic or preventative measures described herein. The methods of "treatment" employ administration to a subject, in need of such treatment, a fusion protein or antibody, or antigen binding fragment thereof, of the present disclosure, for example, a subject in need of a reduced immune response or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

As used herein, the term "vector" is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

It must be noted that, as used in the specification and the appended claims, the singular forms "a," "an" and "the" include plural referents unless the context clearly dictates otherwise.

Multispecific Variable Regions and Antibodies

The present disclosure provides multispecific variable regions capable of binding more than one ELR+ CXC chemokine (e.g., at least two, at least three, at least four, at least five, at least six, at least seven, at least eight, at least nine, at least ten, at least eleven, at least twelve). In some embodiments, the multispecific variable region is a single chain variable fragment (scFv). In some embodiments, the present disclosure also provides isolated monoclonal antibodies, or antigen binding fragments thereof, capable of binding more than one ELR+ CXC chemokine (e.g., at least two, at least three, at least four, at least five, at least six, at least seven, at least eight, at least nine, at least ten, at least eleven, at least twelve).

The ELR+ CXC chemokine system consists of numerous small and structurally similar chemoattractant ligands capable of binding to and activating the related CXCR1 and CXCR2 G protein-coupled receptors (GCPRs) expressed abundantly on the surface of neutrophils (Griffith, J. W. et al. *Annu Rev Immunol* 32, 659-702(2014)). These ligands act either by autocrine or paracrine mechanisms to induce signaling networks that direct neutrophils to sites of inflammation. Studies in animals have demonstrated that genetic deletion of the most promiscuous ELR+ CXC chemokine receptor, CXCR2, can block the development of joint inflammation in anti-type II collagen antibody-induced arthritis (CAIA) (Min, S. H. et al *Biochem Biophy Res Commun* 391, 1080-1086 (2010)), adjuvant-induced arthritis (AIA) (Barsante, M. M. et al *Br J Pharmacol* 153, 992-2001 (2008); Coelho, F. M. et al *Arthritis Rheum* 58, 2329-2337 (2008); Grespan, R. et al *Arthritis Rheum* 58, 2030-2040 (2008)), and K/B×N serum transfer induced arthritis (Jacobs, J. P. et al *Arthritis Rheum* 62, 1921-1932 (2010); Chou, R. C. et al *Immunity* 33, 266-278 (2010)).

Inhibition of ELR+ CXC chemokine-driven signaling has been previously attempted by employing various antagonists against CXCR1 and CXCR2 receptors, including neutralizing antibodies, small molecules and peptide-derived inhibitors. However, these antagonists have shown limited therapeutic effects (Schall, T. J. & Proudfoot, A. E. *Nat Rev Immunol* 11, 355-363 (2011); Szekanecz, Z. & Koch, A. E. *Nat Rev Rheumatol* 12, 5-13 (2016)). Failures of such receptor-based therapies have been attributed to (i) difference between the orthologous rodent (pre-clinical) and human (clinical systems); and (ii) the extremely high doses of antagonist required to guarantee continuous receptor occupancy, such that all receptors in the body are antagonized (Id.).

Accordingly, the present disclosure provides multispecific variable regions, and isolated monoclonal antibodies, or antigen binding fragments thereof, that bind to the ELR+ CXC chemokine ligands themselves. In some embodiments, the multispecific variable regions, and isolated monoclonal antibodies, or antigen binding fragments thereof, described herein, bind to and inhibit or reduce the activity of the ELR+ CXC chemokine ligands.

In some embodiments, the multispecific variable region, or isolated monoclonal antibody, or antigen binding fragment thereof, comprises a heavy chain variable region and a light chain variable region, wherein the heavy chain variable region comprises an amino acid sequence as set forth in SEQ ID NOs: 1, 11 or 21. In some embodiments, the heavy chain variable region comprises the amino acid sequence set forth in SEQ ID NO: 1. In some embodiments, the heavy chain variable region comprises the amino acid sequence set forth in SEQ ID NO: 11. In some embodiments, the heavy chain variable region comprises the amino acid sequence set forth in SEQ ID NO: 21.

In some embodiments, the multispecific variable region, or isolated monoclonal antibody, or antigen binding fragment thereof, comprises a heavy chain variable region and a light chain variable region, wherein the light chain variable region comprises an amino acid sequence as set forth in SEQ ID NOs: 2, 12 or 22. In some embodiments, the light chain variable region comprises the amino acid sequence set forth in SEQ ID NO: 2. In some embodiments, the light chain variable region comprises the amino acid sequence set forth in SEQ ID NO: 12. In some embodiments, the light chain variable region comprises the amino acid sequence set forth in SEQ ID NO: 22.

In some embodiments, the multispecific variable region, or isolated monoclonal antibody, or antigen binding fragment thereof, comprises a heavy chain variable region and a light chain variable region, wherein the heavy chain variable region comprises an amino acid sequence as set forth in SEQ ID NOs: 1, 11 or 21, and wherein the light chain variable region comprises an amino acid sequence as set forth in SEQ ID NOs: 2, 12 or 22.

In some embodiments, the multispecific variable region, or isolated monoclonal antibody, or antigen binding fragment thereof, comprises a heavy chain variable region and a light chain variable region comprising the amino acid sequences set forth in:
  (a) SEQ ID NOs: 1 and 2, respectively;
  (b) SEQ ID NOs: 11 and 12, respectively; or
  (c) SEQ ID NOs: 21 and 22, respectively.

In some embodiments, the multispecific variable region, or isolated monoclonal antibody, or antigen binding fragment thereof, comprises a heavy chain variable region and light chain variable region comprising amino acid sequences having 90% identity to the amino acid sequences set forth in:
  (a) SEQ ID NOs: 1 and 2, respectively;
  (b) SEQ ID NOs: 11 and 12, respectively; or
  (c) SEQ ID NOs: 21 and 22, respectively.

In some embodiments, the multispecific variable region, or isolated monoclonal antibody, or antigen binding fragment thereof, comprises heavy and light chain CDRs selected from the group consisting of:
  (a) heavy chain CDR1, CDR2 and CDR3 sequences set forth in SEQ ID NOs: 5, 6 and 7, respectively, and light chain CDR1, CDR2 and CDR3 sequences set forth in SEQ ID NOs: 8, 9 and 10, respectively;
  (b) heavy chain CDR1, CDR2 and CDR3 sequences set forth in SEQ ID NOs: 15, 16 and 17, respectively, and light chain CDR1, CDR2 and CDR3 sequences set forth in SEQ ID NOs: 18, 19 and 20, respectively; and
  (c) heavy chain CDR1, CDR2 and CDR3 sequences set forth in SEQ ID NOs: 25, 26 and 27, respectively, and light chain CDR1, CDR2 and CDR3 sequences set forth in SEQ ID NOs: 28, 29 and 30, respectively.

In some embodiments, the multispecific variable region, or isolated monoclonal antibody, or antigen binding fragment thereof, comprises heavy chain CDR1, CDR2 and CDR3 sequences set forth in SEQ ID NOs: 5, 6 and 7, respectively, and light chain CDR1, CDR2 and CDR3 sequences set forth in SEQ ID NOs: 8, 9 and 10, respectively.

In some embodiments, the multispecific variable region, or isolated monoclonal antibody, or antigen binding fragment thereof, comprises heavy chain CDR1, CDR2 and CDR3 sequences set forth in SEQ ID NOs: 25, 26 and 27, respectively, and light chain CDR1, CDR2 and CDR3 sequences set forth in SEQ ID NOs: 28, 29 and 30, respectively.

In some embodiments, a multispecific variable region, or isolated monoclonal antibody, or antigen binding fragment thereof, provided herein, binds to human CXCL1, human CXCL2, human CXCL3, human CXCL5, human CXCL6, human CXCL7, human CXCL8, murine CXCL1, murine CXCL2, murine CXCL3, murine CXCL5, murine CXCL7, or any combination thereof.

In some embodiments, a multispecific variable region, or isolated monoclonal antibody, or antigen binding fragment thereof, provided herein, binds to at least two ELR+ CXC chemokines. In some embodiments, a multispecific variable region, or isolated monoclonal antibody, or antigen binding fragment thereof, provided herein, binds to at least four ELR+ CXC chemokines. In some embodiments, a multispecific variable region, or isolated monoclonal antibody provided herein, binds to at least four ELR+ CXC chemokines. In some embodiments, a multispecific variable region, or isolated monoclonal antibody, or antigen binding fragment thereof, provided herein, binds to at least five ELR+ CXC chemokines. In some embodiments, a multispecific variable region, or isolated monoclonal antibody, or antigen binding fragment thereof, provided herein, binds to at least six ELR+ CXC chemokines. In some embodiments, a multispecific variable region, or isolated monoclonal antibody provided herein, binds to at least seven ELR+ CXC chemokines. In some embodiments, a multispecific variable region, or isolated monoclonal antibody provided herein, binds to at least eight ELR+ CXC chemokines. In some embodiments, a multispecific variable region, or isolated monoclonal antibody provided herein, binds to at least nine ELR+ CXC chemokines. In some embodiments, a multispecific variable region, or isolated monoclonal antibody provided herein, binds to at least ten ELR+ CXC chemokines. In some embodiments, a multispecific variable region, or isolated monoclonal antibody provided herein, binds to at least eleven ELR+ CXC chemokines. In some embodiments, a multispecific variable region, or isolated monoclonal antibody provided herein, binds to at least twelve ELR+ CXC chemokines.

In some embodiments, a multispecific variable region, or isolated monoclonal antibody, or antigen binding fragment thereof, provided herein, binds to human CXCL1, human CXCL2, human CXCL3, and murine CXCL1. In some embodiments, a multispecific variable region, or isolated monoclonal antibody, or antigen binding fragment thereof, provided herein, binds to human CXCL1, human CXCL5, human CXCL8, murine CXCL1, murine CXCL2 and murine CXCL5. In some embodiments, a multispecific variable region, or isolated monoclonal antibody, or antigen binding fragment thereof, provided herein, binds to human CXCL1, human CXCL2, human CXCL3, human CXCL5, human CXCL6, human CXCL7, human CXCL8, murine CXCL1, murine CXCL2, murine CXCL3 and murine CXCL5.

In some embodiments, a multispecific variable region, or isolated monoclonal antibody, or antigen binding fragment thereof, provided herein, binds to human ELR+ CXC chemokines. In some embodiments, a multispecific variable region, or isolated monoclonal antibody, or antigen binding fragment thereof, provided herein, binds to murine ELR+ CXC chemokines. In some embodiments, a multispecific variable region, or isolated monoclonal antibody, or antigen binding fragment thereof, provided herein, binds to human and murine ELR+ CXC chemokines. In some embodiments, a multispecific variable region, or isolated monoclonal antibody, or antigen binding fragment thereof, provided herein, binds to human and murine ELR− CXC chemokines (e.g., murine CXCL4, human CXCL4, human CXCL10 and human CXCL11).

In some embodiments, a multispecific variable region, or isolated monoclonal antibody, or antigen binding fragment thereof, provided herein, inhibits or reduces binding of an ELR+ CXC chemokine of interest to its cognate receptor. In some embodiments, a multispecific variable region, or isolated monoclonal antibody, or antigen binding fragment thereof, provided herein, inhibits or reduces binding of an ELR+ CXC chemokine of interest to CXCR2. In some embodiments, a multispecific variable region, or isolated monoclonal antibody, or antigen binding fragment thereof, provided herein, inhibits or reduces binding of an ELR+ CXC chemokine of interest CXCR1. In some embodiments, a multispecific variable region, or isolated monoclonal antibody, or antigen binding fragment thereof, provided herein, inhibits or reduces binding of an ELR+ CXC chemokine of interest to CXCR1 and CXCR2.

Fusion Protein

In some embodiments, the present disclosure provides fusion proteins comprising a multispecific variable region (e.g., scFv) described herein, operably coupled to a polymer. Examples of polymers suitable for use in the fusion proteins described herein, are provided in Strohl, W. R. *BioDrugs*, *Vol.* 29: 215-239 (2015), herein incorporated by reference in its entirety. The coupling of a polymer to multispecific variable region, either covalently or non-covalently, enhances the solubility and stability of the multispecific variable region.

Moreover, in some embodiments, the conjugating of a polymer to a multispecific variable region extends the pharmacokinetic profile (e.g., serum half-life) of the multispecific variable region. In some embodiments, the serum half-life of a fusion protein described herein is increased relative to the multispecific variable region alone. In some embodiments, the serum half-life of a fusion protein described herein is at least 20, 40, 60, 80, 100, 120, 150, 180, 200, 400, 600, 800, or 1000% longer relative to the multispecific variable region alone. In certain embodiments, the serum half-life of a fusion protein described herein is at least 1.5-fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of the multispecific variable region alone. In certain embodiments, the serum half-life of a fusion protein described herein is at least 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours.

In some embodiments, the polymer is an albumin moiety (e.g., serum albumin). In some embodiments, the polymer is an Fc domain. In some embodiments, the polymer is polyethylene glycol (PEG). In some embodiments, the polymer is transferrin. In some embodiments, the polymer is a serum immunoglobulin binding protein. In some embodiments, the polymer is an albumin binding moiety.

Serum Albumin

In some embodiments, the fusion protein comprises a multispecific variable region (e.g., scFv) described herein, operably coupled to an albumin moiety, or fragment thereof. Suitable albumins for use in the fusion proteins can be from human, primate, rodent, bovine, equine, donkey, rabbit, goat, sheep, dog, chicken or pig. In some embodiments, the albumin is a serum albumin, for example, a human serum albumin, primate serum albumin (e.g., chimpanzee serum albumin, gorilla serum albumin), rodent serum albumin (e.g., hamster serum albumin, guinea pig serum albumin, mouse serum albumin and rat serum albumin), bovine serum albumin, equine serum albumin, donkey serum albumin, rabbit serum albumin, goat serum albumin, sheep serum albumin, dog serum albumin, chicken serum albumin, and pig serum albumin.

Serum albumin exploits the FcRn receptor to achieve long half-life in circulation but its plasma persistence is still shorter than full length monoclonal antibodies, thus avoiding "buffering" effects associated with the use of full-length antibody-based strategies (Sand, K. M. et al *Front Immunol* 5, 682 (2014); Mihara, M. e al *Immunology* 74, 55-59 (1991); O'Hear, C. E. & Foote, J. *Proc Natl Acad Sci USA* 102, 40-44 (2005); Haringman, J. J. et al *Arthritis and Rheumatism* 54, 2387-2393 (2006)). Unlike an antibody, serum albumin does not find the FcγR receptors expressed on the surface of immune system cells, thus eluding extra immune system activation and inflammation mediated by antibody-dependent cell-mediated cytotoxicity (ADCC).

In some embodiments, the fusion protein comprises a human serum albumin (HSA), or variants or fragments thereof, such as those disclosed in U.S. Pat. No. 5,876,969, WO 2011/124718, WO 2013/075066, and WO 2011/0514789. In some embodiments, the serum albumin moiety used in the fusion protein described herein, has sequence identity to the sequence of wild-type HSA as set forth in SEQ ID NO: 171. of at least 50%, such as at least 60%, at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

In some embodiments, the fusion protein comprises a mouse serum albumin (MSA), or variants or fragments thereof. In some embodiments, the serum albumin moiety used in the fusion protein described herein, has sequence identity to the sequence of wild-type MSA as set forth in SEQ ID NO: 173. of at least 50%, such as at least 60%, at least 70%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

In some embodiments, the number of alternations, e.g., substitutions, insertions, or deletions in the albumin variants of the present disclosure is 1-20, e.g., 1-10, 1-5, such as 1, 2, 3, 4, 5, 6, 7, 8, 9 or 10 alterations compared to the corresponding wild-type albumin (e.g., HSA or MSA).

In addition to wild-type albumin, albumin variants are considered applicable as fusion partners with the multispecific variable regions (e.g., scFv) of the disclosure. Non-limiting examples of such variants include one or more alterations (e.g., substitutions, deletions, or insertions) in one or more positions corresponding to positions 417, 440, 464, 490, 492, 493, 494, 495, 496, 499, 500, 501, 503, 504, 505, 506, 510, 535, 536, 537, 538, 540, 541, 542, 550, 573, 574, 575, 577, 578, 579, 580, 581, 582 and 584 of HSA (SEQ ID NO: 171). In some embodiments, a variant comprises an alteration of at least one of these positions, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or all of these positions. The substitution(s) may be any substitution(s) where the amino acid in the natural albumin sequence is substituted with a different amino acid selected among the remaining 19 natural occurring amino acids, provided that the substitution(s) increases the half-life of the polypeptide it is fused or conjugated to relative to the polypeptide not fused to the variant or a polypeptide fused to the wild-type albumin. Exemplary variants with altered serum half-life and/or binding to FcRn are those that include one or more of the following amino acid substitutions in HSA (SEQ ID NO: 171), as disclosed in U.S. Published Application No. 2012-0220530: Q417A, Q417H, H440Q, H464Q, A490D, E492G, E492T, E492P, E492H, V493P, V493L, D494N, D494Q, D494A, D494E, D494P, E495Q, E495A, T496A, P499A, K500E, K500G, K500A, K500S, K500C, K500P, K500H, K500F, K500N, K500W, K500T, K500M, K500Y, K500V, K500Q, K500L, K500I, K500R, E501A, E501P, E501Q, N503K, N503D, E503H, A504E, E505K, E505D, T506F, T506S, H510Q, H535Q, K536A, P537A, K538A, K538H, T540S, K541A, K541D, K541G, K541N, K541E, K542P, E542D, D550N, K573Y, K573W, K573P, K573H, K573F, K573V, K573I, K573T, K573N, K573S, K573G, K573M, K573C, K573A, K573E, K573Q, K573R, K573L, K573D, K574N, Q580K, L575F, A577T, A577E, A578R, A578S, S579C, S579T, Q580K, A581D, A582T, G584A (the contents of which are incorporated herein by reference). In particular embodiments, the variant has position 573 of HSA (SEQ ID NO: 171) substituted with proline (P), tryptophan (W), or tyrosine (Y). In some embodiments, the variant comprises multiple alterations, such as substitutions, at positions corresponding to 494 and 496; 492 and 493; 494 and 417; 492 and 503; 492 and 573 (e.g., E492G+K573P, E492G+K573A); and 492, 503, and 573 (e.g., E492G+N503H+K573P). It should be understood that variants containing any alteration (e.g., substitution, insertion, deletion) at any one of the above positions of HSA (SEQ ID NO: 171), or at any other position(s), are suitable for use in the fusion proteins described herein.

In some embodiments, the albumin variant has an increased serum half-life compared to a wild-type albumin. Albumin variants with increased serum half-life, as disclosed in WO2011/051489, include E492G, K500R, N503H, N503K, D550E, K573Y, K573W, K573P, K573H, K573F, K573V, K573I, K573T, K573N, K573S, K573G, K573M, K573C, K573A, K573E, K573Q, K573R, K573L, K573D, K574N, Q580K, E492G+N503K, E492G+N503H, E492G+K573A, E492G+K573P, E492G+N503K+K573P, E492G+N503H+K573P, E492G+N503K+K573A K573P+ L575F+G584A, K573P+A578S+S579T+G584A, K573P+ A577E+A578S+Q580K+A582T, K573P+K574N+A577T+ A578R+S579C+Q580K+A581D+G584A, and E492H+ E501P+N503H+E505D+T506S+T540S+K541E. It will be evident to the skilled artisan that variants with other amino acid substitutions or combinations of amino acid substitutions can be readily tested with routine methods to determine whether they exhibit increased serum half-life.

Some natural variants of albumin also exhibit increased serum half-life, and are suitable for use in the fusion proteins described herein. Such natural HSA variants with increased serum half-life are known in the art, such as E501K, E570K (Iwao et al. 2007, *B.B.A. Proteins and Proteomics* 1774, 1582-90), E505K (Gallino et al., supra), K536E, K574N (Minchiotti et al., *Biochim Biophys Acta* 1987:916:411-418), D550G (Takahashi et al., *PNAS* 1987:84:4413-7), and D550A (Carlson et al., *PNAS* 1992:89:8225-9).

In some embodiments, the variant albumin has an amino acid substitution that increases the affinity of the albumin to FcRn, which correlates with increased serum half-life. Such amino acid substitutions include, but are not limited to, HSA with K573P (i.e., lysine at position 573 substituted with a proline). Routine methods, such as surface plasmon resonance (SPR), as disclosed in WO2011/051489, can be used to determine whether a particular albumin variant exhibits increased affinity to FcRn relative to the corresponding wild-type albumin. It will be evident to the skilled artisan that increased affinity to FcRn can be determined by comparing the binding constants KD of the albumin variant and wild-type albumin. In the context of the present disclosure, variant albumins having a KD that is lower than the KD for natural HSA is considered to have a higher plasma half-life than HSA.

In some embodiments, it may be desirable for the variant albumin, or fragment thereof, to decrease the serum half-life of a fusion protein. Such variant albumins, or fragments thereof, may decrease the binding of the fusion proteins to FcRn relative to non-albumin fused multispecific variable regions in which albumin is the corresponding wild-type albumin. Fusion proteins with decreased serum half-lives, e.g., those with decreased FcRn binding affinity, are useful, for example, for administration to a mammal where a shortened circulation time may be advantageous, e.g., for in vivo diagnostic imaging or in situations where the starting polypeptide has toxic side effects when present in the circulation for prolonged periods. Albumin variants with decreased FcRn binding affinity are also less likely to cross the placenta and, thus, are also useful in the treatment of diseases or disorders in pregnant women. In addition, other applications in which reduced FcRn binding affinity may be desired include those applications in which localization in the brain, kidney, and/or liver is desired. In some embodiments, the fusion proteins described herein exhibit reduced transport across the epithelium of kidney glomeruli from the vasculature. In some embodiments, the fusion proteins described herein exhibit reduced transport across the blood brain barrier (BBB) from the brain, into the vascular space. In some embodiments, a fusion protein with altered FcRn binding comprises at least one albumin domain (e.g., domain III of HSA) having one or more amino acid substitutions within the "FcRn binding region" of an albumin domain. Exemplary albumin variants that exhibit decreased serum half-life are disclosed in, e.g., WO2011/124718, and include Q417A, H464Q, D494N, D494Q, D494A, E495Q, E495A, T496A, P499A, K500E, K500G, K500D, K500A, K500S, K500C, K500P, K500H, K500F, K500N, K500W, K500T, K500M, K500Y, K500V, K500Q, K500L, K500I, K500R, D500N, E501A, E501Q, N503K, N503D, H510Q, H535Q, K536A, P537A, K541G, K541D, K541A, K541N, E492T+N503D, E492G+V493P, D494E+Q417H, E495Q+T496A, D494N+E495Q+T496A, E492G+K538H+K541N+E542D, E492G+V493P+K538H+K541N+E542D, A490D+E492T+V493L+E501P+E503D+A504E+E505K+T506F+K541D. Exemplary natural albumin variants that exhibit decreased serum half-life include D494N (Peach et al., *Biochim Biophys Acta* 1991; 1097:49-54), and K541E and K560E (Iwao et al., *B.B.A. Proteins and Proteomics* 2007; 1774:1582-90).

One or more positions of albumin, or a variant or fragment thereof, can be altered to provide reactive surface residues for, e.g., conjugation with a multispecific variable region. Exemplary positions in HSA (SEQ ID NO: 171) that can be altered to provide conjugation competent cysteine residues include, but are not limited to, those disclosed in WO2010/092135, such as, D1C, A2C, T79C, E82C, E86C, D121C, D129C, S270C, A364C, A504C, E505C, D549C, D562C, A578C, A579C, A581C, L585C, and L595C. Alternatively a cysteine residue may be added to the N or C terminus of albumin. Methods suitable for producing conjugation competent albumin, or a variant or peptide thereof, as well as covalently linking albumin, or a variant or fragment thereof, with a conjugation partner or partners (e.g., a multispecific variable region) are routine in the art and disclosed in, e.g., WO2010/092135 and WO 2009/019314. In some embodiments, the conjugates may conveniently be linked via a free thiol group present on the surface of HSA (amino acid residue 34 of mature HSA) using art-recognized methods.

In addition to the albumin or variants thereof described supra, fragments of albumin, or fragments of variants thereof, are suitable for use as the albumin component of the fusion proteins described herein. Exemplary albumin fragments that are suitable for use in the fusion proteins are disclosed in WO 2011/124718. A fragment of albumin (e.g., a fragment of HSA) will typically be at least 20 amino acids in length, such as at least 40 amino acids, at least 60 amino acids, at least 80 amino acids, at least 100 amino acids, at least 150 amino acids, at least 200 amino acids, at least 300 amino acids, at least 400 amino acids, or at least 500 amino acids in length, and will alter (e.g., increase) the serum half-life of the polypeptide it is fused to (e.g., multispecific variable region) relative to the non-fused polypeptide.

In some embodiments, a fragment may comprise at least one whole sub-domain of albumin. Domains of HSA have been expressed as recombinant proteins (Dockal et al., *JBC* 1999; 274:29303-10), where domain I was defined as consisting of amino acids 1-197 (SEQ ID NO: 175), domain II was defined as consisting of amino acids 189-385 (SEQ ID NO: 176), and domain III was defined as consisting of amino acids 381-585 (SEQ ID NO: 177) of HSA (SEQ ID NO: 171). Partial overlap of the domains occurs given the extended α-helix structure (h10-hl) which exists between domains I and II, and between domains II and III (Peters, 1996, op. cit, Table 2-4). HSA also comprises six sub-domains (sub-domains IA, IB, NA, NB, INA and NIB). Sub-domain IA comprises amino acids 6-105, sub-domain IB comprises amino acids 120-177, sub-domain NA comprises amino acids 200-291, sub-domain NB comprises amino acids 316-369, sub-domain INA comprises amino acids 392-491 and sub-domain NIB comprises amino acids 512-583 of SEQ ID NO: 171.

A fragment may comprise a whole or part of one or more domains or sub-domains as defined above, or any combination of those domains and/or sub-domains. A fragment may comprise or consist of at least 50, 60, 70, 75, 80, 85, 90, 95, 96, 97, 98, or 99% of an albumin or of a domain of an albumin, or a variant or fragment thereof. Additionally, single or multiple heterologous fusions comprising any of the above; or single or multiple heterologous fusions to albumin, or a variant or fragment of any of these may be used. Such fusions include albumin N-terminal fusions, albumin C-terminal fusions and co-N-terminal and C-terminal albumin fusions as exemplified by WO 01/79271. In some embodiments, the fragment of albumin or variant thereof retains the ability to bind to FcRn. In some embodiments, the fusion proteins contain domain III of albumin, or a variant thereof. In some embodiments, the fusion proteins contain domain III of albumin and an additional domain selected from the group consisting of domain I, domain II, and domain III. In some embodiments, the fusion proteins contain domains I, II, and III of albumin.

In certain embodiments, the fusion protein comprises a serum albumin binding protein such as those described in US2005/0287153, US2007/0003549, US2007/0178082, US2007/0269422, US2010/0113339, WO2009/083804, and WO2009/133208, which are herein incorporated by reference in their entirety.

Fc Fragments

In some embodiments, the fusion protein comprises a multispecific variable region described herein, operably coupled to an Fc domain. In some embodiments, the Fc domain comprises the amino acid sequence set forth in SEQ ID NO: 174. It will be understood by those in the art that epitope tags corresponding to 6× his tag on the fusion proteins are optional. The Fc domain does not contain a variable region that binds to antigen. Fc domains useful for producing the fusion proteins disclosed herein may be obtained from a number of different sources. In certain embodiments, an Fc domain of the fusion protein is derived from a human immunoglobulin. In certain embodiments, the Fc domain is from a human IgG1 constant region (SEQ ID NO: 172). The Fc domain of human IgG1 is set forth in SEQ ID NO: 174. It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species. Moreover, the Fc domain or portion thereof may be derived from any immunoglobulin class, including IgM, IgG, IgD, IgA, and IgE, and any immunoglobulin isotype, including IgG1, IgG2, IgG3, and IgG4.

In some embodiments, a fusion protein includes a mutant Fc domain. In some embodiments, a fusion protein includes a mutant, IgG1 Fc domain. In some embodiments, a mutant Fc domain comprises one or more mutations in the hinge, CH2, and/or CH3 domains. In some embodiments, a mutant Fc domain includes a D265A mutation.

A variety of Fc domain gene sequences (e.g., mouse and human constant region gene sequences) are available in the form of publicly accessible deposits. Constant region domains comprising an Fc domain sequence can be selected lacking a particular effector function and/or with a particular modification to reduce immunogenicity. Many sequences of antibodies and antibody-encoding genes have been published and suitable Fc domain sequences (e.g. hinge, CH2, and/or CH3 sequences, or portions thereof) can be derived from these sequences using art recognized techniques. The genetic material obtained using any of the foregoing methods may then be altered or synthesized to obtain polypeptides suitable for use in the methods disclosed herein. It will further be appreciated that the scope of this invention encompasses alleles, variants and mutations of constant region DNA sequences.

Fc domain sequences can be cloned, e.g., using the polymerase chain reaction and primers which are selected to amplify the domain of interest. To clone an Fc domain sequence from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7: 1509); rapid amplification of cDNA ends (Ruberti, F. et al. 1994. J. Immunol. Methods 173:33); antibody leader sequences (Larrick et al. Biochem Biophys Res Commun 1989; 160: 1250). The cloning of antibody sequences is further described in Newman et al., U.S. Pat. No. 5,658,570, filed Jan. 25, 1995, which is herein incorporated by reference.

Fusion proteins disclosed herein may comprise one or more Fc domains (e.g., 2, 3, 4, 5, 6, 7, 8, 9, 10, or more Fc domains). In certain embodiments, the Fc domains may be of different types. In certain embodiments, at least one Fc domain present in the fusion protein comprises a hinge domain or portion thereof. In certain embodiments, the fusion protein disclosed herein comprises at least one Fc domain which comprises at least one CH2 domain or portion thereof. In certain embodiments, the fusion protein disclosed herein comprises at least one Fc domain which comprises at least one CH3 domain or portion thereof. In certain embodiments, the fusion protein disclosed herein comprises at least one Fc domain which comprises at least one CH4 domain or portion thereof. In certain embodiments, the fusion protein disclosed herein comprises at least one Fc domain which comprises at least one hinge domain or portion thereof and at least one CH2 domain or portion thereof (e.g, in the hinge-CH2 orientation). In certain embodiments, the fusion protein disclosed herein comprises at least one Fc domain which comprises at least one CH2 domain or portion thereof and at least one CH3 domain or portion thereof (e.g, in the CH2-CH3 orientation). In certain embodiments, the fusion protein disclosed herein comprises at least one Fc domain comprising at least one hinge domain or portion thereof, at least one CH2 domain or portion thereof, and least one CH3 domain or portion thereof, for example in the orientation hinge-CH2-CH3, hinge-CH3-CH2, or CH2-CH3-hinge.

In certain embodiments, the fusion protein comprises at least one complete Fc region derived from one or more immunoglobulin heavy chains (e.g., an Fc domain including hinge, CH2, and CH3 domains, although these need not be derived from the same antibody). In certain embodiments, the fusion protein comprises at least two complete Fc domains derived from one or more immunoglobulin heavy chains. In certain embodiments, the complete Fc domain is derived from a human IgG immunoglobulin heavy chain (e.g., human IgG1).

In certain embodiments, the fusion protein disclosed herein comprises at least one Fc domain comprising a complete CH3 domain. In certain embodiments, the fusion protein disclosed herein comprises at least one Fc domain comprising a complete CH2 domain. In certain embodiments, the fusion protein disclosed herein comprises at least one Fc domain comprising at least a CH3 domain, and at least one of a hinge region, and a CH2 domain. In certain embodiments, the fusion protein disclosed herein comprises at least one Fc domain comprising a hinge and a CH3 domain. In certain embodiments, the fusion protein disclosed herein comprises at least one Fc domain comprising a hinge, a CH2, and a CH3 domain. In certain embodiments, the Fc domain is derived from a human IgG immunoglobulin heavy chain (e.g., human IgG1).

The constant region domains or portions thereof making up an Fc domain of the fusion protein disclosed herein may be derived from different immunoglobulin molecules. For example, a fusion protein disclosed herein may comprise a CH2 domain or portion thereof derived from an IgG1 molecule and a CH3 region or portion thereof derived from an IgG3 molecule. In another example, the fusion protein comprises an Fc domain comprising a hinge domain derived, in part, from an IgG1 molecule and, in part, from an IgG3 molecule. As set forth herein, it will be understood by one of ordinary skill in the art that an Fc domain may be altered such that it varies in amino acid sequence from a naturally occurring antibody molecule.

In certain embodiments, the fusion protein disclosed herein lacks one or more constant region domains of a complete Fc region, i.e., they are partially or entirely deleted. In certain embodiments, the fusion protein disclosed herein will lack an entire CH2 domain. In certain embodiments, the fusion protein disclosed herein comprise CH2 domain-deleted Fc regions derived from a vector (e.g., from DEC Pharmaceuticals, San Diego) encoding an IgG1 human constant region domain (see, e.g., WO02/060955A2 and WO02/096948A2). This exemplary vector is engineered to delete the CH2 domain and provide a synthetic vector expressing a domain-deleted IgG1 constant region. It will be noted that these exemplary constructs are preferably engineered to fuse a binding CH3 domain directly to a hinge region of the respective Fc domain.

In other constructs it may be desirable to provide a peptide spacer between one or more constituent Fc domains. For example, a peptide spacer may be placed between a hinge region and a CH2 domain and/or between a CH2 and a CH3 domain. For example, compatible constructs could be expressed wherein the CH2 domain has been deleted and the remaining CH3 domain (synthetic or unsynthetic) is joined to the hinge region with a 1-20, 1-10, or 1-5 amino acid peptide spacer. Such a peptide spacer may be added, for instance, to ensure that the regulatory elements of the constant region domain remain free and accessible or that the hinge region remains flexible. Preferably, any linker peptide compatible used in the instant invention will be relatively non-immunogenic and not prevent proper folding of the Fc.

Modified Fc Domains

In certain embodiments, an Fc domain employed in the fusion protein disclosed herein is altered or modified, e.g., by amino acid mutation (e.g., addition, deletion, or substitution). As used herein, the term "Fc domain variant" refers to an Fc domain having at least one amino acid modification, such as an amino acid substitution, as compared to the wild-type Fc from which the Fc domain is derived. For example, wherein the Fc domain is derived from a human IgG1 antibody, a variant comprises at least one amino acid mutation (e.g., substitution) as compared to a wild type amino acid at the corresponding position of the human IgG1 Fc region.

In certain embodiments, the Fc variant comprises a substitution at an amino acid position located in a hinge domain or portion thereof. In certain embodiments, the Fc variant comprises a substitution at an amino acid position located in a CH2 domain or portion thereof. In certain embodiments, the Fc variant comprises a substitution at an amino acid position located in a CH3 domain or portion thereof. In certain embodiments, the Fc variant comprises a substitution at an amino acid position located in a CH4 domain or portion thereof.

In certain embodiments, the fusion protein disclosed herein comprises an Fc variant comprising more than one amino acid substitution. The fusion protein disclosed herein may comprise, for example, 2, 3, 4, 5, 6, 7, 8, 9, 10 or more amino acid substitutions. Preferably, the amino acid substitutions are spatially positioned from each other by an interval of at least 1 amino acid position or more, for example, at least 2, 3, 4, 5, 6, 7, 8, 9, or 10 amino acid positions or more. More preferably, the engineered amino acids are spatially positioned apart from each other by an interval of at least 5, 10, 15, 20, or 25 amino acid positions or more.

In some embodiments, an Fc domain includes changes in the region between amino acids 234-238, including the sequence LLGGP at the beginning of the CH2 domain. In some embodiments, an Fc variant alters Fc mediated effector function, particularly ADCC, and/or decrease binding avidity for Fc receptors. In some aspects, sequence changes closer to the CH2-CH3 junction, at positions such as K322 or P331 can eliminate complement mediated cytotoxicity and/or alter avidity for FcR binding. In some embodiments, an Fc domain incorporates changes at residues P238 and P331, e.g., changing the wild type prolines at these positions to serine. In some embodiments, alterations in the hinge region at one or more of the three hinge cysteines, to encode CCC, SCC, SSC, SCS, or SSS at these residues can also affect FcR binding and molecular homogeneity, e.g., by elimination of unpaired cysteines that may destabilize the folded protein.

Other amino acid mutations in the Fc domain are contemplated to reduce binding to the Fc gamma receptor and Fc gamma receptor subtypes. For example, mutations at positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 322, 324, 327, 329, 330, 331, 333, 334, 335, 337, 338, 340, 356, 360, 373, 376, 378, 379, 382, 388, 389, 398, 414, 416, 419, 430, 434, 435, 437, 438 or 439 of the Fc region can alter binding as described in U.S. Pat. No. 6,737,056, issued May 18, 2004, incorporated herein by reference in its entirety. This patent reported that changing Pro331 in IgG3 to Ser resulted in six fold lower affinity as compared to unmutated IgG3, indicating the involvement of Pro331 in Fc gamma RI binding. In addition, amino acid modifications at positions 234, 235, 236, and 237, 297, 318, 320 and 322 are disclosed as potentially altering receptor binding affinity in U.S. Pat. No. 5,624,821, issued Apr. 29, 1997 and incorporated herein by reference in its entirety.

Further mutations contemplated for use include, e.g., those described in U.S. Pat. App. Pub. No. 2006/0235208, published Oct. 19, 2006 and incorporated herein by reference in its entirety. This publication describes Fc variants that exhibit reduced binding to Fc gamma receptors, reduced antibody dependent cell-mediated cytotoxicity, or reduced complement dependent cytotoxicity, that comprise at least one amino acid modification in the Fc region, including 232G, 234G, 234H, 235D, 235G, 235H, 236I, 236N, 236P, 236R, 237K, 237L, 237N, 237P, 238K, 239R, 265G, 267R, 269R, 270H, 297S, 299A, 299I, 299V, 325A, 325L, 327R, 328R, 329K, 330I, 330L, 330N, 330P, 330R, and 331L (numbering is according to the EU index), as well as double mutants 236R/237K, 236R/325L, 236R/328R, 237K/325L, 237K/328R, 325L/328R, 235G/236R, 267R/269R, 234G/235G, 236R/237K/325L, 236R/325L/328R, 235G/236R/237K, and 237K/325L/328R. Other mutations contemplated for use as described in this publication include 227G, 234D, 234E, 234G, 234I, 234Y, 235D, 235I, 235S, 236S, 239D, 246H, 255Y, 258H, 260H, 264I, 267D, 267E, 268D, 268E, 272H, 272I, 272R, 281D, 282G, 283H, 284E, 293R, 295E, 304T, 324G, 324I, 327D, 327A, 328A, 328D, 328E, 328F, 328I, 328M, 328N, 328Q, 328T, 328V, 328Y, 330I, 330L, 330Y, 332D, 332E, 335D, an insertion of G between positions 235 and 236, an insertion of A between positions 235 and 236, an insertion of S between positions 235 and 236, an insertion of T between positions 235 and 236, an insertion of N between positions 235 and 236, an insertion of D between positions 235 and 236, an insertion of V between positions 235 and 236, an insertion of L between positions 235 and 236, an insertion of G between positions 235 and 236, an insertion of A between positions 235 and 236, an insertion of S between positions 235 and 236, an insertion of T between positions 235 and 236, an insertion of N between positions 235 and 236, an insertion of D between positions 235 and 236, an insertion of V between positions 235 and 236, an insertion of L between positions 235 and 236, an insertion of G between positions 297 and 298, an insertion of A between positions 297 and 298, an insertion of S between positions 297 and 298, an insertion of D between positions 297 and 298, an insertion of G between positions 326 and 327, an insertion of A between positions 326 and 327, an insertion of T between positions 326 and 327, an insertion of D between positions 326 and 327, and an insertion of E between positions 326 and 327 (numbering is according to the EU index). Additionally, mutations described in U.S. Pat. App. Pub. No. 2006/0235208 include 227G/332E, 234D/332E, 234E/332E, 234Y/332E, 234I 332E, 234G/332E, 235I/332E, 235S/332E, 235D/332E, 235E/332E, 236S/332E, 236A/332E, 236S/332D, 236A/332D, 239D/268E, 246H/332E, 255Y/332E, 258H/332E, 260H/332E, 264I 332E, 267E/332E, 267D/332E, 268D/332D, 268E/332D, 268E/332E, 268D/332E, 268E/330Y, 268D/330Y, 272R/332E, 272H/332E, 283H/332E, 284E/332E, 293R/332E, 295E/332E, 304T/332E, 324I 332E, 324G/332E, 324I/332D, 324G/332D, 327D/332E, 328A/332E, 328T/332E, 328V/332E, 328I 332E, 328F/332E, 328Y/332E, 328M/332E, 328D/332E, 328E/332E, 328N/332E, 328Q/332E, 328A/332D, 328T/332D, 328V/332D, 328I 332D, 328F/332D, 328Y/332D, 328M/332D, 328D/332D, 328E/332D, 328N/332D, 328Q/332D, 330L/332E, 330Y/332E, 330I 332E, 332D/330Y, 335D/332E, 239D/332E, 239D/332E/330Y, 239D/332E/330L, 239D/332E/330I, 239D/332E/268E, 239D/332E/268D, 239D/332E/327D, 239D/332E/284E, 239D/268E/330Y, 239D/332E/268E/330Y, 239D/332E/327A, 239D/332E/268E/327A, 239D/332E/330Y/327A, 332E/330Y/268E/327A, 239D/332E/268E/330Y/327A, Insert G>297-298/332E, Insert A>297-298/332E, Insert S>297-298/332E, Insert D>297-298/332E, Insert G>326-327/332E, Insert A>326-327/332E, Insert T>326-327/332E, Insert D>326-327/332E, Insert E>326-327/332E, Insert G>235-236/332E, Insert A>235-236/332E, Insert S>235-236/332E, Insert T>235-236/332E, Insert N>235-236/332E, Insert D>235-236/332E, Insert V>235-236/332E, Insert L>235-236/332E, Insert G>235-236/332D, Insert A>235-236/332D, Insert S>235-236/332D, Insert T>235-236/332D, Insert N>235-236/332D, Insert D>235-236/332D, Insert V>235-236/332D, and Insert L>235-236/332D (numbering according to the EU index) are contemplated for use. The mutant L234A/L235A is described, e.g., in U.S. Pat. App. Pub. No. 2003/0108548, published Jun. 12, 2003 and incorporated herein by reference in its entirety. In embodiments, the described modifications are included either individually or in combination. In certain embodiments, the mutation is D265A in human IgG1.

In certain embodiments, the fusion protein disclosed herein comprises an amino acid substitution to an Fc domain which alters antigen-independent effector functions of the polypeptide, in particular the circulating half-life of the polypeptide.

In certain embodiments, the fusion protein disclosed herein comprises an Fc variant comprising an amino acid substitution which alters the antigen-dependent effector functions of the polypeptide, in particular ADCC or complement activation, e.g., as compared to a wild type Fc region. Such fusion proteins exhibit decreased binding to FcR gamma when compared to wild-type polypeptides and, therefore, mediate reduced effector function. Fc variants with decreased FcR gamma binding affinity are expected to reduce effector function, and such molecules are also useful, for example, for treatment of conditions in which target cell destruction is undesirable, e.g., where normal cells may express target molecules, or where chronic administration of the polypeptide might result in unwanted immune system activation.

In certain embodiments, the fusion protein exhibits altered binding to an activating FcγR (e.g. Fcγl, FcγIIa, or FcγRIIIa). In certain embodiments, the fusion protein exhibits altered binding affinity to an inhibitory FcγR (e.g. FcγRIIb). Exemplary amino acid substitutions which altered FcR or complement binding activity are disclosed in International PCT Publication No. WO05/063815 which is incorporated by reference herein.

The fusion protein disclosed herein may also comprise an amino acid substitution which alters the glycosylation of the fusion protein. For example, the Fc domain of the fusion protein may comprise an Fc domain having a mutation leading to reduced glycosylation (e.g., N- or O-linked glycosylation) or may comprise an altered glycoform of the wild-type Fc domain (e.g., a low fucose or fucose-free glycan). In certain embodiments, the fusion protein has an amino acid substitution near or within a glycosylation motif, for example, an N-linked glycosylation motif that contains the amino acid sequence NXT or NXS. Exemplary amino acid substitutions which reduce or alter glycosylation are disclosed in WO05/018572 and US2007/0111281, the contents of which are incorporated by reference herein. In certain embodiments, the fusion protein disclosed herein comprises at least one Fc domain having engineered cysteine residue or analog thereof which is located at the solvent-exposed surface. In certain embodiments, the fusion protein disclosed herein comprise an Fc domain comprising at least one engineered free cysteine residue or analog thereof that is substantially free of disulfide bonding with a second cysteine residue. Any of the above engineered cysteine residues or analogs thereof may subsequently be conjugated to a functional domain using art-recognized techniques (e.g., conjugated with a thiol-reactive heterobifunctional linker).

In certain embodiments, the fusion protein disclosed herein may comprise a genetically fused Fc domain having two or more of its constituent Fc domains independently selected from the Fc domains described herein. In certain embodiments, the Fc domains are the same. In certain embodiments, at least two of the Fc domains are different. For example, the Fc domains of the fusion protein disclosed herein comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In certain embodiments, the Fc domains of the fusion protein disclosed herein may differ in sequence at one or more amino acid positions. For example, at least two of the Fc domains may differ at about 5 amino acid positions (e.g., 1, 2, 3, 4, or 5 amino acid positions), about 10 positions, about 15 positions, about 20 positions, about 30 positions, about 40 positions, or about 50 positions).

Polyethylene Glycol (PEG)

In certain embodiments, a fusion protein disclosed herein comprises a polyethylene glycol (PEG) domain. PEGylation is well known in the art to confer increased circulation half-life to proteins. Methods of PEGylation are well known and disclosed in, e.g., U.S. Pat. Nos. 7,610,156, 7,847,062, all of which are hereby incorporated by reference.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X-0(CH_2CH_2O)_{n-1}CH_2CH_2OH$, where n is 20 to 2300 and X is H or a terminal modification, e.g., a $C_{1-4}$ alkyl. In certain embodiments, the PEG suitable for use in the methods disclosed herein terminates on one end with hydroxy or methoxy, i.e., X is H or $CH_3$ ("methoxy PEG"). PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and USS, 932,462, both of which are hereby incorporated by reference. One form of PEGs includes two PEG side-chains (PEG2) linked via the primary amino groups of a lysine (Monfardini et al., Bioconjugate Chem 1995; 6:62-9).

In certain embodiments, the fusion protein comprising PEG is produced by site-directed pegylation, particularly by conjugation of PEG to a cysteine moiety at the N- or C-terminus. A PEG moiety may also be attached by other chemistry, including by conjugation to amines. PEG conjugation to peptides or proteins generally involves the activation of PEG and coupling of the activated PEG-intermediates directly to target proteins/peptides or to a linker, which is subsequently activated and coupled to target proteins/peptides (see Abuchowski et al., JBC 1977; 252:3571 and JBC 1977; 252:3582, and Harris et. al., in: Poly(ethylene glycol) Chemistry: Biotechnical and Biomedical Applications; (J. M. Harris ed.) Plenum Press: New York, 1992; Chap. 21 and 22). A variety of molecular mass forms of PEG can be selected, e.g., from about 1,000 Daltons (Da) to 100,000 Da (n is 20 to 2300), for conjugating to the variable region. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270).

One skilled in the art can select a suitable molecular mass for PEG, e.g., based on how the fusion protein comprising PEG will be used therapeutically, the desired dosage, circulation time, resistance to proteolysis, immunogenicity, and other considerations. For a discussion of PEG and its use to enhance the properties of proteins, see N. V. Katre, Advanced Drug Delivery Reviews 1993; 10:91-114.

In certain embodiments, PEG molecules may be activated to react with amino groups on the variable region, such as with lysines (Bencham C. O. et al., Anal. Biochem., 131, 25 (1983); Veronese, F. M. et al., Appl. Biochem., 11, 141 (1985); Zalipsky, S. et al., Polymeric Drugs and Drug Delivery Systems, adrs 9-110 ACS Symposium Series 469 (1999); Zalipsky, S. et al., Europ. Polym. J., 19, 1177-1183 (1983); Delgado, C. et al., Biotechnology and Applied Biochemistry, 12, 119-128 (1990)).

In certain embodiments, carbonate esters of PEG are used to form the fusion protein. N,N'-disuccinimidylcarbonate (DSC) may be used in the reaction with PEG to form active mixed PEG-succinimidyl carbonate that may be subsequently reacted with a nucleophilic group of a linker or an amino group of the variable region (see U.S. Pat. Nos. 5,281,698 and 5,932,462). In a similar type of reaction, 1,1'-(dibenzotriazolyl)carbonate and di-(2-pyridyl)carbonate may be reacted with PEG to form PEG-benzotriazolyl and PEG-pyridyl mixed carbonate (U.S. Pat. No. 5,382,657), respectively. Generation of a fusion protein comprising PEG can be performed according to the methods of the state of the art, for example by reaction of the variable region with electrophilically active PEGs (Shearwater Corp., USA, www.shearwatercorp.com). Preferred PEG reagents suitable for use in the methods disclosed herein are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini, C, et al., Bioconjugate Chem. 6 (1995) 62-69).

In certain embodiments, PEG molecules may be coupled to sulfhydryl groups on the variable region (Sartore, L., et al., Appl. Biochem. Biotechnol., 27, 45 (1991); Morpurgo et al., Biocon. Chem., 7, 363-368 (1996); Goodson et al., Bio/Technology (1990) 8, 343; U.S. Pat. No. 5,766,897). U.S. Pat. Nos. 6,610,281 and 5,766,897 describe exemplary reactive PEG species that may be coupled to sulfhydryl groups.

In certain embodiments where PEG molecules are conjugated to cysteine residues native to the variable region, whereas in certain embodiments, one or more cysteine residues are engineered into the variable region. Mutations may be introduced into the coding sequence of the variable region to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein.

In certain embodiments, the fusion protein comprising PEG comprises one or more PEG molecules covalently attached to a linker.

In certain embodiments, the variable region is pegylated at the C-terminus. In certain embodiments, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., C-Terminal Site-Specific PEGylation of a Truncated Thrombomodulin Mutant with Retention of Full Bioactivity, Bioconjug Chem. 2004; 15(5): 1005-1009. Monopegylation of the variable region can also be achieved according to the general methods described in WO 94/01451. WO 94/01451 describes a method for preparing a recombinant polypeptide with a modified terminal amino acid alpha-carbon reactive group. The steps of the method involve forming the recombinant polypeptide and protecting it with one or more biologically added protecting groups at the N-terminal alpha-amine and C-terminal alpha-carboxyl. The polypeptide can then be reacted with chemical protecting agents to selectively protect reactive side chain groups and thereby prevent side chain groups from being modified. The polypeptide is then cleaved with a cleavage reagent specific for the biological protecting group to form an unprotected terminal amino acid alpha-carbon reactive group. The unprotected terminal amino acid alpha-carbon reactive group is modified with a chemical modifying agent. The side chain protected terminally modified single copy polypeptide is then deprotected at the side chain groups to form a terminally modified recombinant single copy polypeptide. The number and sequence of steps in the method can be varied to achieve selective modification at the N- and/or C-terminal amino acid of the polypeptide.

The ratio of variable region to activated PEG in the conjugation reaction can be from about 1:0.5 to 1:50, between from about 1:1 to 1:30, or from about 1:5 to 1:15. Various aqueous buffers can be used to catalyze the covalent addition of PEG to the variable region, or variants thereof. In certain embodiments, the pH of a buffer used is from about 7.0 to 9.0. In certain embodiments, the pH is in a slightly basic range, e.g., from about 7.5 to 8.5. Buffers having a pKa close to neutral pH range may be used, e.g., phosphate buffer.

Conventional separation and purification techniques known in the art can be used to purify the fusion protein comprising PEG, such as size exclusion (e.g. gel filtration) and ion exchange chromatography. Products may also be separated using SDS-PAGE. Products that may be separated include mono-, di-, tri- poly- and un-pegylated variable regions as well as free PEG. The percentage of mono-PEG conjugates can be controlled by pooling broader fractions around the elution peak to increase the percentage of mono-PEG in the composition.

In certain embodiments, the fusion protein comprising PEG contains one, two or more PEG moieties. In certain embodiments, the PEG moiety(ies) are bound to an amino acid residue which is on the surface of the protein and/or away from the surface that contacts the chemokine of interest. In certain embodiments, the combined or total molecular mass of PEG in the fusion protein comprising PEG is from about 3,000 Da to 60,000 Da, optionally from about 10,000 Da to 36,000 Da. In certain embodiments, PEG of the fusion protein is a substantially linear, straight-chain PEG.

In certain embodiments, the fusion protein comprising PEG will preferably retain at least 25%, 50%, 60%, 70%, 80%, 85%, 90%, 95% or 100% of the biological activity associated with the unmodified protein. In certain embodiments, biological activity refers to the ability to bind the chemokine(s) of interest. The serum clearance rate of the fusion protein comprising PEG may be decreased by about 10%, 20%, 30%, 40%, 50%, 60%, 70%, 80%, or even 90%, relative to the clearance rate of the variable region alone. The fusion protein comprising PEG may have a circulation half-life (t˘) which is enhanced relative to the half-life of the variable region alone. The half-life of the fusion protein comprising PEG, or variants thereof, may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the variable region alone. In certain embodiments, the protein half-life is determined in vitro, such as in a buffered saline solution or in serum. In certain embodiments, the protein half-life is an in vivo circulation half-life, such as the half-life of the protein in the serum or other bodily fluid of an animal.

Other Polymers

In certain embodiments, the fusion protein comprises transferrin, as disclosed in U.S. Pat. Nos. 7,176,278 and 8,158,579, which are herein incorporated by reference in their entirety.

In certain embodiments, the fusion protein comprises a serum immunoglobulin binding protein such as those disclosed in US2007/0178082, which is herein incorporated by reference in its entirety.

In certain embodiments, the fusion protein comprises a fibronectin (Fn)-based scaffold domain protein that binds to serum albumin, such as those disclosed in US2012/0094909, which is herein incorporated by reference in its entirety. Methods of making fibronectin-based scaffold domain proteins are also disclosed in US2012/0094909. A non-limiting example of a Fn3-based extended-PK group is Fn3(HSA), i.e., a Fn3 protein that binds to human serum albumin.

In some embodiments, the fusion protein comprises an XTEN moiety. An XTEN moiety comprises amino acid residues A, E, G, P, S and T. In some embodiments, an XTEN moiety ranges from 36 to 288 amino acid residues in length. Exemplary XTEN moieties are described in WO 2011/123830; Schellenberger V. et al., *Nat Biotechnol.* Vol. 27: 1186-90 (2009); and Geething N C. Et al *PLos One* Vol. 5: e10175 (2010), each of which is herein incorporated by reference in its entirety.

In some embodiments, the fusion protein comprises an ELP moiety. An ELP moiety is a repeating peptide unit containing sequences commonly found in elastin. The ELP sequence contains repeats of V-P-G-x-G, wherein x is any amino acid except proline. ELP moieties can be degraded over time by human elastases, thereby making them biologically degradable. Examples of ELP moieties are described in, Floss, D M. et al *Trends Biotechnol.* Vol. 26: 489-501 (2013); and Floss, D M. et al, *Hoboken: Wiley*, p. 372-98 (2013), each of which is herein incorporated by reference.

In some embodiments, the fusion protein comprises a polymer of repeating amino acids proline, alanine and serine (i.e., PAS moiety). In some embodiments, a PAS moiety comprise 100-20 repeats in length. Exemplary PAS moieties are described in Huang, C. *Curr Opin Biotechnol* Vol. 20: 692-9 (2009), herein incorporated by reference.

Linkers

In some embodiments, the multispecific variable region is operably coupled to a polymer (e.g., serum albumin) via a linker. In some embodiments, the fusion protein includes a plurality of linker domains. In some embodiments, the linker domain is a polypeptide linker. In some embodiments, it is desirable to employ a polypeptide linker to fuse a polymer (e.g., serum albumin) with a multispecific variable region to form a fusion protein described herein.

In some embodiments, the fusion proteins employ a polypeptide linker to join any two or more domains in frame in a single polypeptide chain. In some embodiments, the two or more domains may be independently selected from any of the polymers (e.g., serum albumin), or variants or fragments thereof, or multispecific variable regions discussed herein.

Linkers suitable for fusing the multispecific variable region to the polymer (e.g., serum albumin) are well known in the art, and are disclosed in, e.g., US2010/0210511

US2010/0179094, and US2012/0094909, which are herein incorporated by reference in its entirety. Exemplary linkers include gly- ser polypeptide linkers, glycine-proline polypeptide linkers, and proline-alanine polypeptide linkers, the Fc interlinker from human IgG1 CH2 residues 297-322: NSTYRVVSVLTVLHQDWLNGKEYKCK (SEQ ID NO: 188), and the HSA interlinker from the D3 domain of human serum albumin: FQNALLVRYTKKVPQVSTPTLVEVS (SEQ ID NO: 189). See Fang et al., *Chines. Sci. Bull.,* 2003, 48:1912-1918, incorporated by reference in its entirety. Other linkers are provided, for example, in U.S. Pat. No. 5,525,491; Alfthan et al., *Protein Eng.,* 1995, 8:725-731; Shan et al., *J. Immunol.,* 1999, 162:6589-6595; Newton et al., *Biochemistry,* 1996, 35:545-553; Megeed et al.; *Biomacromolecules,* 2006, 7:999-1004; and Perisic et al., *Structure,* 1994, 12:1217-1226; each of which is incorporated by reference in its entirety. In certain embodiments, the linker is a gly-ser polypeptide linker, i.e., a peptide that consists of glycine and serine residues.

Exemplary gly-ser polypeptide linkers comprise the amino acid sequence Ser(Gly4Ser)n (SEQ ID NO: 183). In certain embodiments, n=1. In certain embodiments, n=2. In certain embodiments, n=3, i.e., Ser(Gly4Ser)3 (SEQ ID NO: 184). In certain embodiments, n=4, i.e., Ser(Gly4Ser)4 (SEQ ID NO: 185). In certain embodiments, n=5. In certain embodiments, n=6. In certain embodiments, n=7. In certain embodiments, n=8. In certain embodiments, n=9. In certain embodiments, n=10. Another exemplary gly-ser polypeptide linker comprises the amino acid sequence Ser(Gly4Ser)n (SEQ ID NO: 186). In certain embodiments, n=1. In certain embodiments, n=2. In certain embodiments, n=3. In certain embodiments, n=4. In certain embodiments, n=5. certain embodiments, n=6. Another exemplary gly-ser polypeptide linker comprises (Gly3Ser)n (SEQ ID NO: 187). In certain embodiments, n=1. In certain embodiments, n=2. In certain embodiments, n=3. In certain embodiments, n=4. In certain embodiments, n=5. In certain embodiments n=6.

In some embodiments, the polypeptide linker is synthetic. As used herein, the term "synthetic" with respect to a polypeptide linker includes peptides (or polypeptides) which comprise an amino acid sequence (which may or may not be naturally occurring) that is linked in a linear sequence of amino acids to a sequence (which may or may not be naturally occurring) to which it is not naturally linked in nature. For example, the polypeptide linker may comprise non-naturally occurring polypeptides which are modified forms of naturally occurring polypeptides (e.g., comprising a mutation such as an addition, substitution or deletion) or which comprise a first amino acid sequence (which may or may not be naturally occurring). Polypeptide linkers may be employed, for instance, to ensure that the variable region, or a variant or fragment thereof, is juxtaposed to ensure proper folding and formation of a functional variable region, or a variant or fragment thereof. Polypeptide linkers may be employed, for instance, to ensure that the polymer (e.g., serum albumin moiety), or a variant or fragment thereof, is juxtaposed to ensure proper folding and formation of a functional polymer (e.g., serum albumin moiety), or a variant or fragment thereof. Preferably, a polypeptide linker will be relatively non-immunogenic and not inhibit any non-covalent association among monomer subunits of a binding protein.

In certain embodiments, the fusion protein comprising a multispecific variable region and a polymer employs a polypeptide linker to join any two or more domains in frame in a single polypeptide chain.

Other linkers that are suitable for use in a fusion protein are known in the art, for example, the serine-rich linkers disclosed in U.S. Pat. No. 5,525,491, the helix forming peptide linkers (e.g., A(EAAAK)nA (n=2-5))(SEQ ID NO: 190) disclosed in Arai et al. (*Protein Eng* 2001; 14:529-32), and the stable linkers disclosed in Chen et al. (*Mol Pharm* 2011; 8:457-65), i.e., the dipeptide linker LE, a thrombin-sensitive disulfide cyclopeptide linker, and the alpha-helix forming linker LEA(EAAAK)4ALEA(EAAAK)$_4$ALE (SEQ ID NO: 191).

In some embodiments, a polypeptide linker for use in the fusion protein described herein, comprises a biologically relevant peptide sequence or a sequence portion thereof. For example, a biologically relevant peptide sequence may include, but is not limited to, sequences derived from an anti-rejection or anti-inflammatory peptide. Said anti-rejection or anti-inflammatory peptides may be selected from the group consisting of a cytokine inhibitory peptide, a cell adhesion inhibitory peptide, a thrombin inhibitory peptide, and a platelet inhibitory peptide. In some embodiments, a polypeptide linker comprises a peptide sequence selected from the group consisting of an IL-1 inhibitory or antagonist peptide sequence, an erythropoietin (EPO)-mimetic peptide sequence, a thrombopoietin (TPO)-mimetic peptide sequence, G-CSF mimetic peptide sequence, a TNF-antagonist peptide sequence, an integrin-binding peptide sequence, a selectin antagonist peptide sequence, an anti-pathogenic peptide sequence, a vasoactive intestinal peptide (VIP) mimetic peptide sequence, a calmodulin antagonist peptide sequence, a mast cell antagonist, a SH3 antagonist peptide sequence, an urokinase receptor (UKR) antagonist peptide sequence, a somatostatin or cortistatin mimetic peptide sequence, and a macrophage and/or T-cell inhibiting peptide sequence. Exemplary peptide sequences, any one of which may be employed as a polypeptide linker, are disclosed in U.S. Pat. No. 6,660,843, which is incorporated by reference herein.

Other exemplary linkers include GS linkers (i.e., (GS)n), GGSG (SEQ ID NO: 192) linkers (i.e., (GGSG)n (SEQ ID NO: 193)), GSAT (SEQ ID NO: 194) linkers, SEG linkers, and GGS linkers (i.e., (GGSGGS)n (SEQ ID NO: 195)), wherein n is a positive integer (e.g., 1, 2, 3, 4, or 5). Other suitable linkers for use in fusion proteins can be found using publicly available databases, such as the Linker Database (ibi.vu.nl/programs/linkerdbwww). The Linker Database is a database of inter-domain linkers in multi-functional enzymes which serve as potential linkers in novel fusion proteins (see, e.g., George et al., *Protein Engineering* 2002; 15:871-9).

It will be understood that variant forms of these exemplary polypeptide linkers can be created by introducing one or more nucleotide substitutions, additions or deletions into the nucleotide sequence encoding a polypeptide linker such that one or more amino acid substitutions, additions or deletions are introduced into the polypeptide linker. Mutations may be introduced by standard techniques, such as site-directed mutagenesis and PCR-mediated mutagenesis.

Polypeptide linkers are at least one amino acid in length and can be of varying lengths. In one embodiment, a polypeptide linker is from about 1 to about 50 amino acids in length. As used in this context, the term "about" indicates +/− two amino acid residues. Since linker length must be a positive integer, the length of from about 1 to about 50 amino acids in length, means a length of from 1 to 48-52 amino acids in length. In another embodiment, a polypeptide linker is from about 10-20 amino acids in length. In another embodiment, a polypeptide linker is from about 15 to about 50 amino acids in length.

In another embodiment, a polypeptide linker is from about 20 to about 45 amino acids in length. In another embodiment, a polypeptide linker is from about 15 to about 25 amino acids in length. In another embodiment, a polypeptide linker is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or 61 or more amino acids in length.

Polypeptide linkers can be introduced into polypeptide sequences using techniques known in the art. Modifications can be confirmed by DNA sequence analysis. Plasmid DNA can be used to transform host cells for stable production of the polypeptides produced.

Exemplary Fusion Proteins

The fusion proteins of the disclosure are modular and can be configured to incorporate various individual domains. For example, in some embodiments, the fusion protein includes a multispecific variable region comprising the heavy and light chain variable regions set forth in SEQ ID NOs: 1 and 2, respectively. In some embodiments, the fusion protein includes a multispecific variable region comprising the heavy and light chain variable regions set forth in SEQ ID NOs: 11 and 12, respectively. In some embodiments, the fusion protein includes a multispecific variable region comprising the heavy and light chain variable regions set forth in SEQ ID NOs: 21 and 22, respectively.

In some embodiments, the multispecific variable region comprises amino acid substitutions that result in the formation of a cysteine bridge, useful for stabilization of the fusion protein. In some embodiments, the multispecific variable region comprises a heavy chain variable region comprising the amino acid substitutions G44C, E44C, or Q105C (Kabat numbering). In some embodiments, the multispecific variable region comprises a light chain variable region comprising the amino acid substitutions A43C or Q100C (Kabat numbering). In some embodiments, the multispecific variable region comprises a heavy chain variable region comprising amino acid substitution E44C, and a light chain variable region comprising amino acid substitution Q100C. In some embodiments, the multispecific variable region comprises a heavy chain variable region comprising amino acid substitution G44C, and a light chain variable region comprising amino acid substitution Q100C. In some embodiments, the multispecific variable region comprises a heavy chain variable region comprising amino acid substitution Q105C, and a light chain variable region comprising amino acid substitution A43C.

In some embodiments, the fusion protein includes the HSA set forth in SEQ ID NO: 171. In some embodiments, the fusion protein includes the MSA set forth in SEQ ID NO: 173. In some embodiments, the fusion protein includes the (Gly4Ser)$_3$ linker domain set forth in SEQ ID NO: 178. In some embodiments, the fusion protein includes the secretory leader sequence set forth in SEQ ID NO: 179. In some embodiments, the fusion protein includes the His tag set forth in SEQ ID NO: 181. It will be understood to the skilled artisan that these individual domains can be operably coupled to each other in any order form a fusion protein that is active (e.g., reduces or inhibits the binding of an ELR+ CXC chemokine to its cognate receptor). For example, as detailed in the specific examples below, the multispecific variable region comprising the heavy and light chain variable regions set forth in SEQ ID NOs: 1 and 2, is operably coupled to MSA. In another example, the multispecific variable region is operably coupled to MSA via a (Gly4Ser)$_3$ linker domain. In yet another example, the fusion protein comprises the secretory leader sequence set forth in SEQ ID NO: 179.

In some embodiments, a fusion protein comprises a multispecific variable region coupled to a wild-type albumin. In some embodiments, the fusion protein comprises a secretory leader sequence, followed by a wild-type MSA, operably coupled via a (Gly4Ser)$_3$ linker domain to a multispecific variable region comprising heavy and light chain variable regions set forth in SEQ ID NOs: 1 and 2, respectively, operably coupled via a (Gly4Ser) linker domain to a His-tag (e.g., SEQ ID NO: 95). In some embodiments, the multispecific variable region comprises the amino acid substitution Q100C within the light chain variable region, and the amino acid substitution G44C within the heavy chain variable region (SEQ ID NO: 98; Kabat numbering). In some embodiments, the multispecific variable region comprises the amino acid substitution A43C within the light chain variable region, and the amino acid substitution Q105C within the heavy chain variable region (SEQ ID NO: 99; Kabat numbering). In one embodiments, the fusion protein lacks the leader sequence and the His-tag (SEQ ID NOs: 160, 163 and 164).

In some embodiments, the fusion protein comprises a secretory leader sequence, followed by a wild-type MSA, operably coupled via a (Gly4Ser)$_3$ linker domain to a multispecific variable region comprising heavy and light chain variable regions set forth in SEQ ID NOs: 11 and 12, respectively, operably coupled via a (Gly4Ser) linker domain to a His-tag (e.g., SEQ ID NO: 96). In some embodiments, the multispecific variable region comprises the amino acid substitution Q100C within the light chain variable region, and the amino acid substitution E44C within the heavy chain variable region (SEQ ID NO: 100; Kabat numbering). In some embodiments, the multispecific variable region comprises the amino acid substitution A43C within the light chain variable region, and the amino acid substitution Q105C within the heavy chain variable region (SEQ ID NO: 101; Kabat numbering). In one embodiments, the fusion protein lacks the leader sequence and the His-tag (SEQ ID NOs: 161, 165 and 166).

In some embodiments, the fusion protein comprises a secretory leader sequence, followed by a wild-type MSA, operably coupled via a (Gly4Ser)$_3$ linker domain to a multispecific variable region comprising heavy and light chain variable regions set forth in SEQ ID NOs: 21 and 22, respectively, operably coupled via a (Gly4Ser) linker domain to a His-tag (e.g., SEQ ID NO: 97). In some embodiments, the multispecific variable region comprises the amino acid substitution Q100C within the light chain variable region, and the amino acid substitution G44C within the heavy chain variable region (SEQ ID NO: 104; Kabat numbering). In some embodiments, the multispecific variable region comprises the amino acid substitution A43C within the light chain variable region, and the amino acid substitution Q105C within the heavy chain variable region (SEQ ID NO: 105; Kabat numbering). In one embodiments, the fusion protein lacks the leader sequence and the His-tag (SEQ ID NO: 162, 169 and 170).

In some embodiments, the fusion protein comprises the amino acid sequence set forth in SEQ ID NO: 95. In some embodiments, the fusion protein is encoded by the nucleic acid set forth in SEQ ID NO: 83. In some embodiments, the fusion protein comprises the amino acid sequence set forth in SEQ ID NO: 96. In some embodiments, the fusion protein is encoded by the nucleic acid set forth in SEQ ID NO: 84. In some embodiments, the fusion protein comprises the amino acid sequence set forth in SEQ ID NO: 97. In some embodiments, the fusion protein is encoded by the nucleic acid set forth in SEQ ID NO: 86.

In some embodiments, the fusion protein comprises the amino acid sequence set forth in SEQ ID NO: 160. In some embodiments, the fusion protein is encoded by the nucleic acid set forth in SEQ ID NO: 149. In some embodiments, the fusion protein comprises the amino acid sequence set forth in SEQ ID NO: 161. In some embodiments, the fusion protein is encoded by the nucleic acid set forth in SEQ ID NO: 150. In some embodiments, the fusion protein comprises the amino acid sequence set forth in SEQ ID NO: 162. In some embodiments, the fusion protein is encoded by the nucleic acid set forth in SEQ ID NO: 151.

Methods of Making Multispecific Variable Regions and Antibodies

The disclosure also provides methods for producing any of the multispecific variable regions, and isolated monoclonal antibodies, or antigen binding fragments thereof, that bind more than one ELR+ CXC chemokine (e.g., at least two, at least three, at least four, at least five, at least six, at least seven), described herein. In some embodiments, the final processed and active form of an ELR+ CXC chemokine protein is used in the methods described herein.

In some embodiments, the methods described herein can involve, or be used in conjunction with, e.g., phage display technologies, bacterial display, yeast surface display, eukaryotic viral display, mammalian cell display, and cell-free (e.g., ribosomal display) antibody screening techniques (see, e.g., Etz et al. (2001) *J Bacteriol* 183:6924-6935; Cornelis (2000) *Curr Opin Biotechnol* 11:450-454; Klemm et al. (2000) *Microbiology* 146:3025-3032; Kieke et al. (1997) *Protein Eng* 10:1303-1310; Yeung et al. (2002) *Biotechnol Prog* 18:212-220; Boder et al. (2000) *Methods Enzymology* 328:430-444; Grabherr et al. (2001) *Comb Chem High Throughput Screen* 4:185-192; Michael et al. (1995) *Gene Ther* 2:660-668; Pereboev et al. (2001) *J Virol* 75:7107-7113; Schaffitzel et al. (1999) *J Immunol Methods* 231:119-135; and Hanes et al. (2000) *Nat Biotechnol* 18:1287-1292).

Methods for identifying multispecific variable regions and/or antibodies using various phage display methods are known in the art. In phage display methods, functional variable region domains are displayed on the surface of phage particles which carry the polynucleotide sequences encoding them. Such phage can be utilized to display antigen-binding domains, such as Fab, Fv, or disulfide-bond stabilized Fv antibody fragments, expressed from a repertoire or combinatorial antibody library (e.g., human or murine). Phage used in these methods are typically filamentous phage such as fd and M13. The antigen binding domains are expressed as a recombinantly fused protein to any of the phage coat proteins pIII, pVIII, or pIX. See, e.g., Shi et al. (2010) *JMB* 397:385-396. Examples of phage display methods that can be used to make the immunoglobulins, or fragments thereof, described herein include those disclosed in Brinkman et al. (1995) *J Immunol Methods* 182:41-50; Ames et al. (1995) *J Immunol Methods* 184:177-186; Kettleborough et al. (1994) *Eur J Immunol* 24:952-958; Persic et al. (1997) *Gene* 187:9-18; Burton et al. (1994) *Advances in Immunology* 57:191-280; and PCT publication nos. WO 90/02809, WO 91/10737, WO 92/01047, WO 92/18619, WO 93/11236, WO 95/15982, and WO 95/20401. Suitable methods are also described in, e.g., U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

In some embodiments, the methods described herein further comprise prioritizing crossreactivity over affinity using directed co-evolution, described in further detail in the Examples. For example, using yeast surface display methods described above, output of each cycle of selection is exposed to a diverse array of antigens of interest (e.g., ELR+ CXC chemokines) in the following cycle. In some embodiments, methods that improve both the binding and affinity of variable regions and antibodies are used. Specifically, a high degree of genetic diversity in the antibody encoding genes can be created using error-prone PCR amplification. Binding affinity can be increased by allowing mutants to evolve through consecutive cycles of equilibrium-based selection using decreasing concentrations of the antigens of interest (e.g., ELR+ CXC chemokines). Concurrently, crossreactivity is increased by exposing the outputs of each cycle of affinity selection towards a different antigen of interest (e.g., different ELR+ CXC chemokine) in the following cycle of selection. Variants whose affinity and crossreactivity towards multiple antigens of interest (e.g., ELR+ CXC chemokines) that are higher than their respective parental clones are collected.

A subpopulation of multispecific variable regions and/or antibodies screened using the above methods can be characterized for their specificity and binding affinity for particular antigens (e.g., chemokines, e.g. ELR+ CXC chemokines) using any immunological or biochemical based method known in the art. For example, specific binding of a multispecific variable region or antibody to a chemokine, may be determined for example using immunological or biochemical based methods such as, but not limited to, an ELISA assay, SPR assays, immunoprecipitation assay, affinity chromatography, and equilibrium dialysis as described above. Immunoassays which can be used to analyze immunospecific binding and cross-reactivity of the antibodies include, but are not limited to, competitive and non-competitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, fluorescent immunoassays, and protein A immunoassays. Such assays are routine and well known in the art.

In embodiments where the selected CDR amino acid sequences are short sequences (e.g., fewer than 10-15 amino acids in length), nucleic acids encoding the CDRs can be chemically synthesized as described in, e.g., Shiraishi et al. (2007) *Nucleic Acids Symposium Series* 51(1):129-130 and U.S. Pat. No. 6,995,259. For a given nucleic acid sequence encoding an acceptor antibody, the region of the nucleic acid sequence encoding the CDRs can be replaced with the chemically synthesized nucleic acids using standard molecular biology techniques. The 5' and 3' ends of the chemically synthesized nucleic acids can be synthesized to comprise sticky end restriction enzyme sites for use in cloning the nucleic acids into the nucleic acid encoding the variable region of the donor antibody.

In some embodiments, the antibodies described herein comprise an altered heavy chain constant region that has reduced (or no) effector function relative to its corresponding unaltered constant region. Effector functions involving the constant region of the antibody may be modulated by altering properties of the constant or Fc region. Altered effector functions include, for example, a modulation in one or more of the following activities: antibody-dependent cellular cytotoxicity (ADCC), complement-dependent cytotoxicity (CDC), apoptosis, binding to one or more Fc-receptors, and pro-inflammatory responses. Modulation refers to an increase, decrease, or elimination of an effector function activity exhibited by a subject antibody containing an altered constant region as compared to the activity of the unaltered form of the constant region. In particular embodiments, modulation includes situations in which an activity is abolished or completely absent.

An altered constant region with altered FcR binding affinity and/or ADCC activity and/or altered CDC activity is a polypeptide which has either an enhanced or diminished FcR binding activity and/or ADCC activity and/or CDC activity compared to the unaltered form of the constant region. An altered constant region which displays increased binding to an FcR binds at least one FcR with greater affinity than the unaltered polypeptide. An altered constant region which displays decreased binding to an FcR binds at least one FcR with lower affinity than the unaltered form of the constant region. Such variants which display decreased binding to an FcR may possess little or no appreciable binding to an FcR, e.g., 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the binding to the FcR as compared to the level of binding of a native sequence immunoglobulin constant or Fc region to the FcR. Similarly, an altered constant region that displays modulated ADCC and/or CDC activity may exhibit either increased or reduced ADCC and/or CDC activity compared to the unaltered constant region. For example, in some embodiments, the antibody comprising an altered constant region can exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the unaltered form of the constant region. An antibody described herein comprising an altered constant region displaying reduced ADCC and/or CDC may exhibit reduced or no ADCC and/or CDC activity.

In some embodiments, an antibody described herein exhibits reduced or no effector function. In some embodiments, an antibody comprises a hybrid constant region, or a portion thereof, such as a G2/G4 hybrid constant region (see e.g., Burton et al. (1992) *Adv Immun* 51:1-18; Canfield et al. (1991) *J Exp Med* 173:1483-1491; and Mueller et al. (1997) *Mol Immunol* 34(6):441-452). See above.

In some embodiments, an antibody may contain an altered constant region exhibiting enhanced or reduced complement dependent cytotoxicity (CDC). Modulated CDC activity may be achieved by introducing one or more amino acid substitutions, insertions, or deletions in an Fc region of the antibody. See, e.g., U.S. Pat. No. 6,194,551. Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See, e.g., Caron et al. (1992) *J Exp Med* 176:1191-1195 and Shopes (1992) *Immunol* 148:2918-2922; PCT publication nos. WO 99/51642 and WO 94/29351; Duncan and Winter (1988) *Nature* 322:738-40; and U.S. Pat. Nos. 5,648,260 and 5,624,821.

It is understood that the above methods can also be used to determine if, e.g., a multispecific variable region does not bind to full length chemokines, e.g., ELR+ CXC chemokines. The above methods can also be used to determine if a multispecific variable region or antibody that specifically binds to more than one ELR+ CXC chemokine also reduces or inhibits the interaction between the chemokines and their cognate receptors (e.g., CXCR1 and CXCR2).

Methods of Making Fusion Proteins

The fusion proteins described herein largely may be made in transformed or transfected host cells using recombinant DNA techniques. To do so, a recombinant DNA molecule coding for the polypeptide is prepared. Methods of preparing such DNA molecules are well known in the art. For instance, sequences coding for the polypeptides could be excised from DNA using suitable restriction enzymes. Alternatively, the DNA molecule could be synthesized using chemical synthesis techniques, such as the phosphoramidate method. Also, a combination of these techniques could be used.

The disclosure also provides a vector capable of expressing the polypeptides in an appropriate host. The vector comprises the DNA molecule that codes for the polypeptides operably coupled to appropriate expression control sequences. Methods of affecting this operative linking, either before or after the DNA molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation. The nucleic acid molecules described above can be contained within a vector that is capable of directing their expression in, for example, a cell that has been transduced with the vector. Accordingly, in addition to polypeptide mutants, expression vectors containing a nucleic acid molecule encoding a mutant and cells transfected with these vectors are among the certain embodiments.

Vectors suitable for use include T7-based vectors for use in bacteria (see, for example, Rosenberg et al., *Gene* 56: 125, 1987), the pMSXND expression vector for use in mammalian cells (Lee and Nathans, *J. Biol. Chem.* 263:3521, 1988), and baculovirus-derived vectors (for example the expression vector pBacPAK5 from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance (neo$^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that are suitable for use include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

The resulting vector having the DNA molecule thereon is used to transform or transfect an appropriate host. This transformation or transfection may be performed using methods well known in the art.

Any of a large number of available and well-known host cells may be used. The selection of a particular host is dependent upon a number of factors recognized by the art. These include, for example, compatibility with the chosen expression vector, toxicity of the peptides encoded by the DNA molecule, rate of transformation or transfection, ease of recovery of the peptides, expression characteristics, biosafety and costs. A balance of these factors must be struck with the understanding that not all hosts may be equally effective for the expression of a particular DNA sequence. Within these general guidelines, useful microbial hosts include bacteria (such as *E. coli*), yeast (such as *Saccharomyces*) and other fungi, insects, plants, mammalian (including human) cells in culture, or other hosts known in the art.

Next, the transformed or transfected host is cultured and purified. Host cells may be cultured under conventional fermentation or culture conditions so that the desired compounds are expressed. Such fermentation and culture conditions are well known in the art. Finally, the peptides are purified from culture by methods well known in the art.

Prokaryotic or eukaryotic cells that contain and express a nucleic acid molecule that encodes a polypeptide mutant are also suitable for use. A cell is a transfected cell, i.e., a cell into which a nucleic acid molecule, for example a nucleic acid molecule encoding a mutant polypeptide, has been introduced by means of recombinant DNA techniques. The progeny of such a cell are also considered suitable for use in the methods disclosed herein.

The precise components of the expression system are not critical. For example, a polypeptide can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed polypeptides can be purified from the expression system using routine biochemical procedures, and can be used, e.g., as therapeutic agents, as described herein.

The fusion proteins may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al., *Biochem Intl* 1985; 10: 394-414; Stewart and Young (1969), Solid Phase Peptide Synthesis; U.S. Pat. No. 3,941,763; Finn et al. (1976), The Proteins (3rd ed.) 2: 105-253; and Erickson et al. (1976), The Proteins (3rd ed.) 2: 257-527. Solid phase synthesis is the preferred technique of making individual peptides since it is the most cost-effective method of making small peptides. Compounds that contain derivatized peptides or which contain non-peptide groups may be synthesized by well-known organic chemistry techniques.

Other methods are of molecule expression/synthesis are generally known in the art to one of ordinary skill.

Modification of Polypeptides

The polypeptides described herein (e.g., fusion proteins, or antibodies or antigen-binding fragments thereof) can be modified following their expression and purification. The modifications can be covalent or non-covalent modifications. Such modifications can be introduced into the polypeptides by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies or fragments.

In some embodiments, the polypeptides can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag (e.g., FLAG (DYKDDDDK (SEQ ID NO: 180)), polyhistidine (6-His; HHHHHH (SEQ ID NO: 181), hemagglutinin (HA; YPYDVPDYA (SEQ ID NO: 182)), glutathione-S-transferase (GST), or maltose-binding protein (MBP)) for use in purifying the antibodies or fragments. Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include, e.g., $^{32}P$, $^{33}P$, $^{14}C$, $^{125}I$, $^{131}I$, $^{35}S$, and $^{3}H$. Suitable fluorescent labels include, without limitation, fluorescein, fluorescein isothiocyanate (FITC), green fluorescent protein (GFP), DyLight™ 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase.

Two proteins (e.g., an antibody and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of the polypeptide. Alternatively, the radioactive label can be included as part of a larger molecule (e.g., $^{125}$I in meta-[$^{125}$I]iodophenyl-N-hydroxysuccinimide ([$^{125}$I]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the polypeptides described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an antibody) are known in the art of protein chemistry. For example, fluorophores can be conjugated to free amino groups (e.g., of lysines) or sulfhydryl groups (e.g., cysteines) of proteins using succinimidyl (NETS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating a polypeptide, with the fluorophore under conditions that facilitate binding of the fluorophore to the protein. See, e.g., Welch and Redvanly (2003) "Handbook of Radiopharmaceuticals: Radiochemistry and Applications," John Wiley and Sons (ISBN 0471495603).

In some embodiments, the polypeptides can be modified, e.g., with a moiety that improves the stabilization and/or retention of the polypeptides in circulation, e.g., in blood, serum, or other tissues. For example, the polypeptide can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476 or HESylated (Fresenius Kabi, Germany; see, e.g., Pavisić et al. (2010) *Int J Pharm* 387(1-2):110-119). The stabilization moiety can improve the stability, or retention of, the polypeptide by at least 1.5 (e.g., at least 2, 5, 10, 15, 20, 25, 30, 40, or 50 or more) fold.

In some embodiments, the polypeptides described herein can be glycosylated. In some embodiments, a polypeptide described herein can be subjected to enzymatic or chemical treatment, or produced from a cell, such that the polypeptide has reduced or absent glycosylation. Methods for producing polypeptides with reduced glycosylation are known in the art and described in, e.g., U.S. Pat. No. 6,933,368; Wright et al. (1991) *EMBO J* 10(10):2717-2723; and Co et al. (1993) *Mol Immunol* 30:1361.

Pharmaceutical Compositions and Modes of Administration

In certain embodiments, the invention provides for a pharmaceutical composition comprising a fusion protein, or an isolated monoclonal antibody, or antigen binding fragment thereof, described herein, with a pharmaceutically acceptable diluent, carrier, solubilizer, emulsifier, preservative and/or adjuvant.

In certain embodiments, acceptable formulation materials preferably are nontoxic to recipients at the dosages and concentrations employed. In certain embodiments, the formulation material(s) are for s.c. and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% Sucrose. In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of the fusion protein, or isolated monoclonal antibody, or antigen binding fragment, described herein.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising a fusion protein, or isolated monoclonal antibody, or antigen binding fragment, described herein, can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising a fusion protein, or isolated monoclonal antibody, or antigen binding fragment, described herein, can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising a fusion protein, or isolated monoclonal antibody, or antigen binding fragment, described herein, in a pharmaceutically acceptable vehicle. In certain embodiments, a vehicle for parenteral injection is sterile distilled water in which a fusion protein, or isolated monoclonal antibody, or antigen binding fragment, described herein, are formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, a fusion protein, or isolated monoclonal antibody, or antigen binding fragment, can be formulated as a dry powder for inhalation. In certain embodiments, an inhalation solution comprising a fusion protein, or isolated monoclonal antibody, or antigen binding fragment, can be formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, it is contemplated that formulations can be administered orally. In certain embodiments, a fusion protein, or isolated monoclonal antibody, or antigen binding fragment, that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of the fusion protein, or isolated monoclonal antibody, or antigen binding fragment. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of the fusion protein, or isolated monoclonal antibody, or antigen binding fragment, in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving a fusion protein, or isolated monoclonal antibody, or antigen binding fragment, in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising a fusion protein, or isolated monoclonal antibody, or antigen binding fragment, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which a fusion protein, or isolated monoclonal antibody, or antigen binding fragment, are being used, the route of administration, and the size (body weight, body surface or organ size) and/or condition (the age and general health) of the patient. In certain embodiments, the clinician can titer the dosage and modify the route of administration to obtain the optimal therapeutic effect.

In certain embodiments, the frequency of dosing will take into account the pharmacokinetic parameters of a fusion protein, or isolated monoclonal antibody, or antigen binding fragment, in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. In certain embodiments, it can be desirable to use a pharmaceutical composition comprising a fusion protein, or isolated monoclonal antibody, or antigen binding fragment, in an ex vivo manner. In such instances, cells, tissues and/or organs that have been removed from the patient are exposed to a pharmaceutical composition comprising a fusion protein, or isolated monoclonal antibody, or antigen binding fragment, after which the cells, tissues and/or organs are subsequently implanted back into the patient.

In certain embodiments, a fusion protein, or isolated monoclonal antibody, or antigen binding fragment, can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

Kits

A kit can include a fusion protein, or isolated monoclonal antibody, or antigen binding fragment, as disclosed herein, and instructions for use. The kits may comprise, in a suitable container, a fusion protein, or isolated monoclonal antibody, or antigen binding fragment, one or more controls, and various buffers, reagents, enzymes and other standard ingredients well known in the art.

The container can include at least one vial, well, test tube, flask, bottle, syringe, or other container means, into which a fusion protein, or isolated monoclonal antibody, or antigen binding fragment, may be placed, and in some instances, suitably aliquoted. Where an additional component is provided, the kit can contain additional containers into which this component may be placed. The kits can also include a means for containing a fusion protein, or isolated monoclonal antibody, or antigen binding fragment, and any other reagent containers in close confinement for commercial sale. Such containers may include injection or blow-molded plastic containers into which the desired vials are retained. Containers and/or kits can include labeling with instructions for use and/or warnings.

Methods of Treatment

The compositions described herein are useful in, inter alia, methods for treating or preventing a variety of autoimmune and related disorders, allergy, inflammation, and/or graft or transplant rejection in a subject. The compositions can be administered to a subject, e.g., a human subject, using a variety of methods that depend, in part, on the route of administration. The route can be, e.g., intravenous injection or infusion (IV), subcutaneous injection (SC), intraperitoneal (IP) injection, intramuscular injection (IM), or intrathecal injection (IT). The injection can be in a bolus or a continuous infusion.

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

In some embodiments, a fusion protein, or antibody or antigen-binding fragment thereof, is therapeutically delivered to a subject by way of local administration.

A suitable dose of a fusion protein, or antibody or antigen-binding fragment thereof described herein, which dose is capable of treating or preventing autoimmune and related disorders in a subject, can depend on a variety of factors including, e.g., the age, sex, and weight of a subject to be treated and the particular inducer compound used. For example, a different dose of a whole antibody may be required to treat a subject with autoimmune disease as compared to the dose of a fusion protein required to treat the same subject. Other factors affecting the dose administered to the subject include, e.g., the type or severity of the autoimmune disorder. For example, a subject having rheumatoid arthritis may require administration of a different dosage than a subject with Guillain-Barre syndrome. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will also depend upon the judgment of the treating medical practitioner (e.g., doctor or nurse). Suitable dosages are described herein.

A pharmaceutical composition can include a therapeutically effective amount of a fusion protein, or antibody or antigen-binding fragment thereof described herein. Such effective amounts can be readily determined by one of ordinary skill in the art based, in part, on the effect of the administered antibody, or the combinatorial effect of the antibody and one or more additional active agents, if more than one agent is used. A therapeutically effective amount of an antibody or fragment thereof described herein can also vary according to factors such as the disease state, age, sex, and weight of the individual, and the ability of the antibody (and one or more additional active agents) to elicit a desired response in the individual, e.g., reduction in tumor growth. For example, a therapeutically effective amount of a fusion protein can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by the therapeutically beneficial effects.

Suitable human doses of any of the fusion proteins, or antibodies or fragments thereof described herein can further be evaluated in, e.g., Phase I dose escalation studies. See, e.g., van Gurp et al. (2008) *Am J Transplantation* 8(8): 1711-1718; Hanouska et al. (2007) *Clin Cancer Res* 13(2, part 1):523-531; and Hetherington et al. (2006) *Antimicrobial Agents and Chemotherapy* 50(10): 3499-3500.

In some embodiments, the composition contains any of the fusion proteins, or antibodies or antigen-binding fragments thereof described herein and one or more (e.g., two, three, four, five, six, seven, eight, nine, 10, or 11 or more) additional therapeutic agents such that the composition as a whole is therapeutically effective. For example, a composition can contain a fusion protein described herein and an anti-inflammatory agent, wherein the fusion protein and agent are each at a concentration that when combined are therapeutically effective for treating or preventing autoimmune and related disorders (e.g., rheumatoid arthritis) in a subject.

Toxicity and therapeutic efficacy of such compositions can be determined by known pharmaceutical procedures in cell cultures or experimental animals (e.g., animal models of any of the cancers described herein). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A fusion protein, or antibody or antigen-binding fragment thereof that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such fusion proteins, or antibodies or antigen-binding fragments thereof lies generally within a range of circulating concentrations of the antibodies or fragments that include the $ED_{50}$ with little or no toxicity. The dosage may vary within this range depending upon the dosage form employed and the route of administration utilized. For a fusion protein described herein, the therapeutically effective dose can be estimated initially from cell culture assays. A dose can be formulated in animal models to achieve a circulating plasma concentration range that includes the $IC_{50}$ (i.e., the concentration of the fusion protein which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration (e.g., to the eye or a joint) is desired, cell culture or animal modeling can be used to determine a dose required to achieve a therapeutically effective concentration within the local site.

In some embodiments, the methods can be performed in conjunction with other therapies for autoimmune and related diseases. For example, the composition can be administered to a subject at the same time, prior to, or after, radiation, surgery, targeted or cytotoxic chemotherapy, anti-inflammatory therapy, steroid therapy, chemoradiotherapy, hormone therapy, immunotherapy, immunosuppressive therapy, antithyroid therapy, antibiotic therapy, gene therapy, cell transplant therapy, precision medicine, genome editing therapy, or other pharmacotherapy.

The compositions described herein (e.g., fusion protein compositions) can be used to treat graft rejection and/or a variety of allergy or autoimmune disorders such as, but not limited to, Crohn's disease, multiple sclerosis, myasthenia gravis, rheumatoid arthritis, Goodpasture's syndrome, T-cell mediated hepatitis, graft vs. host disease, autoimmune uveitis, and/or autoimmune diabetes.

In some embodiments, a fusion protein, or an antibody or an antigen-binding fragment thereof described herein can be administered to a subject as a monotherapy. Alternatively, as described above, the fusion protein, or the antibody or fragment thereof can be administered to a subject as a combination therapy with another treatment, e.g., another treatment for an autoimmune or related disease. For example, the combination therapy can include administering to the subject (e.g., a human patient) one or more additional agents that provide a therapeutic benefit to a subject who has, or is at risk of developing, an autoimmune or related diseases. In some embodiments, a fusion protein, or an antibody and the one or more additional active agents are administered at the same time. In other embodiments, the fusion protein, or antibody or antigen binding fragment thereof is administered first in time and the one or more additional active agents are administered second in time. In some embodiments, the one or more additional active agents are administered first in time and the fusion protein, or antibody or antigen binding fragment thereof is administered second in time.

A fusion protein, or an antibody or an antigen-binding fragment thereof described herein can replace or augment a previously or currently administered therapy. For example, upon treating with a fusion protein, or an antibody or antigen-binding fragment thereof, administration of the one or more additional active agents can cease or diminish, e.g., be administered at lower levels. In some embodiments, administration of the previous therapy can be maintained. In some embodiments, a previous therapy will be maintained until the level of the fusion protein, or the antibody reaches a level sufficient to provide a therapeutic effect. The two therapies can be administered in combination.

Monitoring a subject (e.g., a human patient) for an improvement in an autoimmune or related disease, as defined herein, means evaluating the subject for a change in a disease parameter, e.g., a reduction in inflammation. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for an autoimmune ore related disease described herein.

As ELR+ CXC chemokines are responsible for inducing neutrophil infiltration to sites of inflammation, in some embodiments a fusion protein or an antibody or an antigen-binding fragment thereof described herein, is administered to prevent or block neutrophil infiltration in a subject with an autoimmune disorder. In some embodiments, the fusion protein or antibody, or antigen-binding fragment thereof, prevents or blocks infiltration of neutrophils into the synovial fluid of arthritic joints. Methods of measuring neutrophil infiltration are known in the art. For example, bodily fluid from a subject (e.g., synovial fluid) is collected, cells are isolated and stained with a neutrophil cell marker (e.g., Ly6G), and assessed via flow cytometry. Exemplary methods are described in Miyabe, Y., Kim, N. D., Miyabe, C. & Luster, A. D. Studying Chemokine Control of Neutrophil Migration In Vivo in a Murine Model of Inflammatory Arthritis. *Methods in enzymology* 570, 207-231 (2016), herein incorporated by reference.

EXAMPLES

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

Materials and Methods
Cloning of CXC Chemokines for Mammalian Cell Line Expression Human and murine CXC chemokines undergo proteolysis in vivo resulting in molecules with altered structure and tuned activity. To avoid that in vitro engineered crossreactive binders might not be able to block the mature form in vivo, the final processed and active form of the protein was cloned and produced. The CXC chemokines were produced in mammalian cell lines thus avoiding refolding procedures while preserving their native structure and activity. CXCL chemokines were cloned as C-terminal fusion of the immunoglobulin fragment crystallizable (Fc) domain ($^N$Fc-CXCL$^C$) and as N-terminal fusion of the murine serum albumin (SA) protein ($^N$CXCL-SA$^C$). All mammalian expression vectors were based on gWiz (Genlantis) containing an optimized human cytomegalovirus (CMV) promoter and a Kanamycin antibiotic resistance gene (Kan).

Constructs for expression of $^N$Fc-CXCL$^C$ fusion proteins were generated by using a modified Pfu DNA polymerase-mediated site-directed mutagenesis protocol (Geiser, M., Cebe, R., Drewello, D. & Schmitz, R. Integration of PCR fragments at any specific site within cloning vectors without the use of restriction enzymes and DNA ligase. *Biotechniques* 31, 88-90, 92 (2001)). Pfu Ultra II Fusion HS DNA Polymerase was obtained from Agilent Technologies, DpnI enzyme from New England BioLabs and the oligonucleotide primers from Integrated DNA Technologies. The synthetic DNA coding for the active form of three highly diverse human and murine ELR+ CXC chemokines were obtained from GeneArt Gene Synthesis (Thermo Fisher Scientific). Genes were codon-optimized for expression in mammalian cells. A sequence encoding for Gly-Gly dipeptide spacer (G2, $^N$GG$^C$) followed by a 15 amino acid peptide sequence (AviTag) containing a defined lysine for site-specific biotinylation ($^N$GLNDIFEAQKIEWHE$^C$)(SEQ ID NO: 196) were inserted at the C-terminus of the ELR+ CXC chemokine to obtain $^N$CXCL-G$_2$-AviTag$^C$ synthetic genes. The AviTag sequence for enzymatically biotinylation was placed at the well tolerated C-terminus of the ELR+ CXC chemokines to (i) preserve unaltered the functional N-terminus region, (ii) avoid loss of epitope recognition and (iii) prevent additional structural heterogeneity that could be triggered by performing a chemistry-based amine-reactive succinimidyl esters based biotinylation. The de novo synthesized $^N$CXCL-G$_2$-AviTag$^C$ synthetic sequences were subsequently inserted into a previously modified gWiz expression vector containing a DNA sequence encoding for a secretory leader peptide sequence ($^N$MRVPAQLLGLLLLWLPGARC$^C$)(SEQ ID NO: 197), a Fc domain derived from murine IgG2 heavy-chain constant regions CH2 and CH3, followed by a sequence encoding a hexa-histidine tag (His6; $^N$HHHHHH$^C$)(SEQ ID NO: 181), an eight amino-acid flexible linker ($^N$SSGVDLGT$^C$)(SEQ ID NO: 198) and a Tobacco Etch Virus proteolytic cleavage site (TEV; $^N$ENLYFQ$|_{A/V}{}^C$)(SEQ ID NO: 199) to obtain the final $^N$Fc-His6-linker-TEV-CXCL-G$_2$-AviTag$^C$ fusion proteins (FIG. 1). The His6-tag was inserted between the Fc domain and the TEV cleavage site for further purification steps. The sequence TEV proteolytic cleavage site allowed for a precisely processed N-terminus of the chemokines that was crucial for their activity. All constructs were verified by DNA sequencing (Macrogen) and termed Fc-CXCL fusion proteins (see Table 1 for information about protein accession number SEQ ID NOs: 31-42 for DNA and amino acid sequences).

TABLE 1

| CXCL protein (residues/ accession No.) | Construct for expression | Fusion protein |
|---|---|---|
| Groα/hCXCL1 (38-107/P09341) | gWiz-LS-Fc(mIgG2)-His$_6$-linker-TEV-hCXCL1$^{38-107}$-G$_2$-AviTag | $^N$Fc-hCXCL1$^C$ |
| ENA-78/hCXCL5 (43-114/P42830) | gWiz-LS-Fc(mIgG2)-His$_6$-linker-TEV-hCXCL5$^{43-114}$-G$_2$-AviTag | $^N$Fc-hCXCL5$^C$ |
| IL-8/hCXCL8 (29-99/P10145) | gWiz-LS-Fc(mIgG2)-His$_6$-linker-TEV-hCXCL8$^{29-99}$-G$_2$-AviTag | $^N$Fc-hCXCL8$^C$ |
| KC/mCXCL1 (28-96/P12850) | gWiz-LS-Fc(mIgG2)-His$_6$-linker-TEV-mCXCL1$^{28-96}$-G$_2$-AviTag | $^N$Fc-mCXCL1$^C$ |
| MIP-2/mCXCL2 (31-100/P10889) | gWiz-LS-Fc(mIgG2)-His$_6$-linker-TEV-mCXCL2$^{31-100}$-G$_2$-AviTag | $^N$Fc-mCXCL2$^C$ |
| LIX/mCXCL5 (48-118/P50228) | gWiz-LS-Fc(mIgG2)-His$_6$-linker-TEV-mCXCL5$^{48-118}$-G$_2$-AviTag | $^N$Fc-mCXCL5$^C$ |

Constructs for expression of $^N$CXCL-SA$^C$ fusion proteins were generated by using DNA assembly methods such as Gibson Assembly (New England BioLabs) and In-Fusion Cloning (Clontech Laboratories, Takara Bio) technologies. PfuUltra II Fusion HS DNA Polymerase (Agilent Technologies) and Herculase II Fusion DNA Polymerase (Agilent Technologies) were used for the PCR amplification of the insert and the vector, respectively. DpnI enzyme was obtained from New England Biolabs and the oligonucleotide primers from Integrated DNA Technologies.

The synthetic DNA coding for the active protein form of twelve human and murine (ELR+) CXC chemokines and eight human and murine (ELR−) CXC chemokines were obtained from GeneArt Gene Synthesis (Thermo Fisher Scientific). Genes were codon-optimized for expression in mammalian cells. The de novo synthesized $^N$CXCL$^C$ synthetic sequences were subsequently inserted into a previously modified gWiz expression vector containing a DNA sequence encoding for a secretory leader sequence ($^N$MRVPAQLLGLLLLWLPGARC$^C$)(SEQ ID NO: 197), a ten amino-acid flexible linker ($^N$GGGGSGGGGS$^C$)(SEQ ID NO: 200), sequence encoding for mouse serum albumin (SA) followed by a sequence encoding for a five amino-acid flexible spacer ($^N$GGGGS$^C$)(SEQ ID NO: 201) and a hexa-histidine tag (His6; $^N$HHHHHH$^C$)(SEQ ID NO: 181) to obtain $^N$CXCL-(G$_4$G)$_2$-SA-G$_4$S-His$_6$$^C$ fusion proteins. The process of the leader sequence during the secretory pathway allows for a precisely cleaved N-terminus that is crucial for the activity of the chemokines. Genes encoding $^N$CXCL (G4G)$_2$-SA-G$_4$S-His$_6$$^C$ fusion proteins were further subcloned into a new gWiz expression vector via SalI-HF (New England BioLabs) and MauBI (Thermo Fisher Scientific) restriction enzymes. All constructs were verified by DNA sequencing (Macrogen) and termed $^N$CXCL-SA$^C$ fusion proteins (see Table 2 for information about protein accession number and SEQ ID NOs: 43-82 for DNA and amino-acid sequences).

TABLE 2

| CXCL protein (residues/ accession No.) | Construct for expression | Fusion protein |
|---|---|---|
| Groα/hCXCL1 (35-107/P09341) | gWiz-LS-hCXCL1$^{35-107}$-(Gly$_4$Ser)$_2$-mouse SA-(Gly$_4$Ser)-His$_6$ | $^N$hCXCL1-SA$^C$ |
| Groβ/hCXCL2 (35-107/P19875) | gWiz-LS-hCXCL2$^{35-107}$-(Gly$_4$Ser)$_2$-mouse SA-(Gly$_4$Ser)-His$_6$ | $^N$hCXCL2-SA$^C$ |
| Groγ/hCXCL3 (35-107/P19876) | gWiz-LS-hCXCL3$^{35-107}$-(Gly$_4$Ser)$_2$-mouse SA-(Gly$_4$Ser)-His$_6$ | $^N$hCXCL3-SA$^C$ |
| PF-4/hCXCL4 (32-101/P02776) | gWiz-LS-hCXCL4$^{32-101}$-(Gly$_4$Ser)$_2$-mouse SA-(Gly$_4$Ser)-His$_6$ | $^N$hCXCL4-SA$^C$ |
| ENA-78/hCXCL5 (44-114/P42830) | gWiz-LS-hCXCL5$^{44-114}$-(Gly$_4$Ser)$_2$-mouse SA-(Gly$_4$Ser)-His$_6$ | $^N$hCXCL5-SA$^C$ |
| GCP-2/hCXCL6 (43-114/P80162) | gWiz-LS-hCXCL6$^{43-114}$-(Gly$_4$Ser)$_2$-mouse SA-(Gly$_4$Ser)-His$_6$ | $^N$hCXCL6-SA$^C$ |
| NAP-2/hCXCL7 (59-121/P02775) | gWiz-LS-hCXCL7$^{59-121}$-(Gly$_4$Ser)$_2$-mouse SA-(Gly$_4$Ser)-His$_6$ | $^N$hCXCL7-SA$^C$ |
| IL-8/hCXCL8 (28-99/P10145) | gWiz-LS-hCXCL8$^{28-99}$-(Gly$_4$Ser)$_2$-mouse SA-(Gly$_4$Ser)-His$_6$ | $^N$hCXCL8-SA$^C$ |
| MIG/hCXCL9 (23-125/Q07325) | gWiz-LS-hCXCL9$^{23-125}$-(Gly$_4$Ser)$_2$-mouse SA-(Gly$_4$Ser)-His$_6$ | $^N$hCXCL9-SA$^C$ |
| IP-10/hCXCL10-SA (22-98/P02778) | gWiz-LS-hCXCL10$^{22-98}$-(Gly$_4$Ser)$_2$-mouse SA-(Gly$_4$Ser)-His$_6$ | $^N$hCXCL10-SA$^C$ |
| I-TAC/hCXCL11-SA (22-94/O14625) | gWiz-LS-hCXCL11$^{22-94}$-(Gly$_4$Ser)$_2$-mouse SA-(Gly$_4$Ser)-His$_6$ | $^N$hCXCL11-SA$^C$ |
| KC/mCXCL1-SA (25-96/P12850) | gWiz-LS-mCXCL1$^{25-96}$-(Gly$_4$Ser)$_2$-mouse SA-(Gly$_4$Ser)-His$_6$ | $^N$mCXCL1-SA$^C$ |
| MIP-2/mCXCL2-SA (28-100/P10889) | gWiz-LS-mCXCL2$^{28-100}$-(Gly$_4$Ser)$_2$-mouse SA-(Gly$_4$Ser)-His$_6$ | $^N$mCXCL2-SA$^C$ |
| DCIP-1/mCXCL3-SA (28-100/Q6W5C0) | gWiz-LS-mCXCL3$^{28-100}$-(Gly$_4$Ser)$_2$-mouse SA-(Gly$_4$Ser)-His$_6$ | $^N$mCXCL3-SA$^C$ |
| Pf-4/mCXCL4-SA (30-105/Q9Z126) | gWiz-LS-mCXCL4$^{30-105}$-(Gly$_4$Ser)$_2$-mouse SA-(Gly$_4$Ser)-His$_6$ | $^N$mCXCL4-SA$^C$ |
| LIX/mCXCL5-SA (48-118/P50228) | gWiz-LS-mCXCL5$^{48-118}$-(Gly$_4$Ser)$_2$-mouse SA-(Gly$_4$Ser)-His$_6$ | $^N$mCXCL5-SA$^C$ |
| Nap-2/mCXCL7-SA (48-113/Q9EQI5) | gWiz-LS-mCXCL7$^{48-113}$-(Gly$_4$Ser)$_2$-mouse SA-(Gly$_4$Ser)-His$_6$ | $^N$mCXCL7-SA$^C$ |
| Mig/mCXCL9-SA (22-126/Pl8340) | gWiz-LS-mCXCL9$^{22-126}$-(Gly$_4$Ser)$_2$-mouse SA-(Gly$_4$Ser)-His$_6$ | $^N$mCXCL9-SA$^C$ |
| Ip-10/mCXCL10-SA (22-98/P17515) | gWiz-LS-mCXCL10$^{22-98}$-(Gly$_4$Ser)$_2$-mouse SA-(Gly$_4$Ser)-His$_6$ | $^N$mCXCL10-SA$^C$ |
| I-Tac/mCXCL11-SA (22-100/Q9JHH5) | gWiz-LS-mCXCL11$^{22-100}$-(Gly$_4$Ser)$_2$-mouse SA-(Gly$_4$Ser)-His$_6$ | $^N$mCXCL11-SA$^C$ |

Expression and Purification of Fc Fusion Proteins

Fc fusion proteins $^N$Fc-CXCL$^C$ were expressed by transient transfection of suspension-adapted human embryonic kidney (HEK-293) cells. Protein production was performed either in house using FreeStyle 293 Expression System (Thermo Fisher Scientific) or outsourced to the Protein Expression Core Facility (PECF) of the Life Science Faculty of the EPFL, as described previously (Angelini, A. et al. Bicyclic peptide inhibitor reveals large contact interface with a protease target. *ACS Chem Biol* 7, 817-821 (2012); Angelini, A. et al. Chemical macrocyclization of peptides fused to antibody Fc fragments. *Bioconjug Chem* 23, 1856-1863 (2012); Zhu, E. F. et al. Synergistic innate and adaptive immune response to combination immunotherapy with antitumor antigen antibodies and extended serum half-life IL-2. *Cancer Cell* 27, 489-501 (2015)). At the end of the 7-day phase production, cells were harvested by centrifugation at 15,000×g for 30 minutes at 4° C. on an Avanti JXN-26 Centrifuge (Beckman Coulter). Any additional cell debris was removed from the medium by filtration through 0.22-μm PES membrane filters (Thermo Fisher Scientific) and the clarified medium diluted with 1/10 volume 10×PBS pH 7.4.

Recombinant Fc fusions were captured on a rProtein A Sepharose Fast Flow resin (GE Healthcare), packed on a glass Econo-Column Chromatography column (Bio-Rad), that was previously equilibrated with 10 column volumes (CVs) of 1×PBS pH 7.4. The filter culture media was passed through the resin at a flow rate of approximately 2.5 mL/min at room temperature. The resin was then extensively washed with 10 CVs of 1×PBS pH 7.4 and the recombinant Fc fusions eluted in a single peak by applying 10 CVs of elution Buffer E (50 mM Glycine-HCl, pH 2.7). 2 CVs of neutralizing Buffer N (1 M Tris-HCl pH 8.5) were then immediately added to the eluted Fc fusion proteins to prevent protein denaturation. Eluted Fc fusions were diluted twice with 1×PBS pH 7.4 and concentrated by using 10000 NMWL Amicon Ultra-15 ultrafiltration devices (Millipore) at 4000×g and 4° C. on a Allegra X14R centrifuge (Beckman Coulter). The concentrated Fc fusion proteins were further subjected to size-exclusion chromatography (SEC) by using a Hiprep 26/10 desalting column (GE Healthcare) connected to an AKTApurifier system (GE Healthcare) equilibrated with Buffer T (50 mM Tris-HCl, 100 mM NaCl, 0.5 mM EDTA, pH 8.0). Purified Fc fusion proteins $^N$Fc-CXCL$^C$ in Buffer T were further concentrated to 2 mg/mL by using 10000 NMWL Amicon Ultra-15 ultrafiltration devices (Millipore) at 4000×g and 4° C. on a Allegra X-14R centrifuge (Beckman Coulter) and cleaved by using recombinant TEV protease (0.5 mg/mL). Fc fusion:TEV at a molar ratio of 100:1 were incubated at 4° C. for up to 24 hours in a cleavage Buffer T supplemented with a 10:1 ratio of reduced (GSH) to oxidized (GSSG) L-glutathione (50 mM Tris-HCl, 100 mM NaCl, 0.5 mM EDTA, 3 mM GSH, 0.3 mM GSSG, pH 8.0) and complete protease inhibitor cocktail (Roche).

The further separation of matured cleaved CXC chemokines from the (i) Fc domain, (ii) un-cleaved Fc-CXCL fusion and (iii) recombinant TEV-His6 protease was performed by loading the cleavage mixture on a Ni Sepharose excel affinity resin (GE Healthcare), packed on a glass Econo-Column Chromatography column (Bio-Rad), that was previously equilibrated with 10 CVs of Buffer X (50 mM sodium phosphate, 500 M NaCl, pH 8.0). The mixture was passed through the resin at a flow rate of approximately 1 mL/min at room temperature and the flow-through containing cleaved $^N$CXCL-G$_2$-AviTag$^C$ proteins collected. The purified $^N$CXCL-G$_2$-AviTag$^C$ proteins were further concentrated by using a 3000 NMWL Amicon Ultra-15 ultrafiltration devices (Millipore) at 4000×g and 4° C. on a Allegra X-14R centrifuge (Beckman Coulter) and subjected to SEC by using a HiLoad 16/600 Superdex 75 prep-grade column (GE Healthcare) equilibrated with biotinylation Buffer R (50 mM Bicine, pH 8.3) on an AKTApurifier system (GE Healthcare). Purified $^N$CXCL-G$_2$-AviTag$^C$ proteins in Buffer R were then concentrated to approximately 100 μM by using 3000 NMWL Amicon Ultra-4 ultrafiltration devices (Millipore) at 4000×g and 4° C. on a Allegra X-14R centrifuge (Beckman Coulter).

Biotinylation of $^N$CXCL-G$_2$-AviTag$^C$ proteins was performed by using BirA enzyme (Avidity) according to manufacturer's guidelines. Briefly, enzymatic reaction included 50 nmol $^N$CXCL-G$_2$-AviTag$^C$ protein in Buffer R, 12 μg of recombinant BirA enzyme (3 mg/mL; Avidity), 50 μM d-biotin, 10 mM ATP pH 7.2 and 10 mM MgOAc for a total volume of 1 mL. To ensure complete biotinylation, the reaction was incubated at 4° C. for 48 hours with gentle shacking and jumped started every 12 hours by adding 50 μL of Biomix-A (500 mM Bicine, pH 8.3; Avidity) and 50 μL of Biomix-B (100 mM ATP, 100 mM MgOAc, 500 μM d-biotin; Avidity) to the reaction mix. These conditions were sufficient for complete quantitative reaction yielding one product with expected molecular mass (A mass=226 Da).

Biotinylated $^N$CXCL-G$_2$-AviTag$^C$ proteins were further purified by using either reversed-phase high performance liquid chromatography (RP-HPLC) or SEC. RP-HPLC was performed on a Vydac C18 column (Grace & Co.) connected to a Waters HPLC system (Waters). A flow rate of 1 mL/min and a linear gradient was applied with a mobile phase composed of eluant A (99.9% v/v H2O and 0.1% v/v TFA) and eluant B (99.9% v/v ACN and 0.1% v/v TFA). This step efficiently removed unbound small molecules such as free biotin and ATP along with the BirA enzyme. Purified and biotinylated $^N$CXCL-G$_2$-AviTag$^C$ proteins were lyophilized, dissolved in 1×PBS pH 7.4 to a final protein concentration of approximately 100 μM, flash frozen in liquid nitrogen and stored at −80° C. Alternatively, biotinylated $^N$CXCL-G$_2$-AviTag$^C$ proteins were purified by SEC using a Superdex 75 10/300 GL column (GE Healthcare) equilibrated with 1×PBS pH 7.4 and connected to an AKTApurifier system (GE Healthcare).

The final purified and biotinylated proteins were further concentrated by using 3000 NMWL Amicon Ultra-0.5 centrifugal filter units (Millipore) at 14000×g and 4° C. on a Eppendorf 5702R centrifuge (Eppendorf) to a final protein concentration of approximately 100 μM, flash frozen in liquid nitrogen and stored at −80° C. After purification, the yield of pure and biotinylated $^N$CXCL-G$_2$-AviTag$^C$ proteins ranged from 1 to 5 mg/L of culture. Molecular weights were confirmed by reducing sodium dodecyl sulfate-polyacrylamide gel electrophoresis (SDS-PAGE) using NuPAGE 4-12% Bis-Tris Gels (Thermo Fisher Scientific) in 2-(N-morpholino)ethanesulfonic acid (MES) buffer followed by SimplyBlue SafeStain (Thermo Fisher Scientific) and imaged on the Typhoon Trio imager (GE Healthcare). Biotinylated $^N$CXCL-G$_2$-AviTag$^C$ proteins migrated a single band in SDS-PAGE, with apparent molecular masses of about 8-10 kDa.

Mass Spectrometric Analysis

The molecular mass of each ELR+ CXC chemokine before and after biotinylation was determined with electrospray ionization mass spectrometry (ESI-MS) performed on a quadrupole time-of-flight mass spectrometer (Q-TOF) coupled to a $C^3$ or $C^8$ reversed phase HPLC column for desalting of protein samples. Both LC-MS Agilent 6520 ESI-Q-TOF (Agilent Technologies) and Waters LCT ESI- Q-TOF (Waters) systems, operated in a positive ionization mode, were used. Data were acquired, processed, and analyzed using the Agilent MassHunter (Agilent Technologies) or the MassLynx (Waters) software package. Mass spectrometry (i) confirmed the corrected mass of the purified biotinylated chemokines and (ii) showed that no un-biotinylated protein remains in the final sample.

Selection of Crossreactive Binders From a Naïve Library of Synthetic scFv Displayed on the Surface of Yeast Crossreactive protein binders to human and murine ELR+ CXC chemokines based on the synthetic antibody single-chain variable fragment scaffold (scFv) were isolated using standard yeast surface display technology as previously described (Angelini, A. et al. Protein Engineering and Selection Using Yeast Surface Display. *Methods Mol Biol* 1319, 3-36 (2015)). The yeast-displayed synthetic antibody naïve library "G" was constructed using homologous recombination-based methods as previously described (Angelini, A. et al. Protein Engineering and Selection Using Yeast Surface Display. *Methods Mol Biol* 1319, 3-36 (2015); Van Deventer, J. A., Kelly, R. L., Rajan, S., Wittrup, K. D. & Sidhu, S. S. A switchable yeast display/secretion system. *Protein Eng Des Sel* 28, 317-325 (2015)). The library was constructed to display the synthetic scFv variants on the surface of yeast as C-terminal fusion of the a-agglutinin Aga2 protein ($_N$CXCL-Aga2p$^C$).

Yeast surface display vectors were based on pCT-CON backbone and included a secretory leader sequence ($^N$MQLLRCFSIFSVIASVLA$^C$)(SEQ ID NO: 202), a sequence encoding for the Aga2p protein, a sequence encoding for the influenza hemagglutinin epitope tag (HA; $^N$YPYDVPDYA$^C$)(SEQ ID NO: 182), a fifteen amino-acid flexible linker ($^N$GGGGSGGGGSGGGGS$^C$)(SEQ ID NO: 203), a sequence encoding for the synthetic scFv in the light ($V_L$) to heavy ($V_H$) chain orientation, separated by another fifteen amino-acid flexible linker ($^N$GT-TAASGSSGGSSSGA$^C$)(SEQ ID NO: 204). A sequence encoding for c-myc epitope tag (c-myc; $^N$EQKLISEEDLQ$^C$) (SEQ ID NO: 205) was inserted at the C-terminus of the gene encoding the scFv to obtain $^N$Aga2p-HA-(G$_4$S)$_3$-V$_L$-linker-V$_H$-c-myc$^C$ fusion proteins.

Yeast display selection was performed by using an amount of yeast cells at least ten-fold larger than (i) the initial estimated naïve library size (1×10$^9$ unique clones) or (ii) the number of cells isolated from the previous round of either magnetic bead screening or flow cytometry sorting. The yeast cells display naïve library were grown in SD-CAA medium at 30° C. with shacking (250 rpm) and surface protein expression induced in galactose-containing SG-CAA media for 20 hours at 20° C. with shacking (250 rpm) as previously described (Angelini, A. et al. Protein Engineering and Selection Using Yeast Surface Display. *Methods Mol Biol* 1319, 3-36 (2015)). Before positive selection, yeast populations (1×10$^{10}$) underwent three sequential cycles of "negative" selection using uncoated Dynabeads biotin binder magnetic beads (Thermo Fisher Scientific). Ten-fold diversity library depleted of streptavidin-coated beads binders was screened against highly diverse human (hCXCL1, hCXCL5 and hCXCL8) and murine (mCXCL1, mCXCL1 and mCXCL5) biotinylated ELR+ CXC chemokines captured on magnetic beads. Two iterative cycles of magnetic bead selections followed by four cycles of fluorescence-activated cell sorting (FACS) were applied (FIG. 1B).

Complex positive selection schemes, in which ten-fold of the cell output isolated from a pathway was incubated with a diverse ELR+ CXC chemokine target in the following pathway, were performed to force crossreactivity and thus enhance the probabilities of isolating crossreactive protein binders. Each cycle comprised growth of yeast cells, expression of the synthetic antibodies on the surface, binding to the immobilized CXC ELR+ chemokine ligands, washing and expansion of the isolated bound yeast cells as previously described (Angelini, A. et al. Protein Engineering and Selection Using Yeast Surface Display. *Methods Mol Biol* 1319, 3-36 (2015)). Cells were washed using ice-cold PBSA buffer (1×PBS pH 7.4 supplemented with 0.1% w/v bovine serum albumin fraction V). For FACS, highly crossreactive protein binders were selected using a two-color labeling scheme based on fluorescent-conjugated detection reagents for expression (anti-c-myc epitope tag) and binding to ELR+ CXC chemokine (anti-biotin) at recommended dilutions. Notably, highly avidity magnetic and fluorescently labeled reagents (e.g. streptavidin and neutravidin) saturated with diverse biotinylated ELR+ CXC chemokines were used during the all the six selection cycles.

The use of highly avid reagents increased the likelihood of isolating crossreactive low affinity binders from the naïve library by exploiting the multivalent interaction between yeast cells and the preloaded target. Sorting was performed on BD FACSAria I and III sorter instruments (BD Biosciences) and data evaluated using FlowJo v.10.0.7 software (Tree Star). After six cycles of iterative selections, DNA plasmid was extracted from isolated yeast cells using Zymoprep Yeast Plasmid Miniprep II Kit (Zymo Research). Extracted DNA plasmids were further amplified in *Escherichia coli*, purified and used (i) to reveal the amino acid sequence of each selected protein binder by DNA sequencing (Macrogen), (ii) to transform new yeast cells to determine the binding affinity of single protein binder using yeast cell surface titrations, and (iii) as template to prepare mutagenized DNA for further library generation and co-evolution of both binding affinity and crossreactivity, as described below.

Single Antibody Clone Binding Affinity Characterization Using Yeast Surface Titrations The equilibrium dissociation constant ($K_D$) of each individual selected protein binder towards single CXC chemokines was determined by using yeast surface display titrations as described previously (Angelini, A. et al. Protein Engineering and Selection Using Yeast Surface Display. *Methods Mol Biol* 1319, 3-36 (2015)). Yeast surface display combined to flow cytometry allowed measurement of $K_D$ directly on the surface of yeast cells without the need for additional sub-cloning, expression and purification steps that were instead necessary to characterize protein binders clones isolated using alternative display technologies (VanAntwerp, J. J. & Wittrup, K. D. Fine affinity discrimination by yeast surface display and flow cytometry. *Biotechnol Prog* 16, 31-37 (2000)). Importantly, the $K_D$ values measured using such method have been shown to be consistent with values obtained using alternative techniques for examining binding affinities such as Surface Plasmon Resonance (SPR), Bio-Layer Interferometry (BLI) and Kinetic Exclusion Assay (KinExA flow fluorimeter) (Razai, A. et al. Molecular evolution of antibody affinity for sensitive detection of botulinum neurotoxin type A. *J Mol Biol* 351, 158-169 (2005); Traxlmayr, M. W. et al. Strong Enrichment of Aromatic Residues in Binding Sites from a Charge-Neutralized Hyperthermostable Sso7d Scaffold Library. *J Biol Chem* (2016)).

In brief, DNA plasmids encoding single protein binder clones were transformed into genetically modified *Saccharomyces cerevisiae* yeast cells (EBY100 strain) using Frozen-EZ Yeast Transformation II Kit (Zymo Research) and plated on selective SD-CAA solid agar media. Individual colonies were inoculated in 5 mL SD-SCAA cultures, grown to mid-log phase (OD600=2-5) in SD-CAA media at 30° C. with shacking (250 rpm). Cells were induced in galactose-containing SG-CAA media for 20 hours at 20° C. with shacking (250 rpm) as previously described (Angelini, A. et al. Protein Engineering and Selection Using Yeast Surface Display. *Methods Mol Biol* 1319, 3-36 (2015)). The binding assays were conducted in 96-well plates (Corning) containing $1\times10^4$ induced cells per well. Non-displaying yeast cells ($1\times10^5$) were added to each well and mixed to induced cells to ensure (i) proper cell pelleting and (ii) an excess of soluble CXC chemokine target over total number of yeast displayed protein binders ($5\times10^4$ copies of protein/yeast cell) in solution (Hackel, B. J., Kapila, A. & Wittrup, K. D. Picomolar affinity fibronectin domains engineered utilizing loop length diversity, recursive mutagenesis, and loop shuffling. *Journal of molecular biology* 381, 1238-1252 (2008)). Yeast cells displaying protein binders were incubated with varying concentration of soluble CXC chemokine fusions ($^N$CXCL-SA$^C$) bearing the His6 tag and the primary chicken anti-c-myc epitope tag (1:1000) antibody (Gallus Immunotech) overnight at 4° C. with shaking (150 rpm). Twelve to sixteen different concentrations of pure $^N$CXCL-SA$^C$ fusion proteins, ranging from 10 pM to 10 µM, were applied spanning a range of concentrations ten times both above and below the expected $K_D$ value. After primary incubation, cells were pelleted (2500×g for 5 min at 4° C.) and washed twice with 200 µL ice-cold PBSA buffer. Secondary labeling was performed with goat anti-chicken and mouse anti-His6 epitope tag antibodies conjugated to Alexa Fluor dyes at recommended dilutions.

The 96-well plates were run on a high-throughput plate sampler iQue Screener (IntelliCyt) or individually analyzed on an Accuri C6 Flow Cytometer (BD Accuri Cytometers). Data were evaluated using FlowJo v.10.0.7 software (Tree Star). To ensure that the differences in binding were not due to variations of number of proteins expressed on the surface of yeast cell, the median fluorescence intensity (MFI$_{BIND}$) from binding signal (His6 tag) was normalized to the median fluorescence intensity (MFI$_{DIS}$P) from display signal (c-myc tag). The normalized (binding/display=MFI$_{BIND}$/MFI$_{DIS}$P) median fluorescence intensity as a function of CXC chemokine concentration was used to determine the $K_D$ values for all clones of interest. Values reported here are the results of three independent experiments and are presented as mean (dots)±SE (bars).

Co-Evolution of Protein Binding Affinity and Crossreactivity by Yeast Surface Display Two series of random mutagenesis and FACS-based selections (namely I and II) were applied to improve both the binding affinity and crossreactivity of three crossreactive clones: CK1, CK2 and CK4. Random mutagenesis libraries were generated by error-prone PCR as previously described (Angelini, A. et al. Protein Engineering and Selection Using Yeast Surface Display. *Methods Mol Biol* 1319, 3-36 (2015)). To ensure a mutagenesis rate of approximately 1-2 amino acid mutated residues distributed randomly throughout the entire gene, 1 ng of DNA template encoding the CK1, CK2 and CK4 binders were PCR amplified for 15 cycles using Taq DNA polymerase (New England BioLabs), analogue nucleotides (2 μM 8-oxo-dGTP and 2 μM dPTP) and flanking oligonucleotide primers (forward: 5'-GGAGGCGGTAGCGGAGGCG-GAGGGTCGGCTAGC-3' (SEQ ID NO: 206); reverse: 5'-GTCCTCTTCAGAAATAAGCTTTTGTTCGGAT-3' (SEQ ID NO: 207); Integrated DNA Technologies).

The mutagenized PCR products were further purified, re-amplified for additional 30 cycles in the absence of analogue nucleotides and combined with SalI-HF, NheI-HF and BamHI-HI (New England BioLabs) digested pCT-CON vector at a molar ratio of 2.5:1. Pre-mixed DNA linearized vector and PCR insert (1 μg/μL) was electroporated into freshly prepared *Saccharomyces cerevisiae* EBY100 competent cells, where the full constructs are reassembled via homologous recombination (Angelini, A. et al. Protein Engineering and Selection Using Yeast Surface Display. *Methods Mol Biol* 1319, 3-36 (2015)). Transformed cultures were recovered and expanded in SD-SCAA. Small portions of transformed cells were serially diluted and titrated on SD-SCAA plates to confirm the final reported library sizes (Table 3). Library quality and diversity was further assessed by sequencing twenty colonies of each library. All clones sequenced from the mutagenized libraries were found to be in the expected format. The yeast cells display mutagenized libraries were grown in SD-CAA medium at 30° C. with shacking (250 rpm) and surface protein expression induced in galactose-containing SG-CAA media for 20 hours at 20° C. with shacking (250 rpm) as previously described (Angelini, A. et al. Protein Engineering and Selection Using Yeast Surface Display. *Methods Mol Biol* 1319, 3-36 (2015)).

TABLE 3

| Library name | Template | Library size |
|---|---|---|
| CK1-lib I | CK1 | $1.0\times10^8$ |
| CK2-lib I | CK2 | $2.0\times10^8$ |
| CK4-lib I | CK4 | $8.0\times10^7$ |
| CK1-lib II | CK19 | $3.0\times10^8$ |
| CK2-lib II | CK41 | $5.0\times10^8$ |
| CK4-lib II | CK50 | $4.0\times10^8$ |

An amount of yeast cells at least ten-fold larger than the estimated mutagenized libraries size were screened against human (hCXCL1, hCXCL5 and hCXCL8) and murine (hCXCL1, hCXCL2 and hCXCL5) biotinylated ELR+ CXC chemokines using equilibrium-based selection strategies. Six sequential cycles of FACS were applied. Each cycle comprised growth of yeast cells, expression of the binders on the surface, binding to the immobilized CXC ELR+ chemokine ligands, washing and expansion of the isolated bound yeast cells as previously described (Angelini, A. et al. Protein Engineering and Selection Using Yeast Surface Display. *Methods Mol Biol* 1319, 3-36 (2015)). Complex selection schemes, in which ten-fold of the cell output isolated from a pathway was incubated with a diverse ELR+ CXC chemokine target in the following pathway, were performed to force crossreactivity and thus enhance the probabilities of isolating crossreactive protein binders. Decreasing concentrations [C] of biotinylated CXC ELR+ chemokines up to ten-fold below the measured $K_D$ were used for each round of selection ($[C]=0.1\times K_D$) in order to select for crossreactive clones with improved affinity. Secondary fluorescent-conjugated detection reagents for FACS were constantly alternated to avoid enrichments of clones that could bind to them. Sorting was performed on BD FACSAria I and III sorter instruments (BD Biosciences) and data evaluated using FlowJo v.10.0.7 software (Tree Star). After six cycles of iterative selections, DNA plasmid was extracted from isolated yeast cells and used for further DNA sequencing and single clone characterization as described above.

Combination of Individual Mutations by Site-Directed Mutagenesis Individual mutations from different protein binders were combined to further enhance affinity and specificity. A third step of site directed mutagenesis (namely III) was applied to combine mutations derived from different CK1 and CK2 lineage-derived clones. Site-directed mutagenesis was performed by whole plasmid PCR using QuikChange site directed mutagenesis kit (Agilent Technologies) and pairs of complementary primers carrying single point mutations (Integrated DNA Technologies). The DNA sequences encoding CK63, CK66 and CK72 (CK1 lineage) and CK108, CK111 and CK119 (CK2 lineage) were used as templates to generate fifteen (CK131-CK145) and thirteen (CK146-CK158) variants, respectively, each including different combinations of CDR and FWR mutations. All constructs were verified by DNA sequencing (Macrogen).

Single mutants were displayed on the surface of *Saccharomyces cerevisiae* strain EBY100 using Frozen-EZ Yeast Transformation II Kit (Zymo Research) and plated on selective SD-CAA solid agar media. Individual colonies were inoculated in 5 mL SD-SCAA cultures, grown to mid-log phase (OD600=2-5) in SD-CAA media at 30° C. with shacking (250 rpm). Cells were induced in galactose-containing SG-CAA media for 20 hours at 20° C. with shacking (250 rpm) as previously described (Angelini, A. et al. Protein Engineering and Selection Using Yeast Surface Display. *Methods Mol Biol* 1319, 3-36 (2015)). The equilibrium dissociation constant ($K_D$) of each individual clone towards single CXC chemokines was determined by using yeast surface display titrations combined to flow cytometry as described above.

Figure 6:
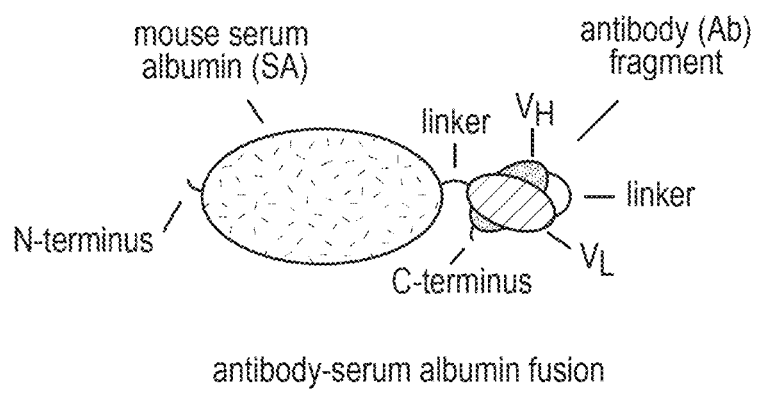
FIG. 6 is a schematic representation of the antibody single-chain variable fragment fused to the C-terminus of mouse serum albumin to generate SA129, SA138 and control $SA^{CTR}$ fusion proteins.

Cloning of Selected Synthetic scFv Fused to Mouse Serum Albumin Protein for Mammalian Cell Line Expression Selected crossreactive synthetic single light ($V_L$) and heavy ($V_H$) chain antibody variable fragments (scFv) were cloned and expressed in mammalian cells as C-terminal fusion of the murine serum albumin (SA) protein ($^N$SA-scFv$^C$). Mammalian expression vectors were based on gWiz (Genlantis). Constructs for expression of $^N$SA-scFv$^C$ fusion proteins were generated by using DNA assembly methods such as Gibson Assembly (New England BioLabs) or In-Fusion Cloning (Clontech Laboratories, Takara Bio) technologies. PfuUltra II Fusion HS DNA Polymerase (Agilent Technologies) and Herculase II Fusion DNA Polymerase (Agilent Technologies) were used for the PCR amplification of the insert and the vector, respectively. DpnI enzyme was obtained from New England Biolabs and oligonucleotide primers from Integrated DNA Technologies. The DNA sequences encoding the scFv ($V_L$-$V_H$ orientation) CK129, CK138 and CK157 as well as separate $V_L$ and $V_H$ domains of CK157 were amplified in a PCR reaction by using the pCT-CON vector as template and following inserted into a previously modified gWiz expression vector containing a DNA sequence encoding for a secretory leader peptide sequence ($^N$MDMRVPAQLLGLLLLWLPGARC$^C$)(SEQ ID NO: 208) followed by a sequence encoding the mouse serum albumin (SA), a fifteen amino-acid flexible linker ($^N$GGGGSGGGGSGGGGS$^C$)(SEQ ID NO: 203). A sequence encoding for a five amino-acid flexible linker ($^N$GGGGS$^C$)(SEQ ID NO: 201) followed by a hexa-histidine tag (His6; $^N$HHHHHH$^C$)(SEQ ID NO: 181) was inserted at the C-terminus of the gene encoding the scFv to obtain the final $^N$SA-(G$_4$S)$_3$-scFv-G$_4$S-His$_6{}^C$, $^N$SA-(G$_4$S)$_3$ V$_L$-G$_4$S-HiS$_6{}^C$ and $^N$SA(G$_4$S)$_3$-V$_H$-His6$^C$ fusion proteins (FIG. 6). In a similar fashion, the control scFv ($V_H$-$V_L$ orientation) targeting the human carcinoembryonic antigen (CEA) (Graff, C. P., Chester, K., Begent, R. & Wittrup, K. D. Directed evolution of an anti-carcinoembryonic antigen scFv with a 4-day monovalent dissociation half-time at 37 degrees C. *Protein Eng Des Sel* 17, 293-304 (2004)) was fused at the C-terminus of mouse serum albumin. The stability of the each scFv was further improved by connecting the $V_L$ and $V_H$ domains via an intermolecular disulfide bond (ds). The addition of stabilizing intermolecular disulfide bridges is reported to increase the percent of monomeric forms by permanently fixing monomer: dimer ratios during the purification steps. Two of the most favorable locations were selected for the introduction of pairs of cysteine residues into each single scFv (ds1: $V_L$100 and $V_H$44; ds2: $V_L$43 and $V_H$105; Kabat numbering system) (Reiter, Y. et al. Stabilization of the Fv fragments in recombinant immunotoxins by disulfide bonds engineered into conserved framework regions. *Biochemistry* 33, 5451-5459 (1994); Jung, S. H., Pastan, I. & Lee, B. Design of interchain disulfide bonds in the framework region of the Fv fragment of the monoclonal antibody B3. *Proteins* 19, 35-47 (1994); Weatherill, E. E. et al. Towards a universal disulphide stabilised single chain Fv format: importance of interchain disulphide bond location and vL-vH orientation. *Protein Eng Des Sel* 25, 321-329 (2012); Kabat, E. A., Wu, T. T., Perry, H., Gottesman, K. and Foeller, C. Sequences of Proteins of Immunological Interest, Edn. Fifth Edition. (1991)) and their relative effects on expression, percent monomer formation and retention of antigen binding compared. Cysteine residues were introduced into each scFv by site-directed mutagenesis using DNA assembly methods such as Gibson-Assembly (New England BioLabs) or In-Fusion Cloning (Clontech Laboratories, Takara Bio) technologies and standard oligonucleotide primers carrying single point mutations (Integrated DNA Technologies). Final genes encoding $^N$SA-(G$_4$S)$_3$-scFv-G$_4$S-His6$^C$, $^N$SA-(G$_4$S)$_3$-scFv-ds1-G$_4$S-His6$^C$, $^N$SA-(G$_4$S)$_3$-scFv-ds2-G$_4$S-His6$^C$, $^N$SA(G$_4$S)$_3$-V$_L$-G$_4$S-His6$^C$ and $^N$SA-(G4S)$_3$-V$_H$-G4S-His6$^C$ fusion proteins were further subcloned into a new gWiz expression vector via NotI-HF and XbaI (New England BioLabs) restriction enzymes. All constructs were verified by DNA sequencing (Macrogen, Cambridge, Mass.) and termed $^N$CXCL-SA$^C$ fusion proteins (see Table 4 for information about protein accession number and SEQ ID NOs: 83-106 for DNA and amino-acid sequences). The serum albumin-antibody fusion formats were used for all in vitro and in vivo studies.

TABLE 4

| Fusion protein (code name) | Construct for expression |
|---|---|
| $^N$SA-CK138$^C$ (SA138) | gWiz-LS-mouse SA-(Gly$_4$Ser)$_3$-scFv (V$_L$-V$_H$) CK138-(Gly$_4$Ser)-His$_6$ |
| $^N$SA-CK157$^C$ (SA157) | gWiz-LS-mouse SA-(Gly$_4$Ser)$_3$-scFv (V$_L$-V$_H$) CK157-(Gly$_4$Ser)-His$_6$ |
| $^N$SA-CK129$^C$ (SA129) | gWiz-LS-mouse SA-(Gly$_4$Ser)$_3$-scFv (V$_L$-V$_H$) CK129-(Gly$_4$Ser)-His$_6$ |
| $^N$SA-CK138-ds1$^C$ (SA138-ds1) | gWiz-LS-mouse SA-(Gly$_4$Ser)$_3$-scFv (V$_L$-V$_H$) CK138-ds1 (V$_L$100$^{Q>C}$/V$_H$44$^{G>C}$)-(Gly$_4$Ser)-His$_6$ |

TABLE 4-continued

| Fusion protein (code name) | Construct for expression |
|---|---|
| $^N$SA-CK138-ds2$^C$ (SA138-ds2) | gWiz-LS-mouse SA-(Gly$_4$Ser)$_3$-scFv (V$_L$-V$_H$) CK138-ds2 (V$_L$43$^{A>C}$/V$_H$105$^{Q>C}$)-(Gly$_4$Ser)-His$_6$ |
| $^N$SA-CK157-ds1$^C$ (SA157-ds1) | gWiz-LS-mouse SA-(Gly$_4$Ser)$_3$-scFv (V$_L$-V$_H$) CK157-ds1 (V$_L$100$^{Q>C}$/V$_H$44$^{E>C}$)-(Gly$_4$Ser)-His$_6$ |
| $^N$SA-CK157-ds2$^C$ (SA157-ds2) | gWiz-LS-mouse SA-(Gly$_4$Ser)$_3$-scFv (V$_L$-V$_H$) CK157-ds2 (V$_L$43$^{A>C}$/V$_H$105$^{Q>C}$)-(Gly$_4$Ser)-His$_6$ |
| $^N$SA-CK157-VL$^C$ (SA157-VL) | gWiz-LS-mouse SA-(Gly$_4$Ser)-V$_L$ CK157-HiS$_6$ |
| $^N$SA-CK157-VH$^C$ (SA157-VH) | gWiz-LS-mouse SA-(Gly$_4$Ser)-V$_H$ CK157-HiS$_6$ |
| $^N$SA-CK129-ds1$^C$ (SA129-ds1) | gWiz-LS-mouse SA-(Gly$_4$Ser)$_3$-scFv (V$_L$-V$_H$) CK129-ds1 (V$_L$100$^{Q>C}$/V$_H$44$^{G>C}$)-(Gly$_4$Ser)-His$_6$ |
| $^N$SA-CK129-ds2$^C$ (SA129-ds2) | gWiz-LS-mouse SA-(Gly$_4$Ser)$_3$-scFv (V$_L$-V$_H$) CK129-ds2 (V$_L$43$^{A>C}$/V$_H$105$^{Q>C}$)-(Gly$_4$Ser)-His$_6$ |
| $^N$SA-sm3e-ds$^C$ (SActr) | gWiz-LS-mouse SA-(Gly$_4$Ser)$_3$-scFv (V$_H$-V$_L$) sm3E-ds (V$_H$44$^{R>C}$/V$_L$100$^{G>C}$)-(Gly$_4$Ser)-His$_6$ |

Expression and Purification of Serum Albumin Fusion Proteins

Serum albumin (SA) fusion proteins $^N$CXCL-SA$^C$ and $^N$SA-scFv$^C$ were expressed by transient transfection of suspension-adapted human embryonic kidney (HEK-293) cells. Protein production was performed either in house using FreeStyle 293 Expression System (Thermo Fisher Scientific) or outsourced to the Protein Expression Core Facility (PECF) of the Life Science Faculty of the EPFL, as described previously (Angelini, A. et al. Bicyclic peptide inhibitor reveals large contact interface with a protease target. *ACS Chem Biol* 7, 817-821 (2012); Angelini, A. et al. Chemical macrocyclization of peptides fused to antibody Fc fragments. *Bioconjug Chem* 23, 1856-1863 (2012); Zhu, E. F. et al. Synergistic innate and adaptive immune response to combination immunotherapy with anti-tumor antigen antibodies and extended serum half-life IL-2. *Cancer Cell* 27, 489-501 (2015)). At the end of the 7-day phase production, cells were harvested by centrifugation at 15,000×g for 30 minutes at 4° C. on an Avanti JXN-26 Centrifuge (Beckman Coulter). Any additional cell debris was removed from the medium by filtration through 0.22-µm PES membrane filters (Thermo Fisher Scientific) and the clarified medium diluted with ¹/₁₀ volume Buffer A (500 mM sodium phosphate, 5 M NaCl, pH 8.0). Recombinant SA fusions were captured on a Ni Sepharose excel affinity resin (GE Healthcare), packed on a glass Econo-Column chromatography column (Bio-Rad), that was previously equilibrated with 10 CVs of Buffer B (50 mM sodium phosphate, 500 M NaCl, pH 8.0). The medium was passed through the resin at a flow rate of approximately 2.5 mL/min at room temperature. The resin was then extensively washed with 10 CVs of Buffer B and the recombinant SA fusions eluted in a single peak by applying 10 CVs of Buffer C (50 mM sodium phosphate, 500 M NaCl, 500 mM Imidazole, pH 8.0). Eluted SA fusions were following diluted with 10 CVs of Buffer B and concentrated by using 10000 NMWL Amicon Ultra-15 ultrafiltration devices (Millipore) at 4000×g and 4° C. on a Allegra X-14R centrifuge (Beckman Coulter). The concentrated SA fusion proteins were further purified by size exclusion chromatography using a HiLoad 16/600 Superdex 200 prep-grade column (GE Healthcare) equilibrated with 1×PBS pH 7.4 on an AKTApurifier system (GE Healthcare). Purified SA fusion proteins in 1×PBS pH 7.4 were following concentrated to 5 mg/ml ($^N$CXCL-SA$^C$) and 2 mg/mL ($^N$SA-scFv$^C$) final concentration by using 10000 NMWL Amicon Ultra-15 ultrafiltration devices (Millipore) at 4000×g and 4° C. on a Allegra X-14R centrifuge (Beckman Coulter).

Protein concentrations were determined by measuring absorbance at 280 nm using a NanoDrop 2000 spectrophotometer (Thermo Fisher Scientific). Molecular weights were confirmed by reducing sodium dodecyl sulfate-polyacrylamide gel electrophoresis (SDS-PAGE) using NuPAGE 4-12% Bis-Tris Gels (Life Technologies) in 3-(Nmorpholino) propanesulfonic acid (MOPS) buffer followed by SimplyBlue SafeStain (Life Technologies) and imaged on the Typhoon Trio imager (GE Healthcare). All purified SA fusion proteins migrated a single band in SDS-PAGE with an apparent molecular mass of approximately 75 kDa (for $^N$CXCL-SA$^C$), 80 kDa ($^N$SA-V$_L$$^C$ or ($^N$SA-V$_H$$^C$) and 95 kDa ($^N$SA-scFv$^C$). The monodisperse state of concentrated SA fusion proteins was confirmed by size-exclusion chromatography using a Superdex 200 10/300 GL column (GE Healthcare) connected to an AKTApurifier system and equilibrated with 1×PBS pH 7.4. Purified SA fusion proteins were eluted as a single peak at elution volumes (V$_e$) that corresponds to apparent molecular masses ranging between 150 kDa (dimer) and 300 kDa (tetramer) in the case of $^N$SA-CXCL$^C$ fusions while $^N$SA-scFv$^C$ fusions were eluted with V$_e$ that corresponds to apparent molecular masses of about 95 kDa (monomer). Size exclusion chromatography columns and the FPLC system used for purification of $^N$SA-scFv$^C$ fusions for animal studies were pretreated with 1M NaOH to remove endotoxins. Purified $^N$SA-scFv$^C$ fusions were further filtered sterile by passing them through a 0.2 µm syringe filters (Pall Life Sciences) and confirmed to contain minimal levels of endotoxin (<0.1 EU/mL) using the QCL-1000 Limulus Amebocyte Lysate (LAL) chromogenic test following the manufacturer's instructions (Lonza).

Biotinylation of Serum Albumin Fusion Proteins and Commercial Antibodies

Reactive EZ-link sulfo-NHS-LC-biotin (Thermo Fisher Scientific) was dissolved in 1×PBS pH 7.4 to obtain a final concentration of 10 mM. Protein conjugates containing biotin were prepared by incubating serum albumin fusion proteins (at concentrations of 2 mg/mL in 1×PBS pH 7.4) with ten-fold molar excess of EZ-link sulfo-NHS-LC-biotin for 30 minutes at room temperature. Excess of unreacted or hydrolyzed biotinylation reagent was removed using size-exclusion chromatography with Superdex 200 10/300 GL (GE Healthcare) connected to an AKTApurifier system (GE Healthcare) and equilibrated with buffer 1×PBS pH 7.4.

Fractions corresponded to the expected protein pick were pulled and concentrated to a final concentration of 2 mg/mL using 10000 NMWL Amicon Ultra-4 ultrafiltration devices (Millipore) at 4000× g and 4° C. on a Allegra X-14R centrifuge (Beckman Coulter). Final protein concentrations were measured using a NanoDrop 2000 Spectrophotometer (Thermo Fisher Scientific).

Display of CXC Chemokine on Surface of Yeast Cells

The ELR+ and (ELR−) CXC chemokines were displayed on the surface of yeast as N-terminal fusion of the a-agglutinin Aga2 protein ($^N$CXCL-Aga2p$^C$). Yeast surface display vectors were based on pCT backbone (Angelini, A. et al. Protein Engineering and Selection Using Yeast Surface Display. Methods Mol Biol 1319, 3-36 (2015)). Constructs for surface display of $^N$CXCL-Aga2$^C$ fusion proteins were generated by using Gibson Assembly (New England BioLabs) or In-Fusion Cloning (Clontech Laboratories, Takara Bio) technologies. PfuUltra II Fusion HS DNA Polymerase (Agilent Technologies) and Herculase II Fusion DNA Polymerase (Agilent Technologies) were used for the PCR amplification of the insert and the vector, respectively. DpnI enzyme was obtained from New England Biolabs and oligonucleotide primers from Integrated DNA Technologies. The synthetic DNA coding for the active protein form of twelve human and murine ELR+ CXC chemokines and eight human and murine (ELR−) CXC chemokines were obtained from GeneArt Gene Synthesis (Thermo Fisher Scientific).

The de novo synthesized genes encoding for the active processed form of each CXC chemokine were subsequently inserted into a previously modified yeast display pCT vector containing a DNA sequence encoding for a secretory leader sequence ($^N$MKVLIVLLAIFAALPLA-LAQPVISTTVGSAAEGSLDKR$^C$)(SEQ ID NO: 209), a three amino-acid flexible spacer ($^N$GGG$^C$), a sequence encoding for c-myc epitope tag (c-myc; $^N$EQKLISEEDLQ$^C$) (SEQ ID NO: 205) followed by a sequence encoding for the Aga2p protein to obtain $^N$CXCL-(G$_3$)-c-myc-Aga2p$^C$ fusion proteins. The process of the leader sequence during the secretory pathway allows for a precisely cleaved N-terminus that is crucial for the activity of the mature chemokines. Genes encoding $^N$CXCL-(G$_3$)-c-myc-Aga2p$^C$ fusion proteins were further sub-cloned into a new pCT vector via Bpu10I and XhoI (New England BioLabs) restriction enzymes except for MIP-2 for which PstI-HF and XhoI (New England BioLabs) restriction enzymes were used. All constructs were verified by DNA sequencing (Macrogen) and termed $^N$CXCL-Aga2p$^C$ fusion proteins (see Table 5 for information about protein accession number and SEQ ID NOs: 107-146 for DNA and amino-acid sequences).

TABLE 5

| CXCL protein (residues/accession No.) | Construct for expression | Fusion protein |
|---|---|---|
| Groα/hCXCL1 (38-107/P09341) | pCHA-LS-hCXCL1$^{38-107}$-G$_3$-c-myc-Aga2 | $^N$hCXCL1-Aga2$^C$ |
| Groβ/hCXCL2 (38-107/P19875) | pCHA-LS-hCXCL2$^{38-107}$-G$_3$-c-myc-Aga2 | $^N$hCXCL2-Aga2$^C$ |
| Groγ/hCXCL3 (38-107/P19876) | pCHA-LS-hCXCL3$^{38-107}$-G$_3$-c-myc-Aga2 | $^N$hCXCL3-Aga2$^C$ |
| PF-4/hCXCL4 (32-101/P02776) | pCHA-LS-hCXCL4$^{32-101}$-G$_3$-c-myc-Aga2 | $^N$hCXCL4-Aga2$^C$ |
| ENA-78/hCXCL5 (44-114/P42830) | pCHA-LS-hCXCL5$^{44-114}$-G$_3$-c-myc-Aga2 | $^N$hCXCL5-Aga2$^C$ |
| GCP-2/hCXCL6 (44-114/P80162) | pCHA-LS-hCXCL6$^{44-114}$-G$_3$-c-myc-Aga2 | $^N$hCXCL6-Aga2$^C$ |
| NAP-2/hCXCL7 (59-121/P02775) | pCHA-LS-hCXCL7$^{59-121}$-G$_3$-c-myc-Aga2 | $^N$hCXCL7-Aga2$^C$ |
| IL-8/hCXCL8 (29-99/P10145) | pCHA-LS-hCXCL8$^{29-99}$-G$_3$-c-myc-Aga2 | $^N$hCXCL8-Aga2$^C$ |
| MIG/hCXCL9 (23-125/Q07325) | pCHA-LS-hCXCL9$^{23-125}$-G$_3$-c-myc-Aga2 | $^N$hCXCL9-Aga2$^C$ |
| IP-10/hCXCL10-SA (22-98/P02778) | pCHA-LS-hCXCL10$^{22-98}$-G$_3$-c-myc-Aga2 | $^N$hCXCL10-Aga2$^C$ |
| I-TAC/hCXCL11-SA (22-94/O14625) | pCHA-LS-hCXCL11$^{22-94}$-G$_3$-c-myc-Aga2 | $^N$hCXCL11-Aga2$^C$ |
| KC/mCXCL1-SA (28-96/P12850) | pCHA-LS-mCXCL1$^{28-96}$-G$_3$-c-myc-Aga2 | $^N$mCXCL1-Aga2$^C$ |
| MIP-2/mCXCL2-SA (31-100/P10889) | pCHA-LS-mCXCL2$^{31-100}$-G$_3$-c-myc-Aga2 | $^N$mCXCL2-Aga2$^C$ |
| DCIP-1/mCXCL3-SA (31-100/Q6W5C0) | pCHA-LS-mCXCL3$^{31-100}$-G$_3$-c-myc-Aga2 | $^N$mCXCL3-Aga2$^C$ |
| Pf-4/mCXCL4-SA (30-105/Q9Z126) | pCHA-LS-mCXCL4$^{30-105}$-G$_3$-c-myc-Aga2 | $^N$mCXCL4-Aga2$^C$ |
| LIX/mCXCL5-SA (48-118/P50228) | pCHA-LS-mCXCL5$^{48-118}$-G$_3$-c-myc-Aga2 | $^N$mCXCL5-Aga2$^C$ |
| Nap-2/mCXCL7-SA (48-113/Q9EQI5) | pCHA-LS-mCXCL7$^{48-113}$-G$_3$-c-myc-Aga2 | $^N$mCXCL7-Aga2$^C$ |
| Mig/mCXCL9-SA (22-126/P18340) | pCHA-LS-mCXCL9$^{22-126}$-G$_3$-c-myc-Aga2 | $^N$mCXCL9-Aga2$^C$ |
| Ip-10/mCXCL10-SA (22-98/P17515) | pCHA-LS-mCXCL10$^{22-98}$-G$_3$-c-myc-Aga2 | $^N$mCXCL10-Aga2$^C$ |
| I-Tac/mCXCL11-SA (22-100/Q9JHH5) | pCHA-LS-mCXCL11$^{22-100}$-G$_3$-c-myc-Aga2 | $^N$mCXCL11-Aga2$^C$ |

The $^N$CXCL-Aga2p$^C$ fusion proteins were displayed on the surface of Saccharomyces cerevisiae strain EBY100 using a standard protocol as described previously (Angelini, A. et al. Protein Engineering and Selection Using Yeast Surface Display. Methods Mol Biol 1319, 3-36 (2015)).

Briefly, EBY100 yeast cells were transformed with pCT vectors encoding $^N$CXCL-Aga2p$^C$ fusion proteins using Frozen-EZ Yeast Transformation II Kit (Zymo Research). Cells were grown to mid-log phase in SD-CAA media at 30° C. and induced in galactose-containing media SG-CAA for 20 hours at 2° C. Staining of C-terminus c-myc epitope tag indicated that all the CXC chemokines are expressed well on the surface of yeast (approximately 105 copies per cell, a standard for yeast surface display). The proper folding of yeast displayed CXC chemokines was assessed by measuring binding of some displayed CXC chemokines to a panel of commercial neutralizing antibodies.

Epitope Mapping by Alanine-Scanning Mutagenesis

Functional binding residues were identified by alanine-scanning mutagenesis using yeast surface display technology combined to flow cytometry. Yeast surface display has been shown to provide a simple, flexible and robust method for fine resolution epitope mapping of both full-length or single-domain protein (Chao, G., Cochran, J. R. & Wittrup, K. D. Fine epitope mapping of anti-epidermal growth factor receptor antibodies through random mutagenesis and yeast surface display. *J Mol Biol* 342, 539-550 (2004); Cochran, J. R., Kim, Y. S., Olsen, M. J., Bhandari, R. & Wittrup, K. D. Domain-level antibody epitope mapping through yeast surface display of epidermal growth factor receptor fragments. *J Immunol Methods* 287, 147-158 (2004); Levy, R. et al. Fine and domain-level epitope mapping of botulinum neurotoxin type A neutralizing antibodies by yeast surface display. *J Mol Biol* 365, 196-210 (2007); Mata-Fink, J. et al. Rapid conformational epitope mapping of anti-gp120 antibodies with a designed mutant panel displayed on yeast. *J Mol Biol* 425, 444-456 (2013)). Alanine was chosen as a standard replacement residue for the identification of functional epitopes because it is found commonly in both buried and exposed positions, and it is present in all type of secondary structures. Moreover, alanine does not impose new hydrogen bonding, or lead to stearic problems, and is therefore less likely to cause misfolding of the protein (Wells, J. A. Systematic mutational analyses of protein-protein interfaces. *Methods Enzymol* 202, 390-411 (1991); Morrison, K. L. & Weiss, G. A. Combinatorial alanine-scanning. *Curr Opin Chem Biol* 5, 302-307 (2001)). The commonly bound human ELR+ CXC chemokine hCXCL1 (Groα) was selected for alanine-scanning experiments.

Tridimensional structural analysis and literature data were combined to identify Groα residues suitable for mutagenesis (Fairbrother, W. J., Reilly, D., Colby, T. J., Hesselgesser, J. & Horuk, R. The solution structure of melanoma growth stimulating activity. *J Mol Biol* 242, 252-270 (1994); Kim, K. S., Clark-Lewis, I. & Sykes, B. D. Solution structure of GRO/melanoma growth stimulatory activity determined by 1H NMR spectroscopy. *J Biol Chem* 269, 32909-32915 (1994); Poluri, K. M., Joseph, P. R., Sawant, K. V. & Rajarathnam, K. Molecular basis of glycosaminoglycan heparin binding to the chemokine CXCL1 dimer. *J Biol Chem* 288, 25143-25153 (2013); Ravindran, A., Sawant, K. V., Sarmiento, J., Navarro, J. & Rajarathnam, K. Chemokine CXCL1 dimer is a potent agonist for the CXCR2 receptor. *J Biol Chem* 288, 12244-12252 (2013); Sepuru, K. M. & Rajarathnam, K. CXCL1/MGSA Is a Novel Glycosaminoglycan (GAG)-binding Chemokine: STRUCTURAL EVIDENCE FOR TWO DISTINCT NON-OVERLAPPING BINDING DOMAINS. *J Biol Chem* 291, 4247-4255 (2016)). Solvent accessibility of hCXCL1 amino acid residues was determined by using both ASAView (Ahmad, S., Gromiha, M., Fawareh, H. & Sarai, A. ASAView: database and tool for solvent accessibility representation in proteins. *BMC Bioinformatics* 5, 51 (2004)) and PyMOL (PyMOL Molecular Graphics System, Version 1.8 Schrödinger, LLC) tools. Structurally buried hydrophobic amino acids (123, V40, A42, L52, V59, 162 and 163) as well as proline (P20, P31, P33, P54 and P57) and cysteine (C9, C11, C35 and C52) residues that are crucial for overall folding and stability of the chemokine were left unaltered. The wild-type hCXCL1 was displayed on the surface of yeast as the amino terminus fusion of the a-agglutinin Aga2 protein ($^N$hCXCL1$^{WT}$-Aga2p$^C$). Gene encoding $^N$hCXCL1$^{WT}$-(G$_3$)-c-myc-Aga2p$^C$ fusion protein was sub-cloned into a new pCT vector via Bpu10I and XhoI (New England BioLabs) restriction enzymes. The obtained pCT-hCXCL1$^{WT}$-Aga2 vector was used as the template for the site-directed mutagenesis. Mutagenic oligonucleotides were designed to introduce single point mutations at the desired sites and generate fifty-four hCXCL1 variants (pCT-hCXCL1$^{ALAn}$-Aga2, $^N$hCXCL1$^{ALAn}$-Aga2p$^C$; see SEQ ID NOs: 147 and 148 for DNA and amino acid sequences).

Binding of wild-type (hCXCL1$^{WT}$) and single alanine mutants (hCXCL1$^{ALAn}$) displayed on the surface of yeast toward soluble SA129, SA138 and SA157* serum albumin-antibody fusions and two commercial neutralizing antibodies targeting Groα was assessed by using flow cytometry. The wild-type ($^N$hCXCL1$^{WT}$-Aga2p$^C$) and single alanine mutant ($^N$hCXCL1$^{ALAn}$-Aga2p$^C$) fusion proteins were displayed on the surface of *Saccharomyces cerevisiae* strain EBY100 using Frozen-EZ Yeast Transformation II Kit (Zymo Research) as described previously (Angelini, A. et al. Protein Engineering and Selection Using Yeast Surface Display. *Methods Mol Biol* 1319, 3-36 (2015)). Individual colonies were inoculated in 5 mL SD-SCAA cultures, grown to mid-log phase ($OD_{600}$=2-5) in SD-CAA media at 30° C. with shacking (250 rpm) and induced in galactose-containing SG-CAA media for 20 hours at 20° C. with shacking (250 rpm). The binding assays were conducted in 96-well plates (Corning) containing $1\times10^4$ induced cells per well pre-mixed with $1\times10^5$ non-displaying yeast cells.

The level of expression of single wild-type (hCXCL1') and alanine mutants (hCXCL1$^{ALAn}$) displayed on the surface of yeast was assessed by staining the C-terminus c-myc epitope tag. Yeast cells displaying wild-type (hCXCL1$^{WT}$) and single alanine mutants (hCXCL1$^{ALAn}$) were then incubated with soluble serum albumin-antibody fusions SA129, SA138 and SA157* bearing the $His_6$ tag and the primary chicken anti-c-myc epitope tag (1:1000) antibody (Gallus Immunotech) overnight at 4° C. with shaking (150 rpm). The binding epitopes of two commercial mouse derived monoclonal antibodies targeting hCXCL1: Ab275 (clone 20326) and Ab276 (clone 31716) were also determined. High quality epitope maps were achieved by performing the assays at concentrations of soluble serum albumin-antibody fusions and antibodies that were equivalent to their $K_D$ binding values for the wild-type hCXCL1: 2.5 nM for SA129, 100 nM for SA138, 1.5 µM for SA157*, 0.1 nM for Ab275 and 0.25 nM for Ab276. Concentrations higher or lower than that diminished the sensitivity of the assay and made it difficult to differentiate strong from weak binding signals derived from different mutants. At too high concentrations, all the signals were saturated and showed similar binding whereas at too low concentrations, the noise made it difficult to distinguish strong from weak mutants. After primary incubation, cells were pelleted (2500×g for 5 minutes at 4° C.) and washed twice with 200 µL of ice-cold PBSA buffer. Secondary labeling was performed with goat anti-chicken and either mouse anti-His6 epitope tag or goat anti-mouse antibodies conjugated to Alexa Fluor dyes at recommended dilutions. The 96-well plates were run on a high-throughput plate sampler iQue Screener (IntelliCyt). Data were evaluated using FlowJo v.10.0.7 software (Tree Star).

To ensure that the differences in binding were not due to variations of number of proteins expressed on the surface of yeast cell, the median fluorescence intensity ($MFI_{BIND}$) from binding signal (His6 tag or goat anti-mouse antibodies) measured for single wild-type ($hCXCL1^{WT}$) and alanine mutants ($hCXCL1^{ALAn}$) was normalized to the median fluorescence intensity ($MFI_{DISP}$) from display signal (c-myc tag). The normalized (binding/display=$MFI_{BIND}/MFI_{DISP}$) values obtained for each hCXCL1 variant ($hCXCL1^{ALAn}$) were further normalized for the normalized value obtained for the wild-type ($hCXCL1^{WT}$) and plotted as ($MFI_{BIND}^{ALAn}/MFI_{DISP}^{ALAn}$) /($MFI_{BIND}^{WT}/MFI_{DISP}^{WT}$) providing a value, ranging from 0.0 to 1.0, that corresponded to the contribution of each amino acid residues upon binding with the corresponding serum albumin fusion or neutralizing antibody (Table 6). Alanine mutants V26, V28, E39, I41 and L44 exhibited an intense loss of binding when incubated with all soluble serum albumin fusion proteins SA129, SA138, SA157* and neutralizing antibodies Ab275 and Ab276 indicating possible misfolding of the displayed hCXCL1 variants and were therefore excluded. Values reported here are the results of three independent experiments and are presented as mean (dots)±SE (bars).

TABLE 6

Epitope mapping interactions

| | Ab275 | Ab276 | SA129 | SA138 | SA157 |
|---|---|---|---|---|---|
| strong (0.0-0.25) | G17 | L15 | Q13 | L12 | N46 |
| | T43 | G17 | L15 | N46 | |
| | N46 | I18 | I18 | G47 | |
| | G47 | H19 | N46 | R48 | |
| | R48 | N46 | G47 | | |
| | K49 | K61 | R48 | | |
| | | K65 | | | |
| moderate (0.25-0.5) | R8 | Q16 | T14 | R8 | I18 |
| | L12 | K21 | G17 | T14 | H19 |
| | T14 | K45 | G32 | L15 | K21 |
| | L15 | G47 | T43 | G32 | K29 |
| | Q16 | K71 | A50 | A50 | K45 |
| | I18 | | | L67 | G47 |
| | G32 | | | | I58 |
| | K45 | | | | K65 |
| | A50 | | | | K71 |
| weak (0.5-0.75) | Q10 | T14 | N22 | Q13 | N22 |
| | Q13 | N22 | K45 | I18 | |
| | N22 | R48 | E64 | M66 | |
| | N53 | A50 | | | |
| | | I58 | | | |
| | | K60 | | | |
| Total residues | 19 | 18 | 14 | 13 | 11 |

Yeast Display and Competitive Fluorescent-Based Binding Assay

A competitive flow cytometry-based binding assay was performed to further validate the identified hCXCL1 binding epitopes in different ELR+ CXC chemokines. The assays were conducted in 96-well plates (Corning) containing $1\times10^4$ induced cells per well pre-mixed with $1\times10^5$ non-displaying yeast cells. Yeast cells displaying the ELR+ CXC chemokines hCXCL1, hCXCL5, hCXCL8, mCXCL1 and mCXCL2 were pre-incubated at 4° C. with concentration of soluble un-biotinylated protein serum albumin fusions and neutralizing antibodies ("blocking reagents") that are equals to 100-times their $K_D$ values ($C_B$=100 $K_D$). After 90 minutes, soluble biotinylated protein serum albumin fusions and neutralizing antibodies ("detection reagents") were added at concentrations that are equals to their $K_D$ values ($C_D=K_D$).

The incubation time was 30 minutes at 4° C. with shacking (150 rpm). The cells were then pelleted at 2500×g for 5 minutes and 4° C. on an Allegra X-14R centrifuge (Beckman Coulter), and washed twice with 200 μL ice-cold PBSA buffer. Secondary labeling was performed at 4° C. by using goat anti-chicken and either streptavidin or goat anti-mouse and anti-rat antibodies conjugated to Alexa Fluor 647 at recommended dilutions. After 30 minutes, the cells were pelleted at 2500×g for 5 minutes and 4° C. on an Allegra X-14R centrifuge (Beckman Coulter), and washed twice with 200 μL ice-cold PBSA buffer. The 96-well plates were run on a high-throughput flow cytometry plate sampler iQue Screener (IntelliCyt). Data were evaluated using FlowJo v.10.0.7 software (Tree Star). To ensure that the differences in binding were not due to variations of number of proteins expressed on the surface of yeast cell, the determined median binding fluorescence intensities ($MFI_{BIND}$) were normalized to the median display fluorescence intensities ($MFI_{DISP}$). The obtained normalized binding/display ($MFI_{BIND}/MFI_{DISP}$) values were further normalized to the value obtained in the absence of "blocking reagent" providing a percentage value, ranging from 0 to 100%, that corresponded to the residual binding observed upon blocking with the corresponding un-biotinylated serum albumin fusion or neutralizing antibody. Values reported here are the results of two independent experiments and are presented as mean (dots)±SE (bars).

Mammalian Cell Culture and Competitive Fluorescence-Based Binding Assay

The binding of two biotinylated human ELR+ CXC chemokines (hCXCL1 and hCXCL8) to the human CXCR1 and CXCR2 receptors was assessed by using flow cytometry-based binding assay. Human embryonic kidney 293 (HEK293) cells that stably express the human CXCR1 (HEK293-IL8RA) and CXCR2 (HEK293-IL8RB) receptors were used (National Cancer Institute at Frederick, Md.) (Ben-Baruch, A. et al. IL-8 and NAP-2 differ in their capacities to bind and chemoattract 293 cells transfected with either IL-8 receptor type A or type B. *Cytokine* 9, 37-45 (1997)). Transfected HEK293 cells were maintained in DMEM (Thermo Fisher Scientific) supplemented with 10% v/v FBS (Thermo Fisher Scientific), 1% v/v penicillin-streptomycin (Thermo Fisher Scientific), and 0.8 mg/mL G418 (Thermo Fisher Scientific), and grown to approximately 80% confluence in 75 $cm^2$ flasks in a humidified incubator and an atmosphere of 95% air, 5% $CO_2$ at 37° C. Receptor expression levels were determined by flow cytometry using fluorescently labeled monoclonal antibodies against human CXCR1 and CXCR2 receptors on an Accuri C6 Flow Cytometer (BD Accuri Cytometers). Cells were treated with Cell Dissociation Buffer Enzyme Free PBS based buffer (Gibcon), washed twice with cold 1×PBS pH 7.4 and resuspended in cold Cell Binding Assay (CBA) buffer (1×PBS pH 7.4 supplemented with 1% w/v BSA and 0.1% w/v $NaN_3$) to a final density of $1\times10^6$ cells/mL. Cells were then aliquoted (100 μL) in 96-well plates (Corning) and individual wells ($1\times10^5$ cells each) were incubated with various concentrations of biotinylated human ELR+ CXC chemokines (hCXCL1 and hCXCL8) ranging from 0.03 to 300 nM. The incubation time was 30 minutes at 4° C. with shacking (150 rpm). The cells were then pelleted at 600×g for 5 minutes and 4° C. on an Allegra X-14R centrifuge (Beckman Coulter) and washed once with 200 μL ice-cold CBA buffer.

Specific binding of biotinylated ELR+ CXC chemokines to CXCR receptors was detected by incubating the cells with Alexa Fluor 647-labeled Streptavidin (1:200; Thermo Fisher Scientific) for 30 minutes at 4° C. with shaking. Cells were then pelleted at 600×g for 5 minutes and 4° C. on an Allegra X-14R centrifuge (Beckman Coulter), and washed twice with 200 µL ice-cold CBA buffer. Cells were resuspended in 50 µL (2×10$^3$ cell/µL final concentration) of cold CBA buffer and analyzed by flow cytometry on an iQue Screener (IntelliCyt). Data were evaluated using FlowJo v.10.0.7 software (Tree Star). Median fluorescence intensities (MFI) were normalized to the maximal value obtained, expressed as a percentage and plotted as a function of varying ELR+ CXC chemokine concentration. The maximal effective concentrations (EC$_{50}$) were determined by fitting a sigmoidal dose-response curve on GraphPad Prism (GraphPad Software). The same assay was used to assess the ability of crossreactive serum albumin-antibody fusions (SA129, SA138 and SA157*) and commercial neutralizing antibodies (Ab208 and Ab275, R&D Systems) to compete for binding of biotinylated ELR+ CXC chemokines (hCXCL1 and hCXCL8) to their cognate CXCR1 and CXCR2 receptors.

HEK293 cell lines expressing human CXCR1 and CXCR2 receptors were incubated with biotinylated hCXCL1 and hCXCL8 chemokines as "agonist", at final concentration equal to EC$_{50}$ values, in the presence of varying concentrations of "antagonists" (SA129, SA138, SA157*, Ab208 and Ab275), followed by staining with fluorescently labeled streptavidin. Antagonists were serially diluted in 1×PBS pH 7.4 to obtain final concentrations that cover the range from 0.3 nM to 300 nM. Concentrations ranging from 0.03 µM to 30 µM were used for the antagonist SA157*. Median fluorescence intensities (MFI) were normalized to the maximal value obtained, expressed as a percentage and plotted as a function of varying concentrations of "antagonists". The half maximal inhibitory concentration (IC$_{50}$) values were determined by fitting a sigmoidal dose-response curve on GraphPad Prism (GraphPad Software). The ICso values were further converted to inhibition constants K$_i$ by using the Cheng-Prusoff equation K$_i$=IC$_{50}$/([L]/EC$_{50}$+1) where [L] is the fixed concentration of "agonist" biotinylated ELR+ CXC chemokine and EC$_{50}$ is the concentration of "agonist" that results in half maximal activation of the receptor. Values reported here are the results of three independent experiments. The K$_i$ and K$_D$ values, specified in units of molar concentration (mol/L or M) were converted to the pK$_i$ and pK$_D$ scale using pK$_i$=log$_{10}$(K$_i$) and pK$_D$=log$_{10}$(K$_D$), respectively. Higher values of pK$_i$ and pK$_D$ indicate exponentially greater potency. Data are presented as mean (dots)±SE (bars).

Isolation of Neutrophils from Human and Murine Fresh Whole Blood

Human neutrophils were purified directly from human whole blood by immunomagnetic negative selection using EasySep Direct Human Neutrophil Isolation Kit (STEMCELL Technologies). Whole blood from healthy human volunteers was obtained from Research Blood Components, LLC. Blood was collected in sodium-citrate anticoagulant and provided in EDTA vacutainer collection tubes. Murine neutrophils were isolated directly from mouse bone marrow by immunomagnetic negative selection using EasySep Mouse Neutrophils Enrichment Kit (STEMCELL Technologies). The ends of femur and tibia derived from female C57BL/6 mice (Taconic) were cut and the bone marrow cells flushed using a syringe equipped with a 23-gauge needle. Cell clumps and debris were removed by gently passing the cell suspension through a 70 µm mesh nylon strainer.

Both human and murine neutrophils were then pelleted at 1000×g for 5 minutes at 4° C. on a Allegra X-14R centrifuge (Beckman Coulter), the supernatant discarded and the cells washed by adding ice-cold PBE buffer (1×PBS pH 7.4 supplemented with 2 mM EDTA, 0.5% w/v BSA, Ca$^{2+}$ and Mg$^{2+}$ free) to obtain a final cell density of 10$^6$ cells/mL. The washing step was repeated one time more and the washed cells resuspended at 10$^7$ cells/mL in ice-cold PBE buffer. Purity of human neutrophils was assessed by using APC-conjugated anti-human CD16 (clone 3G8, BioLegend), FITC-conjugated anti-human CD66b antibody (clone G10F5; BioLegend) and PE-conjugated anti-human CD45 antibody (clone HI30, BioLegend). Purity of mouse neutrophils was assessed by using APC-conjugated anti-mouse CD11b (clone M1/70; BioLegend) and PE-conjugated anti-mouse Ly-6G/Ly-6C (Gr-1) (clone RB6-8C5; BioLegend). Purified and labeled human and murine neutrophils were further used for calcium signaling experiments.

Competitive Flow Cytometry-Based Intracellular Free Calcium Mobilization Assay

The ability of engineered serum albumin fusion antibody to block the capacity of human and murine ELR+ CXC chemokines to signal through CXCR1 and CXCR2 receptors resulting in an increase of the intracellular calcium concentration was tested on both human and murine freshly purified neutrophils, respectively (June, C. H. & Moore, J. S. Measurement of intracellular ions by flow cytometry. *Curr Protoc Immunol* Chapter 5, Unit 5 5 (2004)). Purified human and murine neutrophils in sterile ice-cold PBE buffer were loaded for 30 minutes at 37° C. in the dark with 2 mM cell permeable ratiometric fluorescent dye Indo-1 AM (Thermo Fisher Scientific) resuspended in 100% v/v dry DMSO to obtain a final concentration of 4 µM. Samples of 10$^6$ cells each were kept aside for autofluorescence measurements and single stained. Indo-1 loaded neutrophils were then pelleted at 1000×g for 5 minutes at 4° C. on a Allegra X-14R centrifuge (Beckman Coulter), the supernatant discarded and the cells washed by adding ice-cold Cell Loading (CL) buffer (1× HBSS, pH 7.4, 0.5% w/v BSA, 1 mM Ca$^{2+}$ and 1 mM Mg$^{2+}$) to obtain a final cell density of 10$^7$ cells/mL. The washing step was repeated one time more and the washed cells were resuspended at 5×10$^6$ cells/mL in ice-cold CL buffer. Aliquots of 10$^6$ cells/tube (200 µL) were prepared, individually pre-warmed at 37° C. for 10 minutes and stimulated with varying concentrations of "agonist" ELR+ CXC chemokines ranging from 0.03 to 300 nM.

Samples were analyzed on a BD LSR II flow cytometer (BD Biosciences). Intracellular calcium levels were measured at 405/30 nm (Indo-1 low) and 485/20 nm (Indo-1 high) emission fluorescence after excitation at 355 nm. Baseline fluorescence was recorded for 60 seconds before the addition of "agonist" ELR+ CXC chemokines and fluorescence measured for an additional 240 seconds. The median fluorescence intensities (MFI) at 405/30 nm and 485/20 nm were recorded, the ratio of two wavelengths calculated (Indo-1 ratio) and plotted as a function of time (seconds). Area under the curve (AUC), calculated as an integral over time, was determined using FlowJo v.10.0.7 software (Tree Star). The obtained values were normalized to the maximal response acquired, expressed as percentage of activity. The maximal effective concentrations (EC$_{50}$) were determined by fitting a sigmoidal dose-response curve on GraphPad Prism (GraphPad Software).

The same assay was used to assess the ability of "antagonist" serum albumin-antibody fusions SA129, SA138 and SA157* to antagonize the ELR+ CXC chemokine-mediated receptors activation and downstream intracellular calcium mobilization. Commercial neutralizing antibodies targeting human CXCL1 (Ab275), CXCL5 (Ab654), CXCL8 (Ab208) and murine CXCL1 (Ab453) and CXCL2 (Ab452) were included as positive controls. Indo-1 loaded neutrophils were incubated with hCXCL1, hCXCL5, hCXCL8, mCXCL1 and mCXCL1 chemokines as "agonist", at final concentration equal to $EC_{50}$ values, in the presence of varying concentrations of "antagonist" serum albumin-antibody fusions and neutralizing antibodies. Antagonists were serially diluted in ice-cold CL buffer to obtain final concentrations that cover the range from 10 pM to 10 µM. Intracellular calcium levels were measured as described above. The obtained values were normalized to the maximal response acquired and expressed as percentage of activity plotted as a function of varying concentrations of "antagonists". Values reported here are the results of three independent experiments. Data are presented as mean (dots)±SE (bars). The half maximal inhibitory concentration ($IC_{50}$) values were determined by fitting a sigmoidal dose-response curve on GraphPad Prism (GraphPad Software). The $IC_{50}$ values were further converted to inhibition constants K by using the Cheng-Prusoff equation and both $pK_i$ and $pK_D$ values determined as described above.

Fluorescent Labeling of Serum Albumin Fusion Proteins

Reactive Alexa Fluor 647 succinimidyl ester (Thermo Fisher Scientific) was dissolved in anhydrous dimethylsulfoxide (DMSO, Sigma-Aldrich) to obtain a final concentration of 10 mg/mL. Protein conjugates containing Alexa Fluor 647 were prepared by incubating proteins (at concentrations of 2 mg/mL in 1×PBS pH 7.4 with 1/10 volume 1 M $K_2HPO_4$, pH 9.0) with two-fold molar excess of Alexa Fluor 647 NHS ester (at 10 mg/mL in DMSO) for 20 minutes at room temperature in the dark. Free dye was removed using size-exclusion chromatography with Superdex 200 10/300 GL (GE Healthcare) connected to an AKTA-purifier system (GE Healthcare) and equilibrated with buffer 1×PBS pH 7.4. Fractions corresponded to the expected protein pick were pulled and concentrated to a final concentration of 2 mg/mL using 10000 NMWL Amicon Ultra-4 ultrafiltration devices (Millipore) at 4000×g and 4° C. on a Allegra X-14R centrifuge (Beckman Coulter). Final protein concentrations and degrees of labeling were measured using a NanoDrop 2000 Spectrophotometer (Thermo Fisher Scientific). Dye-to-protein ratios ranged from 1.0 to 1.5.

Pharmacokinetic Studies in Mice of Serum Albumin-Antibody Fusions

All animal studies were approved by the Massachusetts Institute of Technology Division of Comparative Medicine and carried out according to the federal, state, and local regulations. Female C57BL/6 mice (Taconic) were maintained under specific pathogen-free conditions and used at 6-8 weeks of age. A single bolus/dose (1 mg) of each Alexa Fluor 647-labeled $^N$SA-scFv$^C$ fusions (2 mg/mL) were injected intraperitoneally (i.p.) at 50 mg/kg into 3 mice. At various time points (immediately after injection and at 0.5, 1, 2, 3, 5, 8, 24, 48, 72, 96, 120, 168 hours post injection) blood was collected into heparin-coated capillary tubes (VWR International) and stored at 4° C. in the dark until sample collection was complete. Plasma was obtained after centrifugation (900×g for 5 minutes) and transferred to new capillary tubes. Standard samples were diluted in plasma collected from untreated mice. Serial dilutions (100 µL/well) of the standards (ranging from 0.3 pg/µL to 300 pg/µL) and plasma samples were prepared. Protein fusion concentration was determined by measurement of fluorescent intensity using a Typhoon imager (GE Healthcare) after degree of labeling correction. Fluorescence intensity was quantified using ImageJ software (NIH).

To calculate $^N$SA-scFv$^C$ half-lives, fluorescent measurements were quantified by normalization to a standard curve for each antibody. Starting at the max concentration time point (3 hours for all cases), pharmacokinetic profiles were fit in Graphpad Prism using a two phase non-compartmental model of the following format: $MFI(t)=Aa^{-\alpha t}+Be^{-\beta t}M$. Where A, B, $\alpha$ and $\beta$ represent the systemic clearance rates of a given fusion protein. Fast and slow half-lives, $t_{1/2,\alpha}$ and $t_{1/2,\beta}$ were calculated as $\ln(2)/\alpha$ and $\ln(2)/\beta$, respectively. The total clearance (CL) was calculated by dividing the total dose by the AUC from 0 to infinity. Fits for the three mice in each group were averaged to obtain a single pharmacokinetic curve for each $^N$SA-scFv$^C$ fusion, from which total clearance rate and standard error were calculated. Values reported here are the results of triplicate and data are presented as mean (dots)±SE (bars).

Arthritis Induction and Treatment

All animal studies were approved by the Center for Comparative Medicine (CCM) of the Massachusetts General Hospital (MGH) and carried out according to the federal, state, and local regulations. The inflammatory arthritis serum transfer K/BxN mice model was used (Kouskoff, V. et al. Organ-specific disease provoked by systemic autoimmunity. Cell 87, 811-822 (1996). Mice carrying the KRN T-cell receptor transgene on the C57BL/6 genetic background were mated with NOD mice (Jackson Laboratory) to obtain transgene-positive arthritic K/BxN mice. The presence of the transgene was determined by allele-specific PCR and confirmed by phenotypic assessment. Serum was collected from K/BxN arthritic mice as described (Miyabe, Y., Kim, N. D., Miyabe, C. & Luster, A. D. Studying Chemokine Control of Neutrophil Migration In Vivo in a Murine Model of Inflammatory Arthritis. Methods in enzymology 570, 207-231 (2016)). Experimental arthritis was induced in recipient C57BL/6 by transferring arthritogenic serum containing autoantibodies to the ubiquitous anti-glucose 6-phosphate isomerase (GPI) protein from transgenic 8- to 10-weeks old K/BxN mice to healthy C57BL/6 resulting in synovial pannus formation and both bone and cartilage erosions that mimics the disease that develop spontaneously in transgenic mice. Arthritogenic K/BxN serum (150 µL) was injected intraperitoneally (i.p.) using 26-gauge needle syringe on days 0 and 2 on healthy wild-type C57BL/6 mice (Jackson Laboratory) and disease progress was monitored every other day for 2 weeks as described in the next section.

For the preventative treatment experiments, 500 µL of 2 mg/mL serum albumin fusions were injected i.p. daily starting on day 0 and treated every day for a total of 14 continuative days as follows: group 1 (n=10), mice were treated with SA129 (50 mg/Kg in PBS); group 2 (n=10), mice were treated with SA138 (50 mg/Kg in PBS); group 3 (n=10), mice were treated with control serum-albumin fusion (SA$^m$; 50 mg/Kg in PBS); group 4 (n=10), mice were treated with PBS. For therapeutic treatment, mice were placed into 4 experimental groups so that each group had the same overall clinical score and treated every day for a total of 10 days as follows; Group 1 (n=10), mice were treated with SA129 (50 mg/Kg in PBS); group 2 (n=10), mice were treated with SA138 (50 mg/Kg in PBS); group 3 (n=10), mice were treated with control serum-albumin fusion (SA$^{CTR}$; 50 mg/Kg in PBS); group 4 (n=10), mice were treated with PBS. Paw thickness and clinical scores were determined every other day as described previously (Miyabe, Y., Kim, N. D., Miyabe, C. & Luster, A. D. Studying Chemokine Control of Neutrophil Migration In Vivo in a Murine Model of Inflammatory Arthritis. *Methods in enzymology* 570, 207-231 (2016)). The clinical arthritis score was calculated for each mouse by summing the scores for the four paws: 0=normal; 1=erythema and swelling of one digit; 2=erythema and swelling of two digits or erythema and swelling of ankle joint; 3=erythema and swelling of more than three digits or swelling of two digits and ankle joint; 4=erythema and severe swelling of the ankle, foot and digits with deformity.

Flow Cytometry Analysis and Quantification of Neutrophils in Synovial Fluid

The number of neutrophils that accumulated in the synovial fluid were determined using flow cytometry as previously described (Miyabe, Y., Kim, N. D., Miyabe, C. & Luster, A. D. Studying Chemokine Control of Neutrophil Migration In Vivo in a Murine Model of Inflammatory Arthritis. *Methods in enzymology* 570, 207-231 (2016)). Synovial fluid was obtained from ankle joints of 8- to 10-weeks old C57BL/6 mice (Jackson Laboratory) on day 8 after K/BxN serum injection for all groups. Retrieved synovial fluid cells were resuspended in sterile 1% v/v FCS/PBS to obtain a final concentration of $1\times10^4$ cells/µL. For flow cytometry analysis, cells were incubated with anti-FcγRIII/II antibody (clone 2.4G2; BD Bioscience), and following stained with APC-conjugated anti-murine Ly6G antibody (clone 1A8; BioLegend). Flow cytometry was performed with BD LSRFortessa (BD Bioscience) and analyzed with FlowJo v.10.0.7 software (Tree Star). Neutrophils were identified as Ly6G-positive cells in the granulocyte gate of forward and side scatter plots. Values reported here are the results of triplicate and are presented as mean (dots)±SE (bars).

Histology Analysis

Preventative treated mice (n=3 per group) were sacrificed at day 8 after K/BxN serum injection and paws collected for histology as previously described (Miyabe, Y., Kim, N. D., Miyabe, C. & Luster, A. D. Studying Chemokine Control of Neutrophil Migration In Vivo in a Murine Model of Inflammatory Arthritis. *Methods in enzymology* 570, 207-231 (2016)). Briefly, paws were fixed in 4% v/v formalin solution overnight and decalcified by treatment with 20% EDTA solution for 2 weeks. Samples were then washed with $H_2O$ mQ for at least 10 minutes and embedded in paraffin. Sections of 4 µm thickness were stained with Hematoxylin and Eosin (H&E) staining kit (Wako Pure Chemical Industries), mounted by using Mount-Quick mounting medium (Daido Sangyo Co.) and examined by light microscopy. Values reported here are the results of triplicate and are presented as mean (dots)±SE (bars). Histopathological scoring was performed on H&E stained ankle sections by evaluating both inflammatory cell infiltration and pannus formation as follows. Inflammatory cell infiltration: 0=no change, 1=focal inflammatory cell infiltration, 2=severe and diffuse inflammatory cell infiltration. Pannus formation: 0=no change, 1=pannus formation at one site, 2=pannus formation at two sites, 3=pannus formation at more than three sites. The score of inflammatory cell infiltration and pannus formation were summed to determine a total histopathological score. Visible clinical signs were scored blinded for the origin and treatment of the mice. Because different batches of serum with different potency have been used in different experiments, the measured clinical score values of each experiment were normalized to the maximal value obtained and expressed as a percentage (clinical score %). Values reported here are the results of two independent experiments and are presented as mean (dots)±SE (bars).

Protein Structure Homology Modeling

The protein structure homology models of selected yeast-displayed antibody single-chain variable fragments CK129, CK138 and CK157 have been generated by using protein structure modeling program MODELLER (Sali, A. & Blundell, T. L. Comparative protein modelling by satisfaction of spatial restraints. *J Mol Biol* 234, 779-815 (1993)) and the three-dimensional structure of a highly homologue synthetic antibody fragment as template (PDB ID: 2KH2) (Wilkinson, I. C. et al. High resolution NMR-based model for the structure of a scFv-IL-1beta complex: potential for NMR as a key tool in therapeutic antibody design and development. *J Biol Chem* 284, 31928-31935 (2009)). Protein structures and models were rendered using PyMOL (PyMOL Molecular Graphics System, Version 1.8 Schrödinger, LLC).

Statistical Analysis

All data are presented as mean (dots)±SE (bars). Statistical comparisons were made between each group using one-way analysis of variance (ANOVA) and GraphPad Prism (GraphPad Software). P values: *$P<0.05$,  $P<0.01$, * $P<0.001$; **** $P<0.0001$. ns: non-significant.

Example 1: Generation of Crossreactive Antibodies that Bind a Diverse Array of ELR+ CXC Chemokines To evolve highly crossreactive protein binders toward multiple pro-inflammatory ELR+ CXC chemokines, synthetic single chain variable antibody fragment (scFv) libraries displayed on the surface of yeast were used. Yeast surface display combined with fluorescence-activated cell sorting (FACS) allowed for quantitative selection of protein binders based on both binding affinity and specificity. The synthetic scFv libraries had qualities making them powerful scaffolds for the development of crossreactive binders. Three human (hCXCL1, hCXCL5, and hCXCL8) and three murine (mCXCL1, mCXCL2 and mCXCL5) chemokines were chosen as targets based on their (i) low sequence identity and (ii) proven therapeutic relevance (FIG. 1 and FIG. 2A).

Initially, only one selection pressure was applied, and crossreactivity was prioritized over affinity. To encourage the development of crossreactivity, combinatorial approaches were implemented, in which the output of each cycle of selection was exposed to a diverse array of ELR+ CXC chemokines in the following cycle selection (FIG. 2B). The use of highly avid reagents preloaded with ELR+ CXC chemokines and constant alternation of the detection reagents favored the isolation of weak crossreactive binders while discouraging the enrichment of clones that recognized detection reagents. Subsequent DNA sequences of individual clones revealed eighteen unique antibody clones with varying amino acid compositions and loop lengths within the complementarity-determining regions (CDRs).

Figure 2D:
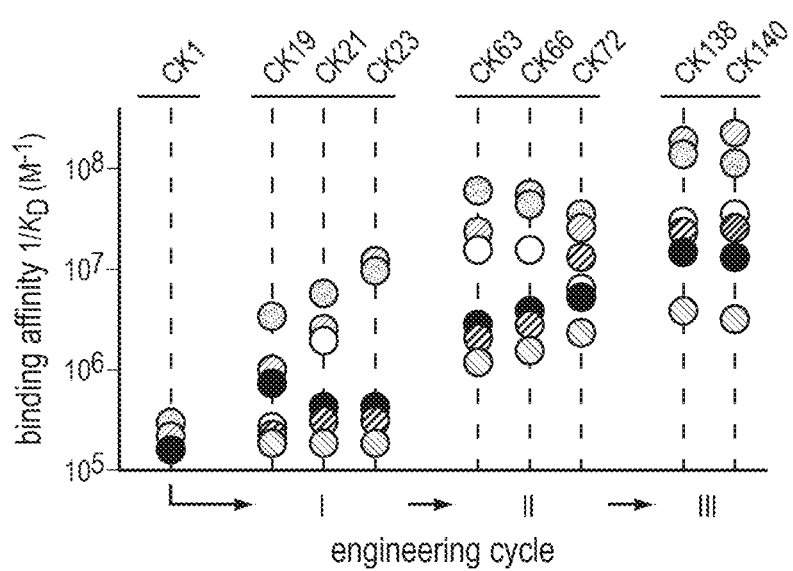
FIGS. 2D-2F provide plots of binding affinities of engineered clones derived from CK1 (FIG. 2D), CK2 (FIG. 2E), and CK4 (FIG. 2F) lineage after two independent processes of selection (I and II), each including the generation of random yeast-display antibody libraries and cycles of flow cytometry sorting, followed by a third round of site-directed mutagenesis (III). Data are represented as inverted equilibrium binding constants ($1/K_D$; $M^{-1}$) and indicate the means of at least three independent experiments.
Figure 2E:
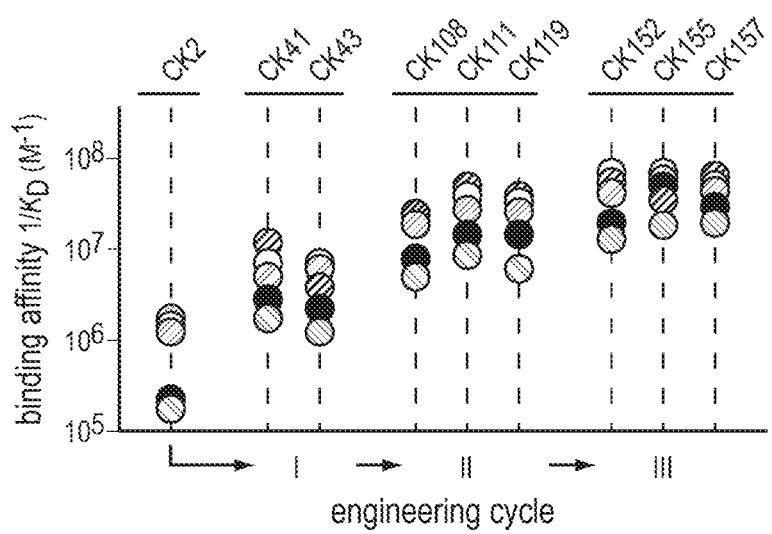
Figure 2F:
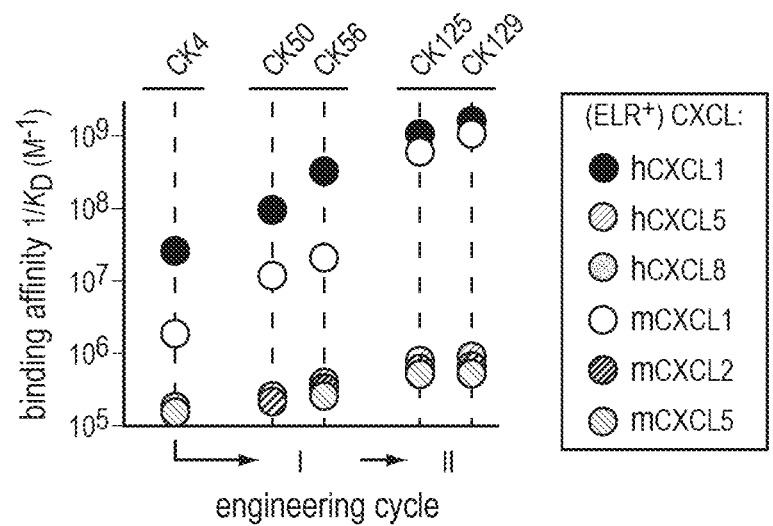

Selected antibodies exhibited diverse affinities and specificities for soluble ELR+ CXC chemokines (FIG. 2C, Table 7). Of these clones, only four (CK1-CK4) recognized at least three different ELR+ CXC chemokines. The most abundant and crossreactive of these antibodies, CK3, recognized the biotinylation sequence located at the C-terminus of each chemokine, thus explaining its crossreactivity and similar binding affinities (FIG. 2C). In addition to the generation of crossreactive binders, six bi-specific and eight mono-specific antibody clones were isolated (FIG. 2C). The presence of numerous mono- and bi-specific antibodies can be explained by the use of highly avid reagents during the selection process. Taken together, these data showed that crossreactive antibodies generally occurred at lower frequency and with weaker binding affinities compared with the mono- and bi-specific antibodies (FIG. 2C).

were sequenced and assessed for binding affinity and crossreactivity towards ELR+ CXC chemokines. In addition, when distinct mutations were found scattered across clones and showed improvement, mutations were combined to investigate the possibility of even further crossreactivity and

TABLE 7

Binding affinities - $K_D \pm SE$ (nM)

|  | Groα | ENA-78 | IL-8 | KC | MIP-2 | LIX | MBP |
|---|---|---|---|---|---|---|---|
| CK1 | >2000 | >2000 | >2000 | N.B. | N.B. | N.B. | N.B. |
| CK2 | >2000 | 605 ± 79 | N.B. | 481 ± 80 | 505 ± 86 | >2000 | N.B. |
| CK3 | N.B. | N.B. | N.B. | N.B. | N.B. | N.B. | N.B. |
| CK3* | 562 ± 88 | 448 ± 73 | 410 ± 61 | 589 ± 75 | 445 ± 69 | 594 ± 81 | 522 ± 79 |
| CK4 | 39.4 ± 7.4 | >2000 | N.B. | 744 ± 93 | N.B. | >2000 | N.B. |
| CK5 | >2000 | N.B. | >2000 | N.B. | N.B. | N.B. | N.B. |
| CK6 | 1675 ± 191 | 1987 ± 228 | N.B. | N.B. | N.B. | N.B. | N.B. |
| CK7 | N.B. | 344 ± 68 | N.B. | N.B. | N.B. | >2000 | N.B. |
| CK8 | 382 ± 73 | N.B. | N.B. | 825 ± 98 | N.B. | N.B. | N.B. |
| CK9 | N.B. | N.B. | N.B. | 221 ± 49 | 278 ± 41 | N.B. | N.B. |
| CK10 | 28.9 ± 4.5 | N.B. | N.B. | 801 ± 107 | N.B. | N.B. | N.B. |
| CK11 | 425 ± 58 | N.B. | N.B. | N.B. | N.B. | N.B. | N.B. |
| CK12 | N.B. | N.B. | N.B. | N.B. | 332 ± 57 | N.B. | N.B. |
| CK13 | N.B. | 297 ± 98 | N.B. | N.B. | N.B. | N.B. | N.B. |
| CK14 | N.B. | N.B. | N.B. | N.B. | N.B. | 269 ± 57 | N.B. |
| CK15 | N.B. | N.B. | N.B. | 251 ± 25 | N.B. | N.B. | N.B. |
| CK16 | N.B. | 102 ± 12 | N.B. | N.B. | N.B. | N.B. | N.B. |
| CK17 | N.B. | N.B. | N.B. | N.B. | N.B. | 106 ± 11 | N.B. |
| CK18 | N.B. | N.B. | 65 ± 6.1 | N.B. | N.B. | N.B. | N.B. |

*= binding affinities measured using biotinylated ELR + CXC chemokines bearing AviTag at C-terminus.
N.B. = no binding

Example 2: Use of Two-Pressure Selection Strategies for Molecular Co-Evolution of Antibody Binding

TABLE 9

Binding affinities - $K_D \pm$ SE (nM)

|  | Groα | ENA-78 | IL-8 | KC | MIP-2 | LIX |
|---|---|---|---|---|---|---|
| CK2 | >2000 | 605 ± 79 | N.B. | 481 ± 80 | 505 ± 86 | >2000 |
| CK41 | 304 ± 44 | 220 ± 65 | N.B. | 143 ± 14 | 75.4 ± 19 | 429 ± 24 |
| CK43 | 368 ± 59 | 154 ± 31 | N.B. | 137 ± 11 | 213 ± 27 | 762 ± 98 |
| CK108 | 110 ± 24 | 40.9 ± 6.4 | N.B. | 39.8 ± 7.5 | 40.6 ± 6.2 | 136 ± 19 |
| CK111 | 62.9 ± 8.4 | 35.3 ± 2.1 | N.B. | 30.5 ± 2.8 | 23.8 ± 2.9 | 97.8 ± 11 |
| CK119 | 56.7 ± 7.2 | 39.3 ± 6.4 | N.B. | 29.8 ± 2.1 | 27.5 ± 3.8 | 116 ± 20 |
| CK152 | 48.4 ± 6.5 | 25.4 ± 2.8 | N.B. | 17.4 ± 2.8 | 21.6 ± 3.1 | 66.5 ± 10 |
| CK155 | 24.1 ± 2.2 | 18.9 ± 2.5 | N.B. | 15.9 ± 2.4 | 33.5 ± 5.5 | 53.7 ± 8.9 |
| CK157 | 36.2 ± 4.3 | 16.9 ± 1.7 | N.B. | 20.6 ± 4.1 | 18.2 ± 3.3 | 57.1 ± 3.9 |

TABLE 10

Binding affinities - $K_D \pm$ SE (nM)

|  | Groα | ENA-78 | IL-8 | KC | MIP-2 | LIX |
|---|---|---|---|---|---|---|
| CK4 | 39.4 ± 7.4 | >2000 | N.B. | 744 ± 93 | N.B. | >2000 |
| CK50 | 3.1 ± 0.5 | >2000 | N.B. | 53.8 ± 3.5 | >2000 | >2000 |
| CK56 | 12.6 ± 2.5 | >2000 | N.B. | 108 ± 4.5 | >2000 |  |
| CK125 | 1.23 ± 0.2 | >2000 | N.B. | 1.31 ± 0.1 | >2000 | >2000 |
| CK129 | 0.79 ± 0.1 | >2000 | N.B. | 0.93 ± 0.1 | >2000 | >2000 |

Importantly, the sequential order in which the ELR+ CXC chemokine targets were exposed to the antibody mutant libraries was critical to the success of the selection process. Among all the possible selection pathways, improvements in both affinity and crossreactivity were observed only when recombinant genetic libraries were screened in order from lowest to highest affinity chemokines (data not shown). However, this was not applicable to the development of CK129, as its parental clone (CK4) already possessed high initial affinity toward hCXCL1 and mCXCL1, but negligible affinity towards the others.

Figure 2G:
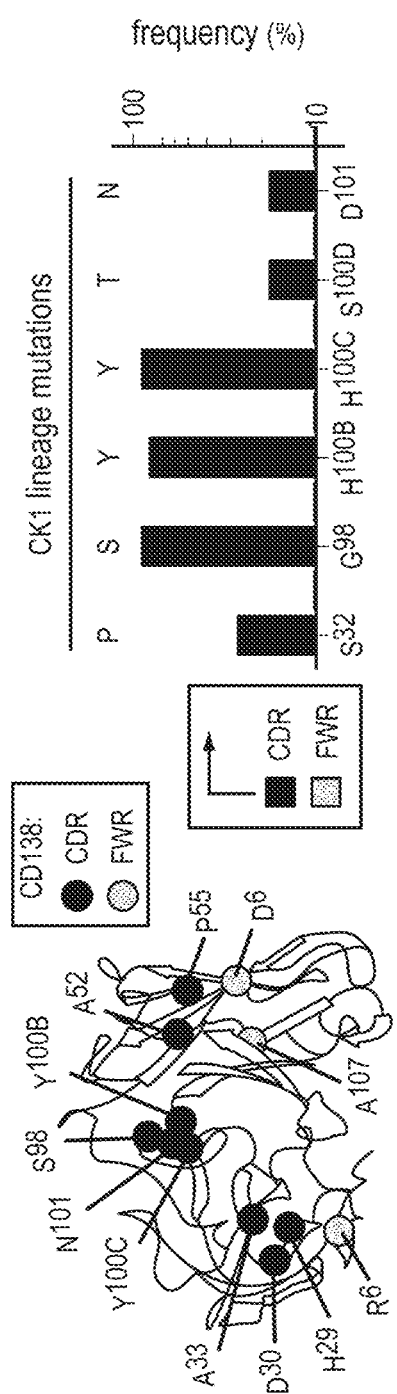
FIGS. 2G and 2H show homology models and frequencies of enriched mutations of engineered CK138 (FIG. 2G) and CK157 (FIG. 2H) antibodies. The $V_L$ and $V_H$ backbones are represented as ribbons (light gray). Mutations acquired during the selection process are depicted as spheres at the Cα positions. Mutated amino acids belonging to CDR loops of CK138 and CK157 are shown in dark circles. Diversified amino acids belonging to FWR regions of CK138 and CK157 are shown in light circles.
Figure 2H:
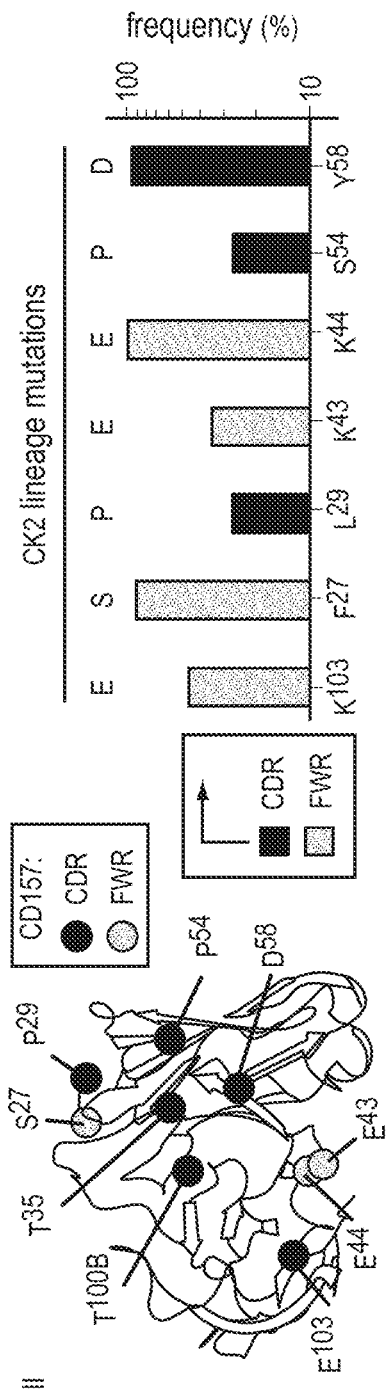

Although reaction conditions that allowed, on average, one to two amino-acid mutations per gene were applied, selected clones from each round of sorting showed higher mutation rates (data not shown). The total number of accumulated mutations within both CDRs and framework regions (FWRs) of variable light ($V_L$) and heavy ($V_H$) chains correlated well with the extent of crossreactivity (data not shown). While the crossreactive antibody CK138 predominantly gathered mutations within the CDRs during the engineering process, CK157 collected numerous mutations within the FWRs (FIGS. 2G and 2H). Both types of mutations were shown to be critical, as reversion of either CDR or FWR mutations to the wild-type amino acids resulted in loss of affinity of CK138 and CK157, respectively, toward ELR+ CXC chemokines (data not shown). Moreover, the FWR mutations were found throughout different clones and cycles of engineering, suggesting strong selection pressure for these residues in conferring high binding crossreactivity and affinity.

Overall, the two-pressure selection approach promoted the evolution of crossreactive binders with improved affinity and revealed the importance of the selection pathway for the achievement of crossreactivity.

Example 3: Engineered Antibodies Bind a Larger Array of Human and Murine CXC Chemokines To assess the extent of crossreactivity of the engineered antibodies, their binding affinity towards all human and murine CXC chemokines were characterized. The chemokine panel included twelve human and mouse ELR+ CXC chemokines (which share 32-90% sequence identity), and eight human and mouse (ELR−) CXC chemokines (which share 18-70% sequence identity). The ELR+ CXC chemokines share 20-51% sequence identity with the (ELR−) CXC chemokines.

To accurately determine the $K_D$ values of the antibodies for the different chemokines, two complementary configurations of chemokines and antibodies in the context of yeast surface display were utilized. Specifically, titrations using (i) soluble CXC chemokines with yeast-displayed antibodies, and (ii) soluble antibodies with yeast-displayed CXC chemokines, were performed. Exploring both orientations was necessary as some CXC chemokines are known to form oligomers when present in high concentration in solution, leading to undesired multivalent binding phenomena (Wang, X., Sharp, J. S., Handel, T. M. & Prestegard, J. H. Chemokine oligomerization in cell signaling and migration. *Prog Mol Biol Transl Sci* 117, 531-578 (2013)). The CXC chemokines were expressed as fusions to the N-terminus of mouse serum albumin (SA), and the engineered CK129, CK138 and CK157 binders as single-chain variable fragments (scFv) fused to the C-terminus of SA, which are referred to as SA129, SA138 and SA157*. SA157* is denoted with an asterisk as it was produced as separate VL and VH domains and then mixed in equimolar amounts, instead of a single chain with a linker.

In both orientations, similar crossreactivity of the engineered binders towards CXC chemokines that were not included in the selection cycles was observed (FIG. 3A). Importantly, this was not merely due to non-specific polyreactivity of the engineered binders, as no binding was detected toward a panel of unrelated proteins (data not shown). Yeast-displayed CK129, CK138 and CK157 bind 7, 12 and 16 soluble CXC chemokines, respectively (FIG. 3A). Similarly, the soluble SA129, SA138 and SA157* bind 4, 11 and 14 yeast-displayed CXC chemokines, respectively (FIG. 3A). With a few exceptions, the $K_D$ values determined using SA129, SA138 and SA157* antibody-fusions with yeast-displayed CXC chemokines were on average 2- to 5-fold higher than those measured in the opposite arrangement (Table 11). The discrepancy in measured $K_D$ values and extent of crossreactivity between the two specular orientations was not surprising and may reflect oligomeric CXC chemokines interacting with multiple yeast-displayed antibodies and therefore, mistaking avidity effects as seemingly higher affinity. This phenomenon appeared to be pronounced for (ELR−) CXC chemokines, such as hCXCL10 and hCXCL4, which are known to form highly avid oligomers in solution (Wang, X., Sharp, J. S., Handel, T. M. & Prestegard, J. H. Chemokine oligomerization in cell signaling and migration. *Prog Mol Biol Transl Sci* 117, 531-578 (2013); Swaminathan, G. J. et al. Crystal structures of oligomeric forms of the IP-10/CXCL10 chemokine. *Structure* 11, 521-532 (2003); Zhang, X., Chen, L., Bancroft, D. P., Lai, C. K. & Maione, T. E. Crystal structure of recombinant human platelet factor 4. *Biochemistry* 33, 8361-8366 (1994)).

Figure 4A:
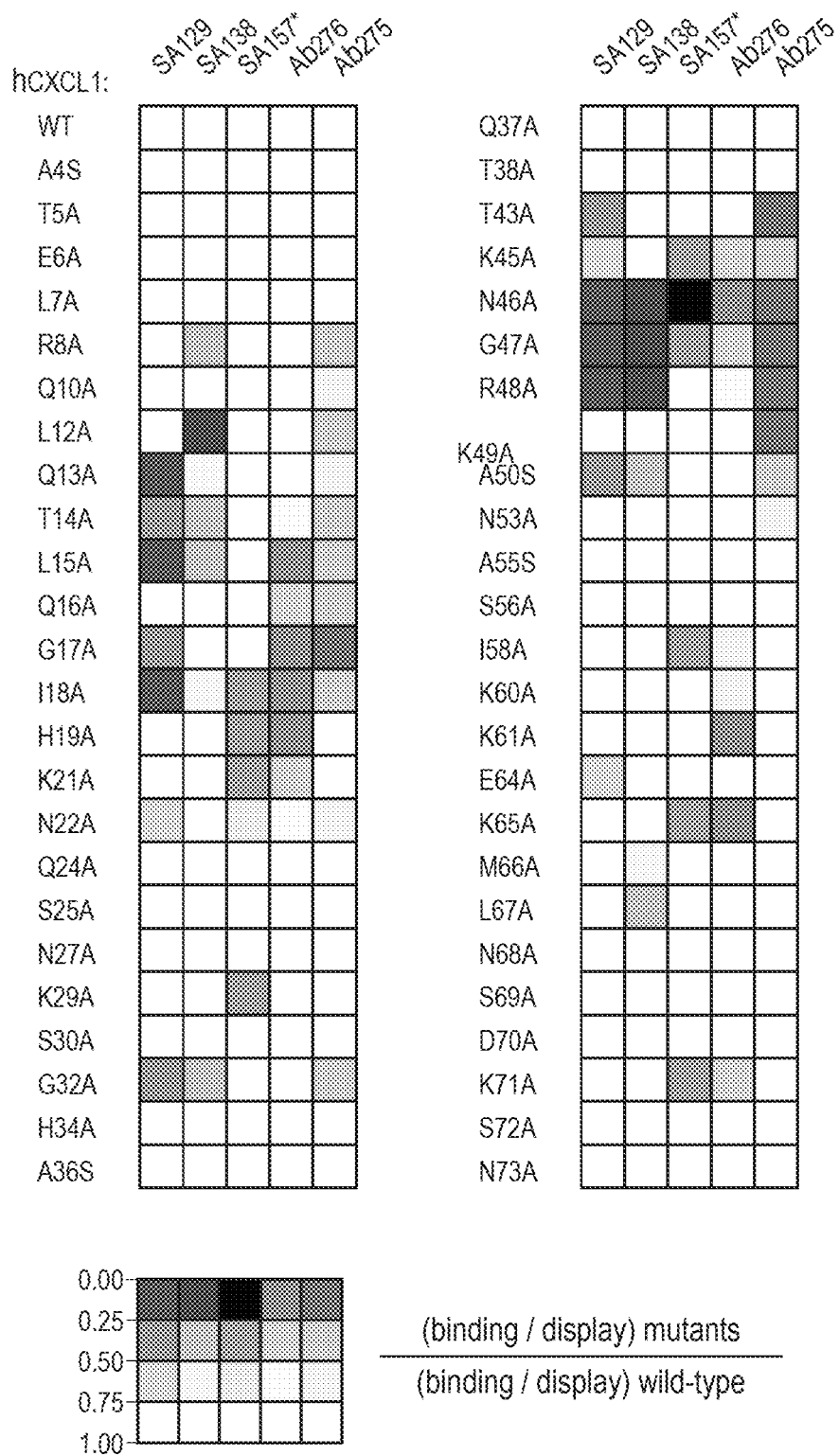
FIG. 4A shows the normalized binding/display intensities of crossreactive protein fusions SA129, SA138 and SA157*, and commercially available antibodies Ab276 and Ab275, to a defined panel of hCXCL1 alanine-mutants, as assessed by flow cytometry. The intensity of color correlates with the strength of the interaction with weak and strong interactions shown in light and dark colors, respectively. h=human.
Figure 4B:
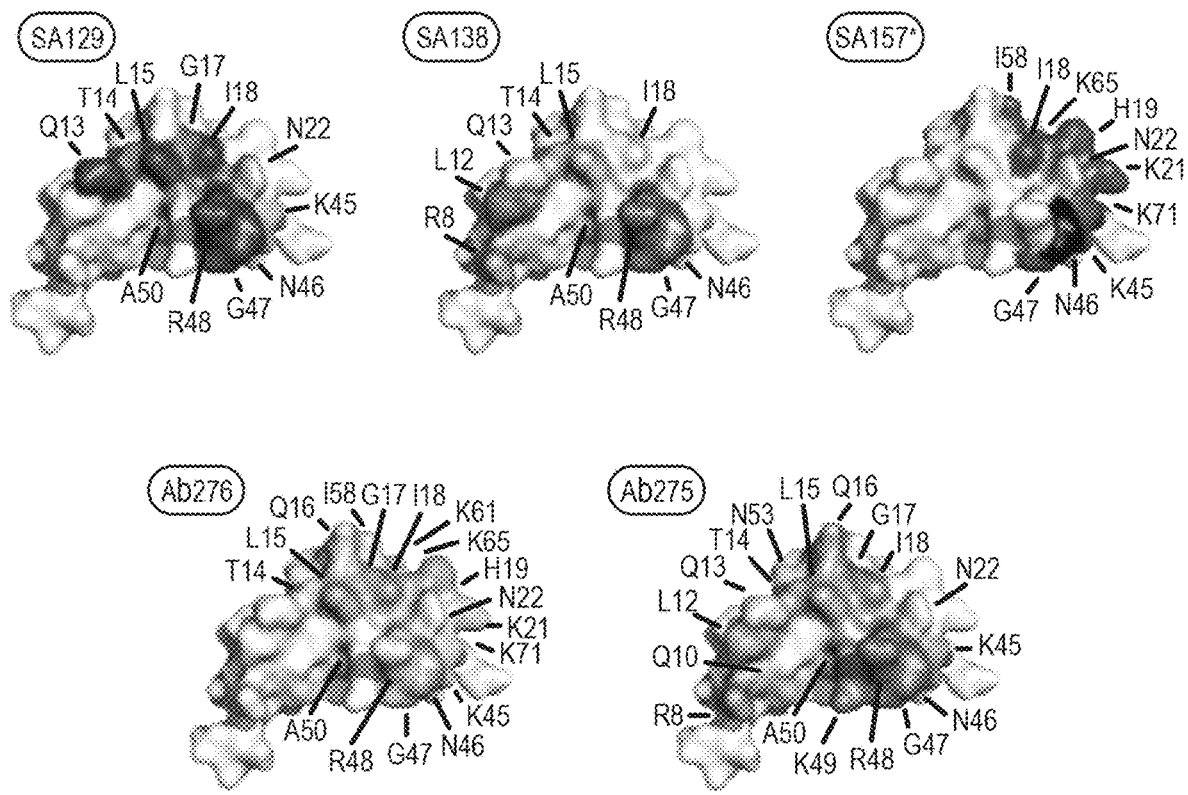
FIG. 4B provides schematics showing residues of hCXCL1 contacted by SA129 (top left), SA138 (top middle), SA157* (top right), Ab276 (bottom left) and Ab275 (bottom right). The intensity of color correlates with the strength of the interaction with weak and strong interactions shown in light and dark colors, respectively.
Figure 4C:
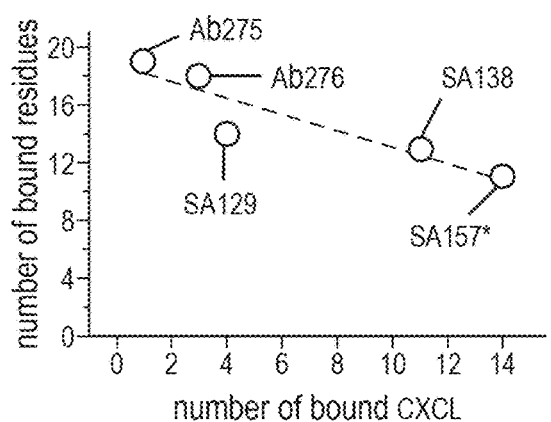
FIG. 4C is a graph showing the number of interacting residues plotted against the number of bound CXC chemokine ligands (CXCL).
Figure 4D:
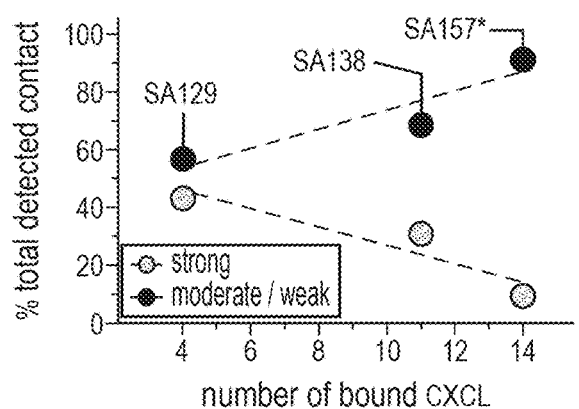
FIG. 4D is a graph showing the percent of strong and combined weak and moderate interactions of each selected protein binders (SA129, SA138 and SA157) plotted against the number of bound CXC chemokines. Weak/moderate and strong interactions are shown in blue and red, respectively.

These data showed that the extent of crossreactivity appeared to correlate both linearly and inversely with binding affinity (FIG. 3C). SA129, which only recognized four chemokines that share significant sequence identity, displayed relatively high affinity for those targets. In contrast, highly crossreactive SA138 and SA157* had overall lower binding affinities toward a larger array of targets.

TABLE 11

| | Binding affinities - $K_D$ ± SE (nM) | | | | | |
|---|---|---|---|---|---|---|
| | CK129/SA129 | | CK138/SA138 | | CK157/SA157* | |
| | Display | | | | | |
| | CK129 | CXCL | CK138 | CXCL | CK157 | CXCL |
| | Soluble | | | | | |
| | CXCL | SA129 | CXCL | SA138 | CXCL | SA157* |
| Groα | 1.0 ± 0.1 | 2.7 ± 0.3 | 41.5 ± 4.5 | 96.7 ± 2.4 | 61.1 ± 5.6 | 1433 ± 108 |
| Groβ | 13.9 ± 1.1 | 43.6 ± 4.1 | 267 ± 38 | 1591 ± 315 | 57.9 ± 4.8 | 853 ± 67 |
| Groγ | 5.7 ± 0.5 | 9.2 ± 0.9 | 349 ± 41 | 836 ± 130 | 53.9 ± 2.1 | 1034 ± 87 |
| ENA-78 | >2000 | N.B. | 5.8 ± 0.5 | 33.7 ± 2.2 | 26.3 ± 2.3 | 2125 ± 269 |
| GCP-2 | N.B. | N.B. | 153 ± 15 | >2000 | 46.6 ± 3.1 | 751 ± 88 |
| NAP-2 | N.B. | N.B. | N.B. | 40.6 ± 1.6 | N.B. | N.B. |
| IL-8 | N.B. | N.B. | 6.9 ± 0.5 | 12.7 ± 0.9 | N.B. | N.B. |
| KC | 1.1 ± 0.1 | 2.9 ± 0.3 | 35.7 ± 3.3 | 29.4 ± 2.8 | 24.3 ± 1.9 | 666 ± 47 |
| MIP-2 | >2000 | N.B. | 29.1 ± 4.1 | 14.7 ± 0.5 | 19.9 ± 1.7 | 591 ± 62 |
| DCIP-1 | N.B. | N.B. | 10.9 ± 1.1 | 31.4 ± 3.1 | 17.4 ± 1.4 | 2647 ± 264 |
| LIX | >2000 | N.B. | 176 ± 21 | 357 ± 33 | 96.9 ± 6.9 | 2018 ± 169 |
| Nap-2 | N.B. | N.B. | N.B. | N.B. | 13.6 ± 0.8 | 528 ± 53 |
| PF-4 | N.B. | N.B. | 167 ± 28 | N.B. | 112 ± 5.1 | >20000 |
| MIG | N.B. | N.B. | N.B. | N.B. | N.B. | N.B. |
| IP-10 | N.B. | N.B. | N.B. | N.B. | 45.5 ± 3.8 | >20000 |
| I-TAC | N.B. | N.B. | N.B. | N.B. | 131 ± 11 | >20000 |
| Pf-4 | N.B. | N.B. | N.B. | N.B. | 17.1 ± 1.2 | 1770 ± 119 |
| Mig | N.B. | N.B. | N.B. | N.B. | N.B. | N.B. |
| Ip-10 | N.B. | N.B. | 500 ± 55 | N.B. | 44.4 ± 3.7 | N.B. |
| I-Tac | N.B. | N.B. | N.B. | N.B. | 124 ± 13 | N.B. |

Example 4: Recognition of Functional Epitopes by Crossreactive Antibodies

Next, fine epitope mapping using alanine-scanning mutagenesis was performed to identify the residues that were directly involved in the interactions. hCXCL1 was chosen as the model chemokine over other ELR+ CXC chemokines because (i) it is recognized by all the engineered crossreactive binders and (ii) it is well-characterized biochemically. First, three-dimensional structural analysis and literate data was combined to identify hCXCL1 amino acid suitable to mutagenesis. Structurally buried hydrophobic amino acids, proline and cysteine residues were left unaltered, as they are crucial for overall folding and stability of the chemokine.

Fifty-four predicted solvent-exposed hCXCL1 residues were selected, individually mutated to alanine, expressed on the surface of yeast, and screened for decreased binding affinity to the soluble SA129, SA138 and SA157* serum-albumin antibody fusions. Five mutants that exhibited an intense loss of binding upon incubation with all the binders were excluded as this phenomenon was likely due to protein misfolding and destabilization of the displayed variants. Next, the binding of the remaining forty-nine hCXCL1 mutants towards soluble SA129, SA138 and SA157* serum albumin antibody-fusions was assessed. Solvent exposed mutations that eliminated or significantly reduced binding affinity were identified, which allowed for determination of residues that were likely critical for the interaction (FIGS. 4A and 4B).

Identification of the epitopes of two commercially available neutralizing antibodies: highly specific Ab275 (binds only hCXCL1) and the crossreactive Ab276 (binds hCXCL1, hCXCL2 and hCXCL3), were also identified. These epitope maps were then compared to the maps assigned to the engineered binders. Similarly to Ab275 and Ab276, SA129 and SA138 bind motifs along the functional N- and 40s-loops that are known to be crucial for the binding of hCXCL1 to its cognate receptor, CXCR2. In contrast, SA157* recognized a distinctive epitope and engaged binding with hCXCL1 residues that are more important for the interaction with the glycosaminoglycans (GAGs). These epitope maps were also consistent with the results from a competitive assay (data not shown).

The residues recognized by the highly crossreactive SA138 and SA157* are conserved among many different chemokines, thus explaining their wide extent of binding crossreactivity. The epitope-mapping data suggested that the degree of crossreactivity inversely correlated with the number of bound residues. The relatively more specific Ab275, Ab276 and SA129 engaged binding with a larger number of hCXCL1 residues than the more crossreactive SA138 and SA157* binders. (FIG. 4C). In contrast, the binding specificity of SA138 and SA157* appeared to be achieved through mostly peripheral long-range weak interactions, and interactions with a few preserved prominent structural conserved residues, such as the hot-spot motif NGF. In contrast, Ab275, Ab276 and SA129 appeared to engage chemokines with much stronger interactions (FIG. 4D).

Figure 5A:
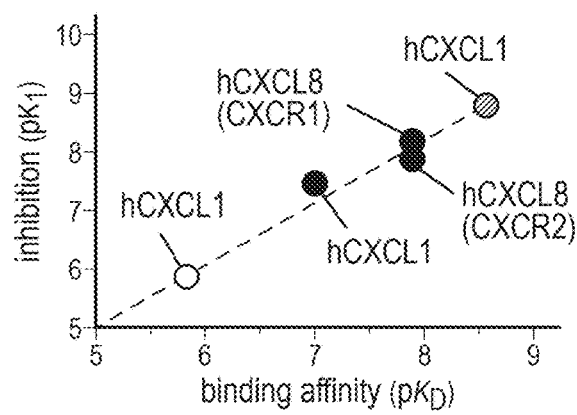
FIG. 5A is a plot showing the ability of serum albumin-antibody fusion SA129 (red), SA138 (blue) and SA157* (gray) to block binding of hCXCL1 and hCXCL8 chemokines to CXCR1 and CXCR2 receptors, assessed by a flow cytometry based assay. The K values were determined, transformed to log $K_i$ and plotted against $pK_D$. h=human.

Example 5: Analysis of Binding of Soluble ELR+ CXC Chemokine Ligands to their Cognate Receptors To measure the potential therapeutic efficacy of the crossreactive binders, the ability of SA129, SA138 and SA157* fusions were tested for their ability to inhibit binding of ELR+ CXC chemokines to their cognate CXCR1 and CXCR2. HEK293 cell lines expressing human CXCR1 and CXCR2 were utilized. Cells were incubated with various concentrations of hCXCL1 and hCXCL8 ligands to determine the half-maximal effective concentrations (EC50) of the interaction. Next, the ability of SA129, SA138 and SA157* to antagonize the interactions between hCXCL1 and hCXCL8 ligands and their cognate receptors was examined. The engineered binders inhibited the ability of hCXCL1 and hCXCL8 chemokines to bind CXCR1 and CXCR2 receptors in a dose dependent manner to various extents (data not shown). Further, the determined inhibitory constants (Ki) correlated well with the previously reported KD values (FIG. 5A). These results show that crossreactive SA129, SA138 and SA157* fusions can markedly interfere with the binding of ELR+ CXC chemokines to both human CXCR1 and CXCR2 in vitro.

Figure 5B:
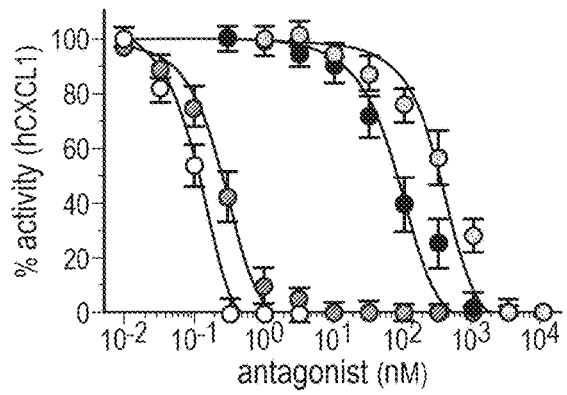
FIGS. 5B and 5C provide plots showing the ability of serum albumin-antibody fusion SA129, SA138 and SA157* to antagonize the ELR+ CXC chemokine-induced receptors activation on mouse and human neutrophils, assessed by flow cytometry intracellular $Ca^{2+}$ mobilization assay. The residual activity of human chemokines (hCXCL1, hCXCL5 and hCXCL8) (FIG. 5B) and mouse chemokines (mCXCL1 and mCXCL2) (FIG. 5C) incubated with varying concentrations of SA129 (red), SA138 (blue), SA157* (gray) and commercial neutralizing antibody (Ab, white). The indicated values are means of three independent experiments. h=human, m=murine.
Figure 5B:
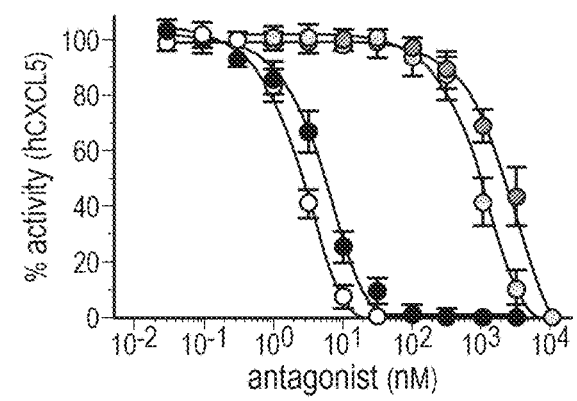
Figure 5B:
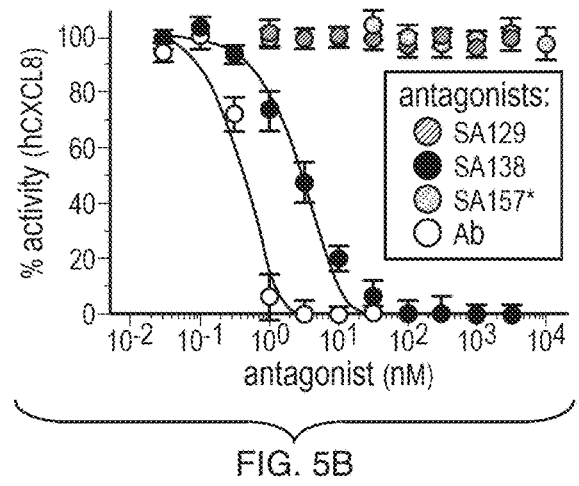
Figure 5C:
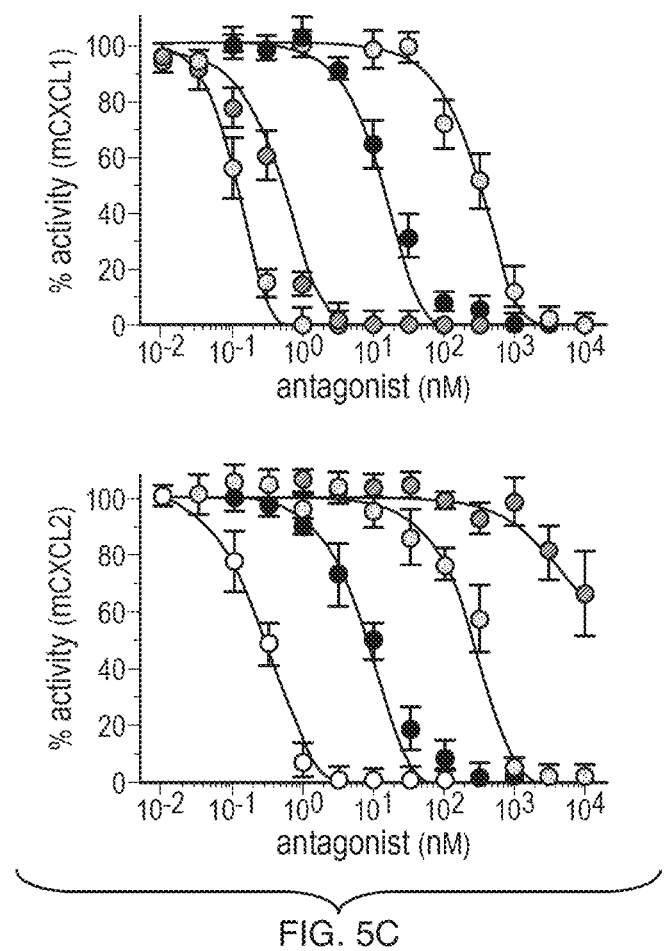
Figure 5D:
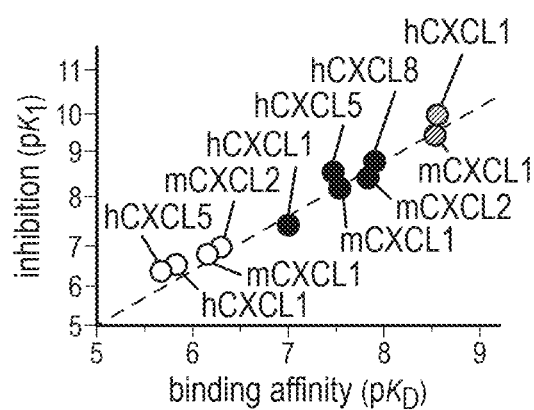
FIG. 5D is a plot showing calculated $pK_i$ correlated linearly with the calculated $pK_D$ suggesting a strict correlation between binding affinity and inhibitory activity. h=human, m=murine.

Next, the ability of the SA129, SA138 and SA157* fusions to antagonize the activation of ELR+ CXC chemokine receptors was assessed. An intracellular calcium mobilization assay was utilized, wherein the assay was in the presence of human and mouse derived neutrophils activated with human (hCXCL1, hCXCL5, and hCXCL8) and murine (mCXCL1 and mCXCL2) ELR+ CXC chemokines, respectively. First, the EC50 of the chemokines on the neutrophils was determined ($0.94\pm0.2$ for hCXCL1; $4.8\pm0.8$ for hCXCL5; $1.29\pm0.4$ for hCXCL8; $0.81\pm0.9$ for mCXCL1; $2.5\pm0.7$ for mCXCL2). Then, changes in intracellular calcium levels were monitored upon pre-incubation of ELR+ CXC chemokines with varying concentrations of SA129, SA138 and SA157* as antagonists. Commercially available neutralizing monoclonal antibodies were used as a positive control. The assays revealed that the engineered binders exhibited inhibitory activity by preventing binding of the human and murine ligands to the receptor in a dose dependent manner (FIGS. 5B and 5C). Again, the calculated K values correlated well with the previously determined $K_D$ affinities (FIG. 5D). Taken together, these data provided strong evidence that engineered crossreactive antibodies are potent inhibitors of ELR+ CXC chemokine signaling in vitro and ex vivo, and have the potential to suppress CXCR1 and CXCR2 activation in vivo.

Example 6: Effect of Crossreactive Serum Albumin-Antibody Fusions on Neutrophil Infiltration In Vivo and Inflammatory Arthritis in Mice Given the promising results from the inhibitory assays, the inhibitory potency of the engineered fusions in the murine serum transfer K/BxN model of autoantibody-induced arthritis was tested. This model displays clinical and histopathological similarities to human rheumatoid arthritis (Christensen, A. D., Haase, C., Cook, A. D. & Hamilton, J. A. K/BxN Serum-Transfer Arthritis as a Model for Human Inflammatory Arthritis. *Front Immunol* 7, 213 (2016); Ditzel, H. J. The K/BxN mouse: a model of human inflammatory arthritis. *Trends Mol Med* 10, 40-45 (2004); Kouskoff, V. et al. Organ-specific disease provoked by systemic autoimmunity. *Cell* 87, 811-822 (1996); Matsumoto, I. et al. How antibodies to a ubiquitous cytoplasmic enzyme may provoke joint-specific autoimmune disease. *Nat Immunol* 3, 360-365 (2002); Ji, H. et al. Arthritis critically dependent on innate immune system players. *Immunity* 16, 157-168 (2002)). The levels of ELR+ CXC chemokines are markedly upregulated in the joints of these arthritic mice and neutrophils, that have upregulated CXCR2 in the joint, are the main effector cells, making K/BxN serum transfer-induced arthritis mice an excellent model to test the therapeutic efficacy of the engineered binders (Chou, R. C. et al. Lipid-cytokine-chemokine cascade drives neutrophil recruitment in a murine model of inflammatory arthritis. *Immunity* 33, 266-278 (2010); Wipke, B. T. & Allen, P. M. Essential role of neutrophils in the initiation and progression of a murine model of rheumatoid arthritis. *J Immunol* 167, 1601-1608 (2001); Jacobs, J. P. et al. Deficiency of CXCR2, but not other chemokine receptors, attenuates autoantibody-mediated arthritis in a murine model. *Arthritis and rheumatism* 62, 1921-1932 (2010)).

Serum albumin-antibody fusions were generated to antagonize circulating small ELR+ CXC chemokines in vivo (FIG. 6). In addition to the SA129 and SA138 fusions described above, an irrelevant SA-fusion ($SA^{CTR}$) was used. The negative control $SA^{CTR}$ encodes SA fused to an antibody fragment that targets the human carcinoembryonic anigen (CEA), a protein that does not exist in mice. To ensure complete inhibition of all ELR+ CXC chemokines present in circulation, relatively high doses of the engineered fusion proteins was administered (i.e., 50 mg/kg). When injected into mice, SA129, SA138 and $SA^{CTR}$ displayed plasma half-lives between 42-47 hours, considerably longer than small synthetic compounds or antibody fragments, but shorter than full length monoclonal antibodies. Despite the high doses of SA129, SA138 and $SA^{CTR}$, the molecules were well tolerated. Treated mice gained weight and exhibited good body condition. Moreover, no signs of splenomegaly as a consequence of neutropenia were detected.

Figure 7A:
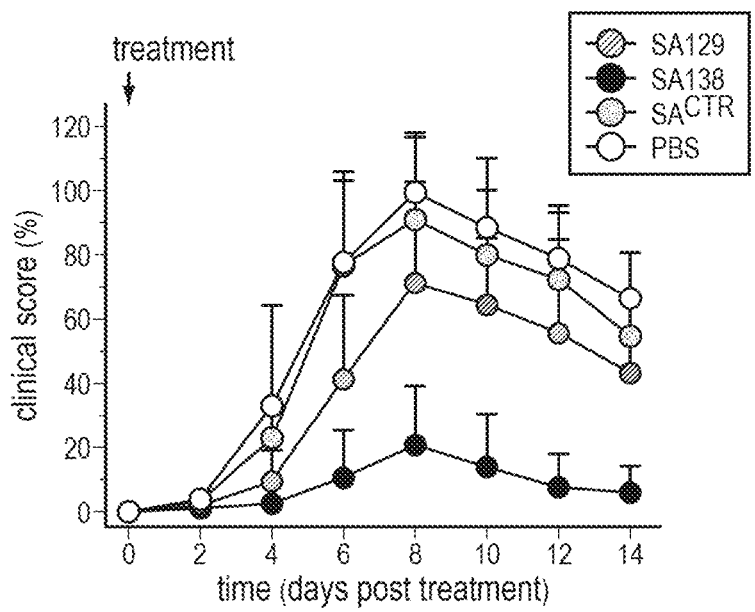
FIG. 7A is a plot showing the percent clinical score of mice treated with serum albumin-antibody fusion proteins on day 0 (preventative regimen). Arrows indicate day begin of treatment. All data are presented as mean (dots)±SE (bars).
Figure 7C:
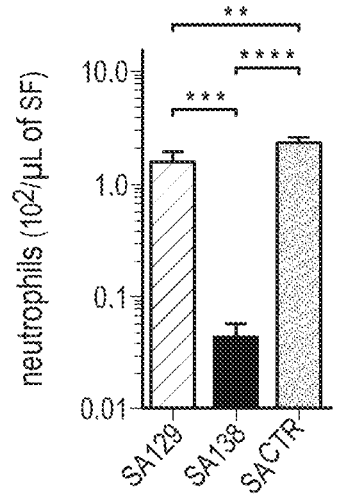
FIG. 7C is a graph showing quantification of purified infiltrating synovial fluid neutrophils (Ly6G+ cells) from the ankles of serum transfer arthritic mice measured at day 8 by flow cytometry (n=3 per condition). Statistical comparisons were made between each group using one-way analysis of variance (ANOVA). P values: *P<0.05,  P<0.01,* P<0.001; **** P<0.0001. ns: non-significant.
Figure 7B:
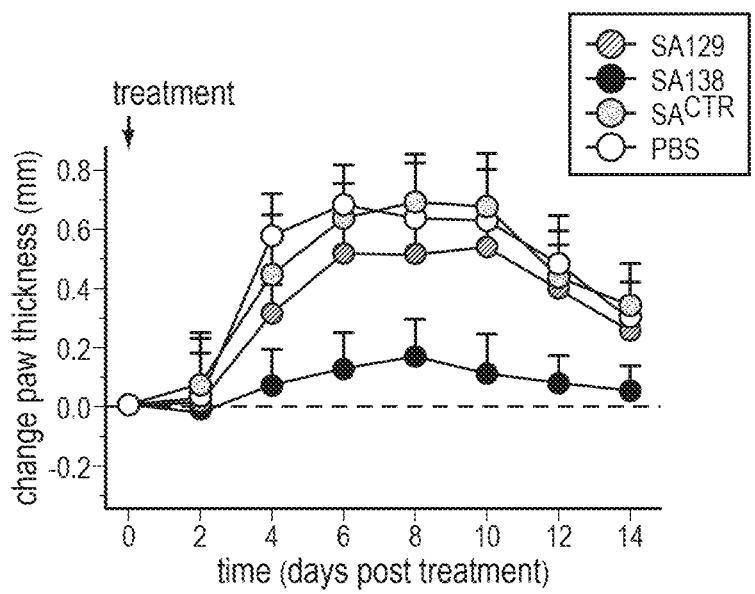
FIG. 7B is a plot showing the change in ankle thickness (mm) of mice treated with serum albumin-antibody fusion proteins on day 0 (preventative regimen). Arrows indicate day begin of treatment. All data are presented as mean (dots)±SE (bars).

Initially the ability of crossreactive SA fusions to prevent the manifestation of the inflammatory arthritis in the K/BxN serum transfer model was assessed. Specifically, mice were treated on the same day as the arthritogenic serum was injected and the progression of the disease evaluated by both blinded clinical scores and measurements of ankle thickness. Mice treated with the more crossreactive SA138, which binds all four murine ELR+ CXC chemokines (mCXCL1, mCXCL2, mCXCL3, and mCXCL5), were protected from developing arthritis, with an approximately 80% reduction of clinical score compared with negative controls at the peak of the disease (day 8 after arthritogenic K/BxN serum transfer and disease initiation; FIGS. 7A and 7B). In contrast, the more specific SA129 that recognizes just one murine ELR+ CXC chemokine (mCXCL1) only moderately reduced joint inflammation, with an approximately 30% reduction of clinical score at day 8 (FIGS. 7A and 7B). Mice treated with $SA^{CTR}$ showed typical clinical signs of untreated mice that received arthritogenic serum and developed inflammatory arthritis with pronounced joint swelling. There were no differences between mice treated with $SA^{CTR}$ or with vehicle (PBS) only (FIGS. 7A and 7B).

Next, the number of synovial fluid neutrophils isolated from the arthritic joints of mice treated with SA129, SA138 and $SA^{CTR}$ fusions was determined. Synovial tissues were harvested at the peak of the disease (day 8 after disease initiation). Mice treated with arthritogenic serum and the broadly crossreactive SA138 had 50- and 70-fold lower levels of infiltrated neutrophils than mice treated with the more specific SA129 and the irrelevant SA$^{CTR}$, respectively (FIG. 7C). These data were consistent with previous clinical score measurements and resembled those observed using mice deficient in CXCR2 (CXCR2$^{-/-}$) injected with arthritogenic serum (Chou, R. C. et al. Lipid-cytokine-chemokine cascade drives neutrophil recruitment in a murine model of inflammatory arthritis. *Immunity* 33, 266-278 (2010); Jacobs, J. P. et al. Deficiency of CXCR2, but not other chemokine receptors, attenuates autoantibody-mediated arthritis in a murine model. *Arthritis and rheumatism* 62, 1921-1932 (2010)).

Figure 7D:
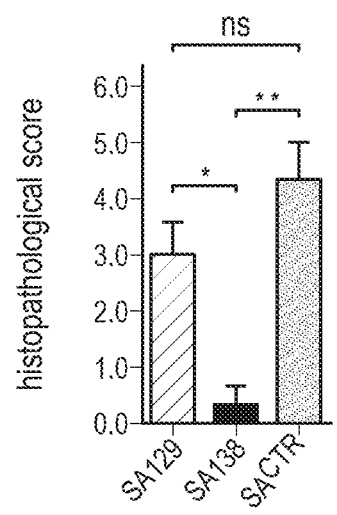
FIG. 7D is a graph showing histopathological scoring of ankle tissue sections of mice treated with SA129, SA138 and control SA$^{CTR}$ on day 8.

Histological analysis and scoring of inflamed ankle sections were also performed. Inflammatory cell infiltration and pannus formation were absent or minimally present in mice treated with the broadly crossreactive SA138 (FIGS. 7D and 7E). Consistent with previous clinical findings, the joints of mice treated with arthritogenic serum and control SA$^{CTR}$ displayed abundant inflammatory cell infiltration and pannus formation. These pathological changes were present, though less pronounced, in mice treated with the more specific SA129 fusion.

Further, the therapeutic efficacy of crossreactive SA fusion in mice with established arthritis was tested. Arthritic mice were treated 4 days after arthritogenic serum transfer, when joint inflammation had developed. The highly crossreactive SA138 reversed inflammation very quickly and provided a remarkable complete resolution of the disease with an approximately 60% reduction of clinical score and 0.3 mm of ankle thickness over control at the peak of the disease (day 8 after disease initiation; FIGS. 7F and 7G). The specific SA129-treated mice exhibited only a modest reduction of both clinical scores (~25%) and ankle thickness (0.1 mm) at day 8 (FIGS. 7F and 7G). The SA$^{CTR}$ and vehicle-treated mice showed no difference in the rate of disease development (FIGS. 7F and 7G). Taken together, these data show that highly crossreactive SA138 fusion efficiently blocked neutrophil infiltration in the synovial tissues, thus preventing and even reversing inflammatory arthritis.

TABLE 12

Sequence Summary

| SEQ ID NO | Description | Sequence |
|---|---|---|
| 1 | CK138 V$_H$ amino acid sequence | EVQLVESDGGLVQPGGSLRLSCAASGFNLSYYGMHWVRQA PGKGLEWVAYIASYPGYTSYADSVKGRFTISADTSKNTAYL QMNSLRAEDTAVYYCARSGYSYSPYYSWFSAGMNYWGQG ALVTVSS |
| 2 | CK138 V$_L$ amino acid sequence | AIQMTRSPSSLSASVGDRVTITCRASQYHDGSAAWYQQKPG KAPKLLIYGASYLYSGVPSRFSGSRSGTDFTLTISSLQPEDFA TYYCQQSSYSLITFGQGTKVEIK |
| 3 | CK138 V$_H$ nucleic acid sequence | GAGGTTCAGCTGGTGGAGTCTGACGGTGGCCTGGTGCAGCCAGGG GGCTCACTCCGTTTGTCCTGTGCAGCTTCTGGCTTCAACCTCTCT TACTACGGTATGCACTGGGTGCGTCAGGCCCCGGGTAAGGGCCTG GAATGGGTTGCATACATTGCTTCTTACCCTGGCTACACTTCTTAT GCCGATAGCGTCAAGGGCCGTTTCACTATAAGCGCAGACACATCC AAAAACACAGCCTACCTACAAATGAACAGCTTAAGAGCTGAGGAC ACTGCCGTCTACTATTGTGCTCGCTCTGGTTACAGTTACTCTCCG TATTATTCTTGGTTCTCTGCTGGTATGAACTACTGGGGTCAAGGA GCCCTGGTCACCGTCTCCTCG |
| 4 | CK138 V$_L$ nucleic acid sequence | GCTATCCAGATGACCCGGTCCCCGAGCTCCCTGTCCGCCTCTGTG GGCGATAGGGTCACCATCACCTGCCGTGCCAGTCAGTACCACGAC GGTTCTGCAGCCTGGTATCAACAGAAACCAGGAAAAGCTCCGAAG CTTCTGATTTACGGTGCATCCTACCTCTACTCTGGAGTCCCTTCC CGCTTCTCTGGTAGCCGTTCCGGGACGGATTTCACTCTGACCATC AGCAGTCTGCAGCCGGAAGACTTCGCAACTTATTACTGTCAGCAA TCTTCTTATTCTCTGATCACGTTCGGACAGGGTACCAAGGTGGAG ATCAAA |
| 5 | CK138 V$_H$ CDR1 | NLSYYGMH |
| 6 | CK138 V$_H$ CDR2 | AYIASYPGYTSY |
| 7 | CK138 V$_H$ CDR3 | RSGYSYSPYYSWFSAGMN |
| 8 | CK138 V$_L$ CDR1 | QYHDGSA |
| 9 | CK138 V$_L$ CDR2 | YGASYL |
| 10 | CK138 V$_L$ CDR3 | QSSYSLIT |
| 11 | CK157 V$_H$ amino acid sequence | EVQLVESGGGLVQPGGSLRLSCAASGSNPYYYGGTHWVRQ APGEELEWVASIGSYPGYTDYADSVKGRFTISADTSKNTAY LQMNSLRAEDTAVYYCARHYYWYDATDYWGQGTLVTVSS |

TABLE 12-continued

Sequence Summary

| SEQ ID NO | Description | Sequence |
|---|---|---|
| 12 | CK157 V$_L$ amino acid sequence | DIQMTQSPSSLSASVGDRVTITCRASQSYGGVAWYQQKPGK APKLLIYSASYLYSGVPSRFSGSRSGTDFTLTISSLQPEDFAT YYCQQPSHLITFGQGTEVEIK |
| 13 | CK157 V$_H$ nucleic acid sequence | GAGGTTCAGCTGGTGGAGTCTGGCGGTGGCCTGGTGCAGCCAGGG GGCTCACTCCGTTTGTCCTGTGCAGCTTCTGGCTCCAACCCCTAC TACTACGGTGGTACGCACTGGGTGCGTCAGGCCCCGGGTGAGGAG CTGGAATGGGTTGCATCTATTGGTTCTTACCCTGGCTACACTGAC TATGCCGATAGCGTCAAGGGCCGTTTCACTATAAGCGCAGACACA TCCAAAAACACAGCCTACCTACAAATGAACAGCTTAAGAGCTGAG GACACTGCCGTCTATTATTGTGCTCGCCATTACTACTGGTACGAT GCTACTGACTACTGGGGTCAAGGAACCCTGGTCACCGTCTCCTCG |
| 14 | CK157 V$_L$ nucleic acid sequence | GATATCCAGATGACCCAGTCCCCGAGCTCCCTGTCCGCCTCTGTG GGCGATAGGGTCACCATCACCTGCCGTGCCAGTCAGTCTTACGGT GGTGTAGCCTGGTATCAACAGAAACCAGGAAAAGCCCCGAAGCTT CTGATTTACTCTGCATCCTACCTCTACTCTGGAGTCCCTTCTCGC TTCTCTGGTAGCCGTTCCGGGACGGATTTCACTCTGACCATCAGC AGTCTGCAGCCGGAAGACTTCGCAACTTATTACTGTCAGCAACCA TCTCATCTGATCACGTTCGGACAGGGTACCGAGGTGGAGATCAAA |
| 15 | CK157 V$_H$ CDR1 | NPYYYGGTH |
| 16 | CK157 V$_H$ CDR2 | ASIGSYPGYTDY |
| 17 | CK157 V$_H$ CDR3 | RHYYWYDATD |
| 18 | CK157 V$_L$ CDR1 | QSYGGV |
| 19 | CK157 V$_L$ CDR2 | YSASYL |
| 20 | CK157 V$_L$ CDR3 | QPSHLIT |
| 21 | CK129 V$_H$ amino acid sequence | EVQLVESGGGLVQPGGSLRLSCAASGFNISSYGSMHWVRQ APGKGLEWVASIYPYSSSTYYADSVKGRFTISADTSKNTAY LQMNSLRAEDTAVYYCARGYGPWYAYSYFALDYWGQGTL VTVSS |
| 22 | CK129 V$_L$ amino acid sequence | DIQMTQSPSPLSASVGDRVTITCRASQYGGYVAWYQQKPG KAPKLLIYGASLLYSGVPSRFSGGRSGTDFTLTISSLQPEDFA TYYCQRGHALITFGQGTKVEIE |
| 23 | CK129 V$_H$ nucleic acid sequence | GAGGTTCAGCTGGTGGAGTCTGGCGGTGGCCTGGTGCAGCCAGGG GGCTCACTCCGTTTATCCTGTGCAGCTTCTGGCTTCAACATCTCT TCTTACGGTTCTATGCACTGGGTGCGTCAGGCCCCGGGTAAGGGC CTGGAATGGGTTGCATCTATTTACCCTTACTCTAGCTCTACTTAC TATGCCGATAGCGTCAAGGGCCGTTTCACTATAAGCGCAGACACA TCCAAAAACACAGCCTACCTACAAATGAACAGCTTAAGAGCTGAG GACACTGCCGTCTATTATTGTGCTCGTGGTTACGGTCCGTGGTAC GCTTACTCTTACTTCGCTTTGGACTACTGGGGTCAAGGAACCCTG GTCACCGTCTCCTCG |
| 24 | CK129 V$_L$ nucleic acid sequence | GATATCCAGATGACCCAGTCCCCGAGCCCCCTGTCCGCCTCTGTG GGCGATAGGGTCACCATCACCTGCCGTGCCAGTCAGTACGGTGGT TACGTAGCCTGGTATCAACAGAAACCAGGAAAAGCTCCGAAGCTT CTGATTTACGGTGCATCCCTTCTCTACTCTGGAGTCCCTTCTCGC TTCTCTGGTGGCCGTTCCGGGACGGATTTCACTCTGACCATCAGC AGTCTGCAGCCGGAAGACTTCGCAACTTATTACTGTCAGCAGGGT CATGCTCTGATCACGTTCGGACAGGGTACCAAGGTGGAGATCGAA |
| 25 | CK129 V$_H$ CDR1 | NISSYGSMH |
| 26 | CK129 V$_H$ CDR2 | ASIYPYSSSTYY |
| 27 | CK129 V$_H$ CDR3 | RGYGPWYAYSYFALD |

TABLE 12-continued

Sequence Summary

| SEQ ID NO | Description | Sequence |
|---|---|---|
| 28 | CK129 $V_L$ CDR1 | QYGGYV |
| 29 | CK129 $V_L$ CDR2 | YGASLLY |
| 30 | CK129 $V_L$ CDR3 | RGHALIT |
| 31 | gWiz-LS-Fc(mIgG2)-His$_6$-linker-TEV-hCXCL1$^{38-107}$-G$_2$-AviTag | <u>ATGAGGGTCCCCGCTCAGCTCCTGGGGCTCCTGCTGCTCTGGCTCCCAGGTGCA CGATGT</u>GAGCCCAGAGTGCCCATAACACAGAACCCCTGTCCTCCACTCAAAGAG TGTCCCCCATGCGCAGCTCCAGACCTCTTGGGTGGACCATCCGTCTTCATCTTC CCTCCAAAGATCAAGGATGTACTCATGATCTCCCTGAGCCCCATGGTCACATGT GTGGTGGTGGATGTGAGCGAGGATGACCCAGACGTCCAGATCAGCTGGTTTGTG AACAACGTGGAAGTACACACAGCTCAGACACAAACCCATAGAGAGGATTACAAC AGTACTCTCCGGGTGGTCAGTGCCCTCCCCATCCAGCACCAGGACTGGATGAGT GGCAAGGAGTTCAAATGCAAGGTCAACAACAGAGCCCTCCCATCCCCCATCGAG AAAACCATCTCAAAACCCAGAGGGCCAGTAAGAGCTCCACAGGTATATGTCTTG CCTCCACCAGCAGAAGAGATGACTAAGAAAGAGTTCAGTCTGACCTGCATGATC ACAGGCTTCTTACCTGCCGAAATTGCTGTGGACTGGACCAGCAATGGGCGTACA GAGCAAAACTACAAGAACACCGCAACAGTCCTGGACTCTGATGGTTCTTACTTC ATGTACAGCAAGCTCAGAGTACAAAAGAGCACTTGGGAAGAGGAAGTCTTTTC GCCTGCTCAGTGGTCCACGAGGGTCTGCACAATCACCTTACGACTAAGACCATC TCCCGGTCTCTGGGTAAACACCATCACCATCATCAC<u>TCTTCTGGCGTGGATCTG GGTACC</u>GAGAACCTGTACTTCCAAGCCACCGAGCTGAGATGCCAGTGCCTGCAG ACCCTGCAGGGCATCCACCCCAAGAACATCCAGAGCGTGAACGTGAAGTCCCCT GGCCCCCACTGCGCCCAGACCGAAGTGATCGCCACCCTGAAGAACGGCCGGAAG GCCTGCCTGAACCCCGCCAGCCCCATCGTGAAGAAAATCATCGAGAAGATGCTG AACAGCGACAAGAGCAAC*GGCGGA*GGCCTGAACGACATCTTCGAGGCCCAGAAA ATCGAGTGGCACGAGTGATGATAA |
| 32 | gWiz-LS-Fc(mIgG2)-His$_6$-linker-TEV-hCXCL5$^{43-114}$-G$_2$-AviTag | <u>ATGAGGGTCCCCGCTCAGCTCCTGGGGCTCCTGCTGCTCTGGCTCCCAGGTGCA CGATGT</u>GAGCCCAGAGTGCCCATAACACAGAACCCCTGTCCTCCACTCAAAGAG TGTCCCCCATGCGCAGCTCCAGACCTCTTGGGTGGACCATCCGTCTTCATCTTC CCTCCAAAGATCAAGGATGTACTCATGATCTCCCTGAGCCCCATGGTCACATGT GTGGTGGTGGATGTGAGCGAGGATGACCCAGACGTCCAGATCAGCTGGTTTGTG AACAACGTGGAAGTACACACAGCTCAGACACAAACCCATAGAGAGGATTACAAC AGTACTCTCCGGGTGGTCAGTGCCCTCCCCATCCAGCACCAGGACTGGATGAGT GGCAAGGAGTTCAAATGCAAGGTCAACAACAGAGCCCTCCCATCCCCCATCGAG AAAACCATCTCAAAACCCAGAGGGCCAGTAAGAGCTCCACAGGTATATGTCTTG CCTCCACCAGCAGAAGAGATGACTAAGAAAGAGTTCAGTCTGACCTGCATGATC ACAGGCTTCTTACCTGCCGAAATTGCTGTGGACTGGACCAGCAATGGGCGTACA GAGCAAAACTACAAGAACACCGCAACAGTCCTGGACTCTGATGGTTCTTACTTC ATGTACAGCAAGCTCAGAGTACAAAAGAGCACTTGGGAAGAGGAAGTCTTTTC GCCTGCTCAGTGGTCCACGAGGGTCTGCACAATCACCTTACGACTAAGACCATC TCCCGGTCTCTGGGTAAACACCATCACCATCATCAC<u>TCTTCTGGCGTGGATCTG GGTACC</u>GAGAACCTGTACTTCCAAGTGCTGCGCGAGCTGAGATGCGTGTGCCTG CAGACCACCCAGGGCGTGCACCCCAAGATGATCAGCAACCTCCAGGTGTTGCC ATCGGCCCCCAGTGCAGCAAGGTGGAAGTGGTGGCCAGCCTGAAGAACGGCAAA GAGATCTGCCTGGACCCCGAGGCCCCATTCCTGAAGAAAGTGATCCAGAAGATC CTGGACGGCGGCAACAAAGAGAAC*GGCGGA*GGCCTGAACGACATCTTCGAGGCC CAGAAAATCGAGTGGCACGAGTGATGATAA |
| 33 | gWiz-LS-Fc(mIgG2)-His$_6$-linker-TEV-hCXCL8$^{29-99}$-G$_2$-AviTag | <u>ATGAGGGTCCCCGCTCAGCTCCTGGGGCTCCTGCTGCTCTGGCTCCCAGGTGCA CGATGT</u>GAGCCCAGAGTGCCCATAACACAGAACCCCTGTCCTCCACTCAAAGAG TGTCCCCCATGCGCAGCTCCAGACCTCTTGGGTGGACCATCCGTCTTCATCTTC CCTCCAAAGATCAAGGATGTACTCATGATCTCCCTGAGCCCCATGGTCACATGT GTGGTGGTGGATGTGAGCGAGGATGACCCAGACGTCCAGATCAGCTGGTTTGTG AACAACGTGGAAGTACACACAGCTCAGACACAAACCCATAGAGAGGATTACAAC AGTACTCTCCGGGTGGTCAGTGCCCTCCCCATCCAGCACCAGGACTGGATGAGT GGCAAGGAGTTCAAATGCAAGGTCAACAACAGAGCCCTCCCATCCCCCATCGAG AAAACCATCTCAAAACCCAGAGGGCCAGTAAGAGCTCCACAGGTATATGTCTTG CCTCCACCAGCAGAAGAGATGACTAAGAAAGAGTTCAGTCTGACCTGCATGATC ACAGGCTTCTTACCTGCCGAAATTGCTGTGGACTGGACCAGCAATGGGCGTACA GAGCAAAACTACAAGAACACCGCAACAGTCCTGGACTCTGATGGTTCTTACTTC ATGTACAGCAAGCTCAGAGTACAAAAGAGCACTTGGGAAGAGGAAGTCTTTTC GCCTGCTCAGTGGTCCACGAGGGTCTGCACAATCACCTTACGACTAAGACCATC TCCCGGTCTCTGGGTAAACACCATCACCATCATCAC<u>TCTTCTGGCGTGGATCTG GGTACC</u>GAGAACCTGTACTTCCAAGCCAAGGAACTGCGCTGCCAGTGCATCAAG ACCTACAGCAAGCCCTTCCACCCCAAGTTCATCAAAGAACTGAGAGTGATCGAG AGCGGCCCTCACTGCGCCAACACCGAGATCATCGTGAAGCTGAGCGACGGCAGA GAGCTGTGCCTGGACCCCAAAGAAAACTGGGTGCAGCGGGTGGTGGAAAAGTTC CTGAAGCGGGCCGAGAACAGC*GGCGGA*GGCCTGAACGACATCTTCGAGGCCCAG AAAATCGAGTGGCACGAGTGATGATAA |

TABLE 12-continued

Sequence Summary

| SEQ ID NO | Description | Sequence |
|---|---|---|
| 34 | gWiz-LS-Fc(mIgG2)-His$_6$-linker-TEV-mCXCL1$^{28-96}$-G$_2$-AviTag | ATGAGGGTCCCCGCTCAGCTCCTGGGGCTCCTGCTGCTCTGGCTCCCAGGTGCA<br>CGATGTGAGCCCAGAGTGCCCATAACACAGAACCCCTGTCCTCCACTCAAAGAG<br>TGTCCCCCATGCGCAGCTCCAGACCTCTTGGGTGGACCATCCGTCTTCATCTTC<br>CCTCCAAAGATCAAGGATGTACTCATGATCTCCCTGAGCCCCATGGTCACATGT<br>GTGGTGGTGGATGTGAGCGAGGATGACCCAGACGTCCAGATCAGCTGGTTTGTG<br>AACAACGTGGAAGTACACACAGCTCAGACACAAACCCATAGAGGAGGATTACAAC<br>AGTACTCTCCGGGTGGTCAGTGCCCTCCCCATCCAGCACCAGGACTGGATGAGT<br>GGCAAGGAGTTCAAATGCAAGGTCAACAACAGAGCCCTCCCATCCCCCATCGAG<br>AAAACCATCTCAAAACCCAGAGGGCCAGTAAGAGCTCCACAGGTATATGTCTTG<br>CCTCCACCAGCAGAAGAGATGACTAAGAAAGAGTTCAGTCTGACCTGCATGATC<br>ACAGGCTTCTTACCTGCCGAAATTGCTGTGGACTGGACCAGCAATGGGCGTACA<br>GAGCAAAACTACAAGAACACCGCAACAGTCCTGGACTCTGATGGTTCTTACTTC<br>ATGTACAGCAAGCTCAGAGTACAAAAGAGCACTTGGGAAAGAGGAAGTCTTTTC<br>GCCTGCTCAGTGGTCCACGAGGGTCTGCACAATCACCTTACGACTAAGACCATC<br>TCCCGGTCTCTGGGTAAACACCATCACCATCATCACTCTTTCTGGCGTGGATCTG<br>GGTACCGAGAACCTGTACTTCCAAGCCAACGAGCTGCGGTGCCAGTGCCTGCAG<br>ACCATGGCCGGCATCCACCTGAAGAACATCCAGAGCCTGAAGGTGCTGCCCAGC<br>GGCCCTCACTGCACCCAGACCGAAGTGATCGCCACCCTGAAGAACGGCAGAGAG<br>GCCTGCCTGGATCCCGAGGCCCCCCTGGTGCAGAAAATCGTGCAGAAATGCTG<br>AAGGGCGTGCCCAAG*GGCGGA*GGCCTGAACGACATCTTCGAGGCCCAGAAAATC<br>GAGTGGCACGAGTGATGATAA |
| 35 | gWiz-LS-Fc(mIgG2)-His$_6$-linker-TEV-mCXCL2$^{31-100}$-G$_2$-AviTag | ATGAGGGTCCCCGCTCAGCTCCTGGGGCTCCTGCTGCTCTGGCTCCCAGGTGCA<br>CGATGTGAGCCCAGAGTGCCCATAACACAGAACCCCTGTCCTCCACTCAAAGAG<br>TGTCCCCCATGCGCAGCTCCAGACCTCTTGGGTGGACCATCCGTCTTCATCTTC<br>CCTCCAAAGATCAAGGATGTACTCATGATCTCCCTGAGCCCCATGGTCACATGT<br>GTGGTGGTGGATGTGAGCGAGGATGACCCAGACGTCCAGATCAGCTGGTTTGTG<br>AACAACGTGGAAGTACACACAGCTCAGACACAAACCCATAGAGGAGGATTACAAC<br>AGTACTCTCCGGGTGGTCAGTGCCCTCCCCATCCAGCACCAGGACTGGATGAGT<br>GGCAAGGAGTTCAAATGCAAGGTCAACAACAGAGCCCTCCCATCCCCCATCGAG<br>AAAACCATCTCAAAACCCAGAGGGCCAGTAAGAGCTCCACAGGTATATGTCTTG<br>CCTCCACCAGCAGAAGAGATGACTAAGAAAGAGTTCAGTCTGACCTGCATGATC<br>ACAGGCTTCTTACCTGCCGAAATTGCTGTGGACTGGACCAGCAATGGGCGTACA<br>GAGCAAAACTACAAGAACACCGCAACAGTCCTGGACTCTGATGGTTCTTACTTC<br>ATGTACAGCAAGCTCAGAGTACAAAAGAGCACTTGGGAAAGAGGAAGTCTTTTC<br>GCCTGCTCAGTGGTCCACGAGGGTCTGCACAATCACCTTACGACTAAGACCATC<br>TCCCGGTCTCTGGGTAAACACCATCACCATCATCACTCTTTCTGGCGTGGATCTG<br>GGTACCGAGAACCTGTACTTCCAAGCCAGCGAGCTGCGGTGCCAGTGCCTGAAA<br>ACCCTGCCCCGGGTGGACTTCAAGAACATCCAGAGCCTGAGCGTGACCCCCCCT<br>GGCCCTCACTGTGCCCAGACCGAAGTGATCGCCACCCTGAAGGGCGGCCAGAAA<br>GTGTGCCTGGACCCCGAGGCCCCCCTGGTGCAGAAGATCATCCAGAAGATCCTG<br>AACAAGGGCAAGGCCAAC*GGCGGA*GGCCTGAACGACATCTTCGAGGCCCAGAAA<br>ATCGAGTGGCACGAGTGATGATAA |
| 36 | gWiz-LS-Fc(mIgG2)-His$_6$-linker-TEV-mCXCL5$^{48-118}$-G$_2$-AviTag | ATGAGGGTCCCCGCTCAGCTCCTGGGGCTCCTGCTGCTCTGGCTCCCAGGTGCA<br>CGATGTGAGCCCAGAGTGCCCATAACACAGAACCCCTGTCCTCCACTCAAAGAG<br>TGTCCCCCATGCGCAGCTCCAGACCTCTTGGGTGGACCATCCGTCTTCATCTTC<br>CCTCCAAAGATCAAGGATGTACTCATGATCTCCCTGAGCCCCATGGTCACATGT<br>GTGGTGGTGGATGTGAGCGAGGATGACCCAGACGTCCAGATCAGCTGGTTTGTG<br>AACAACGTGGAAGTACACACAGCTCAGACACAAACCCATAGAGGAGGATTACAAC<br>AGTACTCTCCGGGTGGTCAGTGCCCTCCCCATCCAGCACCAGGACTGGATGAGT<br>GGCAAGGAGTTCAAATGCAAGGTCAACAACAGAGCCCTCCCATCCCCCATCGAG<br>AAAACCATCTCAAAACCCAGAGGGCCAGTAAGAGCTCCACAGGTATATGTCTTG<br>CCTCCACCAGCAGAAGAGATGACTAAGAAAGAGTTCAGTCTGACCTGCATGATC<br>ACAGGCTTCTTACCTGCCGAAATTGCTGTGGACTGGACCAGCAATGGGCGTACA<br>GAGCAAAACTACAAGAACACCGCAACAGTCCTGGACTCTGATGGTTCTTACTTC<br>ATGTACAGCAAGCTCAGAGTACAAAAGAGCACTTGGGAAAGAGGAAGTCTTTTC<br>GCCTGCTCAGTGGTCCACGAGGGTCTGCACAATCACCTTACGACTAAGACCATC<br>TCCCGGTCTCTGGGTAAACACCATCACCATCATCACTCTTTCTGGCGTGGATCTG<br>GGTACCGAGAACCTGTACTTCCAAGCCACCGAGCTGAGATGCGTGTGCCTGACC<br>GTGACCCCCAAGATCAACCCCAAGCTGATCGCCAACCTGGAAGTGATCCCTGCC<br>GGCCCTCAGTGCCCCACCGTGGAAGTGATTGCCAAGCTGAAGAACCAGAAAGAA<br>GTGTGCCTGGACCCCGAGGCCCCCGTGATCAAGAAGATCATCCAGAAGATCCTG<br>GGCAGCGACAAGAAGAAAGCC*GGCGGA*GGCCTGAACGACATCTTCGAGGCCCAG<br>AAAATCGAGTGGCACGAGTGATGATAA |
| 37 | LS-Fc-His$_6$-linker-TEV-hCXCL1$^{38-107}$-G$_2$-AviTag | <u>MRVPAQLLGLLLLWLPGARC</u>EPRVPITQNPCPPLKECPPCAAPDLLGGPSVFIF<br>PPKIKDVLMISLSPMVTCVVVDVSEDDPDVQISWFVNNVEVHTAQTQTHREDYN<br>STLRVVSALPIQHQDWMSGKEFKCKVNNRALPSPIEKTISKPRGPVRAPQVYVL<br>PPPAAEEMTKKEFSLTCMITGFLPAEIAVDWTSNGRTEQNYKNTATVLDSDGSYF<br>MYSKLRVQKSTWERGSLFACSVVHEGLHNHLTTKTISRSLGKHHHHHHSSGVDL<br>GTENLYFQATELRCQCLQTLQGIHPKNIQSVNVKSPGPHCAQTEVIATLKNGRK<br>ACLNPASPIVKKIIEKMLNSDKSN*GG*GLNDIFEAQKIEWHE-- |

TABLE 12-continued

Sequence Summary

| SEQ ID NO | Description | Sequence |
|---|---|---|
| 38 | LS-Fc-His$_6$-linker-TEV-hCXCL5$^{43-114}$-G$_2$-AviTag | MRVPAQLLGLLLLWLPGARCEPRVPITQNPCPPLKECPPCAAPDLLGGPSVFIF<br>PPKIKDVLMISLSPMVTCVVVDVSEDDPDVQISWFVNNVEVHTAQTQTHREDYN<br>STLRVVSALPIQHQDWMSGKEFKCKVNNRALPSPIEKTISKPRGPVRAPQVYVL<br>PPPAEEMTKKEFSLTCMITGFLPAEIAVDWTSNGRTEQNYKNTATVLDSDGSYF<br>MYSKLRVQKSTWERGSLFACSVVHEGLHNHLTTKTISRSLGKHHHHHHSSGVDL<br>GTENLYFQVLRELRCVCLQTTQGVHPKMISNLQVFAIGPQCSKVEVVASLKNGK<br>EICLDPEAPPLKKVIQKILDGGNKEN*GG*GLNDIFEAQKIEWHE-- |
| 39 | LS-Fc-His$_6$-linker-TEV-hCXCL8$^{29-99}$-G$_2$-AviTag | MRVPAQLLGLLLLWLPGARCEPRVPITQNPCPPLKECPPCAAPDLLGGPSVFIF<br>PPKIKDVLMISLSPMVTCVVVDVSEDDPDVQISWFVNNVEVHTAQTQTHREDYN<br>STLRVVSALPIQHQDWMSGKEFKCKVNNRALPSPIEKTISKPRGPVRAPQVYVL<br>PPPAEEMTKKEFSLTCMITGFLPAEIAVDWTSNGRTEQNYKNTATVLDSDGSYF<br>MYSKLRVQKSTWERGSLFACSVVHEGLHNHLTTKTISRSLGKHHHHHHSSGVDL<br>GTENLYFQAKELRCQCIKTYSKPFHPKFIKELRVIESGPHCANTEIIVKLSDGR<br>ELCLDPKENWVQRVVEKFLKRAENS*GG*GLNDIFEAQKIEWHE-- |
| 40 | LS-Fc-His$_6$-linker-TEV-mCXCL1$^{28-96}$-G$_2$-AviTag | MRVPAQLLGLLLLWLPGARCEPRVPITQNPCPPLKECPPCAAPDLLGGPSVFIF<br>PPKIKDVLMISLSPMVTCVVVDVSEDDPDVQISWFVNNVEVHTAQTQTHREDYN<br>STLRVVSALPIQHQDWMSGKEFKCKVNNRALPSPIEKTISKPRGPVRAPQVYVL<br>PPPAEEMTKKEFSLTCMITGFLPAEIAVDWTSNGRTEQNYKNTATVLDSDGSYF<br>MYSKLRVQKSTWERGSLFACSVVHEGLHNHLTTKTISRSLGKHHHHHHSSGVDL<br>GTENLYFQANELRCQCLQTMAGIHLKNIQSLKVLPSGPHCTQTEVIATLKNGRE<br>ACLDPEAPLVQKIVQKMLKGVPK*GG*GLNDIFEAQKIEWHE-- |
| 41 | LS-Fc-His$_6$-linker-TEV-mCXCL2$^{31-100}$-G$_2$-AviTag | MRVPAQLLGLLLLWLPGARCEPRVPITQNPCPPLKECPPCAAPDLLGGPSVFIF<br>PPKIKDVLMISLSPMVTCVVVDVSEDDPDVQISWFVNNVEVHTAQTQTHREDYN<br>STLRVVSALPIQHQDWMSGKEFKCKVNNRALPSPIEKTISKPRGPVRAPQVYVL<br>PPPAEEMTKKEFSLTCMITGFLPAEIAVDWTSNGRTEQNYKNTATVLDSDGSYF<br>MYSKLRVQKSTWERGSLFACSVVHEGLHNHLTTKTISRSLGKHHHHHHSSGVDL<br>GTENLYFQASELRCQCLKTLPRVDFKNIQSLSVTPPGPHCAQTEVIATLKGGQK<br>VCLDPEAPLVQKIIQKILNKGKAN*GG*GLNDIFEAQKIEWHE-- |
| 42 | LS-Fc-His$_6$-linker-TEV-mCXCL5$^{48-118}$-G$_2$-AviTag | MRVPAQLLGLLLLWLPGARCEPRVPITQNPCPPLKECPPCAAPDLLGGPSVFIF<br>PPKIKDVLMISLSPMVTCVVVDVSEDDPDVQISWFVNNVEVHTAQTQTHREDYN<br>STLRVVSALPIQHQDWMSGKEFKCKVNNRALPSPIEKTISKPRGPVRAPQVYVL<br>PPPAEEMTKKEFSLTCMITGFLPAEIAVDWTSNGRTEQNYKNTATVLDSDGSYF<br>MYSKLRVQKSTWERGSLFACSVVHEGLHNHLTTKTISRSLGKHHHHHHSSGVDL<br>GTENLYFQATELRCVCLTVTPKINPKLIANLEVIPAGPQCPTVEVIAKLKNQKE<br>VCLDPEAPVIKKIIQKILGSDKKKA*GG*GLNDIFEAQKIEWHE-- |
| 43 | gWiz-LS-hCXCL1$^{35-107}$-(Gly$_4$Ser)$_2$-mouse SA-(Gly$_4$Ser)-His$_6$ | ATGAGGGTCCCCGCTCAGCTCCTGGGGCTCCTGCTGCTCTGGCTCCCAGGTGCA<br>CGATGTGCCTCTGTCGCCACCGAGCTGAGATGCCAGTGCCTGCAGACCCTGCAG<br>GGCATCCACCCCAAGAACATCCAGAGCGTGAACGTGAAGTCCCCTGGCCCCCAC<br>TGCGCCCAGACCGAAGTGATCGCCACCCTGAAGAACGGCCGGAAGGCCTGCCTG<br>AACCCCGCCAGCCCCATCGTGAAGAAAATCATCGAGAAGATGCTGAACAGCGAC<br>AAGAGCAACGGTGGAGGCGGTAGCGGAGGCGGAGGGTCGGAAGCACACAAGAGT<br>GAGATCGCCCATCGGTATAATGATTTGGGAGAACAACATTTCAAAGGCCTAGTC<br>CTGATTGCCTTTTCCCAGTATCTCCAGAAATGCTCATACGATGAGCATGCCAAA<br>TTAGTGCAGGAAGTAACAGACTTTGCAAAGACGTGTGTTGCCGATGAGTCTGCC<br>GCCAACTGTGACAAATCCCTTCACACTCTTTTTGGAGATAAGTTGTGTGCCATT<br>CCAAACCTCCGTGAAAACTATGGTGAACTGGCTGACTGCTGTACAAAACAAGAG<br>CCCGAAAGAAACGAATGTTTCCTGCAACACAAAGATGACAACCCCAGCCTGCCA<br>CCATTTGAAAGGCCAGAGGCTGAGGCCATGTGCACCTCCTTTAAGGAAAACCCA<br>ACCACCTTTATGGGACACTATTTGCATGAAGTTGCCAGAAGACATCCTTATTTC<br>TATGCCCCAGAACTTCTTTACTATGCTGAGCAGTACAATGAGATTCTGACCCAG<br>TGTTGTGCAGAGGCTGACAAGGAAAGCTGCCTGACCCCGAAGCTTGATGGTGTG<br>AAGGAGAAAGCATTGGTCTCATGTGTCCGTCAGAGAATGAAGTGTCCAGTATG<br>CAGAAGTTTGGAGAGAGAGCTTTTAAAGCATGGGCAGTAGCTCGTCTGAGCCAG<br>ACATTCCCCAATGCTGACTTTGCAGAAATCACCAAATTGGCAACAGACCTGACC<br>AAAGTCAACAAGGAGTGCTGCCATGGTGACCTGCTGGAATGCGCAGATGACAGG<br>GCGGAACTTGCCAAGTACATGTGTGAAAACCAGGCGACTATCTCCAGCAAACTG<br>CAGACTTGCTGCGATAAACCACTGTTGAAGAAAGCCCACTGTCTTAGTGAGGTG<br>GAGCATGACACCATGCCTGCTGATCTGCCTGCCATTGCTGCTGATTTTGTTGAG<br>GACCAGGAAGTGTGCAAGAACTATGCTGAGGCCAAGGATGTCTTCCTGGGCACG<br>TTCTTGTATGAATATTCAAGAAGACACCCTGATTACTCTGTATCCCTGTTGCTG<br>AGACTTGCTAAGAAATATGAAGCACTCTGGAAAGTGCTGCGCTGAAGCCAAT<br>CCTCCCGCATGCTACGGCACAGTGCTTGCTGAATTTCAGCCTCTTGTAGAAGAG<br>CCTAAGAACTTGGTCAAAACCAACTGTGATCTTTACGAGAAGCTTGGAGAATAT<br>GGATTCCAAAATGCCATTCTAGTTCGCTACACCCAGAAAGCACCTCAGGTGTCA<br>ACCCCAACTCTCGTGGAGGCTGCAAGAAACCTAGGAGAGTGGGCACCAAGTGT<br>TGTACACTTCCTGAAGATCAGAGACTGCCTTGTGTGGAAGACATCTGTCTGCA<br>ATCCTGAACCGTGTGTGTCTGCTGCATGAGAAGACCCCAGTGAGTGAGCATGTT<br>ACCAAGTGCTGTAGTGGATCCCTGGTGGAAAGGCGGCCATGCTTCTCTGCTCTG<br>ACAGTTGATGAAACATATGTCCCCAAAGAGTTTAAAGCTGAGACCTTCACCTTC<br>CACTCTGATATCTGCACACTTCCAGAGAAGGAGAAGCAGATTAAGAAACAAACG |

TABLE 12-continued

Sequence Summary

| SEQ ID NO | Description | Sequence |
|---|---|---|
| | | GCTCTTGCTGAGCTGGTGAAGCACAAGCCCAAGGCTACAGCGGAGCAACTGAAG<br>ACTGTCATGGATGACTTTGCACAGTTCCTGGATACATGTTGCAAGGCTGCTGAC<br>AAGGACACCTGCTTCTCGACTGAGGGTCCAAACCTTGTCACTAGATGCAAAGAC<br>GCCTTAGCC*GGAGGGGGCGGTTCC*CACCATCACCACCATCACTGATAA |
| 44 | gWiz-LS-<br>hCXCL2[35-107]-<br>(Gly4Ser)2-<br>mouse SA-<br>(Gly4Ser)-<br>His6 | ATGAGGGTCCCCGCTCAGCTCCTGGGGCTCCTGCTGCTCTGGCTCCCAGGTGCA<br>*CGATGT*GCTCCTCTGGCCACAGAGCTGAGATGCCAGTGCCTCCAGACACTCCAG<br>GGCATCCACCTGAAGAACATCCAGAGCGTGAAAGTGAAGTCCCCTGGCCCCCAC<br>TGCGCCCAGACAGAAGTGATCGCCACCCTGAAGAATGGCCAGAAGGCCTGCCTG<br>AACCCCGCCAGCCCTATGGTCAAGAAAATCATCGAGAAGATGCTGAAGAACGGC<br>AAGAGCAACGGTGGAGGCGGTAGCGGAGGCGGAGGGTCGGAAGCACACAAGAGT<br>GAGATCGCCCATCGGTATAATGATTTGGGAGAACAACATTTCAAAGGCCTAGTC<br>CTGATTGCCTTTTCCCAGTATCTCCAGAAATGCTCATACGATGAGCATGCCAAA<br>TTAGTGCAGGAAGTAACAGACTTTGCAAAGACGTGTGTTGCCGATGAGTCTGCC<br>GCCAACTGTGACAAATCCCTTCACACTCTTTTTGGAGATAAGTTGTGTGCCATT<br>CCAAACCTCCGTGAAAACTATGGTGAACTGGCTGACTGCTGTACAAAACAAGAG<br>CCCGAAAGAAACGAATGTTTCCTGCAACACAAAGATGACAACCCCAGCCTGCCA<br>CCATTTGAAAGGCCAGAGGCTGAGGCCATGTGCACCTCCTTTAAGGAAAACCCA<br>ACCACCTTTATGGGACACTATTTGCATGAAGTTGCCAGAAGACATCCTTATTTC<br>TATGCCCCAGAACTTCTTTACTATGCTGAGCAGTACAATGAGATTCTGACCCAG<br>TGTTGTGCAGAGGCTGACAAGGAAAGCTGCCTGACCCCGAAGCTTGATGGTGTG<br>AAGGAGAAAGCATTGGTCTCATGTGTCCGTCAGAGAATGAAGTGCTCCAGTATG<br>CAGAAGTTTGGAGAGAGAGCTTTTAAAGCATGGGCAGTAGCTCGTCTGAGCCAG<br>ACATTCCCCAATGCTGACTTTGCAGAAATCACCAAATTGGCAACAGACCTGACC<br>AAAGTCAACAAGGAGTGCTGCCATGGTGACCTGCTGGAATGCGCAGATGACAGG<br>GCGGAACTTGCCAAGTACATGTGTGAAAACCAGGCGACTATCTCCAGCAAACTG<br>CAGACTTGCTGCGATAAACCACTGTTGAAGAAGCCCACTGTCTTAGTGAGGTG<br>GAGCATGACACCATGCCTGCTGATCTGCCTGCCATTGCTGCTGATTTTGTTGAG<br>GACCAGGAAGTGTGCAAGAACTATGCTGAGGCCAAGGATGTCTTCCTGGGCACG<br>TTCTTGTATGAATATTCAAGAAGACACCCTGATTACTCTGTATCCCTGTTGCTG<br>AGACTTGCTAAGAAATATGAAGCCACTCTGGAAAAGTGCTGCGCTGAAGCCAAT<br>CCTCCCGCATGCTACGGCACAGTGCTTGCTGAATTTCAGCCTCTTGTAGAAGAG<br>CCTAAGAACTTGGTCAAAACCAACTGTGATCTTTACGAGAAGCTTGGAGAATAT<br>GGATTCCAAAATGCCATTCTAGTTCGCTACACCCAGAAAAGCACCTCAGGTGTCA<br>ACCCCAACTCTCGTGGAGGCTGCAAGAAACCTAGGAAGAGTGGGCACCAAGTGT<br>TGTACACTTCCTGAAGATCAGAGACTGCCTTGTGTGGAAGACTATCTGTCTGCA<br>ATCCTGAACCGTGTGTCTGCTGCATGAGAAGACCCCAGTGAGTGAGCATGTT<br>ACCAAGTGCTGTAGTGGATCCCTGGTGGAAAGGCGGCCATGCTTCTCTGCTCTG<br>ACAGTTGATGAAACATATGTCCCCAAAGAGTTTAAAGCTGAGACCTTCACCTTC<br>CACTCTGATATCTGCACACTTCCAGAGAAGGAGAAGCAGATTAAGAAACAAACG<br>GCTCTTGCTGAGCTGGTGAAGCACAAGCCCAAGGCTACAGCGGAGCAACTGAAG<br>ACTGTCATGGATGACTTTGCACAGTTCCTGGATACATGTTGCAAGGCTGCTGAC<br>AAGGACACCTGCTTCTCGACTGAGGGTCCAAACCTTGTCACTAGATGCAAAGAC<br>GCCTTAGCC*GGAGGGGGCGGTTCC*CACCATCACCACCATCACTGATAA |
| 45 | gWiz-LS-<br>hCXCL3[35-107]-<br>(Gly4Ser)2-<br>mouse SA-<br>(Gly4Ser)-<br>His6 | ATGAGGGTCCCCGCTCAGCTCCTGGGGCTCCTGCTGCTCTGGCTCCCAGGTGCA<br>*CGATGT*GCCTCTGTCGTGACCGAGCTGAGATGCCAGTGCCTCCAGACACTCCAG<br>GGCATCCACCTGAAGAACATCCAGAGCGTGAACGTGCGGAGCCCTGGCCCTCAT<br>TGTGCCCAGACAGAAGTGATCGCCACCCTGAAGAATGGCCAGAAGGCCTGCCTG<br>AACCCCGCCAGCCCTATGGTCGCAGAAGATCATCGAGAAGATCCTGAACAAGGGC<br>AGCACCAACGGTGGAGGCGGTAGCGGAGGCGGAGGGTCGGAAGCACACAAGAGT<br>GAGATCGCCCATCGGTATAATGATTTGGGAGAACAACATTTCAAAGGCCTAGTC<br>CTGATTGCCTTTTCCCAGTATCTCCAGAAATGCTCATACGATGAGCATGCCAAA<br>TTAGTGCAGGAAGTAACAGACTTTGCAAAGACGTGTGTTGCCGATGAGTCTGCC<br>GCCAACTGTGACAAATCCCTTCACACTCTTTTTGGAGATAAGTTGTGTGCCATT<br>CCAAACCTCCGTGAAAACTATGGTGAACTGGCTGACTGCTGTACAAAACAAGAG<br>CCCGAAAGAAACGAATGTTTCCTGCAACACAAAGATGACAACCCCAGCCTGCCA<br>CCATTTGAAAGGCCAGAGGCTGAGGCCATGTGCACCTCCTTTAAGGAAAACCCA<br>ACCACCTTTATGGGACACTATTTGCATGAAGTTGCCAGAAGACATCCTTATTTC<br>TATGCCCCAGAACTTCTTTACTATGCTGAGCAGTACAATGAGATTCTGACCCAG<br>TGTTGTGCAGAGGCTGACAAGGAAAGCTGCCTGACCCCGAAGCTTGATGGTGTG<br>AAGGAGAAAGCATTGGTCTCATCTGTCCGTCAGAGAATGAAGTGCTCCAGTATG<br>CAGAAGTTTGGAGAGAGAGCTTTTAAAGCATGGGCAGTAGCTCGTCTGAGCCAG<br>ACATTCCCCAATGCTGACTTTGCAGAAATCACCAAATTGGCAACAGACCTGACC<br>AAAGTCAACAAGGAGTGCTGCCATGGTGACCTGCTGGAATGCGCAGATGACAGG<br>GCGGAACTTGCCAAGTACATGTGTGAAAACCAGGCGACTATCTCCAGCAAACTG<br>CAGACTTGCTGCGATAAACCACTGTTGAAGAAGCCCACTGTCTTAGTGAGGTG<br>GAGCATGACACCATGCCTGCTGATCTGCCTGCCATTGCTGCTGATTTTGTTGAG<br>GACCAGGAAGTGTGCAAGAACTATGCTGAGGCCAAGGATGTCTTCCTGGGCACG<br>TTCTTGTATGAATATTCAAGAAGACACCCTGATTACTCTGTATCCCTGTTGCTG<br>AGACTTGCTAAGAAATATGAAGCCACTCTGGAAAAGTGCTGCGCTGAAGCCAAT<br>CCTCCCGCATGCTACGGCACAGTGCTTGCTGAATTTCAGCCTCTTGTAGAAGAG<br>CCTAAGAACTTGGTCAAAACCAACTGTGATCTTTACGAGAAGCTTGGAGAATAT<br>GGATTCCAAAATGCCATTCTAGTTCGCTACACCCAGAAAAGCACCTCAGGTGTCA<br>ACCCCAACTCTCGTGGAGGCTGCAAGAAACCTAGGAAGAGTGGGCACCAAGTGT |

TABLE 12-continued

Sequence Summary

| SEQ ID NO | Description | Sequence |
|---|---|---|
| | | TGTACACTTCCTGAAGATCAGAGACTGCCTTGTGTGGAAGACTATCTGTCTGCA<br>ATCCTGAACCGTGTGTGTCTGCTGCATGAGAAGACCCCAGTGAGTGAGCATGTT<br>ACCAAGTGCTGTAGTGGATCCCTGGTGGAAAGGCGGCCATGCTTCTCTGCTCTG<br>ACAGTTGATGAAACATATGTCCCCAAAGAGTTTAAAGCTGAGACCTTCACCTTC<br>CACTCTGATATCTGCACACTTCCAGAGAAGGAGAAGCAGATTAAGAAACAAACG<br>GCTCTTGCTGAGCTGGTGAAGCACAAGCCCAAGGCTACAGCGGAGCAACTGAAG<br>ACTGTCATGGATGACTTTGCACAGTTCCTGGATACATGTTGCAAGGCTGCTGAC<br>AAGGACACCTGCTTCTCGACTGAGGGTCCAAACCTTGTCACTAGATGCAAAGAC<br>GCCTTAGCC*GGAGGGGGCGGTTCC*CACCATCACCACCATCACTGATAA |
| 46 | gWiz-LS-<br>hCXCL4<sup>32-101</sup>-<br>(Gly<sub>4</sub>Ser)<sub>2</sub>-<br>mouse SA-<br>(Gly<sub>4</sub>Ser) -<br>His<sub>6</sub> | ATGAGGGTCCCCGCTCAGCTCCTGGGGCTCCTGCTGCTCTGGCTCCCAGGTGCA<br>CGATGTGAGGCTGAAGAGGACGGCCATCTCCAGTGCCTGTGCGTGAAAACCACC<br>AGCCAAGTGCGGCCCAGACACATCACCAGCCTGGAAGTGATCAAGGCCGGACCC<br>CACTGTCCTACCGCCCAGCTGATTGCCACCCTGAAGAACGGCCGGAAGATCTGC<br>CTGGACCTCCAGGCCCCCCTGTACAAGAAGATCATCAAGAAGCTGCTGGAAAGC<br>GGTGGAGGCGGTAGCGGAGGCGGAGGGTCGGAAGCACACAAGAGTGAGATCGCC<br>CATCGGTATAATGATTTGGGAGAACAACATTTCAAAGGCCTAGTCCTGATTGCC<br>TTTTCCCAGTATCTCCAGAAATGCTCATACGATGAGCATGCCAAATTAGTGCAG<br>GAAGTAACAGACTTTGCAAAGACGTGTGTTGCCGATGAGTCTGCCGCCAACTGT<br>GACAAATCCCTTCACACTCTTTTTGGAGATAAGTTGTGTGCCATTCCAAACCTC<br>CGTGAAAACTATGGTGAACTGGCTGACTGCTGTACAAAACAAGAGCCCGAAAGA<br>AACGAATGTTTCCTGCAACACAAAGATGACAACCCCAGCCTGCCACCATTTGAA<br>AGGCCAGAGGCTGAGGCCATGTGCACCTCCTTTAAGGAAAACCCAACCACCTTT<br>ATGGGACACTATTTGCATGAAGTTGCCAGAAGACATCCTTATTTCTATGCCCCA<br>GAACTTCTTTACTATGCTGAGCAGTACAATGAGATTCTGACCCAGTGTTGTGCA<br>GAGGCTGACAAGGAAAGCTGCCTGACCCCGAAGCTTGATGGTGTGAAGGAGAAA<br>GCATTGGTCTCATCTGTCCGTCAGAGAATGAAGTGCTCCAGTATGCAGAAGTTT<br>GGAGAGAGAGCTTTTAAAGCATGGGCAGTAGCTCGTCTGAGCCAGACATTCCCC<br>AATGCTGACTTTGCAGAAATCACCAAATTGGCAACAGACCTGACCAAAGTCAAC<br>AAGGAGTGCTGCCATGGTGACCTGCTGGAATGCGCAGATGACAGGGCGGAACTT<br>GCCAAGTACATGTGTGAAAACCAGGCGACTATCTCCAGCAAACTGCAGACTTGC<br>TGCGATAAACCACTGTTGAAGAAAGCCCACTGTCTTAGTGAGGTGGAGCATGAC<br>ACCATGCCTGCTGATCTGCCTGCCATTGCTGCTGATTTTGTTGAGGACCAGGAA<br>GTGTGCAAGAACTATGCTGAGGCAAGGATGTCTTCCTGGGCACGTTCTTGTAT<br>GAATATTCAAGAAGACACCCTGATTACTCTGTATCCCTGTTGCTGAGACTTGCT<br>AAGAAATATGAAGCCACTCTGGAAAAGTGCTGCGCTGAAGCCAATCCTCCCGCA<br>TGCTACGGCACAGTGCTTGCTGAATTTCAGCCTCTTGTAGAAGAGCCTAAGAAC<br>TTGGTCAAAACCAACTGTGATCTTTACGAGAAGCTTGGAGAATATGGATTCCAA<br>AATGCCATTCTAGTTCGCTACACCCAGAAAGCACCTCAGGTGTCAACCCCAACT<br>CTCGTGGAGGCTGCAAGAAACCTAGGAAGAGTGGGCACCAAGTGTTGTACACTT<br>CCTGAAGATCAGAGACTGCCTTGTGTGGAAGACTATCTGTGTGCAATCCTGAAC<br>CGTGTGTGTCTGCTGCATGAGAAGACCCCAGTGAGTGAGCATGTTACCAAGTGC<br>TGTAGTGGATCCCTGGTGGAAAGGCGGCCATGCTTCTCTGCTCTGACAGTTGAT<br>GAAACATATGTCCCCAAAGAGTTTAAAGCTGAGACCTTCACCTTCCACTCTGAT<br>ATCTGCACACTTCCAGAGAAGGAGAAGCAGATTAAGAAACAAACGGCTCTTGCT<br>GAGCTGGTGAAGCACAAGCCCAAGGCTACAGCGGAGCAACTGAAGACTGTCATG<br>GATGACTTTGCACAGTTCCTGGATACATGTTGCAAGGCTGCTGACAAGGACACC<br>TGCTTCTCGACTGAGGGTCCAAACCTTGTCACTAGATGCAAAGACGCCTTAGCC<br>*GGAGGGGGCGGTTCC*CACCATCACCACCATCACTGATAA |
| 47 | gWiz-LS-<br>hCXCL5<sup>44-114</sup>-<br>(Gly<sub>4</sub>Ser)<sub>2</sub>-<br>mouse SA-<br>(Gly<sub>4</sub>Ser) -<br>His<sub>6</sub> | ATGAGGGTCCCCGCTCAGCTCCTGGGGCTCCTGCTGCTCTGGCTCCCAGGTGCA<br>CGATGTCTGCGCGAGCTGAGATGCGTGTGCCTGCAGACCACCCAGGGCGTGCAC<br>CCCAAGATGATCAGCAACCTCCAGGTGTTCGCCATCGGCCCCCAGTGCAGCAAG<br>GTGGAAGTGGTGGCCAGCCTGAAGAACGGCAAAGAGATCTGCCTGGACCCCGAG<br>GCCCCATTCCTGAAGAAAGTGATCCAGAAGATCCTGGACGGCGGCAACAAAGAG<br>AACGGTGGAGGCGGTAGCGGAGGCGGAGGGTCG**GAAGCACACAAGAGTGAGATC<br>GCCCATCGGTATAATGATTTGGGAGAACAACATTTCAAAGGCCTAGTCCTGATT<br>GCCTTTTCCCAGTATCTCCAGAAATGCTCATACGATGAGCATGCCAAATTAGTG<br>CAGGAAGTAACAGACTTTGCAAAGACGTGTGTTGCCGATGAGTCTGCCGCCAAC<br>TGTGACAAATCCCTTCACACTCTTTTTGGAGATAAGTTGTGTGCCATTCCAAAC<br>CTCCGTGAAAACTATGGTGAACTGGCTGACTGCTGTACAAAACAAGAGCCCGAA<br>AGAAACGAATGTTTCCTGCAACACAAAGATGACAACCCCAGCCTGCCACCATTT<br>GAAAGGCCAGAGGCTGAGGCCATGTGCACCTCCTTTAAGGAAAACCCAACCACC<br>TTTATGGGACACTATTTGCATGAAGTTGCCAGAAGACATCCTTATTTCTATGCC<br>CCAGAACTTCTTTACTATGCTGAGCAGTACAATGAGATTCTGACCCAGTGTTGT<br>GCAGAGGCTGACAAGGAAAGCTGCCTGACCCCGAAGCTTGATGGTGTGAAGGAG<br>AAAGCATTGGTCTCATCTGTCCGTCAGAGAATGAAGTGCTCCAGTATGCAGAAG<br>TTTGGAGAGAGAGCTTTTAAAGCATGGGCAGTAGCTCGTCTGAGCCAGACATTC<br>CCCAATGCTGACTTTGCAGAAATCACCAAATTGGCAACAGACCTGACCAAAGTC<br>AACAAGGAGTGCTGCCATGGTGACCTGCTGGAATGCGCAGATGACAGGGCGGAA<br>CTTGCCAAGTACATGTGTGAAAACCAGGCGACTATCTCCAGCAAACTGCAGACT<br>TGCTGCGATAAACCACTGTTGAAGAAAGCCCACTGTCTTAGTGAGGTGGAGCAT<br>GACACCATGCCTGCTGATCTGCCTGCCATTGCTGCTGATTTTGTTGAGGACCAG<br>GAAGTGTGCAAGAACTATGCTGAGGCAAGGATGTCTTCCTGGGCACGTTCTTG<br>TATGAATATTCAAGAAGACACCCTGATTACTCTGTATCCCTGTTGCTGAGACTT |

TABLE 12-continued

Sequence Summary

| SEQ ID NO | Description | Sequence |
|---|---|---|
| | | GCTAAGAAATATGAAGCCACTCTGGAAAAGTGCTGCGCTGAAGCCAATCCTCCC<br>GCATGCTACGGCACAGTGCTTGCTGAATTTCAGCCTCTTGTAGAAGAGCCTAAG<br>AACTTGGTCAAAACCAACTGTGATCTTTACGAGAAGCTTGGAGAATATGGATTC<br>CAAAATGCCATTCTAGTTCGCTACACCCAGAAAGCACCTCAGGTGTCAACCCCA<br>ACTCTCGTGGAGGCTGCAAGAAACCTAGGAAGAGTGGGCACCAAGTGTTGTACA<br>CTTCCTGAAGATCAGAGACTGCCTTGTGTGGAAGACTATCTGTCTGCAATCCTG<br>AACCGTGTGTGTCTGCTGCATGAGAAGACCCCAGTGAGTGAGCATGTTACCAAG<br>TGCTGTAGTGGATCCCTGGTGGAAAGGCGGCCATGCTTCTCTGCTCTGACAGTT<br>GATGAAACATATGTCCCCAAAGAGTTTAAAGCTGAGACCTTCACCTTCCACTCT<br>GATATCTGCACACTTCCAGAGAAGGAGAAGCAGATTAAGAAACAAACGGCTCTT<br>GCTGAGCTGGTGAAGCACAAGCCCAAGGCTACAGCGGAGCAACTGAAGACTGTC<br>ATGGATGACTTTGCACAGTTCCTGGATACATGTTGCAAGGCTGCTGACAAGGAC<br>ACCTGCTTCTCGACTGAGGGTCCAAACCTTGTCACTAGATGCAAAGACGCCTTA<br>GCC*GGAGGGGGCGGTTCC*CACCATCACCACCATCACTGATAA |
| 48 | gWiz-LS-hCXCL6<sup>43-114</sup>-(Gly<sub>4</sub>Ser)<sub>2</sub>-mouse SA-(Gly<sub>4</sub>Ser)-His<sub>6</sub> | <u>ATG</u>AGGGTCCCCGCTCAGCTCCTGGGGCTCCTGCTGCTCTGGCTCCCAGGTGCA<br><u>CGATGT</u>GTGCTGACCGAGCTGCGGTGCACCTGTCTGAGAGTGACCCTGCGCGTG<br>AACCCCAAGACCATCGGCAAGCTCCAGGTGTTCCCTGCCGGCCCTCAGTGCAGC<br>AAGGTGGAAGTGGTGGCCAGCCTGAAAAACGGAAAACAAGTGTGCCTGGACCCC<br>GAGGCCCCATTCCTGAAGAAAGTGATCCAGAAGATCCTGGACAGCGGCAACAAG<br>AAGAACGGTGGAGGCGGTAGCGGAGGCGGAGGGTCGGAAGCACACAAGAGTGAG<br>ATCGCCCATCGGTATAATGATTTGGGAGAACAACATTTCAAAGGCCTAGTCCTG<br>ATTGCCTTTTCCCAGTATCTCCAGAAATGCTCATACGATGAGCATGCCAAATTA<br>GTGCAGGAAGTAACAGACTTTGCAAAGACGTGTGTTGCCGATGAGTCTGCCGCC<br>AACTGTGACAAATCCCTTCACACTCTTTTTGGAGATAAGTTGTGTGCCATTCCA<br>AACCTCCGTGAAAACTATGGTGAACTGGCTGACTGCTGTACAAAACAAGAGCCC<br>GAAAGAAACGAATGTTTCCTGCAACACAAAGATGACAACCCCAGCCTGCCACCA<br>TTTGAAAGGCCAGAGGCTGAGGCCATGTGCACCTCCTTTAAGGAAAACCCAACC<br>ACCTTTATGGGACACTATTTGCATGAAGTTGCCAGAAGACATCCTTATTTCTAT<br>GCCCCAGAACTTCTTTACTATGCTGAGCAGTACAATGAGATTCTGACCCAGTGT<br>TGTGCAGAGGCTGACAAGGAAAGCTGCCTGACCCCGAAGCTTGATGGTGTGAAG<br>GAGAAAGCATTGGTCTCATGTGTCCGTCAGAGAATGAAGTGCTCCAGTATGCAG<br>AAGTTTGGAGAGAGAGCTTTTAAAGCATGGGCAGTAGCTCGTCTGAGCCAGACA<br>TTCCCCAATGCTGACTTTGCAGAAATCACCAAATTGGCAACAGACCTGACCAAA<br>GTCAACAAGGAGTGCTGCCATGGTGACCTGCTGGAATGCGCAGATGACAGGGCG<br>GAACTTGCCAAGTACATGTGTGAAAACCAGGCGACTATCTCCAGCAAACTGCAG<br>ACTTGCTGCGATAAACACTGTTGAAGAAAGCCCACTGTCTTAGTGAGGTGGAG<br>CATGACACCATGCCTGCTGATCTGCCTGCCATTGCTGCTGATTTTGTTGAGGAC<br>CAGGAAGTGTGCAAGAACTATGCTGAGGCCAAGGATGTCTTCCTGGGCACGTTC<br>TTGTATGAATATTCAAGAAGACACCCTGATTACTCTGTATCCCTGTTGCTGAGA<br>CTTGCTAAGAAATATGAAGCCACTCTGGAAAAGTGCTGCGCTGAAGCCAATCCT<br>CCCGCATGCTACGGCACAGTGCTTGCTGAATTTCAGCCTCTTGTAGAAGAGCCT<br>AAGAACTTGGTCAAAACCAACTGTGATCTTTACGAGAAGCTTGGAGAATATGGA<br>TTCCAAAATGCCATTCTAGTTCGCTACACCCAGAAAGCACCTCAGGTGTCAACC<br>CCAACTCTCGTGGAGGCTGCAAGAAACCTAGGAAGAGTGGGCACCAAGTGTTGT<br>ACACTTCCTGAAGATCAGAGACTGCCTTGTGTGGAAGACTATCTGTCTGCAATC<br>CTGAACCGTGTGTGTCTGCTGCATGAGAAGACCCCAGTGAGTGAGCATGTTACC<br>AAGTGCTGTAGTGGATCCCTGGTGGAAAGGCGGCCATGCTTCTCTGCTCTGACA<br>GTTGATGAAACATATGTCCCCAAAGAGTTTAAAGCTGAGACCTTCACCTTCCAC<br>TCTGATATCTGCACACTTCCAGAGAAGGAGAAGCAGATTAAGAAACAAACGGCT<br>CTTGCTGAGCTGGTGAAGCACAAGCCCAAGGCTACAGCGGAGCAACTGAAGACT<br>GTCATGGATGACTTTGCACAGTTCCTGGATACATGTTGCAAGGCTGCTGACAAG<br>GACACCTGCTTCTCGACTGAGGGTCCAAACCTTGTCACTAGATGCAAAGACGCC<br>TTAGCC*GGAGGGGGCGGTTCC*CACCATCACCACCATCACTGATAA |
| 49 | gWiz-LS-hCXCL7<sup>59-121</sup>-(Gly<sub>4</sub>Ser)<sub>2</sub>-mouse SA-(Gly<sub>4</sub>Ser)-His<sub>6</sub> | <u>ATG</u>AGGGTCCCCGCTCAGCTCCTGGGGCTCCTGCTGCTCTGGCTCCCAGGTGCA<br><u>CGATGT</u>GCCGAGCTGCGGTGCATGTGCATCAAGACCACCAGCGGAATCCACCCC<br>AAGAATATCCAGTCCCTGGAAGTGATTGGCAAGGGCACCCACTGCAACCAGGTG<br>GAAGTGATTGCCACACACTGAAAGACGGCCGGAAGATCTGCCTGGACCCTGACGCC<br>CCCAGAATCAAGAAAATCGTGCAGAAAAAGCTGGGTGGAGGCGGTAGCGGAGGC<br>GGAGGGTCGGAAGCACACAAGAGTGAGATCGCCCATCGGTATAATGATTTGGGA<br>GAACAACATTTCAAAGGCCTAGTCCTGATTGCCTTTTCCCAGTATCTCCAGAAA<br>TGCTCATACGATGAGCATGCCAAATTAGTGCAGGAAGTAACAGACTTTGCAAAG<br>ACGTGTGTTGCCGATGAGTCTGCCGCCAACTGTGACAAATCCCTTCACACTCTT<br>TTTGGAGATAAGTTGTGTGCCATTCCAAACCTCCGTGAAAACTATGGTGAACTG<br>GCTGACTGCTGTACAAAACAAGAGCCCGAAAGAAACGAATGTTTCCTGCAACAC<br>AAAGATGACAACCCCAGCCTGCCACCATTTGAAAGGCCAGAGGCTGAGGCCATG<br>TGCACCTCCTTTAAGGAAAACCCAACCACCTTTATGGGACACTATTTGCATGAA<br>GTTGCCAGAAGACATCCTTATTTCTATGCCCCAGAACTTCTTTACTATGCTGAG<br>CAGTACAATGAGATTCTGACCCAGTGTTGTGCAGAGGCTGACAAGGAAAGCTGC<br>CTGACCCCGAAGCTTGATGGTGTGAAGGAGAAAGCATTGGTCTCATCTGTCCGT<br>CAGAGAATGAAGTGCTCCAGTATGCAGAAGTTTGGAGAGAGAGCTTTTAAAGCA<br>TGGGCAGTAGCTCGTCTGAGCCAGACATTCCCCAATGCTGACTTTGCAGAAATC<br>ACCAAATTGGCAACAGACCTGACCAAAGTCAACAAGGAGTGCTGCCATGGTGAC<br>CTGCTGGAATGCGCAGATGACAGGGCGGAACTTGCCAAGTACATGTGTGAAAAC |

TABLE 12-continued

Sequence Summary

| SEQ ID NO | Description | Sequence |
|---|---|---|
|  |  | CAGGCGACTATCTCCAGCAAACTGCAGACTTGCTGCGATAAACCACTGTTGAAG<br>AAAGCCCACTGTCTTAGTGAGGTGGAGCATGACACCATGCCTGCTGATCTGCCT<br>GCCATTGCTGCTGATTTTGTTGAGGACCAGGAAGTGTGCAAGAACTATGCTGAG<br>GCCAAGGATGTCTTCCTGGGCACGTTCTTGTATGAATATTCAAGAAGACACCCT<br>GATTACTCTGTATCCCTGTTGCTGAGACTTGCTAAGAAATATGAAGCCACTCTG<br>GAAAAGTGCTGCGCTGAAGCCAATCCTCCCGCATGCTACGGCACAGTGCTTGCT<br>GAATTTCAGCCTCTTGTAGAAGAGCCTAAGAACTTGGTCAAAACCAACTGTGAT<br>CTTTACGAGAAGCTTGGAGAATATGGATTCCAAAATGCCATTCTAGTTCGCTAC<br>ACCCAGAAAGCACCTCAGGTGTCAACCCCAACTCTCGTGGAGGCTGCAAGAAAC<br>CTAGGAAGAGTGGGCACCAAGTGTTGTACACTTCCTGAAGATCAGAGACTGCCT<br>TGTGTGGAAGACTATCTGTCTGCAATCCTGAACCGTGTGTGTCTGCTGCATGAG<br>AAGACCCCAGTGAGTGAGCATGTTACCAAGTGCTGTAGTGGATCCCTGGTGGAA<br>AGGCGGCCATGCTTCTCTGCTCTGACAGTTGATGAAACATATGTCCCCAAAGAG<br>TTTAAAGCTGAGACCTTCACCTTCCACTCTGATATCTGCACACTTCCAGAGAAG<br>GAGAAGCAGATTAAGAAACAAACGGCTCTTGCTGAGCTGGTGAAGCACAAGCCC<br>AAGGCTACAGCGGAGCAACTGAAGACTGTCATGGATGACTTTGCACAGTTCCTG<br>GATACATGTTGCAAGGCTGCTGACAAGGACACCTGCTTCTCGACTGAGGGTCCA<br>AACCTTGTCACTAGATGCAAAGACGCCTTAGCC<u>*GGAGGGGGCGGTTCC*</u>CACCAT<br>CACCACCATCACTGATAA |
| 50 | gWiz-LS-<br>hCXCL8<sup>28-99</sup>-<br>(Gly<sub>4</sub>Ser)<sub>2</sub>-<br>mouse SA-<br>(Gly<sub>4</sub>Ser)-<br>His<sub>6</sub> | ATGAGGGTCCCCGCTCAGCTCCTGGGGCTCCTGCTGCTCTGGCTCCCAGGTGCA<br>CGATGTAGCGCCAAAGAACTGCGGTGCCAGTGCATCAAGACCTACAGCAAGCCC<br>TTCCACCCCAAGTTCATCAAAGAACTGAGAGTGATCGAGAGCGGCCCTCACTGC<br>GCCAACACCGAGATCATCGTGAAGCTGAGCGACGGCAGAGAGCTGTGCCTGGAC<br>CCCAAAGAAAACTGGGTGCAGCGGGTGGTGGAAAAGTTCCTGAAGCGGGCCGAG</b><br>AACAGCGGTGGAGGCGGTAGCGGAGGCGGAGGGTCG**GAAGCACACAAGAGTGAG<br>ATCGCCCATCGGTATAATGATTTGGGAGAACAACATTTCAAAGGCCTAGTCCTG<br>ATTGCCTTTTCCCAGTATCTCCAGAAATGCTCATACGATGAGCATGCCAAATTA<br>GTGCAGGAAGTAACAGACTTTGCAAAGACGTGTGTTGCCGATGAGTCTGCCGCC<br>AACTGTGACAAATCCCTTCACACTCTTTTTGGAGATAAGTTGTGTGCCATTCCA<br>AACCTCCGTGAAAACTATGGTGAACTGGCTGACTGCTGTACAAAACAAGAGCCC<br>GAAAGAAACGAATGTTTCCTGCAACACAAAGATGACAACCCCAGCCTGCCACCA<br>TTTGAAAGGCCAGAGGCTGAGGCCATGTGCACCTCCTTTAAGGAAAACCCAACC<br>ACCTTTATGGGACACTATTTGCATGAAGTTGCCAGAAGACATCCTTATTTCTAT<br>GCCCCAGAACTTCTTTACTATGCTGAGCAGTACAATGAGATTCTGACCCAGTGT<br>TGTGCAGAGGCTGACAAGGAAAGCTGCCTGACCCCGAAGCTTGATGGTGTGAAG<br>GAGAAAGCATTGGTCTCATCTGTCCGTCAGAGAATGAAGTGCTCCAGTATGCAG<br>AAGTTTGGAGAGAGAGCTTTTAAAGCATGGGCAGTAGCTCGTCTGAGCCAGACA<br>TTCCCCAATGCTGACTTTGCAGAAATCACCAAATTGGCAACAGACCTGACCAAA<br>GTCAACAAGGAGTGCTGCCATGGTGACCTGCTGGAATGCGCAGATGACAGGGCG<br>GAACTTGCCAAGTACATGTGTGAAAACCAGGCGACTATCTCCAGCAAACTGCAG<br>ACTTGCTGCGATAAACCACTGTTGAAGAAAGCCCACTGTCTTAGTGAGGTGGAG<br>CATGACACCATGCCTGCTGATCTGCCTGCCATTGCTGCTGATTTTGTTGAGGAC<br>CAGGAAGTGTGCAAGAACTATGCTGAGGCCAAGGATGTCTTCCTGGGCACGTTC<br>TTGTATGAATATTCAAGAAGACACCCTGATTACTCTGTATCCCTGTTGCTGAGA<br>CTTGCTAAGAAATATGAAGCCACTCTGGAAAAGTGCTGCGCTGAAGCCAATCCT<br>CCCGCATGCTACGGCACAGTGCTTGCTGAATTTCAGCCTCTTGTAGAAGAGCCT<br>AAGAACTTGGTCAAAACCAACTGTGATCTTTACGAGAAGCTTGGAGAATATGGA<br>TTCCAAAATGCCATTCTAGTTCGCTACACCCAGAAAGCACCTCAGGTGTCAACC<br>CCAACTCTCGTGGAGGCTGCAAGAAACCTAGGAAGAGTGGGCACCAAGTGTTGT<br>ACACTTCCTGAAGATCAGAGACTGCCTTGTGTGGAAGACTATCTGTCTGCAATC<br>CTGAACCGTGTGTGTCTGCTGCATGAGAAGACCCCAGTGAGTGAGCATGTTACC<br>AAGTGCTGTAGTGGATCCCTGGTGGAAAGGCGGCCATGCTTCTCTGCTCTGACA<br>GTTGATGAAACATATGTCCCCAAAGAGTTTAAAGCTGAGACCTTCACCTTCCAC<br>TCTGATATCTGCACACTTCCAGAGAAGGAGAAGCAGATTAAGAAACAAACGGCT<br>CTTGCTGAGCTGGTGAAGCACAAGCCCAAGGCTACAGCGGAGCAACTGAAGACT<br>GTCATGGATGACTTTGCACAGTTCCTGGATACATGTTGCAAGGCTGCTGACAAG<br>GACACCTGCTTCTCGACTGAGGGTCCAAACCTTGTCACTAGATGCAAAGACGCC<br>TTAGCC<u>*GGAGGGGGCGGTTCC*</u>CACCATCACCACCATCACTGATAA |
| 51 | gWiz-LS-<br>hCXCL9<sup>23-125</sup>-<br>(Gly<sub>4</sub>Ser)<sub>2</sub>-<br>mouse SA-<br>(Gly<sub>4</sub>Ser)-<br>His<sub>6</sub> | ATGAGGGTCCCCGCTCAGCTCCTGGGGCTCCTGCTGCTCTGGCTCCCAGGTGCA<br>CGATGTACCCCGTCGTCGGAAGGGCAGATGCAGCTGTATCAGCACCAACCAG<br>GGCACCATCCATCTCCAGTCTCTGAAGGACCTGAAGCAGTTCGCCCCCAGCCCC<br>AGCTGCGAGAAGATCGAGATTATCGCCACACTGAAAAACGGGGTGCAGACCTGC<br>CTGAACCCCGACAGCGCCGACGTGAAAGAACTGATCAAGAAATGGGAGAAACAG<br>GTGTCCCAGAAGAAGAAGCAGAAGAACGGAAAGAAGCACCAGAAAAAGAAAGTG<br>CTGAAAGTGCGGAAGTCCCAGCGGAGCCGGCAGAAGAAAACCACAGGTGGAGGC<br>GGTAGCGGAGGCGGAGGGTCGGAAGCACACAAGAGTGAGATCGCCCATCGGTAT<br>AATGATTTGGGAGAACAACATTTCAAAGGCCTAGTCCTGATTGCCTTTTCCCAG<br>TATCTCCAGAAATGCTCATACGATGAGCATGCCAAATTAGTGCAGGAAGTAACA<br>GACTTTGCAAAGACGTGTGTTGCCGATGAGTCTGCCGCCAACTGTGACAAATCC<br>CTTCACACTCTTTTTGGAGATAAGTTGTGTGCCATTCCAAACCTCCGTGAAAAC<br>TATGGTGAACTGGCTGACTGCTGTACAAAACAAGAGCCCGAAAGAAACGAATGT<br>TTCCTGCAACACAAAGATGACAACCCCAGCCTGCCACCATTTGAAAGGCCAGAG<br>GCTGAGGCCATGTGCACCTCCTTTAAGGAAAACCCAACCACCTTTATGGGACAC |

TABLE 12-continued

Sequence Summary

| SEQ ID NO | Description | Sequence |
|---|---|---|
| | | TATTTGCATGAAGTTGCCAGAAGACATCCTTATTTCTATGCCCCAGAACTTCTT<br>TACTATGCTGAGCAGTACAATGAGATTCTGACCCAGTGTTGTGCAGAGGCTGAC<br>AAGGAAAGCTGCCTGACCCCGAAGCTTGATGGTGTGAAGGAAAGCATTGGTC<br>TCATCTGTCCGTCAGAGAATGAAGTGCTCCAGTATGCAGAAGTTTGGAGAGAGA<br>GCTTTTAAAGCATGGGCAGTAGCTCGTCTGAGCCAGACATTCCCCAATGCTGAC<br>TTTGCAGAAATCACCAAATTGGCAACAGACCTGACCAAAGTCAACAAGGAGTGC<br>TGCCATGGTGACCTGCTGGAATGCGCAGATGACAGGGCGGAACTTGCCAAGTAC<br>ATGTGTGAAAACCAGGCGACTATCTCCAGCAAACTGCAGACTTGCTGCGATAAA<br>CCACTGTTGAAGAAAGCCCACTGTCTTAGTGAGGTGGAGCATGACACCATGCCT<br>GCTGATCTGCCTGCCATTGCTGCTGATTTTGTTGAGGACCAGGAAGTGTGCAAG<br>AACTATGCTGAGGCCAAGGATGTCTTCCTGGGCACGTTCTTGTATGAATATTCA<br>AGAAGACACCCTGATTACTCTGTATCCCTGTTGCTGAGACTTGCTAAGAAATAT<br>GAAGCCACTCTGGAAAAGTGCTGCGCTGAAGCCAATCCTCCCGCATGCTACGGC<br>ACAGTGCTTGCTGAATTTCAGCCTCTTGTAGAAGAGCCTAAGAACTTGGTCAAA<br>ACCAACTGTGATCTTTACGAGAAGCTTGGAGAATATGGATTCCAAAATGCCATT<br>CTAGTTCGCTACACCCAGAAAGCACCTCAGGTGTCAACCCCAACTCTCGTGGAG<br>GCTGCAAGAAACCTAGGAAGAGTGGGCACCAAGTGTTGTACACTTCCTGAAGAT<br>CAGAGACTGCCTTGTGTGGAAGACTATCTGTCTGCAATCCTGAACCGTGTGTGT<br>CTGCTGCATGAGAAGACCCCAGTGAGTGAGCATGTTACCAAGTGCTGTAGTGGA<br>TCCCTGGTGGAAAGGCGGCCATGCTTCTCTGCTCTGACAGTTGATGAAACATAT<br>GTCCCCAAAGAGTTTAAAGCTGAGACCTTCACCTTCCACTCTGATATCTGCACA<br>CTTCCAGAGAAGGAGAAGCAGATTAAGAAACAAACGGCTCTTGCTGAGCTGGTG<br>AAGCACAAGCCCAAGGCTACAGCGGAGCAACTGAAGACTGTCATGGATGACTTT<br>GCACAGTTCCTGGATACATGTTGCAAGGCTGCTGACAAGGACACCTGCTTCTCG<br>ACTGAGGGTCCAAACCTTGTCACTAGATGCAAAGACGCCTTAGC<u>*GGAGGGGGC*</u><br><u>*GGTTCC*</u>CACCATCACCACCATCACTGATAA |
| 52 | gWiz-LS-<br>hCXCL10<sup>22-98</sup>-<br>(Gly<sub>4</sub>Ser)<sub>2</sub>-<br>mouse SA-<br>(Gly<sub>4</sub>Ser)-<br>His<sub>6</sub> | <u>ATG</u>AGGGTCCCCGCTCAGCTCCTGGGGCTCCTGCTGCTCTGGCTCCCAGGTGCA<br><u>CGATG</u>TGTGCCTCTGAGCAGAACCGTGCGGTGCACCTGTATCAGCATCAGCAAC<br>CAGCCCGTGAACCCCAGAAGCCTGGAAAAGCTGGAAATCATCCCCGCCAGCCAG<br>TTCTGCCCCAGAGTGGAAATTATCGCCACCATGAAGAAGAAAGGCGAGAAGCGG<br>TGCCTGAACCCCGAGAGCAAGGCCATCAAGAACCTGCTGAAGGCCGTGTCCAAA<br>GAGCGGAGCAAGCGGAGCCCAGGTGGCGGTAGCGGAGGCGGAGGGTCGGAA<br>GCACACAAGAGTGAGATCGCCCATCGGTATAATGATTTGGGAGAACAACATTTC<br>AAAGGCCTAGTCCTGATTGCCTTTTCCCAGTATCTCCAGAAATGCTCATACGAT<br>GAGCATGCCAAATTAGTGCAGGAAGTAACAGACTTTGCAAAGACGTGTGTTGCC<br>GATGAGTCTGCCGCCAACTGTGACAAATCCCTTCACACTCTTTTTGGAGATAAG<br>TTGTGTGCCATTCCAAACCTCCGTGAAAACTATGGTGAACTGGCTGACTGCTGT<br>ACAAAACAAGAGCCCGAAAGAAACGAATGTTTCCTGCAACACAAAGATGACAAC<br>CCCAGCCTGCCACCATTTGAAAGGCCAGAGGCTGAGGCCATGTGCACCTCCTTT<br>AAGGAAAACCCAACCACCTTTATGGGACACTATTTGCATGAAGTTGCCAGAAGA<br>CATCCTTATTTCTATGCCCCAGAACTTCTTTACTATGCTGAGCAGTACAATGAG<br>ATTCTGACCCAGTGTTGTGCAGAGGCTGACAAGGAAAGCTGCCTGACCCCGAAG<br>CTTGATGGTGTGAAGGAGAAAGCATTGGTCTCATCTGTCCGTCAGAGAATGAAG<br>TGCTCCAGTATGCAGAAGTTTGGAGAGAGAGCTTTTAAAGCATGGGCAGTAGCT<br>CGTCTGAGCCAGACATTCCCCAATGCTGACTTTGCAGAAATCACCAAATTGGCA<br>ACAGACCTGACCAAAGTCAACAAGGAGTGCTGCCATGGTGACCTGCTGGAATGC<br>GCAGATGACAGGGCGGAACTTGCCAAGTACATGTGTGAAAACCAGGCGACTATC<br>TCCAGCAAACTGCAGACTTGCTGCGATAAACCACTGTTGAAGAAAGCCCACTGT<br>CTTAGTGAGGTGGAGCATGACACCATGCCTGCTGATCTGCCTGCCATTGCTGCT<br>GATTTTGTTGAGGACCAGGAAGTGTGCAAGAACTATGCTGAGGCCAAGGATGTC<br>TTCCTGGGCACGTTCTTGTATGAATATTCAAGAAGACACCCTGATTACTCTGTA<br>TCCCTGTTGCTGAGACTTGCTAAGAAATATGAAGCCACTCTGGAAAAGTGCTGC<br>GCTGAAGCCAATCCTCCCGCATGCTACGGCACAGTGCTTGCTGAATTTCAGCCT<br>CTTGTAGAAGAGCCTAAGAACTTGGTCAAAACCAACTGTGATCTTTACGAGAAG<br>CTTGGAGAATATGGATTCCAAAATGCCATTCTAGTTCGCTACACCCAGAAAGCA<br>CCTCAGGTGTCAACCCCAACTCTCGTGGAGGCTGCAAGAAACCTAGGAAGAGTG<br>GGCACCAAGTGTTGTACACTTCCTGAAGATCAGAGACTGCCTTGTGTGGAAGAC<br>TATCTGTCTGCAATCCTGAACCGTGTGTGTCTGCTGCATGAGAAGACCCCAGTG<br>AGTGAGCATGTTACCAAGTGCTGTAGTGGATCCCTGGTGGAAAGGCGGCCATGC<br>TTCTCTGCTCTGACAGTTGATGAAACATATGTCCCCAAAGAGTTTAAAGCTGAG<br>ACCTTCACCTTCCACTCTGATATCTGCACACTTCCAGAGAAGGAGAAGCAGATT<br>AAGAAACAAACGGCTCTTGCTGAGCTGGTGAAGCACAAGCCCAAGGCTACAGCG<br>GAGCAACTGAAGACTGTCATGGATGACTTTGCACAGTTCCTGGATACATGTTGC<br>AAGGCTGCTGACAAGGACACCTGCTTCTCGACTGAGGGTCCAAACCTTGTCACT<br>AGATGCAAAGACGCCTTAGC<u>*GGAGGGGGCGGTTCC*</u>CACCATCACCACCATCAC<br>TGATAA |
| 53 | gWiz-LS-<br>hCXCL11<sup>22-94</sup>-<br>(Gly<sub>4</sub>Ser)<sub>2</sub>-<br>mouse SA-<br>(Gly<sub>4</sub>Ser)-<br>His<sub>6</sub> | <u>ATG</u>AGGGTCCCCGCTCAGCTCCTGGGGCTCCTGCTGCTCTGGCTCCCAGGTGCA<br><u>CGATG</u>TTTCCCCATGTTCAAGCGGGGCAGATGCCTGTGCATCGGCCCTGGCGTG<br>AAAGCCGTGAAGGTGGCCGATATCGAGAAGGCCAGCATCATGTACCCCAGCAAC<br>AACTGCGACAAGATCGAAGTGATCATCACCCTGAAAGAGAACAAGGGCCAGAGA<br>TGCCTGAATCCCAAGTCCAAGCAGGCCCGGCTGATCATCAAGAAGGTGGAACGG<br>AAGAACTTCGGTGGAGGCGGTAGCGGAGGCGGAGGGTCGGAAGCACACAAGAGT<br>GAGATCGCCCATCGGTATAATGATTTGGGAGAACAACATTTCAAAGGCCTAGTC |

TABLE 12-continued

Sequence Summary

| SEQ ID NO | Description | Sequence |
|---|---|---|
| | | CTGATTGCCTTTTCCCAGTATCTCCAGAAATGCTCATACGATGAGCATGCCAAA<br>TTAGTGCAGGAAGTAACAGACTTTGCAAAGACGTGTGTTGCCGATGAGTCTGCC<br>GCCAACTGTGACAAATCCCTTCACACTCTTTTTGGAGATAAGTTGTGTGCCATT<br>CCAAACCTCCGTGAAAACTATGGTGAACTGGCTGACTGCTGTACAAAACAAGAG<br>CCCGAAAGAAACGAATGTTTCCTGCAACACAAAGATGACAACCCCAGCCTGCCA<br>CCATTTGAAAGGCCAGAGGCTGAGGCCATGTGCACCTCCTTTAAGGAAAACCCA<br>ACCACCTTTATGGGACACTATTTGCATGAAGTTGCCAGAAGACATCCTTATTTC<br>TATGCCCCAGAACTTCTTTACTATGCTGAGCAGTACAATGAGATTCTGACCCAG<br>TGTTGTGCAGAGGCTGACAAGGAAAGCTGCCTGACCCCGAAGCTTGATGGTGTG<br>AAGGAGAAAGCATTGGTCTCATGTGTCCGTCAGAGAATGAAGTGCTCCAGTATG<br>CAGAAGTTTGGAGAGAGAGCTTTTAAAGCATGGGCAGTAGCTCGTCTGAGCCAG<br>ACATTCCCCAATGCTGACTTTGCAGAAATCACCAAATTGGCAACAGACCTGACC<br>AAAGTCAACAAGGAGTGCTGCCATGGTGACCTGCTGGAATGCGCAGATGACAGG<br>GCGGAACTTGCCAAGTACATGTGTGAAAACCAGGCGACTATCTCCAGCAAACTG<br>CAGACTTGCTGCGATAAACCACTGTTGAAGAAAGCCCACTGTCTTAGTGAGGTG<br>GAGCATGACACCATGCCTGCTGATCTGCCTGCCATTGCTGCTGATTTTGTTGAG<br>GACCAGGAAGTGTGCAAGAACTATGCTGAGGCCAAGGATGTCTTCCTGGGCACG<br>TTCTTGTATGAATATTCAAGAAGACACCCTGATTACTCTGTATCCCTGTTGCTG<br>AGACTTGCTAAGAAATATGAAGCCACTCTGGAAAAGTGCTGCGCTGAAGCCAAT<br>CCTCCCGCATGCTACGGCACAGTGCTTGCTGAATTTCAGCCTCTTGTAGAAGAG<br>CCTAAGAACTTGGTCAAAACCAACTGTGATCTTTACGAGAAGCTTGGAGAATAT<br>GGATTCCAAAATGCCATTCTAGTTCGCTACACCCAGAAAGCACCTCAGGTGTCA<br>ACCCCAACTCTCGTGGAGGCTGCAAGAAACCTAGGAAGAGTGGGCACCAAGTGT<br>TGTACACTTCCTGAAGATCAGAGACTGCCTTGTGTGGAAGACTATCTGTCTGCA<br>ATCCTGAACCGTGTGTGTCTGCTGCATGAGAAGACCCCAGTGAGTGAGCATGTT<br>ACCAAGTGCTGTAGTGGATCCCTGGTGGAAAGGCGGCCATGCTTCTCTGCTCTG<br>ACAGTTGATGAAACATATGTCCCCAAAGAGTTTAAAGCTGAGACCTTCACCTTC<br>CACTCTGATATCTGCACACTTCCAGAGAAGGAGAAGCAGATTAAGAAACAAACG<br>GCTCTTGCTGAGCTGGTGAAGCACAAGCCCAAGGCTACAGCGGAGCAACTGAAG<br>ACTGTCATGGATGACTTTGCACAGTTCCTGGATACATGTTGCAAGGCTGCTGAC<br>AAGGACACCTGCTTCTCGACTGAGGGTCCAAACCTTGTCACTAGATGCAAAGAC<br>GCCTTAGCC_GGAGGGGGCGGTTCC_CACCATCACCACCATCACTGATAA |
| 54 | gWiz-LS-<br>mCXCL1[25-96]-<br>(Gly4Ser)2-<br>mouse SA-<br>(Gly4Ser)-<br>His6 | ATGAGGGTCCCCGCTCAGCTCCTGGGGCTCCTGCTGCTCTGGCTCCCAGGTGCA<br>CGATGTGCCCTATTGCCAACGAGCTGCGGTGCCAGTGCCTGCAGACCATGGCC<br>GGCATCCACCTGAAGAACATCCAGAGCCTGAAGGTGCTGCCCAGCGGCCCTCAC<br>TGCACCCAGACCGAAGTGATCGCCACCCTGAAGAACGGCAGAGAGGCCTGCCTG<br>GATCCCGAGGCCCCCCTGGTGCAGAAAATCGTGCAGAAAATGCTGAAGGGCGTG<br>CCCAAGGGTGGAGGCGGTAGCGGAGGCGGAGGGTCGGAAGCACACAAGAGTGAG<br>ATCGCCCATCGGTATAATGATTTGGGAGAACAACATTTCAAAGGCCTAGTCCTG<br>ATTGCCTTTTCCCAGTATCTCCAGAAATGCTCATACGATGAGCATGCCAAATTA<br>GTGCAGGAAGTAACAGACTTTGCAAAGACGTGTGTTGCCGATGAGTCTGCCGCC<br>AACTGTGACAAATCCCTTCACACTCTTTTTGGAGATAAGTTGTGTGCCATTCCA<br>AACCTCCGTGAAAACTATGGTGAACTGGCTGACTGCTGTACAAAACAAGAGCCC<br>GAAAGAAACGAATGTTTCCTGCAACACAAAGATGACAACCCCAGCCTGCCACCA<br>TTTGAAAGGCCAGAGGCTGAGGCCATGTGCACCTCCTTTAAGGAAAACCCAACC<br>ACCTTTATGGGACACTATTTGCATGAAGTTGCCAGAAGACATCCTTATTTCTAT<br>GCCCCAGAACTTCTTTACTATGCTGAGCAGTACAATGAGATTCTGACCCAGTGT<br>TGTGCAGAGGCTGACAAGGAAAGCTGCCTGACCCCGAAGCTTGATGGTGTGAAG<br>GAGAAAGCATTGGTCTCATGTGTCCGTCAGAGAATGAAGTGCTCCAGTATGCAG<br>AAGTTTGGAGAGAGAGCTTTTAAAGCATGGGCAGTAGCTCGTCTGAGCCAGACA<br>TTCCCCAATGCTGACTTTGCAGAAATCACCAAATTGGCAACAGACCTGACCAAA<br>GTCAACAAGGAGTGCTGCCATGGTGACCTGCTGGAATGCGCAGATGACAGGGCG<br>GAACTTGCCAAGTACATGTGTGAAAACCAGGCGACTATCTCCAGCAAACTGCAG<br>ACTTGCTGCGATAAACCACTGTTGAAGAAAGCCCACTGTCTTAGTGAGGTGGAG<br>CATGACACCATGCCTGCTGATCTGCCTGCCATTGCTGCTGATTTTGTTGAGGAC<br>CAGGAAGTGTGCAAGAACTATGCTGAGGCCAAGGATGTCTTCCTGGGCACGTTC<br>TTGTATGAATATTCAAGAAGACACCCTGATTACTCTGTATCCCTGTTGCTGAGA<br>CTTGCTAAGAAATATGAAGCCACTCTGGAAAAGTGCTGCGCTGAAGCCAATCCT<br>CCCGCATGCTACGGCACAGTGCTTGCTGAATTTCAGCCTCTTGTAGAAGAGCCT<br>AAGAACTTGGTCAAAACCAACTGTGATCTTTACGAGAAGCTTGGAGAATATGGA<br>TTCCAAAATGCCATTCTAGTTCGCTACACCCAGAAAGCACCTCAGGTGTCAACC<br>CCAACTCTCGTGGAGGCTGCAAGAAACCTAGGAAGAGTGGGCACCAAGTGTTGT<br>ACACTTCCTGAAGATCAGAGACTGCCTTGTGTGGAAGACTATCTGTCTGCAATC<br>CTGAACCGTGTGTGTCTGCTGCATGAGAAGACCCCAGTGAGTGAGCATGTTACC<br>AAGTGCTGTAGTGGATCCCTGGTGGAAAGGCGGCCATGCTTCTCTGCTCTGACA<br>GTTGATGAAACATATGTCCCCAAAGAGTTTAAAGCTGAGACCTTCACCTTCCAC<br>TCTGATATCTGCACACTTCCAGAGAAGGAGAAGCAGATTAAGAAACAAACGGCT<br>CTTGCTGAGCTGGTGAAGCACAAGCCCAAGGCTACAGCGGAGCAACTGAAGACT<br>GTCATGGATGACTTTGCACAGTTCCTGGATACATGTTGCAAGGCTGCTGACAAG<br>GACACCTGCTTCTCGACTGAGGGTCCAAACCTTGTCACTAGATGCAAAGACGCC<br>TTAGCC_GGAGGGGGCGGTTCC_CACCATCACCACCATCACTGATAA** |
| 55 | gWiz-LS-<br>mCXCL2[28-100]- | ATGAGGGTCCCCGCTCAGCTCCTGGGGCTCCTGCTGCTCTGGCTCCCAGGTGCA<br>CGATGTGCCGTCGTGGCCAGCGAGCTGCGGTGCCAGTGCCTGAAAACCCTGCCC |

TABLE 12-continued

Sequence Summary

| SEQ ID NO | Description | Sequence |
|---|---|---|
| | (Gly$_4$Ser)$_2$-mouse SA-(Gly$_4$Ser)-His$_6$ | CGGGTGGACTTCAAGAACATCCAGAGCCTGAGCGTGACCCCCCCTGGCCCTCAC TGTGCCCAGACCGAAGTGATCGCCACCCTGAAGGGCGGCCAGAAAGTGTGCCTG GACCCCGAGGCCCCCCTGGTGCAGAAGATCATCCAGAAGATCCTGAACAAGGGC AAGGCCAACGGTGGAGGCGGTAGCGGAGGCGGAGGGTCGGAAGCACACAAGAGT GAGATCGCCCATCGGTATAATGATTTGGGAGAACAACATTTCAAAGGCCTAGTC CTGATTGCCTTTTCCCAGTATCTCCAGAAATGCTCATACGATGAGCATGCCAAA TTAGTGCAGGAAGTAACAGACTTTGCAAAGACGTGTGTTGCCGATGAGTCTGCC GCCAACTGTGACAAATCCCTTCACACTCTTTTTGGAGATAAGTTGTGTGCCATT CCAAACCTCCGTGAAAACTATGGTGAACTGGCTGACTGCTGTACAAAACAAGAG CCCGAAAGAAACGAATGTTTCCTGCAACACAAAGATGACAACCCCAGCCTGCCA CCATTTGAAAGGCCAGAGGCTGAGGCCATGTGCACCTCCTTTAAGGAAAACCCA ACCACCTTTATGGGACACTATTTGCATGAAGTTGCCAGAAGACATCCTTATTTC TATGCCCCAGAACTTCTTTACTATGCTGAGCAGTACAATGAGATTCTGACCCAG TGTTGTGCAGAGGCTGACAAGGAAAGCTGCCTGACCCCGAAGCTTGATGGTGTG AAGGAGAAAGCATTGGTCTCATGTGTCCGTCAGAGAATGAAGTGCTCCAGTATG CAGAAGTTTGGAGAGAGAGCTTTTAAAGCATGGGCAGTAGCTCGTCTGAGCCAG ACATTCCCCAATGCTGACTTTGCAGAAATCACCAAATTGGCAACAGACCTGACC AAAGTCAACAAGGAGTGCTGCCATGGTGACCTGCTGGAATGCGCAGATGACAGG GCGGAACTTGCCAAGTACATGTGTGAAAACCAGGCGACTATCTCCAGCAAACTG CAGACTTGCTGCGATAAACCACTGTTGAAGAAAGCCCACTGTCTTAGTGAGGTG GAGCATGACACCATGCCTGCTGATCTGCCTGCCATTGCTGCTGATTTTGTTGAG GACCAGGAAGTGTGCAAGAACTATGCTGAGGCCAAGGATGTCTTCCTGGGCACG TTCTTGTATGAATATTCAAGAAGACACCCTGATTACTCTGTATCCCTGTTGCTG AGACTTGCTAAGAAATATGAAGCCACTCTGGAAAAGTGCTGCGCTGAAGCCAAT CCTCCCGCATGCTACGGCACAGTGCTTGCTGAATTTCAGCCTCTTGTAGAAGAG CCTAAGAACTTGGTCAAAACCAACTGTGATCTTTACGAGAAGCTTGGAGAATAT GGATTCCAAAATGCCATTCTAGTTCGCTACACCCAGAAAGCACCTCAGGTGTCA ACCCCAACTCTCGTGGAGGCTGCAAGAAACCTAGGAAGAGTGGGCACCAAGTGT TGTACACTTCCTGAAGATCAGAGACTGCCTTGTGTGGAAGACTATCTGTCTGCA ATCCTGAACCGTGTGTGTCTGCTGCATGAGAAGACCCCAGTGAGTGAGCATGTT ACCAAGTGCTGTAGTGGATCCCTGGTGGAAAGGCGGCCATGCTTCTCTGCTCTG ACAGTTGATGAAACATATGTCCCCAAAGAGTTTAAAGCTGAGACCTTCACCTTC CACTCTGATATCTGCACACTTCCAGAGAAGGAGAAGCAGATTAAGAAACAAACG GCTCTTGCTGAGCTGGTGAAGCACAAGCCCAAGGCTACAGCGGAGCAACTGAAG ACTGTCATGGATGACTTTGCACAGTTCCTGGATACATGTTGCAAGGCTGCTGAC AAGGACACCTGCTTCTCGACTGAGGGTCCAAACCTTGTCACTAGATGCAAAGAC GCCTTAGCC*GGAGGGGGCGGTTCC*CACCATCACCACCATCACTGATAA |
| 56 | gWiz-LS-mCXCL3$^{28-100}$-(Gly$_4$Ser)$_2$-mouse SA-(Gly$_4$Ser)-His$_6$ | <u>ATG</u><u>AGGGTCCCCGCTCAGCTCCTGGGGCTCCTGCTGCTCTGGCTCCCAGGTGCA CGATGT</u>GCTGTGGTGGCCTCTGAGCTGAGATGCCAGTGCCTGAACACCCTGCCC CGGGTGGACTTCGAGACAATCCAGAGCCTGACCGTGACCCCCCCTGGCCCTCAC TGTACCCAGACAGAAGTGATCGCCACCCTGAAGGACGGCCAGGAAGTGTGCCTG AATCCCCAGGGCCCCAGACTCCAGATCATCATCAAGAAGATCCTGAAGTCCGGC AAGAGCAGCGGTGGAGGCGGTAGCGGAGGCGGAGGGTCGGAAGCACACAAGAGT GAGATCGCCCATCGGTATAATGATTTGGGAGAACAACATTTCAAAGGCCTAGTC CTGATTGCCTTTTCCCAGTATCTCCAGAAATGCTCATACGATGAGCATGCCAAA TTAGTGCAGGAAGTAACAGACTTTGCAAAGACGTGTGTTGCCGATGAGTCTGCC GCCAACTGTGACAAATCCCTTCACACTCTTTTTGGAGATAAGTTGTGTGCCATT CCAAACCTCCGTGAAAACTATGGTGAACTGGCTGACTGCTGTACAAAACAAGAG CCCGAAAGAAACGAATGTTTCCTGCAACACAAAGATGACAACCCCAGCCTGCCA CCATTTGAAAGGCCAGAGGCTGAGGCCATGTGCACCTCCTTTAAGGAAAACCCA ACCACCTTTATGGGACACTATTTGCATGAAGTTGCCAGAAGACATCCTTATTTC TATGCCCCAGAACTTCTTTACTATGCTGAGCAGTACAATGAGATTCTGACCCAG TGTTGTGCAGAGGCTGACAAGGAAAGCTGCCTGACCCCGAAGCTTGATGGTGTG AAGGAGAAAGCATTGGTCTCATCTGTCCGTCAGAGAATGAAGTGCTCCAGTATG CAGAAGTTTGGAGAGAGAGCTTTTAAAGCATGGGCAGTAGCTCGTCTGAGCCAG ACATTCCCCAATGCTGACTTTGCAGAAATCACCAAATTGGCAACAGACCTGACC AAAGTCAACAAGGAGTGCTGCCATGGTGACCTGCTGGAATGCGCAGATGACAGG GCGGAACTTGCCAAGTACATGTGTGAAAACCAGGCGACTATCTCCAGCAAACTG CAGACTTGCTGCGATAAACCACTGTTGAAGAAAGCCCACTGTCTTAGTGAGGTG GAGCATGACACCATGCCTGCTGATCTGCCTGCCATTGCTGCTGATTTTGTTGAG GACCAGGAAGTGTGCAAGAACTATGCTGAGGCCAAGGATGTCTTCCTGGGCACG TTCTTGTATGAATATTCAAGAAGACACCCTGATTACTCTGTATCCCTGTTGCTG AGACTTGCTAAGAAATATGAAGCCACTCTGGAAAAGTGCTGCGCTGAAGCCAAT CCTCCCGCATGCTACGGCACAGTGCTTGCTGAATTTCAGCCTCTTGTAGAAGAG CCTAAGAACTTGGTCAAAACCAACTGTGATCTTTACGAGAAGCTTGGAGAATAT GGATTCCAAAATGCCATTCTAGTTCGCTACACCCAGAAAGCACCTCAGGTGTCA ACCCCAACTCTCGTGGAGGCTGCAAGAAACCTAGGAAGAGTGGGCACCAAGTGT TGTACACTTCCTGAAGATCAGAGACTGCCTTGTGTGGAAGACTATCTGTCTGCA ATCCTGAACCGTGTGTGTCTGCTGCATGAGAAGACCCCAGTGAGTGAGCATGTT ACCAAGTGCTGTAGTGGATCCCTGGTGGAAAGGCGGCCATGCTTCTCTGCTCTG ACAGTTGATGAAACATATGTCCCCAAAGAGTTTAAAGCTGAGACCTTCACCTTC CACTCTGATATCTGCACACTTCCAGAGAAGGAGAAGCAGATTAAGAAACAAACG GCTCTTGCTGAGCTGGTGAAGCACAAGCCCAAGGCTACAGCGGAGCAACTGAAG ACTGTCATGGATGACTTTGCACAGTTCCTGGATACATGTTGCAAGGCTGCTGAC** |

TABLE 12-continued

Sequence Summary

| SEQ ID NO | Description | Sequence |
|---|---|---|
| | | AAGGACACCTGCTTCTCGACTGAGGGTCCAAACCTTGTCACTAGATGCAAAGAC<br>GCCTTAGCC*GGAGGGGGCGGTTCC*CACCATCACCACCATCACTGATAA |
| 57 | gWiz-LS-<br>mCXCL4[30-105]-<br>(Gly4Ser)2-<br>mouse SA-<br>(Gly4Ser)-<br>His6 | ATGAGGGTCCCCGCTCAGCTCCTGGGGCTCCTGCTGCTCTGGCTCCCAGGTGCA<br>CGATGTGTGACATCTGCCGGCCCTGAGGAAAGCGACGGCGATCTGTCTTGCGTG<br>TGCGTGAAAACCATCAGCAGCGGCATCCACCTGAAGCACATCACCAGCCTGGAA<br>GTGATCAAGGCCGGCAGGCACTGTGCCGTGCCTCAGCTGATTGCCACCCTGAAG<br>AACGGCCGGAAGATCTGCCTGGACAGACAGGCCCCCCTGTACAAGAAAGTGATT<br>AAGAAGATCCTGGAAAGCGGTGGAGGCGGTAGCGGAGGCGGAGGGTCGGAAGCA<br>CACAAGAGTGAGATCGCCCATCGGTATAATGATTTGGGAGAACAACATTTCAAA<br>GGCCTAGTCCTGATTGCCTTTTCCCAGTATCTCCAGAAATGCTCATACGATGAG<br>CATGCCAAATTAGTGCAGGAAGTAACAGACTTTGCAAAGACGTGTGTTGCCGAT<br>GAGTCTGCCGCCAACTGTGACAAATCCCTTCACACTCTTTTTGGAGATAAGTTG<br>TGTGCCATTCCAAACCTCCGTGAAAACTATGGTGAACTGGCTGACTGCTGTACA<br>AAACAAGAGCCCGAAAGAAACGAATGTTTCCTGCAACACAAAGATGACAACCCC<br>AGCCTGCCACCATTTGAAAGGCCAGAGGCTGAGGCCATGTGCACCTCCTTTAAG<br>GAAAACCCAACCACCTTTATGGGACACTATTTGCATGAAGTTGCCAGAAGACAT<br>CCTTATTTCTATGCCCCAGAACTTCTTTACTATGCTGAGCAGTACAATGAGATT<br>CTGACCCAGTGTTGTGCAGAGGCTGACAAGGAAAGCTGCCTGACCCCGAAGCTT<br>GATGGTGTGAAGGAGAAAGCATTGGTCTCATCTGTCCGTCAGAGAATGAAGTGC<br>TCCAGTATGCAGAAGTTTGGAGAGAGAGCTTTTAAAGCATGGGCAGTAGCTCGT<br>CTGAGCCAGACATTCCCCAATGCTGACTTTGCAGAAATCACCAAATTGGCAACA<br>GACCTGACCAAAGTCAACAAGGAGTGCTGCCATGGTGACCTGCTGGAATGCGCA<br>GATGACAGGGCGGAACTTGCCAAGTACATGTGTGAAAACCAGGCGACTATCTCC<br>AGCAAACTGCAGACTTGCTGCGATAAACCACTGTTGAAGAAAGCCCACTGTCTT<br>AGTGAGGTGGAGCATGACACCATGCCTGCTGATCTGCCTGCCATTGCTGCTGAT<br>TTTGTTGAGGACCAGGAAGTGTGCAAGAACTATGCTGAGGCAAGGATGTCTTC<br>CTGGGCACGTTCTTGTATGAATATTCAAGAAGACACCCTGATTACTCTGTATCC<br>CTGTTGCTGAGACTTGCTAAGAAATATGAAGCCACTCTGGAAAAGTGCTGCGCT<br>GAAGCCAATCCTCCCGCATGCTACGGCACAGTGCTTGCTGAATTTCAGCCTCTT<br>GTAGAAGAGCCTAAGAACTTGGTCAAAACCAACTGTGATCTTTACGAGAAGCTT<br>GGAGAATATGGATTCCAAAATGCCATTCTAGTTCGCTACACCCAGAAAGCACCT<br>CAGGTGTCAACCCCAACTCTCGTGGAGGCTGCAAGAAACCTAGGAAGAGTGGGC<br>ACCAAGTGTTGTACACTTCCTGAAGATCAGAGACTGCCTTGTGTGGAAGACTAT<br>CTGTCTGCAATCCTGAACCGTGTGTGTCTGCTGCATGAGAAGACCCCAGTGAGT<br>GAGCATGTTACCAAGTGCTGTAGTGGATCCCTGGTGGAAAGGCGGCCATGCTTC<br>TCTGCTCTGACAGTTGATGAAACATATGTCCCCAAAGAGTTTAAAGCTGAGACC<br>TTCACCTTCCACTCTGATATCTGCACACTTCCAGAGAAGGAGAAGCAGATTAAG<br>AAACAAACGGCTCTTGCTGAGCTGGTGAAGCACAAGCCCAAGGCTACAGCGGAG<br>CAACTGAAGACTGTCATGGATGACTTTGCACAGTTCCTGGATACATGTTGCAAG<br>GCTGCTGACAAGGACACCTGCTTCTCGACTGAGGGTCCAAACCTTGTCACTAGA<br>TGCAAAGACGCCTTAGCC*GGAGGGGGCGGTTCC*CACCATCACCACCATCACTGA<br>TAA |
| 58 | gWiz-LS-<br>mCXCL5[48-118]-<br>(Gly4Ser)2-<br>mouse SA-<br>(Gly4Ser)-<br>His6 | ATGAGGGTCCCCGCTCAGCTCCTGGGGCTCCTGCTGCTCTGGCTCCCAGGTGCA<br>CGATGTGCCACCGAGCTGAGATGCGTGTGCCTGACCGTGACCCCCAAGATCAAC<br>CCCAAGCTGATCGCCAACCTGGAAGTGATCCCTGCCGGCCCTCAGTGCCCCACC<br>GTGGAAGTGATTGCCAAGCTGAAGAACCAGAAAGAAGTGTGCCTGGACCCCGAG<br>GCCCCCGTGATCAAGAAGATCATCCAGAAGATCCTGGGCAGCGACAAGAAGAAA<br>GCCGGTGGAGGCGGTAGCGGAGGCGGAGGGTCGGAAGCACACAAGAGTGAGATC<br>GCCCATCGGTATAATGATTTGGGAGAACAACATTTCAAAGGCCTAGTCCTGATT<br>GCCTTTTCCCAGTATCTCCAGAAATGCTCATACGATGAGCATGCCAAATTAGTG<br>CAGGAAGTAACAGACTTTGCAAAGACGTGTGTTGCCGATGAGTCTGCCGCCAAC<br>TGTGACAAATCCCTTCACACTCTTTTTGGAGATAAGTTGTGTGCCATTCCAAAC<br>CTCCGTGAAAACTATGGTGAACTGGCTGACTGCTGTACAAAACAAGAGCCCGAA<br>AGAAACGAATGTTTCCTGCAACACAAAGATGACAACCCCAGCCTGCCACCATTT<br>GAAAGGCCAGAGGCTGAGGCCATGTGCACCTCCTTTAAGGAAAACCCAACCACC<br>TTTATGGGACACTATTTGCATGAAGTTGCCAGAAGACATCCTTATTTCTATGCC<br>CCAGAACTTCTTTACTATGCTGAGCAGTACAATGAGATTCTGACCCAGTGTTGT<br>GCAGAGGCTGACAAGGAAAGCTGCCTGACCCCGAAGCTTGATGGTGTGAAGGAG<br>AAAGGATTGGTCTCATGTGTCCGTCAGAGAATGAAGTGCTCCAGTATGCAGAAG<br>TTTGGAGAGAGAGCTTTTAAAGCATGGGCAGTAGCTCGTCTGAGCCAGACATTC<br>CCCAATGCTGACTTTGCAGAAATCACCAAATTGGCAACAGACCTGACCAAAGTC<br>AACAAGGAGTGCTGCCATGGTGACCTGCTGGAATGCGCAGATGACAGGGCGGAA<br>CTTGCCAAGTACATGTGTGAAAACCAGGCGACTATCTCCAGCAAACTGCAGACT<br>TGCTGCGATAAACCACTGTTGAAGAAAGCCCACTGTCTTAGTGAGGTGGAGCAT<br>GACACCATGCCTGCTGATCTGCCTGCCATTGCTGCTGATTTTGTTGAGGACCAG<br>GAAGTGTGCAAGAACTATGCTGAGGCAAGGATGTCTTCCTGGGCACGTTCTTG<br>TATGAATATTCAAGAAGACACCCTGATTACTCTGTATCCCTGTTGCTGAGACTT<br>GCTAAGAAATATGAAGCCACTCTGGAAAAGTGCTGCGCTGAAGCCAATCCTCCC<br>GCATGCTACGGCACAGTGCTTGCTGAATTTCAGCCTCTTGTAGAAGAGCCTAAG<br>AACTTGGTCAAAACCAACTGTGATCTTTACGAGAAGCTTGGAGAATATGGATTC<br>CAAAATGCCATTCTAGTTCGCTACACCCAGAAAGCACCTCAGGTGTCAACCCCA<br>ACTCTCGTGGAGGCTGCAAGAAACCTAGGAAGAGTGGGCACCAAGTGTTGTACA<br>CTTCCTGAAGATCAGAGACTGCCTTGTGTGGAAGACTATCTGTCTGCAATCCTG |

TABLE 12-continued

Sequence Summary

| SEQ ID NO | Description | Sequence |
|---|---|---|
| | | AACCGTGTGTGTCTGCTGCATGAGAAGACCCCAGTGAGTGAGCATGTTACCAAG<br>TGCTGTAGTGGATCCCTGGTGGAAAGGCGGCCATGCTTCTCTGCTCTGACAGTT<br>GATGAAACATATGTCCCCAAAGAGTTTAAAGCTGAGACCTTCACCTTCCACTCT<br>GATATCTGCACACTTCCAGAGAAGGAGAAGCAGATTAAGAAACAAACGGCTCTT<br>GCTGAGCTGGTGAAGCACAAGCCCAAGGCTACAGCGGAGCAACTGAAGACTGTC<br>ATGGATGACTTTGCACAGTTCCTGGATACATGTTGCAAGGCTGCTGACAAGGAC<br>ACCTGCTTCTCGACTGAGGGTCCAAACCTTGTCACTAGATGCAAAGACGCCTTA<br>GCC*GGAGGGGGCGGTTCC*CACCATCACCACCATCACTGATAA |
| 59 | gWiz-LS-<br>mCXCL7[48-113]-<br>(Gly₄Ser)₂-<br>mouse SA-<br>(Gly₄Ser)-<br>His₆ | ATGAGGGTCCCCGCTCAGCTCCTGGGGCTCCTGCTGCTCTGGCTCCCAGGTGCA<br>CGATGTATCGAGCTGCGGTGCCGGTGCACCAACACCATCAGCGGCATCCCTTTC<br>AACAGCATCAGCCTCGTGAACGTGTACAGACCCGGCGTGCACTGCGCCGACGTG<br>GAAGTGATTGCTACACTGAAGAATGGGCAGAAAACCTGCCTGGACCCCAACGCC<br>CCTGGCGTGAAGCGGATCGTGATGAAGATTCTGAAGGCTACGGTGGAGGCGGT<br>AGCGGAGGCGGAGGGTCGGAAGCACACAAGAGTGAGATCGCCCATCGGTATAAT<br>GATTTGGGAGAACAACATTTCAAAGGCCTAGTCCTGATTGCCTTTTCCCAGTAT<br>CTCCAGAAATGCTCATACGATGAGCATGCCAAATTAGTGCAGGAAGTAACAGAC<br>TTTGCAAAGACGTGTGTTGCCGATGAGTCTGCCGCCAACTGTGACAAATCCCTT<br>CACACTCTTTTTGGAGATAAGTTGTGTGCCATTCCAAACCTCCGTGAAAACTAT<br>GGTGAACTGGCTGACTGCTGTACAAAACAAGAGCCCGAAAGAAACGAATGTTTC<br>CTGCAACACAAAGATGACAACCCCAGCCTGCCACCATTTGAAAGGCCAGAGGCT<br>GAGGCCATGTGCACCTCCTTTAAGGAAAACCCAACCACCTTTATGGGACACTAT<br>TTGCATGAAGTTGCCAGAAGACATCCTTATTTCTATGCCCCAGAACTTCTTTAC<br>TATGCTGAGCAGTACAATGAGATTCTGACCCAGTGTTGTGCAGAGGCTGACAAG<br>GAAAGCTGCCTGACCCCGAAGCTTGATGGTGTGAAGGAGAAAGCATTGGTCTCA<br>TCTGTCCGTCAGAGAATGAAGTGCTCCAGTATGCAGAAGTTTGGAGAGAGAGCT<br>TTTAAAGCATGGGCAGTAGCTCGTCTGAGCCAGACATTCCCCAATGCTGACTTT<br>GCAGAAATCACCAAATTGGCAACAGACCTGACCAAAGTCAACAAGGAGTGCTGC<br>CATGGTGACCTGCTGGAATGCGCAGATGACAGGGCGGAACTTGCCAAGTACATG<br>TGTGAAAACCAGGCGACTATCTCCAGCAAACTGCAGACTTGCTGCGATAAACCA<br>CTGTTGAAGAAAGCCCACTGTCTTAGTGAGGTGGAGCATGACACCATGCCTGCT<br>GATCTGCCTGCCATTGCTGCTGATTTTGTTGAGGACCAGGAAGTGTGCAAGAAC<br>TATGCTGAGGCCAAGGATGTCTTCCTGGGCACGTTCTTGTATGAATATTCAAGA<br>AGACACCCTGATTACTCTGTATCCCTGTTGCTGAGACTTGCTAAGAAATATGAA<br>GCCACTCTGGAAAAGTGCTGCGCTGAAGCCAATCCTCCCGCATGCTACGGCACA<br>GTGCTTGCTGAATTTCAGCCTCTTGTAGAAGAGCCTAAGAACTTGGTCAAAACC<br>AACTGTGATCTTTACGAGAAGCTTGGAGAATATGGATTCCAAAATGCCATTCTA<br>GTTCGCTACACCCAGAAAGCACCTCAGGTGTCAACCCCAACTCTCGTGGAGGCT<br>GCAAGAAACCTAGGAAGAGTGGGCACCAAGTGTTGTACACTTCCTGAAGATCAG<br>AGACTGCCTTGTGTGGAAGACTATCTGTCTGCAATCCTGAACCGTGTGTGTCTG<br>CTGCATGAGAAGACCCCAGTGAGTGAGCATGTTACCAAGTGCTGTAGTGGATCC<br>CTGGTGGAAAGGCGGCCATGCTTCTCTGCTCTGACAGTTGATGAAACATATGTC<br>CCCAAAGAGTTTAAAGCTGAGACCTTCACCTTCCACTCTGATATCTGCACACTT<br>CCAGAGAAGGAGAAGCAGATTAAGAAACAAACGGCTCTTGCTGAGCTGGTGAAG<br>CACAAGCCCAAGGCTACAGCGGAGCAACTGAAGACTGTCATGGATGACTTTGCA<br>CAGTTCCTGGATACATGTTGCAAGGCTGCTGACAAGGACACCTGCTTCTCGACT<br>GAGGGTCCAAACCTTGTCACTAGATGCAAAGACGCCTTAGCC*GGAGGGGGCGGT*<br>*TCC*CACCATCACCACCATCACTGATAA |
| 60 | gWiz-LS-<br>mCXCL9[22-126]-<br>(Gly₄Ser)₂-<br>mouse SA-<br>(Gly₄Ser)-<br>His₆ | ATGAGGGTCCCCGCTCAGCTCCTGGGGCTCCTGCTGCTCTGGCTCCCAGGTGCA<br>CGATGTACCCTCGTGATCCGGAACGCCCGGTGCAGCTGTATCAGCACCAGCAGA<br>GGCACCATCCACTACAAGAGCCTGAAGGATCTGAAGCAGTTCGCCCCCAGCCCC<br>AACTGCAACAAGACCGAGATTATCGCCACACTGAAAAACGGGGACCAGACCTGT<br>CTGGACCCCGACAGCGCCAACGTGAAGAAACTGATGAAGGAATGGGAGAAGAAG<br>ATCAGCCAGAAGAAGAAGCAGAAGCGGGCAAGAAACACCAGAAAAACATGAAG<br>AACCGGAAGCCCAAGACCCCCAGAGCCGGCGGAGATCCAGAAAGACCACAGGT<br>GGAGGCGGTAGCGGAGGCGGAGGGTCGGAAGCACACAAGAGTGAGATCGCCCAT<br>CGGTATAATGATTTGGGAGAACAACATTTCAAAGGCCTAGTCCTGATTGCCTTT<br>TCCCAGTATCTCCAGAAATGCTCATACGATGAGCATGCCAAATTAGTGCAGGAA<br>GTAACAGACTTTGCAAAGACGTGTGTTGCCGATGAGTCTGCCGCCAACTGTGAC<br>AAATCCCTTCACACTCTTTTTGGAGATAAGTTGTGTGCCATTCCAAACCTCCGT<br>GAAAACTATGGTGAACTGGCTGACTGCTGTACAAAACAAGAGCCCGAAAGAAAC<br>GAATGTTTCCTGCAACACAAAGATGACAACCCCAGCCTGCCACCATTTGAAAGG<br>CCAGAGGCTGAGGCCATGTGCACCTCCTTTAAGGAAAACCCAACCACCTTTATG<br>GGACACTATTTGCATGAAGTTGCCAGAAGACATCCTTATTTCTATGCCCCAGAA<br>CTTCTTTACTATGCTGAGCAGTACAATGAGATTCTGACCCAGTGTTGTGCAGAG<br>GCTGACAAGGAAAGCTGCCTGACCCCGAAGCTTGATGGTGTGAAGGAGAAAGCA<br>TTGGTCTCATCTGTCCGTCAGAGAATGAAGTGCTCCAGTATGCAGAAGTTTGGA<br>GAGAGAGCTTTTAAAGCATGGGCAGTAGCTCGTCTGAGCCAGACATTCCCCAAT<br>GCTGACTTTGCAGAAATCACCAAATTGGCAACAGACCTGACCAAAGTCAACAAG<br>GAGTGCTGCCATGGTGACCTGCTGGAATGCGCAGATGACAGGGCGGAACTTGCC<br>AAGTACATGTGTGAAAACCAGGCGACTATCTCCAGCAAACTGCAGACTTGCTGC<br>GATAAACCACTGTTGAAGAAAGCCCACTGTCTTAGTGAGGTGGAGCATGACACC<br>ATGCCTGCTGATCTGCCTGCCATTGCTGCTGATTTTGTTGAGGACCAGGAAGTG<br>TGCAAGAACTATGCTGAGGCCAAGGATGTCTTCCTGGGCACGTTCTTGTATGAA |

TABLE 12-continued

Sequence Summary

| SEQ ID NO | Description | Sequence |
|---|---|---|
| | | TATTCAAGAAGACACCCTGATTACTCTGTATCCCTGTTGCTGAGACTTGCTAAG<br>AAATATGAAGCCACTCTGGAAAAGTGCTGCGCTGAAGCCAATCCTCCCGCATGC<br>TACGGCACAGTGCTTGCTGAATTTCAGCCTCTTGTAGAAGAGCCTAAGAACTTG<br>GTCAAAACCAACTGTGATCTTTACGAGAAGCTTGGAGAATATGGATTCCAAAAT<br>GCCATTCTAGTTCGCTACACCCAGAAAGCACCTCAGGTGTCAACCCCAACTCTC<br>GTGGAGGCTGCAAGAAACCTAGGAAGAGTGGGCACCAAGTGTTGTACACTTCCT<br>GAAGATCAGAGACTGCCTTGTGTGGAAGACTATCTGTCTGCAATCCTGAACCGT<br>GTGTGTCTGCTGCATGAGAAGACCCCAGTGAGTGAGCATGTTACCAAGTGCTGT<br>AGTGGATCCCTGGTGGAAAGGCGGCCATGCTTCTCTGCTCTGACAGTTGATGAA<br>ACATATGTCCCCAAAGAGTTTAAAGCTGAGACCTTCACCTTCCACTCTGATATC<br>TGCACACTTCCAGAGAAGGAGAAGCAGATTAAGAAACAAACGGCTCTTGCTGAG<br>CTGGTGAAGCACAAGCCCAAGGCTACAGCGGAGCAACTGAAGACTGTCATGGAT<br>GACTTTGCACAGTTCCTGGATACATGTTGCAAGGCTGCTGACAAGGACACCTGC<br>TTCTCGACTGAGGGTCCAAACCTTGTCACTAGATGCAAAGACGCCTTAGCC<u>GGA<br>GGGGGCGGTTCC</u>CACCATCACCACCATCACTGATAA |
| 61 | gWiz-LS-<br>mCXCL10$^{22\text{-}98}$-<br>(Gly$_4$Ser)$_2$-<br>mouse SA-<br>(Gly$_4$Ser)-<br>His$_6$ | ATGAGGGTCCCCGCTCAGCTCCTGGGGCTCCTGCTGCTCTGGCTCCCAGGTGCA<br><u>CGATG</u>TATCCCACTGGCCAGAACCGTGCGGTGCAACTGCATCCACATCGACGAT<br>GGCCCCGTGCGGATGAGAGCCATCGGCAAGCTGGAAATCATCCCCGCCAGCCTG<br>AGCTGCCCCAGAGTGGAAATTATCGCCACCATGAAGAAGAACGACGAGCAGCGG<br>TGCCTGAACCCCGAGAGCAAGACCATCAAGAACCTGATGAAGGCCTTTAGCCAG<br>AAGCGGAGCAAGAGGGCCCCAGGTGGAGGCGGTAGCGGAGGCGGAGGGTCGGAA<br>GCACACAAGAGTGAGATCGCCCATCGGTATAATGATTTGGGAGAACAACATTTC<br>AAAGGCCTAGTCCTGATTGCCTTTTCCCAGTATCTCCAGAAATGCTCATACGAT<br>GAGCATGCCAAATTAGTGCAGGAAGTAACAGACTTTGCAAAGACGTGTGTTGCC<br>GATGAGTCTGCCGCCAACTGTGACAAATCCCTTCACACTCTTTTTGGAGATAAG<br>TTGTGTGCCATTCCAAACCTCCGTGAAAACTATGGTGAACTGGCTGACTGCTGT<br>ACAAAACAAGAGCCCGAAAGAAACGAATGTTTCCTGCAACACAAAGATGACAAC<br>CCCAGCCTGCCACCATTTGAAAGGCCAGAGGCTGAGGCCATGTGCACCTCCTTT<br>AAGGAAAACCCAACCACCTTTATGGGACACTATTTGCATGAAGTTGCCAGAAGA<br>CATCCTTATTTCTATGCCCCAGAACTTCTTTACTATGCTGAGCAGTACAATGAG<br>ATTCTGACCCAGTGTTGTGCAGAGGCTGACAAGGAAAGCTGCCTGACCCCGAAG<br>CTTGATGGTGTGAAGGAGAAAGCATTGGTCTCATCTGTCCGTCAGAGAATGAAG<br>TGCTCCAGTATGCAGAAGTTTGGAGAGAGAGCTTTTAAAGCATGGGCAGTAGCT<br>CGTCTGAGCCAGACATTCCCCAATGCTGACTTTGCAGAAATCACCAAATTGGCA<br>ACAGACCTGACCAAAGTCAACAAGGAGTGCTGCCATGGTGACCTGCTGGAATGC<br>GCAGATGACAGGGCGGAACTTGCCAAGTACATGTGTGAAAACCAGGCGACTATC<br>TCCAGCAAACTGCAGACTTGCTGCGATAAACCACTGTTGAAGAAAGCCCACTGT<br>CTTAGTGAGGTGGAGCATGACACCATGCCTGCTGATCTGCCTGCCATTGCTGCT<br>GATTTTGTTGAGGACCAGGAAGTGTGCAAGAACTATGCTGAGGCCAAGGATGTC<br>TTCCTGGGCACGTTCTTGTATGAATATTCAAGAAGACACCCTGATTACTCTGTA<br>TCCCTGTTGCTGAGACTTGCTAAGAAATATGAAGCCACTCTGGAAAAGTGCTGC<br>GCTGAAGCCAATCCTCCCGCATGCTACGGCACAGTGCTTGCTGAATTTCAGCCT<br>CTTGTAGAAGAGCCTAAGAACTTGGTCAAAACCAACTGTGATCTTTACGAGAAG<br>CTTGGAGAATATGGATTCCAAAATGCCATTCTAGTTCGCTACACCCAGAAAGCA<br>CCTCAGGTGTCAACCCCAACTCTCGTGGAGGCTGCAAGAAACCTAGGAAGAGTG<br>GGCACCAAGTGTTGTACACTTCCTGAAGATCAGAGACTGCCTTGTGTGGAAGAC<br>TATCTGTCTGCAATCCTGAACCGTGTGTGTCTGCTGCATGAGAAGACCCCAGTG<br>AGTGAGCATGTTACCAAGTGCTGTAGTGGATCCCTGGTGGAAAGGCGGCCATGC<br>TTCTCTGCTCTGACAGTTGATGAAACATATGTCCCCAAAGAGTTTAAAGCTGAG<br>ACCTTCACCTTCCACTCTGATATCTGCACACTTCCAGAGAAGGAGAAGCAGATT<br>AAGAAACAAACGGCTCTTGCTGAGCTGGTGAAGCACAAGCCCAAGGCTACAGCG<br>GAGCAACTGAAGACTGTCATGGATGACTTTGCACAGTTCCTGGATACATGTTGC<br>AAGGCTGCTGACAAGGACACCTGCTTCTCGACTGAGGGTCCAAACCTTGTCACT<br>AGATGCAAAGACGCCTTAGCC<u>GGAGGGGGCGGTTCC</u>CACCATCACCACCATCAC<br>TGATAA |
| 62 | gWiz-LS-<br>mCXCL11$^{22\text{-}100}$-<br>(Gly$_4$Ser)$_2$-<br>mouse SA-<br>(Gly$_4$Ser)-<br>His$_6$ | ATGAGGGTCCCCGCTCAGCTCCTGGGGCTCCTGCTGCTCTGGCTCCCAGGTGCA<br><u>CGATG</u>TTTCCTGATGTTCAAGCAGGGCCGGTGCCTGTGCATCGGCCCTGGAATG<br>AAGGCCGTGAAGATGGCCGAGATCGAGAAGGCCAGCGTGATCTACCCCAGCAAC<br>GGCTGCGACAAGGTGGAAGTGATCGTGACCATGAAGGCCCACAAGCGGCAGAGA<br>TGCCTGGACCCCAGATCCAAGCAGCCCGGCTGATCATGCAGGCTATCGAGAAG<br>AAGAATTTCCTGCGGCGGCAGAACATGGGTGGAGGCGGTAGCGGAGGCGGAGGG<br>TCGGAAGCACACAAGAGTGAGATCGCCCATCGGTATAATGATTTGGGAGAACAA<br>CATTTCAAAGGCCTAGTCCTGATTGCCTTTTCCCAGTATCTCCAGAAATGCTCA<br>TACGATGAGCATGCCAAATTAGTGCAGGAAGTAACAGACTTTGCAAAGACGTGT<br>GTTGCCGATGAGTCTGCCGCCAACTGTGACAAATCCCTTCACACTCTTTTTGGA<br>GATAAGTTGTGTGCCATTCCAAACCTCCGTGAAAACTATGGTGAACTGGCTGAC<br>TGCTGTACAAAACAAGAGCCCGAAAGAAACGAATGTTTCCTGCAACACAAAGAT<br>GACAACCCCAGCCTGCCACCATTTGAAAGGCCAGAGGCTGAGGCCATGTGCACC<br>TCCTTTAAGGAAAACCCAACCACCTTTATGGGACACTATTTGCATGAAGTTGCC<br>AGAAGACATCCTTATTTCTATGCCCCAGAACTTCTTTACTATGCTGAGCAGTAC<br>AATGAGATTCTGACCCAGTGTTGTGCAGAGGCTGACAAGGAAAGCTGCCTGACC<br>CCGAAGCTTGATGGTGTGAAGGAGAAAGCATTGGTCTCATCTGTCCGTCAGAGA<br>ATGAAGTGCTCCAGTATGCAGAAGTTTGGAGAGAGAGCTTTTAAAGCATGGGCA |

TABLE 12-continued

Sequence Summary

| SEQ ID NO | Description | Sequence |
|---|---|---|
| | | GTAGCTCGTCTGAGCCAGACATTCCCCAATGCTGACTTTGCAGAAATCACCAAA<br>TTGGCAACAGACCTGACCAAAGTCAACAAGGAGTGCTGCCATGGTGACCTGCTG<br>GAATGCGCAGATGACAGGGCGGAACTTGCCAAGTACATGTGTGAAAACCAGGCG<br>ACTATCTCCAGCAAACTGCAGACTTGCTGCGATAAACCACTGTTGAAGAAAGCC<br>CACTGTCTTAGTGAGGTGGAGCATGACACCATGCCTGCTGATCTGCCTGCCATT<br>GCTGCTGATTTTGTTGAGGACCAGGAAGTGTGCAAGAACTATGCTGAGGCCAAG<br>GATGTCTTCCTGGGCACGTTCTTGTATGAATATTCAAGAAGACACCCTGATTAC<br>TCTGTATCCCTGTTGCTGAGACTTGCTAAGAAATATGAAGCCACTCTGGAAAAG<br>TGCTGCGCTGAAGCCAATCCTCCCGCATGCTACGGCACAGTGCTTGCTGAATTT<br>CAGCCTCTTGTAGAAGAGCCTAAGAACTTGGTCAAAACCAACTGTGATCTTTAC<br>GAGAAGCTTGGAGAATATGGATTCCAAAATGCCATTCTAGTTCGCTACACCCAG<br>AAAGCCACCTCAGGTGTCAACCCCAACTCTCGTGGAGGCTGCAAGAAACCTAGGA<br>AGAGTGGGCACCAAGTGTTGTACACTTCCTGAAGATCAGAGACTGCCTTGTGTG<br>GAAGACTATCTGTGTGCAATCCTGAACCGTGTGTGTGCTGCATGAGAAGACC<br>CCAGTGAGTGAGCATGTTACCAAGTGCTGTAGTGGATCCCTGGTGGAAAGGCGG<br>CCATGCTTCTCTGCTCTGACAGTTGATGAAACATATGTCCCCAAAGAGTTTAAA<br>GCTGAGACCTTCACCTTCCACTCTGATATCTGCACACTTCCAGAGAAGGAGAAG<br>CAGATTAAGAAACAAACGGCTCTTGCTGAGCTGGTGAAGCACAAGCCCAAGGCT<br>ACAGCGGAGCAACTGAAGACTGTCATGGATGACTTTGCACAGTTCCTGGATACA<br>TGTTGCAAGGCTGCTGACAAGGACACCTGCTTCTCGACTGAGGGTCCAAACCTT<br>GTCACTAGATGCAAAGACGCCTTAGCC<u>GGAGGGGGCGGTTCC</u>CACCATCACCAC<br>CATCACTGATAA |
| 63 | LS-hCXCL1$^{35-107}$-(Gly$_4$Ser)$_2$-mouse SA-(Gly$_4$Ser)-His$_6$ | <u>MRVPAQLLGLLLLWLPGARC</u>ASVATELRCQCLQTLQGIHPKNIQSVNVKSPGPH<br>CAQTEVIATLKNGRKACLNPASPIVKKIIEKMLNSDKSNGGGGSGGGGSEAHKS<br>EIAHRYNDLGEQHFKGLVLIAFSQYLQKCSYDEHAKLVQEVTDFAKTCVADESA<br>ANCDKSLHTLFGDKLCAIPNLRENYGELADCCTKQEPERNECFLQHKDDNPSLP<br>PFERPEAEAMCTSFKENPTTFMGHYLHEVARRHPYFYAPELLYYAEQYNEILTQ<br>CCAEADKESCLTPKLDGVKEKALVSSVRQRMKCSSMQKFGERAFKAWAVARLSQ<br>TFPNADFAEITKLATDLTKVNKECCHGDLLECADDRAELAKYMCENQATISSKL<br>QTCCDKPLLKKAHCLSEVEHDTMPADLPAIAADFVEDQEVCKNYAEAKDVFLGT<br>FLYEYSRRHPDYSVSLLLRLAKKYEATLEKCCAEANPPACYGTVLAEFQPLVEE<br>PKNLVKTNCDLYEKLGEYGFQNAILVRYTQKAPQVSTPTLVEAARNLGRVGTKC<br>CTLPEDQRLPCVEDYLSAILNRVCLLHEKTPVSEHVTKCCSGSLVERRPCFSAL<br>TVDETYVPKEFKAETFTFHSDICTLPEKEKQIKKQTALAELVKHKPKATAEQLK<br>TVMDDFAQFLDTCCKAADKDTCFSTEGPNLVTRCKDALA<u>GGGGS</u>HHHHHH-- |
| 64 | LS-hCXCL2$^{35-107}$-(Gly$_4$Ser)$_2$-mouse SA-(Gly$_4$Ser)-His$_6$ | <u>MRVPAQLLGLLLLWLPGARC</u>APLATELRCQCLQTLQGIHLKNIQSVKVKSPGPH<br>CAQTEVIATLKNGQKACLNPASPMVKKIIEKMLKNGKSNGGGGSGGGGSEAHKS<br>EIAHRYNDLGEQHFKGLVLIAFSQYLQKCSYDEHAKLVQEVTDFAKTCVADESA<br>ANCDKSLHTLFGDKLCAIPNLRENYGELADCCTKQEPERNECFLQHKDDNPSLP<br>PFERPEAEAMCTSFKENPTTFMGHYLHEVARRHPYFYAPELLYYAEQYNEILTQ<br>CCAEADKESCLTPKLDGVKEKALVSSVRQRMKCSSMQKFGERAFKAWAVARLSQ<br>TFPNADFAEITKLATDLTKVNKECCHGDLLECADDRAELAKYMCENQATISSKL<br>QTCCDKPLLKKAHCLSEVEHDTMPADLPAIAADFVEDQEVCKNYAEAKDVFLGT<br>FLYEYSRRHPDYSVSLLLRLAKKYEATLEKCCAEANPPACYGTVLAEFQPLVEE<br>PKNLVKTNCDLYEKLGEYGFQNAILVRYTQKAPQVSTPTLVEAARNLGRVGTKC<br>CTLPEDQRLPCVEDYLSAILNRVCLLHEKTPVSEHVTKCCSGSLVERRPCFSAL<br>TVDETYVPKEFKAETFTFHSDICTLPEKEKQIKKQTALAELVKHKPKATAEQLK<br>TVMDDFAQFLDTCCKAADKDTCFSTEGPNLVTRCKDALA<u>GGGGS</u>HHHHHH-- |
| 65 | LS-hCXCL3$^{35-107}$-(Gly$_4$Ser)$_2$-mouse SA-(Gly$_4$Ser)-His$_6$ | <u>MRVPAQLLGLLLLWLPGARC</u>ASVVTELRCQCLQTLQGIHLKNIQSVNVRSPGPH<br>CAQTEVIATLKNGKKACLNPASPMVQKIILNKGSTNGGGGSGGGGSEAHKS<br>EIAHRYNDLGEQHFKGLVLIAFSQYLQKCSYDEHAKLVQEVTDFAKTCVADESA<br>ANCDKSLHTLFGDKLCAIPNLRENYGELADCCTKQEPERNECFLQHKDDNPSLP<br>PFERPEAEAMCTSFKENPTTFMGHYLHEVARRHPYFYAPELLYYAEQYNEILTQ<br>CCAEADKESCLTPKLDGVKEKALVSSVRQRMKCSSMQKFGERAFKAWAVARLSQ<br>TFPNADFAEITKLATDLTKVNKECCHGDLLECADDRAELAKYMCENQATISSKL<br>QTCCDKPLLKKAHCLSEVEHDTMPADLPAIAADFVEDQEVCKNYAEAKDVFLGT<br>FLYEYSRRHPDYSVSLLLRLAKKYEATLEKCCAEANPPACYGTVLAEFQPLVEE<br>PKNLVKTNCDLYEKLGEYGFQNAILVRYTQKAPQVSTPTLVEAARNLGRVGTKC<br>CTLPEDQRLPCVEDYLSAILNRVCLLHEKTPVSEHVTKCCSGSLVERRPCFSAL<br>TVDETYVPKEFKAETFTFHSDICTLPEKEKQIKKQTALAELVKHKPKATAEQLK<br>TVMDDFAQFLDTCCKAADKDTCFSTEGPNLVTRCKDALA<u>GGGGS</u>HHHHHH-- |
| 66 | LS-hCXCL4$^{32-101}$-(Gly$_4$Ser)$_2$-mouse SA-(Gly$_4$Ser)-His$_6$ | <u>MRVPAQLLGLLLLWLPGARC</u>EAEEDGDLQCLCVKTTSQVRPRHITSLEVIKAGP<br>HCPTAQLIATLKNGRKICLDLQAPLYKKIIKKLLESGGGGSGGGGSEAHKSEIA<br>HRYNDLGEQHFKGLVLIAFSQYLQKCSYDEHAKLVQEVTDFAKTCVADESAANC<br>DKSLHTLFGDKLCAIPNLRENYGELADCCTKQEPERNECFLQHKDDNPSLPPFE<br>RPEAEAMCTSFKENPTTFMGHYLHEVARRHPYFYAPELLYYAEQYNEILTQCCA<br>EADKESCLTPKLDGVKEKALVSSVRQRMKCSSMQKFGERAFKAWAVARLSQTFP<br>NADFAEITKLATDLTKVNKECCHGDLLECADDRAELAKYMCENQATISSKLQTC<br>CDKPLLKKAHCLSEVEHDTMPADLPAIAADFVEDQEVCKNYAEAKDVFLGTFLY<br>EYSRRHPDYSVSLLLRLAKKYEATLEKCCAEANPPACYGTVLAEFQPLVEEPKN<br>LVKTNCDLYEKLGEYGFQNAILVRYTQKAPQVSTPTLVEAARNLGRVGTKCCTL |

TABLE 12-continued

Sequence Summary

| SEQ ID NO | Description | Sequence |
|---|---|---|
| | | PEDQRLPCVEDYLSAILNRVCLLHEKTPVSEHVTKCCSGSLVERRPCFSALTVD ETYVPKEFKAETFTFHSDICTLPEKEKQIKKQTALAELVKHKPKATAEQLKTVM DDFAQFLDTCCKAADKDTCFSTEGPNLVTRCKDALA*GGGGS*HHHHHH-- |
| 67 | LS-hCXCL5$^{44-114}$-(Gly$_4$Ser)$_2$-mouse SA-(Gly$_4$Ser)-His$_6$ | MRVPAQLLGLLLLWLPGARCLRELRCVCLQTTQGVHPKMISNLQVFAIGPQCSK VEVVASLKNGKEICLDPEAPFLKKVIQKILDGGNKENGGGGSGGGGSEAHKSEI AHRYNDLGEQHFKGLVLIAFSQYLQKCSYDEHAKLVQEVTDFAKTCVADESAAN CDKSLHTLFGDKLCAIPNLRENYGELADCCTKQEPERNECFLQHKDDNPSLPPF ERPEAEAMCTSFKENPTTFMGHYLHEVARRHPYFYAPELLYYAEQYNEILTQCC AEADKESCLTPKLDGVKEKALVSSVRQRMKCSSMQKFGERAFKAWAVARLSQTF PNADFAEITKLATDLTKVNKECCHGDLLECADDRAELAKYMCENQATISSKLQT CCDKPLLKKAHCLSEVEHDTMPADLPAIAADFVEDQEVCKNYAEAKDVFLGTFL YEYSRRHPDYSVSLLLRLAKKYEATLEKCCAEANPPACYGTVLAEFQPLVEEPK NLVKTNCDLYEKLGEYGFQNAILVRYTQKAPQVSTPTLVEAARNLGRVGTKCCT LPEDQRLPCVEDYLSAILNRVCLLHEKTPVSEHVTKCCSGSLVERRPCFSALTV DETYVPKEFKAETFTFHSDICTLPEKEKQIKKQTALAELVKHKPKATAEQLKTV MDDFAQFLDTCCKAADKDTCFSTEGPNLVTRCKDALA*GGGGS*HHHHHH-- |
| 68 | LS-hCXCL6$^{43-114}$-(Gly$_4$Ser)$_2$-mouse SA-(Gly$_4$Ser)-His$_6$ | MRVPAQLLGLLLLWLPGARCVLTELRCTCLRVTLRVNPKTIGKLQVFPAGPQCS KVEVVASLKNGKQVCLDPEAPFLKKVIQKILDSGNKKNGGGGSGGGGSEAHKSE IAHRYNDLGEQHFKGLVLIAFSQYLQKCSYDEHAKLVQEVTDFAKTCVADESAA NCDKSLHTLFGDKLCAIPNLRENYGELADCCTKQEPERNECFLQHKDDNPSLPP FERPEAEAMCTSFKENPTTFMGHYLHEVARRHPYFYAPELLYYAEQYNEILTQC CAEADKESCLTPKLDGVKEKALVSSVRQRMKCSSMQKFGERAFKAWAVARLSQT FPNADFAEITKLATDLTKVNKECCHGDLLECADDRAELAKYMCENQATISSKLQ TCCDKPLLKKAHCLSEVEHDTMPADLPAIAADFVEDQEVCKNYAEAKDVFLGTF LYEYSRRHPDYSVSLLLRLAKKYEATLEKCCAEANPPACYGTVLAEFQPLVEEP KNLVKTNCDLYEKLGEYGFQNAILVRYTQKAPQVSTPTLVEAARNLGRVGTKCC TLPEDQRLPCVEDYLSAILNRVCLLHEKTPVSEHVTKCCSGSLVERRPCFSALT VDETYVPKEFKAETFTFHSDICTLPEKEKQIKKQTALAELVKHKPKATAEQLKT VMDDFAQFLDTCCKAADKDTCFSTEGPNLVTRCKDALA*GGGGS*HHHHHH-- |
| 69 | LS-hCXCL7$^{59-121}$-(Gly$_4$Ser)$_2$-mouse SA-(Gly$_4$Ser)-His$_6$ | MRVPAQLLGLLLLWLPGARCAELRCMCIKTTSGIHPKNIQSLEVIGKGTHCNQV EVIATLKDGRKICLDPDAPRIKKIVQKKLGGGGSGGGGSEAHKSEIAHRYNDLG EQHFKGLVLIAFSQYLQKCSYDEHAKLVQEVTDFAKTCVADESAANCDKSLHTL FGDKLCAIPNLRENYGELADCCTKQEPERNECFLQHKDDNPSLPPFERPEAEAM CTSFKENPTTFMGHYLHEVARRHPYFYAPELLYYAEQYNEILTQCCAEADKESC LTPKLDGVKEKALVSSVRQRMKCSSMQKFGERAFKAWAVARLSQTFPNADFAEI TKLATDLTKVNKECCHGDLLECADDRAELAKYMCENQATISSKLQTCCDKPLLK KAHCLSEVEHDTMPADLPAIAADFVEDQEVCKNYAEAKDVFLGTFLYEYSRRHP DYSVSLLLRLAKKYEATLEKCCAEANPPACYGTVLAEFQPLVEEPKNLVKTNCD LYEKLGEYGFQNAILVRYTQKAPQVSTPTLVEAARNLGRVGTKCCTLPEDQRLP CVEDYLSAILNRVCLLHEKTPVSEHVTKCCSGSLVERRPCFSALTVDETYVPKE FKAETFTFHSDICTLPEKEKQIKKQTALAELVKHKPKATAEQLKTVMDDFAQFL DTCCKAADKDTCFSTEGPNLVTRCKDALA*GGGGS*HHHHHH-- |
| 70 | LS-hCXCL8$^{28-99}$-(Gly$_4$Ser)$_2$-mouse SA-(Gly$_4$Ser)-His$_6$ | MRVPAQLLGLLLLWLPGARCSAKELRCQCIKTYSKPFHPKFIKELRVIESGPHC ANTEIIVKLSDGRELCLDPKENWVQRVVEKFLKRAENSGGGGSGGGGSEAHKSE IAHRYNDLGEQHFKGLVLIAFSQYLQKCSYDEHAKLVQEVTDFAKTCVADESAA NCDKSLHTLFGDKLCAIPNLRENYGELADCCTKQEPERNECFLQHKDDNPSLPP FERPEAEAMCTSFKENPTTFMGHYLHEVARRHPYFYAPELLYYAEQYNEILTQC CAEADKESCLTPKLDGVKEKALVSSVRQRMKCSSMQKFGERAFKAWAVARLSQT FPNADFAEITKLATDLTKVNKECCHGDLLECADDRAELAKYMCENQATISSKLQ TCCDKPLLKKAHCLSEVEHDTMPADLPAIAADFVEDQEVCKNYAEAKDVFLGTF LYEYSRRHPDYSVSLLLRLAKKYEATLEKCCAEANPPACYGTVLAEFQPLVEEP KNLVKTNCDLYEKLGEYGFQNAILVRYTQKAPQVSTPTLVEAARNLGRVGTKCC TLPEDQRLPCVEDYLSAILNRVCLLHEKTPVSEHVTKCCSGSLVERRPCFSALT VDETYVPKEFKAETFTFHSDICTLPEKEKQIKKQTALAELVKHKPKATAEQLKT VMDDFAQFLDTCCKAADKDTCFSTEGPNLVTRCKDALA*GGGGS*HHHHHH-- |
| 71 | LS-hCXCL9$^{23-115}$-(Gly$_4$Ser)$_2$-mouse SA-(Gly$_4$Ser)-His$_6$ | MRVPAQLLGLLLLWLPGARCTPVVRKGRCSCISTNQGTIHLQSLKDLKQFAPSP SCEKIEIIATLKNGVQTCLNPDSADVKELIKKWEKQVSQKKKQKNGKKHQKKKV LKVRKSQRSRQKKTTGGGGSGGGGSEAHKSEIAHRYNDLGEQHFKGLVLIAFSQ YLQKCSYDEHAKLVQEVTDFAKTCVADESAANCDKSLHTLFGDKLCAIPNLREN YGELADCCTKQEPERNECFLQHKDDNPSLPPFERPEAEAMCTSFKENPTTFMGH YLHEVARRHPYFYAPELLYYAEQYNEILTQCCAEADKESCLTPKLDGVKEKALV SSVRQRMKCSSMQKFGERAFKAWAVARLSQTFPNADFAEITKLATDLTKVNKEC CHGDLLECADDRAELAKYMCENQATISSKLQTCCDKPLLKKAHCLSEVEHDTMP ADLPAIAADFVEDQEVCKNYAEAKDVFLGTFLYEYSRRHPDYSVSLLLRLAKKY EATLEKCCAEANPPACYGTVLAEFQPLVEEPKNLVKTNCDLYEKLGEYGFQNAI LVRYTQKAPQVSTPTLVEAARNLGRVGTKCCTLPEDQRLPCVEDYLSAILNRVC LLHEKTPVSEHVTKCCSGSLVERRPCFSALTVDETYVPKEFKAETFTFHSDICT LPEKEKQIKKQTALAELVKHKPKATAEQLKTVMDDFAQFLDTCCKAADKDTCFS TEGPNLVTRCKDALA*GGGGS*HHHHHH-- |

TABLE 12-continued

Sequence Summary

| SEQ ID NO | Description | Sequence |
|---|---|---|
| 72 | LS-hCXCL10$^{22-98}$-(Gly$_4$Ser)$_2$-mouse SA-(Gly$_4$Ser)-His$_6$ | MRVPAQLLGLLLLWLPGARCVPLSRTVRCTCISISNQPVNPRSLEKLEIIPASQ FCPRVEIIATMKKKGEKRCLNPESKAIKNLLKAVSKERSKRSPGGGGSGGGGSE AHKSEIAHRYNDLGEQHFKGLVLIAFSQYLQKCSYDEHAKLVQEVTDFAKTCVA DESAANCDKSLHTLFGDKLCAIPNLRENYGELADCCTKQEPERNECFLQHKDDN PSLPPFERPEAEAMCTSFKENPTTFMGHYLHEVARRHPYFYAPELLYYAEQYNE ILTQCCAEADKESCLTPKLDGVKEKALVSSVRQRMKCSSMQKFGERAFKAWAVA RLSQTFPNADFAEITKLATDLTKVNKECCHGDLLECADDRAELAKYMCENQATI SSKLQTCCDKPLLKKAHCLSEVEHDTMPADLPAIAADFVEDQEVCKNYAEAKDV FLGTFLYEYSRRHPDYSVSLLLRLAKKYEATLEKCCAEANPPACYGTVLAEFQP LVEEPKNLVKTNCDLYEKLGEYGFQNAILVRYTQKAPQVSTPTLVEAARNLGRV GTKCCTLPEDQRLPCVEDYLSAILNRVCLLHEKTPVSEHVTKCCSGSLVERRPC FSALTVDETYVPKEFKAETFTFHSDICTLPEKEKQIKKQTALAELVKHKPKATA EQLKTVMDDFAQFLDTCCKAADKDTCFSTEGPNLVTRCKDALA*GGGGS*HHHHHH-- |
| 73 | LS-hCXCL11$^{22-94}$-(Gly$_4$Ser)$_2$-mouse SA-(Gly$_4$Ser)-His$_6$ | MRVPAQLLGLLLLWLPGARCFPMFKRGRCLCIGPGVKAVKVADIEKASIMYPSN NCDKIEVIITLKENKGQRCLNPKSKQARLIIKKVERKNFGGGGSGGGGSEAHKS EIAHRYNDLGEQHFKGLVLIAFSQYLQKCSYDEHAKLVQEVTDFAKTCVADESA ANCDKSLHTLFGDKLCAIPNLRENYGELADCCTKQEPERNECFLQHKDDNPSLP PFERPEAEAMCTSFKENPTTFMGHYLHEVARRHPYFYAPELLYYAEQYNEILTQ CCAEADKESCLTPKLDGVKEKALVSSVRQRMKCSSMQKFGERAFKAWAVARLSQ TFPNADFAEITKLATDLTKVNKECCHGDLLECADDRAELAKYMCENQATISSKL QTCCDKPLLKKAHCLSEVEHDTMPADLPAIAADFVEDQEVCKNYAEAKDVFLGT FLYEYSRRHPDYSVSLLLRLAKKYEATLEKCCAEANPPACYGTVLAEFQPLVEE PKNLVKTNCDLYEKLGEYGFQNAILVRYTQKAPQVSTPTLVEAARNLGRVGTKC CTLPEDQRLPCVEDYLSAILNRVCLLHEKTPVSEHVTKCCSGSLVERRPCFSAL TVDETYVPKEFKAETFTFHSDICTLPEKEKQIKKQTALAELVKHKPKATAEQLK TVMDDFAQFLDTCCKAADKDTCFSTEGPNLVTRCKDALA*GGGGS*HHHHHH-- |
| 74 | LS-mCXCL1$^{25-96}$-(Gly$_4$Ser)$_2$-mouse SA-(Gly$_4$Ser)-His$_6$ | MRVPAQLLGLLLLWLPGARCAPIANELRCQCLQTMAGIHLKNIQSLKVLPSGPH CTQTEVIATLKNGREACLDPEAPLVQKIVQKMLKGVPKGGGGSGGGGSEAHKSE IAHRYNDLGEQHFKGLVLIAFSQYLQKCSYDEHAKLVQEVTDFAKTCVADESAA NCDKSLHTLFGDKLCAIPNLRENYGELADCCTKQEPERNECFLQHKDDNPSLPP FERPEAEAMCTSFKENPTTFMGHYLHEVARRHPYFYAPELLYYAEQYNEILTQC CAEADKESCLTPKLDGVKEKALVSSVRQRMKCSSMQKFGERAFKAWAVARLSQT FPNADFAEITKLATDLTKVNKECCHGDLLECADDRAELAKYMCENQATISSKLQ TCCDKPLLKKAHCLSEVEHDTMPADLPAIAADFVEDQEVCKNYAEAKDVFLGTF LYEYSRRHPDYSVSLLLRLAKKYEATLEKCCAEANPPACYGTVLAEFQPLVEEP KNLVKTNCDLYEKLGEYGFQNAILVRYTQKAPQVSTPTLVEAARNLGRVGTKCC TLPEDQRLPCVEDYLSAILNRVCLLHEKTPVSEHVTKCCSGSLVERRPCFSALT VDETYVPKEFKAETFTFHSDICTLPEKEKQIKKQTALAELVKHKPKATAEQLKT VMDDFAQFLDTCCKAADKDTCFSTEGPNLVTRCKDALA*GGGGS*HHHHHH-- |
| 75 | LS-mCXCL2$^{28-100}$-(Gly$_4$Ser)$_2$-mouse SA-(Gly$_4$Ser)-His$_6$ | MRVPAQLLGLLLLWLPGARCAVVASELRCQCLKTLPRVDFKNIQSLSVTPPGPH CAQTEVIATLKGGQKVCLDPEAPLVQKIIQKILNKGKANGGGGSGGGGSEAHKS EIAHRYNDLGEQHFKGLVLIAFSQYLQKCSYDEHAKLVQEVTDFAKTCVADESA ANCDKSLHTLFGDKLCAIPNLRENYGELADCCTKQEPERNECFLQHKDDNPSLP PFERPEAEAMCTSFKENPTTFMGHYLHEVARRHPYFYAPELLYYAEQYNEILTQ CCAEADKESCLTPKLDGVKEKALVSSVRQRMKCSSMQKFGERAFKAWAVARLSQ TFPNADFAEITKLATDLTKVNKECCHGDLLECADDRAELAKYMCENQATISSKL QTCCDKPLLKKAHCLSEVEHDTMPADLPAIAADFVEDQEVCKNYAEAKDVFLGT FLYEYSRRHPDYSVSLLLRLAKKYEATLEKCCAEANPPACYGTVLAEFQPLVEE PKNLVKTNCDLYEKLGEYGFQNAILVRYTQKAPQVSTPTLVEAARNLGRVGTKC CTLPEDQRLPCVEDYLSAILNRVCLLHEKTPVSEHVTKCCSGSLVERRPCFSAL TVDETYVPKEFKAETFTFHSDICTLPEKEKQIKKQTALAELVKHKPKATAEQLK TVMDDFAQFLDTCCKAADKDTCFSTEGPNLVTRCKDALA*GGGGS*HHHHHH-- |
| 76 | LS-mCXCL3$^{28-100}$-(Gly$_4$Ser)$_2$-mouse SA-(Gly$_4$Ser)-His$_6$ | MRVPAQLLGLLLLWLPGARCAVVASELRCQCLNTLPRVDFETIQSLTVTPPGPH CTQTEVIATLKDGQEVCLNPQGPRLQIIIKKILSGKSSGGGGSGGGGSEAHKS EIAHRYNDLGEQHFKGLVLIAFSQYLQKCSYDEHAKLVQEVTDFAKTCVADESA ANCDKSLHTLFGDKLCAIPNLRENYGELADCCTKQEPERNECFLQHKDDNPSLP PFERPEAEAMCTSFKENPTTFMGHYLHEVARRHPYFYAPELLYYAEQYNEILTQ CCAEADKESCLTPKLDGVKEKALVSSVRQRMKCSSMQKFGERAFKAWAVARLSQ TFPNADFAEITKLATDLTKVNKECCHGDLLECADDRAELAKYMCENQATISSKL QTCCDKPLLKKAHCLSEVEHDTMPADLPAIAADFVEDQEVCKNYAEAKDVFLGT FLYEYSRRHPDYSVSLLLRLAKKYEATLEKCCAEANPPACYGTVLAEFQPLVEE PKNLVKTNCDLYEKLGEYGFQNAILVRYTQKAPQVSTPTLVEAARNLGRVGTKC CTLPEDQRLPCVEDYLSAILNRVCLLHEKTPVSEHVTKCCSGSLVERRPCFSAL TVDETYVPKEFKAETFTFHSDICTLPEKEKQIKKQTALAELVKHKPKATAEQLK TVMDDFAQFLDTCCKAADKDTCFSTEGPNLVTRCKDALA*GGGGS*HHHHHH-- |
| 77 | LS-mCXCL4$^{30-105}$-(Gly$_4$Ser)$_2$-mouse SA- | MRVPAQLLGLLLLWLPGARCVTSAGPEESDGDLSCVCVKTISSGIHLKHITSLE VIKAGRHCAVPQLIATLKNGRKICLDRQAPLYKKVIKKILESGGGGGSGGGGSEA HKSEIAHRYNDLGEQHFKGLVLIAFSQYLQKCSYDEHAKLVQEVTDFAKTCVAD ESAANCDKSLHTLFGDKLCAIPNLRENYGELADCCTKQEPERNECFLQHKDDNP |

TABLE 12-continued

Sequence Summary

| SEQ ID NO | Description | Sequence |
|---|---|---|
| | (Gly₄Ser)-His₆ | SLPPFERPEAEAMCTSFKENPTTFMGHYLHEVARRHPYFYAPELLYYAEQYNEI<br>LTQCCAEADKESCLTPKLDGVKEKALVSSVRQRMKCSSMQKFGERAFKAWAVAR<br>LSQTFPNADFAEITKLATDLTKVNKECCHGDLLECADDRAELAKYMCENQATIS<br>SKLQTCCDKPLLKKAHCLSEVEHDTMPADLPAIAADFVEDQEVCKNYAEAKDVF<br>LGTFLYEYSRRHPDYSVSLLLRLAKKYEATLEKCCAEANPPACYGTVLAEFQPL<br>VEEPKNLVKTNCDLYEKLGEYGFQNAILVRYTQKAPQVSTPTLVEAARNLGRVG<br>TKCCTLPEDQRLPCVEDYLSAILNRVCLLHEKTPVSEHVTKCCSGSLVERRPCF<br>SALTVDETYVPKEFKAETFTFHSDICTLPEKEKQIKKQTALAELVKHKPKATAE<br>QLKTVMDDFAQFLDTCCKAADKDTCFSTEGPNLVTRCKDALA*GGGGS*HHHHHH-- |
| 78 | LS-mCXCL5⁴⁸⁻¹¹⁸-(Gly₄Ser)₂-mouse SA-(Gly₄Ser)-His₆ | <u>MRVPAQLLGLLLLWLPGARC</u>ATELRCVCLTVTPKINPKLIANLEVIPAGPQCPT<br>VEVIAKLKNQKEVCLDPEAPVIKKIIQKILGSDKKAGGGGSGGGGSEAHKSEI<br>AHRYNDLGEQHFKGLVLIAFSQYLQKCSYDEHAKLVQEVTDFAKTCVADESAAN<br>CDKSLHTLFGDKLCAIPNLRENYGELADCCTKQEPERNECFLQHKDDNPSLPPF<br>ERPEAEAMCTSFKENPTTFMGHYLHEVARRHPYFYAPELLYYAEQYNEILTQCC<br>AEADKESCLTPKLDGVKEKALVSSVRQRMKCSSMQKFGERAFKAWAVARLSQTF<br>PNADFAEITKLATDLTKVNKECCHGDLLECADDRAELAKYMCENQATISSKLQT<br>CCDKPLLKKAHCLSEVEHDTMPADLPAIAADFVEDQEVCKNYAEAKDVFLGTFL<br>YEYSRRHPDYSVSLLLRLAKKYEATLEKCCAEANPPACYGTVLAEFQPLVEEPK<br>NLVKTNCDLYEKLGEYGFQNAILVRYTQKAPQVSTPTLVEAARNLGRVGTKCCT<br>LPEDQRLPCVEDYLSAILNRVCLLHEKTPVSEHVTKCCSGSLVERRPCFSALTV<br>DETYVPKEFKAETFTFHSDICTLPEKEKQIKKQTALAELVKHKPKATAEQLKTV<br>MDDFAQFLDTCCKAADKDTCFSTEGPNLVTRCKDALA*GGGGS*HHHHHH-- |
| 79 | LS-mCXCL7⁴⁸⁻¹¹³-(Gly₄Ser)₂-mouse SA-(Gly₄Ser)-His₆ | <u>MRVPAQLLGLLLLWLPGARC</u>IELRCRCTNTISGIPFNSISLVNVYRPGVHCADV<br>EVIATLKNGQKTCLDPNAPGVKRIVMKILEGYGGGGSGGGGSEAHKSEIAHRYN<br>DLGEQHFKGLVLIAFSQYLQKCSYDEHAKLVQEVTDFAKTCVADESAANCDKSL<br>HTLFGDKLCAIPNLRENYGELADCCTKQEPERNECFLQHKDDNPSLPPFERPEA<br>EAMCTSFKENPTTFMGHYLHEVARRHPYFYAPELLYYAEQYNEILTQCCAEADK<br>ESCLTPKLDGVKEKALVSSVRQRMKCSSMQKFGERAFKAWAVARLSQTFPNADF<br>AEITKLATDLTKVNKECCHGDLLECADDRAELAKYMCENQATISSKLQTCCDKP<br>LLKKAHCLSEVEHDTMPADLPAIAADFVEDQEVCKNYAEAKDVFLGTFLYEYSR<br>RHPDYSVSLLLRLAKKYEATLEKCCAEANPPACYGTVLAEFQPLVEEPKNLVKT<br>NCDLYEKLGEYGFQNAILVRYTQKAPQVSTPTLVEAARNLGRVGTKCCTLPEDQ<br>RLPCVEDYLSAILNRVCLLHEKTPVSEHVTKCCSGSLVERRPCFSALTVDETYV<br>PKEFKAETFTFHSDICTLPEKEKQIKKQTALAELVKHKPKATAEQLKTVMDDFA<br>QFLDTCCKAADKDTCFSTEGPNLVTRCKDALA*GGGGS*HHHHHH-- |
| 80 | LS-mCXCL9²²⁻¹²⁶-(Gly₄Ser)₂-mouse SA-(Gly₄Ser)-His₆ | <u>MRVPAQLLGLLLLWLPGARC</u>TLVIRNARCSCISTSRGTIHYKSLKDLKQFAPSP<br>NCNKTEIIATLKNGDQTCLDPDSANVKKLMKEWEKKISQKKKQKRGKKHQKNMK<br>NRKPKTPQSRRRSRKTTGGGGSGGGGSEAHKSEIAHRYNDLGEQHFKGLVLIAF<br>SQYLQKCSYDEHAKLVQEVTDFAKTCVADESAANCDKSLHTLFGDKLCAIPNLR<br>ENYGELADCCTKQEPERNECFLQHKDDNPSLPPFERPEAEAMCTSFKENPTTFM<br>GHYLHEVARRHPYFYAPELLYYAEQYNEILTQCCAEADKESCLTPKLDGVKEKA<br>LVSSVRQRMKCSSMQKFGERAFKAWAVARLSQTFPNADFAEITKLATDLTKVNK<br>ECCHGDLLECADDRAELAKYMCENQATISSKLQTCCDKPLLKKAHCLSEVEHDT<br>MPADLPAIAADFVEDQEVCKNYAEAKDVFLGTFLYEYSRRHPDYSVSLLLRLAK<br>KYEATLEKCCAEANPPACYGTVLAEFQPLVEEPKNLVKTNCDLYEKLGEYGFQN<br>AILVRYTQKAPQVSTPTLVEAARNLGRVGTKCCTLPEDQRLPCVEDYLSAILNR<br>VCLLHEKTPVSEHVTKCCSGSLVERRPCFSALTVDETYVPKEFKAETFTFHSDI<br>CTLPEKEKQIKKQTALAELVKHKPKATAEQLKTVMDDFAQFLDTCCKAADKDTC<br>FSTEGPNLVTRCKDALA*GGGGS*HHHHHH-- |
| 81 | LS-mCXCL10²²⁻⁹⁸-(Gly₄Ser)₂-mouse SA-(Gly₄Ser)-His₆ | <u>MRVPAQLLGLLLLWLPGARC</u>IPLARTVRCNCIHIDDGPVRMRAIGKLEIIPASL<br>SCPRVEIIATMKKNDEQRCLNPESKTIKNLMKAFSQKRSKRAPGGGGSGGGGSE<br>AHKSEIAHRYNDLGEQHFKGLVLIAFSQYLQKCSYDEHAKLVQEVTDFAKTCVA<br>DESAANCDKSLHTLFGDKLCAIPNLRENYGELADCCTKQEPERNECFLQHKDDN<br>PSLPPFERPEAEAMCTSFKENPTTFMGHYLHEVARRHPYFYAPELLYYAEQYNE<br>ILTQCCAEADKESCLTPKLDGVKEKALVSSVRQRMKCSSMQKFGERAFKAWAVA<br>RLSQTFPNADFAEITKLATDLTKVNKECCHGDLLECADDRAELAKYMCENQATI<br>SSKLQTCCDKPLLKKAHCLSEVEHDTMPADLPAIAADFVEDQEVCKNYAEAKDV<br>FLGTFLYEYSRRHPDYSVSLLLRLAKKYEATLEKCCAEANPPACYGTVLAEFQP<br>LVEEPKNLVKTNCDLYEKLGEYGFQNAILVRYTQKAPQVSTPTLVEAARNLGRV<br>GTKCCTLPEDQRLPCVEDYLSAILNRVCLLHEKTPVSEHVTKCCSGSLVERRPC<br>FSALTVDETYVPKEFKAETFTFHSDICTLPEKEKQIKKQTALAELVKHKPKATA<br>EQLKTVMDDFAQFLDTCCKAADKDTCFSTEGPNLVTRCKDALA*GGGGS*HHHHHH<br>-- |
| 82 | LS-mCXCL11²²⁻¹⁰⁰-(Gly₄Ser)₂-mouse SA-(Gly₄Ser)-His₆ | <u>MRVPAQLLGLLLLWLPGARC</u>FLMFKQGRCLCIGPGMKAVKMAEIEKASVIYPSN<br>GCDKVEVIVTMKAHKRQRCLDPRSKQARLIMQAIEKKNFLRRQNMGGGGSGGGG<br>SEAHKSEIAHRYNDLGEQHFKGLVLIAFSQYLQKCSYDEHAKLVQEVTDFAKTC<br>VADESAANCDKSLHTLFGDKLCAIPNLRENYGELADCCTKQEPERNECFLQHKD<br>DNPSLPPFERPEAEAMCTSFKENPTTFMGHYLHEVARRHPYFYAPELLYYAEQY<br>NEILTQCCAEADKESCLTPKLDGVKEKALVSSVRQRMKCSSMQKFGERAFKAWA |

TABLE 12-continued

Sequence Summary

| SEQ ID NO | Description | Sequence |
|---|---|---|
| | | VARLSQTFPNADFAEITKLATDLTKVNKECCHGDLLECADDRAELAKYMCENQA TISSKLQTCCDKPLLKKAHCLSEVEHDTMPADLPAIAADFVEDQEVCKNYAEAK DVFLGTFLYEYSRRHPDYSVSLLLRLAKKYEATLEKCCAEANPPACYGTVLAEF QPLVEEPKNLVKTNCDLYEKLGEYGFQNAILVRYTQKAPQVSTPTLVEAARNLG RVGTKCCTLPEDQRLPCVEDYLSAILNRVCLLHEKTPVSEHVTKCCSGSLVERR PCFSALTVDETYVPKEFKAETFTFHSDICTLPEKEKQIKKQTALAELVKHKPKA TAEQLKTVMDDFAQFLDTCCKAADKDTCFSTEGPNLVTRCKDALA*GGGGS*HHHH HH-- |
| 83 | gWiz-LS-mouse SA-(Gly$_4$Ser)$_3$-scFv (V$_L$-V$_H$) CK138-(Gly$_4$Ser)-His$_6$ | ATGGACATGAGAGTGCCTGCTCAGCTGCTGGGCCTGCTGCTGCTGTGGCTGCCT GGTGCTAGATGCGAAGCACACAAGAGTGAGATCGCCCATCGGTATAATGATTTG GGAGAACAACATTTCAAAGGCCTAGTCCTGATTGCCTTTTCCCAGTATCTCCAG AAATGCTCATACGATGAGCATGCCAAATTAGTGCAGGAAGTAACAGACTTTGCA AAGACGTGTGTTGCCGATGAGTCTGCCGCCAACTGTGACAAATCCCTTCACACT CTTTTTGGAGATAAGTTGTGTGCCATTCCAAACCTCCGTGAAAACTATGGTGAA CTGGCTGACTGCTGTACAAAACAAGAGCCCGAAAGAAACGAATGTTTCCTGCAA CACAAAGATGACAACCCCAGCCTACCACCATTTGAAAGGCCAGAGGCTGAGGCC ATGTGCACCTCCTTTAAGGAAAACCCAACCACCTTTATGGGACACTATTTGCAT GAAGTTGCCAGAAGACATCCTTATTTCTATGCCCCAGAACTTCTTTACTATGCT GAGCAGTACAATGAGATTCTGACCCAGTGTTGTGCAGAGGCTGACAAGGAAAGC TGCCTGACCCCGAAGCTTGATGGTGTGAAGGAGAAAGCATTGGTCTCATCTGTC CGTCAGAGAATGAAGTGCTCCAGTATGCAGAAGTTTGGAGAGAGAGCTTTTAAA GCATGGGCAGTAGCTCGTCTGAGCCAGACATTCCCCAATGCTGACTTTGCAGAA ATCACCAAATTGGCAACAGACCTGACCAAAGTCAACAAGGAGTGCTGCCATGGT GACCTGCTGGAATGCGCAGATGACAGGGCGGAACTTGCCAAGTACATGTGTGAA AACCAGGCGACTATCTCCAGCAAACTGCAGACTTGCTGCGATAAACCACTGTTG AAGAAAGCCCACTGTCTTAGTGAGGTGGAGCATGACACCATGCCTGCTGATCTG CCTGCCATTGCTGCTGATTTTGTTGAGGACCAGGAAGTGTGCAAGAACTATGCT GAGGCCAAGGATGTCTTCCTGGGCACGTTCTTGTATGAATATTCAAGAAGACAC CCTGATTACTCTGTATCCCTGTTGCTGAGACTTGCTAAGAAATATGAAGCCACT CTGGAAAAGTGCTGCGCTGAAGCCAATCCTCCCGCATGCTACGGCACAGTGCTT GCTGAATTTCAGCCTCTTGTAGAAGAGCCTAAGAACTTGGTCAAAACCAACTGT GATCTTTACGAGAAGCTTGGAGAATATGGATTCCAAAATGCCATTCTAGTTCGC TACACCCAGAAAGCACCTCAGGTGTCAACCCCAACTCTCGTGGAGGCTGCAAGA AACCTAGGAAGAGTGGGCACCAAGTGTTGTACACTTCCTGAAGATCAGAGACTG CCTTGTGTGGAAGACTATCTGTCTGCAATCCTGAACCGTGTGTGTCTGCTGCAT GAGAAGACCCCAGTGAGTGAGCATGTTACCAAGTGCTGTAGTGGATCCCTGGTG GAAAGGCGGCCATGCTTCTCTGCTCTGACAGTTGATGAAACATATGTCCCCAAA GAGTTTAAAGCTGAGACCTTCACCTTCCACTCTGATATCTGCACACTTCCAGAG AAGGAGAAGCAGATTAAGAAACAAACGGCTCTTGCTGAGCTGGTGAAGGACAAG CCCAAGGCTACAGCGGAGCAACTGAAGACTGTCATGGATGACTTTGCACAGTTC CTGGATACATGTTGCAAGGCTGCTGACAAGGACACCTGCTTCTCGACTGAGGGT CCAAACCTTGTCACTAGATGCAAAGACGCCTTAGCC*GGTGGAGGAGGCTCTGGT GGAGGCGGTAGCGGAGGCGGAGGGTCG*GCTATCCAGATGACCCGGTCCCCGAGC TCCCTGTCCGCCTCTGTGGGCGATAGGGTCACCATCACCTGCCGTGCCAGTCAG TACCACGACGGTTCTGCAGCCTGGTATCAACAGAAACCAGGAAAAGCTCCGAAG CTTCTGATTTACGGTGCATCCTACCTCTACTCTGGAGTCCCTTCCCGCTTCTCT GGTAGCCGTTCCGGGACGGATTTCACTCTGACCATCAGCAGTCTGCAGCCGGAA GACTTCGCAACTTATTACTGTCAGCAATCTTCTTATTCTCTGATCACGTTCGGA CAGGGTACCAAGGTGGAGATCAAAGGTACTACTGCCGCTAGTGGTAGTAGTGGT GGCAGTAGCAGTGGTGCCGAGGTTCAGCTGGTGGAGTCTGACGGTGGCCTGGTG CAGCCAGGGGGCTCACTCCGTTTGTCCTGTGCAGCTTCTGGCTTCAACCTCTCT TACTACGGTATGCACTGGGTGCGTCAGGCCCCGGGTAAGGGCCTGGAATGGGTT GCATACATTGCTTCTTACCCTGGCTACACTTCTTATGCCGATAGCGTCAAGGGC CGTTTCACTATAAGCGCAGACACATCCAAAAACACAGCCTACCTACAAATGAAC AGCTTAAGAGCTGAGGACACTGCCGTCTACTATTGTGCTCGCTCTGGTTACAGT TACTCTCCGTATTATTCTTGGTTCTCTGCTGGTATGAACTACTGGGGTCAAGGA GCCCTGGTCACCGTCTCCTCG*GGAGGGGGCGGTTCC*CACCATCACCACCATCAC TGATAG |
| 84 | gWiz-LS-mouse SA-(Gly$_4$Ser)$_3$-scFv (V$_L$-V$_H$) CK157-(Gly$_4$Ser)-His$_6$ | ATGGACATGAGAGTGCCTGCTCAGCTGCTGGGCCTGCTGCTGCTGTGGCTGCCT GGTGCTAGATGCGAAGCACACAAGAGTGAGATCGCCCATCGGTATAATGATTTG GGAGAACAACATTTCAAAGGCCTAGTCCTGATTGCCTTTTCCCAGTATCTCCAG AAATGCTCATACGATGAGCATGCCAAATTAGTGCAGGAAGTAACAGACTTTGCA AAGACGTGTGTTGCCGATGAGTCTGCCGCCAACTGTGACAAATCCCTTCACACT CTTTTTGGAGATAAGTTGTGTGCCATTCCAAACCTCCGTGAAAACTATGGTGAA CTGGCTGACTGCTGTACAAAACAAGAGCCCGAAAGAAACGAATGTTTCCTGCAA CACAAAGATGACAACCCCAGCCTACCACCATTTGAAAGGCCAGAGGCTGAGGCC ATGTGCACCTCCTTTAAGGAAAACCCAACCACCTTTATGGGACACTATTTGCAT GAAGTTGCCAGAAGACATCCTTATTTCTATGCCCCAGAACTTCTTTACTATGCT GAGCAGTACAATGAGATTCTGACCCAGTGTTGTGCAGAGGCTGACAAGGAAAGC TGCCTGACCCCGAAGCTTGATGGTGTGAAGGAGAAAGCATTGGTCTCATCTGTC CGTCAGAGAATGAAGTGCTCCAGTATGCAGAAGTTTGGAGAGAGAGCTTTTAAA GCATGGGCAGTAGCTCGTCTGAGCCAGACATTCCCCAATGCTGACTTTGCAGAA ATCACCAAATTGGCAACAGACCTGACCAAAGTCAACAAGGAGTGCTGCCATGGT |

TABLE 12-continued

Sequence Summary

| SEQ ID NO | Description | Sequence |
|---|---|---|
| | | GACCTGCTGGAATGCGCAGATGACAGGGCGGAACTTGCCAAGTACATGTGTGAA<br>AACCAGGCGACTATCTCCAGCAAACTGCAGACTTGCTGCGATAAACCACTGTTG<br>AAGAAAGCCCACTGTCTTAGTGAGGTGGAGCATGACACCATGCCTGCTGATCTG<br>CCTGCCATTGCTGCTGATTTTGTTGAGGACCAGGAAGTGTGCAAGAACTATGCT<br>GAGGCCAAGGATGTCTTCCTGGGCACGTTCTTGTATGAATATTCAAGAAGACAC<br>CCTGATTACTCTGTATCCCTGTTGCTGAGACTTGCTAAGAAATATGAAGCCACT<br>CTGGAAAAGTGCTGCGCTGAAGCCAATCCTCCCGCATGCTACGGCACAGTGCTT<br>GCTGAATTTCAGCCTCTTGTAGAAGAGCCTAAGAACTTGGTCAAAACCAACTGT<br>GATCTTTACGAGAAGCTTGGAGAATATGGATTCCAAAATGCCATTCTAGTTCGC<br>TACACCCAGAAAGCACCTCAGGTGTCAACCCCAACTCTCGTGGAGGCTGCAAGA<br>AACCTAGGAAGAGTGGGCACCAAGTGTTGTACACTTCCTGAAGATCAGAGACTG<br>CCTTGTGTGGAAGACTATCTGTCTGCAATCCTGAACCGTGTGTGTCTGCTGCAT<br>GAGAAGACCCCAGTGAGTGAGCATGTTACCAAGTGCTGTAGTGGATCCCTGGTG<br>GAAAGGCGGCCATGCTTCTCTGCTCTGACAGTTGATGAAACATATGTCCCCAAA<br>GAGTTTAAAGCTGAGACCTTCACCTTCCACTCTGATATCTGCACACTTCCAGAG<br>AAGGAGAAGCAGATTAAGAAACAAACGGCTCTTGCTGAGCTGGTGAAGGACAAG<br>CCCAAGGCTACAGCGGAGCAACTGAAGACTGTCATGGATGACTTTGCACAGTTC<br>CTGGATACATGTTGCAAGGCTGCTGACAAGGACACCTGCTTCTCGACTGAGGGT<br>CCAAACCTTGTCACTAGATGCAAAGACGCCTTAGCC<u>GGTGGAGGAGGCTCTGGT</u><br><u>GGAGGCGGTAGCGGAGGCGGAGGGTCG</u>GATATCAGATGACCCAGTCCCCGAGC<br>TCCCTGTCCGCCTCTGTGGGCGATAGGGTCACCATCACCTGCCGTGCCAGTCAG<br>TCTTACGGTGGTGTAGCCTGGTATCAACAGAAACCAGGAAAAGCCCCGAAGCTT<br>CTGATTTACTCTGCATCCTACCTCTACTCTGGAGTCCCTTCTCGCTTCTCTGGT<br>AGCCGTTCCGGGACGGATTTCACTCTGACCATCAGCAGTCTGCAGCCGGAAGAC<br>TTCGCAACTTATTACTGTCAGCAACCATCTCATCTGATCACGTTCGGACAGGGT<br>ACCGAGGTGGAGATCAAAGGTACTACTGCCGCTAGTGGTAGTAGTGGTGGCAGT<br>AGCAGTGGTGCCGAGGTTCAGCTGGTGGAGTCTGGCGGTGGCCTGGTGCAGCCA<br>GGGGGCTCACTCCGTTTGTCCTGTGCAGCTTCTGGCTCCAACCCCTACTACTAC<br>GGTGGTACGCACTGGGTGCGTCAGGCCCCGGGTGAGGAGCTGGAATGGGTTGCA<br>TCTATTGGTTCTTACCCTGGCTACACTGACTATGCCGATAGCGTCAAGGGCCGT<br>TTCACTATAAGCGCAGACACATCCAAAAACACAGCCTACCTACAAATGAACAGC<br>TTAAGAGCTGAGGACACTGCCGTCTATTATTGTGCTCGCCATTACTACTGGTAC<br>GATGCTACTGACTACTGGGGTCAAGGAACCCTGGTCACCGTCTCCTCG<u>GGAGGG</u><br><u>GGCGGTTCC</u>CACCATCACCACCATCACTGATAG |
| 85 | gWiz-LS-<br>mouse SA-<br>(Gly$_4$Ser)$_3$-<br>scFv (V$_L$-<br>V$_H$) CK129-<br>(Gly$_4$Ser)-<br>His$_6$ | ATGGACATGAGAGTGCCTGCTCAGCTGCTGGGCCTGCTGCTGCTGTGGCTGCCT<br>GGTGCTAGATGCGAAGCACACAAGAGTGAGATCGCCCATCAGTATAATGATTTG<br>GGAGAACAACATTTCAAAGGCCTAGTCCTGATTGCCTTTTCCCAGTATCTCCAG<br>AAATGCTCATACGATGAGCATGCCAAATTAGTGCAGGAAGTAACAGACTTTGCA<br>AAGACGTGTGTTGCCGATGAGTCTGCCGCCAACTGTGACAAATCCCTTCACACT<br>CTTTTTGGAGATAAGTTGTGTGCCATTCCAAACCTCCGTGAAAACTATGGTGAA<br>CTGGCTGACTGCTGTACAAAACAAGAGCCCGAAAGAAACGAATGTTTCCTGCAA<br>CACAAAGATGACAACCCCAGCCTACCACCATTTGAAAGGCCAGAGGCTGAGGCC<br>ATGTGCACCTCCTTTAAGGAAAACCCAACCACCTTTATGGGACACTATTTGCAT<br>GAAGTTGCCAGAAGACATCCTTATTTCTATGCCCCAGAACTTCTTTACTATGCT<br>GAGCAGTACAATGAGATTCTGACCCAGTGTTGTGCAGAGGCTGACAAGGAAAGC<br>TGCCTGACCCCGAAGCTTGATGGTGTGAAGGAGAAAGCATTGGTCTCATCTGTC<br>CGTCAGAGAATGAAGTGCTCCAGTATGCAGAAGTTTGGAGAGAGAGCTTTTAAA<br>GCATGGGCAGTAGCTCGTCTGAGCCAGACATTCCCCAATGCTGACTTTGCAGAA<br>ATCACCAAATTGGCAACAGACCTGACCAAAGTCAACAAGGAGTGCTGCCATGGT<br>GACCTGCTGGAATGCGCAGATGACAGGGCGGAACTTGCCAAGTACATGTGTGAA<br>AACCAGGCGACTATCTCCAGCAAACTGCAGACTTGCTGCGATAAACCACTGTTG<br>AAGAAAGCCCACTGTCTTAGTGAGGTGGAGCATGACACCATGCCTGCTGATCTG<br>CCTGCCATTGCTGCTGATTTTGTTGAGGACCAGGAAGTGTGCAAGAACTATGCT<br>GAGGCCAAGGATGTCTTCCTGGGCACGTTCTTGTATGAATATTCAAGAAGACAC<br>CCTGATTACTCTGTATCCCTGTTGCTGAGACTTGCTAAGAAATATGAAGCCACT<br>CTGGAAAAGTGCTGCGCTGAAGCCAATCCTCCCGCATGCTACGGCACAGTGCTT<br>GCTGAATTTCAGCCTCTTGTAGAAGAGCCTAAGAACTTGGTCAAAACCAACTGT<br>GATCTTTACGAGAAGCTTGGAGAATATGGATTCCAAAATGCCATTCTAGTTCGC<br>TACACCCAGAAAGCACCTCAGGTGTCAACCCCAACTCTCGTGGAGGCTGCAAGA<br>AACCTAGGAAGAGTGGGCACCAAGTGTTGTACACTTCCTGAAGATCAGAGACTG<br>CCTTGTGTGGAAGACTATCTGTCTGCAATCCTGAACCGTGTGTGTCTGCTGCAT<br>GAGAAGACCCCAGTGAGTGAGCATGTTACCAAGTGCTGTAGTGGATCCCTGGTG<br>GAAAGGCGGCCATGCTTCTCTGCTCTGACAGTTGATGAAACATATGTCCCCAAA<br>GAGTTTAAAGCTGAGACCTTCACCTTCCACTCTGATATCTGCACACTTCCAGAG<br>AAGGAGAAGCAGATTAAGAAACAAACGGCTCTTGCTGAGCTGGTGAAGGACAAG<br>CCCAAGGCTACAGCGGAGCAACTGAAGACTGTCATGGATGACTTTGCACAGTTC<br>CTGGATACATGTTGCAAGGCTGCTGACAAGGACACCTGCTTCTCGACTGAGGGT<br>CCAAACCTTGTCACTAGATGCAAAGACGCCTTAGCC<u>GGTGGAGGAGGCTCTGGT</u><br><u>GGAGGCGGTAGCGGAGGCGGAGGGTCG</u>GCTAGCGATATCCAGATGACCCAGTCC<br>CCGAGCCCCTGTCCGCCTCTGTGGGCGATAGGGTCACCATCACCTGCCGTGCC<br>AGTCAGTACGGTGGTTACGTAGCCTGGTATCAACAGAAACCAGGAAAAGCTCCG<br>AAGCTTCTGATTTACGGTGCATCCCTTTCTCTACTCTGGAGTCCCTTCTCGCTTC<br>TCTGGTGGCCGTTCCGGGACGGATTTCACTCTGACCATCAGCAGTCTGCAGCCG<br>GAAGACTTCGCAACTTATTACTGTCAGCGAGGTCATGCTCTGATCACGTTCGGA |

TABLE 12-continued

Sequence Summary

| SEQ ID NO | Description | Sequence |
|---|---|---|
|  |  | CAGGGTACCAAGGTGGAGATCGAAGGTACTACTGCCGCTAGTGGTAGTAGTGGT<br>GGCAGTAGCAGTGGTGCCGAGGTTCAGCTGGTGGAGTCTGGCGGTGGCCTGGTG<br>CAGCCAGGGGGCTCACTCCGTTTATCCTGTGCAGCTTCTGGCTTCAACATCTCT<br>TCTTACGGTTCTATGCACTGGGTGCGTCAGGCCCCGGGTAAGGGGCCTGGAATGG<br>GTTGCATCTATTTACCCTTACTCTAGCTCTACTTACTATGCCGATAGCGTCAAG<br>GGCCGTTTCACTATAAGCGCAGACACATCCAAAAACACAGCCTACCTACAAATG<br>AACAGCTTAAGAGCTGAGGACACTGCCGTCTATTATTGTGCTCGTGGTTACGGT<br>CCGTGGTACGCTTACTCTTACTTCGCTTTGGACTACTGGGGTCAAGGAACCCTG<br>GTCACCGTCTCCTCG<u>GGAGGGGGCGGTTCC</u>CACCATCACCACCATCACTGATAG |
| 86 | gWiz-LS-<br>mouse SA-<br>(Gly₄Ser)₃-<br>scFv (V<sub>L</sub>-<br>V<sub>H</sub>) CK138-<br>ds1<br>(V<sub>L</sub>100<sup>Q>C</sup>/<br>V<sub>H</sub>44<sup>G>C</sup>)-<br>(Gly₄Ser)-<br>His₆ | ATGGACATGAGAGTGCCTGCTCAGCTGCTGGGCCTGCTGCTGCTGTGGCTGCCT<u>GGTGCTAGATGC</u>GAAGCACACAAGAGTGAGATCGCCCATCGGTATAATGATTTG<br>GGAGAACAACATTTCAAAGGCCTAGTCCTGATTGCCTTTTCCCAGTATCTCCAG<br>AAATGCTCATACGATGAGCATGCCAAATTAGTGCAGGAAGTAACAGACTTTGCA<br>AAGACGTGTGTTGCCGATGAGTCTGCCGCCAACTGTGACAAATCCCTTCACACT<br>CTTTTTGGAGATAAGTTGTGTGCCATTCCAAACCTCCGTGAAAACTATGGTGAA<br>CTGGCTGACTGCTGTACAAAACAAGAGCCCGAAAGAAACGAATGTTTCCTGCAA<br>CACAAAGATGACAACCCCAGCCTACCACCATTTGAAAGGCCAGAGGCTGAGGCC<br>ATGTGCACCTCCTTTAAGGAAAACCCAACCACCTTTATGGGACACTATTTGCAT<br>GAAGTTGCCAGAAGACATCCTTATTTCTATGCCCCAGAACTTCTTTACTATGCT<br>GAGCAGTACAATGAGATTCTGACCCAGTGTTGTGCAGAGGCTGACAAGGAAAGC<br>TGCCTGACCCCGAAGCTTGATGGTGTGAAGGAGAAAGCATTGGTCTCATCTGTC<br>CGTCAGAGAATGAAGTGCTCCAGTATGCAGAAGTTTGGAGAGAGAGCTTTTAAA<br>GCATGGGCAGTAGCTCGTCTGAGCCAGACATTCCCCAATGCTGACTTTGCAGAA<br>ATCACCAAATTGGCAACAGACCTGACCAAAGTCAACAAGGAGTGCTGCCATGGT<br>GACCTGCTGGAATGCGCAGATGACAGGGCGGAACTTGCCAAGTACATGTGTGAA<br>AACCAGGCGACTATCTCCAGCAAACTGCAGACTTGCTGCGATAAACCACTGTTG<br>AAGAAAGCCCACTGTCTTAGTGAGGTGGAGCATGACACCATGCCTGCTGATCTG<br>CCTGCCATTGCTGCTGATTTTGTTGAGGACCAGGAAGTGTGCAAGAACTATGCT<br>GAGGCCAAGGATGTCTTCCTGGGCACGTTCTTGTATGAATATTCAAGAAGACAC<br>CCTGATTACTCTGTATCCCTGTTGCTGAGACTTGCTAAGAAATATGAAGCCACT<br>CTGGAAAAGTGCTGCGCTGAAGCCAATCCTCCCGCATGCTACGGCACAGTGCTT<br>GCTGAATTTCAGCCTCTTGTAGAAGAGCCTAAGAACTTGGTCAAAACCAACTGT<br>GATCTTTACGAGAAGCTTGGAGAATATGGATTCCAAAATGCCATTCTAGTTCGC<br>TACACCCAGAAAGCACCTCAGGTGTCAACCCCAACTCTCGTGGAGGCTGCAAGA<br>AACCTAGGAAGAGTGGGCACCAAGTGTTGTACACTTCCTGAAGATCAGAGACTG<br>CCTTGTGTGGAAGACTATCTGTCTGCAATCCTGAACCGTGTGTCTGCTGCAT<br>GAGAAGACCCCAGTGAGTGAGCATGTTACCAAGTGCTGTAGTGGATCCCTGGTG<br>GAAAGGCGGCCATGCTTCTCTGCTCTGACAGTTGATGAAACATATGTCCCCAAA<br>GAGTTTAAAGCTGAGACCTTCACCTTCCACTCTGATATCTGCACACTTCCAGAG<br>AAGGAGAAGCAGATTAAGAAACAAACGGCTCTTGCTGAGCTGGTGAAGCACAAG<br>CCCAAGGCTACAGCGGAGCAACTGAAGACTGTCATGGATGACTTTGCACAGTTC<br>CTGGATACATGTTGCAAGGCTGCTGACAAGGACACCTGCTTCTCGACTGAGGGT<br>CCAAACCTTGTCACTAGATGCAAAGACGCCTTAGCC<u>GGTGGAGGAGGCTCTGGT</u><u>GGAGGCGGTAGCGGAGGCGGAGGGTCG</u>GCTATCCAGATGACCCGGTCCCCGAGC<br>TCCCTGTCCGCCTCTGTGGGCGATAGGGTCACCATCACCTGCCGTGCCAGTCAG<br>TACCACGACGGTTCTGCAGCCTGGTATCAACAGAAACCAGGAAAAGCTCCGAAG<br>CTTCTGATTTACGGTGCATCCTACCTCTACTCTGGAGTCCCTTCCCGCTTCTCT<br>GGTAGCCGTTCCGGGACGGATTTCACTCTGACCATCAGCAGTCTGCAGCCGGAA<br>GACTTCGCAACTTATTACTGTCAGCAATCTTCTTATTCTCTGATCACGTTCGGA<br>*TGC*GGTACCAAGGTGGAGATCAAAGGTACTACTGCCGCTAGTGGTAGTAGTGGT<br>GGCAGTAGCAGTGGTGCCGAGGTTCAGCTGGTGGAGTCTGACGGTGGCCTGGTG<br>CAGCCAGGGGGCTCACTCCGTTTGTCCTGTGCAGCTTCTGGCTTCAACCTCTCT<br>TACTACGGTATGCACTGGGTGCGTCAGGCCCCGGGTAA*G*GCCTGGAATGGGTT<br>GCATACATTGCTTCTTACCCTGGCTACACTTCTTATGCCGATAGCGTCAAGGGC<br>CGTTTCACTATAAGCGCAGACACATCCAAAAACACAGCCTACCTACAAATGAAC<br>AGCTTAAGAGCTGAGGACACTGCCGTCTACTATTGTGCTCGCTCTGGTTACAGT<br>TACTCTCCGTATTATTCTTGGTTCTCTGCTGGTATGAACTACTGGGGTCAAGGA<br>GCCCTGGTCACCGTCTCCTCG<u>GGAGGGGGCGGTTCC</u>CACCATCACCACCATCAC<br>TGATAG |
| 87 | gWiz-LS-<br>mouse SA-<br>(Gly₄Ser)₃-<br>scFv (V<sub>L</sub>-<br>V<sub>H</sub>) CK138-<br>ds2<br>(V<sub>L</sub>43<sup>A>C</sup>/<br>V<sub>H</sub>105<sup>Q>C</sup>)-<br>(Gly₄Ser)-<br>His₆ | ATGGACATGAGAGTGCCTGCTCAGCTGCTGGGCCTGCTGCTGCTGTGGCTGCCT<u>GGTGCTAGATGC</u>GAAGCACACAAGAGTGAGATCGCCCATCGGTATAATGATTTG<br>GGAGAACAACATTTCAAAGGCCTAGTCCTGATTGCCTTTTCCCAGTATCTCCAG<br>AAATGCTCATACGATGAGCATGCCAAATTAGTGCAGGAAGTAACAGACTTTGCA<br>AAGACGTGTGTTGCCGATGAGTCTGCCGCCAACTGTGACAAATCCCTTCACACT<br>CTTTTTGGAGATAAGTTGTGTGCCATTCCAAACCTCCGTGAAAACTATGGTGAA<br>CTGGCTGACTGCTGTACAAAACAAGAGCCCGAAAGAAACGAATGTTTCCTGCAA<br>CACAAAGATGACAACCCCAGCCTACCACCATTTGAAAGGCCAGAGGCTGAGGCC<br>ATGTGCACCTCCTTTAAGGAAAACCCAACCACCTTTATGGGACACTATTTGCAT<br>GAAGTTGCCAGAAGACATCCTTATTTCTATGCCCCAGAACTTCTTTACTATGCT<br>GAGCAGTACAATGAGATTCTGACCCAGTGTTGTGCAGAGGCTGACAAGGAAAGC<br>TGCCTGACCCCGAAGCTTGATGGTGTGAAGGAGAAAGCATTGGTCTCATCTGTC<br>CGTCAGAGAATGAAGTGCTCCAGTATGCAGAAGTTTGGAGAGAGAGCTTTTAAA<br>GCATGGGCAGTAGCTCGTCTGAGCCAGACATTCCCCAATGCTGACTTTGCAGAA |

TABLE 12-continued

Sequence Summary

| SEQ ID NO | Description | Sequence |
|---|---|---|
| | | ATCACCAAATTGGCAACAGACCTGACCAAAGTCAACAAGGAGTGCTGCCATGGT<br>GACCTGCTGGAATGCGCAGATGACAGGGCGGAACTTGCCAAGTACATGTGTGAA<br>AACCAGGCGACTATCTCCAGCAAACTGCAGACTTGCTGCGATAAACCACTGTTG<br>AAGAAAGCCCACTGTCTTAGTGAGGTGGAGCATGACACCATGCCTGCTGATCTG<br>CCTGCCATTGCTGCTGATTTTGTTGAGGACCAGGAAGTGTGCAAGAACTATGCT<br>GAGGCCAAGGATGTCTTCCTGGGCACGTTCTTGTATGAATATTCAAGAAGACAC<br>CCTGATTACTCTGTATCCCTGTTGCTGAGACTTGCTAAGAAATATGAAGCCACT<br>CTGGAAAAGTGCTGCGCTGAAGCCAATCCTCCCGCATGCTACGGCACAGTGCTT<br>GCTGAATTTCAGCCTCTTGTAGAAGAGCCTAAGAACTTGGTCAAAACCAACTGT<br>GATCTTTACGAGAAGCTTGGAGAATATGGATTCCAAAATGCCATTCTAGTTCGC<br>TACACCCAGAAAGCACCTCAGGTGTCAACCCCAACTCTCGTGGAGGCTGCAAGA<br>AACCTAGGAAGAGTGGGCACCAAGTGTTGTACACTTCCTGAAGATCAGAGACTG<br>CCTTGTGTGGAAGACTATCTGTCTGCAATCCTGAACCGTGTGTGTCTGCTGCAT<br>GAGAAGACCCCAGTGAGTGAGCATGTTACCAAGTGCTGTAGTGGATCCCTGGTG<br>GAAAGGCGGCCATGCTTCTCTGCTCTGACAGTTGATGAAACATATGTCCCCAAA<br>GAGTTTAAAGCTGAGACCTTCACCTTCCACTCTGATATCTGCACACTTCCAGAG<br>AAGGAGAAGCAGATTAAGAAACAAACGGCTCTTGCTGAGCTGGTGAAGCACAAG<br>CCCAAGGCTACAGCGGAGCAACTGAAGACTGTCATGGATGACTTTGCACAGTTC<br>CTGGATACATGTTGCAAGGCTGCTGACAAGGACACCTGCTTCTCGACTGAGGGT<br>CCAAACCTTGTCACTAGATGCAAAGACGCCTTAGCC*GGTGGAGGAGGCTCTGGT*<br>*GGAGGCGGTAGCGGAGGCGGAGGGTCG*GCTAGCGCTATCCAGATGACCCGGTCC<br>CCGAGCTCCCTGTCCGCCTCTGTGGGCGATAGGGTCACCATCACCTGCCGTGCC<br>AGTCAGTACCACGACGGTTCTGCAGCCTGGTATCAACAGAAACCAGGAAAA*TGC*<br>CCGAAGCTTCTGATTTACGGTGCATCCTACCTCTACTCTGGAGTCCCTTCCCGC<br>TTCTCTGGTAGCCGTTCCGGGACGGATTTCACTCTGACCATCAGCAGTCTGCAG<br>CCGGAAGACTTCGCAACTTATTACTGTCAGCAATCTTCTTATTCTCTGATCACG<br>TTCGGACAGGGTACCAAGGTGGAGATCAAAGGTACTACTGCCGCTAGTGGTAGT<br>AGTGGTGGCAGTAGCAGTGGTGCCGAGGTTCAGCTGGTGGAGTCTGACGGTGGC<br>CTGGTGCAGCCAGGGGGCTCACTCCGTTTGTCCTGTGCAGCTTCTGGCTTCAAC<br>CTCTCTTACTACGGTATGCACTGGGTGCGTCAGGCCCCGGGTAAGGGCCTGGAA<br>TGGGTTGCATACATTGCTTCTTACCCTGGCTACACTTCTTATGCCGATAGCGTC<br>AAGGGCCGTTTCACTATAAGCGCAGACACATCCAAAAACACAGCCTACCTACAA<br>ATGAACAGCTTAAGAGCTGAGGACACTGCCGTCTACTATTGTGCTGCTCTGGT<br>TACAGTTACTCTCCGTATTATTCTTGGTTCTCTGCTGGTATGAACTACTGGGGT<br>*TGC*GGAGCCCTGGTCACCGTCTCCTCG*GGAGGGGGCGGTTCC*CACCATCACCAC<br>CATCACTGATAG |
| 88 | gWiz-LS-<br>mouse SA-<br>(Gly₄Ser)₃-<br>scFv (V$_L$-<br>V$_H$) CK157-<br>ds1<br>(V$_L$100$^{Q>C}$/<br>V$_H$44$^{E>C}$) -<br>(Gly₄Ser) -<br>His₆ | ATGGACATGAGAGTGCCTGCTCAGCTGCTGGGCCTGCTGCTGCTGTGGCTGCCT<br><u>GGTGCTAGATGC</u>GAAGCACACAAGAGTGAGATCGCCCATCGGTATAATGATTTG<br>GGAGAACAACATTTCAAAGGCCTAGTCCTGATTGCCTTTTCCCAGTATCTCCAG<br>AAATGCTCATACGATGAGCATGCCAAATTAGTGCAGGAAGTAACAGACTTTGCA<br>AAGACGTGTGTTGCCGATGAGTCTGCCGCCAACTGTGACAAATCCCTTCACACT<br>CTTTTTGGAGATAAGTTGTGTGCCATTCCAAACCTCCGTGAAAACTATGGTGAA<br>CTGGCTGACTGCTGTACAAAACAAGAGCCCGAAAGAAACGAATGTTTCCTGCAA<br>CACAAAGATGACAACCCCAGCCTACCACCATTTGAAAGGCCAGAGGCTGAGGCC<br>ATGTGCACCTCCTTTAAGGAAAACCCAACCACCTTTATGGGACACTATTTGCAT<br>GAAGTTGCCAGAAGACATCCTATTTCTATGCCCCAGAACTTCTTTACTATGCT<br>GAGCAGTACAATGAGATTCTGACCCAGTGTTGTGCAGAGGCTGACAAGGAAAGC<br>TGCCTGACCCCGAAGCTTGATGGTGTGAAGGAGAAAGCATTGGTCTCATCTGTC<br>CGTCAGAGAATGAAGTGCTCCAGTATGCAGAAGTTTGGAGAGAGAGCTTTTAAA<br>GCATGGGCAGTAGCTCGTCTGAGCCAGACATTCCCCAATGCTGACTTTGCAGAA<br>ATCACCAAATTGGCAACAGACCTGACCAAAGTCAACAAGGAGTGCTGCCATGGT<br>GACCTGCTGGAATGCGCAGATGACAGGGCGGAACTTGCCAAGTACATGTGTGAA<br>AACCAGGCGACTATCTCCAGCAAACTGCAGACTTGCTGCGATAAACCACTGTTG<br>AAGAAAGCCCACTGTCTTAGTGAGGTGGAGCATGACACCATGCCTGCTGATCTG<br>CCTGCCATTGCTGCTGATTTTGTTGAGGACCAGGAAGTGTGCAAGAACTATGCT<br>GAGGCCAAGGATGTCTTCCTGGGCACGTTCTTGTATGAATATTCAAGAAGACAC<br>CCTGATTACTCTGTATCCCTGTTGCTGAGACTTGCTAAGAAATATGAAGCCACT<br>CTGGAAAAGTGCTGCGCTGAAGCCAATCCTCCCGCATGCTACGGCACAGTGCTT<br>GCTGAATTTCAGCCTCTTGTAGAAGAGCCTAAGAACTTGGTCAAAACCAACTGT<br>GATCTTTACGAGAAGCTTGGAGAATATGGATTCCAAAATGCCATTCTAGTTCGC<br>TACACCCAGAAAGCACCTCAGGTGTCAACCCCAACTCTCGTGGAGGCTGCAAGA<br>AACCTAGGAAGAGTGGGCACCAAGTGTTGTACACTTCCTGAAGATCAGAGACTG<br>CCTTGTGTGGAAGACTATCTGTCTGCAATCCTGAACCGTGTGTGTCTGCTGCAT<br>GAGAAGACCCCAGTGAGTGAGCATGTTACCAAGTGCTGTAGTGGATCCCTGGTG<br>GAAAGGCGGCCATGCTTCTCTGCTCTGACAGTTGATGAAACATATGTCCCCAAA<br>GAGTTTAAAGCTGAGACCTTCACCTTCCACTCTGATATCTGCACACTTCCAGAG<br>AAGGAGAAGCAGATTAAGAAACAAACGGCTCTTGCTGAGCTGGTGAAGCACAAG<br>CCCAAGGCTACAGCGGAGCAACTGAAGACTGTCATGGATGACTTTGCACAGTTC<br>CTGGATACATGTTGCAAGGCTGCTGACAAGGACACCTGCTTCTCGACTGAGGGT<br>CCAAACCTTGTCACTAGATGCAAAGACGCCTTAGCC<u>*GGTGGAGGAGGCTCTGGT*</u><br><u>*GGAGGCGGTAGCGGAGGCGGAGGGTCG*</u>GATATCCAGATGACCCAGTCCCCGAGC<br>TCCCTGTCCGCCTCTGTGGGCGATAGGGTCACCATCACCTGCCGTGCCAGTCAG<br>TCTTACGGTGGTGTAGCCTGGTATCAACAGAAACCAGGAAAAGCCCCGAAGCTT<br>CTGATTTACTCTGCATCCTACCTCTACTCTGGAGTCCCTTCTCGCTTCTCTGGT |

TABLE 12-continued

Sequence Summary

| SEQ ID NO | Description | Sequence |
|---|---|---|
| | | AGCCGTTCCGGGACGGATTTCACTCTGACCATCAGCAGTCTGCAGCCGGAAGAC<br>TTCGCAACTTATTACTGTCAGCAACCATCTCATCTGATCACGTTCGGA*TGC*GGT<br>ACCGAGGTGGAGATCAAAGGTACTACTGCCGCTAGTGGTAGTAGTGGTGGCAGT<br>AGCAGTGGTGCCGAGGTTCAGCTGGTGGAGTCTGGCGGTGGCCTGGTGCAGCCA<br>GGGGGCTCACTCCGTTTGTCCTGTGCAGCTTCTGGCTCCAACCCCTACTACTAC<br>GGTGGTACGCACTGGGTGCGTCAGGCCCGGGTGAG*TGC*CTGGAATGGGTTGCA<br>TCTATTGGTTCTTACCCTGGCTACACTGACTATGCCGATAGCGTCAAGGGCCGT<br>TTCACTATAAGCGCAGACACATCCAAAAACACAGCCTACCTACAAATGAACAGC<br>TTAAGAGCTGAGGACACTGCCGTCTATTATTGTGCTCGCCATTACTACTGGTAC<br>GATGCTACTGACTACTGGGGTCAAGGAACCCTGGTCACCGTCTCCTCG<u>GGAGGG<br>GGCGGTTCC</u>CACCATCACCACCATCACTGATAG |
| 89 | gWiz-LS-<br>mouse SA-<br>(Gly₄Ser)₃-<br>scFv (V$_L$-<br>V$_H$) CK157-<br>ds2<br>(V$_L$43$^{A>C}$/<br>V$_H$105$^{Q>C}$)-<br>(Gly₄Ser)-<br>His₆ | ATGGACATGAGAGTGCCTGCTCAGCTGCTGGGCCTGCTGCTGCTGTGGCTGCCT<br>GGTGCTAGATGCGAAGCACACAAGAGTGAGATCGCCCATCGGTATAATGATTTC<br>GGAGAACAACATTTCAAAGGCCTAGTCCTGATTGCCTTTTCCCAGTATCTCCAC<br>AAATGCTCATACGATGAGCATGCCAAATTAGTGCAGGAAGTAACAGACTTTGCA<br>AAGACGTGTGTTGCCGATGAGTCTGCCGCCAACTGTGACAAATCCCTTCACACT<br>CTTTTTGGAGATAAGTTGTGTGCCATTCCAAACCTCCGTGAAAACTATGGTGAA<br>CTGGCTGACTGCTGTACAAAACAAGAGCCCGAAAGAAACGAATGTTTCCTGCAA<br>CACAAAGATGACAACCCCAGCCTACCACCATTTGAAAGGCCAGAGGCTGAGGCC<br>ATGTGCACCTCCTTTAAGGAAAACCCAACCACCTTTATGGGACACTATTTGCAT<br>GAAGTTGCCAGAAGACATCCTTATTTCTATGCCCCAGAACTTCTTTACTATGCT<br>GAGCAGTACAATGAGATTCTGACCCAGTGTTGTGCAGAGGCTGACAAGGAAAGC<br>TGCCTGACCCCGAAGCTTGATGGTGTGAAGGAGAAAGCATTGGTCTCATCTGTC<br>CGTCAGAGAATGAAGTGCTCCAGTATGCAGAAGTTTGGAGAGAGAGCTTTTAAA<br>GCATGGGCAGTAGCTCGTCTGAGCCAGACATTCCCCAATGCTGACTTTGCAGAA<br>ATCACCAAATTGGCAACAGACCTGACCAAAGTCAACAAGGAGTGCTGCCATGGT<br>GACCTGCTGGAATGCGCAGATGACAGGGCGGAACTTGCCAAGTACATGTGTGAA<br>AACCAGGCGACTATCTCCAGCAAACTGCAGACTTGCTGCGATAAACCACTGTTG<br>AAGAAAGCCCACTGTCTTAGTGAGGTGGAGCATGACACCATGCCTGCTGATCTG<br>CCTGCCATTGCTGCTGATTTTGTTGAGGACCAGGAAGTGTGCAAGAACTATGCT<br>GAGGCCAAGGATGTCTTCCTGGGCACGTTCTTGTATGAATATTCAAGAAGACAC<br>CCTGATTACTCTGTATCCCTGTTGCTGAGACTTGCTAAGAAATATGAAGCCACT<br>CTGGAAAAGTGCTGCGCTGAAGCCAATCCTCCCGCATGCTACGGCACAGTGCTT<br>GCTGAATTTCAGCCTCTTGTAGAAGAGCCTAAGAACTTGGTCAAAACCAACTGT<br>GATCTTTACGAGAAGCTTGGAGAATATGGATTCCAAAATGCCATTCTAGTTCGC<br>TACACCCAGAAAGCACCTCAGGTGTCAACCCCAACTCTCGTGGAGGCTGCAAGA<br>AACCTAGGAAGAGTGGGCACCAAGTGTTGTACACTTCCTGAAGATCAGAGACTG<br>CCTTGTGTGGAAGACTATCTGTCTGCAATCCTGAACCGTGTGTGTCTGCTGCAT<br>GAGAAGACCCCAGTGAGTGAGCATGTTACCAAGTGCTGTAGTGGATCCCTGGTG<br>GAAAGGCGGCCATGCTTCTCTGCTCTGACAGTTGATGAAACATATGTCCCCAAA<br>GAGTTTAAAGCTGAGACCTTCACCTTCCACTCTGATATCTGCACACTTCCAGAG<br>AAGGAGAAGCAGATTAAGAAACAAACGGCTCTTGCTGAGCTGGTGAAGCACAAG<br>CCCAAGGCTACAGCGGAGCAACTGAAGACTGTCATGGATGACTTTGCACAGTTC<br>CTGGATACATGTTGCAAGGCTGCTGACAAGGACACCTGCTTCTCGACTGAGGGT<br>CCAAACCTTGTCACTAGATGCAAAGACGCCTTAGCC<u>GGTGGAGGAGGCTCTGGT<br>GGAGGCGGTAGCGGAGGCGGAGGGTCG</u>GATATCCAGATGACCCAGTCCCCGAGC<br>TCCCTGTCCGCCTCTGTGGGCGATAGGGTCACCATCACCTGCCGTGCCAGTCAG<br>TCTTACGGTGGTGTAGCCTGGTATCAACAGAAACCAGGAAAA*TGC*CCCGAAGCTT<br>CTGATTTACTCTGCATCCTACCTCTACTCTGGAGTCCCTTCTCGCTTCTCTGGT<br>AGCCGTTCCGGGACGGATTTCACTCTGACCATCAGCAGTCTGCAGCCGGAAGAC<br>TTCGCAACTTATTACTGTCAGCAACCATCTCATCTGATCACGTTCGGACAGGGT<br>ACCGAGGTGGAGATCAAAGGTACTACTGCCGCTAGTGGTAGTAGTGGTGGCAGT<br>AGCAGTGGTGCCGAGGTTCAGCTGGTGGAGTCTGGCGGTGGCCTGGTGCAGCCA<br>GGGGGCTCACTCCGTTTGTCCTGTGCAGCTTCTGGCTCCAACCCCTACTACTAC<br>GGTGGTACGCACTGGGTGCGTCAGGCCCGGGTGAGGAGCTGGAATGGGTTGCA<br>TCTATTGGTTCTTACCCTGGCTACACTGACTATGCCGATAGCGTCAAGGGCCGT<br>TTCACTATAAGCGCAGACACATCCAAAAACACAGCCTACCTACAAATGAACAGC<br>TTAAGAGCTGAGGACACTGCCGTCTATTATTGTGCTCGCCATTACTACTGGTAC<br>GATGCTACTGACTACTGGGGT*TGC*GGAACCCTGGTCACCGTCTCCTCG<u>GGAGGG<br>GGCGGTTCC</u>CACCATCACCACCATCACTGATAG |
| 90 | gWiz-LS-<br>mouse SA-<br>(Gly₄Ser)-V$_L$<br>CK157-His₆ | ATGGACATGAGAGTGCCTGCTCAGCTGCTGGGCCTGCTGCTGCTGTGGCTGCCT<br>GGTGCTAGATGCGAAGCACACAAGAGTGAGATCGCCCATCGGTATAATGATTTG<br>GGAGAACAACATTTCAAAGGCCTAGTCCTGATTGCCTTTTCCCAGTATCTCCAG<br>AAATGCTCATACGATGAGCATGCCAAATTAGTGCAGGAAGTAACAGACTTTGCA<br>AAGACGTGTGTTGCCGATGAGTCTGCCGCCAACTGTGACAAATCCCTTCACACT<br>CTTTTTGGAGATAAGTTGTGTGCCATTCCAAACCTCCGTGAAAACTATGGTGAA<br>CTGGCTGACTGCTGTACAAAACAAGAGCCCGAAAGAAACGAATGTTTCCTGCAA<br>CACAAAGATGACAACCCCAGCCTACCACCATTTGAAAGGCCAGAGGCTGAGGCC<br>ATGTGCACCTCCTTTAAGGAAAACCCAACCACCTTTATGGGACACTATTTGCAT<br>GAAGTTGCCAGAAGACATCCTTATTTCTATGCCCCAGAACTTCTTTACTATGCT<br>GAGCAGTACAATGAGATTCTGACCCAGTGTTGTGCAGAGGCTGACAAGGAAAGC<br>TGCCTGACCCCGAAGCTTGATGGTGTGAAGGAGAAAGCATTGGTCTCATCTGTC<br>CGTCAGAGAATGAAGTGCTCCAGTATGCAGAAGTTTGGAGAGAGAGCTTTTAAA |

TABLE 12-continued

Sequence Summary

| SEQ ID NO | Description | Sequence |
|---|---|---|
| | | GCATGGGCAGTAGCTCGTCTGAGCCAGACATTCCCCAATGCTGACTTTGCAGAA ATCACCAAATTGGCAACAGACCTGACCAAAGTCAACAAGGAGTGCTGCCATGGT GACCTGCTGGAATGCGCAGATGACAGGGCGGAACTTGCCAAGTACATGTGTGAA AACCAGGCGACTATCTCCAGCAAACTGCAGACTTGCTGCGATAAACCACTGTTG AAGAAAGCCCACTGTCTTAGTGAGGTGGAGCATGACACCATGCCTGCTGATCTG CCTGCCATTGCTGCTGATTTTGTTGAGGACCAGGAAGTGTGCAAGAACTATGCT GAGGCCAAGGATGTCTTCCTGGGCACGTTCTTGTATGAATATTCAAGAAGACAC CCTGATTACTCTGTATCCCTGTTGCTGAGACTTGCTAAGAAATATGAAGCCACT CTGGAAAAGTGCTGCGCTGAAGCCAATCCTCCCGCATGCTACGGCACAGTGCTT GCTGAATTTCAGCCTCTTGTAGAAGAGCCTAAGAACTTGGTCAAAACCAACTGT GATCTTTACGAGAAGCTTGGAGAATATGGATTCCAAAATGCCATTCTAGTTCGC TACACCCAGAAAGCACCTCAGGTGTCAACCCCAACTCTCGTGGAGGCTGCAAGA AACCTAGGAAGAGTGGGCACCAAGTGTTGTACACTTCCTGAAGATCAGAGACTG CCTTGTGTGGAAGACTATCTGTCTGCAATCCTGAACCGTGTGTGTCTGCTGCAT GAGAAGACCCCAGTGAGTGAGCATGTTACCAAGTGCTGTAGTGGATCCCTGGTG GAAAGGCGGCCATGCTTCTCTGCTCTGACAGTTGATGAAACATATGTCCCCAAA GAGTTTAAAGCTGAGACCTTCACCTTCCACTCTGATATCTGCACACTTCCAGAG AAGGAGAAGCAGATTAAGAAACAAACGGCTCTTGCTGAGCTGGTGAAGCACAAG CCCAAGGCTACAGCGGAGCAACTGAAGACTGTCATGGATGACTTTGCACAGTTC CTGGATACATGTTGCAAGGCTGCTGACAAGGACACCTGCTTCTCGACTGAGGGT CCAAACCTTGTCACTAGATGCAAAGACGCCTTAGCC<u>GGTGGAGGAGGCTCTGGT GGAGGCGGTAGCGGAGGCGGAGGGTCG</u>GATATCCAGATGACCCAGTCCCCGAGC TCCCTGTCCGCCTCTGTGGGCGATAGGGTCACCATCACCTGCCGTGCCAGTCAG TCTTACGGTGGTAGCTGGTATCAACAGAAACCAGGAAAAGCCCCGAAGCTT CTGATTTACTCTGCATCCTACCTCTACTCTGGAGTCCCTTCTCGCTTCTCTGGT AGCCGTTCCGGGACGGATTTCACTCTGACCATCAGCAGTCTGCAGCCGGAAGAC TTCGCAACTTATTACTGTCAGCAACCATCTCATCTGATCACGTTCGGACAGGGT ACCGAGGTGGAGATCAAA<u>GGAGGGGGCGGTTCC</u>CACCATCACCACCATCACTGA TAG |
| 91 | gWiz-LS-mouse SA-(Gly$_4$Ser)-V$_H$ CK157-His$_6$ | ATG<u>GACATGAGAGTGCCTGCTCAGCTGCTGGGCCTGCTGCTGCTGTGGCTGCCT GGTGCTAGATGC</u>GAAGCACACAAGAGTGAGATCGCCCATCGGTATAATGATTTG GGAGAACAACATTTCAAAGGCCTAGTCCTGATTGCCTTTTCCCAGTATCTCCAG AAATGCTCATACGATGAGCATGCCAAATTAGTGCAGGAAGTAACAGACTTTGCA AAGACGTGTGTTGCCGATGAGTCTGCCGCCAACTGTGACAAATCCCTTCACACT CTTTTTTGGAGATAAGTTGTGTGCCATTCCAAACCTCCGTGAAAACTATGGTGAA CTGGCTGACTGCTGTACAAAACAAGAGCCCGAAAGAAACGAATGTTTCCTGCAA CACAAAGATGACAACCCCAGCCTACCACCATTTGAAAGGCCAGAGGCTGAGGCC ATGTGCACCTCCTTTAAGGAAAACCCAACCACCTTTATGGGACACTATTTGCAT GAAGTTGCCAGAAGACATCCTTATTTCTATGCCCCAGAACTTCTTTACTATGCT GAGCAGTACAATGAGATTCTGACCCAGTGTTGTGCAGAGGCTGACAAGGAAAGC TGCCTGACCCCGAAGCTTGATGGTGTGAAGGAGAAAGCATTGGTCTCATCTGTC CGTCAGAGAATGAAGTGCTCCAGTATGCAGAAGTTTGGAGAGAGAGCTTTTAAA GCATGGGCAGTAGCTCGTCTGAGCCAGACATTCCCCAATGCTGACTTTGCAGAA ATCACCAAATTGGCAACAGACCTGACCAAAGTCAACAAGGAGTGCTGCCATGGT GACCTGCTGGAATGCGCAGATGACAGGGCGGAACTTGCCAAGTACATGTGTGAA AACCAGGCGACTATCTCCAGCAAACTGCAGACTTGCTGCGATAAACCACTGTTG AAGAAAGCCCACTGTCTTAGTGAGGTGGAGCATGACACCATGCCTGCTGATCTG CCTGCCATTGCTGCTGATTTTGTTGAGGACCAGGAAGTGTGCAAGAACTATGCT GAGGCCAAGGATGTCTTCCTGGGCACGTTCTTGTATGAATATTCAAGAAGACAC CCTGATTACTCTGTATCCCTGTTGCTGAGACTTGCTAAGAAATATGAAGCCACT CTGGAAAAGTGCTGCGCTGAAGCCAATCCTCCCGCATGCTACGGCACAGTGCTT GCTGAATTTCAGCCTCTTGTAGAAGAGCCTAAGAACTTGGTCAAAACCAACTGT GATCTTTACGAGAAGCTTGGAGAATATGGATTCCAAAATGCCATTCTAGTTCGC TACACCCAGAAAGCACCTCAGGTGTCAACCCCAACTCTCGTGGAGGCTGCAAGA AACCTAGGAAGAGTGGGCACCAAGTGTTGTACACTTCCTGAAGATCAGAGACTG CCTTGTGTGGAAGACTATCTGTCTGCAATCCTGAACCGTGTGTGTCTGCTGCAT GAGAAGACCCCAGTGAGTGAGCATGTTACCAAGTGCTGTAGTGGATCCCTGGTG GAAAGGCGGCCATGCTTCTCTGCTCTGACAGTTGATGAAACATATGTCCCCAAA GAGTTTAAAGCTGAGACCTTCACCTTCCACTCTGATATCTGCACACTTCCAGAG AAGGAGAAGCAGATTAAGAAACAAACGGCTCTTGCTGAGCTGGTGAAGCACAAG CCCAAGGCTACAGCGGAGCAACTGAAGACTGTCATGGATGACTTTGCACAGTTC CTGGATACATGTTGCAAGGCTGCTGACAAGGACACCTGCTTCTCGACTGAGGGT CCAAACCTTGTCACTAGATGCAAAGACGCCTTAGCC<u>GGTGGAGGAGGCTCTGGT GGAGGCGGTAGCGGAGGCGGAGGGTCG</u>GCCGAGGTTCAGCTGGTGGAGTCTGGC GGTGGCCTGGTGCAGCCAGGGGGCTCACTCCGTTTGTCCTGTGCAGCTTCTGGC TCCAACCCCTACTACTACGGTGGTACGCACTGGGTGCGTCAGGCCCCGGGTGAG GAGCTGGAATGGGTTGCATCTATTGGTTCTTACCCTGGCTACACTGACTATGCC GATAGCGTCAAGGGCCGTTTCACTATAAGCGCAGACACATCCAAAAACACAGCC TACCTACAAATGAACAGCTTAAGAGCTGAGGACACTGCCGTCTATTATTGTGCT CGCCATTACTACTGGTACGATGCTACTGACTACTGGGGTCAAGGAACCCTGGTC ACCGTCTCCTCG<u>GGAGGGGGCGGTTCC</u>CACCATCACCACCATCACTGATAG |
| 92 | gWiz-LS-mouse SA- | ATG<u>GACATGAGAGTGCCTGCTCAGCTGCTGGGCCTGCTGCTGCTGTGGCTGCCT GGTGCTAGATGC</u>GAAGCACACAAGAGTGAGATCGCCCATCGGTATAATGATTTG |

TABLE 12-continued

Sequence Summary

| SEQ ID NO | Description | Sequence |
|---|---|---|
| | (Gly$_4$Ser)$_3$-scFv (V$_L$-V$_H$) CK129-ds1 (V$_L$100$^{Q>C}$/V$_H$44$^{G>C}$)-(Gly$_4$Ser)-His$_6$ | GGAGAACAACATTTCAAAGGCCTAGTCCTGATTGCCTTTTCCCAGTATCTCCAG<br>AAATGCTCATACGATGAGCATGCCAAATTAGTGCAGGAAGTAACAGACTTTGCA<br>AAGACGTGTGTTGCCGATGAGTCTGCCGCCAACTGTGACAAATCCCTTCACACT<br>CTTTTTGGAGATAAGTTGTGTGCCATTCCAAACCTCCGTGAAAACTATGGTGAA<br>CTGGCTGACTGCTGTACAAAACAAGAGCCCGAAAGAAACGAATGTTCCTGCAA<br>CACAAAGATGACAACCCCAGCCTACCACCATTTGAAAGGCCAGAGGCTGAGGCC<br>ATGTGCACCTCCTTTAAGGAAAACCCAACCACCTTTATGGGACACTATTTGCAT<br>GAAGTTGCCAGAAGACATCCTTATTTCTATGCCCCAGAACTTCTTTACTATGCT<br>GAGCAGTACAATGAGATTCTGACCCAGTGTTGTGCAGAGGCTGACAAGGAAAGC<br>TGCCTGACCCCGAAGCTTGATGGTGTGAAGGAGAAAGCATTGGTCTCATCTGTC<br>CGTCAGAGAATGAAGTGCTCCAGTATGCAGAAGTTTGGAGAGAGAGCTTTTAAA<br>GCATGGGCAGTAGCTCGTCTGAGCCAGACATTCCCCAATGCTGACTTTGCAGAA<br>ATCACCAAATTGGCAACAGACCTGACCAAAGTCAACAAGGAGTGCTGCCATGGT<br>GACCTGCTGGAATGCGCAGATGACAGGGCGGAACTTGCCAAGTACATGTGTGAA<br>AACCAGGCGACTATCTCCAGCAAACTGCAGACTTGCTGCGATAAACCACTGTTG<br>AAGAAAGCCCACTGTCTTAGTGAGGTGGAGCATGACACCATGCCTGCTGATCTG<br>CCTGCCATTGCTGCTGATTTTGTTGAGGACCAGGAAGTGTGCAAGAACTATGCT<br>GAGGCCAAGGATGTCTTCCTGGGCACGTTCTTGTATGAATATTCAAGAAGACAC<br>CCTGATTACTCTGTATCCCTGTTGCTGAGACTTGCTAAGAAATATGAAGCCACT<br>CTGGAAAAGTGCTGCGCTGAAGCCAATCCTCCCGCATGCTACGGCACAGTGCTT<br>GCTGAATTTCAGCCTCTTGTAGAAGAGCCTAAGAACTTGGTCAAAACCAACTGT<br>GATCTTTACGAGAAGCTTGGAGAATATGGATTCCAAAATGCCATTCTAGTTCGC<br>TACACCCAGAAAGCACCTCAGGTGTCAACCCCAACTCTCGTGGAGGCTGCAAGA<br>AACCTAGGAAGAGTGGGCACCAAGTGTTGTACACTTCCTGAAGATCAGAGACTG<br>CCTTGTGTGGAAGACTATCTGTCTGCAATCCTGAACCGTGTGTGTCTGCTGCAT<br>GAGAAGACCCCAGTGAGTGAGCATGTTACCAAGTGCTGTAGTGGATCCCTGGTG<br>GAAAGGCGGCCATGCTTCTCTGCTCTGACAGTTGATGAAACATATGTCCCCAAA<br>GAGTTTAAAGCTGAGACCTTCACCTTCCACTCTGATATCTGCACACTTCCAGAG<br>AAGGAGAAGCAGATTAAGAAACAAACGGCTCTTGCTGAGCTGGTGAAGCACAAG<br>CCCAAGGCTACAGCGGAGCAACTGAAGACTGTCATGGATGACTTTGCACAGTTC<br>CTGGATACATGTTGCAAGGCTGCTGACAAGGACACCTGCTTCTCGACTGAGGGT<br>CCAAACCTTGTCACTAGATGCAAAGACGCCTTAGC<u>GGTGGAGGAGGCTCTGGT</u><br><u>GGAGGCGGTAGCGGAGGCGGAGGGTCG</u>GATATCCAGATGACCCAGTCCCCGAGC<br>CCCCTGTCCGCCTCTGTGGGCGATAGGGTCACCATCACCTGCCGTGCCAGTCAG<br>TACGGTGGTTACGTAGCCTGGTATCAACAGAAACCAGGAAAAGCTCCGAAGCTT<br>CTGATTTACGGTGCATCCCTTCTCTACTCTGGAGTCCCTTCTCGCTTCTCTGGT<br>GGCCGTTCCGGGACGGATTTCACTCTGACCATCAGCAGTCTGCAGCCGGAAGAC<br>TTCGCAACTTATTACTGTCAGCGAGGTCATGCTCTGATCACGTTCGGA<i>TGC</i>GGT<br>ACCAAGGTGGAGATCGAAGGTACTACTGCCGCTAGTGGTAGTAGTGGTGGCAGT<br>AGCAGTGGTGCCGAGGTTCAGCTGGTGGAGTCTGGCGGTGGCCTGGTGCAGCCA<br>GGGGGGCTCACTCCGTTTATCCTGTGCAGCTTCTGGCTTCAACATCTCTTCTTAC<br>GGTTCTATGCACTGGGTGCGTCAGGCCCCGGGTAAG<i>T</i>GCCTGGAATGGGTTGCA<br>TCTATTTACCCTTACTCTAGCTCTACTTACTATGCCGATAGCGTCAAGGGCCGT<br>TTCACTATAAGCGCAGACACATCCAAAAACACAGCCTACCTACAAATGAACAGC<br>TTAAGAGCTGAGGACACTGCCGTCTATTATTGTGCTCGTGGTTACGGTCCGTGG<br>TACGCTTACTCTTACTTCGCTTTGGACTACTGGGGTCAAGGAACCCTGGTCACC<br>GTCTCCTCG<u>GGAGGGGGCGGTTCC</u>CACCATCACCACCATCACTGATAG |
| 93 | gWiz-LS-mouse SA-(Gly$_4$Ser)$_3$-scFv (V$_L$-V$_H$) CK129-ds2 (V$_L$43$^{A>C}$/V$_H$105$^{Q>C}$)-(Gly$_4$Ser)-His$_6$ | ATGGACATGAGAGTGCCTGCTCAGCTGCTGGGCCTGCTGCTGCTGTGGCTGCCT<br><u>GGTGCTAGATGC</u>GAAGCACACAAGAGTGAGATCGCCCATCGGTATAATGATTTG<br>GGAGAACAACATTTCAAAGGCCTAGTCCTGATTGCCTTTTCCCAGTATCTCCAG<br>AAATGCTCATACGATGAGCATGCCAAATTAGTGCAGGAAGTAACAGACTTTGCA<br>AAGACGTGTGTTGCCGATGAGTCTGCCGCCAACTGTGACAAATCCCTTCACACT<br>CTTTTTGGAGATAAGTTGTGTGCCATTCCAAACCTCCGTGAAAACTATGGTGAA<br>CTGGCTGACTGCTGTACAAAACAAGAGCCCGAAAGAAACGAATGTTCCTGCAA<br>CACAAAGATGACAACCCCAGCCTACCACCATTTGAAAGGCCAGAGGCTGAGGCC<br>ATGTGCACCTCCTTTAAGGAAAACCCAACCACCTTTATGGGACACTATTTGCAT<br>GAAGTTGCCAGAAGACATCCTTATTTCTATGCCCCAGAACTTCTTTACTATGCT<br>GAGCAGTACAATGAGATTCTGACCCAGTGTTGTGCAGAGGCTGACAAGGAAAGC<br>TGCCTGACCCCGAAGCTTGATGGTGTGAAGGAGAAAGCATTGGTCTCATCTGTC<br>CGTCAGAGAATGAAGTGCTCCAGTATGCAGAAGTTTGGAGAGAGAGCTTTTAAA<br>GCATGGGCAGTAGCTCGTCTGAGCCAGACATTCCCCAATGCTGACTTTGCAGAA<br>ATCACCAAATTGGCAACAGACCTGACCAAAGTCAACAAGGAGTGCTGCCATGGT<br>GACCTGCTGGAATGCGCAGATGACAGGGCGGAACTTGCCAAGTACATGTGTGAA<br>AACCAGGCGACTATCTCCAGCAAACTGCAGACTTGCTGCGATAAACCACTGTTG<br>AAGAAAGCCCACTGTCTTAGTGAGGTGGAGCATGACACCATGCCTGCTGATCTG<br>CCTGCCATTGCTGCTGATTTTGTTGAGGACCAGGAAGTGTGCAAGAACTATGCT<br>GAGGCCAAGGATGTCTTCCTGGGCACGTTCTTGTATGAATATTCAAGAAGACAC<br>CCTGATTACTCTGTATCCCTGTTGCTGAGACTTGCTAAGAAATATGAAGCCACT<br>CTGGAAAAGTGCTGCGCTGAAGCCAATCCTCCCGCATGCTACGGCACAGTGCTT<br>GCTGAATTTCAGCCTCTTGTAGAAGAGCCTAAGAACTTGGTCAAAACCAACTGT<br>GATCTTTACGAGAAGCTTGGAGAATATGGATTCCAAAATGCCATTCTAGTTCGC<br>TACACCCAGAAAGCACCTCAGGTGTCAACCCCAACTCTCGTGGAGGCTGCAAGA<br>AACCTAGGAAGAGTGGGCACCAAGTGTTGTACACTTCCTGAAGATCAGAGACTG<br>CCTTGTGTGGAAGACTATCTGTCTGCAATCCTGAACCGTGTGTGTCTGCTGCAT |

TABLE 12-continued

Sequence Summary

| SEQ ID NO | Description | Sequence |
|---|---|---|
| | | GAGAAGACCCCAGTGAGTGAGCATGTTACCAAGTGCTGTAGTGGATCCCTGGTG<br>GAAAGGCGGCCATGCTTCTCTGCTCTGACAGTTGATGAAACATATGTCCCCAAA<br>GAGTTTAAAGCTGAGACCTTCACCTTCCACTCTGATATCTGCACACTTCCAGAG<br>AAGGAGAAGCAGATTAAGAAACAAACGGCTCTTGCTGAGCTGGTGAAGGACAAG<br>CCCAAGGCTACAGCGGAGCAACTGAAGACTGTCATGGATGACTTTGCACAGTTC<br>CTGGATACATGTTGCAAGGCTGCTGACAAGGACACCTGCTTCTCGACTGAGGGT<br>CCAAACCTTGTCACTAGATGCAAAGACGCCTTAGCC*GGTGGAGGAGGCTCTGGT*<br>*GGAGGCGGTAGCGGAGGCGGAGGGTCG*GATATCCAGATGACCCAGTCCCCGAGC<br>CCCCTGTCCGCCTCTGTGGGCGATAGGGTCACCATCACCTGCCGTGCCAGTCAG<br>TACGGTGGTTACGTAGCCTGGTATCAACAGAAACCAGGAAAA*TGC*CCGAAGCTT<br>CTGATTTACGGTGCATCCCTTCTCTACTCTGGAGTCCCTTCTCGCTTCTCTGGT<br>GGCCGTTCCGGGACGGATTTCACTCTGACCATCAGCAGTCTGCAGCCGGAAGAC<br>TTCGCAACTTATTACTGTCAGCGAGGTCATGCTCTGATCACGTTCGGACAGGGT<br>ACCAAGGTGGAGATCGAAGGTACTACTGCCGCTAGTGGTAGTAGTGGTGGCAGT<br>AGCAGTGGTGCCGAGGTTCAGCTGGTGGAGTCTGGCGGTGGCCTGGTGCAGCCA<br>GGGGGCTCACTCCGTTTATCCTGTGCAGCTTCTGGCTTCAACATCTCTTCTTAC<br>GGTTCTATGCACTGGGTGCGTCAGGCCCCGGGTAAGGGCCTGGAATGGGTTGCA<br>TCTATTTACCCTTACTCTAGCTCTACTTACTATGCCGATAGCGTCAAGGGCCGT<br>TTCACTATAAGCGCAGACACATCCAAAAACACAGCCTACCTACAAATGAACAGC<br>TTAAGAGCTGAGGACACTGCCGTCTATTATTGTGCTCGTGGTTACGGTCCGTGG<br>TACGCTTACTCTTACTTCGCTTTGGACTACTGGGGT*TGC*GGAACCCTGGTCACC<br>GTCTCCTCG*GGAGGGGGCGGTTCC*CACCATCACCACCATCACTGATAG |
| 94 | gWiz-LS-<br>mouse SA-<br>(Gly$_4$Ser)$_3$-<br>scFv (V$_H$-<br>V$_L$) sm3E-ds<br>(V$_H$44$^{R>G}$/<br>V$_L$100$^{G>C}$)-<br>(Gly$_4$Ser)-<br>His$_6$ | ATGGACATGAGAGTGCCTGCTCAGCTGCTGGGCCTGCTGCTGCTGTGGCTGCCT<br>GGTGCTAGATGCGAAGCACACAAGAGTGAGATCGCCCATCGGTATAATGATTTG<br>GGAGAACAACATTTCAAAGGCCTAGTCCTGATTGCCTTTTCCCAGTATCTCCAG<br>AAATGCTCATACGATGAGCATGCCAAATTAGTGCAGGAAGTAACAGACTTTGCA<br>AAGACGTGTGTTGCCGATGAGTCTGCCGCCAACTGTGACAAATCCCTTCACACT<br>CTTTTTGGAGATAAGTTGTGTGCCATTCCAAACCTCCGTGAAAACTATGGTGAA<br>CTGGCTGACTGCTGTACAAAACAAGAGCCCGAAAGAAACGAATGTTTCCTGCAA<br>CACAAAGATGACAACCCCAGCCTACCACCATTTGAAAGGCCAGAGGCTGAGGCC<br>ATGTGCACCTCCTTTAAGGAAAACCCAACCACCTTTATGGGACACTATTTGCAT<br>GAAGTTGCCAGAAGACATCCTTATTTCTATGCCCCAGAACTTCTTTACTATGCT<br>GAGCAGTACAATGAGATTCTGACCCAGTGTTGTGCAGAGGCTGACAAGGAAAGC<br>TGCCTGACCCCGAAGCTTGATGGTGTGAAGGAGAAAGCATTGGTCTCATCTGTC<br>CGTCAGAGAATGAAGTGCTCCAGTATGCAGAAGTTTGGAGAGAGAGCTTTTAAA<br>GCATGGGCAGTAGCTCGTCTGAGCCAGACATTCCCCAATGCTGACTTTGCAGAA<br>ATCACCAAATTGGCAACAGACCTGACCAAAGTCAACAAGGAGTGCTGCCATGGT<br>GACCTGCTGGAATGCGCAGATGACAGGGCGGAACTTGCCAAGTACATGTGTGAA<br>AACCAGGCGACTATCTCCAGCAAACTGCAGACTTGCTGCGATAAACCACTGTTG<br>AAGAAAGCCCACTGTCTTAGTGAGGTGGAGCATGACACCATGCCTGCTGATCTG<br>CCTGCCATTGCTGCTGATTTTGTTGAGGACCAGGAAGTGTGCAAGAACTATGCT<br>GAGGCCAAGGATGTCTTCCTGGGCACGTTCTTGTATGAATATTCAAGAAGACAC<br>CCTGATTACTCTGTATCCCTGTTGCTGAGACTTGCTAAGAAATATGAAGCCACT<br>CTGGAAAAGTGCTGCGCTGAAGCCAATCCTCCCGCATGCTACGGCACAGTGCTT<br>GCTGAATTTCAGCCTCTTGTAGAAGAGCCTAAGAACTTGGTCAAAACCAACTGT<br>GATCTTTACGAGAAGCTTGGAGAATATGGATTCCAAAATGCCATTCTAGTTCGC<br>TACACCCAGAAAGCACCTCAGGTGTCAACCCCAACTCTCGTGGAGGCTGCAAGA<br>AACCTAGGAAGAGTGGGCACCAAGTGTTGTACACTTCCTGAAGATCAGAGACTG<br>CCTTGTGTGGAAGACTATCTGTCTGCAATCCTGAACCGTGTGTGTCTGCTGCAT<br>GAGAAGACCCCAGTGAGTGAGCATGTTACCAAGTGCTGTAGTGGATCCCTGGTG<br>GAAAGGCGGCCATGCTTCTCTGCTCTGACAGTTGATGAAACATATGTCCCCAAA<br>GAGTTTAAAGCTGAGACCTTCACCTTCCACTCTGATATCTGCACACTTCCAGAG<br>AAGGAGAAGCAGATTAAGAAACAAACGGCTCTTGCTGAGCTGGTGAAGGACAAG<br>CCCAAGGCTACAGCGGAGCAACTGAAGACTGTCATGGATGACTTTGCACAGTTC<br>CTGGATACATGTTGCAAGGCTGCTGACAAGGACACCTGCTTCTCGACTGAGGGT<br>CCAAACCTTGTCACTAGATGCAAAGACGCCTTAGCC*GGTGGAGGAGGCTCTGGT*<br>*GGAGGCGGTAGCGGAGGCGGAGGGTCG*CAAGTTAAACTGGAACAGTCCGGTGCT<br>GAAGTTGTCAAACCAGGTGCTTCCGTGAAGTTGTCCTGTAAAGCCTCTGGTTTT<br>AACATCAAGGATTCGTATATGCATTGGTTGAGACAAGGGCCAGGACAA*TGT*TTG<br>GAATGGATTGGCTGGATTGATCCAGAAGAATGGTGATACCGAGTACGCTCCTAAA<br>TTTCAGGGAAAGGCTACTTTTACTACCGACACTTCCGCTAATACCGCATACTTG<br>GGCTTATCTTCCTTGAGACCAGAGGACACTGCCGTATACTACTGCAACGAAGGG<br>ACACCAACTGGTCCTTACTATTTCGACTACTGGGGACAAGGTACCTTAGTTACT<br>GTCTCTAGCGGTGGCGGAGGTTCAGGCGGTGGAGGGTCTGGAGGTGGCGGTAGT<br>GAAAATGTGCTGACCCAATCTCCAAGCTCCATGTCTGTTTCTGTTGGCGATAGA<br>GTAACCATCGCTTGTAGCGCATCCTCTAGTGTCCCATATATGCACTGGCTTCAA<br>CAGAAGCCAGGTAAAAGCCCAAAGTTGTTGATTTATTTGACATCCAACTTGGCT<br>TCTGGAGTGCCTTCAAGGTTTTCTGGTTCCGGCTCAGGAACCGATTATAGTTTG<br>ACTATTAGCTCAGTGCAGCCAGAGGATGCTGCAACCTACTATTGCCAGCAAAGG<br>TCCTCATATCCACTGACTTTCGGG*TGT*GGAACGAAGTTGGAAATCAAG*GGAGGG*<br>*GGCGGTTCC*CACCATCACCACCATCACTGATAG |
| 95 | LS-mouse<br>SA- | MDMRVPAQLLGLLLLWLPGARCEAHKSEIAHRYNDLGEQHFKGLVLIAFSQYLQ<br>KCSYDEHAKLVQEVTDFAKTCVADESAANCDKSLHTLFGDKLCAIPNLRENYGE |

TABLE 12-continued

Sequence Summary

| SEQ ID NO | Description | Sequence |
|---|---|---|
| | (Gly$_4$Ser)$_3$-scFv (V$_L$-V$_H$) CK138-(Gly$_4$Ser)-His$_6$ | LADCCTKQEPERNECFLQHKDDNPSLPPFERPEAEAMCTSFKENPTTFMGHYLH EVARRHPYFYAPELLYYAEQYNEILTQCCAEADKESCLTPKLDGVKEKALVSSV RQRMKCSSMQKFGERAFKAWAVARLSQTFPNADFAEITKLATDLTKVNKECCHG DLLECADDRAELAKYMCENQATISSKLQTCCDKPLLKKAHCLSEVEHDTMPADL PAIAADFVEDQEVCKNYAEAKDVFLGTFLYEYSRRHPDYSVSLLLRLAKKYEAT LEKCCAEANPPACYGTVLAEFQPLVEEPKNLVKTNCDLYEKLGEYGFQNAILVR YTQKAPQVSTPTLVEAARNLGRVGTKCCTLPEDQRLPCVEDYLSAILNRVCLLH EKTPVSEHVTKCCSGSLVERRPCFSALTVDETYVPKEFKAETFTFHSDICTLPE KEKQIKKQTALAELVKHKPKATAEQLKTVMDDFAQFLDTCCKAADKDTCFSTEG PNLVTRCKDALA*GGGGSGGGGSGGGGS*ASAIQMTRSPSSLSASVGDRVTITCRA SQYHDGSAAWYQQKPGKAPKLLIYGASYLYSGVPSRFSGSRSGTDFTLTISSLQ PEDFATYYCQQSSYSLITFGQGTKVEIKGTTAASGSSGGSSSGAEVQLVESDGG LVQPGGSLRLSCAASGFNLSYYGMHWVRQAPGKGLEWVAYIASYPGYTSYADSV KGRFTISADTSKNTAYLQMNSLRAEDTAVYYCARSGYSYSPYYSWFSAGMNYWG QGALVTVSS*GGGGS***HHHHHH-- |
| 96 | LS-mouse SA-(Gly$_4$Ser)$_3$-scFv (V$_L$-V$_H$) CK157-(Gly$_4$Ser)-His$_6$ | MDMRVPAQLLGLLLLWLPGARCEAHKSEIAHRYNDLGEQHFKGLVLIAFSQYLQ KCSYDEHAKLVQEVTDFAKTCVADESAANCDKSLHTLFGDKLCAIPNLRENYGE LADCCTKQEPERNECFLQHKDDNPSLPPFERPEAEAMCTSFKENPTTFMGHYLH EVARRHPYFYAPELLYYAEQYNEILTQCCAEADKESCLTPKLDGVKEKALVSSV RQRMKCSSMQKFGERAFKAWAVARLSQTFPNADFAEITKLATDLTKVNKECCHG DLLECADDRAELAKYMCENQATISSKLQTCCDKPLLKKAHCLSEVEHDTMPADL PAIAADFVEDQEVCKNYAEAKDVFLGTFLYEYSRRHPDYSVSLLLRLAKKYEAT LEKCCAEANPPACYGTVLAEFQPLVEEPKNLVKTNCDLYEKLGEYGFQNAILVR YTQKAPQVSTPTLVEAARNLGRVGTKCCTLPEDQRLPCVEDYLSAILNRVCLLH EKTPVSEHVTKCCSGSLVERRPCFSALTVDETYVPKEFKAETFTFHSDICTLPE KEKQIKKQTALAELVKHKPKATAEQLKTVMDDFAQFLDTCCKAADKDTCFSTEG PNLVTRCKDALA*GGGGSGGGGSGGGGS*ASDIQMTQSPSSLSASVGDRVTITCRA SQSYGGVAWYQQKPGKAPKLLIYSASYLYSGVPSRFSGSRSGTDFTLTISSLQP EDFATYYCQQPSHLITFGQGTEVEIKGTTAASGSSGGSSSGAEVQLVESGGGLV QPGGSLRLSCAASGSNPYYYGGTHWVRQAPGEELEWVASIGSYPGYTDYADSVK GRFTISADTSKNTAYLQMNSLRAEDTAVYYCARHYYWYDATDYWGQGTLVTVSS *GGGGS*HHHHHH-- |
| 97 | LS-mouse SA-(Gly$_4$Ser)$_3$-scFv (V$_L$-V$_H$) CK129-(Gly$_4$Ser)-His$_6$ | MDMRVPAQLLGLLLLWLPGARCEAHKSEIAHRYNDLGEQHFKGLVLIAFSQYLQ KCSYDEHAKLVQEVTDFAKTCVADESAANCDKSLHTLFGDKLCAIPNLRENYGE LADCCTKQEPERNECFLQHKDDNPSLPPFERPEAEAMCTSFKENPTTFMGHYLH EVARRHPYFYAPELLYYAEQYNEILTQCCAEADKESCLTPKLDGVKEKALVSSV RQRMKCSSMQKFGERAFKAWAVARLSQTFPNADFAEITKLATDLTKVNKECCHG DLLECADDRAELAKYMCENQATISSKLQTCCDKPLLKKAHCLSEVEHDTMPADL PAIAADFVEDQEVCKNYAEAKDVFLGTFLYEYSRRHPDYSVSLLLRLAKKYEAT LEKCCAEANPPACYGTVLAEFQPLVEEPKNLVKTNCDLYEKLGEYGFQNAILVR YTQKAPQVSTPTLVEAARNLGRVGTKCCTLPEDQRLPCVEDYLSAILNRVCLLH EKTPVSEHVTKCCSGSLVERRPCFSALTVDETYVPKEFKAETFTFHSDICTLPE KEKQIKKQTALAELVKHKPKATAEQLKTVMDDFAQFLDTCCKAADKDTCFSTEG PNLVTRCKDALA*GGGGSGGGGSGGGGS*ASDIQMTQSPSPLSASVGDRVTITCRA SQYGGYVAWYQQKPGKAPKLLIYGASLLYSGVPSRFSGGRSGTDFTLTISSLQP EDFATYYCQRGHALITFGQGTKVEIEGTTAASGSSGGSSSGAEVQLVESGGGLV QPGGSLRLSCAASGFNISSYGSMHWVRQAPGKGLEWVASIYPYSSSTYYADSVK GRFTISADTSKNTAYLQMNSLRAEDTAVYYCARGYGPWYAYSYFALDYWGQGTL VTVSS*GGGGS***HHHHHH-- |
| 98 | LS-mouse SA-(Gly$_4$Ser)$_3$-scFv (V$_L$-V$_H$) CK138-ds1 (V$_L$100$^{Q>C}$/V$_H$44$^{G>C}$)-(Gly$_4$Ser)-His$_6$ | MDMRVPAQLLGLLLLWLPGARCEAHKSEIAHRYNDLGEQHFKGLVLIAFSQYLQ KCSYDEHAKLVQEVTDFAKTCVADESAANCDKSLHTLFGDKLCAIPNLRENYGE LADCCTKQEPERNECFLQHKDDNPSLPPFERPEAEAMCTSFKENPTTFMGHYLH EVARRHPYFYAPELLYYAEQYNEILTQCCAEADKESCLTPKLDGVKEKALVSSV RQRMKCSSMQKFGERAFKAWAVARLSQTFPNADFAEITKLATDLTKVNKECCHG DLLECADDRAELAKYMCENQATISSKLQTCCDKPLLKKAHCLSEVEHDTMPADL PAIAADFVEDQEVCKNYAEAKDVFLGTFLYEYSRRHPDYSVSLLLRLAKKYEAT LEKCCAEANPPACYGTVLAEFQPLVEEPKNLVKTNCDLYEKLGEYGFQNAILVR YTQKAPQVSTPTLVEAARNLGRVGTKCCTLPEDQRLPCVEDYLSAILNRVCLLH EKTPVSEHVTKCCSGSLVERRPCFSALTVDETYVPKEFKAETFTFHSDICTLPE KEKQIKKQTALAELVKHKPKATAEQLKTVMDDFAQFLDTCCKAADKDTCFSTEG PNLVTRCKDALA*GGGGSGGGGSGGGGS*AS**AIQMTRSPSSLSASVGDRVTITCRA SQYHDGSAAWYQQKPGKAPKLLIYGASYLYSGVPSRFSGSRSGTDFTLTISSLQ PEDFATYYCQQSSYSLITFG*C*GTKVEIKGTTAASGSSGGSSSGAEVQLVESDGG LVQPGGSLRLSCAASGFNLSYYGMHWVRQAPGK*C*LEWVAYIASYPGYTSYADSV KGRFTISADTSKNTAYLQMNSLRAEDTAVYYCARSGYSYSPYYSWFSAGMNYWG QGALVTVSS*GGGGS*HHHHHH-- |
| 99 | LS-mouse SA-(Gly$_4$Ser)$_3$-scFv (V$_L$-V$_H$) CK138- | MDMRVPAQLLGLLLLWLPGARCEAHKSEIAHRYNDLGEQHFKGLVLIAFSQYLQ KCSYDEHAKLVQEVTDFAKTCVADESAANCDKSLHTLFGDKLCAIPNLRENYGE LADCCTKQEPERNECFLQHKDDNPSLPPFERPEAEAMCTSFKENPTTFMGHYLH EVARRHPYFYAPELLYYAEQYNEILTQCCAEADKESCLTPKLDGVKEKALVSSV RQRMKCSSMQKFGERAFKAWAVARLSQTFPNADFAEITKLATDLTKVNKECCHG |

TABLE 12-continued

Sequence Summary

| SEQ ID NO | Description | Sequence |
|---|---|---|
| | ds2 (V$_L$43$^{A>C}$/V$_H$105$^{Q>C}$)-(Gly$_4$Ser)-His$_6$ | DLLECADDRAELAKYMCENQATISSKLQTCCDKPLLKKAHCLSEVEHDTMPADL PAIAADFVEDQEVCKNYAEAKDVFLGTFLYEYSRRHPDYSVSLLLRLAKKYEAT LEKCCAEANPPACYGTVLAEFQPLVEEPQPLVEEPKNLVKTNCDLYEKLGEYGFQNAILVR YTQKAPQVSTPTLVEAARNLGRVGTKCCTLPEDQRLPCVEDYLSAILNRVCLLH EKTPVSEHVTKCCSGSLVERRPCFSALTVDETYVPKEFKAETFTFHSDICTLPE KEKQIKKQTALAELVKHKPKATAEQLKTVMDDFAQFLDTCCKAADKDTCFSTEG PNLVTRCKDALA*GGGGSGGGGSGGGGS*ASAIQMTRSPSSLSASVGDRVTTTCRA SQYHDGSAAWYQQKPGKCPKLLIYGASYLYSGVPSRFSGSRSGTDFTLTISSLQ PEDFATYYCQQSSYSLITFGQGTKVEIKGTTAASGSSGGSSSGAEVQLVESDGG LVQPGGSLRLSCAASGFNLSYYGMHWVRQAPGKGLEWVAYIASYPGYTSYADSV KGRFTISADTSKNTAYLQMNSLRAEDTAVYYCARSGYSYSPYYSWFSAGMNYWG CGALVTVSS*GGGGS*HHHHHH-- |
| 100 | LS-mouse SA-(Gly$_4$Ser)$_3$-scFv (V$_L$-V$_H$) CK157-ds1 (V$_L$100$^{Q>C}$/V$_H$44$^{E>C}$)-(Gly$_4$Ser)-His$_6$ | MDMRVPAQLLGLLLLWLPGARCEAHKSEIAHRYNDLGEQHFKGLVLIAFSQYLQ KCSYDEHAKLVQEVTDFAKTCVADESAANCDKSLHTLFGDKLCAIPNLRENYGE LADCCTKQEPERNECFLQHKDDNPSLPPFERPEAEAMCTSFKENPTTFMGHYLH EVARRHPYFYAPELLYYAEQYNEILTQCCAEADKESCLTPKLDGVKEKALVSSV RQRMKCSSMQKFGERAFKAWAVARLSQTFPNADFAEITKLATDLTKVNKECCHG DLLECADDRAELAKYMCENQATISSKLQTCCDKPLLKKAHCLSEVEHDTMPADL PAIAADFVEDQEVCKNYAEAKDVFLGTFLYEYSRRHPDYSVSLLLRLAKKYEAT LEKCCAEANPPACYGTVLAEFQPLVEEPKNLVKTNCDLYEKLGEYGFQNAILVR YTQKAPQVSTPTLVEAARNLGRVGTKCCTLPEDQRLPCVEDYLSAILNRVCLLH EKTPVSEHVTKCCSGSLVERRPCFSALTVDETYVPKEFKAETFTFHSDICTLPE KEKQIKKQTALAELVKHKPKATAEQLKTVMDDFAQFLDTCCKAADKDTCFSTEG PNLVTRCKDALA*GGGGSGGGGSGGGGS*ASDIQMTQSPSSLSASVGDRVTITCRA SQSYGGVAWYQQKPGKAPKLLIYSASYLYSGVPSRFSGSRSGTDFTLTISSLQP EDFATYYCQQPSHLITFGCGTEVEIKGTTAASGSSGGSSSGAEVQLVESGGGLV QPGGSLRLSCAASGSNPYYYGGTHWVRQAPGECLEWVASIGSYPGYTDYADSVK GRFTISADTSKNTAYLQMNSLRAEDTAVYYCARHYYWYDATDYWGQGTLVTVSS  *GGGGS*HHHHHH-- |
| 101 | LS-mouse SA-(Gly$_4$Ser)3-scFv (V$_L$-V$_H$) CK157-ds2 (V$_L$43$^{A>C}$/V$_H$105$^{Q>C}$)-(Gly$_4$Ser)-His$_6$ | MDMRVPAQLLGLLLLWLPGARCEAHKSEIAHRYNDLGEQHFKGLVLIAFSQYLQ KCSYDEHAKLVQEVTDFAKTCVADESAANCDKSLHTLFGDKLCAIPNLRENYGE LADCCTKQEPERNECFLQHKDDNPSLPPFERPEAEAMCTSFKENPTTFMGHYLH EVARRHPYFYAPELLYYAEQYNEILTQCCAEADKESCLTPKLDGVKEKALVSSV RQRMKCSSMQKFGERAFKAWAVARLSQTFPNADFAEITKLATDLTKVNKECCHG DLLECADDRAELAKYMCENQATISSKLQTCCDKPLLKKAHCLSEVEHDTMPADL PAIAADFVEDQEVCKNYAEAKDVFLGTFLYEYSRRHPDYSVSLLLRLAKKYEAT LEKCCAEANPPACYGTVLAEFQPLVEEPKNLVKTNCDLYEKLGEYGFQNAILVR YTQKAPQVSTPTLVEAARNLGRVGTKCCTLPEDQRLPCVEDYLSAILNRVCLLH EKTPVSEHVTKCCSGSLVERRPCFSALTVDETYVPKEFKAETFTFHSDICTLPE KEKQIKKQTALAELVKHKPKATAEQLKTVMDDFAQFLDTCCKAADKDTCFSTEG PNLVTRCKDALA*GGGGSGGGGSGGGGS*ASDIQMTQSPSSLSASVGDRVTITCRA SQSYGGVAWYQQKPGKCPKLLIYSASYLYSGVPSRFSGSRSGTDFTLTISSLQP EDFATYYCQQPSHLITFGQGTEVEIKGTTAASGSSGGSSSGAEVQLVESGGGLV QPGGSLRLSCAASGSNPYYYGGTHWVRQAPGEELEWVASIGSYPGYTDYADSVK GRFTISADTSKNTAYLQMNSLRAEDTAVYYCARHYYWYDATDYWGCGTLVTVSS  *GGGGS*HHHHHH-- |
| 102 | LS-mouse SA-(Gly$_4$Ser)-V$_L$ CK157-His$_6$ | MDMRVPAQLLGLLLLWLPGARCEAHKSEIAHRYNDLGEQHFKGLVLIAFSQYLQ KCSYDEHAKLVQEVTDFAKTCVADESAANCDKSLHTLFGDKLCAIPNLRENYGE LADCCTKQEPERNECFLQHKDDNPSLPPFERPEAEAMCTSFKENPTTFMGHYLH EVARRHPYFYAPELLYYAEQYNEILTQCCAEADKESCLTPKLDGVKEKALVSSV RQRMKCSSMQKFGERAFKAWAVARLSQTFPNADFAEITKLATDLTKVNKECCHG DLLECADDRAELAKYMCENQATISSKLQTCCDKPLLKKAHCLSEVEHDTMPADL PAIAADFVEDQEVCKNYAEAKDVFLGTFLYEYSRRHPDYSVSLLLRLAKKYEAT LEKCCAEANPPACYGTVLAEFQPLVEEPKNLVKTNCDLYEKLGEYGFQNAILVR YTQKAPQVSTPTLVEAARNLGRVGTKCCTLPEDQRLPCVEDYLSAILNRVCLLH EKTPVSEHVTKCCSGSLVERRPCFSALTVDETYVPKEFKAETFTFHSDICTLPE KEKQIKKQTALAELVKHKPKATAEQLKTVMDDFAQFLDTCCKAADKDTCFSTEG PNLVTRCKDALA*GGGGSGGGGSGGGGS*ASDIQMTQSPSSLSASVGDRVTITCRA SQSYGGVAWYQQKPGKAPKLLIYSASYLYSGVPSRFSGSRSGTDFTLTISSLQP EDFATYYCQQPSHLITFGQGTEVEIK*GGGGS*HHHHHH-- |
| 103 | LS-mouse SA-(Gly$_4$Ser)-V$_H$ CK157-His$_6$ | MDMRVPAQLLGLLLLWLPGARCEAHKSEIAHRYNDLGEQHFKGLVLIAFSQYLQ KCSYDEHAKLVQEVTDFAKTCVADESAANCDKSLHTLFGDKLCAIPNLRENYGE LADCCTKQEPERNECFLQHKDDNPSLPPFERPEAEAMCTSFKENPTTFMGHYLH EVARRHPYFYAPELLYYAEQYNEILTQCCAEADKESCLTPKLDGVKEKALVSSV RQRMKCSSMQKFGERAFKAWAVARLSQTFPNADFAEITKLATDLTKVNKECCHG DLLECADDRAELAKYMCENQATISSKLQTCCDKPLLKKAHCLSEVEHDTMPADL PAIAADFVEDQEVCKNYAEAKDVFLGTFLYEYSRRHPDYSVSLLLRLAKKYEAT LEKCCAEANPPACYGTVLAEFQPLVEEPKNLVKTNCDLYEKLGEYGFQNAILVR YTQKAPQVSTPTLVEAARNLGRVGTKCCTLPEDQRLPCVEDYLSAILNRVCLLH EKTPVSEHVTKCCSGSLVERRPCFSALTVDETYVPKEFKAETFTFHSDICTLPE KEKQIKKQTALAELVKHKPKATAEQLKTVMDDFAQFLDTCCKAADKDTCFSTEG |

TABLE 12-continued

Sequence Summary

| SEQ ID NO | Description | Sequence |
|---|---|---|
| | | PNLVTRCKDALA*GGGGSGGGGSGGGGS*ASAEVQLVESGGGLVQPGGSLRLSCAA SGSNPYYYGGTHWVRQAPGEELEWVASIGSYPGYTDYADSVKGRFTISADTSKN TAYLQMNSLRAEDTAVYYCARHYYWYDATDYWGQGTLVTVSS*GGGGS*HHHHHH-- |
| 104 | LS-mouse SA-(Gly$_4$Ser)$_3$-scFv (V$_L$-V$_H$) CK129-ds1 (V$_L$100$^{Q>C}$/V$_H$44$^{G>C}$)-(Gly$_4$Ser)-His$_6$ | MDMRVPAQLLGLLLLWLPGARCEAHKSEIAHRYNDLGEQHFKGLVLIAFSQYLQ KCSYDEHAKLVQEVTDFAKTCVADESAANCDKSLHTLFGDKLCAIPNLRENYGE LADCCTKQEPERNECFLQHKDDNPSLPPFERPEAEAMCTSFKENPTTFMGHYLH EVARRHPYFYAPELLYYAEQYNEILTQCCAEADKESCLTPKLDGVKEKALVSSV RQRMKCSSMQKFGERAFKAWAVARLSQTFPNADFAEITKLATDLTKVNKECCHG DLLECADDRAELAKYMCENQATISSKLQTCCDKPLLKKAHCLSEVEHDTMPADL PAIAADFVEDQEVCKNYAEAKDVFLGTFLYEYSRRHPDYSVSLLLRLAKKYEAT LEKCCAEANPPACYGTVLAEFQPLVEEPKNLVKTNCDLYEKLGEYGFQNAILVR YTQKAPQVSTPTLVEAARNLGRVGTKCCTLPEDQRLPCVEDYLSAILNRVCLLH EKTPVSEHVTKCCSGSLVERRPCFSALTVDETYVPKEFKAETFTFHSDICTLPE KEKQIKKQTALAELVKHKPKATAEQLKTVMDDFAQFLDTCCKAADKDTCFSTEG PNLVTRCKDALA*GGGGSGGGGSGGGGS*ASDIQMTQSPSPLSASVGDRVTITCRA SQYGGYVAWYQQKPGKAPKLLIYGASLLYSGVPSRFSGGRSGTDFTLTISSLQP EDFATYYCQRGHALITFGCGTKVEIEGTTAASGSSGGSSSGAEVQLVESGGGLV QPGGSLRLSCAASGFNISSYGSMHWVRQAPGKC**LEWVASIYPYSSSTYYADSVK GRFTISADTSKNTAYLQMNSLRAEDTAVYYCARGYGPWYAYSYFALDYWGQGTL VTVSS*GGGGS*HHHHHH-- |
| 105 | LS-mouse SA-(Gly$_4$Ser)$_3$-scFv (V$_L$-V$_H$) CK129-ds2 (V$_L$43$^{A>C}$/V$_H$105$^{Q>C}$)-(Gly$_4$Ser)-His$_6$ | MDMRVPAQLLGLLLLWLPGARCEAHKSEIAHRYNDLGEQHFKGLVLIAFSQYLQ KCSYDEHAKLVQEVTDFAKTCVADESAANCDKSLHTLFGDKLCAIPNLRENYGE LADCCTKQEPERNECFLQHKDDNPSLPPFERPEAEAMCTSFKENPTTFMGHYLH EVARRHPYFYAPELLYYAEQYNEILTQCCAEADKESCLTPKLDGVKEKALVSSV RQRMKCSSMQKFGERAFKAWAVARLSQTFPNADFAEITKLATDLTKVNKECCHG DLLECADDRAELAKYMCENQATISSKLQTCCDKPLLKKAHCLSEVEHDTMPADL PAIAADFVEDQEVCKNYAEAKDVFLGTFLYEYSRRHPDYSVSLLLRLAKKYEAT LEKCCAEANPPACYGTVLAEFQPLVEEPKNLVKTNCDLYEKLGEYGFQNAILVR YTQKAPQVSTPTLVEAARNLGRVGTKCCTLPEDQRLPCVEDYLSAILNRVCLLH EKTPVSEHVTKCCSGSLVERRPCFSALTVDETYVPKEFKAETFTFHSDICTLPE KEKQIKKQTALAELVKHKPKATAEQLKTVMDDFAQFLDTCCKAADKDTCFSTEG PNLVTRCKDALA*GGGGSGGGGSGGGGS*ASDIQMTQSPSPLSASVGDRVTITCRA SQYGGYVAWYQQKPGKCPKLLIYGASLLYSGVPSRFSGGRSGTDFTLTISSLQP EDFATYYCQRGHALITFGQGTKVEIEGTTAASGSSGGSSSGAEVQLVESGGGLV QPGGSLRLSCAASGFNISSYGSMHWVRQAPGKGLEWVASIYPYSSSTYYADSVK GRFTISADTSKNTAYLQMNSLRAEDTAVYYCARGYGPWYAYSYFALDYWGC**GTL VTVSS*GGGGS*HHHHHH-- |
| 106 | LS-mouse SA-(Gly$_4$Ser)$_3$-scFv (V$_H$-V$_L$) sm3E-ds (V$_H$44$^{R>C}$/V$_L$100$^{G>C}$)-(Gly$_4$Ser)-His$_6$ | MDMRVPAQLLGLLLLWLPGARCEAHKSEIAHRYNDLGEQHFKGLVLIAFSQYLQ KCSYDEHAKLVQEVTDFAKTCVADESAANCDKSLHTLFGDKLCAIPNLRENYGE LADCCTKQEPERNECFLQHKDDNPSLPPFERPEAEAMCTSFKENPTTFMGHYLH EVARRHPYFYAPELLYYAEQYNEILTQCCAEADKESCLTPKLDGVKEKALVSSV RQRMKCSSMQKFGERAFKAWAVARLSQTFPNADFAEITKLATDLTKVNKECCHG DLLECADDRAELAKYMCENQATISSKLQTCCDKPLLKKAHCLSEVEHDTMPADL PAIAADFVEDQEVCKNYAEAKDVFLGTFLYEYSRRHPDYSVSLLLRLAKKYEAT LEKCCAEANPPACYGTVLAEFQPLVEEPKNLVKTNCDLYEKLGEYGFQNAILVR YTQKAPQVSTPTLVEAARNLGRVGTKCCTLPEDQRLPCVEDYLSAILNRVCLLH EKTPVSEHVTKCCSGSLVERRPCFSALTVDETYVPKEFKAETFTFHSDICTLPE KEKQIKKQTALAELVKHKPKATAEQLKTVMDDFAQFLDTCCKAADKDTCFSTEG PNLVTRCKDALA*GGGGSGGGGSGGGGS*ASQVKLEQSGAEVVKPGASVKLSCKAS GFNIKDSYMHWLRQGPGQCLEWIGWIDPENGDTEYAPKFQGKATFTTDTSANTA YLGLSSLRPEDTAVYYCNEGTPTPGPYYFDYWGQGTLVTVSSGGGGSGGGGSGGG GSENVLTQSPSSMSVSVGDRVTIACSASSSVPYMHWLQQKPGKSPKLLIYLTSN LASGVPSRFSGSGSGTDYSLTISSVQPEDAATYYCQQRSSYPLTFGC**GTKLEIK *GGGGS*HHHHHH-- |
| 107 | pCHA-LS-hCXCL1$^{38-107}$-G$_3$-c-myc-Aga2 | ATGAAGGTTTTGATTGTCTTGTTGGCTATCTTCGCTGCTTTGCCATTGGCCTTA GCTCAACCGGTTATTTCTACTACCGTCGGTTCCGCTGCAGAAGGCTCTTTGGAC AAGAGAGCCACCGAGCTGAGATGCCAGTGCCTGCAGACCTGCAGGGCATCCAC CCCAAGAACATCCAGAGCGTGAACGTGAAGTCCCCTGGCCCCCACTGCGCCCAG ACCGAAGTGATCGCCACCCTGAAGAACGGCCGGAAGGCCTGCCTGAACCCCGCC AGCCCCATCGTGAAGAAAATCATCGAGAAGATGCTGAACAGCGACAAGAGCAAC *GGCGGAGGC*GAACAAAAGCTTATCTCCGAAGAAGACTTGCAGGAACTGACAACT ATATGCGAGCAAATCCCCTCACCAACTTTAGAATCGACGCCGTACTCTTTGTCA ACGACTACTATTTTGGCCAACGGGAAGGCAATGCAAGGAGTTTTTGAATATTAC AAATCAGTAACGTTTGTCAGTAATTGCGGTTCTCACCCCTCAACAACTAGCAAA GGCAGCCCCATAAACACACAGTATGTTTTTTAA |
| 108 | pCHA-LS-hCXCL2$^{38-107}$-G$_3$-c-myc-Aga2 | ATGAAGGTTTTGATTGTCTTGTTGGCTATCTTCGCTGCTTTGCCATTGGCCTTA GCTCAACCGGTTATTTCTACTACCGTCGGTTCCGCTGCAGAAGGCTCTTTGGAC AAGAGAGCCACAGAGCTGAGATGCCAGTGCCTCCAGACACTCCAGGGCATCCAC CTGAAGAACATCCAGAGCGTGAAAGTGAAGTCCCCTGGCCCCCACTGCGCCCAG |

TABLE 12-continued

Sequence Summary

| SEQ ID NO | Description | Sequence |
|---|---|---|
| | | ACAGAAGTGATCGCCACCCTGAAGAATGGCCAGAAGGCCTGCCTGAACCCCGCC<br>AGCCCTATGGTCAAGAAAATCATCGAGAAGATGCTGAAGAACGGCAAGAGCAAC<br>*GGCGGAGGC*GAACAAAAGCTTATCTCCGAAGAAGACTTGCAGGAACTGACAACT<br>ATATGCGAGCAAATCCCCTCACCAACTTTAGAATCGACGCCGTACTCTTTGTCA<br>ACGACTACTATTTTGGCCAACGGGAAGGCAATGCAAGGAGTTTTTGAATATTAC<br>AAATCAGTAACGTTTGTCAGTAATTGCGGTTCTCACCCCTCAACAACTAGCAAA<br>GGCAGCCCCATAAACACACAGTATGTTTTTTAA |
| 109 | pCHA-LS-<br>hCXCL3$^{38-107}$-<br>G$_3$-c-<br>myc-Aga2 | ATG<u>AAGGTTTTGATTGTCTTGTTGGCTATCTTCGCTGCTTTGCCATTGGCTTA<br>GCTCAACCGGTTATTTCTACTACCGTCGGTTCCGCTGCAGAAGGCTCTTTGGAC<br>AAGAGA</u>GTGACCGAGCTGAGATGCCAGTGCCTCCAGACACTCCAGGGCATCCAC<br>CTGAAGAACATCCAGAGCGTGAACGTGCGGAGCCCTGGCCCTCATTGTGCCCAG<br>ACAGAAGTGATCGCCACCCTGAAGAATGGCAAGAAGGCCTGCCTGAACCCCGCC<br>AGCCCTATGGTGCAGAAGATCATCGAGAAGATCCTGAACAAGGGCAGCACCAAC<br>*GGCGGAGGC*GAACAAAAGCTTATCTCCGAAGAAGACTTGCAGGAACTGACAACT<br>ATATGCGAGCAAATCCCCTCACCAACTTTAGAATCGACGCCGTACTCTTTGTCA<br>ACGACTACTATTTTGGCCAACGGGAAGGCAATGCAAGGAGTTTTTGAATATTAC<br>AAATCAGTAACGTTTGTCAGTAATTGCGGTTCTCACCCCTCAACAACTAGCAAA<br>GGCAGCCCCATAAACACACAGTATGTTTTTTAA |
| 110 | pCHA-LS-<br>hCXCL4$^{32-101}$-<br>G$_3$-c-<br>myc-Aga2 | ATG<u>AAGGTTTTGATTGTCTTGTTGGCTATCTTCGCTGCTTTGCCATTGGCTTA<br>GCTCAACCGGTTATTTCTACTACCGTCGGTTCCGCTGCAGAAGGCTCTTTGGAC<br>AAGAGA</u>GAGGCTGAAGAGGACGGCGATCTCCAGTGCCTGTGCGTGAAAACCACC<br>AGCCAAGTGCGGCCCAGACAACATCACCAGCCTGGAAGTGATCAAGGCCGGACCC<br>CACTGTCCTACCGCCCAGCTGATTGCCACCCTGAAGAACGGCCGGAAGATCTGC<br>CTGGACCTCCAGGCCCCCCTGTACAAGAAGATCATCAAGAAGCTGCTGGAAAGC<br>*GGCGGAGGC*GAACAAAAGCTTATCTCCGAAGAAGACTTGCAGGAACTGACAACT<br>ATATGCGAGCAAATCCCCTCACCAACTTTAGAATCGACGCCGTACTCTTTGTCA<br>ACGACTACTATTTTGGCCAACGGGAAGGCAATGCAAGGAGTTTTTGAATATTAC<br>AAATCAGTAACGTTTGTCAGTAATTGCGGTTCTCACCCCTCAACAACTAGCAAA<br>GGCAGCCCCATAAACACACAGTATGTTTTTTAA |
| 111 | pCHA-LS-<br>hCXCL5$^{44-114}$-<br>G$_3$-c-<br>myc-Aga2 | ATG<u>AAGGTTTTGATTGTCTTGTTGGCTATCTTCGCTGCTTTGCCATTGGCTTA<br>GCTCAACCGGTTATTTCTACTACCGTCGGTTCCGCTGCAGAAGGCTCTTTGGAC<br>AAGAGA</u>CTGCGCGAGCTGAGATGCGTGTGCCTGCAGACCACCCAGGGCGTGCAC<br>CCCAAGATGATCAGCAACCTCCAGGTGTTCGCCATCGGCCCCCAGTGCAGCAAG<br>GTGGAAGTGGTGGCCAGCCTGAAGAACGGCAAAGAGATCTGCCTGGACCCCGAG<br>GCCCCATTCCTGAAGAAAGTGATCCAGAAGATCCTGGACGGCGGCAACAAAGAG<br>AAC*GGCGGAGGC*GAACAAAAGCTTATCTCCGAAGAAGACTTGCAGGAACTGACA<br>ACTATATGCGAGCAAATCCCCTCACCAACTTTAGAATCGACGCCGTACTCTTTG<br>TCAACGACTACTATTTTGGCCAACGGGAAGGCAATGCAAGGAGTTTTTGAATAT<br>TACAAATCAGTAACGTTTGTCAGTAATTGCGGTTCTCACCCCTCAACAACTAGC<br>AAAGGCAGCCCCATAAACACACAGTATGTTTTTTAA |
| 112 | pCHA-LS-<br>hCXCL6$^{44-114}$-<br>G$_3$-c-<br>myc-Aga2 | ATG<u>AAGGTTTTGATTGTCTTGTTGGCTATCTTCGCTGCTTTGCCATTGGCTTA<br>GCTCAACCGGTTATTTCTACTACCGTCGGTTCCGCTGCAGAAGGCTCTTTGGAC<br>AAGAGA</u>CTGACCGAGCTGCGGTGCACCTGTCTGAGAGTGACCCTGCGCGTGAAC<br>CCCAAGACCATCGGCAAGCTCCAGGTGTTCCCTGCCGGCCCTCAGTGCAGCAAG<br>GTGGAAGTGGTGGCCAGCCTGAAAAACGGAAAACAAGTGTGCCTGGACCCCGAG<br>GCCCCATTCCTGAAGAAAGTGATCCAGAAGATCCTGGACAGCGGCAACAAGAAG<br>AAC*GGCGGAGGC*GAACAAAAGCTTATCTCCGAAGAAGACTTGCAGGAACTGACA<br>ACTATATGCGAGCAAATCCCCTCACCAACTTTAGAATCGACGCCGTACTCTTTG<br>TCAACGACTACTATTTTGGCCAACGGGAAGGCAATGCAAGGAGTTTTTGAATAT<br>TACAAATCAGTAACGTTTGTCAGTAATTGCGGTTCTCACCCCTCAACAACTAGC<br>AAAGGCAGCCCCATAAACACACAGTATGTTTTTTAA |
| 113 | pCHA-LS-<br>hCXCL7$^{59-121}$-<br>G$_3$-c-<br>myc-Aga2 | ATG<u>AAGGTTTTGATTGTCTTGTTGGCTATCTTCGCTGCTTTGCCATTGGCTTA<br>GCTCAACCGGTTATTTCTACTACCGTCGGTTCCGCTGCAGAAGGCTCTTTGGAC<br>AAGAGA</u>GCCGAGCTGCGGTGCATGTGCATCAAGACCACCAGCGGAATCCACCCC<br>AAGAATATCCAGTCCCTGGAAGTGATTGGCAAGGGCACCCACTGCAACCAGGTG<br>GAAGTGATTGCCACACTGAAAGACGGCCGGAAGATCTGCCTGGACCCTGACGCC<br>CCCAGAATCAAGAAAATCGTGCAGAAAAAGCTG<br>*GGCGGAGGC*GAACAAAAGCTTATCTCCGAAGAAGACTTGCAGGAACTGACAACT<br>ATATGCGAGCAAATCCCCTCACCAACTTTAGAATCGACGCCGTACTCTTTGTCA<br>ACGACTACTATTTTGGCCAACGGGAAGGCAATGCAAGGAGTTTTTGAATATTAC<br>AAATCAGTAACGTTTGTCAGTAATTGCGGTTCTCACCCCTCAACAACTAGCAAA<br>GGCAGCCCCATAAACACACAGTATGTTTTTTAA |
| 114 | pCHA-LS-<br>hCXCL8$^{29-99}$-<br>G$_3$-c-<br>myc-Aga2 | ATG<u>AAGGTTTTGATTGTCTTGTTGGCTATCTTCGCTGCTTTGCCATTGGCTTA<br>GCTCAACCGGTTATTTCTACTACCGTCGGTTCCGCTGCAGAAGGCTCTTTGGAC<br>AAGAGA</u>GCCAAGAACTGCGGTGCCAGTGCATCAAGACCTACAGCAAGCCCTTC<br>CACCCCAAGTTCATCAAAGAACTGAGAGTGATCGAGAGCGGCCCTCACTGCGCC<br>AACACCGAGATCATCGTGAAGCTGAGCGACGGCAGAGAGCTGTGCCTGGACCCC<br>AAAGAAAACTGGGTGCAGCGGGTGGTGGAAAAGTTCCTGAAGCGGGCCGAGAAC<br>AGC*GGCGGAGGC*GAACAAAAGCTTATCTCCGAAGAAGACTTGCAGGAACTGACA |

TABLE 12-continued

Sequence Summary

| SEQ ID NO | Description | Sequence |
|---|---|---|
| | | ACTATATGCGAGCAAATCCCCTCACCAACTTTAGAATCGACGCCGTACTCTTTG<br>TCAACGACTACTATTTTGGCCAACGGGAAGGCAATGCAAGGAGTTTTTGAATAT<br>TACAAATCAGTAACGTTTGTCAGTAATTGCGGTTCTCACCCCTCAACAACTAGC<br>AAAGGCAGCCCCATAAACACACAGTATGTTTTTTAA |
| 115 | pCHA-LS-<br>hCXCL9[23-115]-<br>G$_3$-c-<br>myc-Aga2 | ATG<u>AAGGTTTTGATTGTCTTGTTGGCTATCTTCGCTGCTTTGCCATTGGCCTTA<br>GCTCAACCGGTTATTTCTACTACCGTCGGTTCCGCTGCAGAAGGCTCTTTGGAC<br>AAGAGA</u>ACCCCGTCGTGCGGAAGGGCAGATGCAGCTGTATCAGCACCAACCAG<br>GGCACCATCCATCTCCAGTCTCTGAAGGACCTGAAGCAGTTCGCCCCCAGCCCC<br>AGCTGCGAGAAGATCGAGATTATCGCCACACTGAAAAACGGGGTGCAGACCTGC<br>CTGAACCCCGACAGCGCCGACGTGAAAGAACTGATCAAGAAATGGGAGAAACAG<br>GTGTCCCAGAAGAAGAAGCAGAAGAACGGGAAGAAGCACCAGAAAAAGAAAGTG<br>CTGAAAGTGCGGAAGTCCCAGCGGAGCCGGCAGAAGAAAACCACA*GGCGGAGGC*<br>GAACAAAAGCTTATCTCCGAAGAAGACTTGCAGGAACTGACAACTATATGCGAG<br>CAAATCCCCTCACCAACTTTAGAATCGACGCCGTACTCTTTGTCAACGACTACT<br>ATTTTGGCCAACGGGAAGGCAATGCAAGGAGTTTTTGAATATTACAAATCAGTA<br>ACGTTTGTCAGTAATTGCGGTTCTCACCCCTCAACAACTAGCAAAGGCAGCCCC<br>ATAAACACACAGTATGTTTTTTAA |
| 116 | pCHA-LS-<br>hCXCL10[22-98]-<br>G$_3$-c-<br>myc-Aga2 | ATG<u>AAGGTTTTGATTGTCTTGTTGGCTATCTTCGCTGCTTTGCCATTGGCCTTA<br>GCTCAACCGGTTATTTCTACTACCGTCGGTTCCGCTGCAGAAGGCTCTTTGGAC<br>AAGAGA</u>GTGCCTCTGAGCAGAACCGTGCGGTGCACCTGTATCAGCATCAGCAAC<br>CAGCCCGTGAACCCCAGAAGCCTGGAAAAGCTGGAAATCATCCCCGCCAGCCAG<br>TTCTGCCCCAGAGTGGAAATTATCGCCACCATGAAGAAGAAAGGCGAGAAGCGG<br>TGCCTGAACCCCGAGAGCAAGGCCATCAAGAACCTGCTGAAGGCCGTGTCCAAA<br>GAGCGGAGCAAGCGGAGCCCA*GGCGGAGGC*GAACAAAAGCTTATCTCCGAAGAA<br>GACTTGCAGGAACTGACAACTATATGCGAGCAAATCCCCTCACCAACTTTAGAA<br>TCGACGCCGTACTCTTTGTCAACGACTACTATTTTGGCCAACGGGAAGGCAATG<br>CAAGGAGTTTTTGAATATTACAAATCAGTAACGTTTGTCAGTAATTGCGGTTCT<br>CACCCCTCAACAACTAGCAAAGGCAGCCCCATAAACACACAGTATGTTTTTTAA |
| 117 | pCHA-LS-<br>hCXCL11[22-94]-<br>G3-c-<br>myc-Aga2 | ATG<u>AAGGTTTTGATTGTCTTGTTGGCTATCTTCGCTGCTTTGCCATTGGCCTTA<br>GCTCAACCGGTTATTTCTACTACCGTCGGTTCCGCTGCAGAAGGCTCTTTGGAC<br>AAGAGA</u>TTCCCCATGTTCAAGCGGGGCAGATGCCTGTGCATCGGCCCTGGCGTG<br>AAAGCCGTGAAGGTGGCCGATATCGAGAAGGCCAGCATCATGTACCCCAGCAAC<br>AACTGCGACAAGATCGAAGTGATCATCACCCTGAAAGAGAACAAGGGCCAGAGA<br>TGCCTGAATCCCAAGTCCAAGCAGGCCCGGCTGATCATCAAGAAGGTGGAACGG<br>AAGAACTTC*GGCGGAGGC*GAACAAAAGCTTATCTCCGAAGAAGACTTGCAGGAA<br>CTGACAACTATATGCGAGCAAATCCCCTCACCAACTTTAGAATCGACGCCGTAC<br>TCTTTGTCAACGACTACTATTTTGGCCAACGGGAAGGCAATGCAAGGAGTTTTT<br>GAATATTACAAATCAGTAACGTTTGTCAGTAATTGCGGTTCTCACCCCTCAACA<br>ACTAGCAAAGGCAGCCCCATAAACACACAGTATGTTTTTTAA |
| 118 | pCHA-LS-<br>mCXCL1[28-96]-<br>G$_3$-c-<br>myc-Aga2 | ATG<u>AAGGTTTTGATTGTCTTGTTGGCTATCTTCGCTGCTTTGCCATTGGCCTTA<br>GCTCAACCGGTTATTTCTACTACCGTCGGTTCCGCTGCAGAAGGCTCTTTGGAC<br>AAGAGA</u>GCCAACGAGCTGCGGTGCCAGTGCCTGCAGACCATGGCCGGCATCCAC<br>CTGAAGAACATCCAGAGCCTGAAGGTGCTGCCCAGCGGCCCTCACTGCACCCAG<br>ACCGAAGTGATCGCCACCCTGAAGAACGGCAGAGAGGCCTGCCTGGATCCCGAG<br>GCCCCCCTGGTGCAGAAAATCGTGCAGAAAATGCTGAAGGGCGTGCCCAAG*GGC<br>GGAGGC*GAACAAAAGCTTATCTCCGAAGAAGACTTGCAGGAACTGACAACTATA<br>TGCGAGCAAATCCCCTCACCAACTTTAGAATCGACGCCGTACTCTTTGTCAACG<br>ACTACTATTTTGGCCAACGGGAAGGCAATGCAAGGAGTTTTTGAATATTACAAA<br>TCAGTAACGTTTGTCAGTAATTGCGGTTCTCACCCCTCAACAACTAGCAAAGGC<br>AGCCCCATAAACACACAGTATGTTTTTTAA |
| 119 | pCHA-LS-<br>mCXCL2[31-100]-<br>G$_3$-c-<br>myc-Aga2 | ATG<u>AAGGTTTTGATTGTCTTGTTGGCTATCTTCGCTGCTTTGCCATTGGCCTTA<br>GCTCAACCGGTTATTTCTACTACCGTCGGTTCCGCTGCAGAAGGCTCTTTGGAC<br>AAGAGA</u>GCCAGCGAGCTGCGGTGCCAGTGCCTGAAAACCCTGCCCCGGGTGGAC<br>TTCAAGAACATCCAGAGCCTGAGCGTGACCCCCCCTGGCCCTCACTGTGCCCAG<br>ACCGAAGTGATCGCCACCCTGAAGGGCGGCCAGAAAGTGTGCCTGGACCCCGAG<br>GCCCCCCTGGTGCAGAAGATCATCCAGAAGATCCTGAACAAGGGCAAGGCCAAC<br>*GGCGGAGGC*GAACAAAAGCTTATCTCCGAAGAAGACTTGCAGGAACTGACAACT<br>ATATGCGAGCAAATCCCCTCACCAACTTTAGAATCGACGCCGTACTCTTTGTCA<br>ACGACTACTATTTTGGCCAACGGGAAGGCAATGCAAGGAGTTTTTGAATATTAC<br>AAATCAGTAACGTTTGTCAGTAATTGCGGTTCTCACCCCTCAACAACTAGCAAA<br>GGCAGCCCCATAAACACACAGTATGTTTTTTAA |
| 120 | pCHA-LS-<br>mCXCL3[31-100]-<br>G$_3$-c-<br>myc-Aga2 | ATG<u>AAGGTTTTGATTGTCTTGTTGGCTATCTTCGCTGCTTTGCCATTGGCCTTA<br>GCTCAACCGGTTATTTCTACTACCGTCGGTTCCGCTGCAGAAGGCTCTTTGGAC<br>AAGAGA</u>GCCTCTGAGCTGAGATGCCAGTGCCTGAACACCCTGCCCCGGGTGGAC<br>TTCGAGACAATCCAGAGCCTGACCGTGACCCCCCCTGGCCCTCACTGTACCCAG<br>ACAGAAGTGATCGCCACCCTGAAGGACGGCCAGGAAGTGTGCCTGAATCCCCAG<br>GGCCCCAGACTCCAGATCATCATCAAGAAGATCCTGAAGTCCGGCAAGAGCAGC<br>*GGCGGAGGC*GAACAAAAGCTTATCTCCGAAGAAGACTTGCAGGAACTGACAACT<br>ATATGCGAGCAAATCCCCTCACCAACTTTAGAATCGACGCCGTACTCTTTGTCA |

TABLE 12-continued

Sequence Summary

| SEQ ID NO | Description | Sequence |
|---|---|---|
| | | ACGACTACTATTTTGGCCAACGGGAAGGCAATGCAAGGAGTTTTTGAATATTAC<br>AAATCAGTAACGTTTGTCAGTAATTGCGGTTCTCACCCCTCAACAACTAGCAAA<br>GGCAGCCCCATAAACACACAGTATGTTTTTTAA |
| 121 | pCHA-LS-<br>mCXCL4[30-105]-<br>G$_3$-c-<br>myc-Aga2 | ATG<u>AAGGTTTTGATTGTCTTGTTGGCTATCTTCGCTGCTTTGCCATTGGCCTTA</u><br><u>GCTCAACCGGTTATTTCTACTACCGTCGGTTCCGCTGCAGAAGGCTCTTTGGAC</u><br><u>AAGAGA</u>GTGACATCTGCCGGCCCTGAGGAAAGCGACGGCGATCTGTCTTGCGTG<br>TGCGTGAAAACCATCAGCAGCGGCATCCACCTGAAGCACATCACCAGCCTGGAA<br>GTGATCAAGGCCGGCAGGCACTGTGCCGTGCCTCAGCTGATTGCCACCCTGAAG<br>AACGGCCGGAAGATCTGCCTGGACAGACAGGCCCCCCTGTACAAGAAAGTGATT<br>AAGAAGATCCTGGAAAGC*GGCGGAGGC*GAACAAAAGCTTATCTCCGAAGAAGAC<br>TTGCAGGAACTGACAACTATATGCGAGCAAATCCCCTCACCAACTTTAGAATCG<br>ACGCCGTACTCTTTGTCAACGACTACTATTTTGGCCAACGGGAAGGCAATGCAA<br>GGAGTTTTTGAATATTACAAATCAGTAACGTTTGTCAGTAATTGCGGTTCTCAC<br>CCCTCAACAACTAGCAAAGGCAGCCCCATAAACACACAGTATGTTTTTTAA |
| 122 | pCHA-LS-<br>mCXCL5[48-118]-<br>G$_3$-c-<br>myc-Aga2 | ATG<u>AAGGTTTTGATTGTCTTGTTGGCTATCTTCGCTGCTTTGCCATTGGCCTTA</u><br><u>GCTCAACCGGTTATTTCTACTACCGTCGGTTCCGCTGCAGAAGGCTCTTTGGAC</u><br><u>AAGAGA</u>GCCACCGAGCTGAGATGCGTGTGCCTGACCGTGACCCCCAAGATCAAC<br>CCCAAGCTGATCGCCAACCTGGAAGTGATCCCTGCCGGCCCTCAGTGCCCCACC<br>GTGGAAGTGATTGCCAAGCTGAAGAACCAGAAAGAAGTGTGCCTGGACCCCGAG<br>GCCCCCGTGATCAAGAAGATCATCCAGAAGATCCTGGGCAGCGACAAGAAGAAA<br>GCC*GGCGGAGGC*GAACAAAAGCTTATCTCCGAAGAAGACTTGCAGGAACTGACA<br>ACTATATGCGAGCAAATCCCCTCACCAACTTTAGAATCGACGCCGTACTCTTTG<br>TCAACGACTACTATTTTGGCCAACGGGAAGGCAATGCAAGGAGTTTTTGAATAT<br>TACAAATCAGTAACGTTTGTCAGTAATTGCGGTTCTCACCCCTCAACAACTAGC<br>AAAGGCAGCCCCATAAACACACAGTATGTTTTTTAA |
| 123 | pCHA-LS-<br>mCXCL7[48-113]-<br>G$_3$-c-<br>myc-Aga2 | ATG<u>AAGGTTTTGATTGTCTTGTTGGCTATCTTCGCTGCTTTGCCATTGGCCTTA</u><br><u>GCTCAACCGGTTATTTCTACTACCGTCGGTTCCGCTGCAGAAGGCTCTTTGGAC</u><br><u>AAGAGA</u>ATCGAGCTGCGGTGCCGGTGCACCAACACCATCAGCGGCATCCCTTTC<br>AACAGCATCAGCCTCGTGAACGTGTACAGACCCGGCCGTGCACTGCGCCGACGTG<br>GAAGTGATTGCTACACTGAAGAATGGGCAGAAAACCTGCCTGGACCCCAACGCC<br>CCTGGCGTGAAGCGGATCGTGATGAAGATTCTGGAAGGCTAC*GGCGGAGGC*GAA<br>CAAAAGCTTATCTCCGAAGAAGACTTGCAGGAACTGACAACTATATGCGAGCAA<br>ATCCCCTCACCAACTTTAGAATCGACGCCGTACTCTTTGTCAACGACTACTATT<br>TTGGCCAACGGGAAGGCAATGCAAGGAGTTTTTGAATATTACAAATCAGTAACG<br>TTTGTCAGTAATTGCGGTTCTCACCCCTCAACAACTAGCAAAGGCAGCCCCATA<br>AACACACAGTATGTTTTTTAA |
| 124 | pCHA-LS-<br>mCXCL9[22-126]-<br>G$_3$-c-<br>myc-Aga2 | ATG<u>AAGGTTTTGATTGTCTTGTTGGCTATCTTCGCTGCTTTGCCATTGGCCTTA</u><br><u>GCTCAACCGGTTATTTCTACTACCGTCGGTTCCGCTGCAGAAGGCTCTTTGGAC</u><br><u>AAGAGA</u>ACCCTCGTGATCCGGAACGCCCGGTGCAGCTGTATCAGCACCAGCAGA<br>GGCACCATCCACTACAAGAGCCTGAAGGATCTGAAGCAGTTCGCCCCCAGCCCC<br>AACTGCAACAAGACCGAGATTATCGCCACACTGAAAAACGGGGACCAGACCTGT<br>CTGGACCCCGACAGCGCCAACGTGAAGAAACTGATGAAGGAATGGGAGAAGAAG<br>ATCAGCCAGAAGAAGAAGCAGAAGCGGGCAAGAAACACCAGAAAAACATGAAG<br>AACCGGAAGCCCAAGACCCCCAGAGCCGGCGGAGATCCAGAAAGACCACA*GGC<br>GGAGGC*GAACAAAAGCTTATCTCCGAAGAAGACTTGCAGGAACTGACAACTATA<br>TGCGAGCAAATCCCCTCACCAACTTTAGAATCGACGCCGTACTCTTTGTCAACG<br>ACTACTATTTTGGCCAACGGGAAGGCAATGCAAGGAGTTTTTGAATATTACAAA<br>TCAGTAACGTTTGTCAGTAATTGCGGTTCTCACCCCTCAACAACTAGCAAAGGC<br>AGCCCCATAAACACACAGTATGTTTTTTAA |
| 125 | pCHA-LS-<br>mCXCL10[22-98]-<br>G$_3$-c-<br>myc-Aga2 | ATG<u>AAGGTTTTGATTGTCTTGTTGGCTATCTTCGCTGCTTTGCCATTGGCCTTA</u><br><u>GCTCAACCGGTTATTTCTACTACCGTCGGTTCCGCTGCAGAAGGCTCTTTGGAC</u><br><u>AAGAGA</u>ATCCCACTGGCCAGAACCGTGCGGTGCAACTGCATCCACATCGACGAT<br>GGCCCCGTGCGGATGAGAGCCATCGGCAAGCTGGAAATCATCCCCGCCAGCCTG<br>AGCTGCCCCAGAGTGGAAATTATCGCCACCATGAAGAAGAACGACGAGCAGCGG<br>TGCCTGAACCCCGAGAGCAAGACCATCAAGAACCTGATGAAGGCCTTTAGCCAG<br>AAGCGGAGCAAGAGGGCCCCA*GGCGGAGGC*GAACAAAAGCTTATCTCCGAAGAA<br>GACTTGCAGGAACTGACAACTATATGCGAGCAAATCCCCTCACCAACTTTAGAA<br>TCGACGCCGTACTCTTTGTCAACGACTACTATTTTGGCCAACGGGAAGGCAATG<br>CAAGGAGTTTTTGAATATTACAAATCAGTAACGTTTGTCAGTAATTGCGGTTCT<br>CACCCCTCAACAACTAGCAAAGGCAGCCCCATAAACACACAGTATGTTTTTTAA |
| 126 | pCHA-LS-<br>mCXCL11[22-100]-<br>G$_3$-c-<br>myc-Aga2 | ATG<u>AAGGTTTTGATTGTCTTGTTGGCTATCTTCGCTGCTTTGCCATTGGCCTTA</u><br><u>GCTCAACCGGTTATTTCTACTACCGTCGGTTCCGCTGCAGAAGGCTCTTTGGAC</u><br><u>AAGAGA</u>TTCCTGATGTTCAAGCAGGGCCGGTGCCTGTGCATCGGCCCTGGAATG<br>AAGGCCGTGAAGATGGCCGAGATCGAGAAGGCCAGCGTGATCTACCCCAGCAAC<br>GGCTGCGACAAGGTGGAAGTGATCGTGACCATGAAGGCCCACAAGCGGCAGAGA<br>TGCCTGGACCCCAGATCCAAGCAGGCCCGGCTGATCATGCAGGCTATCGAGAAG<br>AAGAATTTCCTGCGGCGGCAGAACATG*GGCGGAGGC*GAACAAAAGCTTATCTCC<br>GAAGAAGACTTGCAGGAACTGACAACTATATGCGAGCAAATCCCCTCACCAACT<br>TTAGAATCGACGCCGTACTCTTTGTCAACGACTACTATTTTGGCCAACGGGAAG |

TABLE 12-continued

Sequence Summary

| SEQ ID NO | Description | Sequence |
|---|---|---|
| | | GCAATGCAAGGAGTTTTTGAATATTACAAATCAGTAACGTTTGTCAGTAATTGC GGTTCTCACCCCTCAACAACTAGCAAAGGCAGCCCCATAAACACACAGTATGTT TTTTAA |
| 127 | LS-hCXCL1$^{38-107}$-G$_3$-c-myc-Aga2 | <u>MKVLIVLLAIFAALPLALAQPVISTTVGSAAEGSLDKR</u>ATELRCQCLQTLQGIH PKNIQSVNVKSPGPHCAQTEVIATLKNGRKACLNPASPIVKKIIEKMLNSDKSN <u>*GGG*</u>EQKLISEEDLQELTTICEQIPSPTLESTPYSLSTTTILANGKAMQGVFEYY KSVTFVSNCGSHPSTTSKGSPINTQYVF- |
| 128 | LS-hCXCL2$^{38-107}$-G$_3$-c-myc-Aga2 | <u>MKVLIVLLAIFAALPLALAQPVISTTVGSAAEGSLDKR</u>ATELRCQCLQTLQGIH LKNIQSVKVKSPGPHCAQTEVIATLKNGQKACLNPASPMVKKIIEKMLKNGKSN <u>*GGG*</u>EQKLISEEDLQELTTICEQIPSPTLESTPYSLSTTTILANGKAMQGVFEYY KSVTFVSNCGSHPSTTSKGSPINTQYVF- |
| 129 | LS-hCXCL3$^{38-107}$-G$_3$-c-myc-Aga2 | <u>MKVLIVLLAIFAALPLALAQPVISTTVGSAAEGSLDKR</u>VTELRCQCLQTLQGIH LKNIQSVNVRSPGPHCAQTEVIATLKNGKKACLNPASPMVQKIIEKILNKGSTN <u>*GGG*</u>EQKLISEEDLQELTTICEQIPSPTLESTPYSLSTTTILANGKAMQGVFEYY KSVTFVSNCGSHPSTTSKGSPINTQYVF- |
| 130 | LS-hCXCL4$^{32-101}$-G$_3$-c-myc-Aga2 | <u>MKVLIVLLAIFAALPLALAQPVISTTVGSAAEGSLDKR</u>EAEEDGDLQCLCVKTT SQVRPRHITSLEVIKAGPHCPTAQLIATLKNGRKICLDLQAPLYKKIIKKLLES <u>*GGG*</u>EQKLISEEDLQELTTICEQIPSPTLESTPYSLSTTTILANGKAMQGVFEYY KSVTFVSNCGSHPSTTSKGSPINTQYVF- |
| 131 | LS-hCXCL5$^{44-114}$-G$_3$-c-myc-Aga2 | <u>MKVLIVLLAIFAALPLALAQPVISTTVGSAAEGSLDKR</u>LRELRCVCLQTTQGVH PKMISNLQVFAIGPQCSKVEVVASLKNGKEICLDPEAPFLKKVIQKILDGGNKE N<u>*GGG*</u>EQKLISEEDLQELTTICEQIPSPTLESTPYSLSTTTILANGKAMQGVFEY YKSVTFVSNCGSHPSTTSKGSPINTQYVF- |
| 132 | LS-hCXCL6$^{44-114}$-G$_3$-c-myc-Aga2 | <u>MKVLIVLLAIFAALPLALAQPVISTTVGSAAEGSLDKR</u>LTELRCTCLRVTLRVN PKTIGKLQVFPAGPQCSKVEVVASLKNGKQVCLDPEAPFLKKVIQKILDSGNKK N<u>*GGG*</u>EQKLISEEDLQELTTICEQIPSPTLESTPYSLSTTTILANGKAMQGVFEY YKSVTFVSNCGSHPSTTSKGSPINTQYVF- |
| 133 | LS-hCXCL7$^{59-121}$-G$_3$-c-myc-Aga2 | <u>MKVLIVLLAIFAALPLALAQPVISTTVGSAAEGSLDKR</u>AELRCMCIKTTSGIHP KNIQSLEVIGKGTHCNQVEVIATLKDGRKICLDPDAPRIKKIVQKKL <u>*GGG*</u>EQKLISEEDLQELTTICEQIPSPTLESTPYSLSTTTILANGKAMQGVFEYY KSVTFVSNCGSHPSTTSKGSPINTQYVF- |
| 134 | LS-hCXCL8$^{29-99}$-G$_3$-c-myc-Aga2 | <u>MKVLIVLLAIFAALPLALAQPVISTTVGSAAEGSLDKR</u>AKELRCQCIKTYSKPF HPKFIKELRVIESGPHCANTEIIVKLSDGRELCLDPKENWVQRIVEKFLKRAEN S<u>*GGG*</u>EQKLISEEDLQELTTICEQIPSPTLESTPYSLSTTTILANGKAMQGVFEY YKSVTFVSNCGSHPSTTSKGSPINTQYVF- |
| 135 | LS-hCXCL9$^{23-115}$-G$_3$-c-myc-Aga2 | <u>MKVLIVLLAIFAALPLALAQPVISTTVGSAAEGSLDKR</u>TPVVRKGRCSCISTNQ GTIHLQSLKDLKQFAPSPSCEKIEIIATLKNGVQTCLNPDSADVKELIKKWEKQ VSQKKKQKNGKKHQKKKVLKVRKSQRSRQKKTT<u>*GGG*</u>EQKLISEEDLQELTTICE QIPSPTLESTPYSLSTTTILANGKAMQGVFEYYKSVTFVSNCGSHPSTTSKGSP INTQYVF- |
| 136 | LS-hCXCL10$^{22-98}$-G$_3$-c-myc-Aga2 | <u>MKVLIVLLAIFAALPLALAQPVISTTVGSAAEGSLDKR</u>VPLSRTVRCTCISISN QPVNPRSLEKLEIIPASQFCPRVEIIATMKKKGEKRCLNPESKAIKNLLKAVSK ERSKRSP<u>*GGG*</u>EQKLISEEDLQELTTICEQIPSPTLESTPYSLSTTTILANGKAM QGVFEYYKSVTFVSNCGSHPSTTSKGSPINTQYVF- |
| 137 | LS-hCXCL11$^{22-94}$-G$_3$-c-myc-Aga2 | <u>MKVLIVLLAIFAALPLALAQPVISTTVGSAAEGSLDKR</u>FPMFKRGRCLCIGPGV KAVKVADIEKASIMYPSNNCDKIEVIITLKENKGQRCLNPKSKQARLIIKKVER KNF<u>*GGG*</u>EQKLISEEDLQELTTICEQIPSPTLESTPYSLSTTTILANGKAMQGVF EYYKSVTFVSNCGSHPSTTSKGSPINTQYVF- |
| 138 | LS-mCXCL1$^{28-96}$-G$_3$-c-myc-Aga2 | <u>MKVLIVLLAIFAALPLALAQPVISTTVGSAAEGSLDKR</u>ANELRCQCLQTMAGIH LKNIQSLKVLPSGPHCTQTEVIATLKNGREACLDPEAPLVQKIVQKMLKGVPK*G GG*EQKLISEEDLQELTTICEQIPSPTLESTPYSLSTTTILANGKAMQGVFEYYK SVTFVSNCGSHPSTTSKGSPINTQYVF- |
| 139 | LS-mCXCL2$^{31-100}$-G$_3$-c-myc-Aga2 | <u>MKVLIVLLAIFAALPLALAQPVISTTVGSAAEGSLDKR</u>ASELRCQCLKTLPRVD FKNIQSLSVTPPGPHCAQTEVIATLKGGQKVCLDPEAPLVQKIIQKILNKGKAN <u>*GGG*</u>EQKLISEEDLQELTTICEQIPSPTLESTPYSLSTTTILANGKAMQGVFEYY KSVTFVSNCGSHPSTTSKGSPINTQYVF- |
| 140 | LS-mCXCL3$^{31-100}$-G$_3$-c-myc-Aga2 | <u>MKVLIVLLAIFAALPLALAQPVISTTVGSAAEGSLDKR</u>ASELRCQCLNTLPRVD FETIQSLTVTPPGPHCTQTEVIATLKDGQEVCLNPQGPRLQIIIKKILSGKSS <u>*GGG*</u>EQKLISEEDLQELTTICEQIPSPTLESTPYSLSTTTILANGKAMQGVFEYY KSVTFVSNCGSHPSTTSKGSPINTQYVF- |

TABLE 12-continued

Sequence Summary

| SEQ ID NO | Description | Sequence |
|---|---|---|
| 141 | LS-mCXCL4[30-105]-G$_3$-c-myc-Aga2 | MKVLIVLLAIFAALPLALAQPVISTTVGSAAEGSLDKRVTSAGPEESDGDLSCV CVKTISSGIHLKHITSLEVIKAGRHCAVPQLIATLKNGRKICLDRQAPLYKKVI KKILES_GGG_EQKLISEEDLQELTTICEQIPSPTLESTPYSLSTTTILANGKAMQ GVFEYYKSVTFVSNCGSHPSTTSKGSPINTQYVF- |
| 142 | LS-mCXCL5[48-118]-G$_3$-c-myc-Aga2 | MKVLIVLLAIFAALPLALAQPVISTTVGSAAEGSLDKRATELRCVCLTVTPKIN PKLIANLEVIPAGPQCPTVEVIAKLKNQKEVCLDPEAPVIKKIIQKILGSDKKK AGGGEQKLISEEDLQELTTICEQIPSPTLESTPYSLSTTTILANGKAMQGVFEY YKSVTFVSNCGSHPSTTSKGSPINTQYVF- |
| 143 | LS-mCXCL7[48-113]-G$_3$-c-myc-Aga2 | MKVLIVLLAIFAALPLALAQPVISTTVGSAAEGSLDKRIELRCRCTNTISGIPF NSISLVNVYRPGVHCADVEVIATLKNGQKTCLDPNAPGVKRIVMKILEGY_GGG_E QKLISEEDLQELTTICEQIPSPTLESTPYSLSTTTILANGKAMQGVFEYYKSVT FVSNCGSHPSTTSKGSPINTQYVF- |
| 144 | LS-mCXCL9[22-126]-G$_3$-c-myc-Aga2 | MKVLIVLLAIFAALPLALAQPVISTTVGSAAEGSLDKRTLVIRNARCSCISTSR GTIHYKSLKDLKQFAPSPNCNKTEIIATLKNGDQTCLDPDSANVKKLMKEWEKK ISQKKKQKRGKKHQKNMKNRKPKTPQSRRRSRKTT_GGG_EQKLISEEDLQELTTI CEQIPSPTLESTPYSLSTTTILANGKAMQGVFEYYKSVTFVSNCGSHPSTTSKG SPINTQYVF- |
| 145 | LS-mCXCL10[22-98]-G$_3$-c-myc-Aga2 | MKVLIVLLAIFAALPLALAQPVISTTVGSAAEGSLDKRIPLARTVRCNCIHIDD GPVRMRAIGKLEIIPASLSCPRVEIIATMKKNDEQRCLNPESKTIKNLMKAFSQ KRSKRAP_GGG_EQKLISEEDLQELTTICEQIPSPTLESTPYSLSTTTILANGKAM QGVFEYYKSVTFVSNCGSHPSTTSKGSPINTQYVF- |
| 146 | LS-mCXCL11[22-100]-G$_3$-c-myc-Aga2 | MKVLIVLLAIFAALPLALAQPVISTTVGSAAEGSLDKRFLMFKQGRCLCIGPGM KAVKMAEIEKASVIYPSNGCDKVEVIVTMKAHKRQRCLDPRSKQARLIMQAIEK KNFLRRQNM_GGG_EQKLISEEDLQELTTICEQIPSPTLESTPYSLSTTTILANGK AMQGVFEYYKSVTFVSNCGSHPSTTSKGSPINTQYVF- |
| 147 | pCHA-LS-hCXCL1-G$_3$-c-myc-Aga2 | ATGAAGGTTTTGATTGTCTTGTTGGCTATCTTCGCTGCTTTGCCA TTGGCCTTAGCTCAACCGGTTATTTCTACTACCGTCGGTTCCGCT GCAGAAGGCTCTTTGGACAAGAGAGCCACCGAGCTGAGATGCCAG TGCCTGCAGACCCTGCAGGGCATCCACCCCAAGAACATCCAGAGC GTGAACGTGAAGTCCCCTGGCCCCCACTGCGCCCAGACCGAAGTG ATCGCCACCCTGAAGAACGGCCGGAAGGCCTGCCTGAACCCCGCC AGCCCCATCGTGAAGAAAATCATCGAGAAGATGCTGAACAGCGAC AAGAGCAAC_GGCGGAGGC_GAACAAAAGCTTATCTCCGAAGAAGAC TTGCAGGAACTGACAACTATATGCGAGCAAATCCCCTCACCAACT TTAGAATCGACGCCGTACTCTTTGTCAACGACTACTATTTTGGCC AACGGGAAGGCAATGCAAGGAGTTTTTGAATATTACAAATCAGTA ACGTTTGTCAGTAATTGCGGTTCTCACCCCTCAACAACTAGCAAA GGCAGCCCCATAAACACACAGTATGTTTTTTAA |
| 148 | LS-hCXCL1-G$_3$-c-myc-Aga2 | MKVLIVLLAIFAALPLALAQPVISTTVGSAAEGSLDKRATELRCQ CLQTLQGIHPKNIQSVNVKSPGPHCAQTEVIATLKNGRKACLNPA SPIVKKIIEKMLNSDKSN_GGG_**EQKLISEEDLQELTTICEQIPSPT LESTPYSLSTTTILANGKAMQGVFEYYKSVTFVSNCGSHPSTTSK GSPINTQYVF- |
| 149 | mouse SA-(Gly$_4$Ser)$_3$-scFv (V$_L$-V$_H$) CK138 | ATGGAAGCACACAAGAGTGAGATCGCCCATCGGTATAATGATTTGGGAGAACAA CATTTCAAAGGCCTAGTCCTGATTGCCTTTTCCCAGTATCTCCAGAAATGCTCA TACGATGAGCATGCCAAATTAGTGCAGGAAGTAACAGACTTTGCAAAGACGTGT GTTGCCGATGAGTCTGCCGCCAACTGTGACAAATCCCTTCACACTCTTTTTGGA GATAAGTTGTGTGCCATTCCAAACCTCCGTGAAAACTATGGTGAACTGGCTGAC TGCTGTACAAAACAAGAGCCCGAAAGAAACGAATGTTTCCTGCAACACAAAGAT GACAACCCCAGCCTACCACCATTTGAAAGGCCAGAGGCTGAGGCCATGTGCACC TCCTTTAAGGAAAACCCAACCACCTTTATGGGACACTATTTGCATGAAGTTGCC AGAAGACATCCTTATTTCTATGCCCCAGAACTTCTTTACTATGCTGAGCAGTAC AATGAGATTCTGACCCAGTGTTGTGCAGAGGCTGACAAGGAAAGCTGCCTGACC CCGAAGCTTGATGGTGTGAAGGAGAAAGCATTGGTCTCATCTGTCCGTCAGAGA ATGAAGTGCTCCAGTATGCAGAAGTTTGGAGAGAGAGCTTTTAAAGCATGGGCA GTAGCTCGTCTGAGCCAGACATTCCCAATGCTGACTTTGCAGAAATCACCAAA TTGGCAACAGACCTGACCAAAGTCAACAAGGAGTGCTGCCATGGTGACCTGCTG GAATGCGCAGATGACAGGGCGGAACTTGCCAAGTACATGTGTGAAAACCAGGCG ACTATCTCCAGCAAACTGCAGACTTGCTGCGATAAACCACTGTTGAAGAAAGCC CACTGTCTTAGTGAGGTGGAGCATGACACCATGCCTGCTGATCTGCCTGCCATT GCTGCTGATTTTGTTGAGGACCAGGAAGTGTGCAAGAACTATGCTGAGGCCAAG GATGTCTTCCTGGGCACGTTCTTGTATGAATATTCAAGAAGACACCCTGATTAC TCTGTATCCCTGTTGCTGAGACTTGCTAAGAAATATGAAGCCACTCTGGAAAAG TGCTGCGCTGAAGCCAATCCTCCCGCATGCTACGGCACAGTGCTTGCTGAATTT CAGCCTCTTGTAGAAGAGCCTAAGAACTTGGTCAAAACCAACTGTGATCTTTAC GAGAAGCTTGGAGAATATGGATTCCAAAATGCCATTCTAGTTCGCTACACCCAG AAAGCACCTCAGGTGTCAACCCCAACTCTCGTGGAGGCTGCAAGAAACCTAGGA |

TABLE 12-continued

Sequence Summary

| SEQ ID NO | Description | Sequence |
|---|---|---|
| | | AGAGTGGGCACCAAGTGTTGTACACTTCCTGAAGATCAGAGACTGCCTTGTGTG<br>GAAGACTATCTGTGTGCAATCCTGAACCGTGTGTGTGCTGCATGAGAAGACC<br>CCAGTGAGTGAGCATGTTACCAAGTGCTGTAGTGGATCCCTGGTGGAAAGGCGG<br>CCATGCTTCTCTGCTCTGACAGTTGATGAAACATATGTCCCCAAAGAGTTTAAA<br>GCTGAGACCTTCACCTTCCACTCTGATATCTGCACACTTCCAGAGAAGGAGAAG<br>CAGATTAAGAAACAAACGGCTCTTGCTGAGCTGGTGAAGCACAAGCCCAAGGCT<br>ACAGCGGAGCAACTGAAGACTGTCATGGATGACTTTGCACAGTTCCTGGATACA<br>TGTTGCAAGGCTGCTGACAAGGACACCTGCTTCTCGACTGAGGGTCCAAACCTT<br>GTCACTAGATGCAAAGACGCCTTAGCC<u>GGTGGAGGAGGCTCTGGTGGAGGCGGT</u><br><u>AGCGGAGGCGGAGGGTCG</u>GCTATCCAGATGACCCGGTCCCCGAGCTCCCTGTCC<br>GCCTCTGTGGGCGATAGGGTCACCATCACCTGCCGTGCCAGTCAGTACCACGAC<br>GGTTCTGCAGCCTGGTATCAACAGAAACCAGGAAAAGCTCCGAAGCTTCTGATT<br>TACGGTGCATCCTACCTCTACTCTGGAGTCCCTTCCCGCTTCTCTGGTAGCCGT<br>TCCGGGACGGATTTCACTCTGACCATCAGCAGTCTGCAGCCGGAAGACTTCGCA<br>ACTTATTACTGTCAGCAATCTTCTTATTCTCTGATCACGTTCGGACAGGGTACC<br>AAGGTGGAGATCAAAGGTACTACTGCCGCTAGTGGTAGTAGTGGTGGCAGTAGC<br>AGTGGTGCCGAGGTTCAGCTGGTGGAGTCTGACGGTGGCCTGGTGCAGCCAGGG<br>GGCTCACTCCGTTTGTCCTGTGCAGCTTCTGGCTTCAACCTCTCTTACTACGGT<br>ATGCACTGGGTGCGTCAGGCCCCGGGTAAGGGCCTGGAATGGGTTGCATACATT<br>GCTTCTTACCCTGGCTACACTTCTTATGCCGATAGCGTCAAGGGCCGTTTCACT<br>ATAAGCGCAGACACATCCAAAAACACAGCCTACCTACAAATGAACAGCTTAAGA<br>GCTGAGGACACTGCCGTCTACTATTGTGCTCGCTCTGGTTACAGTTACTCTCCG<br>TATTATTCTTGGTTCTCTGCTGGTATGAACTACTGGGGTCAAGGAGCCCTGGTC<br>ACCGTCTCCTCGTGATAG |
| 150 | mouse SA-<br>(Gly$_4$Ser)$_3$-<br>scFv (V$_L$-<br>V$_H$) CK157 | ATGCGAAGCACACAAGAGTGAGATCGCCCATCGGTATAATGATTTGGGAGAACA<br>ACATTTCAAAGGCCTAGTCCTGATTGCCTTTTCCCAGTATCTCCAGAAATGCTC<br>ATACGATGAGCATGCCAAATTAGTGCAGGAAGTAACAGACTTTGCAAAGACGTG<br>TGTTGCCGATGAGTCTGCCGCCAACTGTGACAAATCCCTTCACACTCTTTTTGG<br>AGATAAGTTGTGTGCCATTCCAAACCTCCGTGAAAACTATGGTGAACTGGCTGA<br>CTGCTGTACAAAACAAGAGCCCGAAAGAAACGAATGTTTCCTGCAACACAAAGA<br>TGACAACCCCAGCCTACCACCATTTGAAAGGCCAGAGGCTGAGGCCATGTGCAC<br>CTCCTTTAAGGAAAACCCAACCACCTTTATGGGACACTATTTGCATGAAGTTGC<br>CAGAAGACATCCTTATTTCTATGCCCCAGAACTTCTTTACTATGCTGAGCAGTA<br>CAATGAGATTCTGACCCAGTGTTGTGCAGAGGCTGACAAGGAAAGCTGCCTGAC<br>CCCGAAGCTTGATGGTGTGAAGGAGAAAGCATTGGTCTCATCTGTCCGTCAGAG<br>AATGAAGTGCTCCAGTATGCAGAAGTTTGGAGAGAGAGCTTTTAAAGCATGGGC<br>AGTAGCTCGTCTGAGCCAGACATTCCCCAATGCTGACTTTGCAGAAATCACCAA<br>ATTGGCAACAGACCTGACCAAAGTCAACAAGGAGTGCTGCCATGGTGACCTGCT<br>GGAATGCGCAGATGACAGGGCGGAACTTGCCAAGTACATGTGTGAAAACCAGGC<br>GACTATCTCCAGCAAACTGCAGACTTGCTGCGATAAACCACTGTTGAAGAAAGC<br>CCACTGTCTTAGTGAGGTGGAGCATGACACCATGCCTGCTGATCTGCCTGCCAT<br>TGCTGCTGATTTTGTTGAGGACCAGGAAGTGTGCAAGAACTATGCTGAGGCCAA<br>GGATGTCTTCCTGGGCACGTTCTTGTATGAATATTCAAGAAGACACCCTGATTA<br>CTCTGTATCCCTGTTGCTGAGACTTGCTAAGAAATATGAAGCCACTCTGGAAAA<br>GTGCTGCGCTGAAGCCAATCCTCCCGCATGCTACGGCACAGTGCTTGCTGAATT<br>TCAGCCTCTTGTAGAAGAGCCTAAGAACTTGGTCAAAACCAACTGTGATCTTTA<br>CGAGAAGCTTGGAGAATATGGATTCCAAAATGCCATTCTAGTTCGCTACACCCA<br>GAAAGCACCTCAGGTGTCAACCCCAACTCTCGTGGAGGCTGCAAGAAACCTAGG<br>AAGAGTGGGCACCAAGTGTTGTACACTTCCTGAAGATCAGAGACTGCCTTGTGT<br>GGAAGACTATCTGTGTGCAATCCTGAACCGTGTGTGTGCTGCATGAGAAGAC<br>CCCAGTGAGTGAGCATGTTACCAAGTGCTGTAGTGGATCCCTGGTGGAAAGGCG<br>GCCATGCTTCTCTGCTCTGACAGTTGATGAAACATATGTCCCCAAAGAGTTTAA<br>AGCTGAGACCTTCACCTTCCACTCTGATATCTGCACACTTCCAGAGAAGGAGAA<br>GCAGATTAAGAAACAAACGGCTCTTGCTGAGCTGGTGAAGCACAAGCCCAAGGC<br>TACAGCGGAGCAACTGAAGACTGTCATGGATGACTTTGCACAGTTCCTGGATAC<br>ATGTTGCAAGGCTGCTGACAAGGACACCTGCTTCTCGACTGAGGGTCCAAACCT<br>TGTCACTAGATGCAAAGACGCCTTAGCC<u>GGTGGAGGAGGCTCTGGTGGAGGCGG</u><br><u>TAGCGGAGGCGGAGGGTCG</u>GATATCCAGATGACCCAGTCCCCGAGCTCCCTGTC<br>CGCCTCTGTGGGCGATAGGGTCACCATCACCTGCCGTGCCAGTCAGTCTTACGG<br>TGGTGTAGCCTGGTATCAACAGAAACCAGGAAAAGCCCCGAAGCTTCTGATTTA<br>CTCTGCATCCTACCTCTACTCTGGAGTCCCTTCTCGCTTCTCTGGTAGCCGTTC<br>CGGGACGGATTTCACTCTGACCATCAGCAGTCTGCAGCCGGAAGACTTCGCAAC<br>TTATTACTGTCAGCAACCATCTCATCTGATCACGTTCGGACAGGGTACCGAGGT<br>GGAGATCAAAGGTACTACTGCCGCTAGTGGTAGTAGTGGTGGCAGTAGCAGTGG<br>TGCCGAGGTTCAGCTGGTGGAGTCTGGCGGTGGCCTGGTGCAGCCAGGGGGCTC<br>ACTCCGTTTGTCCTGTGCAGCTTCTGGCTCCAACCCCTACTACTACGGTGGTAC<br>GCACTGGGTGCGTCAGGCCCCGGGTGAGGAGCTGGAATGGGTTGCATCTATTGG<br>TTCTTACCCTGGCTACACTGACTATGCCGATAGCGTCAAGGGCCGTTTCACTAT<br>AAGCGCAGACACATCCAAAAACACAGCCTACCTACAAATGAACAGCTTAAGAGC<br>TGAGGACACTGCCGTCTATTATTGTGCTCGCCATTACTACTGGTACGATGCTAC<br>TGACTACTGGGGTCAAGGAACCCTGGTCACCGTCTCCTCGTGATAG |
| 151 | mouse SA-<br>(Gly$_4$Ser)$_3$- | ATGGAAGCACACAAGAGTGAGATCGCCCATCGGTATAATGATTTGGGAGAACAA<br>CATTTCAAAGGCCTAGTCCTGATTGCCTTTTCCCAGTATCTCCAGAAATGCTCA |

TABLE 12-continued

Sequence Summary

| SEQ ID NO | Description | Sequence |
|---|---|---|
| | scFv (V$_L$-V$_H$) CK129 | TACGATGAGCATGCCAAATTAGTGCAGGAAGTAACAGACTTTGCAAAGACGTGT<br>GTTGCCGATGAGTCTGCCGCCAACTGTGACAAATCCCTTCACACTCTTTTTGGA<br>GATAAGTTGTGTGCCATTCCAAACCTCCGTGAAAACTATGGTGAACTGGCTGAC<br>TGCTGTACAAAACAAGAGCCCGAAAGAAACGAATGTTTCCTGCAACACAAAGAT<br>GACAACCCCAGCCTACCACCATTTGAAAGGCCAGAGGCTGAGGCCATGTGCACC<br>TCCTTTAAGGAAAACCCAACCACCTTTATGGGACACTATTTGCATGAAGTTGCC<br>AGAAGACATCCTTATTTCTATGCCCCAGAACTTCTTTACTATGCTGAGCAGTAC<br>AATGAGATTCTGACCCAGTGTTGTGCAGAGGCTGACAAGGAAAGCTGCCTGACC<br>CCGAAGCTTGATGGTGTGAAGGAGAAAGCATTGGTCTCATCTGTCCGTCAGAGA<br>ATGAAGTGCTCCAGTATGCAGAAGTTTGGAGAGAGAGCTTTTAAAGCATGGGCA<br>GTAGCTCGTCTGAGCCAGACATTCCCCAATGCTGACTTTGCAGAAATCACCAAA<br>TTGGCAACAGACCTGACCAAAGTCAACAAGGAGTGCTGCCATGGTGACCTGCTG<br>GAATGCGCAGATGACAGGGCGGAACTTGCCAAGTACATGTGTGAAAACCAGGCG<br>ACTATCTCCAGCAAACTGCAGACTTGCTGCGATAAACCACTGTTGAAGAAAGCC<br>CACTGTCTTAGTGAGGTGGAGCATGACACCATGCCTGCTGATCTGCCTGCCATT<br>GCTGCTGATTTTGTTGAGGACCAGGAAGTGTGCAAGAACTATGCTGAGGCCAAG<br>GATGTCTTCCTGGGCACGTTCTTGTATGAATATTCAAGAAGACACCCTGATTAC<br>TCTGTATCCCTGTTGCTGAGACTTGCTAAGAAATATGAAGCCACTCTGGAAAAG<br>TGCTGCGCTGAAGCCAATCCTCCCGCATGCTACGGCACAGTGCTTGCTGAATTT<br>CAGCCTCTTGTAGAAGAGCCTAAGAACTTGGTCAAAACCAACTGTGATCTTTAC<br>GAGAAGCTTGAGAATATGGATTCCAAAATGCCATTCTAGTTCGCTACACCCAG<br>AAAGCACCTCAGGTGTCAACCCCAACTCTCGTGGAGGCTGCAAGAAACCTAGGA<br>AGAGTGGGCACCAAGTGTTGTACACTTCCTGAAGATCAGAGACTGCCTTGTGTG<br>GAAGACTATCTGTGTGCAATCCTGAACCGTGTGTGTGCTGCATGAGAAGACC<br>CCAGTGAGTGAGCATGTTACCAAGTGCTGTAGTGGATCCCTGGTGGAAAGGCGG<br>CCATGCTTCTCTGCTCTGACAGTTGATGAAACATATGTCCCCAAAGAGTTTAAA<br>GCTGAGACCTTCACCTTCCACTCTGATATCTGCACACTTCCAGAGAAGGAGAAG<br>CAGATTAAGAAACAAACGGCTCTTGCTGAGCTGGTGAAGCACAAGCCCAAGGCT<br>ACAGCGGAGCAACTGAAGACTGTCATGGATGACTTTGCACAGTTCCTGGATACA<br>TGTTGCAAGGCTGCTGACAAGGACACCTGCTTCTCGACTGAGGGTCCAAACCTT<br>GTCACTAGATGCAAAGACGCCTTAGC<u>GGTGGAGGAGGCTCTGGTGGAGGCGGT<br>AGCGGAGGCGGAGGGTCG</u>GCTAGCGATATCCAGATGACCCAGTCCCCGAGCCCC<br>CTGTCCGCCTCTGTGGGCGATAGGGTCACCATCACCTGCCGTGCCAGTCAGTAC<br>GGTGGTTACGTAGCCTGGTATCAACAGAAACCAGGAAAAGCTCCGAAGCTTCTG<br>ATTTACGGTGCATCCCTTCTCTACTCTGGAGTCCCTTCTCGCTTCTCTGGTGGC<br>CGTTCCGGGACGGATTTCACTCTGACCATCAGCAGTCTGCAGCCGGAAGACTTC<br>GCAACTTATTACTGTCAGCAGGTCATGCTCTGATCACGTTCGGACAGGGTACC<br>AAGGTGGAGATCGAAGGTACTACTGCCGCTAGTGGTAGTAGTGGTGGCAGTAGC<br>AGTGGTGCCGAGGTTCAGCTGGTGGAGTCTGGCGGTGGCCTGGTGCAGCCAGGG<br>GGCTCACTCCGTTTATCCTGTGCAGCTTCTGGCTTCAACATCTCTTCTTACGGT<br>TCTATGCACTGGGTGCGTCAGGCCCCGGGTAAGGGCCTGGAATGGGTTGCATCT<br>ATTTACCCTTACTCTAGCTCTACTTACTATGCCGATAGCGTCAAGGGCCGTTTC<br>ACTATAAGCGCAGACACATCCAAAAACACAGCCTACCTACAAATGAACAGCTTA<br>AGAGCTGAGGACACTGCCGTCTATTATTGTGCTCGTGGTTACGGTCCGTGGTAC<br>GCTTACTCTTACTTCGCTTTGGACTACTGGGGTCAAGGAACCCTGGTCACCGTC<br>TCCTCGTGATAG |
| 152 | mouse SA-(Gly$_4$Ser)$_3$-scFv (V$_L$-V$_H$) CK138-ds1<br>(V$_L$100$^{Q>C}$/V$_H$44$^{G>C}$) | ATGGAAGCACACAAGAGTGAGATCGCCCATCGGTATAATGATTTGGGAGAACAA<br>CATTTCAAAGGCCTAGTCCTGATTGCCTTTTCCCAGTATCTCCAGAAATGCTCA<br>TACGATGAGCATGCCAAATTAGTGCAGGAAGTAACAGACTTTGCAAAGACGTGT<br>GTTGCCGATGAGTCTGCCGCCAACTGTGACAAATCCCTTCACACTCTTTTTGGA<br>GATAAGTTGTGTGCCATTCCAAACCTCCGTGAAAACTATGGTGAACTGGCTGAC<br>TGCTGTACAAAACAAGAGCCCGAAAGAAACGAATGTTTCCTGCAACACAAAGAT<br>GACAACCCCAGCCTACCACCATTTGAAAGGCCAGAGGCTGAGGCCATGTGCACC<br>TCCTTTAAGGAAAACCCAACCACCTTTATGGGACACTATTTGCATGAAGTTGCC<br>AGAAGACATCCTTATTTCTATGCCCCAGAACTTCTTTACTATGCTGAGCAGTAC<br>AATGAGATTCTGACCCAGTGTTGTGCAGAGGCTGACAAGGAAAGCTGCCTGACC<br>CCGAAGCTTGATGGTGTGAAGGAGAAAGCATTGGTCTCATCTGTCCGTCAGAGA<br>ATGAAGTGCTCCAGTATGCAGAAGTTTGGAGAGAGAGCTTTTAAAGCATGGGCA<br>GTAGCTCGTCTGAGCCAGACATTCCCCAATGCTGACTTTGCAGAAATCACCAAA<br>TTGGCAACAGACCTGACCAAAGTCAACAAGGAGTGCTGCCATGGTGACCTGCTG<br>GAATGCGCAGATGACAGGGCGGAACTTGCCAAGTACATGTGTGAAAACCAGGCG<br>ACTATCTCCAGCAAACTGCAGACTTGCTGCGATAAACCACTGTTGAAGAAAGCC<br>CACTGTCTTAGTGAGGTGGAGCATGACACCATGCCTGCTGATCTGCCTGCCATT<br>GCTGCTGATTTTGTTGAGGACCAGGAAGTGTGCAAGAACTATGCTGAGGCCAAG<br>GATGTCTTCCTGGGCACGTTCTTGTATGAATATTCAAGAAGACACCCTGATTAC<br>TCTGTATCCCTGTTGCTGAGACTTGCTAAGAAATATGAAGCCACTCTGGAAAAG<br>TGCTGCGCTGAAGCCAATCCTCCCGCATGCTACGGCACAGTGCTTGCTGAATTT<br>CAGCCTCTTGTAGAAGAGCCTAAGAACTTGGTCAAAACCAACTGTGATCTTTAC<br>GAGAAGCTTGAGAATATGGATTCCAAAATGCCATTCTAGTTCGCTACACCCAG<br>AAAGCACCTCAGGTGTCAACCCCAACTCTCGTGGAGGCTGCAAGAAACCTAGGA<br>AGAGTGGGCACCAAGTGTTGTACACTTCCTGAAGATCAGAGACTGCCTTGTGTG<br>GAAGACTATCTGTGTGCAATCCTGAACCGTGTGTGTGCTGCATGAGAAGACC<br>CCAGTGAGTGAGCATGTTACCAAGTGCTGTAGTGGATCCCTGGTGGAAAGGCGG<br>CCATGCTTCTCTGCTCTGACAGTTGATGAAACATATGTCCCCAAAGAGTTTAAA |

TABLE 12-continued

Sequence Summary

| SEQ ID NO | Description | Sequence |
|---|---|---|
| | | GCTGAGACCTTCACCTTCCACTCTGATATCTGCACACTTCCAGAGAAGGAGAAG<br>CAGATTAAGAAACAAACGGCTCTTGCTGAGCTGGTGAAGCACAAGCCCAAGGCT<br>ACAGCGGAGCAACTGAAGACTGTCATGGATGACTTTGCACAGTTCCTGGATACA<br>TGTTGCAAGGCTGCTGACAAGGACACCTGCTTCTCGACTGAGGGTCCAAACCTT<br>GTCACTAGATGCAAAGACGCCTTAGCC<u>GGTGGAGGAGGCTCTGGTGGAGGCGGT</u><br><u>AGCGGAGGCGGAGGGTCG</u>GCTATCCAGATGACCCGGTCCCCGAGCTCCCTGTCC<br>GCCTCTGTGGGCGATAGGGTCACCATCACCTGCCGTGCCAGTCAGTACCACGAC<br>GGTTCTGCAGCCTGGTATCAACAGAAACCAGGAAAAGCTCCGAAGCTTCTGATT<br>TACGGTGCATCCTACCTCTACTCTGGAGTCCCTTCCCGCTTCTCTGGTAGCCGT<br>TCCGGGACGGATTTCACTCTGACCATCAGCAGTCTGCAGCCGGAAGACTTCGCA<br>ACTTATTACTGTCAGCAATCTTCTTATTCTCTGATCACGTTCGGA<i>TGC</i>GGTACC<br>AAGGTGGAGATCAAAGGTACTACTGCCGCTAGTGGTAGTAGTGGTGGCAGTAGC<br>AGTGGTGCCGAGGTTCAGCTGGTGGAGTCTGACGGTGGCCTGGTGCAGCCAGGG<br>GGCTCACTCCGTTTGTCCTGTGCAGCTTCTGGCTTCAACCTCTCTTACTACGGT<br>ATGCACTGGGTGCGTCAGGCCCCGGGTAAG<i>T</i>GCCTGGAATGGGTTGCATACATT<br>GCTTCTTACCCTGGCTACACTTCTTATGCCGATAGCGTCAAGGGCCGTTTCACT<br>ATAAGCGCAGACACATCCAAAAACACAGCCTACCTACAAATGAACAGCTTAAGA<br>GCTGAGGACACTGCCGTCTACTATTGTGCTCGCTCTGGTTACAGTTACTCTCCG<br>TATTATTCTTGGTTCTCTGCTGGTATGAACTACTGGGGTCAAGGAGCCCTGGTC<br>ACCGTCTCCTCGTGATAG |
| 153 | mouse SA-<br>(Gly$_4$Ser)$_3$-<br>scFv (V$_L$-<br>V$_H$) CK138-<br>ds2<br>(V$_L$43$^{A>C}$/<br>V$_H$105$^{Q>C}$) | ATGGAAGCACACAAGAGTGAGATCGCCCATCGGTATAATGATTTGGGAGAACAA<br>CATTTCAAAGGCCTAGTCCTGATTGCCTTTTCCCAGTATCTCCAGAAATGCTCA<br>TACGATGAGCATGCCAAATTAGTGCAGGAAGTAACAGACTTTGCAAAGACGTGT<br>GTTGCCGATGAGTCTGCCGCCAACTGTGACAAATCCCTTCACACTCTTTTTGGA<br>GATAAGTTGTGTGCCATTCCAAACCTCCGTGAAAACTATGGTGAACTGGCTGAC<br>TGCTGTACAAAACAAGAGCCCGAAAGAAACGAATGTTTCCTGCAACACAAAGAT<br>GACAACCCCAGCCTACCACCATTTGAAAGGCCAGAGGCTGAGGCCATGTGCACC<br>TCCTTTAAGGAAAACCCAACCACCTTTATGGGACACTATTTGCATGAAGTTGCC<br>AGAAGACATCCTTATTCTATGCCCCAGAACTTCTTTACTATGCTGAGCAGTAC<br>AATGAGATTCTGACCCAGTGTTGTGCAGAGGCTGACAAGGAAAGCTGCCTGACC<br>CCGAAGCTTGATGGTGTGAAGGAGAAAGCATTGGTCTCATCTGTCCGTCAGAGA<br>ATGAAGTGCTCCAGTATGCAGAAGTTTGGAGAGAGAGCTTTTAAAGCATGGGCA<br>GTAGCTCGTCTGAGCCAGACATTCCCCAATGCTGACTTTGCAGAAATCACCAAA<br>TTGGCAACAGACCTGACCAAAGTCAACAAGGAGTGCTGCCATGGTGACCTGCTG<br>GAATGCGCAGATGACAGGGCGGAACTTGCCAAGTACATGTGTGAAAACCAGGCG<br>ACTATCTCCAGCAAACTGCAGACTTGCTGCGATAAACCACTGTTGAAGAAAGCC<br>CACTGTCTTAGTGAGGTGGAGCATGACACCATGCCTGCTGATCTGCCTGCCATT<br>GCTGCTGATTTTGTTGAGGACCAGGAAGTGTGCAAGAACTATGCTGAGGCCAAG<br>GATGTCTTCCTGGGCACGTTCTTGTATGAATATTCAAGAAGACACCCTGATTAC<br>TCTGTATCCCTGTTGCTGAGACTTGCTAAGAAATATGAAGCCACTCTGGAAAAG<br>TGCTGCGCTGAAGCCAATCCTCCCGCATGCTACGGCACAGTGCTTGCTGAATTT<br>CAGCCTCTTGTAGAAGAGCCTAAGAACTTGGTCAAAACCAACTGTGATCTTTAC<br>GAGAAGCTTGGAGAATATGGATTCCAAAATGCCATTCTAGTTCGCTACACCCAG<br>AAAGCACCTCAGGTGTCAACCCCAACTCTCGTGGAGGCTGCAAGAAACCTAGGA<br>AGAGTGGGCACCAAGTGTTGTACACTTCCTGAAGATCAGAGACTGCCTTGTGTG<br>GAAGACTATCTGTGTGCAATCCTGAACCGTGTGTGTGTGCTGCATGAGAAGACC<br>CCAGTGAGTGAGCATGTTACCAAGTGCTGTAGTGGATCCCTGGTGGAAAGGCGG<br>CCATGCTTCTCTGCTCTGACAGTTGATGAAACATATGTCCCCAAAGAGTTTAAA<br>GCTGAGACCTTCACCTTCCACTCTGATATCTGCACACTTCCAGAGAAGGAGAAG<br>CAGATTAAGAAACAAACGGCTCTTGCTGAGCTGGTGAAGCACAAGCCCAAGGCT<br>ACAGCGGAGCAACTGAAGACTGTCATGGATGACTTTGCACAGTTCCTGGATACA<br>TGTTGCAAGGCTGCTGACAAGGACACCTGCTTCTCGACTGAGGGTCCAAACCTT<br>GTCACTAGATGCAAAGACGCCTTAGCC<u>GGTGGAGGAGGCTCTGGTGGAGGCGGT</u><br><u>AGCGGAGGCGGAGGGTCG</u>GCTAGCGCTATCCAGATGACCCGGTCCCCGAGCTCC<br>CTGTCCGCCTCTGTGGGCGATAGGGTCACCATCACCTGCCGTGCCAGTCAGTAC<br>CACGACGGTTCTGCAGCCTGGTATCAACAGAAACCAGGAAAA<i>TGC</i>CCGAAGCTT<br>CTGATTTACGGTGCATCCTACCTCTACTCTGGAGTCCCTTCCCGCTTCTCTGGT<br>AGCCGTTCCGGGACGGATTTCACTCTGACCATCAGCAGTCTGCAGCCGGAAGAC<br>TTCGCAACTTATTACTGTCAGCAATCTTCTTATTCTCTGATCACGTTCGGACAG<br>GGTACCAAGGTGGAGATCAAAGGTACTACTGCCGCTAGTGGTAGTAGTGGTGGC<br>AGTAGCAGTGGTGCCGAGGTTCAGCTGGTGGAGTCTGACGGTGGCCTGGTGCAG<br>CCAGGGGGCTCACTCCGTTTGTCCTGTGCAGCTTCTGGCTTCAACCTCTCTTAC<br>TACGGTATGCACTGGGTCGTCAGGCCCGGGTAAGGGCCTGGAATGGGTTGCA<br>TACATTGCTTCTTACCCTGGCTACACTTCTTATGCCGATAGCGTCAAGGGCCGT<br>TTCACTATAAGCGCAGACACATCCAAAAACACAGCCTACCTACAAATGAACAGC<br>TTAAGAGCTGAGGACACTGCCGTCTACTATTGTGCTCGCTCTGGTTACAGTTAC<br>TCTCCGTATTATTCTTGGTTCTCTGCTGGTATGAACTACTGGGGT<i>TGC</i>GGAGCC<br>CTGGTCACCGTCTCCTCGTGATAG |
| 154 | mouse SA-<br>(Gly$_4$Ser)$_3$-<br>scFv (V$_L$-<br>V$_H$) CK157-<br>ds1 | ATGGAAGCACACAAGAGTGAGATCGCCCATCGGTATAATGATTTGGGAGAACAA<br>CATTTCAAAGGCCTAGTCCTGATTGCCTTTTCCCAGTATCTCCAGAAATGCTCA<br>TACGATGAGCATGCCAAATTAGTGCAGGAAGTAACAGACTTTGCAAAGACGTGT<br>GTTGCCGATGAGTCTGCCGCCAACTGTGACAAATCCCTTCACACTCTTTTTGGA<br>GATAAGTTGTGTGCCATTCCAAACCTCCGTGAAAACTATGGTGAACTGGCTGAC |

TABLE 12-continued

Sequence Summary

| SEQ ID NO | Description | Sequence |
|---|---|---|
| | ($V_L100^{Q>C}$/ $V_H44^{E>C}$) | TGCTGTACAAAACAAGAGCCCGAAAGAAACGAATGTTTCCTGCAACACAAAGAT<br>GACAACCCCAGCCTACCACCATTTGAAAGGCCAGAGGCTGAGGCCATGTGCACC<br>TCCTTTAAGGAAAACCCAACCACCTTTATGGGACACTATTTGCATGAAGTTGCC<br>AGAAGACATCCTTATTTCTATGCCCCAGAACTTCTTTACTATGCTGAGCAGTAC<br>AATGAGATTCTGACCCAGTGTTGTGCAGAGGCTGACAAGGAAAGCTGCCTGACC<br>CCGAAGCTTGATGGTGTGAAGGAGAAAGCATTGGTCTCATCTGTCCGTCAGAGA<br>ATGAAGTGCTCCAGTATGCAGAAGTTTGGAGAGAGAGCTTTTAAAGCATGGGCA<br>GTAGCTCGTCTGAGCCAGACATTCCCCAATGCTGACTTTGCAGAAATCACCAAA<br>TTGGCAACAGACCTGACCAAAGTCAACAAGGAGTGCTGCCATGGTGACCTGCTG<br>GAATGCGCAGATGACAGGCGGAACTTGCCAAGTACATGTGTGAAAACCAGGCG<br>ACTATCTCCAGCAAACTGCAGACTTGCTGCGATAAACCACTGTTGAAGAAAGCC<br>CACTGTCTTAGTGAGGTGGAGCATGACACCATGCCTGCTGATCTGCCTGCCATT<br>GCTGCTGATTTTGTTGAGGACCAGGAAGTGTGCAAGAACTATGCTGAGGCCAAG<br>GATGTCTTCCTGGGCACGTTCTTGTATGAATATTCAAGAAGACACCCTGATTAC<br>TCTGTATCCCTGTTGCTGAGACTTGCTAAGAAATATGAAGCCACTCTGGAAAAG<br>TGCTGCGCTGAAGCCAATCCTCCCGCATGCTACGGCACAGTGCTTGCTGAATTT<br>CAGCCTCTTGTAGAAGAGCCTAAGAACTTGGTCAAAACCAACTGTGATCTTTAC<br>GAGAAGCTTGGAGAATATGGATTCCAAAATGCCATTCTAGTTCGCTACACCCAG<br>AAAGCACCTCAGGTGTCAACCCCAACTCTCGTGGAGGCTGCAAGAAACCTAGGA<br>AGAGTGGGCACCAAGTGTTGTACACTTCCTGAAGATCAGAGACTGCCTTGTGTG<br>GAAGACTATCTGTGTGCAATCCTGAACCGTGTGTGTGCTGCATGAGAAGACC<br>CCAGTGAGTGAGCATGTTACCAAGTGCTGTAGTGGATCCCTGGTGGAAAGGCGG<br>CCATGCTTCTCTGCTCTGACAGTTGATGAAACATATGTCCCCAAAGAGTTTAAA<br>GCTGAGACCTTCACCTTCCACTCTGATATCTGCACACTTCCAGAGAAGGAGAAG<br>CAGATTAAGAAACAAACGGCTCTTGCTGAGCTGGTGAAGCACAAGCCCAAGGCT<br>ACAGCGGAGCAACTGAAGACTGTCATGGATGACTTTGCACAGTTCCTGGATACA<br>TGTTGCAAGGCTGCTGACAAGGACACCTGCTTCTCGACTGAGGGTCCAAACCTT<br>GTCACTAGATGCAAAGACGCCTTAGCC<u>*GGTGGAGGAGGCTCTGGTGGAGGCGGT*</u><br><u>*AGCGGAGGCGGAGGGTCG*</u>GATATCCAGATGACCCAGTCCCCGAGCTCCCTGTCC<br>GCCTCTGTGGGCGATAGGGTCACCATCACCTGCCGTGCCAGTCAGTCTTACGGT<br>GGTGTAGCCTGGTATCAACAGAAACCAGGAAAAGCCCCGAAGCTTCTGATTTAC<br>TCTGCATCCTACCTCTACTCTGGAGTCCCTTCTCGCTTCTCTGGTAGCCGTTCC<br>GGGACAGATTTCACTCTGACCATCAGCAGTCTGCAGCCGGAAGACTTCGCAACT<br>TATTACTGTCAGCAACCATCTCATCTGATCACGTTCGGA*TGC*GGTACCGAGGTG<br>GAGATCAAAGGTACTACTGCCGCTAGTGGTAGTAGTGGTGGCAGTAGCAGTGGT<br>GCCGAGGTTCAGCTGGTGGAGTCTGGCGGTGGCCTGGTGCAGCCAGGGGGCTCA<br>CTCCGTTTGTCCTGTGCAGCTTCTGGCTCCAACCCCTACTACTACGGTGGTACG<br>CACTGGGTGCGTCAGGCCCCGGGTGAG*TGC*CTGGAATGGGTTGCATCTATTGGT<br>TCTTACCCTGGCTACACTGACTATGCCGATAGCGTCAAGGGCCGTTTCACTATA<br>AGCGCAGACACATCCAAAAACACAGCCTACCTACAAATGAACAGCTTAAGAGCT<br>GAGGACACTGCCGTCTATTATTGTGCTCGCCATTACTACTGGTACGATGCTACT<br>GACTACTGGGGTCAAGGAACCCTGGTCACCGTCTCCTCGTGATAG |
| 155 | mouse SA-($Gly_4Ser$)$_3$-scFv ($V_L$-$V_H$) CK157-ds2 ($V_L43^{A>C}$/ $V_H105^{Q>C}$) | ATGGAAGCACACAAGAGTGAGATCGCCCATCGGTATAATGATTTGGGAGAACAA<br>CATTTCAAAGGCCTAGTCCTGATTGCCTTTTCCCAGTATCTCCAGAAATGCTCA<br>TACGATGAGCATGCCAAATTAGTGCAGGAAGTAACAGACTTTGCAAAGACGTGT<br>GTTGCCGATGAGTCTGCCGCCAACTGTGACAAATCCCTTCACACTCTTTTTGGA<br>GATAAGTTGTGTGCCATTCCAAACCTCCGTGAAAACTATGGTGAACTGGCTGAC<br>TGCTGTACAAAACAAGAGCCCGAAAGAAACGAATGTTTCCTGCAACACAAAGAT<br>GACAACCCCAGCCTACCACCATTTGAAAGGCCAGAGGCTGAGGCCATGTGCACC<br>TCCTTTAAGGAAAACCCAACCACCTTTATGGGACACTATTTGCATGAAGTTGCC<br>AGAAGACATCCTTATTTCTATGCCCCAGAACTTCTTTACTATGCTGAGCAGTAC<br>AATGAGATTCTGACCCAGTGTTGTGCAGAGGCTGACAAGGAAAGCTGCCTGACC<br>CCGAAGCTTGATGGTGTGAAGGAGAAAGCATTGGTCTCATCTGTCCGTCAGAGA<br>ATGAAGTGCTCCAGTATGCAGAAGTTTGGAGAGAGAGCTTTTAAAGCATGGGCA<br>GTAGCTCGTCTGAGCCAGACATTCCCCAATGCTGACTTTGCAGAAATCACCAAA<br>TTGGCAACAGACCTGACCAAAGTCAACAAGGAGTGCTGCCATGGTGACCTGCTG<br>GAATGCGCAGATGACAGGCGGAACTTGCCAAGTACATGTGTGAAAACCAGGCG<br>ACTATCTCCAGCAAACTGCAGACTTGCTGCGATAAACCACTGTTGAAGAAAGCC<br>CACTGTCTTAGTGAGGTGGAGCATGACACCATGCCTGCTGATCTGCCTGCCATT<br>GCTGCTGATTTTGTTGAGGACCAGGAAGTGTGCAAGAACTATGCTGAGGCCAAG<br>GATGTCTTCCTGGGCACGTTCTTGTATGAATATTCAAGAAGACACCCTGATTAC<br>TCTGTATCCCTGTTGCTGAGACTTGCTAAGAAATATGAAGCCACTCTGGAAAAG<br>TGCTGCGCTGAAGCCAATCCTCCCGCATGCTACGGCACAGTGCTTGCTGAATTT<br>CAGCCTCTTGTAGAAGAGCCTAAGAACTTGGTCAAAACCAACTGTGATCTTTAC<br>GAGAAGCTTGGAGAATATGGATTCCAAAATGCCATTCTAGTTCGCTACACCCAG<br>AAAGCACCTCAGGTGTCAACCCCAACTCTCGTGGAGGCTGCAAGAAACCTAGGA<br>AGAGTGGGCACCAAGTGTTGTACACTTCCTGAAGATCAGAGACTGCCTTGTGTG<br>GAAGACTATCTGTGTGCAATCCTGAACCGTGTGTGTGCTGCATGAGAAGACC<br>CCAGTGAGTGAGCATGTTACCAAGTGCTGTAGTGGATCCCTGGTGGAAAGGCGG<br>CCATGCTTCTCTGCTCTGACAGTTGATGAAACATATGTCCCCAAAGAGTTTAAA<br>GCTGAGACCTTCACCTTCCACTCTGATATCTGCACACTTCCAGAGAAGGAGAAG<br>CAGATTAAGAAACAAACGGCTCTTGCTGAGCTGGTGAAGCACAAGCCCAAGGCT<br>ACAGCGGAGCAACTGAAGACTGTCATGGATGACTTTGCACAGTTCCTGGATACA<br>TGTTGCAAGGCTGCTGACAAGGACACCTGCTTCTCGACTGAGGGTCCAAACCTT |

TABLE 12-continued

Sequence Summary

| SEQ ID NO | Description | Sequence |
|---|---|---|
| | | GTCACTAGATGCAAAGACGCCTTAGCC*GGTGGAGGAGGCTCTGGTGGAGGCGGT*<br>*AGCGGAGGCGGAGGGTCG*GATATCCAGATGACCCAGTCCCCGAGCTCCCTGTCC<br>GCCTCTGTGGGCGATAGGGTCACCATCACCTGCCGTGCCAGTCAGTCTTACGGT<br>GGTGTAGCCTGGTATCAACAGAAACCAGGAAAA*TG*CCCGAAGCTTCTGATTTAC<br>TCTGCATCCTACCTCTACTCTGGAGTCCCTTCTCGCTTCTCTGGTAGCCGTTCC<br>GGGACGGATTTCACTCTGACCATCAGCAGTCTGCAGCCGGAAGACTTCGCAACT<br>TATTACTGTCAGCAACCATCTCATCTGATCACGTTCGGACAGGGTACCGAGGTG<br>GAGATCAAAGGTACTACTGCCGCTAGTGGTAGTAGTGGTGGCAGTAGCAGTGGT<br>GCCGAGGTTCAGCTGGTGGAGTCTGGCGGTGGCCTGGTGCAGCCAGGGGGCTCA<br>CTCCGTTTGTCCTGTGCAGCTTCTGGCTCCAACCCCTACTACTACGGTGGTACG<br>CACTGGGTGCGTCAGGCCCCGGGTGAGGAGCTGGAATGGGTTGCATCTATTGGT<br>TCTTACCCTGGCTACACTGACTATGCCGATAGCGTCAAGGGCCGTTTCACTATA<br>AGCGCAGACACATCCAAAAACACAGCCTACCTACAAATGAACAGCTTAAGAGCT<br>GAGGACACTGCCGTCTATTATTGTGCTCGCCATTACTACTGGTACGATGCTACT<br>GACTACTGGGGT*TGC*GGAACCCTGGTCACCGTCTCCTCGTGATAG |
| 156 | mouse SA-<br>(Gly₄Ser)-V_L<br>CK157 | ATGGAAGCACACAAGAGTGAGATCGCCCATCGGTATAATGATTTGGGAGAACAA<br>CATTTCAAAGGCCTAGTCCTGATTGCCTTTTCCCAGTATCTCCAGAAATGCTCA<br>TACGATGAGCATGCCAAATTAGTGCAGGAAGTAACAGACTTTGCAAAGACGTGT<br>GTTGCCGATGAGTCTGCCGCCAACTGTGACAAATCCCTTCACACTCTTTTTGGA<br>GATAAGTTGTGTGCCATTCCAAACCTCCGTGAAAACTATGGTGAACTGGCTGAC<br>TGCTGTACAAAACAAGAGCCCGAAAGAAACGAATGTTTCCTGCAACACAAAGAT<br>GACAACCCCAGCCTACCACCATTTGAAAGGCCAGAGGCTGAGGCCATGTGCACC<br>TCCTTTAAGGAAAACCCAACCACCTTTATGGGACACTATTTGCATGAAGTTGCC<br>AGAAGACATCCTTATTTCTATGCCCCAGAACTTCTTTACTATGCTGAGCAGTAC<br>AATGAGATTCTGACCCAGTGTTGTGCAGAGGCTGACAAGGAAAGCTGCCTGACC<br>CCGAAGCTTGATGGTGTGAAGGAGAAAGCATTGGTCTCATCTGTCCGTCAGAGA<br>ATGAAGTGCTCCAGTATGCAGAAGTTTGGAGAGAGAGCTTTTAAAGCATGGGCA<br>GTAGCTCGTCTGAGCCAGACATTCCCCAATGCTGACTTTGCAGAAATCACCAAA<br>TTGGCAACAGACCTGACCAAAGTCAACAAGGAGTGCTGCCATGGTGACCTGCTG<br>GAATGCGCAGATGACAGGGCGGAACTTGCCAAGTACATGTGTGAAAACCAGGCG<br>ACTATCTCCAGCAAACTGCAGACTTGCTGCGATAAACCACTGTTGAAGAAAGCC<br>CACTGTCTTAGTGAGGTGGAGCATGACACCATGCCTGCTGATCTGCCTGCCATT<br>GCTGCTGATTTTGTTGAGGACCAGGAAGTGTGCAAGAACTATGCTGAGGCCAAG<br>GATGTCTTCCTGGGCACGTTCTTGTATGAATATTCAAGAAGACACCCTGATTAC<br>TCTGTATCCCTGTTGCTGAGACTTGCTAAGAAATATGAAGCCACTCTGGAAAAG<br>TGCTGCGCTGAAGCCAATCCTCCCGCATGCTACGGCACAGTGCTTGCTGAATTT<br>CAGCCTCTTGTAGAAGAGCCTAAGAACTTGGTCAAAACCAACTGTGATCTTTAC<br>GAGAAGCTTGGAGAATATGGATTCCAAAATGCCATTCTAGTTCGCTACACCCAG<br>AAAGCACCTCAGGTGTCAACCCCAACTCTCGTGGAGGCTGCAAGAAACCTAGGA<br>AGAGTGGGCACCAAGTGTTGTACACTTCCTGAAGATCAGAGACTGCCTTGTGTG<br>GAAGACTATCTGTGTGCAATCCTGAACCGTGTGTGTGTGCTGCATGAGAAGACC<br>CCAGTGAGTGAGCATGTTACCAAGTGCTGTAGTGGATCCCTGGTGGAAAGGCGG<br>CCATGCTTCTCTGCTCTGACAGTTGATGAAACATATGTCCCCAAAGAGTTTAAA<br>GCTGAGACCTTCACCTTCCACTCTGATATCTGCACACTTCCAGAGAAGGAGAAG<br>CAGATTAAGAAACAAACGGCTCTTGCTGAGCTGGTGAAGCACAAGCCCAAGGCT<br>ACAGCGGAGCAACTGAAGACTGTCATGGATGACTTTGCACAGTTCCTGGATACA<br>TGTTGCAAGGCTGCTGACAAGGACACCTGCTTCTCGACTGAGGGTCCAAACCTT<br>GTCACTAGATGCAAAGACGCCTTAGCC*GGTGGAGGAGGCTCTGGTGGAGGCGGT*<br>*AGCGGAGGCGGAGGGTCG*GATATCCAGATGACCCAGTCCCCGAGCTCCCTGTCC<br>GCCTCTGTGGGCGATAGGGTCACCATCACCTGCCGTGCCAGTCAGTCTTACGGT<br>GGTGTAGCCTGGTATCAACAGAAACCAGGAAAAGCCCCGAAGCTTCTGATTTAC<br>TCTGCATCCTACCTCTACTCTGGAGTCCCTTCTCGCTTCTCTGGTAGCCGTTCC<br>GGGACGGATTTCACTCTGACCATCAGCAGTCTGCAGCCGGAAGACTTCGCAACT<br>TATTACTGTCAGCAACCATCTCATCTGATCACGTTCGGACAGGGTACCGAGGTG<br>GAGATCAAATGATAG |
| 157 | mouse SA-<br>(Gly₄Ser)-<br>V_H CK157 | ATGGAAGCACACAAGAGTGAGATCGCCCATCGGTATAATGATTTGGGAGAACAA<br>CATTTCAAAGGCCTAGTCCTGATTGCCTTTTCCCAGTATCTCCAGAAATGCTCA<br>TACGATGAGCATGCCAAATTAGTGCAGGAAGTAACAGACTTTGCAAAGACGTGT<br>GTTGCCGATGAGTCTGCCGCCAACTGTGACAAATCCCTTCACACTCTTTTTGGA<br>GATAAGTTGTGTGCCATTCCAAACCTCCGTGAAAACTATGGTGAACTGGCTGAC<br>TGCTGTACAAAACAAGAGCCCGAAAGAAACGAATGTTTCCTGCAACACAAAGAT<br>GACAACCCCAGCCTACCACCATTTGAAAGGCCAGAGGCTGAGGCCATGTGCACC<br>TCCTTTAAGGAAAACCCAACCACCTTTATGGGACACTATTTGCATGAAGTTGCC<br>AGAAGACATCCTTATTTCTATGCCCCAGAACTTCTTTACTATGCTGAGCAGTAC<br>AATGAGATTCTGACCCAGTGTTGTGCAGAGGCTGACAAGGAAAGCTGCCTGACC<br>CCGAAGCTTGATGGTGTGAAGGAGAAAGCATTGGTCTCATCTGTCCGTCAGAGA<br>ATGAAGTGCTCCAGTATGCAGAAGTTTGGAGAGAGAGCTTTTAAAGCATGGGCA<br>GTAGCTCGTCTGAGCCAGACATTCCCCAATGCTGACTTTGCAGAAATCACCAAA<br>TTGGCAACAGACCTGACCAAAGTCAACAAGGAGTGCTGCCATGGTGACCTGCTG<br>GAATGCGCAGATGACAGGGCGGAACTTGCCAAGTACATGTGTGAAAACCAGGCG<br>ACTATCTCCAGCAAACTGCAGACTTGCTGCGATAAACCACTGTTGAAGAAAGCC<br>CACTGTCTTAGTGAGGTGGAGCATGACACCATGCCTGCTGATCTGCCTGCCATT<br>GCTGCTGATTTTGTTGAGGACCAGGAAGTGTGCAAGAACTATGCTGAGGCCAAG |

TABLE 12-continued

Sequence Summary

| SEQ ID NO | Description | Sequence |
|---|---|---|
| | | GATGTCTTCCTGGGCACGTTCTTGTATGAATATTCAAGAAGACACCCTGATTAC<br>TCTGTATCCCTGTTGCTGAGACTTGCTAAGAAATATGAAGCCACTCTGGAAAAG<br>TGCTGCGCTGAAGCCAATCCTCCCGCATGCTACGGCACAGTGCTTGCTGAATTT<br>CAGCCTCTTGTAGAAGAGCCTAAGAACTTGGTCAAAACCAACTGTGATCTTTAC<br>GAGAAGCTTGGAGAATATGGATTCCAAAATGCCATTCTAGTTCGCTACACCCAG<br>AAAGCACCTCAGGTGTCAACCCCAACTCTCGTGGAGGCTGCAAGAAACCTAGGA<br>AGAGTGGGCACCAAGTGTTGTACACTTCCTGAAGATCAGAGACTGCCTTGTGTG<br>GAAGACTATCTGTGTGCAATCCTGAACCGTGTGTGTGCTGCATGAGAAGACC<br>CCAGTGAGTGAGCATGTTACCAAGTGCTGTAGTGGATCCCTGGTGGAAAGGCGG<br>CCATGCTTCTCTGCTCTGACAGTTGATGAAACATATGTCCCCAAAGAGTTTAAA<br>GCTGAGACCTTCACCTTCCACTCTGATATCTGCACACTTCCAGAGAAGGAGAAG<br>CAGATTAAGAAACAAACGGCTCTTGCTGAGCTGGTGAAGCACAAGCCCAAGGCT<br>ACAGCGGAGCAACTGAAGACTGTCATGGATGACTTTGCACAGTTCCTGGATACA<br>TGTTGCAAGGCTGCTGACAAGGACACCTGCTTCTCGACTGAGGGTCCAAACCTT<br>GTCACTAGATGCAAAGACGCCTTAGCC*GGTGGAGGAGGCTCTGGTGGAGGCGGT*<br>*AGCGGAGGCGGAGGGTCG*GCCGAGGTTCAGCTGGTGGAGTCTGGCGGTGGCCTG<br>GTGCAGCCAGGGGGCTCACTCCGTTTGTCCTGTGCAGCTTCTGGCTCCAACCCC<br>TACTACTACGGTGGTACGCACTGGGTGCGTCAGGCCCCGGGTGAGGAGCTGGAA<br>TGGGTTGCATCTATTGGTTCTTACCCTGGCTACACTGACTATGCCGATAGCGTC<br>AAGGGCCGTTTCACTATAAGCGCAGACACATCCAAAAACACAGCCTACCTACAA<br>ATGAACAGCTTAAGAGCTGAGGACACTGCCGTCTATTATTGTGCTCGCCATTAC<br>TACTGGTACGATGCTACTGACTACTGGGGTCAAGGAACCCTGGTCACCGTCTCC<br>TCGTGATAG |
| 158 | mouse SA-<br>(Gly$_4$Ser)$_3$-<br>scFv (V$_L$-<br>V$_H$) CK129-<br>ds1<br>(V$_L$100$^{Q>C}$/<br>V$_H$44$^{G>C}$) | ATGGAAGCACACAAGAGTGAGATCGCCCATCGGTATAATGATTTGGGAGAACAA<br>CATTTCAAAGGCCTAGTCCTGATTGCCTTTTCCCAGTATCTCCAGAAATGCTCA<br>TACGATGAGCATGCCAAATTAGTGCAGGAAGTAACAGACTTTGCAAAGACGTGT<br>GTTGCCGATGAGTCTGCCGCCAACTGTGACAAATCCCTTCACACTCTTTTTGGA<br>GATAAGTTGTGTGCCATTCCAAACCTCCGTGAAAACTATGGTGAACTGGCTGAC<br>TGCTGTACAAAACAAGAGCCCGAAAGAAACGAATGTTTCCTGCAACACAAAGAT<br>GACAACCCCAGCCTACCACCATTTGAAAGGCCAGAGGCTGAGGCCATGTGCACC<br>TCCTTTAAGGAAAACCCAACCACCTTTATGGGACACTATTTGCATGAAGTTGCC<br>AGAAGACATCCTTATTTCTATGCCCCAGAACTTCTTTACTATGCTGAGCAGTAC<br>AATGAGATTCTGACCCAGTGTTGTGCAGAGGCTGACAAGGAAAGCTGCCTGACC<br>CCGAAGCTTGATGGTGTGAAGGAGAAAGCATTGGTCTCATCTGTCCGTCAGAGA<br>ATGAAGTGCTCCAGTATGCAGAAGTTTGGAGAGAGAGCTTTTAAAGCATGGGCA<br>GTAGCTCGTCTGAGCCAGACATTCCCCAATGCTGACTTTGCAGAAATCACCAAA<br>TTGGCAACAGACCTGACCAAAGTCAACAAGGAGTGCTGCCATGGTGACCTGCTG<br>GAATGCGCAGATGACAGGGCGGAACTTGCCAAGTACATGTGTGAAAACCAGGCG<br>ACTATCTCCAGCAAACTGCAGACTTGCTGCGATAAACCACTGTTGAAGAAAGCC<br>CACTGTCTTAGTGAGGTGGAGCATGACACCATGCCTGCTGATCTGCCTGCCATT<br>GCTGCTGATTTTGTTGAGGACCAGGAAGTGTGCAAGAACTATGCTGAGGCCAAG<br>GATGTCTTCCTGGGCACGTTCTTGTATGAATATTCAAGAAGACACCCTGATTAC<br>TCTGTATCCCTGTTGCTGAGACTTGCTAAGAAATATGAAGCCACTCTGGAAAAG<br>TGCTGCGCTGAAGCCAATCCTCCCGCATGCTACGGCACAGTGCTTGCTGAATTT<br>CAGCCTCTTGTAGAAGAGCCTAAGAACTTGGTCAAAACCAACTGTGATCTTTAC<br>GAGAAGCTTGGAGAATATGGATTCCAAAATGCCATTCTAGTTCGCTACACCCAG<br>AAAGCACCTCAGGTGTCAACCCCAACTCTCGTGGAGGCTGCAAGAAACCTAGGA<br>AGAGTGGGCACCAAGTGTTGTACACTTCCTGAAGATCAGAGACTGCCTTGTGTG<br>GAAGACTATCTGTCTGCAATCCTGAACCGTGTGTGTCTGCTGCATGAGAAGACC<br>CCAGTGAGTGAGCATGTTACCAAGTGCTGTAGTGGATCCCTGGTGGAAAGGCGG<br>CCATGCTTCTCTGCTCTGACAGTTGATGAAACATATGTCCCCAAAGAGTTTAAA<br>GCTGAGACCTTCACCTTCCACTCTGATATCTGCACACTTCCAGAGAAGGAGAAG<br>CAGATTAAGAAACAAACGGCTCTTGCTGAGCTGGTGAAGCACAAGCCCAAGGCT<br>ACAGCGGAGCAACTGAAGACTGTCATGGATGACTTTGCACAGTTCCTGGATACA<br>TGTTGCAAGGCTGCTGACAAGGACACCTGCTTCTCGACTGAGGGTCCAAACCTT<br>GTCACTAGATGCAAAGACGCCTTAGCC*GGTGGAGGAGGCTCTGGTGGAGGCGGT*<br>*AGCGGAGGCGGAGGGTCG*GATATCCAGATGACCCAGTCCCCGAGCCCCCTGTCC<br>GCCTCTGTGGGCGATAGGGTCACCATCACCTGCCGTGCCAGTCAGTACGGTGGT<br>TACGTAGCCTGGTATCAACAGAAACCAGGAAAAGCTCCGAAGCTTCTGATTTAC<br>GGTGCATCCCTTCTCTACTCTGGAGTCCCTTCTCGCTTCTCTGGTGGCCGTTCC<br>GGGACGGATTTCACTCTGACCATCAGCAGTCTGCAGCCGGAAGACTTCGCAACT<br>TATTACTGTCAGCGAGGTCATGCTCTGATCACGTTCGGA*TGC*GGTACCAAGGTG<br>GAGATCGAAGGTACTACTGCCGCTAGTGGTAGTAGTGGTGGCAGTAGCAGTGGT<br>GCCGAGGTTCAGCTGGTGGAGTCTGGCGGTGGCCTGGTGCAGCCAGGGGGCTCA<br>CTCCGTTTATCCTGTGCAGCTTCTGGCTTCAACATCTCTTCTTACGGTTCTATG<br>CACTGGGTGCGTCAGGCCCCGGGTAAG*T*GCCTGGAATGGGTTGCATCTATTTAC<br>CCTTACTCTAGCTCTACTTACTATGCCGATAGCGTCAAGGGCCGTTTCACTATA<br>AGCGCAGACACATCCAAAAACACAGCCTACCTACAAATGAACAGCTTAAGAGCT<br>GAGGACACTGCCGTCTATTATTGTGCTCGTGGTTACGGTCCGTGGTACGCTTAC<br>TCTTACTTCGCTTTGGACTACTGGGGTCAAGGAACCCTGGTCACCGTCTCCTCG<br>TGATAG |
| 159 | mouse SA-<br>(Gly$_4$Ser)$_3$- | ATGGAAGCACACAAGAGTGAGATCGCCCATCGGTATAATGATTTGGGAGAACAA<br>CATTTCAAAGGCCTAGTCCTGATTGCCTTTTCCCAGTATCTCCAGAAATGCTCA |

TABLE 12-continued

Sequence Summary

| SEQ ID NO | Description | Sequence |
|---|---|---|
|  | scFv (V$_L$-V$_H$) CK129-ds2 (V$_L$43$^{A>C}$/V$_H$105$^{Q>C}$) | TACGATGAGCATGCCAAATTAGTGCAGGAAGTAACAGACTTTGCAAAGACGTGT<br>GTTGCCGATGAGTCTGCCGCCAACTGTGACAAATCCCTTCACACTCTTTTTGGA<br>GATAAGTTGTGTGCCATTCCAAACCTCCGTGAAAACTATGGTGAACTGGCTGAC<br>TGCTGTACAAAACAAGAGCCCGAAAGAAACGAATGTTTCCTGCAACACAAAGAT<br>GACAACCCCAGCCTACCACCATTTGAAAGGCCAGAGGCTGAGGCCATGTGCACC<br>TCCTTTAAGGAAAACCCAACCACCTTTATGGGACACTATTTGCATGAAGTTGCC<br>AGAAGACATCCTTATTTCTATGCCCCAGAACTTCTTTACTATGCTGAGCAGTAC<br>AATGAGATTCTGACCCAGTGTTGTGCAGAGGCTGACAAGGAAAGCTGCCTGACC<br>CCGAAGCTTGATGGTGTGAAGGAGAAAGCATTGGTCTCATCTGTCCGTCAGAGA<br>ATGAAGTGCTCCAGTATGCAGAAGTTTGGAGAGAGAGCTTTTAAAGCATGGGCA<br>GTAGCTCGTCTGAGCCAGACATTCCCCAATGCTGACTTTGCAGAAATCACCAAA<br>TTGGCAACAGACCTGACCAAAGTCAACAAGGAGTGCTGCCATGGTGACCTGCTG<br>GAATGCGCAGATGACAGGGCGGAACTTGCCAAGTACATGTGTGAAAACCAGGCG<br>ACTATCTCCAGCAAACTGCAGACTTGCTGCGATAAACCACTGTTGAAGAAAGCC<br>CACTGTCTTAGTGAGGTGGAGCATGACACCATGCCTGCTGATCTGCCTGCCATT<br>GCTGCTGATTTTGTTGAGGACCAGGAAGTGTGCAAGAACTATGCTGAGGCCAAG<br>GATGTCTTCCTGGGCACGTTCTTGTATGAATATTCAAGAAGACACCCTGATTAC<br>TCTGTATCCCTGTTGCTGAGACTTGCTAAGAAATATGAAGCCACTCTGGAAAAG<br>TGCTGCGCTGAAGCCAATCCTCCCGCATGCTACGGCACAGTGCTTGCTGAATTT<br>CAGCCTCTTGTAGAAGAGCCTAAGAACTTGGTCAAAACCAACTGTGATCTTTAC<br>GAGAAGCTTGAGAATATGGATTCCAAAATGCCATTCTAGTTCGCTACACCCAG<br>AAAGCACCTCAGGTGTCAACCCCAACTCTCGTGGAGGCTGCAAGAAACCTAGGA<br>AGAGTGGGCACCAAGTGTTGTACACTTCCTGAAGATCAGAGACTGCCTTGTGTG<br>GAAGACTATCTGTCTGCAATCCTGAACCGTGTGTGTCTGCTGCATGAGAAGACC<br>CCAGTGAGTGAGCATGTTACCAAGTGCTGTAGTGGATCCCTGGTGGAAAGGCGG<br>CCATGCTTCTCTGCTCTGACAGTTGATGAAACATATGTCCCCAAAGAGTTTAAA<br>GCTGAGACCTTCACCTTCCACTCTGATATCTGCACACTTCCAGAGAAGGAGAAG<br>CAGATTAAGAAACAAACGGCTCTTGCTGAGCTGGTGAAGCACAAGCCCAAGGCT<br>ACAGCGGAGCAACTGAAGACTGTCATGGATGACTTTGCACAGTTCCTGGATACA<br>TGTTGCAAGGCTGCTGACAAGGACACCTGCTTCTCGACTGAGGGTCCAAACCTT<br>GTCACTAGATGCAAAGACGCCTTAGC*GGTGGAGGAGGCTCTGGTGGAGGCGGT<br>AGCGGAGGCGGAGGGTCG*GATATCCAGATGACCCAGTCCCCGAGCCCCCTGTCC<br>GCCTCTGTGGGCGATAGGGTCACCATCACCTGCCGTGCCAGTCAGTACGGTGGT<br>TACGTAGCCTGGTATCAACAGAAACCAGGAAAA*TGC*CCGAAGCTTCTGATTTAC<br>GGTGCATCCCTTCTCTACTCTGGAGTCCCTTCTCGCTTCTCTGGTGGCCGTTCC<br>GGGACGGATTTCACTCTGACCATCAGCAGTCTGCAGCCGGAAGACTTCGCAACT<br>TATTACTGTCAGCGAGGTCATGCTCTGATCACGTTCGGACAGGGTACCAAGGTG<br>GAGATCGAAGGTACTACTGCCGCTAGTGGTAGTAGTGGTGGCAGTAGCAGTGGT<br>GCCGAGGTTCAGCTGGTGGAGTCTGGCGGTGGCCTGGTGCAGCCAGGGGGCTCA<br>CTCCGTTTATCCTGTGCAGCTTCTGGCTTCAACATCTCTTCTTACGGTTCTATG<br>CACTGGGTGCGTCAGGCCCCGGGTAAGGGCCTGGAATGGTTTGCATCTATTTAC<br>CCTTACTCTAGCTCTACTTACTATGCCGATAGCGTCAAGGGCCGTTTCACTATA<br>AGCGCAGACACATCCAAAAACACAGCCTACCTACAAATGAACAGCTTAAGAGCT<br>GAGGACACTGCCGTCTATTATTGTGCTCGTGGTTACGGTCCGTGGTACGCTTAC<br>TCTTACTTCGCTTTGGACTACTGGGGT*TGC*GGAACCCTGGTCACCGTCTCCTCG<br>TGATAG |
| 160 | mouse SA-(Gly$_4$Ser)$_3$-scFv (V$_L$-V$_H$) CK138 | EAHKSEIAHRYNDLGEQHFKGLVLIAFSQYLQKCSYDEHAKLVQEVTDFAKTCV<br>ADESAANCDKSLHTLFGDKLCAIPNLRENYGELADCCTKQEPERNECFLQHKDD<br>NPSLPPFERPEAEAMCTSFKENPTTFMGHYLHEVARRHPYFYAPELLYYAEQYN<br>EILTQCCAEADKESCLTPKLDGVKEKALVSSVRQRMKCSSMQKFGERAFKAWAV<br>ARLSQTFPNADFAEITKLATDLTKVNKECCHGDLLECADDRAELAKYMCENQAT<br>ISSKLQTCCDKPLLKKAHCLSEVEHDTMPADLPAIAADFVEDQEVCKNYAEAKD<br>VFLGTFLYEYSRRHPDYSVSLLLRLAKKYEATLEKCCAEANPPACYGTVLAEFQ<br>PLVEEPKNLVKTNCDLYEKLGEYGFQNAILVRYTQKAPQVSTPTLVEAARNLGR<br>VGTKCCTLPEDQRLPCVEDYLSAILNRVCLLHEKTPVSEHVTKCCSGSLVERRP<br>CFSALTVDETYVPKEFKAETFTFHSDICTLPEKEKQIKKQTALAELVKHKPKAT<br>AEQLKTVMDDFAQFLDTCCKAADKDTCFSTEGPNLVTRCKDALA*GGGGSGGGGS<br>GGGGS*ASAIQMTRSPSSLSASVGDRVTITCRASQYHDGSAAWYQQKPGKAPKLL<br>IYGASYLYSGVPSRFSGSRSGTDFTLTISSLQPEDFATYYCQQSSYSLITFGQG<br>TKVEIKGTTAASGSSGGSSSGAEVQLVESDGGLVQPGGSLRLSCAASGFNLSYY<br>GMHWVRQAPGKGLEWVAYIASYPGYTSYADSVKGRFTISADTSKNTAYLQMNSL<br>RAEDTAVYYCARSGYSYSPYYSWFSAGMNYWGQGALVTVSS-- |
| 161 | mouse SA-(Gly$_4$Ser)$_3$-scFv (V$_L$-V$_H$) CK157 | EAHKSEIAHRYNDLGEQHFKGLVLIAFSQYLQKCSYDEHAKLVQEVTDFAKTCV<br>ADESAANCDKSLHTLFGDKLCAIPNLRENYGELADCCTKQEPERNECFLQHKDD<br>NPSLPPFERPEAEAMCTSFKENPTTFMGHYLHEVARRHPYFYAPELLYYAEQYN<br>EILTQCCAEADKESCLTPKLDGVKEKALVSSVRQRMKCSSMQKFGERAFKAWAV<br>ARLSQTFPNADFAEITKLATDLTKVNKECCHGDLLECADDRAELAKYMCENQAT<br>ISSKLQTCCDKPLLKKAHCLSEVEHDTMPADLPAIAADFVEDQEVCKNYAEAKD<br>VFLGTFLYEYSRRHPDYSVSLLLRLAKKYEATLEKCCAEANPPACYGTVLAEFQ<br>PLVEEPKNLVKTNCDLYEKLGEYGFQNAILVRYTQKAPQVSTPTLVEAARNLGR<br>VGTKCCTLPEDQRLPCVEDYLSAILNRVCLLHEKTPVSEHVTKCCSGSLVERRP<br>CFSALTVDETYVPKEFKAETFTFHSDICTLPEKEKQIKKQTALAELVKHKPKAT<br>AEQLKTVMDDFAQFLDTCCKAADKDTCFSTEGPNLVTRCKDALA*GGGGSGGGGS* |

TABLE 12-continued

Sequence Summary

| SEQ ID NO | Description | Sequence |
|---|---|---|
| | | GGGGSASDIQMTQSPSSLSASVGDRVTITCRASQSYGGVAWYQQKPGKAPKLLI YSASYLYSGVPSRFSGSRSGTDFTLTISSLQPEDFATYYCQQPSHLITFGQGTE VEIKGTTAASGSSGGSSSGAEVQLVESGGGLVQPGGSLRLSCAASGSNPYYYGG THWVRQAPGEELEWVASIGSYPGYTDYADSVKGRFTISADTSKNTAYLQMNSLR AEDTAVYYCARHYYWYDATDYWGQGTLVTVSS-- |
| 162 | mouse SA-(Gly4Ser)3-scFv (V$_L$-V$_H$) CK129 | EAHKSEIAHRYNDLGEQHFKGLVLIAFSQYLQKCSYDEHAKLVQEVTDFAKTCV ADESAANCDKSLHTLFGDKLCAIPNLRENYGELADCCTKQEPERNECFLQHKDD NPSLPPFERPEAEAMCTSFKENPTTFMGHYLHEVARRHPYFYAPELLYYAEQYN EILTQCCAEADKESCLTPKLDGVKEKALVSSVRQRMKCSSMQKFGERAFKAWAV ARLSQTFPNADFAEITKLATDLTKVNKECCHGDLLECADDRAELAKYMCENQAT ISSKLQTCCDKPLLKKAHCLSEVEHDTMPADLPAIAADFVEDQEVCKNYAEAKD VFLGTFLYEYSRRHPDYSVSLLLRLAKKYEATLEKCCAEANPPACYGTVLAEFQ PLVEEPKNLVKTNCDLYEKLGEYGFQNAILVRYTQKAPQVSTPTLVEAARNLGR VGTKCCTLPEDQRLPCVEDYLSAILNRVCLLHEKTPVSEHVTKCCSGSLVERRP CFSALTVDETYVPKEFKAETFTFHSDICTLPEKEKQIKKQTALAELVKHKPKAT AEQLKTVMDDFAQFLDTCCKAADKDTCFSTEGPNLVTRCKDALAGGGGSGGGGS GGGGSASDIQMTQSPSPLSASVGDRVTITCRASQYGGYVAWYQQKPGKAPKLLI YGASLLYSGVPSRFSGGRSGTDFTLTISSLQPEDFATYYCQRGHALITFGQGTK VEIEGTTAASGSSGGSSSGAEVQLVESGGGLVQPGGSLRLSCAASGFNISSYGS MHWVRQAPGKGLEWVASIYPYSSSTYYADSVKGRFTISADTSKNTAYLQMNSLR AEDTAVYYCARGYGPWYAYSYFALDYWGQGTLVTVSS-- |
| 163 | mouse SA-(Gly4Ser)3-scFv (V$_L$-V$_H$) CK138-ds1 (V$_L$100$^{Q>C}$/V$_H$44$^{G>C}$) | EAHKSEIAHRYNDLGEQHFKGLVLIAFSQYLQKCSYDEHAKLVQEVTDFAKTCV ADESAANCDKSLHTLFGDKLCAIPNLRENYGELADCCTKQEPERNECFLQHKDD NPSLPPFERPEAEAMCTSFKENPTTFMGHYLHEVARRHPYFYAPELLYYAEQYN EILTQCCAEADKESCLTPKLDGVKEKALVSSVRQRMKCSSMQKFGERAFKAWAV ARLSQTFPNADFAEITKLATDLTKVNKECCHGDLLECADDRAELAKYMCENQAT ISSKLQTCCDKPLLKKAHCLSEVEHDTMPADLPAIAADFVEDQEVCKNYAEAKD VFLGTFLYEYSRRHPDYSVSLLLRLAKKYEATLEKCCAEANPPACYGTVLAEFQ PLVEEPKNLVKTNCDLYEKLGEYGFQNAILVRYTQKAPQVSTPTLVEAARNLGR VGTKCCTLPEDQRLPCVEDYLSAILNRVCLLHEKTPVSEHVTKCCSGSLVERRP CFSALTVDETYVPKEFKAETFTFHSDICTLPEKEKQIKKQTALAELVKHKPKAT AEQLKTVMDDFAQFLDTCCKAADKDTCFSTEGPNLVTRCKDALAGGGGSGGGGS GGGGSASAIQMTRSPSSLSASVGDRVTITCRASQYHDGSAAWYQQKPGKAPKLL IYGASYLYSGVPSRFSGSRSGTDFTLTISSLQPEDFATYYCQQSSYSLITFGCG TKVEIKGTTAASGSGGSSSGAESVQLVESDGGLVQPGGSLRLSCAASGFNLSYY GMHWVRQAPGKCLEWVAYIASYPGYTSYADSVKGRFTISADTSKNTAYLQMNSL RAEDTAVYYCARSGYSYSPYYSWFSAGMNYWGQGALVTVSS-- |
| 164 | mouse SA-(Gly4Ser)3-scFv (V$_L$-V$_H$) CK138-ds2 (V$_L$43$^{A>C}$/V$_H$105$^{Q>C}$) | EAHKSEIAHRYNDLGEQHFKGLVLIAFSQYLQKCSYDEHAKLVQEVTDFAKTCV ADESAANCDKSLHTLFGDKLCAIPNLRENYGELADCCTKQEPERNECFLQHKDD NPSLPPFERPEAEAMCTSFKENPTTFMGHYLHEVARRHPYFYAPELLYYAEQYN EILTQCCAEADKESCLTPKLDGVKEKALVSSVRQRMKCSSMQKFGERAFKAWAV ARLSQTFPNADFAEITKLATDLTKVNKECCHGDLLECADDRAELAKYMCENQAT ISSKLQTCCDKPLLKKAHCLSEVEHDTMPADLPAIAADFVEDQEVCKNYAEAKD VFLGTFLYEYSRRHPDYSVSLLLRLAKKYEATLEKCCAEANPPACYGTVLAEFQ PLVEEPKNLVKTNCDLYEKLGEYGFQNAILVRYTQKAPQVSTPTLVEAARNLGR VGTKCCTLPEDQRLPCVEDYLSAILNRVCLLHEKTPVSEHVTKCCSGSLVERRP CFSALTVDETYVPKEFKAETFTFHSDICTLPEKEKQIKKQTALAELVKHKPKAT AEQLKTVMDDFAQFLDTCCKAADKDTCFSTEGPNLVTRCKDALAGGGGSGGGGS GGGGSASAIQMTRSPSSLSASVGDRVTITCRASQYHDGSAAWYQQKPGKCPKLL IYGASYLYSGVPSRFSGSRSGTDFTLTISSLQPEDFATYYCQQSSYSLITFGQG TKVEIKGTTAASGSGGSSSGAEVQLVESDGGLVQPGGSLRLSCAASGFNLSYY GMHWVRQAPGKGLEWVAYIASYPGYTSYADSVKGRFTISADTSKNTAYLQMNSL RAEDTAVYYCARSGYSYSPYYSWFSAGMNYWGCGALVTVSS-- |
| 165 | mouse SA-(Gly4Ser)3-scFv (V$_L$-V$_H$) CK157-ds1 (V$_L$100$^{Q>C}$/V$_H$44$^{E>C}$) | EAHKSEIAHRYNDLGEQHFKGLVLIAFSQYLQKCSYDEHAKLVQEVTDFAKTCV ADESAANCDKSLHTLFGDKLCAIPNLRENYGELADCCTKQEPERNECFLQHKDD NPSLPPFERPEAEAMCTSFKENPTTFMGHYLHEVARRHPYFYAPELLYYAEQYN EILTQCCAEADKESCLTPKLDGVKEKALVSSVRQRMKCSSMQKFGERAFKAWAV ARLSQTFPNADFAEITKLATDLTKVNKECCHGDLLECADDRAELAKYMCENQAT ISSKLQTCCDKPLLKKAHCLSEVEHDTMPADLPAIAADFVEDQEVCKNYAEAKD VFLGTFLYEYSRRHPDYSVSLLLRLAKKYEATLEKCCAEANPPACYGTVLAEFQ PLVEEPKNLVKTNCDLYEKLGEYGFQNAILVRYTQKAPQVSTPTLVEAARNLGR VGTKCCTLPEDQRLPCVEDYLSAILNRVCLLHEKTPVSEHVTKCCSGSLVERRP CFSALTVDETYVPKEFKAETFTFHSDICTLPEKEKQIKKQTALAELVKHKPKAT AEQLKTVMDDFAQFLDTCCKAADKDTCFSTEGPNLVTRCKDALAGGGGSGGGGS GGGGSASDIQMTQSPSSLSASVGDRVTITCRASQSYGGVAWYQQKPGKAPKLLI YSASYLYSGVPSRFSGSRSGTDFTLTISSLQPEDFATYYCQQPSHLITFGCGTE VEIKGTTAASGSSGGSSSGAEVQLVESGGGLVQPGGSLRLSCAASGSNPYYYGG THWVRQAPGECLEWVASIGSYPGYTDYADSVKGRFTISADTSKNTAYLQMNSLR AEDTAVYYCARHYYWYDATDYWGQGTLVTVSS-- |

TABLE 12-continued

Sequence Summary

| SEQ ID NO | Description | Sequence |
|---|---|---|
| 166 | mouse SA-(Gly4Ser)3-scFv (V$_L$-V$_H$) CK157-ds2 (V$_L$43$^{A>C}$/V$_H$105$^{Q>C}$) | EAHKSEIAHRYNDLGEQHFKGLVLIAFSQYLQKCSYDEHAKLVQEVTDFAKTCV<br>ADESAANCDKSLHTLFGDKLCAIPNLRENYGELADCCTKQEPERNECFLQHKDD<br>NPSLPPFERPEAEAMCTSFKENPTTFMGHYLHEVARRHPYFYAPELLYYAEQYN<br>EILTQCCAEADKESCLTPKLDGVKEKALVSSVRQRMKCSSMQKFGERAFKAWAV<br>ARLSQTFPNADFAEITKLATDLTKVNKECCHGDLLECADDRAELAKYMCENQAT<br>ISSKLQTCCDKPLLKKAHCLSEVEHDTMPADLPAIAADFVEDQEVCKNYAEAKD<br>VFLGTFLYEYSRRHPDYSVSLLLRLAKKYEATLEKCCAEANPPACYGTVLAEFQ<br>PLVEEPKNLVKTNCDLYEKLGEYGFQNAILVRYTQKAPQVSTPTLVEAARNLGR<br>VGTKCCTLPEDQRLPCVEDYLSAILNRVCLLHEKTPVSEHVTKCCSGSLVERRP<br>CFSALTVDETYVPKEFKAETFTFHSDICTLPEKEKQIKKQTALAELVKHKPKAT<br>AEQLKTVMDDFAQFLDTCCKAADKDTCFSTEGPNLVTRCKDALA*GGGGSGGGGS*<br>*GGGGS*ASDIQMTQSPSSLSASVGDRVTITCRASQSYGGVAWYQQKPGK*C* PKLLI<br>YSASYLYSGVPSRFSGSRSGTDFTLTISSLQPEDFATYYCQQPSHLITFGQGTE<br>VEIKGTTAASGSSGGSSSGAEVQLVESGGGLVQPGGSLRLSCAASGSNPYYYGG<br>THWVRQAPGEELEWVASIGSYPGYTDYADSVKGRFTISADTSKNTAYLQMNSLR<br>AEDTAVYYCARHYYWYDATDYWC*GTLVTVSS-- |
| 167 | mouse SA-(Gly4Ser)-V$_L$ CK157 | EAHKSEIAHRYNDLGEQHFKGLVLIAFSQYLQKCSYDEHAKLVQEVTDFAKTCV<br>ADESAANCDKSLHTLFGDKLCAIPNLRENYGELADCCTKQEPERNECFLQHKDD<br>NPSLPPFERPEAEAMCTSFKENPTTFMGHYLHEVARRHPYFYAPELLYYAEQYN<br>EILTQCCAEADKESCLTPKLDGVKEKALVSSVRQRMKCSSMQKFGERAFKAWAV<br>ARLSQTFPNADFAEITKLATDLTKVNKECCHGDLLECADDRAELAKYMCENQAT<br>ISSKLQTCCDKPLLKKAHCLSEVEHDTMPADLPAIAADFVEDQEVCKNYAEAKD<br>VFLGTFLYEYSRRHPDYSVSLLLRLAKKYEATLEKCCAEANPPACYGTVLAEFQ<br>PLVEEPKNLVKTNCDLYEKLGEYGFQNAILVRYTQKAPQVSTPTLVEAARNLGR<br>VGTKCCTLPEDQRLPCVEDYLSAILNRVCLLHEKTPVSEHVTKCCSGSLVERRP<br>CFSALTVDETYVPKEFKAETFTFHSDICTLPEKEKQIKKQTALAELVKHKPKAT<br>AEQLKTVMDDFAQFLDTCCKAADKDTCFSTEGPNLVTRCKDALA*GGGGSGGGGS*<br>*GGGGS*ASDIQMTQSPSSLSASVGDRVTITCRASQSYGGVAWYQQKPGKAPKLLI<br>YSASYLYSGVPSRFSGSRSGTDFTLTISSLQPEDFATYYCQQPSHLITFGQGTE<br>VEIK-- |
| 168 | mouse SA-(Gly4Ser)-V$_H$ CK157 | EAHKSEIAHRYNDLGEQHFKGLVLIAFSQYLQKCSYDEHAKLVQEVTDFAKTCV<br>ADESAANCDKSLHTLFGDKLCAIPNLRENYGELADCCTKQEPERNECFLQHKDD<br>NPSLPPFERPEAEAMCTSFKENPTTFMGHYLHEVARRHPYFYAPELLYYAEQYN<br>EILTQCCAEADKESCLTPKLDGVKEKALVSSVRQRMKCSSMQKFGERAFKAWAV<br>ARLSQTFPNADFAEITKLATDLTKVNKECCHGDLLECADDRAELAKYMCENQAT<br>ISSKLQTCCDKPLLKKAHCLSEVEHDTMPADLPAIAADFVEDQEVCKNYAEAKD<br>VFLGTFLYEYSRRHPDYSVSLLLRLAKKYEATLEKCCAEANPPACYGTVLAEFQ<br>PLVEEPKNLVKTNCDLYEKLGEYGFQNAILVRYTQKAPQVSTPTLVEAARNLGR<br>VGTKCCTLPEDQRLPCVEDYLSAILNRVCLLHEKTPVSEHVTKCCSGSLVERRP<br>CFSALTVDETYVPKEFKAETFTFHSDICTLPEKEKQIKKQTALAELVKHKPKAT<br>AEQLKTVMDDFAQFLDTCCKAADKDTCFSTEGPNLVTRCKDALA*GGGGSGGGGS*<br>*GGGGS*ASAEVQLVESGGGLVQPGGSLRLSCAASGSNPYYYGGTHWVRQAPGEEL<br>EWVASIGSYPGYTDYADSVKGRFTISADTSKNTAYLQMNSLRAEDTAVYYCARH<br>YYWYDATDYWGQGTLVTVSS-- |
| 169 | mouse SA-(Gly4Ser)3-scFv (V$_L$-V$_H$) CK129-ds1 (V$_L$100$^{Q>C}$/V$_H$44$^{G>C}$) | EAHKSEIAHRYNDLGEQHFKGLVLIAFSQYLQKCSYDEHAKLVQEVTDFAKTCV<br>ADESAANCDKSLHTLFGDKLCAIPNLRENYGELADCCTKQEPERNECFLQHKDD<br>NPSLPPFERPEAEAMCTSFKENPTTFMGHYLHEVARRHPYFYAPELLYYAEQYN<br>EILTQCCAEADKESCLTPKLDGVKEKALVSSVRQRMKCSSMQKFGERAFKAWAV<br>ARLSQTFPNADFAEITKLATDLTKVNKECCHGDLLECADDRAELAKYMCENQAT<br>ISSKLQTCCDKPLLKKAHCLSEVEHDTMPADLPAIAADFVEDQEVCKNYAEAKD<br>VFLGTFLYEYSRRHPDYSVSLLLRLAKKYEATLEKCCAEANPPACYGTVLAEFQ<br>PLVEEPKNLVKTNCDLYEKLGEYGFQNAILVRYTQKAPQVSTPTLVEAARNLGR<br>VGTKCCTLPEDQRLPCVEDYLSAILNRVCLLHEKTPVSEHVTKCCSGSLVERRP<br>CFSALTVDETYVPKEFKAETFTFHSDICTLPEKEKQIKKQTALAELVKHKPKAT<br>AEQLKTVMDDFAQFLDTCCKAADKDTCFSTEGPNLVTRCKDALA*GGGGSGGGGS*<br>*GGGGS*ASDIQMTQSPSPLSASVGDRVTITCRASQYGGYVAWYQQKPGKAPKLLI<br>**YGASLLYSGVPSRFSGGRSGTDFTLTISSLQPEDFATYYCQRGHALITFC*GTK<br>VEIEGGTTAASGSSGGSSSGAEVQLVESGGGLVQPGGSLRLSCAASGFNISSYGS<br>MHWVRQAPGK*C*LEWVASIYPYSSSTYYADSVKGRFTISADTSKNTAYLQMNSLR<br>AEDTAVYYCARGYGPWYAYSYFALDYWGQGTLVTVSS**-- |
| 170 | mouse SA-(Gly4Ser)3-scFv (V$_L$-V$_H$) CK129-ds2 (V$_L$43$^{A>C}$/V$_H$105$^{Q>C}$) | EAHKSEIAHRYNDLGEQHFKGLVLIAFSQYLQKCSYDEHAKLVQEVTDFAKTCV<br>ADESAANCDKSLHTLFGDKLCAIPNLRENYGELADCCTKQEPERNECFLQHKDD<br>NPSLPPFERPEAEAMCTSFKENPTTFMGHYLHEVARRHPYFYAPELLYYAEQYN<br>EILTQCCAEADKESCLTPKLDGVKEKALVSSVRQRMKCSSMQKFGERAFKAWAV<br>ARLSQTFPNADFAEITKLATDLTKVNKECCHGDLLECADDRAELAKYMCENQAT<br>ISSKLQTCCDKPLLKKAHCLSEVEHDTMPADLPAIAADFVEDQEVCKNYAEAKD<br>VFLGTFLYEYSRRHPDYSVSLLLRLAKKYEATLEKCCAEANPPACYGTVLAEFQ<br>PLVEEPKNLVKTNCDLYEKLGEYGFQNAILVRYTQKAPQVSTPTLVEAARNLGR<br>VGTKCCTLPEDQRLPCVEDYLSAILNRVCLLHEKTPVSEHVTKCCSGSLVERRP<br>CFSALTVDETYVPKEFKAETFTFHSDICTLPEKEKQIKKQTALAELVKHKPKAT |

TABLE 12-continued

Sequence Summary

| SEQ ID NO | Description | Sequence |
|---|---|---|
| | | AEQLKTVMDDFAQFLDTCCKAADKDTCFSTEGPNLVTRCKDALA*GGGGSGGGGS* *GGGGS*ASDIQMTQSPSPLSASVGDRVTITCRASQYGGYVAWYQQKPGKCPKLLI YGASLLYSGVPSRFSGGRSGTDFTLTISSLQPEDFATYYCQRGHALITFGQGTK VEIEGTTAASGSSGGSSSGAEVQLVESGGGLVQPGGSLRLSCAASGFNISSYGS MHWVRQAPGKGLEWVASIYPYSSSTYYADSVKGRFTISADTSKNTAYLQMNSLR AEDTAVYYCARGYGPWYAYSYFALDYWGCGTLVTVSS-- |
| 171 | Human serum albumin (mature) (HSA) | DAHKSEVAHRFKDLGEENFKALVLIAFAQYLQQCPFEDHVKLVNEVTEFAKTCV ADESAENCDKSLHTLFGDKLCTVATLRETYGEMADCCAKQEPERNECFLQHKDD NPNLPRLVRPEVDVMCTAFHDNEETFLKKYLYEIARRHPYFYAPELLFFAKRYK AAFTECCQAADKAACLLPKLDELRDEGKASSAKQRLKCASLQKFGERAFKAWAV ARLSQRFPKAEFAEVSKLVTDLTKVHTECCHGDLLECADDRADLAKYICENQDS ISSKLKECCEKPLLEKSHCIAEVENDEMPADLPSLAADFVESKDVCKNYAEAKD VFLGMFLYEYARRHPDYSVVLLLRLAKTYETTLEKCCAAADPHECYAKVFDEFK PLVEEPQNLIKQNCELFEQLGEYKFQNALLVRYTKKVPQVSTPTLVEVSRNLGK VGSKCCKHPEAKRMPCAEDYLSWLNQLCVLHEKTPVSDRVTKCCTESLVNRRP CFSALEVDETYVPKEFNAETFTFHADICTLSEKERQIKKQTALVELVKHKPKAT KEQLKAVMDDFAAFVEKCCKADDKETCFAEEGKKLVAASQAALGL |
| 172 | Human IgG1 constant region (amino acid sequence) | ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKKVEPKSCDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKC KVSNKALPAPIEKTISKAKGQPREPQVYTLPPSRDELTKNQV SLTCLVKGFYPSDIAVEWESNGQPENNYKTTPPVLDSDGSFF LYSKLTVDKSRWQQGNVFSCSVMHEALHNHYTQKSLSLSP GK |
| 173 | Mouse serum albumin | EAHKSEIAHRYNDLGEQHFKGLVLIAFSQYLQKCSYDEHAKLVQEVTDFAKTCV ADESAANCDKSLHTLFGDKLCAIPNLRENYGELADCCTKQEPERNECFLQHKDD NPSLPPFERPEAEAMCTSFKENPTTFMGHYLHEVARRHPYFYAPELLYYAEQYN EILTQCCAEADKESCLTPKLDGVKEKALVSSVRQRMKCSSMQKFGERAFKAWAV ARLSQTFPNADFAEITKLATDLTKVNKECCHGDLLECADDRAELAKYMCENQAT ISSKLQTCCDKPLLKKAHCLSEVEHDTMPADLPAIAADFVEDQEVCKNYAEAKD VFLGTFLYEYSRRHPDYSVSLLLRLAKKYEATLEKCCAEANPPACYGTVLAEFQ PLVEEPKNLVKTNCDLYEKLGEYGFQNAILVRYTQKAPQVSTPTLVEAARNLGR VGTKCCTLPEDQRLPCVEDYLSAILNRVCLLHEKTPVSEHVTKCCSGSLVERRP CFSALTVDETYVPKEFKAETFTFHSDICTLPEKEKQIKKQTALAELVKHKPKAT AEQLKTVMDDFAQFLDTCCKAADKDTCFSTEGPNLVTRCKDALA |
| 174 | Human IgG1 Fc domain (amino acid sequence) | EPKSCDKTHTCPPCPAPELLGGPSVFLFPPKPKDTLMISRTPE VTCVVVDVSHEDPEVKFNWYVDGVEVHNAKTKPREEQYN STYRVVSVLTVLHQDWLNGKEYKCKVSNKALPAPIEKTISK AKGQPREPQVYTLPPSRDELTKNQVSLTCLVKGFYPSDIAVE WESNGQPENNYKTTPPVLDSDGSFFLYSKLTVDKSRWQQG NVFSCSVMHEALHNHYTQKSLSLSPGK |
| 175 | HSA domain I | DAHKSEVAHRFKDLGEENFKALVLIAFAQYLQQCPFEDHVKLVNEVTEFAKTCV ADESAENCDKSLHTLFGDKLCTVATLRETYGEMADCCAKQEPERNECFLQHKDD NPNLPRLVRPEVDVMCTAFHDNEETFLKKYLYEIARRHPYFYAPELLFFAKRYK AAFTECCQAADKAACLLPKLDELRDEGKASSAKQR |
| 176 | HSA domain II | GKASSAKQRLKCASLQKFGERAFKAWAVARLSQRFPKAEFAEVSKLVTDLTKVH TECCHGDLLECADDRADLAKYICENQDSISSKLKECCEKPLLEKSHCIAEVEND EMPADLPSLAADFVESKDVCKNYAEAKDVFLGMFLYEYARRHPDYSVVLLLRLA KTYETTLEKCCAAADPHECYAKVFDEFKPLVEEPQ |
| 177 | HSA domain III | NLIKQNCELFEQLGEYKFQNALLVRYTKKVPQVSTPTLVEVSRNLGKVGSKCCK HPEAKRMPCAEDYLSWLNQLCVLHEKTPVSDRVTKCCTESLVNRRPCFSALEV DETYVPKEFNAETFTFHADICTLSEKERQIKKQTALVELVKHKPKATKEQLKAV MDDFAAFVEKCCKADDKETCFAEEGKKLVAASQAALGL |
| 178 | (Gly$_4$Ser)$_3$ linker domain | GGGGSGGGGSGGGGS |
| 179 | Secretory leader sequence | MDMRVPAQLLGLLLLWLPGARC |
| 180 | FLAG tag | DYKDDDDK |

TABLE 12-continued

Sequence Summary

| SEQ ID NO | Description | Sequence |
|---|---|---|
| 181 | Polyhistidine (6-His) | HHHHHH |
| 182 | Hemagglutinin | YPYDVPDYA |

The invention claimed is:

1. A fusion protein, comprising a multispecific variable region operably coupled to a polymer, wherein the multispecific variable region comprises heavy chain CDR1, CDR2 and CDR3 sequences set forth in SEQ ID NOs: 5, 6 and 7, respectively, and light chain CDR1, CDR2 and CDR3 sequences set forth in SEQ ID NOs: 8, 9 and 10, respectively.

2. The fusion protein of claim 1, wherein the multispecific variable region is operably coupled to the C-terminus of the polymer, or to the N-terminus of the polymer.

3. The fusion protein of claim 1, wherein the multispecific variable region is operably coupled to the polymer via a linker.

4. The fusion protein of claim 3, wherein the linker is a Gly-Ser linker.

5. The fusion protein of claim 1, wherein the polymer is a serum albumin moiety or an Fc domain.

6. The fusion protein of claim 1, wherein the multispecific variable region is a scFv.

7. The fusion protein of claim 1, wherein the multispecific variable region comprises a heavy chain variable region and a light chain variable region, wherein
   the heavy chain variable region comprises an amino acid sequence as set forth in SEQ ID NO: 1;
   (ii) the light chain variable region comprises an amino acid sequence as set forth in SEQ ID NO: 2; or
   (iii) a combination of (i)-(ii).

8. A method of blocking neutrophil infiltration in a subject with inflammatory arthritis, the method comprising administering an effective amount of the fusion protein of claim 1.

9. A method of blocking neutrophil infiltration in a subject with an autoimmune disorder, the method comprising administering an effective amount of the fusion protein of claim 1.

10. The fusion protein of claim 1, wherein the fusion protein comprises an amino acid sequence having at least 90% identity to an amino acid sequence selected from the group consisting of SEQ ID NO: 95, 98, 99, 160, 163, and 164.

11. The fusion protein of claim 1, wherein the fusion protein comprises an amino acid sequence selected from the group consisting of SEQ ID NOs: 95, 98, 99, 160, 163, and 164.

12. A fusion protein, comprising a multispecific variable region operably coupled to a serum albumin moiety, wherein the multispecific variable region comprises heavy chain CDR1, CDR2 and CDR3 sequences set forth in SEQ ID NOs: 5, 6 and 7, respectively, and light chain CDR1, CDR2 and CDR3 sequences set forth in SEQ ID NOs: 8, 9 and 10, respectively.

13. The fusion protein of claim 12, wherein the multispecific variable region comprises heavy and light chain variable regions, wherein the heavy chain variable region and the light chain variable region comprise amino acid sequences having at least 90% identity to the amino acid sequences set forth in SEQ ID NOs: 1 and 2.

14. The fusion protein of claim 12, wherein the multispecific variable region comprises heavy and light chain variable regions, wherein the heavy chain variable region and the light chain variable region comprise amino acid sequences set forth in SEQ ID NOs: 1 and 2.

15. An isolated monoclonal antibody, or binding fragment thereof comprising heavy chain CDR1, CDR2 and CDR3 sequences set forth in SEQ ID NOs: 5, 6 and 7, respectively, and light chain CDR1, CDR2 and CDR3 sequences set forth in SEQ ID NOs: 8, 9 and 10, respectively.

* * * * *

SEQUENCE LISTING

<160> NUMBER OF SEQ ID NOS: 209

<210> SEQ ID NO 1
<211> LENGTH: 127
<212> TYPE: PRT
<213> ORGANISM: Artificial Sequence
<220> FEATURE:
<223> OTHER INFORMATION: Synthetic: CK138 VH amino acid sequence

<400> SEQUENCE: 1

Glu Val Gln Leu Val Glu Ser Asp Gly Gly Leu Val Gln Pro Gly Gly
1               5                   10                  15

Ser Leu Arg Leu Ser Cys Ala Ala Ser Gly Phe Asn Leu Ser Tyr Tyr
            20                  25                  30

Gly Met His Trp Val Arg Gln Ala Pro Gly Lys Gly Leu Glu Trp Val
        35                  40                  45

Ala Tyr Ile Ala Ser Tyr Pro Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Ser Tyr Ser Pro Tyr Tyr Ser Trp Phe Ser Ala
            100                 105                 110

Gly Met Asn Tyr Trp Gly Gln Gly Ala Leu Val Thr Val Ser Ser
        115                 120                 125

<210> SEQ ID NO 2
<211> LENGTH: 107
<212> TYPE: PRT
<213> ORGANISM: Artificial Sequence
<220> FEATURE:
<223> OTHER INFORMATION: Synthetic: CK138 VL amino acid sequence

<400> SEQUENCE: 2

Ala Ile Gln Met Thr Arg Ser Pro Ser Ser Leu Ser Ala Ser Val Gly
1               5                   10                  15

Asp Arg Val Thr Ile Thr Cys Arg Ala Ser Gln Tyr His Asp Gly Ser
            20                  25                  30

Ala Ala Trp Tyr Gln Gln Lys Pro Gly Lys Ala Pro Lys Leu Leu Ile
        35                  40                  45

Tyr Gly Ala Ser Tyr Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Tyr Ser Leu Ile

```
                85                  90                  95
Thr Phe Gly Gln Gly Thr Lys Val Glu Ile Lys
            100                 105

<210> SEQ ID NO 3
<211> LENGTH: 381
<212> TYPE: DNA
<213> ORGANISM: Artificial Sequence
<220> FEATURE:
<223> OTHER INFORMATION: Synthetic: CK138 VH nucleic acid sequence

<400> SEQUENCE: 3
gaggttcagc tggtggagtc tgacggtggc ctggtgcagc caggggggctc actccgtttg     60 tcctgtgcag cttctggctt caacctctct tactacggta tgcactgggt gcgtcaggcc    120
ccgggtaagg gcctggaatg ggttgcatac attgcttctt accctggcta cacttcttat    180
gccgatagcg tcaagggccg tttcactata agcgcagaca catccaaaaa cacagcctac    240
ctacaaatga acagcttaag agctgaggac actgccgtct actattgtgc tcgctctggt    300
tacagttact ctccgtatta ttcttggttc tctgctggta tgaactactg gggtcaagga    360
gccctggtca ccgtctcctc g                                              381

<210> SEQ ID NO 4
<211> LENGTH: 321
<212> TYPE: DNA
<213> ORGANISM: Artificial Sequence
<220> FEATURE:
<223> OTHER INFORMATION: Synthetic: CK138 VL nucleic acid sequence

<400> SEQUENCE: 4
gctatccaga tgacccggtc cccgagctcc ctgtccgcct ctgtgggcga tagggtcacc     60
atcacctgcc gtgccagtca gtaccacgac ggttctgcag cctggtatca acagaaacca    120
ggaaaagctc cgaagcttct gatttacggt gcatcctacc tctactctgg agtcccttcc    180
cgcttctctg gtagccgttc cgggacggat ttcactctga ccatcagcag tctgcagccg    240
gaagacttcg caacttatta ctgtcagcaa tcttcttatt ctctgatcac gttcggacag    300
ggtaccaagg tggagatcaa a                                              321

<210> SEQ ID NO 5
<211> LENGTH: 8
<212> TYPE: PRT
<213> ORGANISM: Artificial Sequence
<220> FEATURE:
<223> OTHER INFORMATION: Synthetic: CK138 VH CDR1

<400> SEQUENCE: 5

Asn Leu Ser Tyr Tyr Gly Met His
1               5

<210> SEQ ID NO 6
<211> LENGTH: 12
<212> TYPE: PRT
<213> ORGANISM: Artificial Sequence
<220> FEATURE:
<223> OTHER INFORMATION: Synthetic: CK138 VH CDR2

<400> SEQUENCE: 6

Ala Tyr Ile Ala Ser Tyr Pro Gly Tyr Thr Ser Tyr
1               5                   10

<210> SEQ ID NO 7
```

```
<211> LENGTH: 18
<212> TYPE: PRT
<213> ORGANISM: Artificial Sequence
<220> FEATURE:
<223> OTHER INFORMATION: Synthetic: CK138 VH CDR3

<400> SEQUENCE: 7

Arg Ser Gly Tyr Ser Tyr Ser Pro Tyr Tyr Ser Trp Phe Ser Ala Gly
1               5                   10                  15

Met Asn

<210> SEQ ID NO 8
<211> LENGTH: 7
<212> TYPE: PRT
<213> ORGANISM: Artificial Sequence
<220> FEATURE:
<223> OTHER INFORMATION: Synthetic: CK138 VL CDR1

<400> SEQUENCE: 8

Gln Tyr His Asp Gly Ser Ala
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic: CK138 VL CDR2

<400> SEQUENCE: 9

Tyr Gly Ala Ser Tyr Leu
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic: CK138 VL CDR3

<400> SEQUENCE: 10

Gln Ser Ser Tyr Ser Leu Ile Thr
1               5

<210> SEQ ID NO 11
<211> LENGTH: 120
<212> TYPE: PRT
<213> ORGANISM: Artificial Sequence
<220> FEATURE:
<223> OTHER INFORMATION: Synthetic: CK157 VH amino acid sequence

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Asn Pro Tyr Tyr Tyr
            20                  25                  30

Gly Gly Thr His Trp Val Arg Gln Ala Pro Gly Glu Glu Leu Glu Trp
        35                  40                  45

Val Ala Ser Ile Gly Ser Tyr Pro Gly Tyr Thr Asp Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95
```

Cys Ala Arg His Tyr Tyr Trp Tyr Asp Ala Thr Asp Tyr Trp Gly Gln
            100                 105                 110

Gly Thr Leu Val Thr Val Ser Ser
        115                 120

<210> SEQ ID NO 12
<211> LENGTH: 105
<212> TYPE: PRT
<213> ORGANISM: Artificial Sequence
<220> FEATURE:
<223> OTHER INFORMATION: Synthetic: CK157 VL amino acid sequence

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Tyr Gly Gly Val
            20                  25                  30

Ala Trp Tyr Gln Gln Lys Pro Gly Lys Ala Pro Lys Leu Leu Ile Tyr
        35                  40                  45

Ser Ala Ser Tyr Leu Tyr Ser Gly Val Pro Ser Arg Phe Ser Gly Ser
    50                  55                  60

Arg Ser Gly Thr Asp Phe Thr Leu Thr Ile Ser Ser Leu Gln Pro Glu
65                  70                  75                  80

Asp Phe Ala Thr Tyr Tyr Cys Gln Gln Pro Ser His Leu Ile Thr Phe
                85                  90                  95

Gly Gln Gly Thr Glu Val Glu Ile Lys
            100                 105

<210> SEQ ID NO 13
<211> LENGTH: 360
<212> TYPE: DNA
<213> ORGANISM: Artificial Sequence
<220> FEATURE:
<223> OTHER INFORMATION: Synthetic: CK157 VH nucleic acid sequence

<400> SEQUENCE: 13
gaggttcagc tggtggagtc tggcggtggc ctggtgcagc caggggctc actccgtttg      60 tcctgtgcag cttctggctc caaccctac tactacggtg gtacgcactg ggtgcgtcag    120
gccccgggtg aggagctgga atgggttgca tctattggtt cttaccctgg ctacactgac    180
tatgccgata gcgtcaaggg ccgtttcact ataagcgcag acacatccaa aacacagcc    240 tacctacaaa tgaacagctt aagagctgag gacactgccg tctattattg tgctcgccat    300
tactactggt acgatgctac tgactactgg ggtcaaggaa ccctggtcac cgtctcctcg    360

<210> SEQ ID NO 14
<211> LENGTH: 315
<212> TYPE: DNA
<213> ORGANISM: Artificial Sequence
<220> FEATURE:
<223> OTHER INFORMATION: Synthetic: CK157 VL nucleic acid sequence

<400> SEQUENCE: 14
gatatccaga tgacccagtc cccgagctcc ctgtccgcct ctgtgggcga tagggtcacc     60
atcacctgcc gtgccagtca gtcttacggt ggtgtagcct ggtatcaaca gaaaccagga    120
aaagccccga agcttctgat ttactctgca tcctacctct actctggagt cccttctcgc    180
ttctctggta gccgttccgg gacggatttc actctgacca tcagcagtct gcagccggaa    240
gacttcgcaa cttattactg tcagcaacca tctcatctga tcacgttcgg acagggtacc    300
gaggtggaga tcaaa                                             315

<210> SEQ ID NO 15
<211> LENGTH: 9
<212> TYPE: PRT
<213> ORGANISM: Artificial Sequence
<220> FEATURE:
<223> OTHER INFORMATION: Synthetic: CK157 VH CDR1

<400> SEQUENCE: 15

Asn Pro Tyr Tyr Tyr Gly Gly Thr His
1               5

<210> SEQ ID NO 16
<211> LENGTH: 12
<212> TYPE: PRT
<213> ORGANISM: Artificial Sequence
<220> FEATURE:
<223> OTHER INFORMATION: Synthetic: CK157 VH CDR2

<400> SEQUENCE: 16

Ala Ser Ile Gly Ser Tyr Pro Gly Tyr Thr Asp Tyr
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic: CK157 VH CDR3

<400> SEQUENCE: 17

Arg His Tyr Tyr Trp Tyr Asp Ala Thr Asp
1               5                   10

<210> SEQ ID NO 18
<211> LENGTH: 6
<212> TYPE: PRT
<213> ORGANISM: Artificial Sequence
<220> FEATURE:
<223> OTHER INFORMATION: Synthetic: CK157 VL CDR1

<400> SEQUENCE: 18

Gln Ser Tyr Gly Gly Val
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic: CK157 VL CDR2

<400> SEQUENCE: 19

Tyr Ser Ala Ser Tyr Leu
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic: CK157 VL CDR3

<400> SEQUENCE: 20

Gln Pro Ser His Leu Ile Thr

<210> SEQ ID NO 21
<211> LENGTH: 125
<212> TYPE: PRT
<213> ORGANISM: Artificial Sequence
<220> FEATURE:
<223> OTHER INFORMATION: Synthetic: CK129 VH amino acid sequence

<400> SEQUENCE: 21

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Ser Ser Tyr
            20                  25                  30
Gly Ser Met His Trp Val Arg Gln Ala Pro Gly Lys Gly Leu Glu Trp
        35                  40                  45
Val Ala Ser Ile Tyr Pro Tyr Ser Ser Thr Tyr Tyr Ala Asp Ser
    50                  55                  60
Val Lys Gly Arg Phe Thr Ile Ser Ala Asp Thr Ser Lys Asn Thr Ala
65                  70                  75                  80
Tyr Leu Gln Met Asn Ser Leu Arg Ala Glu Asp Thr Ala Val Tyr Tyr
                85                  90                  95
Cys Ala Arg Gly Tyr Gly Pro Trp Tyr Ala Tyr Ser Tyr Phe Ala Leu
            100                 105                 110
Asp Tyr Trp Gly Gln Gly Thr Leu Val Thr Val Ser Ser
        115                 120                 125
```

<210> SEQ ID NO 22
<211> LENGTH: 105
<212> TYPE: PRT
<213> ORGANISM: Artificial Sequence
<220> FEATURE:
<223> OTHER INFORMATION: Synthetic: CK129 VL amino acid sequence

<400> SEQUENCE: 22

```
Asp Ile Gln Met Thr Gln Ser Pro Ser Leu Ser Ala Ser Val Gly
1               5                   10                  15
Asp Arg Val Thr Ile Thr Cys Arg Ala Ser Gln Tyr Gly Gly Tyr Val
            20                  25                  30
Ala Trp Tyr Gln Gln Lys Pro Gly Lys Ala Pro Lys Leu Leu Ile Tyr
        35                  40                  45
Gly Ala Ser Leu Leu Tyr Ser Gly Val Pro Ser Arg Phe Ser Gly Gly
    50                  55                  60
Arg Ser Gly Thr Asp Phe Thr Leu Thr Ile Ser Ser Leu Gln Pro Glu
65                  70                  75                  80
Asp Phe Ala Thr Tyr Tyr Cys Gln Arg Gly His Ala Leu Ile Thr Phe
                85                  90                  95
Gly Gln Gly Thr Lys Val Glu Ile Glu
            100                 105
```

<210> SEQ ID NO 23
<211> LENGTH: 375
<212> TYPE: DNA
<213> ORGANISM: Artificial Sequence
<220> FEATURE:
<223> OTHER INFORMATION: Synthetic: CK129 VH nucleic acid sequence

<400> SEQUENCE: 23
gaggttcagc tggtggagtc tggcggtggc ctggtgcagc caggggggctc actccgttta    60

```
tcctgtgcag cttctggctt caacatctct tcttacggtt ctatgcactg ggtgcgtcag    120
gccccgggta agggcctgga atgggttgca tctatttacc cttactctag ctctacttac    180
tatgccgata gcgtcaaggg ccgtttcact ataagcgcag acacatccaa aaacacagcc    240
tacctacaaa tgaacagctt aagagctgag gacactgccg tctattattg tgctcgtggt    300
tacggtccgt ggtacgctta ctcttacttc gctttggact actggggtca aggaaccctg    360
gtcaccgtct cctcg                                                    375
```

```
<210> SEQ ID NO 24
<211> LENGTH: 315
<212> TYPE: DNA
<213> ORGANISM: Artificial Sequence
<220> FEATURE:
<223> OTHER INFORMATION: Synthetic: CK129 VL nucleic acid sequence

<400> SEQUENCE: 24
```

```
gatatccaga tgacccagtc cccgagcccc ctgtccgcct ctgtgggcga tagggtcacc     60
atcacctgcc gtgccagtca gtacggtggt tacgtagcct ggtatcaaca gaaaccagga    120
aaagctccga agcttctgat ttacggtgca tcccttctct actctggagt cccttctcgc    180
ttctctggtg gccgttccgg gacggatttc actctgacca tcagcagtct gcagccggaa    240
gacttcgcaa cttattactg tcagcgaggt catgctctga tcacgttcgg acagggtacc    300
aaggtggaga tcgaa                                                    315
```

```
<210> SEQ ID NO 25
<211> LENGTH: 9
<212> TYPE: PRT
<213> ORGANISM: Artificial Sequence
<220> FEATURE:
<223> OTHER INFORMATION: Synthetic: CK129 VH CDR1

<400> SEQUENCE: 25

Asn Ile Ser Ser Tyr Gly Ser Met His
1               5
```

```
<210> SEQ ID NO 26
<211> LENGTH: 12
<212> TYPE: PRT
<213> ORGANISM: Artificial Sequence
<220> FEATURE:
<223> OTHER INFORMATION: Synthetic: CK129 VH CDR2

<400> SEQUENCE: 26

Ala Ser Ile Tyr Pro Tyr Ser Ser Ser Thr Tyr Tyr
1               5                   10
```

```
<210> SEQ ID NO 27
<211> LENGTH: 15
<212> TYPE: PRT
<213> ORGANISM: Artificial Sequence
<220> FEATURE:
<223> OTHER INFORMATION: Synthetic: CK129 VH CDR3

<400> SEQUENCE: 27

Arg Gly Tyr Gly Pro Trp Tyr Ala Tyr Ser Tyr Phe Ala Leu Asp
1               5                   10                  15
```

```
<210> SEQ ID NO 28
<211> LENGTH: 6
<212> TYPE: PRT
<213> ORGANISM: Artificial Sequence
<220> FEATURE:
```

<223> OTHER INFORMATION: Synthetic: CK129 VL CDR1

<400> SEQUENCE: 28

Gln Tyr Gly Gly Tyr Val
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic: CK129 VL CDR2

<400> SEQUENCE: 29

Tyr Gly Ala Ser Leu Leu Tyr
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic: CK129 VL CDR3

<400> SEQUENCE: 30

Arg Gly His Ala Leu Ile Thr
1               5

<210> SEQ ID NO 31
<211> LENGTH: 1104
<212> TYPE: DNA
<213> ORGANISM: Artificial Sequence
<220> FEATURE:
<223> OTHER INFORMATION: Synthetic:
     gWiz-LS-Fc(mIgG2)-His6-linker-TEV-hCXCL138-107-G2-AviTag

<400> SEQUENCE: 31

```
atgagggtcc ccgctcagct cctggggctc ctgctgctct ggctcccagg tgcacgatgt      60
gagcccagag tgcccataac acagaacccc tgtcctccac tcaaagagtg tccccccatgc    120
gcagctccag acctcttggg tggaccatcc gtcttcatct ccctccaaa gatcaaggat      180
gtactcatga tctccctgag ccccatggtc acatgtgtgg tggtggatgt gagcgaggat    240
gacccagacg tccagatcag ctggtttgtg aacaacgtgg aagtacacac agctcagaca    300
caaacccata gagaggatta caacagtact ctccgggtgg tcagtgccct cccatccag    360
caccaggact ggatgagtgg caaggagttc aaatgcaagg tcaacaacag agccctccca   420
tcccccatcg agaaaaccat ctcaaaaccc agagggccag taagagctcc acaggtatat   480
gtcttgcctc caccagcaga agatgactaa gaaaagagt tcagtctgac ctgcatgatc    540
acaggcttct acctgccgga aattgctgtg gactggacca gcaatgggcg tacagagcaa   600
aactacaaga caccgcaac agtcctggac tctgatggtt cttacttcat gtacagcaag    660
ctcagagtac aaaagagcac ttgggaaaga ggaagtcttt tcgcctgctc agtggtccac   720
gagggtctgc acaatcacct tacgactaag accatctccc ggtctctggg taaacaccat   780
caccatcatc actcttctgg cgtggatctg ggtaccgaga acctgtactt ccaagccacc   840
gagctgagat gccagtgcct gcagaccctg cagggcatcc accccaagaa catccagagc   900
gtgaacgtga gtcccctgg ccccactgc gcccagaccg aagtgatcgc cacctgaag   960
aacgccggaa aggcctgcct gaaccccgcc agccccatcg tgaagaaaat catcgagaag  1020
atgctgaaca gcgacaagag caacggcgga ggcctgaacg acatcttcga ggcccagaaa 1080
```

```
atcgagtggc acgagtgatg ataa                                      1104
```

<210> SEQ ID NO 32
<211> LENGTH: 1110
<212> TYPE: DNA
<213> ORGANISM: Artificial Sequence
<220> FEATURE:
<223> OTHER INFORMATION: Synthetic:
     gWiz-LS-Fc(mIgG2)-His6-linker-TEV-hCXCL543-114-G2-AviTag

<400> SEQUENCE: 32

```
atgagggtcc ccgctcagct cctggggctc ctgctgctct ggctcccagg tgcacgatgt    60
gagcccagag tgcccataac acagaacccc tgtcctccac tcaaagagtg tcccccatgc   120
gcagctccag acctcttggg tggaccatcc gtcttcatct ccctccaaa gatcaaggat    180
gtactcatga tctccctgag ccccatggtc acatgtgtgg tggtggatgt gagcgaggat   240
gacccagacg tccagatcag ctggtttgtg aacaacgtgg aagtacacac agctcagaca   300
caaacccata gagaggatta caacagtact ctccgggtgg tcagtgccct ccccatccag   360
caccaggact ggatgagtgg caaggagttc aaatgcaagg tcaacaacag agccctccca   420
tcccccatcg agaaaaccat ctcaaaaccc agagggccag taagagctcc acaggtatat   480
gtcttgcctc caccagcaga gagatgact aagaaagagt tcagtctgac ctgcatgatc   540
acaggcttct tacctgccga aattgctgtg gactggacca gcaatgggcg tacagagcaa   600
aactacaaga caccgcaac agtcctggac tctgatggtt cttacttcat gtacagcaag   660
ctcagagtac aaaagagcac ttgggaaaga ggaagtcttt tcgcctgctc agtggtccac   720
gagggtctgc acaatcacct tacgactaag accatctccc ggtctctggg taaacaccat   780
caccatcatc actcttctgg cgtggatctg ggtaccgaga acctgtactt ccaagtgctg   840
cgcgagctga atgcgtgtg cctgcagacc acccagggcg tgcacccaa gatgatcagc   900
aacctccagg tgttcgccat cggcccccag tgcagcaagg tggaagtggt ggccagcctg   960
aagaacggca agagatctg cctggacccc gaggccccat tcctgaagaa agtgatccag  1020
aagatcctgg acggcggcaa caaagagaac ggcggaggcc tgaacgacat cttcgaggcc  1080
cagaaaatcg agtggcacga gtgatgataa                                  1110
```

<210> SEQ ID NO 33
<211> LENGTH: 1107
<212> TYPE: DNA
<213> ORGANISM: Artificial Sequence
<220> FEATURE:
<223> OTHER INFORMATION: Synthetic:
     gWiz-LS-Fc(mIgG2)-His6-linker-TEV-hCXCL829-99-G2-AviTag

<400> SEQUENCE: 33

```
atgagggtcc ccgctcagct cctggggctc ctgctgctct ggctcccagg tgcacgatgt    60
gagcccagag tgcccataac acagaacccc tgtcctccac tcaaagagtg tcccccatgc   120
gcagctccag acctcttggg tggaccatcc gtcttcatct ccctccaaa gatcaaggat    180
gtactcatga tctccctgag ccccatggtc acatgtgtgg tggtggatgt gagcgaggat   240
gacccagacg tccagatcag ctggtttgtg aacaacgtgg aagtacacac agctcagaca   300
caaacccata gagaggatta caacagtact ctccgggtgg tcagtgccct ccccatccag   360
caccaggact ggatgagtgg caaggagttc aaatgcaagg tcaacaacag agccctccca   420
tcccccatcg agaaaaccat ctcaaaaccc agagggccag taagagctcc acaggtatat   480
```

```
gtcttgcctc caccagcaga agagatgact aagaaagagt tcagtctgac ctgcatgatc    540
acaggcttct tacctgccga aattgctgtg gactggacca gcaatgggcg tacagagcaa    600
aactacaaga acaccgcaac agtcctggac tctgatggtt cttacttcat gtacagcaag    660
ctcagagtac aaaagagcac ttgggaaaga ggaagtcttt tcgcctgctc agtggtccac    720
gagggtctgc acaatcacct tacgactaag accatctccc ggtctctggg taaacaccat    780
caccatcatc actcttctgg cgtggatctg ggtaccgaga acctgtactt ccaagccaaa    840
gaactgcggt gccagtgcat caagacctac agcaagccct ccacccccaa gttcatcaaa    900
gaactgagag tgatcgagag cggccctcac tgcgccaaca ccgagatcat cgtgaagctg    960
agcgacggca gagagctgtg cctggacccc aaagaaaact gggtgcagcg ggtggtggaa   1020
aagttcctga gcgggccga gaacagcggc ggaggcctga cgacatctt cgaggcccag   1080 aaaatcgagt ggcacgagtg atgataa                                      1107

<210> SEQ ID NO 34
<211> LENGTH: 1101
<212> TYPE: DNA
<213> ORGANISM: Artificial Sequence
<220> FEATURE:
<223> OTHER INFORMATION: Synthetic:
      gWiz-LS-Fc(mIgG2)-His6-linker-TEV-mCXCL128-96-G2-AviTag

<400> SEQUENCE: 34
atgagggtcc ccgctcagct cctggggctc ctgctgctct ggctcccagg tgcacgatgt     60
gagcccagag tgcccataac acagaacccc tgtcctccac tcaaagagtg tccccccatgc   120 gcagctccag acctcttggg tggaccatcc gtcttcatct tccctccaaa gatcaaggat    180
gtactcatga tctccctgag ccccatggtc acatgtgtgg tggtggatgt gagcgaggat    240
gacccagacg tccagatcag ctggtttgtg aacaacgtgg aagtacacac agctcagaca    300
caaacccata gagaggatta caacagtact ctccgggtgg tcagtgccct ccccatccag    360
caccaggact ggatgagtgg caaggagttc aaatgcaagg tcaacaacag agccctccca    420
tcccccatcg agaaaaccat ctcaaaaccc agagggccag taagagctcc acaggtatat    480
gtcttgcctc caccagcaga agagatgact aagaaagagt tcagtctgac ctgcatgatc    540
acaggcttct tacctgccga aattgctgtg gactggacca gcaatgggcg tacagagcaa    600
aactacaaga acaccgcaac agtcctggac tctgatggtt cttacttcat gtacagcaag    660
ctcagagtac aaaagagcac ttgggaaaga ggaagtcttt tcgcctgctc agtggtccac    720
gagggtctgc acaatcacct tacgactaag accatctccc ggtctctggg taaacaccat    780
caccatcatc actcttctgg cgtggatctg ggtaccgaga acctgtactt ccaagccaac    840
gagctgcggt gccagtgcct gcagaccatg gccggcatcc acctgaagaa catccagagc    900
ctgaaggtgc tgcccagcgg ccctcactgc acccagaccg aagtgatcgc caccctgaag    960
aacggcagag aggcctgcct ggatcccgag gccccctgg tgcagaaaat cgtgcagaaa   1020
atgctgaagg gcgtgcccaa gggcggaggc ctgaacgaca tcttcgaggc cagaaaatc   1080 gagtggcacg agtgatgata a                                            1101

<210> SEQ ID NO 35
<211> LENGTH: 1104
<212> TYPE: DNA
<213> ORGANISM: Artificial Sequence
<220> FEATURE:
<223> OTHER INFORMATION: Synthetic:
      gWiz-LS-Fc(mIgG2)-His6-linker-TEV-mCXCL231-100-G2-AviTag
```

<400> SEQUENCE: 35

```
atgagggtcc ccgctcagct cctggggctc ctgctgctct ggctcccagg tgcacgatgt      60
gagcccagag tgcccataac acagaacccc tgtcctccac tcaaagagtg tcccccatgc     120
gcagctccag acctcttggg tggaccatcc gtcttcatct ccctccaaa gatcaaggat      180
gtactcatga tctccctgag ccccatggtc acatgtgtgg tggtggatgt gagcgaggat     240
gacccagacg tccagatcag ctggtttgtg aacaacgtgg aagtacacac agctcagaca     300
caaacccata gagaggatta acagtact ctccgggtgg tcagtgccct ccccatccag      360
caccaggact ggatgagtgg caaggagttc aaatgcaagg tcaacaacag agccctccca     420
tcccccatcg agaaaaccat ctcaaaaccc agagggccag taagagctcc acaggtatat     480
gtcttgcctc caccagcaga agagatgact aagaaagagt tcagtctgac ctgcatgatc     540
acaggcttct acctgccga aattgctgtg gactggacca gcaatgggcg tacagagcaa     600
aactacaaga acaccgcaac agtcctggac tctgatggtt cttacttcat gtacagcaag     660
ctcagagtac aaaagagcac ttgggaaaga ggaagtcttt tcgcctgctc agtggtccac     720
gagggtctgc acaatcacct tacgactaag accatctccc ggtctctggg taaacaccat     780
caccatcatc actcttctgg cgtggatctg ggtaccgaga acctgtactt ccaagccagc     840
gagctgcggt gccagtgcct gaaaaccctg ccccggggtgg acttcaagaa catccagagc     900
ctgagcgtga ccccccctgg ccctcactgt gcccagaccg aagtgatcgc caccctgaag     960
ggcggccaga agtgtgcct ggaccccgag gccccctgg tgcagaagat catccagaag     1020
atcctgaaca agggcaaggc caacggcgga ggcctgaacg acatcttcga ggcccagaaa    1080
atcgagtggc acgagtgatg ataa                                           1104
```

<210> SEQ ID NO 36
<211> LENGTH: 1107
<212> TYPE: DNA
<213> ORGANISM: Artificial Sequence
<220> FEATURE:
<223> OTHER INFORMATION: Synthetic:
      gWiz-LS-Fc(mIgG2)-His6-linker-TEV-mCXCL548-118-G2-AviTag

<400> SEQUENCE: 36

```
atgagggtcc ccgctcagct cctggggctc ctgctgctct ggctcccagg tgcacgatgt      60
gagcccagag tgcccataac acagaacccc tgtcctccac tcaaagagtg tcccccatgc     120
gcagctccag acctcttggg tggaccatcc gtcttcatct ccctccaaa gatcaaggat      180
gtactcatga tctccctgag ccccatggtc acatgtgtgg tggtggatgt gagcgaggat     240
gacccagacg tccagatcag ctggtttgtg aacaacgtgg aagtacacac agctcagaca     300
caaacccata gagaggatta acagtact ctccgggtgg tcagtgccct ccccatccag      360
caccaggact ggatgagtgg caaggagttc aaatgcaagg tcaacaacag agccctccca     420
tcccccatcg agaaaaccat ctcaaaaccc agagggccag taagagctcc acaggtatat     480
gtcttgcctc caccagcaga agagatgact aagaaagagt tcagtctgac ctgcatgatc     540
acaggcttct acctgccga aattgctgtg gactggacca gcaatgggcg tacagagcaa     600
aactacaaga acaccgcaac agtcctggac tctgatggtt cttacttcat gtacagcaag     660
ctcagagtac aaaagagcac ttgggaaaga ggaagtcttt tcgcctgctc agtggtccac     720
gagggtctgc acaatcacct tacgactaag accatctccc ggtctctggg taaacaccat     780
caccatcatc actcttctgg cgtggatctg ggtaccgaga acctgtactt ccaagccacc     840
```

```
gagctgagat gcgtgtgcct gaccgtgacc cccaagatca accccaagct gatcgccaac    900
ctggaagtga tccctgccgg ccctcagtgc ccaccgtgg aagtgattgc caagctgaag    960
aaccagaaag aagtgtgcct ggaccccgag gcccccgtga tcaagaagat catccagaag   1020
atcctgggca gcgacaagaa gaaagccggc ggaggcctga cgacatctt cgaggcccag   1080 aaaatcgagt ggcacgagtg atgataa                                      1107
```

<210> SEQ ID NO 37
<211> LENGTH: 365
<212> TYPE: PRT
<213> ORGANISM: Artificial Sequence
<220> FEATURE:
<223> OTHER INFORMATION: Synthetic: LS-Fc-His6-linker-TEV-hCXCL138-107-G2-AviTag

<400> SEQUENCE: 37

```
Met Arg Val Pro Ala Gln Leu Leu Gly Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Asp Val Ser Glu Asp
65              70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys His His His His His His Ser Ser Gly Val Asp Leu Gly Thr
            260                 265                 270

Glu Asn Leu Tyr Phe Gln Ala Thr Glu Leu Arg Cys Gln Cys Leu Gln
        275                 280                 285

Thr Leu Gln Gly Ile His Pro Lys Asn Ile Gln Ser Val Asn Val Lys
    290                 295                 300
```

```
Ser Pro Gly Pro His Cys Ala Gln Thr Glu Val Ile Ala Thr Leu Lys
305                 310                 315                 320

Asn Gly Arg Lys Ala Cys Leu Asn Pro Ala Ser Pro Ile Val Lys Lys
            325                 330                 335

Ile Ile Glu Lys Met Leu Asn Ser Asp Lys Ser Asn Gly Gly Gly Leu
        340                 345                 350

Asn Asp Ile Phe Glu Ala Gln Lys Ile Glu Trp His Glu
    355                 360                 365

<210> SEQ ID NO 38
<211> LENGTH: 367
<212> TYPE: PRT
<213> ORGANISM: Artificial Sequence
<220> FEATURE:
<223> OTHER INFORMATION: Synthetic: LS-Fc-His6-linker-TEV-hCXCL543-114-
      G2-AviTag

<400> SEQUENCE: 38

Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
50                  55                  60

Ser Leu Ser Pro Met Val Thr Cys Val Val Asp Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys His His His His His Ser Ser Gly Val Asp Leu Gly Thr
            260                 265                 270

Glu Asn Leu Tyr Phe Gln Val Leu Arg Glu Leu Arg Cys Val Cys Leu
        275                 280                 285

Gln Thr Thr Gln Gly Val His Pro Lys Met Ile Ser Asn Leu Gln Val
290                 295                 300
```

```
Phe Ala Ile Gly Pro Gln Cys Ser Lys Val Glu Val Ala Ser Leu
305                 310                 315                 320

Lys Asn Gly Lys Glu Ile Cys Leu Asp Pro Glu Ala Pro Phe Leu Lys
            325                 330                 335

Lys Val Ile Gln Lys Ile Leu Asp Gly Gly Asn Lys Glu Asn Gly Gly
            340                 345                 350

Gly Leu Asn Asp Ile Phe Glu Ala Gln Lys Ile Glu Trp His Glu
        355                 360                 365
```

<210> SEQ ID NO 39
<211> LENGTH: 366
<212> TYPE: PRT
<213> ORGANISM: Artificial Sequence
<220> FEATURE:
<223> OTHER INFORMATION: Synthetic: LS-Fc-His6-linker-TEV-hCXCL829-99-
      G2-AviTag

<400> SEQUENCE: 39

```
Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
50                  55                  60

Ser Leu Ser Pro Met Val Thr Cys Val Val Asp Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys His His His His His His Ser Ser Gly Val Asp Leu Gly Thr
            260                 265                 270

Glu Asn Leu Tyr Phe Gln Ala Lys Glu Leu Arg Cys Gln Cys Ile Lys
        275                 280                 285

Thr Tyr Ser Lys Pro Phe His Pro Lys Phe Ile Lys Glu Leu Arg Val
```

```
                    290                 295                 300

Ile Glu Ser Gly Pro His Cys Ala Asn Thr Glu Ile Ile Val Lys Leu
305                 310                 315                 320

Ser Asp Gly Arg Glu Leu Cys Leu Asp Pro Lys Glu Asn Trp Val Gln
                    325                 330                 335

Arg Val Val Glu Lys Phe Leu Lys Arg Ala Glu Asn Ser Gly Gly Gly
                    340                 345                 350

Leu Asn Asp Ile Phe Glu Ala Gln Lys Ile Glu Trp His Glu
                355                 360                 365

<210> SEQ ID NO 40
<211> LENGTH: 364
<212> TYPE: PRT
<213> ORGANISM: Artificial Sequence
<220> FEATURE:
<223> OTHER INFORMATION: Synthetic: LS-Fc-His6-linker-TEV-mCXCL128-96-
      G2-AviTag

<400> SEQUENCE: 40

Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
                20                  25                  30

Pro Leu Lys Glu Cys Pro Pro Cys Ala Ala Pro Asp Leu Leu Gly Gly
            35                  40                  45

Pro Ser Val Phe Ile Phe Pro Pro Lys Ile Lys Asp Val Leu Met Ile
50                  55                  60

Ser Leu Ser Pro Met Val Thr Cys Val Val Asp Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
                100                 105                 110

Val Val Ser Ala Leu Pro Ile Gln His Gln Asp Trp Met Ser Gly Lys
            115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys His His His His His His Ser Ser Gly Val Asp Leu Gly Thr
            260                 265                 270

Glu Asn Leu Tyr Phe Gln Ala Asn Glu Leu Arg Cys Gln Cys Leu Gln
        275                 280                 285
```

```
Thr Met Ala Gly Ile His Leu Lys Asn Ile Gln Ser Leu Lys Val Leu
    290                 295                 300

Pro Ser Gly Pro His Cys Thr Gln Thr Glu Val Ile Ala Thr Leu Lys
305                 310                 315                 320

Asn Gly Arg Glu Ala Cys Leu Asp Pro Glu Ala Pro Leu Val Gln Lys
                325                 330                 335

Ile Val Gln Lys Met Leu Lys Gly Val Pro Lys Gly Gly Leu Asn
            340                 345                 350

Asp Ile Phe Glu Ala Gln Lys Ile Glu Trp His Glu
            355                 360

<210> SEQ ID NO 41
<211> LENGTH: 365
<212> TYPE: PRT
<213> ORGANISM: Artificial Sequence
<220> FEATURE:
<223> OTHER INFORMATION: Synthetic: LS-Fc-His6-linker-TEV-mCXCL231-100-
      G2-AviTag

<400> SEQUENCE: 41

Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
                20                  25                  30

Pro Leu Lys Glu Cys Pro Pro Cys Ala Ala Pro Asp Leu Leu Gly Gly
            35                  40                  45

Pro Ser Val Phe Ile Phe Pro Pro Lys Ile Lys Asp Val Leu Met Ile
50                  55                  60

Ser Leu Ser Pro Met Val Thr Cys Val Val Asp Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys His His His His His His Ser Ser Gly Val Asp Leu Gly Thr
            260                 265                 270

Glu Asn Leu Tyr Phe Gln Ala Ser Glu Leu Arg Cys Gln Cys Leu Lys
        275                 280                 285
```

```
Thr Leu Pro Arg Val Asp Phe Lys Asn Ile Gln Ser Leu Ser Val Thr
        290                 295                 300

Pro Pro Gly Pro His Cys Ala Gln Thr Glu Val Ile Ala Thr Leu Lys
305                 310                 315                 320

Gly Gly Gln Lys Val Cys Leu Asp Pro Glu Ala Pro Leu Val Gln Lys
                325                 330                 335

Ile Ile Gln Lys Ile Leu Asn Lys Gly Lys Ala Asn Gly Gly Gly Leu
        340                 345                 350

Asn Asp Ile Phe Glu Ala Gln Lys Ile Glu Trp His Glu
        355                 360                 365

<210> SEQ ID NO 42
<211> LENGTH: 366
<212> TYPE: PRT
<213> ORGANISM: Artificial Sequence
<220> FEATURE:
<223> OTHER INFORMATION: Synthetic: LS-Fc-His6-linker-TEV-mCXCL548-118-
      G2-AviTag

<400> SEQUENCE: 42

Met Arg Val Pro Ala Gln Leu Leu Gly Leu Leu Leu Trp Leu Pro
1               5                   10                  15

Gly Ala Arg Cys Glu Pro Arg Val Pro Ile Thr Gln Asn Pro Cys Pro
                20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
50                  55                  60

Ser Leu Ser Pro Met Val Thr Cys Val Val Asp Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
        100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
        130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
        180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
        210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys His His His His His His Ser Ser Gly Val Asp Leu Gly Thr
        260                 265                 270

Glu Asn Leu Tyr Phe Gln Ala Thr Glu Leu Arg Cys Val Cys Leu Thr
```

|  | 275 |  |  | 280 |  |  | 285 |  |  |  |  |
|---|---|---|---|---|---|---|---|---|---|---|---|
| Val | Thr | Pro | Lys | Ile | Asn | Pro | Lys | Leu | Ile | Ala | Asn Leu Glu Val Ile |
|  | 290 |  |  | 295 |  |  | 300 |  |  |  |  |

Pro Ala Gly Pro Gln Cys Pro Thr Val Glu Val Ile Ala Lys Leu Lys
305 310 315 320

Asn Gln Lys Glu Val Cys Leu Asp Pro Glu Ala Pro Val Ile Lys Lys
 325 330 335

Ile Ile Gln Lys Ile Leu Gly Ser Asp Lys Lys Lys Ala Gly Gly Gly
 340 345 350

Leu Asn Asp Ile Phe Glu Ala Gln Lys Ile Glu Trp His Glu
 355 360 365

<210> SEQ ID NO 43
<211> LENGTH: 2100
<212> TYPE: DNA
<213> ORGANISM: Artificial Sequence
<220> FEATURE:
<223> OTHER INFORMATION: Synthetic: gWiz-LS-hCXCL135-107-(Gly4Ser)2-
      mouse SA-(Gly4Ser)-His6

<400> SEQUENCE: 43

```
atgagggtcc ccgctcagct cctggggctc ctgctgctct ggctcccagg tgcacgatgt      60
gcctctgtcg ccaccgagct gagatgccag tgcctgcaga ccctgcaggg catccacccc     120
aagaacatcc agagcgtgaa cgtgaagtcc cctggccccc actgcgccca gaccgaagtg     180
atcgccaccc tgaagaacgg ccggaaggcc tgcctgaacc ccgccagccc catcgtgaag     240
aaaatcatcg agaagatgct gaacagcgac aagagcaacg tggaggcgg tagcggaggc     300 ggagggtcgg aagcacacaa gagtgagatc gcccatcggt ataatgattt gggagaacaa     360
catttcaaag gctagtcct gattgccttt tcccagtatc tccagaaatg ctcatacgat     420
gagcatgcca aattagtgca ggaagtaaca gactttgcaa agacgtgtgt tgccgatgag     480
tctgccgcca actgtgacaa atcccttcac actcttttg gagataagtt gtgtgccatt     540
ccaaacctcc gtgaaaacta tggtgaactg gctgactgct gtacaaaaca agagcccgaa     600
agaaacgaat gtttcctgca cacaaagat gacaaccca gcctgccacc atttgaaagg     660
ccagaggctg aggccatgtg cacctccttt aaggaaaacc caaccacctt tatgggacac     720
tatttgcatg aagttgccag aagacatcct tatttctatg ccccagaact tctttactat     780
gctgagcagt acaatgagat tctgacccag tgttgtgcag aggctgacaa ggaaagctgc     840
ctgaccccga agcttgatgg tgtgaaggag aaagcattgg tctcatctgt ccgtcagaga     900
atgaagtgct ccagtatgca aagtttggaa gagagagctt ttaaagcatg gcagtagct      960 cgtctgagcc agacattccc caatgctgac tttgcagaaa tcaccaaatt ggcaacagac    1020
ctgaccaaag tcaacaagga gtgctgccat ggtgacctgc tggaatgcgc agatgacagg    1080
gcggaacttg ccaagtacat gtgtgaaaac caggcgacta tctccagcaa actgcagact    1140
tgctgcgata accactgtt gaagaaagcc cactgtctta gtgaggtgga gcatgacacc    1200
atgcctgctg atctgcctgc cattgctgct gattttgttg aggaccagga agtgtgcaag    1260
aactatgctg aggccaagga tgtcttcctg ggcacgttct tgtatgaata ttcaagaaga    1320
caccctgatt actctgtatc cctgttgctg agacttgcta agaaatatga agccactctg    1380
gaaaagtgct gcgctgaagc caatcctccc gcatgctacg gcacagtgct tgctgaattt    1440
cagcctcttg tagaagagcc taagaacttg gtcaaaacca actgtgatct ttacgagaag    1500
cttggagaat atggattcca aaatgccatt ctagttcgct acacccagaa agcacctcag    1560
```

```
gtgtcaaccc caactctcgt ggaggctgca agaaacctag gaagagtggg caccaagtgt    1620
tgtacacttc ctgaagatca gagactgcct tgtgtggaag actatctgtc tgcaatcctg    1680
aaccgtgtgt gtctgctgca tgagaagacc ccagtgagtg agcatgttac caagtgctgt    1740
agtggatccc tggtggaaag gcggccatgc ttctctgctc tgacagttga tgaaacatat    1800
gtccccaaag agtttaaagc tgagaccttc accttccact ctgatatctg cacacttcca    1860
gagaaggaga agcagattaa gaaacaaacg gctcttgctg agctggtgaa gcacaagccc    1920
aaggctacag cggagcaact gaagactgtc atggatgact ttgcacagtt cctggataca    1980
tgttgcaagg ctgctgacaa ggacacctgc ttctcgactg agggtccaaa ccttgtcact    2040
agatgcaaag acgccttagc cggagggggc ggttcccacc atcaccacca tcactgataa    2100
```

<210> SEQ ID NO 44
<211> LENGTH: 2100
<212> TYPE: DNA
<213> ORGANISM: Artificial Sequence
<220> FEATURE:
<223> OTHER INFORMATION: Synthetic: gWiz-LS-hCXCL235-107-(Gly4Ser)2-
      mouse SA-(Gly4Ser)-His6

<400> SEQUENCE: 44

```
atgagggtcc ccgctcagct cctggggctc ctgctgctct ggctcccagg tgcacgatgt      60
gctcctctgg ccacagagct gagatgccag tgcctccaga cactccaggg catccacctg     120
aagaacatcc agagcgtgaa agtgaagtcc cctggccccc actgcgccca gacagaagtg     180
atcgccaccc tgaagaatgg ccagaaggcc tgcctgaacc ccgccagccc tatggtcaag     240
aaaatcatcg agaagatgct gaagaacggc aagagcaacg gtggaggcgg tagcggaggc     300
ggagggtcgg aagcacacaa gagtgagatc gcccatcggt ataatgattt gggagaacaa     360
catttcaaag gcctagtcct gattgccttt tcccagtatc tccagaaatg ctcatacgat     420
gagcatgcca aattagtgca ggaagtaaca gactttgcaa agacgtgtgt tgccgatgag     480
tctgccgcca actgtgacaa atcccttcac actcttttg gagataagtt gtgtgccatt     540
ccaaacctcc gtgaaaacta tggtgaactg gctgactgct gtacaaaaca agagcccgaa     600
agaaacgaat gtttcctgca acacaaagat gacaacccca gcctgccacc atttgaaagg     660
ccagaggctg aggccatgtg cacctccttt aaggaaaacc caaccacctt atgggacac     720 tatttgcatg aagttgccag aagacatcct tatttctatg ccccagaact tctttactat     780
gctgagcagt acaatgagat tctgacccag tgttgtgcag aggctgacaa ggaaagctgc     840
ctgaccccga gcttgatgg tgtgaaggag aaagcattgg tctcatctgt ccgtcagaga     900
atgaagtgct ccagtatgca gaagtttgga gagagagctt ttaaagcatg gcagtagct     960 cgtctgagcc agacattccc caatgctgac tttgcagaaa tcaccaaatt ggcaacagac    1020
ctgaccaaag tcaacaagga gtgctgccat ggtgacctgc tggaatgcgc agatgacagg    1080
gcggaacttg ccaagtacat gtgtgaaaac caggcgacta tctccagcaa actgcagact    1140
tgctgcgata aaccactgtt gaagaaagcc cactgtctta gtgaggtgga gcatgacacc    1200
atgcctgctg atctgcctgc cattgctgct gattttgttg aggaccagga agtgtgcaag    1260
aactatgctg aggccaagga tgtcttcctg ggcacgttct tgtatgaata ttcaagaaga    1320
caccctgatt actctgtatc cctgttgctg agacttgcta agaaatatga agccactctg    1380
gaaaagtgct gcgctgaagc caatcctccc gcatgctacg gcacagtgct tgctgaattt    1440
cagcctcttg tagaagagcc taagaacttg gtcaaaacca actgtgatct ttacgagaag    1500
```

```
cttggagaat atggattcca aaatgccatt ctagttcgct acacccagaa agcacctcag    1560
gtgtcaaccc caactctcgt ggaggctgca agaaacctag gaagagtggg caccaagtgt    1620
tgtacacttc ctgaagatca gagactgcct tgtgtggaag actatctgtc tgcaatcctg    1680
aaccgtgtgt gtctgctgca tgagaagacc ccagtgagtg agcatgttac caagtgctgt    1740
agtggatccc tggtggaaag gcggccatgc ttctctgctc tgacagttga tgaaacatat    1800
gtccccaaag agtttaaagc tgagaccttc accttccact ctgatatctg cacacttcca    1860
gagaaggaga agcagattaa gaaacaaacg gctcttgctg agctggtgaa gcacaagccc    1920
aaggctacag cggagcaact gaagactgtc atggatgact ttgcacagtt cctggataca    1980
tgttgcaagg ctgctgacaa ggacacctgc ttctcgactg agggtccaaa ccttgtcact    2040
agatgcaaag acgccttagc cggagggggc ggttcccacc atcaccacca tcactgataa    2100
```

<210> SEQ ID NO 45
<211> LENGTH: 2100
<212> TYPE: DNA
<213> ORGANISM: Artificial Sequence
<220> FEATURE:
<223> OTHER INFORMATION: Synthetic: gWiz-LS-hCXCL335-107-(Gly4Ser)2-
      mouse SA-(Gly4Ser)-His6

<400> SEQUENCE: 45

```
atgggggtcc ccgctcagct cctggggctc ctgctgctct ggctcccagg tgcacgatgt      60
gcctctgtcg tgaccgagct gagatgccag tgcctccaga cactccaggg catccacctg     120
aagaacatcc agagcgtgaa cgtgcggagc cctggcccct cattgtgccca gacagaagtg    180 atcgccaccc tgaagaatgg caagaaggcc tgcctgaacc ccgccagccc tatggtgcag    240
aagatcatcg agaagatcct gaacaagggc agcaccaacg gtggaggcgg tagcggaggc    300
ggagggtcgg aagcacacaa gagtgagatc gcccatcggt ataatgattt gggagaacaa    360
catttcaaag gcctagtcct gattgccttt tcccagtatc tccagaaatg ctcatacgat    420
gagcatgcca aattagtgca ggaagtaaca gactttgcaa agacgtgtgt tgccgatgag    480
tctgccgcca actgtgacaa atcccttcac actctttttg gagataagtt gtgtgccatt    540
ccaaacctcc gtgaaaacta tggtgaactg gctgactgct gtacaaaaca agagcccgaa    600
agaaacgaat gttcctgcaa cacaaagat gacaacccca gcctgccacc atttgaaagg    660
ccagaggctg aggccatgtg cacctccttt aaggaaaacc caaccacctt tatgggacac    720
tatttgcatg aagttgccag aagacatcct tatttctatg ccccagaact tctttactat    780
gctgagcagt acaatgagat tctgacccag tgttgtgcag aggctgacaa ggaaagctgc    840
ctgaccccga gcttgatgg tgtgaaggag aaagcattgg tctcatctgt ccgtcagaga    900
atgaagtgct ccagtatgca aagtttgga gagagagctt ttaaagcatg gcagtagct    960 cgtctgagcc agacattccc caatgctgac tttgcagaaa tcaccaaatt ggcaacagac    1020
ctgaccaaag tcaacaagga gtgctgccat ggtgacctgc tggaatgcgc agatgacagg    1080
gcggaacttg ccaagtacat gtgtgaaaac caggcgacta tctccagcaa actgcagact    1140
tgctgcgata aaccactgtt gaagaaagcc cactgtctta gtgaggtgga gcatgacacc    1200
atgcctgctg atctgcctgc cattgctgct gattttgttg aggaccagga agtgtgcaag    1260
aactatgcta aggccaagga tgtcttcctg ggcacgttct tgtatgaata ttcaagaaga    1320
caccctgatt actctgtatc cctgttgctg agacttgcta agaaatatga agccactctg    1380
gaaaagtgct gcgctgaagc caatcctccc gcatgctacg gcacagtgct tgctgaattt    1440
```

```
cagcctcttg tagaagagcc taagaacttg gtcaaaacca actgtgatct ttacgagaag    1500
cttggagaat atggattcca aaatgccatt ctagttcgct acacccagaa agcacctcag    1560
gtgtcaaccc caactctcgt ggaggctgca agaaacctag gaagagtggg caccaagtgt    1620
tgtacacttc ctgaagatca gagactgcct tgtgtggaag actatctgtc tgcaatcctg    1680
aaccgtgtgt gtctgctgca tgagaagacc ccagtgagtg agcatgttac caagtgctgt    1740
agtggatccc tggtggaaag gcggccatgc ttctctgctc tgacagttga tgaaacatat    1800
gtccccaaag agtttaaagc tgagaccttc accttccact ctgatatctg cacacttcca    1860
gagaaggaga agcagattaa gaaacaaacg gctcttgctg agctggtgaa gcacaagccc    1920
aaggctacag cggagcaact gaagactgtc atggatgact ttgcacagtt cctggataca    1980
tgttgcaagg ctgctgacaa ggacacctgc ttctcgactg agggtccaaa ccttgtcact    2040
agatgcaaag acgccttagc cggaggggc ggttcccacc atcaccacca tcactgataa    2100
```

<210> SEQ ID NO 46
<211> LENGTH: 2091
<212> TYPE: DNA
<213> ORGANISM: Artificial Sequence
<220> FEATURE:
<223> OTHER INFORMATION: Synthetic: gWiz-LS-hCXCL432-101-(Gly4Ser)2-
      mouse SA-(Gly4Ser)-His6

<400> SEQUENCE: 46

```
atgagggtcc ccgctcagct cctggggctc ctgctgctct ggctcccagg tgcacgatgt     60
gaggctgaag aggacggcga tctccagtgc ctgtgcgtga aaaccaccag ccaagtgcgg    120
cccagacaca tcaccagcct ggaagtgatc aaggccggac cccactgtcc taccgcccag    180
ctgattgcca ccctgaagaa cggccggaag atctgcctgg acctccaggc cccctgtac    240 aagaagatca tcaagaagct gctggaaagc ggtggaggcg gtagcggagg cggagggtcg    300
gaagcacaca gagtgagat cgcccatcgg tataatgatt gggagaacac acatttcaaa    360
ggcctagtcc tgattgcctt ttcccagtat ctccagaaat gctcatacga tgagcatgcc    420
aaattagtgc aggaagtaac agactttgca aagacgtgtg ttgccgatga gtctgccgcc    480
aactgtgaca aatcccttca cactctttt ggagataagt tgtgtgccat ccaaacctc     540 cgtgaaaact atggtgaact ggctgactgc tgtacaaaac aagagcccga agaaacgaa    600 tgtttcctgc aacacaaaga tgacaacccc agcctgccac catttgaaag ccagagggct    660
gaggccatgt gcacctcctt taaggaaaac ccaaccacct tatgggaca ctatttgcat    720 gaagttgcca aagacatcc ttatttctat gccccagaac ttcttactca tgctgagcag    780
tacaatgaga ttctgaccca gtgttgtgca gaggctgaca ggaaaagctg cctgaccccg    840
aagcttgatg tgtgaagga gaaagcattg gtctcatctg tccgtcagag aatgaagtgc    900
tccagtatgc agaagtttgg agagagagct tttaaagcat gggcagtagc tcgtctgagc    960
cagacattcc ccaatgctga cttttgcagaa atcaccaaat tggcaacaga cctgaccaaa   1020
gtcaacaagg agtgctgcca tggtgacctg ctggaatgcg cagatgacag gcggaactt    1080 gccaagtaca tgtgtgaaaa ccaggcgact atctccagca aactgcagac ttgctgcgat   1140
aaaccactgt tgaagaaagc ccactgtctt agtgaggtgg agcatgacac catgcctgct   1200
gatctgcctg ccattgctgc tgattttgtt gaggaccagg aagtgtgcaa gaactatgct   1260
gaggccaagg atgtcttcct gggcacgttc ttgtatgaat attcaagaag acaccctgat   1320
tactctgtat ccctgttgct gagacttgct aagaaatatg aagccactct ggaaaagtgc   1380
```

```
tgcgctgaag ccaatcctcc cgcatgctac ggcacagtgc ttgctgaatt tcagcctctt    1440
gtagaagagc ctaagaactt ggtcaaaacc aactgtgatc tttacgagaa gcttggagaa    1500
tatggattcc aaaatgccat tctagttcgc tacacccaga agcacctca ggtgtcaacc     1560 ccaactctcg tggaggctgc aagaaaccta ggaagagtgg gcaccaagtg ttgtacactt    1620
cctgaagatc agagactgcc ttgtgtggaa gactatctgt ctgcaatcct gaaccgtgtg    1680
tgtctgctgc atgagaagac cccagtgagt gagcatgtta ccaagtgctg tagtggatcc    1740
ctggtggaaa ggcggccatg cttctctgct ctgacagttg atgaaacata tgtccccaaa    1800
gagtttaaag ctgagacctt caccttccac tctgatatct gcacacttcc agagaaggag    1860
aagcagatta gaaacaaac ggctcttgct gagctggtga agcacaagcc caaggctaca     1920
gcggagcaac tgaagactgt catggatgac tttgcacagt tcctggatac atgttgcaag    1980
gctgctgaca aggacacctg cttctcgact gagggtccaa accttgtcac tagatgcaaa    2040
gacgccttag ccggaggggg cggttcccac catcaccacc atcactgata a             2091

<210> SEQ ID NO 47
<211> LENGTH: 2094
<212> TYPE: DNA
<213> ORGANISM: Artificial Sequence
<220> FEATURE:
<223> OTHER INFORMATION: Synthetic: gWiz-LS-hCXCL544-114-(Gly4Ser)2-
      mouse SA-(Gly4Ser)-His6

<400> SEQUENCE: 47
atgagggtcc ccgctcagct cctggggctc ctgctgctct ggctcccagg tgcacgatgt      60
ctgcgcgagc tgagatgcgt gtgcctgcag accacccagg gcgtgcaccc caagatgatc     120
agcaacctcc aggtgttcgc catcggcccc cagtgcagca aggtggaagt ggtggccagc     180
ctgaagaacg gcaaagagat ctgcctggac cccgaggccc cattcctgaa gaaagtgatc    240
cagaagatcc tggacggcgg caacaaagag aacggtggag gcggtagcgg aggcggaggg    300
tcggaagcac acaagagtga gatcgcccat cggtataatg atttgggaga acaacatttc    360
aaaggcctag tcctgattgc cttttcccag tatctccaga atgctcata cgatgagcat     420 gccaaattag tgcaggaagt aacagacttt gcaaagacgt gtgttgccga tgagtctgcc    480
gccaactgtg acaaatccct tcacactctt tttggagata gttgtgtgc cattccaaac    540 ctccgtgaaa actatggtga actggctgac tgctgtacaa acaagagcc gaaagaaac      600 gaatgttttc tgcaacacaa agatgacaac cccagcctgc caccatttga aaggccagag    660
gctgaggcca tgtgcacctc ctttaaggaa aacccaacca cctttatggg acactatttg    720
catgaagttg ccagaagaca tccttatttc tatgccccag aacttcttta ctatgctgag    780
cagtacaatg agattctgac ccagtgttgt gcagaggctg acaaggaaag ctgcctgacc    840
ccgaagcttg atggtgtgaa ggagaaagca ttggtctcat ctgtccgtca gagaatgaag    900
tgctccagta tgcagaagtt tggagagaga gcttttaaag catgggcagt agctcgtctg    960
agccagacat tccccaatgc tgactttgca gaaatcacca attggcaac agacctgacc    1020 aaagtcaaca aggagtgctg ccatggtgac ctgctggaat cgcagatga cagggcggaa    1080 cttgccaagt acatgtgtga aaaccaggcg actatctcca gcaaactgca gacttgctgc    1140
gataaaccac tgttgaagaa agcccactgt cttagtgagg tggagcatga caccatgcct    1200
gctgatctgc ctgccattgc tgctgatttt gttgaggacc aggaagtgtg caagaactat    1260
gctgaggcca aggatgtctt cctgggcacg ttccttgtatg aatattcaag aagacaccct    1320
```

```
gattactctg tatccctgtt gctgagactt gctaagaaat atgaagccac tctggaaaag    1380
tgctgcgctg aagccaatcc tcccgcatgc tacggcacag tgcttgctga atttcagcct    1440
cttgtagaag agcctaagaa cttggtcaaa ccaactgtg atctttacga gaagcttgga    1500
gaatatggat tccaaaatgc cattctagtt cgctacaccc agaaagcacc tcaggtgtca    1560
accccaactc tcgtggaggc tgcaagaaac ctaggaagag tgggcaccaa gtgttgtaca    1620
cttcctgaag atcagagact gccttgtgtg aagactatc tgtctgcaat cctgaaccgt    1680
gtgtgtctgc tgcatgagaa accccagtg agtgagcatg ttaccaagtg ctgtagtgga    1740
tccctggtgg aaaggcggcc atgcttctct gctctgacag ttgatgaaac atatgtcccc    1800
aaagagttta agctgagac cttcaccttc cactctgata tctgcacact tccagagaag    1860
gagaagcaga ttaagaaaca aacggctctt gctgagctgg tgaagcacaa gcccaaggct    1920
acagcggagc aactgaagac tgtcatggat gactttgcac agttcctgga tacatgttgc    1980
aaggctgctg acaaggacac ctgcttctcg actgagggtc aaaccttgt cactagatgc    2040 aaagacgcct tagccggagg gggcggttcc caccatcacc accatcactg ataa          2094

<210> SEQ ID NO 48
<211> LENGTH: 2097
<212> TYPE: DNA
<213> ORGANISM: Artificial Sequence
<220> FEATURE:
<223> OTHER INFORMATION: Synthetic: gWiz-LS-hCXCL643-114-(Gly4Ser)2-
      mouse SA-(Gly4Ser)-His6

<400> SEQUENCE: 48
atgagggtcc ccgctcagct cctggggctc ctgctgctct ggctcccagg tgcacgatgt      60
gtgctgaccg agctgcggtg cacctgtctg agagtgaccc tgcgcgtgaa ccccaagacc     120
atcggcaagc tccaggtgtt ccctgccggc cctcagtgca gcaaggtgga agtggtggcc     180
agcctgaaaa acggaaaaca agtgtgcctg accccgagg ccccattcct gaagaaagtg     240
atccagaaga tcctggacag cggcaacaag aagaacggtg gaggcggtag cggaggcgga     300
gggtcggaag cacacaagag tgagatcgcc catcggtata tgatttggg agaacaacat     360 ttcaaaggcc tagtcctgat tgccttttcc cagtatctcc agaaatgctc atacgatgag     420
catgccaaat tagtgcagga agtaacagac tttgcaaaga cgtgtgttgc cgatgagtct     480
gccgccaact gtgacaaatc ccttcacact cttttttggag ataagttgtg tgccattcca     540
aacctccgtg aaaactatgg tgaactggct gactgctgta caaaacaaga gcccgaaaga     600
aacgaatgtt tcctgcaaca caagatgac aaccccagcc tgccaccatt tgaaaggcca     660
gaggctgagg ccatgtgcac ctcctttaag gaaaacccaa ccacctttat gggacactat     720
ttgcatgaag ttgccagaag acatccttat ttctatgccc cagaacttct ttactatgct     780
gagcagtaca tgagattct gacccagtgt tgtgcagagg ctgacaagga aagctgcctg     840
accccgaagc ttgatggtgt gaaggagaaa gcattggtct catctgtccg tcagagaatg     900
aagtgctcca gtatgcagaa gtttggagag agagctttta aagcatgggc agtagctcgt     960
ctgagccaga cattccccaa tgctgacttt gcagaaatca ccaaattggc aacagacctg    1020
accaaagtca caaggagtg ctgccatggt gacctgctgg aatgcgcaga tgacagggcg    1080
gaacttgcca gtacatgtg tgaaaaccag gcgactatct ccagcaaact gcagacttgc    1140
tgcgataaac cactgttgaa gaaagccac tgtcttagtg aggtggagca tgacaccatg    1200
cctgctgatc tgcctgccat tgctgctgat tttgttgagg accaggaagt gtgcaagaac    1260
```

```
tatgctgagg ccaaggatgt cttcctgggc acgttcttgt atgaatattc aagaagacac   1320
cctgattact ctgtatccct gttgctgaga cttgctaaga aatatgaagc cactctggaa   1380
aagtgctgcg ctgaagccaa tcctcccgca tgctacggca cagtgcttgc tgaatttcag   1440
cctcttgtag aagagcctaa gaacttggtc aaaaccaact gtgatcttta cgagaagctt   1500
ggagaatatg gattccaaaa tgccattcta gttcgctaca cccagaaagc acctcaggtg   1560
tcaaccccaa ctctcgtgga ggctgcaaga aacctaggaa gagtgggcac caagtgttgt   1620
acacttcctg aagatcagag actgccttgt gtggaagact atctgtctgc aatcctgaac   1680
cgtgtgtgtc tgctgcatga aagaccccca gtgagtgagc atgttaccaa gtgctgtagt   1740
ggatccctgg tggaaaggcg gccatgcttc tctgctctga cagttgatga acatatgtc    1800 cccaaagagt ttaaagctga gaccttcacc ttccactctg atatctgcac acttccagag   1860
aaggagaagc agattaagaa acaaacggct cttgctgagc tggtgaagca caagcccaag   1920
gctacagcgg agcaactgaa gactgtcatg atgactttg cacagttcct ggatacatgt    1980
tgcaaggctg ctgacaagga cacctgcttc tcgactgagg gtccaaacct tgtcactaga   2040
tgcaaagacg ccttagccgg aggggcggt tcccaccatc accaccatca ctgataa       2097
```

<210> SEQ ID NO 49
<211> LENGTH: 2070
<212> TYPE: DNA
<213> ORGANISM: Artificial Sequence
<220> FEATURE:
<223> OTHER INFORMATION: Synthetic: gWiz-LS-hCXCL759-121-(Gly4Ser)2-
     mouse SA-(Gly4Ser)-His6

<400> SEQUENCE: 49

```
atgagggtcc ccgctcagct cctggggctc ctgctgctct ggctcccagg tgcacgatgt    60
gccgagctgc ggtgcatgtg catcaagacc accagcggaa tccaccccaa gaatatccag   120
tccctggaag tgattggcaa gggcacccac tgcaaccagg tggaagtgat tgccacactg   180
aaagacggcc ggaagatctg cctggaccct gacgccccca gaatcaagaa aatcgtgcag   240
aaaaagctgg gtggaggcgg tagcggaggc ggagggtcgg aagcacacaa gagtgagatc   300
gcccatcggt ataatgattt gggagaacaa catttcaaag gcctagtcct gattgccttt   360
tcccagtatc tccagaaatg ctcatacgat gagcatgcca aattagtgca ggaagtaaca   420
gactttgcaa agacgtgtgt tgccgatgag tctgccgcca actgtgacaa tccccttcac   480 actcttttg gagataagtt gtgtgccatt ccaaacctcc gtgaaaacta tggtgaactg   540
gctgactgct gtacaaaaca agagcccgaa agaaacgaat gtttcctgca acacaaagat   600
gacaacccca gcctgccacc atttgaaagg ccagaggctg aggccatgtg cacctccttt   660
aaggaaaacc caaccacctt tatgggacac tatttgcatg aagttgccag aagacatcct   720
tatttctatg cccagaact tctttactat gctgagcagt acaatgagat tctgaccccag   780 tgttgtgcag aggctgacaa ggaaagctgc ctgaccccga gcttgatgg tgtgaaggag   840 aaagcattgg tctcatctgt ccgtcagaga atgaagtgct ccagtatgca aagtttgga    900 gagagagctt taaagcatg gcagtagct cgtctgagcc agacattccc caatgctgac    960
tttgcagaaa tcaccaaatt ggcaacagac ctgaccaaag tcaacaagga gtgctgccat  1020
ggtgacctgc tggaatgcgc agatgacagg gcggaacttg ccaagtacat gtgtgaaaac  1080
caggcgacta tctccagcaa actgcagact tgctgcgata aaccactgtt gaagaaagcc  1140
cactgtctta gtgaggtgga gcatgacacc atgcctgctg atctgcctgc cattgctgct  1200
```

```
gattttgttg aggaccagga agtgtgcaag aactatgctg aggccaagga tgtcttcctg    1260
ggcacgttct tgtatgaata ttcaagaaga caccctgatt actctgtatc cctgttgctg    1320
agacttgcta agaaatatga agccactctg gaaaagtgct gcgctgaagc caatcctccc    1380
gcatgctacg gcacagtgct tgctgaattt cagcctcttg tagaagagcc taagaacttg    1440
gtcaaaacca actgtgatct ttacgagaag cttggagaat atggattcca aaatgccatt    1500
ctagttcgct acacccagaa agcacctcag gtgtcaaccc caactctcgt ggaggctgca    1560
agaaacctag aagagtggg caccaagtgt tgtacacttc ctgaagatca gagactgcct    1620
tgtgtggaag actatctgtc tgcaatcctg aaccgtgtgt gtctgctgca tgagaagacc    1680
ccagtgagtg agcatgttac caagtgctgt agtggatccc tggtggaaag gcggccatgc    1740
ttctctgctc tgacagttga tgaaacatat gtccccaaag agtttaaagc tgagaccttc    1800
accttccact ctgatatctg cacacttcca gagaaggaga agcagattaa gaaacaaacg    1860
gctcttgctg agctggtgaa gcacaagccc aaggctacag cggagcaact gaagactgtc    1920
atggatgact ttgcacagtt cctggataca tgttgcaagg ctgctgacaa ggacacctgc    1980
ttctcgactg agggtccaaa ccttgtcact agatgcaaag acgccttagc cggagggggc    2040
ggttcccacc atcaccacca tcactgataa                                      2070
```

<210> SEQ ID NO 50
<211> LENGTH: 2097
<212> TYPE: DNA
<213> ORGANISM: Artificial Sequence
<220> FEATURE:
<223> OTHER INFORMATION: Synthetic: gWiz-LS-hCXCL828-99-(Gly4Ser)2-mouse
    SA-(Gly4Ser)-His6

<400> SEQUENCE: 50

```
atgagggtcc ccgctcagct cctggggctc ctgctgctct ggctcccagg tgcacgatgt     60
agcgccaaag aactgcggtg ccagtgcatc aagacctaca gcaagccctt ccaccccaag    120
ttcatcaaag aactgagagt gatcgagagc ggccctcact cgccaacac cgagatcatc     180 gtgaagctga gcgacggcag agagctgtgc ctggacccca agaaaaactg ggtgcagcgg    240
gtggtggaaa agttcctgaa gcgggccgag aacagcggtg gaggcggtag cggaggcgga    300
gggtcggaag cacacaagag tgagatcgcc catcggtata tgatttggg agaacaacat    360 ttcaaaggcc tagtcctgat tgccttttcc cagtatctcc agaaatgctc atacgatgag    420
catgccaaat tagtgcagga agtaacagac tttgcaaaga cgtgtgttgc cgatgagtct    480
gccgccaact gtgacaaatc ccttcacact ctttttggag ataagttgtg tgccattcca    540
aacctccgtg aaaactatgg tgaactggct gactgctgta aaaacaaga gcccgaaaga    600 aacgaatgtt tcctgcaaca caaagatgac aaccccagcc tgccaccatt tgaaaggcca    660
gaggctgagg ccatgtgcac ctcctttaag gaaaacccaa ccacctttat gggacactat    720
ttgcatgaag ttgccagaag acatcctat ttctatgccc cagaacttct ttactatgct    780
gagcagtaca atgagattct gacccagtgt tgtgcagagg ctgacaagga agctgcctg    840 accccgaagc ttgatggtgt gaaggagaaa gcattggtct catctgtccg tcagagaatg    900
aagtgctcca gtatgcagaa gtttggagag agagctttta agcatgggc agtagctcgt    960 ctgagccaga cattccccaa tgctgacttt gcagaaatca ccaaattggc aacagaccug   1020
accaaagtca caaggagtg ctgccatggt gacctgctgg aatgcgcaga tgacagggcg   1080
gaacttgcca gtacatgtg tgaaaaccag gcgactatct ccagcaaact gcagacttgc   1140
```

```
tgcgataaac cactgttgaa gaaagcccac tgtcttagtg aggtggagca tgacaccatg   1200
cctgctgatc tgcctgccat tgctgctgat tttgttgagg accaggaagt gtgcaagaac   1260
tatgctgagg ccaaggatgt cttcctgggc acgttcttgt atgaatattc aagaagacac   1320
cctgattact ctgtatccct gttgctgaga cttgctaaga aatatgaagc cactctggaa   1380
aagtgctgcg ctgaagccaa tcctcccgca tgctacggca cagtgcttgc tgaatttcag   1440
cctcttgtag aagagcctaa gaacttggtc aaaaccaact gtgatcttta cgagaagctt   1500
ggagaatatg gattccaaaa tgccattcta gttcgctaca cccagaaagc acctcaggtg   1560
tcaaccccaa ctctcgtgga ggctgcaaga aacctaggaa gagtgggcac caagtgttgt   1620
acacttcctg aagatcagag actgccttgt gtggaagact atctgtctgc aatcctgaac   1680
cgtgtgtgtc tgctgcatga agaccccca gtgagtgagc atgttaccaa gtgctgtagt   1740
ggatccctgg tggaaaggcg gccatgcttc tctgctctga cagttgatga acatatgtc   1800 cccaaagagt ttaaagctga gaccttcacc ttccactctg atatctgcac acttccagag   1860
aaggagaagc agattaagaa acaaacggct cttgctgagc tggtgaagca aagcccaag   1920 gctacagcgg agcaactgaa gactgtcatg atgactttg cacagttcct ggatacatgt   1980
tgcaaggctg ctgacaagga cacctgcttc tcgactgagg gtccaaacct tgtcactaga   2040
tgcaaagacg ccttagccgg aggggcggt tcccaccatc accaccatca ctgataa      2097

<210> SEQ ID NO 51
<211> LENGTH: 2190
<212> TYPE: DNA
<213> ORGANISM: Artificial Sequence
<220> FEATURE:
<223> OTHER INFORMATION: Synthetic: gWiz-LS-hCXCL923-125-(Gly4Ser)2-
      mouse SA-(Gly4Ser)-His6

<400> SEQUENCE: 51
atgagggtcc ccgctcagct cctggggctc ctgctgctct ggctcccagg tgcacgatgt     60
acccccgtcg tgcggaaggg cagatgcagc tgtatcagca ccaaccaggg caccatccat    120
ctccagtctc tgaaggacct gaagcagttc gcccccagcc ccagctgcga gaagatcgag    180
attatcgcca cactgaaaaa cggggtgcag acctgcctga accccgacag cgccgacgtg    240
aaagaactga tcaagaaatg ggagaaacag gtgtcccaga gaagaagca gaagaacgga    300 aagaagcacc agaaaagaa agtgctgaaa gtgcggaagt cccagcggag ccggcagaag    360
aaaaccacag gtggaggcgg tagcggaggc ggagggtcgg aagcacacaa gagtgagatc    420
gcccatcggt ataatgatt gggagaacaa catttcaaag gcctagtcct gattgccttt    480
tcccagtatc tccagaaatg ctcatacgat gagcatgcca attagtgca ggaagtaaca    540 gactttgcaa agacgtgtgt tgccgatgag tctgccgcca actgtgacaa atcccttcac    600 actcttttg gagataagtt gtgtgccatt ccaaacctcc gtgaaaacta tggtgaactg    660
gctgactgct gtacaaaaca agagcccgaa agaaacgaat gtttcctgca acacaaagat    720 gacaaccca gcctgccacc atttgaaagg ccagaggctg aggccatgtg cacctccttt    780
aaggaaaacc caaccacctt tatgggacac tatttgcatg aagttgccag aagacatcct    840
tatttctatg ccccagaact tctttactat gctgagcagt acaatgagat tctgacccag    900
tgttgtgcag aggctgacaa ggaaagctgc tgaccccga gcttgatgg tgtgaaggag    960 aaagcattgg tctcatctgt ccgtcagaga atgaagtgct ccagtatgca gaagtttgga   1020
gagagagctt ttaaagcatg gcagtagct cgtctgagcc agacattccc caatgctgac   1080
```

```
tttgcagaaa tcaccaaatt ggcaacagac ctgaccaaag tcaacaagga gtgctgccat    1140
ggtgacctgc tggaatgcgc agatgacagg gcggaacttg ccaagtacat gtgtgaaaac    1200
caggcgacta tctccagcaa actgcagact tgctgcgata aaccactgtt gaagaaagcc    1260
cactgtctta gtgaggtgga gcatgacacc atgcctgctg atctgcctgc cattgctgct    1320
gattttgttg aggaccagga agtgtgcaag aactatgctg aggccaagga tgtcttcctg    1380
ggcacgttct tgtatgaata ttcaagaaga cccctgatt actctgtatc cctgttgctg    1440
agacttgcta agaaatatga agccactctg gaaaagtgct gcgctgaagc caatcctccc    1500
gcatgctacg gcacagtgct tgctgaattt cagcctcttg tagaagagcc taagaacttg    1560
gtcaaaacca actgtgatct ttacgagaag cttggagaat atggattcca aaatgccatt    1620
ctagttcgct acacccagaa agcacctcag gtgtcaaccc caactctcgt ggaggctgca    1680
agaaacctag aagagtggg caccaagtgt tgtacacttc ctgaagatca gagactgcct    1740
tgtgtggaag actatctgtc tgcaatcctg aaccgtgtgt gtctgctgca tgagaagacc    1800
ccagtgagtg agcatgttac caagtgctgt agtggatccc tggtggaaag gcggccatgc    1860
ttctctgctc tgacagttga tgaaacatat gtccccaaag agtttaaagc tgagaccttc    1920
accttccact ctgatatctg cacacttcca gagaaggaga agcagattaa gaaacaaacg    1980
gctcttgctg agctggtgaa gcacaagccc aaggctacag cggagcaact gaagactgtc    2040
atggatgact ttgcacagtt cctggataca tgttgcaagg ctgctgacaa ggacacctgc    2100
ttctcgactg agggtccaaa ccttgtcact agatgcaaag acgccttagc cggagggggc    2160
ggttcccacc atcaccacca tcactgataa                                    2190

<210> SEQ ID NO 52
<211> LENGTH: 2112
<212> TYPE: DNA
<213> ORGANISM: Artificial Sequence
<220> FEATURE:
<223> OTHER INFORMATION: Synthetic: gWiz-LS-hCXCL1022-98-(Gly4Ser)2-
      mouse SA-(Gly4Ser)-His6

<400> SEQUENCE: 52
atgagggtcc ccgctcagct cctggggctc ctgctgctct ggctcccagg tgcacgatgt     60
gtgcctctga gcagaaccgt gcggtgcacc tgtatcagca tcagcaacca gcccgtgaac    120
cccagaagcc tggaaaagct ggaaatcatc cccgccagcc agttctgccc cagagtggaa    180
attatcgcca ccatgaagaa gaaaggcgag aagcggtgcc tgaaccccga gagcaaggcc    240
atcaagaacc tgctgaaggc cgtgtccaaa gagcggcagca gcggagccc aggtggaggc    300 ggtagcggag gcgagggtc ggaagcacac aagagtgaga tcgcccatcg gtataatgat    360
ttgggagaac aacatttcaa aggcctagtc ctgattgcct tttcccagta tctccagaaa    420
tgctcatacg atgagcatgc caaattagtg caggaagtaa cagactttgc aaagacgtgt    480
gttgccgatg agtctgccgc caactgtgac aaaatccctt cacactcttt tggagataag    540
ttgtgtgcca ttccaaacct ccgtgaaaac tatggtgaac tggctgactg ctgtacaaaa    600
caagagcccg aaagaaacga atgtttcctg caacacaaag atgacaaccc cagcctgcca    660
ccatttgaaa ggccagaggc tgaggccatg tgcacctcct taaggaaaa cccaaccacc    720 tttatgggac actatttgca tgaagttgcc agaagacatc cttatttcta tgccccagaa    780
cttctttact atgctgagca gtacaatgag attctgaccc agtgttgtgc agaggctgac    840
aaggaaagct gcctgacccc gaagcttgat ggtgtgaagg agaaagcatt ggtctcatct    900
```

```
gtccgtcaga gaatgaagtg ctccagtatg cagaagtttg gagagagagc tttaaagca      960 tgggcagtag ctcgtctgag ccagacattc cccaatgctg actttgcaga aatcaccaaa     1020
ttggcaacag acctgaccaa agtcaacaag gagtgctgcc atggtgacct gctggaatgc     1080
gcagatgaca gggcggaact tgccaagtac atgtgtgaaa accaggcgac tatctccagc     1140
aaactgcaga cttgctgcga taaaccactg ttgaagaaag cccactgtct tagtgaggtg     1200
gagcatgaca ccatgcctgc tgatctgcct gccattgctg ctgattttgt tgaggaccag     1260
gaagtgtgca agaactatgc tgaggccaag gatgtcttcc tgggcacgtt cttgtatgaa     1320
tattcaagaa gacaccctga ttactctgta tccctgttgc tgagacttgc taagaaatat     1380
gaagccactc tggaaaagtg ctgcgctgaa gccaatcctc ccgcatgcta cggcacagtg     1440
cttgctgaat tcagcctctc tgtagaagag cctaagaact tggtcaaaac caactgtgat     1500
ctttacgaga agcttggaga atatggattc caaaatgcca ttctagttcg ctacacccag     1560
aaagcacctc aggtgtcaac cccaactctc gtggaggctg caagaaacct aggaagagtg     1620
ggcaccaagt gttgtacact tcctgaagat cagagactgc cttgtgtgga agactatctg     1680
tctgcaatcc tgaaccgtgt gtgtctgctg catgagaaga ccccagtgag tgagcatgtt     1740
accaagtgct gtagtggatc cctggtggaa aggcggccat gcttctctgc tctgacagtt     1800
gatgaaacat atgtccccaa agagtttaaa gctgagacct tcaccttcca ctctgatatc     1860
tgcacacttc cagagaagga gaagcagatt aagaaacaaa cggctcttgc tgagctggtg     1920
aagcacaagc ccaaggctac agcggagcaa ctgaagactg tcatggatga ctttgcacag     1980
ttcctggata catgttgcaa ggctgctgac aaggacacct gcttctcgac tgagggtcca     2040
aaccttgtca ctagatgcaa agacgcctta gccggagggg gcggttccca ccatcaccac     2100
catcactgat aa                                                          2112

<210> SEQ ID NO 53
<211> LENGTH: 2100
<212> TYPE: DNA
<213> ORGANISM: Artificial Sequence
<220> FEATURE:
<223> OTHER INFORMATION: Synthetic: gWiz-LS-hCXCL1122-94-(Gly4Ser)2-
      mouse SA-(Gly4Ser)-His6

<400> SEQUENCE: 53
atgagggtcc ccgctcagct cctggggctc ctgctgctct ggctcccagg tgcacgatgt       60
ttccccatgt tcaagcgggg cagatgcctg tgcatcggcc tggcgtgaa agccgtgaag       120 gtggccgata tcgagaaggc cagcatcatg taccccagca caactgcga caagatcgaa       180 gtgatcatca ccctgaaaga gaacaagggc cagagatgcc tgaatcccaa gtccaagcag       240
gcccggctga tcatcaagaa ggtggaacgg aagaacttcg gtgaggcgg tagcggaggc       300 ggaggggtcgg aagcacacaa gagtgagatc gcccatcggt ataatgattt gggagaacaa       360
catttcaaag gcctagtcct gattgccttt tcccagtatc tccagaaatg ctcatacgat       420
gagcatgcca aattagtgca ggaagtaaca gactttgcaa agacgtgtgt tgccgatgag       480
tctgccgcca actgtgacaa atcccttcac actctttttg gagataagtt gtgtgccatt       540
ccaaacctcc gtgaaaacta tgtggaactg gctgactgct acaaaaacaa agagcccgaa       600
agaaacgaat gtttcctgca acacaaagat gacaacccca gcctgccacc atttgaaagg       660
ccagaggctg aggccatgtg cacctccttt aaggaaaacc caaccacctt tatgggacac       720
tatttgcatg aagttgccag aagacatcct tatttctatg ccccagaact tctttactat       780
```

-continued

```
gctgagcagt acaatgagat tctgacccag tgttgtgcag aggctgacaa ggaaagctgc    840
ctgaccccga agcttgatgg tgtgaaggag aaagcattgg tctcatctgt ccgtcagaga    900
atgaagtgct ccagtatgca gaagtttgga gagagagctt ttaaagcatg gcagtagct    960 cgtctgagcc agacattccc caatgctgac tttgcagaaa tcaccaaatt ggcaacagac   1020
ctgaccaaag tcaacaagga gtgctgccat ggtgacctgc tggaatgcgc agatgacagg   1080
gcggaacttg ccaagtacat gtgtgaaaac caggcgacta tctccagcaa actgcagact   1140
tgctgcgata aaccactgtt gaagaaagcc cactgtctta gtgaggtgga gcatgacacc   1200
atgcctgctg atctgcctgc cattgctgct gattttgttg aggaccagga agtgtgcaag   1260
aactatgctg aggccaagga tgtcttcctg ggcacgttct tgtatgaata ttcaagaaga   1320
caccctgatt actctgtatc cctgttgctg agacttgcta agaaatatga agccactctg   1380
gaaaagtgct gcgctgaagc caatcctccc gcatgctacg gcacagtgct tgctgaattt   1440
cagcctcttg tagaagagcc taagaacttg gtcaaaacca actgtgatct ttacgagaag   1500
cttggagaat atggattcca aaatgccatt ctagttcgct acacccagaa agcacctcag   1560
gtgtcaaccc caactctcgt ggaggctgca agaaacctag aagagtggg caccaagtgt   1620 tgtacacttc ctgaagatca gagactgcct tgtgtggaag actatctgtc tgcaatcctg   1680
aaccgtgtgt gtctgctgca tgagaagacc ccagtgagtg agcatgttac caagtgctgt   1740
agtggatccc tggtggaaag gcggccatgc ttctctgctc tgacagttga tgaaacatat   1800
gtccccaaag agtttaaagc tgagaccttc accttccact ctgatatctg cacacttcca   1860
gagaaggaga agcagattaa gaaacaaacg gctcttgctg agctggtgaa gcacaagccc   1920
aaggctacag cggagcaact gaagactgtc atggatgact ttgcacagtt cctggataca   1980
tgttgcaagg ctgctgacaa ggacacctgc ttctcgactg agggtccaaa ccttgtcact   2040
agatgcaaag acgccttagc cggaggggc ggttcccacc atcaccacca tcactgataa   2100
```

<210> SEQ ID NO 54
<211> LENGTH: 2097
<212> TYPE: DNA
<213> ORGANISM: Artificial Sequence
<220> FEATURE:
<223> OTHER INFORMATION: Synthetic: gWiz-LS-mCXCL125-96-(Gly4Ser)2-mouse
      SA-(Gly4Ser)-His6

<400> SEQUENCE: 54

```
atgagggtcc ccgctcagct cctggggctc ctgctgctct ggctcccagg tgcacgatgt     60 gccccctattg ccaacgagct gcggtgccag tgcctgcaga ccatggccgg catccacctg    120
aagaacatcc agagcctgaa ggtgctgccc agcggccctc actgcaccca gaccgaagtg    180
atcgccaccc tgaagaacgg cagagaggcc tgcctggatc ccgaggcccc cctggtgcag    240
aaaatcgtgc agaaaatgct gaagggcgtg cccaagggtg gaggcggtag cggaggcgga    300
gggtcggaag cacacaagag tgagatcgcc catcggtata tgatttggg agaacaacat    360 ttcaaaggcc tagtcctgat tgccttttcc cagtatctcc agaaatgctc atacgatgag    420
catgccaaat tagtgcagga agtaacagac tttgcaaaga cgtgtgttgc cgatgagtct    480
gccgccaact gtgacaaatc ccttcacact ctttttggag ataagttgtg tgccattcca    540
aacctccgtg aaaactatgg tgaactggct gactgctgta caaaacaaga gcccgaaaga    600
aacgaatgtt tcctgcaaca caagatgac aaccccagcc tgccaccatt tgaaggcca    660 gaggctgagg ccatgtgcac ctccttaag gaaaacccaa ccaccttat gggacactat    720
```

```
ttgcatgaag ttgccagaag acatccttat ttctatgccc agaacttct ttactatgct    780
gagcagtaca atgagattct gacccagtgt tgtgcagagg ctgacaagga aagctgcctg    840
accccgaagc ttgatggtgt gaaggagaaa gcattggtct catctgtccg tcagagaatg    900
aagtgctcca gtatgcagaa gtttggagag agagctttta agcatgggc agtagctcgt    960
ctgagccaga cattccccaa tgctgacttt gcagaaatca ccaaattggc aacagacctg   1020
accaaagtca acaaggagtg ctgccatggt gacctgctgg aatgcgcaga tgacagggcg   1080
gaacttgcca agtacatgtg tgaaaaccag gcgactatct ccagcaaact gcagacttgc   1140
tgcgataaac cactgttgaa gaaagcccac tgtcttagtg aggtggagca tgacaccatg   1200
cctgctgatc tgcctgccat tgctgctgat tttgttgagg accaggaagt gtgcaagaac   1260
tatgctgagg ccaaggatgt cttcctgggc acgttcttgt atgaatattc aagaagacac   1320
cctgattact ctgtatccct gttgctgaga cttgctaaga aatatgaagc cactctggaa   1380
aagtgctgcg ctgaagccaa tcctcccgca tgctacggca cagtgcttgc tgaatttcag   1440
cctcttgtag aagagcctaa gaacttggtc aaaaccaact gtgatcttta cgagaagctt   1500
ggagaatatg gattccaaaa tgccattcta gttcgctaca cccagaaagc acctcaggtg   1560
tcaaccccaa ctctcgtgga ggctgcaaga aacctaggaa gagtgggcac caagtgttgt   1620
acacttcctg aagatcagag actgccttgt gtggaagact atctgtctgc aatcctgaac   1680
cgtgtgtgtc tgctgcatga aagaccccca gtgagtgagc atgttaccaa gtgctgtagt   1740
ggatccctgg tggaaaggcg ccatgcttc tctgctctga cagttgatga acatatgtc   1800
cccaaagagt ttaaagctga gaccttcacc ttccactctg atatctgcac acttccagag   1860
aaggagaagc agattaagaa acaaacggct cttgctgagc tggtgaagca caagcccaag   1920
gctacagcgg agcaactgaa gactgtcatg gatgactttg cacagttcct ggatacatgt   1980
tgcaaggctg ctgacaagga cacctgcttc tcgactgagg gtccaaacct tgtcactaga   2040
tgcaaagacg ccttagccgg aggggggcgt tcccaccatc accaccatca ctgataa      2097
```

<210> SEQ ID NO 55
<211> LENGTH: 2100
<212> TYPE: DNA
<213> ORGANISM: Artificial Sequence
<220> FEATURE:
<223> OTHER INFORMATION: Synthetic: gWiz-LS-mCXCL228-100-(Gly4Ser)2-
      mouse SA-(Gly4Ser)-His6

<400> SEQUENCE: 55

```
atgagggtcc ccgctcagct cctggggctc ctgctgctct ggctcccagg tgcacgatgt     60
gccgtcgtgg ccagcgagct gcggtgccag tgcctgaaaa ccctgccccg ggtggacttc    120
aagaacatcc agagcctgag cgtgacccc cctggccctc actgtgccca gaccgaagtg    180
atcgccaccc tgaagggcgg ccagaaagtg tgcctggacc ccgaggcccc cctggtgcag    240
aagatcatcc agaagatcct gaacaaggc aaggccaacg tggaggcgg tagcggaggc    300
ggagggtcgg aagcacacaa gagtgagatc gcccatcggt ataatgattt gggagaacaa    360
catttcaaag gcctagtcct gattgccttt tcccagtatc tccagaaatg ctcatacgat    420
gagcatgcca aattagtgca ggaagtaaca gactttgcaa agacgtgtgt tgccgatgag    480
tctgccgcca actgtgacaa atcccttcac actctttttg gagataagtt gtgtgccatt    540
ccaaacctcc gtgaaaacta tggtgaactg gctgactgct gtacaaaaca agagcccgaa    600
agaaacgaat gtttcctgca acacaaagat gacaacccca gcctgccacc atttgaaagg    660
```

```
ccagaggctg aggccatgtg cacctccttt aaggaaaacc caaccacctt tatgggacac    720
tatttgcatg aagttgccag aagacatcct tatttctatg ccccagaact tctttactat    780
gctgagcagt acaatgagat tctgacccag tgttgtgcag aggctgacaa ggaaagctgc    840
ctgaccccga agcttgatgg tgtgaaggag aaagcattgg tctcatctgt ccgtcagaga    900
atgaagtgct ccagtatgca gaagtttgga gagagagctt ttaaagcatg gcagtagct     960 cgtctgagcc agacattccc caatgctgac tttgcagaaa tcaccaaatt ggcaacagac   1020
ctgaccaaag tcaacaagga gtgctgccat ggtgacctgc tggaatgcgc agatgacagg   1080
gcggaacttg ccaagtacat gtgtgaaaac caggcgacta ctccagcaa actgcagact    1140 tgctgcgata aaccactgtt gaagaaagcc cactgtctta gtgaggtgga gcatgacacc   1200
atgcctgctg atctgcctgc cattgctgct gattttgttg aggaccagga agtgtgcaag   1260
aactatgctg aggccaagga tgtcttcctg ggcacgttct tgtatgaata ttcaagaaga   1320
caccctgatt actctgtatc cctgttgctg agacttgcta agaaatatga agccactctg   1380
gaaaagtgct gcgctgaagc caatcctccc gcatgctacg gcacagtgct tgctgaattt   1440
cagcctcttg tagaagagcc taagaacttg gtcaaaacca actgtgatct ttacgagaag   1500
cttggagaat atggattcca aaatgccatt ctagttcgct acacccagaa agcacctcag   1560
gtgtcaaccc caactctcgt ggaggctgca agaaacctag aagagtggg caccaagtgt   1620 tgtacacttc ctgaagatca gagactgcct tgtgtggaag actatctgtc tgcaatcctg   1680
aaccgtgtgt gtctgctgca tgagaagacc ccagtgagtg agcatgttac caagtgctgt   1740
agtggatccc tggtggaaag gcggccatgc ttctctgctc tgacagttga tgaaacatat   1800
gtccccaaag agtttaaagc tgagaccttc accttccact ctgatatctg cacacttcca   1860
gagaaggaga agcagattaa gaaacaaacg gctcttgctg agctggtgaa gcacaagccc   1920
aaggctacag cggagcaact gaagactgtc atggatgact ttgcacagtt cctggataca   1980
tgttgcaagg ctgctgacaa ggacacctgc ttctcgactg agggtccaaa ccttgtcact   2040
agatgcaaag acgccttagc cggagggggc ggttcccacc atcaccacca tcactgataa   2100
```

<210> SEQ ID NO 56
<211> LENGTH: 2100
<212> TYPE: DNA
<213> ORGANISM: Artificial Sequence
<220> FEATURE:
<223> OTHER INFORMATION: Synthetic: gWiz-LS-mCXCL328-100-(Gly4Ser)2-
    mouse SA-(Gly4Ser)-His6

<400> SEQUENCE: 56

```
atgagggtcc ccgctcagct cctggggctc ctgctgctct ggctcccagg tgcacgatgt     60
gctgtggtgg cctctgagct gagatgccag tgcctgaaca ccctgccccg ggtggacttc    120
gagacaatcc agagcctgac cgtgaccccc ctggccctc actgtacccca gacagaagtg    180 atcgccaccc tgaaggacgg ccaggaagtg tgcctgaatc cccagggccc cagactccag    240
atcatcatca gaagatcct gaagtccggc aagagcagcg tggaggcgg tagcggaggc    300 ggagggtcgg aagcacacaa gagtgagatc gcccatcggt ataatgattt gggagaacaa    360
catttcaaag gcctagtcct gattgccttt tcccagtatc tccagaaatg ctcatacgat    420
gagcatgcca aattagtgca ggaagtaaca gactttgcaa agacgtgtgt tgccgatgag    480
tctgccgcca actgtgacaa atcccttcac actcttttg gagataagtt gtgtgccatt    540
ccaaacctcc gtgaaaacta tggtgaactg gctgactgct gtacaaaaca agagcccgaa    600
```

```
agaaacgaat gtttcctgca acacaaagat gacaacccca gcctgccacc atttgaaagg    660
ccagaggctg aggccatgtg cacctccttt aaggaaaacc caaccacctt tatgggacac    720
tatttgcatg aagttgccag aagacatcct tatttctatg ccccagaact tctttactat    780
gctgagcagt acaatgagat tctgacccag tgttgtgcag aggctgacaa ggaaagctgc    840
ctgaccccga agcttgatgg tgtgaaggag aaagcattgg tctcatctgt ccgtcagaga    900
atgaagtgct ccagtatgca gaagtttgga gagagagctt ttaaagcatg ggcagtagct    960
cgtctgagcc agacattccc caatgctgac tttgcagaaa tcaccaaatt ggcaacagac   1020
ctgaccaaag tcaacaagga gtgctgccat ggtgacctgc tggaatgcgc agatgacagg   1080
gcggaacttg ccaagtacat gtgtgaaaac caggcgacta tctccagcaa actgcagact   1140
tgctgcgata aaccactgtt gaagaaagcc cactgtctta gtgaggtgga gcatgacacc   1200
atgcctgctg atctgcctgc cattgctgct gattttgttg aggaccagga agtgtgcaag   1260
aactatgctg aggccaagga tgtcttcctg ggcacgttct tgtatgaata ttcaagaaga   1320
caccctgatt actctgtatc cctgttgctg agacttgcta agaaatatga agccactctg   1380
gaaaagtgct cgctgaagc caatcctccc gcatgctacg gcacagtgct tgctgaattt   1440
cagcctcttg tagaagagcc taagaacttg gtcaaaacca actgtgatct ttacgagaag   1500
cttggagaat atggattcca aaatgccatt ctagttcgct acacccagaa agcacctcag   1560
gtgtcaaccc caactctcgt ggaggctgca agaaacctag gaagagtggg caccaagtgt   1620
tgtacacttc ctgaagatca gagactgcct tgtgtggaag actatctgtc tgcaatcctg   1680
aaccgtgtgt gtctgctgca tgagaagacc ccagtgagtg agcatgttac caagtgctgt   1740
agtggatccc tggtggaaag gcggccatgc ttctctgctc tgacagttga tgaaacatat   1800
gtccccaaag agtttaaagc tgagaccttc accttccact ctgatatctg cacacttcca   1860
gagaaggaga agcagattaa gaaacaaacg gctcttgctg agctggtgaa gcacaagccc   1920
aaggctacag cggagcaact gaagactgtc atggatgact ttgcacagtt cctggataca   1980
tgttgcaagg ctgctgacaa ggacacctgc ttctcgactg agggtccaaa ccttgtcact   2040
agatgcaaag acgccttagc cggaggggc ggttcccacc atcaccacca tcactgataa   2100
```

<210> SEQ ID NO 57
<211> LENGTH: 2109
<212> TYPE: DNA
<213> ORGANISM: Artificial Sequence
<220> FEATURE:
<223> OTHER INFORMATION: Synthetic: gWiz-LS-mCXCL430-105-(Gly4Ser)2-
      mouse SA-(Gly4Ser)-His6

<400> SEQUENCE: 57

```
atgagggtcc ccgctcagct cctggggctc ctgctgctct ggctcccagg tgcacgatgt     60 gtgcacatctg ccggccctga ggaaagcgac ggcgatctgt cttgcgtgtg cgtgaaaacc    120
atcagcagcg gcatccacct gaagcacatc accagcctgg aagtgatcaa ggccggcagg    180
cactgtgccg tgcctcagct gattgccacc ctgaagaacg gccggaagat ctgcctggac    240
agacaggccc cctgtacaa gaaagtgatt aagaagatcc tggaaagcgg tggaggcggt    300
agcggaggcg gagggtcgga agcacacaag agtgagatcg cccatcggta taatgatttg    360
ggagaacaac atttcaaagg cctagtcctg attgccttt cccagtatct ccagaaatgc    420
tcatacgatg agcatgccaa attagtgcag gaagtaacag actttgcaaa gacgtgtgtt    480
gccgatgagt ctgccgccaa ctgtgacaaa tcccttcaca ctcttttttgg agataagttg    540
```

```
tgtgccattc caaacctccg tgaaaactat ggtgaactgg ctgactgctg tacaaaacaa    600
gagcccgaaa gaaacgaatg tttcctgcaa cacaaagatg acaacccag cctgccacca    660 tttgaaaggc cagaggctga ggccatgtgc acctccttta aggaaaaccc aaccacctt    720 atgggacact atttgcatga agttgccaga agacatcctt atttctatgc cccagaactt    780
ctttactatg ctgagcagta caatgagatt ctgacccagt gttgtgcaga ggctgacaag    840
gaaagctgcc tgaccccgaa gcttgatggt gtgaaggaga agcattggt ctcatctgtc     900 cgtcagagaa tgaagtgctc cagtatgcag aagtttggag agagctttt taaagcatgg    960 gcagtagctc gtctgagcca gacattcccc aatgctgact ttgcagaaat caccaaattg    1020
gcaacagacc tgaccaaagt caacaaggag tgctgccatg gtgacctgct ggaatgcgca    1080
gatgacaggg cggaacttgc caagtacatg tgtgaaaacc aggcgactat ctccagcaaa    1140
ctgcagactt gctgcgataa accactgttg aagaaagccc actgtcttag tgaggtggag    1200
catgacacca tgcctgctga tctgcctgcc attgctgctg attttgttga ggaccaggaa    1260
gtgtgcaaga actatgctga ggccaaggat gtcttcctgg gcacgttctt gtatgaatat    1320
tcaagaagac ccctgattca ctctgtatcc ctgttgctga cttgctaa gaaatatgaa      1380 gccactctgg aaaagtgctg cgctgaagcc aatcctcccg catgctacgg cacagtgctt    1440
gctgaatttc agcctcttgt agaagagcct aagaacttgg tcaaaaccaa ctgtgatctt    1500
tacgagaagc ttggagaata tggattccaa aatgccattc tagttcgcta cacccagaaa    1560
gcacctcagg tgtcaacccc aactctcgtg gaggctgcaa gaaacctagg aagagtgggc    1620
accaagtgtt gtacacttcc tgaagatcag agactgcctt gtgtggaaga ctatctgtct    1680
gcaatcctga accgtgtgtg tctgctgcat gagaagaccc cagtgagtga gcatgttacc    1740
aagtgctgta gtggatccct ggtggaaagg cggccatgct tctctgctct gacagttgat    1800
gaaacatatg tccccaaaga gtttaaagct gagaccttca ccttccactc tgatatctgc    1860
acacttccag agaaggagaa gcagattaag aaacaaacgg ctcttgctga gctggtgaag    1920
cacaagccca aggctacagc ggagcaactg aagactgtca tggatgactt tgcacagttc    1980
ctggatacat gttgcaaggc tgctgacaag gacacctgct tctcgactga gggtccaaac    2040
cttgtcacta gatgcaaaga cgccttagcc ggaggggcg gttcccacca tcaccaccat    2100
cactgataa                                                            2109
```

<210> SEQ ID NO 58
<211> LENGTH: 2094
<212> TYPE: DNA
<213> ORGANISM: Artificial Sequence
<220> FEATURE:
<223> OTHER INFORMATION: Synthetic: gWiz-LS-mCXCL548-118-(Gly4Ser)2-
      mouse SA-(Gly4Ser)-His6

<400> SEQUENCE: 58

```
atgagggtcc ccgctcagct cctggggctc ctgctgctct ggctcccagg tgcacgatgt    60
gccaccgagc tgagatgcgt gtgcctgacc gtgacccca agatcaaccc caagctgatc    120
gccaacctgg aagtgatccc tgccggccct cagtgcccca ccgtgaagt gattgccaag    180 ctgaagaacc agaaagaagt gtgcctggac cccgaggccc ccgtgatcaa gaagatcatc    240
cagaagatcc tggcagcgca caagaagaaa ccggtggag gcggtagcgg aggcggaggg    300
tcggaagcac acaagagtga gatcgcccat cggtataatg atttgggaga acaacatttc    360
aaaggcctag tcctgattgc cttttcccag tatctccaga aatgctcata cgatgagcat    420
```

```
gccaaattag tgcaggaagt aacagacttt gcaaagacgt gtgttgccga tgagtctgcc    480
gccaactgtg acaaatccct tcacactctt tttggagata agttgtgtgc cattccaaac    540
ctccgtgaaa actatggtga actggctgac tgctgtacaa acaagagcc cgaaagaaac     600 gaatgtttcc tgcaacacaa agatgacaac cccagcctgc caccatttga aggccagag     660 gctgaggcca tgtgcacctc ctttaaggaa aacccaacca cctttatggg acactatttg    720
catgaagttg ccagaagaca tccttatttc tatgccccag aacttcttta ctatgctgag    780
cagtacaatg agattctgac ccagtgttgt gcagaggctg acaaggaaag ctgcctgacc    840
ccgaagcttg atggtgtgaa ggagaaagca ttggtctcat ctgtccgtca gagaatgaag    900
tgctccagta tgcagaagtt tggagagaga gcttttaaag catgggcagt agctcgtctg    960
agccagacat tccccaatgc tgactttgca gaaatcacca aattggcaac agacctgacc   1020
aaagtcaaca aggagtgctg ccatggtgac ctgctggaat gcgcagatga cagggcggaa   1080
cttgccaagt acatgtgtga aaaccaggcg actatctcca gcaaactgca gacttgctgc   1140
gataaaccac tgttgaagaa agcccactgt cttagtgagg tggagcatga ccaccatgcct  1200 gctgatctgc ctgccattgc tgctgatttt gttgaggacc aggaagtgtg caagaactat   1260
gctgaggcca aggatgtctt cctgggcacg ttcttgtatg aatattcaag aagacaccct   1320
gattactctg tatccctgtt gctgagactt gctaagaaat atgaagccac tctggaaaag   1380
tgctgcgctg aagccaatcc tcccgcatgc tacggcacag tgcttgctga atttcagcct   1440
cttgtagaag agcctaagaa cttggtcaaa accaactgtg atctttacga agcttgga    1500 gaatatggat ccaaaatgc cattctagtt cgctacaccc agaaagcacc tcaggtgtca   1560
accccaactc tcgtggaggc tgcaagaaac ctaggaagag tgggcaccaa gtgttgtaca   1620
cttcctgaag atcagagact gccttgtgtg gaagactatc tgtctgcaat cctgaaccgt   1680
gtgtgtctgc tgcatgagaa daccccagtg agtgagcatg ttaccaagtg ctgtagtgga   1740
tccctggtgg aaaggcggcc atgcttctct gctctgacag ttgatgaaac atatgtcccc   1800
aaagagttta agctgagac cttcaccttc cactctgata tctgcacact tccagagaag   1860
gagaagcaga ttaagaaaca aacggctctt gctgagctgg tgaagcacaa gcccaaggct   1920
acagcggagc aactgaagac tgtcatggat gactttgcac agttcctgga tacatgttgc   1980
aaggctgctg acaaggacac ctgcttctcg actgagggtc caaaccttgt cactagatgc   2040
aaagacgcct tagccggagg gggcggttcc caccatcacc accatcactg ataa         2094
```

<210> SEQ ID NO 59
<211> LENGTH: 2079
<212> TYPE: DNA
<213> ORGANISM: Artificial Sequence
<220> FEATURE:
<223> OTHER INFORMATION: Synthetic: gWiz-LS-mCXCL748-113-(Gly4Ser)2-
      mouse SA-(Gly4Ser)-His6

<400> SEQUENCE: 59

```
atgagggtcc ccgctcagct cctggggctc ctgctgctct ggctcccagg tgcacgatgt     60
atcgagctgc ggtgccggtg caccaacacc atcagcggca tcccttttcaa cagcatcagc   120 ctcgtgaacg tgtacagacc cggcgtgcac tgcgccgacg tggaagtgat tgctacactg    180
aagaatgggc agaaaaccctg cctggacccc aacgcccctg cgtgaagcg gatcgtgatg    240 aagattctgg aaggctacgg tggaggcggt agcggaggcg gagggtcgga agcacacaag    300
agtgagatcg cccatcggta taatgatttg ggagaacaac atttcaaagg cctagtcctg    360
```

```
attgccttt  cccagtatct  ccagaaatgc  tcatacgatg  agcatgccaa  attagtgcag       420
gaagtaacag  actttgcaaa  gacgtgtgtt  gccgatgagt  ctgccgccaa  ctgtgacaaa       480
tcccttcaca  ctcttttgg   agataagttg  tgtgccattc  caaacctccg  tgaaaactat       540
ggtgaactgg  ctgactgctg  tacaaaacaa  gagcccgaaa  gaaacgaatg  tttcctgcaa       600
cacaaagatg  acaaccccag  cctgccacca  tttgaaaggc  cagaggctga  ggccatgtgc       660
acctccttta  aggaaaaccc  aaccaccttt  atgggacact  atttgcatga  agttgccaga       720
agacatcctt  atttctatgc  cccagaactt  ctttactatg  ctgagcagta  caatgagatt       780
ctgacccagt  gttgtgcaga  ggctgacaag  gaaagctgcc  tgaccccgaa  gcttgatggt       840
gtgaaggaga  agcattggt   ctcatctgtc  cgtcagagaa  tgaagtgctc  cagtatgcag       900
aagtttggag  agagagcttt  taaagcatgg  gcagtagctc  gtctgagcca  gacattcccc       960
aatgctgact  ttgcagaaat  caccaaattg  gcaacagacc  tgaccaaagt  caacaaggag      1020
tgctgccatg  gtgacctgct  ggaatgcgca  gatgacaggg  cggaacttgc  caagtacatg      1080
tgtgaaaacc  aggcgactat  ctccagcaaa  ctgcagactt  gctgcgataa  accactgttg      1140
aagaaagccc  actgtcttag  tgaggtggag  catgacacca  tgcctgctga  tctgcctgcc      1200
attgctgctg  attttgttga  ggaccaggaa  gtgtgcaaga  actatgctga  ggccaaggat      1260
gtcttcctgg  gcacgttctt  gtatgaatat  tcaagaagac  ccctgattac  tctgtatcc       1320 ctgttgctga  gacttgctaa  gaaatatgaa  gccactctgg  aaaagtgctg  cgctgaagcc      1380
aatcctcccg  catgctacgg  cacagtgctt  gctgaatttc  agcctcttgt  agaagagcct      1440
aagaacttgg  tcaaaaccaa  ctgtgatctt  tacgagaagc  ttggagaata  tggattccaa      1500
aatgccattc  tagttcgcta  cacccagaaa  gcacctcagg  tgtcaacccc  aactctcgtg      1560
gaggctgcaa  gaaacctagg  aagagtgggc  accaagtgtt  gtacacttcc  tgaagatcag      1620
agactgcctt  gtgtggaaga  ctatctgtct  gcaatcctga  accgtgtgtg  tctgctgcat      1680
gagaagaccc  cagtgagtga  gcatgttacc  aagtgctgta  gtggatccct  ggtggaaagg      1740
cggccatgct  ctctgctctc  tgacagttgat  gaaacatatg  tccccaaaga  gtttaaagct      1800
gagaccttca  ccttccactc  tgatatctgc  acacttccag  agaaggagaa  gcagattaag      1860
aaacaaacgg  ctcttgctga  gctggtgaag  cacaagccca  aggctacagc  ggagcaactg      1920
aagactgtca  tggatgactt  tgcacagttc  ctggatacat  gttgcaaggc  tgctgacaag      1980
gacacctgct  tctcgactga  gggtccaaac  cttgtcacta  gatgcaaaga  cgccttagcc      2040
ggagggggcg  gttcccacca  tcaccaccat  cactgataa                              2079

<210> SEQ ID NO 60
<211> LENGTH: 2196
<212> TYPE: DNA
<213> ORGANISM: Artificial Sequence
<220> FEATURE:
<223> OTHER INFORMATION: Synthetic: gWiz-LS-mCXCL922-126-(Gly4Ser)2-
      mouse SA-(Gly4Ser)-His6

<400> SEQUENCE: 60
atgagggtcc  ccgctcagct  cctggggctc  ctgctgctct  ggctcccagg  tgcacgatgt        60
accctcgtga  tccggaacgc  ccggtgcagc  tgtatcagca  ccagcagagg  caccatccac       120
tacaagagcc  tgaaggatct  gaagcagttc  gcccccagcc  caactgcaa   caagaccgag       180 attatcgcca  cactgaaaaa  cggggaccag  acctgtctgg  accccgacag  cgccaacgtg       240
aagaaactga  tgaaggaatg  ggagaagaag  atcagccaga  agaagaagca  gaagcggggc       300
```
aagaaacacc agaaaaacat gaagaaccgg aagcccaaga ccccccagag ccggcggaga    360
tccagaaaga ccacaggtgg aggcggtagc ggaggcggag ggtcggaagc acacaagagt    420
gagatcgccc atcggtataa tgatttggga gaacaacatt tcaaaggcct agtcctgatt    480
gccttttccc agtatctcca gaaatgctca tacgatgagc atgccaaatt agtgcaggaa    540
gtaacagact ttgcaaagac gtgtgttgcc gatgagtctg ccgccaactg tgacaaatcc    600
cttcacactc tttttggaga taagttgtgt gccattccaa acctccgtga aaactatggt    660
gaactggctg actgctgtac aaaacaagag cccgaaagaa cgaatgtttt cctgcaacac    720
aaagatgaca accccagcct gccaccattt gaaaggccag aggctgaggc catgtgcacc    780
tcctttaagg aaaacccaac cacctttatg ggacactatt tgcatgaagt tgccagaaga    840
catccttatt tctatgcccc agaacttctt tactatgctg agcagtacaa tgagattctg    900
acccagtgtt gtgcagaggc tgacaaggaa agctgcctga ccccgaagct tgatggtgtg    960
aaggagaaag cattggtctc atctgtccgt cagagaatga agtgctccag tatgcagaag   1020
tttggagaga gagcttttaa agcatgggca gtagctcgtc tgagccagac attccccaat   1080
gctgactttg cagaaatcac caaattggca acagacctga ccaaagtcaa caaggagtgc   1140
tgccatggtg acctgctgga atgcgcagat acagggcgg aacttgccaa gtacatgtgt   1200
gaaaaccagg cgactatctc cagcaaactg cagacttgct gcgataaacc actgttgaag   1260
aaagcccact gtcttagtga ggtggagcat gacaccatgc ctgctgatct gcctgccatt   1320
gctgctgatt tgttgagga ccaggaagtg tgcaagaact atgctgaggc caaggatgtc   1380
ttcctgggca cgttcttgta tgaatattca agaagacacc ctgattactc tgtatccctg   1440
ttgctgagac ttgctaagaa atatgaagcc actctggaaa agtgctgcgc tgaagccaat   1500
cctcccgcat gctacggcac agtgcttgct gaatttcagc ctcttgtaga agagcctaag   1560
aacttggtca aaaccaactg tgatctttac gagaagcttg gagaatatgg attccaaaat   1620
gccattctag ttcgctacac ccagaaagca cctcaggtgt caaccccaac tctcgtggag   1680
gctgcaagaa acctaggaag agtgggcacc aagtgttgta cacttcctga agatcagaga   1740
ctgccttgtg tggaagacta tctgtctgca atcctgaacc gtgtgtgtct gctgcatgag   1800 aagacccccag tgagtgagca tgttaccaag tgctgtagtg gatccctggt ggaaaggcgg   1860
ccatgcttct ctgctctgac agttgatgaa acatatgtcc ccaaagagtt taaagctgag   1920
accttcacct ccactctga tatctgcaca cttccagaga aggagaagca gattaagaaa   1980
caaacggctc ttgctgagct ggtgaagcac aagcccaagg ctacagcgga gcaactgaag   2040
actgtcatgg atgactttgc acagttcctg gatacatgtt gcaaggctgc tgacaaggac   2100
acctgcttct cgactgaggg tccaaacctt gtcactagat gcaaagacgc cttagccgga   2160 ggggcggtt cccaccatca ccaccatcac tgataa   2196

<210> SEQ ID NO 61
<211> LENGTH: 2112
<212> TYPE: DNA
<213> ORGANISM: Artificial Sequence
<220> FEATURE:
<223> OTHER INFORMATION: Synthetic: gWiz-LS-mCXCL1022-98-(Gly4Ser)2-
      mouse SA-(Gly4Ser)-His6

<400> SEQUENCE: 61
atgagggtcc ccgctcagct cctggggctc ctgctgctct ggctcccagg tgcacgatgt     60
atcccactgg ccagaaccgt gcggtgcaac tgcatccaca tcgacgatgg ccccgtgcgg    120

```
atgagagcca tcggcaagct ggaaatcatc cccgccagcc tgagctgccc cagagtggaa      180
attatcgcca ccatgaagaa gaacgacgag cagcggtgcc tgaacccccga gagcaagacc     240 atcaagaacc tgatgaaggc ctttagccag aagcggagca gagggcccc aggtggaggc       300 ggtagcggag gcggagggtc ggaagcacac aagagtgaga tcgcccatcg gtataatgat      360
ttgggagaac aacatttcaa aggcctagtc ctgattgcct tttcccagta tctccagaaa      420
tgctcatacg atgagcatgc caaattagtc aggaagtaa cagactttgc aaagacgtgt       480
gttgccgatg agtctgccgc caactgtgac aaatcccttc acactctttt tggagataag      540
ttgtgtgcca ttccaaacct ccgtgaaaac tatggtgaac tggctgactg ctgtacaaaa      600
caagagcccg aaagaaacga atgtttcctg caacacaaag atgacaaccc cagcctgcca      660
ccatttgaaa ggccagaggc tgaggccatg tgcacctcct taaggaaaaa cccaaccacc      720
tttatgggac actatttgca tgaagttgcc agaagacatc cttatttcta tgccccagaa      780
cttctttact atgctgagca gtacaatgag attctgaccc agtgttgtgc agaggctgac      840
aaggaaagct gcctgacccc gaagcttgat ggtgtgaagg agaaagcatt ggtctcatct      900
gtccgtcaga gaatgaagtg ctccagtatg cagaagtttg gagagagagc ttttaaagca      960
tgggcagtag ctcgtctgag ccagacattc cccaatgctg actttgcaga aatcaccaaa     1020
ttggcaacag acctgaccaa agtcaacaag gagtgctgcc atggtgacct gctggaatgc     1080
gcagatgaca gggcggaact tgccaagtac atgtgtgaaa accaggcgac tatctccagc     1140
aaactgcaga cttgctgcga taaaccactg ttgaagaaag cccactgtct tagtgaggtg     1200
gagcatgaca ccatgcctgc tgatctgcct gccattgctg ctgattttgt tgaggaccag     1260
gaagtgtgca gaactatgc tgaggccaag gatgtcttcc tgggcacgtt cttgtatgaa      1320
tattcaagaa gacaccctga ttactctgta tccctgttgc tgagacttgc taagaaatat     1380
gaagccactc tggaaaagtg ctgcgctgaa gccaatcctc ccgcatgcta cggcacagtg     1440
cttgctgaat tcagcctct tgtagaagag cctaagaact tggtcaaaac caactgtgat      1500
ctttacgaga agcttggaga atatggattc caaaatgcca ttctagttcg ctacacccag     1560
aaagcacctc aggtgtcaac cccaactctc gtggaggctg caagaaacct aggaagagtg     1620
ggcaccaagt gttgtacact tcctgaagat cagagactgc cttgtgtgga agactatctg     1680
tctgcaatcc tgaaccgtgt gtgtctgctg catgagaaga ccccagtgag tgagcatgtt     1740
accaagtgct gtagtggatc cctggtggaa aggcggccat gcttctctgc tctgacagtt     1800
gatgaaacat atgtcccccaa agagtttaaa gctgagacct tcaccttcca ctctgatatc     1860
tgcacacttc cagagaagga gaagcagatt aagaaacaaa cggctcttgc tgagctggtg     1920
aagcacaagc ccaaggctac agcggagcaa ctgaagactg tcatggatga ctttgcacag     1980
ttcctggata catgttgcaa ggctgctgac aaggacacct gcttctcgac tgagggtcca     2040
aaccttgtca ctagatgcaa agacgcctta gccggagggg gcggttccca ccatcaccac     2100
catcactgat aa                                                          2112
```

<210> SEQ ID NO 62
<211> LENGTH: 2118
<212> TYPE: DNA
<213> ORGANISM: Artificial Sequence
<220> FEATURE:
<223> OTHER INFORMATION: Synthetic: gWiz-LS-mCXCL1122-100-(Gly4Ser)2-
      mouse SA-(Gly4Ser)-His6

<400> SEQUENCE: 62

```
atgagggtcc ccgctcagct cctggggctc ctgctgctct ggctcccagg tgcacgatgt    60
ttcctgatgt tcaagcaggg ccggtgcctg tgcatcggcc tggaatgaa ggccgtgaag    120 atggccgaga tcgagaaggc cagcgtgatc taccccagca acggctgcga caaggtggaa    180
gtgatcgtga ccatgaaggc ccacaagcgg cagagatgcc tggaccccag atccaagcag    240
gcccggctga tcatgcaggc tatcgagaag aagaatttcc tgcggcggca gaacatgggt    300
ggaggcggta gcgaggcgg agggtcggaa gcacacaaga gtgagatcgc ccatcggtat    360
aatgatttgg gagaacaaca tttcaaaggc ctagtcctga ttgccttttc ccagtatctc    420
cagaaatgct catacgatga gcatgccaaa ttagtgcagg aagtaacaga ctttgcaaag    480
acgtgtgttg ccgatgagtc tgccgccaac tgtgacaaat cccttcacac tctttttgga    540
gataagttgt gtgccattcc aaacctccgt gaaaactatg gtgaactggc tgactgctgt    600
acaaaacaag agcccgaaag aaacgaatgt ttcctgcaac acaaagatga caaccccagc    660
ctgccaccat ttgaaaggcc agaggctgag gccatgtgca cctcctttaa ggaaaaccca    720 accacctta tgggacacta tttgcatgaa gttgccagaa gacatcctta tttctatgcc    780
ccagaacttc tttactatgc tgagcagtac aatgagattc tgacccagtg ttgtgcagag    840
gctgacaagg aaagctgcct gaccccgaag cttgatggtg tgaaggagaa agcattggtc    900
tcatctgtcc gtcagagaat gaagtgctcc agtatgcaga agtttggaga gagagctttt    960
aaagcatggg cagtagctcg tctgagccag acattcccca atgctgactt tgcagaaatc    1020
accaaattgg caacagacct gaccaaagtc aacaaggagt gctgccatgg tgacctgctg    1080
gaatgcgcag atgacagggc ggaacttgcc aagtacatgt gtgaaaacca ggcgactatc    1140
tccagcaaac tgcagacttg ctgcgataaa ccactgttga gaaagccca ctgtctagt    1200 gaggtggagc atgacaccat gcctgctgat ctgcctgcca ttgctgctga ttttgttgag    1260
gaccaggaag tgtgcaagaa ctatgctgag gccaaggatg tcttcctggg cacgttcttg    1320
tatgaatatt caagaagaca ccctgattac tctgtatccc tgttgctgag acttgctaag    1380
aaatatgaag ccactctgga aaagtgctgc gctgaagcca atcctcccgc atgctacggc    1440
acagtgcttg ctgaatttca gcctcttgta gaagagccta gaacttggt caaaaccaac    1500 tgtgatcttt acgagaagct ggagaatat ggattccaaa atgccattct agttcgctac    1560
acccagaaag cacctcaggt gtcaaccca actctcgtgg aggctgcaag aaacctagga    1620
agagtgggca ccaagtgttg tacacttcct gaagatcaga gactgccttg tgtggaagac    1680
tatctgtctg caatcctgaa ccgtgtgtgt ctgctgcatg agaagacccc agtgagtgag    1740
catgttacca gtgctgtag tggatccctg gtggaaaggc ggccatgctt ctctgctctg    1800
acagttgatg aaacatatgt ccccaaagag tttaaagctg agaccttcac cttccactct    1860
gatatctgca cacttccaga aaggagaag cagattaaga acaaacggc tcttgctgag    1920 ctggtgaagc acaagcccaa ggctacagcg agcaactga agactgtcat ggatgacttt    1980
gcacagttcc tggatacatg ttgcaaggct gctgacaagg acacctgctt ctcgactgag    2040
ggtccaaacc ttgtcactag atgcaaagac gccttagccg gagggggcgg ttcccaccat    2100
caccaccatc actgataa                                                 2118
```

<210> SEQ ID NO 63
<211> LENGTH: 698
<212> TYPE: PRT
<213> ORGANISM: Artificial Sequence
<220> FEATURE:

<223> OTHER INFORMATION: Synthetic: LS-hCXCL135-107-(Gly4Ser)2-mouse SA-(Gly4Ser)-His6

<400> SEQUENCE: 63

| | | | | | | | | | | | | | | |
|---|---|---|---|---|---|---|---|---|---|---|---|---|---|---|
| Met | Arg | Val | Pro | Ala | Gln | Leu | Leu | Gly | Leu | Leu | Leu | Trp | Leu | Pro |
| 1 | | | | 5 | | | | | 10 | | | | | 15 |
| Gly | Ala | Arg | Cys | Ala | Ser | Val | Ala | Thr | Glu | Leu | Arg | Cys | Gln | Cys | Leu |
| | | | 20 | | | | | 25 | | | | | 30 | | |
| Gln | Thr | Leu | Gln | Gly | Ile | His | Pro | Lys | Asn | Ile | Gln | Ser | Val | Asn | Val |
| | | | 35 | | | | | 40 | | | | | 45 | | |
| Lys | Ser | Pro | Gly | Pro | His | Cys | Ala | Gln | Thr | Glu | Val | Ile | Ala | Thr | Leu |
| | 50 | | | | | 55 | | | | | 60 | | | | |
| Lys | Asn | Gly | Arg | Lys | Ala | Cys | Leu | Asn | Pro | Ala | Ser | Pro | Ile | Val | Lys |
| 65 | | | | | 70 | | | | | 75 | | | | | 80 |
| Lys | Ile | Ile | Glu | Lys | Met | Leu | Asn | Ser | Asp | Lys | Ser | Asn | Gly | Gly | Gly |
| | | | | 85 | | | | | 90 | | | | | 95 | |
| Gly | Ser | Gly | Gly | Gly | Gly | Ser | Glu | Ala | His | Lys | Ser | Glu | Ile | Ala | His |
| | | | 100 | | | | | 105 | | | | | 110 | | |
| Arg | Tyr | Asn | Asp | Leu | Gly | Glu | Gln | His | Phe | Lys | Gly | Leu | Val | Leu | Ile |
| | | | 115 | | | | | 120 | | | | | 125 | | |
| Ala | Phe | Ser | Gln | Tyr | Leu | Gln | Lys | Cys | Ser | Tyr | Asp | Glu | His | Ala | Lys |
| 130 | | | | | 135 | | | | | 140 | | | | | |
| Leu | Val | Gln | Glu | Val | Thr | Asp | Phe | Ala | Lys | Thr | Cys | Val | Ala | Asp | Glu |
| 145 | | | | | 150 | | | | | 155 | | | | | 160 |
| Ser | Ala | Ala | Asn | Cys | Asp | Lys | Ser | Leu | His | Thr | Leu | Phe | Gly | Asp | Lys |
| | | | | 165 | | | | | 170 | | | | | 175 | |
| Leu | Cys | Ala | Ile | Pro | Asn | Leu | Arg | Glu | Asn | Tyr | Gly | Glu | Leu | Ala | Asp |
| | | | 180 | | | | | 185 | | | | | 190 | | |
| Cys | Cys | Thr | Lys | Gln | Glu | Pro | Glu | Arg | Asn | Glu | Cys | Phe | Leu | Gln | His |
| | | | 195 | | | | | 200 | | | | | 205 | | |
| Lys | Asp | Asp | Asn | Pro | Ser | Leu | Pro | Pro | Phe | Glu | Arg | Pro | Glu | Ala | Glu |
| | 210 | | | | | 215 | | | | | 220 | | | | |
| Ala | Met | Cys | Thr | Ser | Phe | Lys | Glu | Asn | Pro | Thr | Thr | Phe | Met | Gly | His |
| 225 | | | | | 230 | | | | | 235 | | | | | 240 |
| Tyr | Leu | His | Glu | Val | Ala | Arg | Arg | His | Pro | Tyr | Phe | Tyr | Ala | Pro | Glu |
| | | | | 245 | | | | | 250 | | | | | 255 | |
| Leu | Leu | Tyr | Tyr | Ala | Glu | Gln | Tyr | Asn | Glu | Ile | Leu | Thr | Gln | Cys | Cys |
| | | | 260 | | | | | 265 | | | | | 270 | | |
| Ala | Glu | Ala | Asp | Lys | Glu | Ser | Cys | Leu | Thr | Pro | Lys | Leu | Asp | Gly | Val |
| | | | 275 | | | | | 280 | | | | | 285 | | |
| Lys | Glu | Lys | Ala | Leu | Val | Ser | Ser | Val | Arg | Gln | Arg | Met | Lys | Cys | Ser |
| | 290 | | | | | 295 | | | | | 300 | | | | |
| Ser | Met | Gln | Lys | Phe | Gly | Glu | Arg | Ala | Phe | Lys | Ala | Trp | Ala | Val | Ala |
| 305 | | | | | 310 | | | | | 315 | | | | | 320 |
| Arg | Leu | Ser | Gln | Thr | Phe | Pro | Asn | Ala | Asp | Phe | Ala | Glu | Ile | Thr | Lys |
| | | | | 325 | | | | | 330 | | | | | 335 | |
| Leu | Ala | Thr | Asp | Leu | Thr | Lys | Val | Asn | Lys | Glu | Cys | Cys | His | Gly | Asp |
| | | | 340 | | | | | 345 | | | | | 350 | | |
| Leu | Leu | Glu | Cys | Ala | Asp | Asp | Arg | Ala | Glu | Leu | Ala | Lys | Tyr | Met | Cys |
| | | | 355 | | | | | 360 | | | | | 365 | | |
| Glu | Asn | Gln | Ala | Thr | Ile | Ser | Ser | Lys | Leu | Gln | Thr | Cys | Cys | Asp | Lys |
| | 370 | | | | | 375 | | | | | 380 | | | | |
| Pro | Leu | Leu | Lys | Lys | Ala | His | Cys | Leu | Ser | Glu | Val | Glu | His | Asp | Thr |
| 385 | | | | | 390 | | | | | 395 | | | | | 400 |

```
Met Pro Ala Asp Leu Pro Ala Ile Ala Ala Asp Phe Val Glu Asp Gln
                405                 410                 415

Glu Val Cys Lys Asn Tyr Ala Glu Ala Lys Asp Val Phe Leu Gly Thr
            420                 425                 430

Phe Leu Tyr Glu Tyr Ser Arg Arg His Pro Asp Tyr Ser Val Ser Leu
        435                 440                 445

Leu Leu Arg Leu Ala Lys Lys Tyr Glu Ala Thr Leu Glu Lys Cys Cys
450                 455                 460

Ala Glu Ala Asn Pro Pro Ala Cys Tyr Gly Thr Val Leu Ala Glu Phe
465                 470                 475                 480

Gln Pro Leu Val Glu Glu Pro Lys Asn Leu Val Lys Thr Asn Cys Asp
                485                 490                 495

Leu Tyr Glu Lys Leu Gly Glu Tyr Gly Phe Gln Asn Ala Ile Leu Val
            500                 505                 510

Arg Tyr Thr Gln Lys Ala Pro Gln Val Ser Thr Pro Thr Leu Val Glu
        515                 520                 525

Ala Ala Arg Asn Leu Gly Arg Val Gly Thr Lys Cys Cys Thr Leu Pro
530                 535                 540

Glu Asp Gln Arg Leu Pro Cys Val Glu Asp Tyr Leu Ser Ala Ile Leu
545                 550                 555                 560

Asn Arg Val Cys Leu Leu His Glu Lys Thr Pro Val Ser Glu His Val
                565                 570                 575

Thr Lys Cys Cys Ser Gly Ser Leu Val Glu Arg Arg Pro Cys Phe Ser
            580                 585                 590

Ala Leu Thr Val Asp Glu Thr Tyr Val Pro Lys Glu Phe Lys Ala Glu
        595                 600                 605

Thr Phe Thr Phe His Ser Asp Ile Cys Thr Leu Pro Glu Lys Glu Lys
610                 615                 620

Gln Ile Lys Lys Gln Thr Ala Leu Ala Glu Leu Val Lys His Lys Pro
625                 630                 635                 640

Lys Ala Thr Ala Glu Gln Leu Lys Thr Val Met Asp Asp Phe Ala Gln
                645                 650                 655

Phe Leu Asp Thr Cys Cys Lys Ala Ala Asp Lys Asp Thr Cys Phe Ser
            660                 665                 670

Thr Glu Gly Pro Asn Leu Val Thr Arg Cys Lys Asp Ala Leu Ala Gly
        675                 680                 685

Gly Gly Gly Ser His His His His His His
690                 695

<210> SEQ ID NO 64
<211> LENGTH: 698
<212> TYPE: PRT
<213> ORGANISM: Artificial Sequence
<220> FEATURE:
<223> OTHER INFORMATION: Synthetic: LS-hCXCL235-107-(Gly4Ser)2-mouse SA-
      (Gly4Ser)-His6

<400> SEQUENCE: 64

Met Arg Val Pro Ala Gln Leu Leu Gly Leu Leu Leu Leu Trp Leu Pro
1               5                   10                  15

Gly Ala Arg Cys Ala Pro Leu Ala Thr Glu Leu Arg Cys Gln Cys Leu
            20                  25                  30

Gln Thr Leu Gln Gly Ile His Leu Lys Asn Ile Gln Ser Val Lys Val
        35                  40                  45

Lys Ser Pro Gly Pro His Cys Ala Gln Thr Glu Val Ile Ala Thr Leu
```

```
            50                  55                  60
Lys Asn Gly Gln Lys Ala Cys Leu Asn Pro Ala Ser Pro Met Val Lys
 65                  70                  75                  80

Lys Ile Ile Glu Lys Met Leu Lys Asn Gly Lys Ser Asn Gly Gly Gly
                 85                  90                  95

Gly Ser Gly Gly Gly Ser Glu Ala His Lys Ser Glu Ile Ala His
                100                 105                 110

Arg Tyr Asn Asp Leu Gly Glu Gln His Phe Lys Gly Leu Val Leu Ile
                115                 120                 125

Ala Phe Ser Gln Tyr Leu Gln Lys Cys Ser Tyr Asp Glu His Ala Lys
            130                 135                 140

Leu Val Gln Glu Val Thr Asp Phe Ala Lys Thr Cys Val Ala Asp Glu
145                 150                 155                 160

Ser Ala Ala Asn Cys Asp Lys Ser Leu His Thr Leu Phe Gly Asp Lys
                165                 170                 175

Leu Cys Ala Ile Pro Asn Leu Arg Glu Asn Tyr Gly Glu Leu Ala Asp
                180                 185                 190

Cys Cys Thr Lys Gln Glu Pro Glu Arg Asn Glu Cys Phe Leu Gln His
            195                 200                 205

Lys Asp Asp Asn Pro Ser Leu Pro Pro Phe Glu Arg Pro Glu Ala Glu
210                 215                 220

Ala Met Cys Thr Ser Phe Lys Glu Asn Pro Thr Thr Phe Met Gly His
225                 230                 235                 240

Tyr Leu His Glu Val Ala Arg Arg His Pro Tyr Phe Tyr Ala Pro Glu
                245                 250                 255

Leu Leu Tyr Tyr Ala Glu Gln Tyr Asn Glu Ile Leu Thr Gln Cys Cys
                260                 265                 270

Ala Glu Ala Asp Lys Glu Ser Cys Leu Thr Pro Lys Leu Asp Gly Val
            275                 280                 285

Lys Glu Lys Ala Leu Val Ser Ser Val Arg Gln Arg Met Lys Cys Ser
            290                 295                 300

Ser Met Gln Lys Phe Gly Glu Arg Ala Phe Lys Ala Trp Ala Val Ala
305                 310                 315                 320

Arg Leu Ser Gln Thr Phe Pro Asn Ala Asp Phe Ala Glu Ile Thr Lys
                325                 330                 335

Leu Ala Thr Asp Leu Thr Lys Val Asn Lys Glu Cys Cys His Gly Asp
                340                 345                 350

Leu Leu Glu Cys Ala Asp Asp Arg Ala Glu Leu Ala Lys Tyr Met Cys
            355                 360                 365

Glu Asn Gln Ala Thr Ile Ser Ser Lys Leu Gln Thr Cys Cys Asp Lys
            370                 375                 380

Pro Leu Leu Lys Lys Ala His Cys Leu Ser Glu Val Glu His Asp Thr
385                 390                 395                 400

Met Pro Ala Asp Leu Pro Ala Ile Ala Ala Asp Phe Val Glu Asp Gln
                405                 410                 415

Glu Val Cys Lys Asn Tyr Ala Glu Ala Lys Asp Val Phe Leu Gly Thr
                420                 425                 430

Phe Leu Tyr Glu Tyr Ser Arg Arg His Pro Asp Tyr Ser Val Ser Leu
            435                 440                 445

Leu Leu Arg Leu Ala Lys Lys Tyr Glu Ala Thr Leu Glu Lys Cys Cys
            450                 455                 460

Ala Glu Ala Asn Pro Pro Ala Cys Tyr Gly Thr Val Leu Ala Glu Phe
465                 470                 475                 480
```

```
Gln Pro Leu Val Glu Glu Pro Lys Asn Leu Val Lys Thr Asn Cys Asp
                485                 490                 495

Leu Tyr Glu Lys Leu Gly Glu Tyr Gly Phe Gln Asn Ala Ile Leu Val
            500                 505                 510

Arg Tyr Thr Gln Lys Ala Pro Gln Val Ser Thr Pro Thr Leu Val Glu
        515                 520                 525

Ala Ala Arg Asn Leu Gly Arg Val Gly Thr Lys Cys Cys Thr Leu Pro
    530                 535                 540

Glu Asp Gln Arg Leu Pro Cys Val Glu Asp Tyr Leu Ser Ala Ile Leu
545                 550                 555                 560

Asn Arg Val Cys Leu Leu His Glu Lys Thr Pro Val Ser Glu His Val
                565                 570                 575

Thr Lys Cys Cys Ser Gly Ser Leu Val Glu Arg Arg Pro Cys Phe Ser
            580                 585                 590

Ala Leu Thr Val Asp Glu Thr Tyr Val Pro Lys Glu Phe Lys Ala Glu
        595                 600                 605

Thr Phe Thr Phe His Ser Asp Ile Cys Thr Leu Pro Glu Lys Glu Lys
    610                 615                 620

Gln Ile Lys Lys Gln Thr Ala Leu Ala Glu Leu Val Lys His Lys Pro
625                 630                 635                 640

Lys Ala Thr Ala Glu Gln Leu Lys Thr Val Met Asp Asp Phe Ala Gln
                645                 650                 655

Phe Leu Asp Thr Cys Cys Lys Ala Ala Asp Lys Asp Thr Cys Phe Ser
            660                 665                 670

Thr Glu Gly Pro Asn Leu Val Thr Arg Cys Lys Asp Ala Leu Ala Gly
        675                 680                 685

Gly Gly Gly Ser His His His His His His
    690                 695

<210> SEQ ID NO 65
<211> LENGTH: 698
<212> TYPE: PRT
<213> ORGANISM: Artificial Sequence
<220> FEATURE:
<223> OTHER INFORMATION: Synthetic: LS-hCXCL335-107-(Gly4Ser)2-mouse SA-
      (Gly4Ser)-His6

<400> SEQUENCE: 65

Met Arg Val Pro Ala Gln Leu Leu Gly Leu Leu Leu Leu Trp Leu Pro
1               5                   10                  15

Gly Ala Arg Cys Ala Ser Val Val Thr Glu Leu Arg Cys Gln Cys Leu
            20                  25                  30

Gln Thr Leu Gln Gly Ile His Leu Lys Asn Ile Gln Ser Val Asn Val
        35                  40                  45

Arg Ser Pro Gly Pro His Cys Ala Gln Thr Glu Val Ile Ala Thr Leu
    50                  55                  60

Lys Asn Gly Lys Lys Ala Cys Leu Asn Pro Ala Ser Pro Met Val Gln
65                  70                  75                  80

Lys Ile Ile Glu Lys Ile Leu Asn Lys Gly Ser Thr Asn Gly Gly Gly
                85                  90                  95

Gly Ser Gly Gly Gly Gly Ser Glu Ala His Lys Ser Glu Ile Ala His
            100                 105                 110

Arg Tyr Asn Asp Leu Gly Glu Gln His Phe Lys Gly Leu Val Leu Ile
        115                 120                 125

Ala Phe Ser Gln Tyr Leu Gln Lys Cys Ser Tyr Asp Glu His Ala Lys
```

```
            130                 135                 140
Leu Val Gln Glu Val Thr Asp Phe Ala Lys Thr Cys Val Ala Asp Glu
145                 150                 155                 160

Ser Ala Ala Asn Cys Asp Lys Ser Leu His Thr Leu Phe Gly Asp Lys
                165                 170                 175

Leu Cys Ala Ile Pro Asn Leu Arg Glu Asn Tyr Gly Glu Leu Ala Asp
                180                 185                 190

Cys Cys Thr Lys Gln Glu Pro Glu Arg Asn Glu Cys Phe Leu Gln His
            195                 200                 205

Lys Asp Asp Asn Pro Ser Leu Pro Pro Phe Glu Arg Pro Glu Ala Glu
        210                 215                 220

Ala Met Cys Thr Ser Phe Lys Glu Asn Pro Thr Thr Phe Met Gly His
225                 230                 235                 240

Tyr Leu His Glu Val Ala Arg Arg His Pro Tyr Phe Tyr Ala Pro Glu
                245                 250                 255

Leu Leu Tyr Tyr Ala Glu Gln Tyr Asn Glu Ile Leu Thr Gln Cys Cys
                260                 265                 270

Ala Glu Ala Asp Lys Glu Ser Cys Leu Thr Pro Lys Leu Asp Gly Val
            275                 280                 285

Lys Glu Lys Ala Leu Val Ser Ser Val Arg Gln Arg Met Lys Cys Ser
        290                 295                 300

Ser Met Gln Lys Phe Gly Glu Arg Ala Phe Lys Ala Trp Ala Val Ala
305                 310                 315                 320

Arg Leu Ser Gln Thr Phe Pro Asn Ala Asp Phe Ala Glu Ile Thr Lys
                325                 330                 335

Leu Ala Thr Asp Leu Thr Lys Val Asn Lys Glu Cys Cys His Gly Asp
                340                 345                 350

Leu Leu Glu Cys Ala Asp Asp Arg Ala Glu Leu Ala Lys Tyr Met Cys
            355                 360                 365

Glu Asn Gln Ala Thr Ile Ser Ser Lys Leu Gln Thr Cys Cys Asp Lys
        370                 375                 380

Pro Leu Leu Lys Lys Ala His Cys Leu Ser Glu Val Glu His Asp Thr
385                 390                 395                 400

Met Pro Ala Asp Leu Pro Ala Ile Ala Ala Asp Phe Val Glu Asp Gln
                405                 410                 415

Glu Val Cys Lys Asn Tyr Ala Glu Ala Lys Asp Val Phe Leu Gly Thr
                420                 425                 430

Phe Leu Tyr Glu Tyr Ser Arg Arg His Pro Asp Tyr Ser Val Ser Leu
            435                 440                 445

Leu Leu Arg Leu Ala Lys Lys Tyr Glu Ala Thr Leu Glu Lys Cys Cys
        450                 455                 460

Ala Glu Ala Asn Pro Pro Ala Cys Tyr Gly Thr Val Leu Ala Glu Phe
465                 470                 475                 480

Gln Pro Leu Val Glu Glu Pro Lys Asn Leu Val Lys Thr Asn Cys Asp
                485                 490                 495

Leu Tyr Glu Lys Leu Gly Glu Tyr Gly Phe Gln Asn Ala Ile Leu Val
                500                 505                 510

Arg Tyr Thr Gln Lys Ala Pro Gln Val Ser Thr Pro Thr Leu Val Glu
            515                 520                 525

Ala Ala Arg Asn Leu Gly Arg Val Gly Thr Lys Cys Cys Thr Leu Pro
        530                 535                 540

Glu Asp Gln Arg Leu Pro Cys Val Glu Asp Tyr Leu Ser Ala Ile Leu
545                 550                 555                 560
```

```
Asn Arg Val Cys Leu Leu His Glu Lys Thr Pro Val Ser Glu His Val
                565                 570                 575

Thr Lys Cys Cys Ser Gly Ser Leu Val Glu Arg Arg Pro Cys Phe Ser
            580                 585                 590

Ala Leu Thr Val Asp Glu Thr Tyr Val Pro Lys Glu Phe Lys Ala Glu
        595                 600                 605

Thr Phe Thr Phe His Ser Asp Ile Cys Thr Leu Pro Glu Lys Glu Lys
    610                 615                 620

Gln Ile Lys Lys Gln Thr Ala Leu Ala Glu Leu Val Lys His Lys Pro
625                 630                 635                 640

Lys Ala Thr Ala Glu Gln Leu Lys Thr Val Met Asp Asp Phe Ala Gln
                645                 650                 655

Phe Leu Asp Thr Cys Cys Lys Ala Ala Asp Lys Asp Thr Cys Phe Ser
            660                 665                 670

Thr Glu Gly Pro Asn Leu Val Thr Arg Cys Lys Asp Ala Leu Ala Gly
        675                 680                 685

Gly Gly Gly Ser His His His His His His
    690                 695

<210> SEQ ID NO 66
<211> LENGTH: 695
<212> TYPE: PRT
<213> ORGANISM: Artificial Sequence
<220> FEATURE:
<223> OTHER INFORMATION: Synthetic: LS-hCXCL432-101-(Gly4Ser)2-mouse SA-
      (Gly4Ser)-His6

<400> SEQUENCE: 66

Met Arg Val Pro Ala Gln Leu Leu Gly Leu Leu Leu Leu Trp Leu Pro
1               5                   10                  15

Gly Ala Arg Cys Glu Ala Glu Glu Asp Gly Asp Leu Gln Cys Leu Cys
                20                  25                  30

Val Lys Thr Thr Ser Gln Val Arg Pro Arg His Ile Thr Ser Leu Glu
            35                  40                  45

Val Ile Lys Ala Gly Pro His Cys Pro Thr Ala Gln Leu Ile Ala Thr
50                  55                  60

Leu Lys Asn Gly Arg Lys Ile Cys Leu Asp Leu Gln Ala Pro Leu Tyr
65                  70                  75                  80

Lys Lys Ile Ile Lys Lys Leu Leu Glu Ser Gly Gly Gly Gly Ser Gly
                85                  90                  95

Gly Gly Gly Ser Glu Ala His Lys Ser Glu Ile Ala His Arg Tyr Asn
                100                 105                 110

Asp Leu Gly Glu Gln His Phe Lys Gly Leu Val Leu Ile Ala Phe Ser
            115                 120                 125

Gln Tyr Leu Gln Lys Cys Ser Tyr Asp Glu His Ala Lys Leu Val Gln
        130                 135                 140

Glu Val Thr Asp Phe Ala Lys Thr Cys Val Ala Asp Glu Ser Ala Ala
145                 150                 155                 160

Asn Cys Asp Lys Ser Leu His Thr Leu Phe Gly Asp Lys Leu Cys Ala
                165                 170                 175

Ile Pro Asn Leu Arg Glu Asn Tyr Gly Glu Leu Ala Asp Cys Cys Thr
            180                 185                 190

Lys Gln Glu Pro Glu Arg Asn Glu Cys Phe Leu Gln His Lys Asp Asp
        195                 200                 205

Asn Pro Ser Leu Pro Pro Phe Glu Arg Pro Glu Ala Glu Ala Met Cys
```

```
                210                 215                 220
Thr Ser Phe Lys Glu Asn Pro Thr Thr Phe Met Gly His Tyr Leu His
225                 230                 235                 240

Glu Val Ala Arg Arg His Pro Tyr Phe Tyr Ala Pro Glu Leu Leu Tyr
                245                 250                 255

Tyr Ala Glu Gln Tyr Asn Glu Ile Leu Thr Gln Cys Cys Ala Glu Ala
                260                 265                 270

Asp Lys Glu Ser Cys Leu Thr Pro Lys Leu Asp Gly Val Lys Glu Lys
                275                 280                 285

Ala Leu Val Ser Ser Val Arg Gln Arg Met Lys Cys Ser Ser Met Gln
290                 295                 300

Lys Phe Gly Glu Arg Ala Phe Lys Ala Trp Ala Val Ala Arg Leu Ser
305                 310                 315                 320

Gln Thr Phe Pro Asn Ala Asp Phe Ala Glu Ile Thr Lys Leu Ala Thr
                325                 330                 335

Asp Leu Thr Lys Val Asn Lys Glu Cys Cys His Gly Asp Leu Leu Glu
                340                 345                 350

Cys Ala Asp Asp Arg Ala Glu Leu Ala Lys Tyr Met Cys Glu Asn Gln
                355                 360                 365

Ala Thr Ile Ser Ser Lys Leu Gln Thr Cys Cys Asp Lys Pro Leu Leu
                370                 375                 380

Lys Lys Ala His Cys Leu Ser Glu Val Glu His Asp Thr Met Pro Ala
385                 390                 395                 400

Asp Leu Pro Ala Ile Ala Ala Asp Phe Val Glu Asp Gln Glu Val Cys
                405                 410                 415

Lys Asn Tyr Ala Glu Ala Lys Asp Val Phe Leu Gly Thr Phe Leu Tyr
                420                 425                 430

Glu Tyr Ser Arg Arg His Pro Asp Tyr Ser Val Ser Leu Leu Leu Arg
                435                 440                 445

Leu Ala Lys Lys Tyr Glu Ala Thr Leu Glu Lys Cys Cys Ala Glu Ala
                450                 455                 460

Asn Pro Pro Ala Cys Tyr Gly Thr Val Leu Ala Glu Phe Gln Pro Leu
465                 470                 475                 480

Val Glu Glu Pro Lys Asn Leu Val Lys Thr Asn Cys Asp Leu Tyr Glu
                485                 490                 495

Lys Leu Gly Glu Tyr Gly Phe Gln Asn Ala Ile Leu Val Arg Tyr Thr
                500                 505                 510

Gln Lys Ala Pro Gln Val Ser Thr Pro Thr Leu Val Glu Ala Ala Arg
                515                 520                 525

Asn Leu Gly Arg Val Gly Thr Lys Cys Cys Thr Leu Pro Glu Asp Gln
530                 535                 540

Arg Leu Pro Cys Val Glu Asp Tyr Leu Ser Ala Ile Leu Asn Arg Val
545                 550                 555                 560

Cys Leu Leu His Glu Lys Thr Pro Val Ser Glu His Val Thr Lys Cys
                565                 570                 575

Cys Ser Gly Ser Leu Val Glu Arg Arg Pro Cys Phe Ser Ala Leu Thr
                580                 585                 590

Val Asp Glu Thr Tyr Val Pro Lys Glu Phe Lys Ala Glu Thr Phe Thr
                595                 600                 605

Phe His Ser Asp Ile Cys Thr Leu Pro Glu Lys Glu Lys Gln Ile Lys
                610                 615                 620

Lys Gln Thr Ala Leu Ala Glu Leu Val Lys His Lys Pro Lys Ala Thr
625                 630                 635                 640
```

```
Ala Glu Gln Leu Lys Thr Val Met Asp Asp Phe Ala Gln Phe Leu Asp
                645                 650                 655

Thr Cys Cys Lys Ala Ala Asp Lys Asp Thr Cys Phe Ser Thr Glu Gly
            660                 665                 670

Pro Asn Leu Val Thr Arg Cys Lys Asp Ala Leu Ala Gly Gly Gly Gly
        675                 680                 685

Ser His His His His His
    690             695

<210> SEQ ID NO 67
<211> LENGTH: 696
<212> TYPE: PRT
<213> ORGANISM: Artificial Sequence
<220> FEATURE:
<223> OTHER INFORMATION: Synthetic: LS-hCXCL544-114-(Gly4Ser)2-mouse SA-
      (Gly4Ser)-His6

<400> SEQUENCE: 67

Met Arg Val Pro Ala Gln Leu Leu Gly Leu Leu Leu Leu Trp Leu Pro
1               5                   10                  15

Gly Ala Arg Cys Leu Arg Glu Leu Arg Cys Val Cys Leu Gln Thr Thr
            20                  25                  30

Gln Gly Val His Pro Lys Met Ile Ser Asn Leu Gln Val Phe Ala Ile
        35                  40                  45

Gly Pro Gln Cys Ser Lys Val Glu Val Val Ala Ser Leu Lys Asn Gly
    50                  55                  60

Lys Glu Ile Cys Leu Asp Pro Glu Ala Pro Phe Leu Lys Lys Val Ile
65                  70                  75                  80

Gln Lys Ile Leu Asp Gly Gly Asn Lys Glu Asn Gly Gly Gly Gly Ser
                85                  90                  95

Gly Gly Gly Gly Ser Glu Ala His Lys Ser Glu Ile Ala His Arg Tyr
            100                 105                 110

Asn Asp Leu Gly Glu Gln His Phe Lys Gly Leu Val Leu Ile Ala Phe
        115                 120                 125

Ser Gln Tyr Leu Gln Lys Cys Ser Tyr Asp Glu His Ala Lys Leu Val
    130                 135                 140

Gln Glu Val Thr Asp Phe Ala Lys Thr Cys Val Ala Asp Glu Ser Ala
145                 150                 155                 160

Ala Asn Cys Asp Lys Ser Leu His Thr Leu Phe Gly Asp Lys Leu Cys
                165                 170                 175

Ala Ile Pro Asn Leu Arg Glu Asn Tyr Gly Glu Leu Ala Asp Cys Cys
            180                 185                 190

Thr Lys Gln Glu Pro Glu Arg Asn Glu Cys Phe Leu Gln His Lys Asp
        195                 200                 205

Asp Asn Pro Ser Leu Pro Pro Phe Glu Arg Pro Glu Ala Glu Ala Met
    210                 215                 220

Cys Thr Ser Phe Lys Glu Asn Pro Thr Thr Phe Met Gly His Tyr Leu
225                 230                 235                 240

His Glu Val Ala Arg Arg His Pro Tyr Phe Tyr Ala Pro Glu Leu Leu
                245                 250                 255

Tyr Tyr Ala Glu Gln Tyr Asn Glu Ile Leu Thr Gln Cys Cys Ala Glu
            260                 265                 270

Ala Asp Lys Glu Ser Cys Leu Thr Pro Lys Leu Asp Gly Val Lys Glu
        275                 280                 285

Lys Ala Leu Val Ser Ser Val Arg Gln Arg Met Lys Cys Ser Ser Met
```

```
              290                 295                 300
Gln Lys Phe Gly Glu Arg Ala Phe Lys Ala Trp Ala Val Ala Arg Leu
305                 310                 315                 320

Ser Gln Thr Phe Pro Asn Ala Asp Phe Ala Glu Ile Thr Lys Leu Ala
                325                 330                 335

Thr Asp Leu Thr Lys Val Asn Lys Glu Cys Cys His Gly Asp Leu Leu
                340                 345                 350

Glu Cys Ala Asp Asp Arg Ala Glu Leu Ala Lys Tyr Met Cys Glu Asn
                355                 360                 365

Gln Ala Thr Ile Ser Ser Lys Leu Gln Thr Cys Cys Asp Lys Pro Leu
            370                 375                 380

Leu Lys Lys Ala His Cys Leu Ser Glu Val Glu His Asp Thr Met Pro
385                 390                 395                 400

Ala Asp Leu Pro Ala Ile Ala Ala Asp Phe Val Glu Asp Gln Glu Val
                405                 410                 415

Cys Lys Asn Tyr Ala Glu Ala Lys Asp Val Phe Leu Gly Thr Phe Leu
                420                 425                 430

Tyr Glu Tyr Ser Arg Arg His Pro Asp Tyr Ser Val Ser Leu Leu Leu
            435                 440                 445

Arg Leu Ala Lys Lys Tyr Glu Ala Thr Leu Glu Lys Cys Cys Ala Glu
450                 455                 460

Ala Asn Pro Pro Ala Cys Tyr Gly Thr Val Leu Ala Glu Phe Gln Pro
465                 470                 475                 480

Leu Val Glu Glu Pro Lys Asn Leu Val Lys Thr Asn Cys Asp Leu Tyr
                485                 490                 495

Glu Lys Leu Gly Glu Tyr Gly Phe Gln Asn Ala Ile Leu Val Arg Tyr
            500                 505                 510

Thr Gln Lys Ala Pro Gln Val Ser Thr Pro Thr Leu Val Glu Ala Ala
            515                 520                 525

Arg Asn Leu Gly Arg Val Gly Thr Lys Cys Cys Thr Leu Pro Glu Asp
530                 535                 540

Gln Arg Leu Pro Cys Val Glu Asp Tyr Leu Ser Ala Ile Leu Asn Arg
545                 550                 555                 560

Val Cys Leu Leu His Glu Lys Thr Pro Val Ser Glu His Val Thr Lys
                565                 570                 575

Cys Cys Ser Gly Ser Leu Val Glu Arg Arg Pro Cys Phe Ser Ala Leu
            580                 585                 590

Thr Val Asp Glu Thr Tyr Val Pro Lys Glu Phe Lys Ala Glu Thr Phe
            595                 600                 605

Thr Phe His Ser Asp Ile Cys Thr Leu Pro Glu Lys Glu Lys Gln Ile
            610                 615                 620

Lys Lys Gln Thr Ala Leu Ala Glu Leu Val Lys His Lys Pro Lys Ala
625                 630                 635                 640

Thr Ala Glu Gln Leu Lys Thr Val Met Asp Asp Phe Ala Gln Phe Leu
                645                 650                 655

Asp Thr Cys Cys Lys Ala Ala Asp Lys Asp Thr Cys Phe Ser Thr Glu
                660                 665                 670

Gly Pro Asn Leu Val Thr Arg Cys Lys Asp Ala Leu Ala Gly Gly Gly
            675                 680                 685

Gly Ser His His His His His His
    690                 695

<210> SEQ ID NO 68
```

<211> LENGTH: 697
<212> TYPE: PRT
<213> ORGANISM: Artificial Sequence
<220> FEATURE:
<223> OTHER INFORMATION: Synthetic: LS-hCXCL643-114-(Gly4Ser)2-mouse SA-
      (Gly4Ser)-His6

<400> SEQUENCE: 68

```
Met Arg Val Pro Ala Gln Leu Leu Gly Leu Leu Leu Trp Leu Pro
1               5                   10                  15

Gly Ala Arg Cys Val Leu Thr Glu Leu Arg Cys Thr Cys Leu Arg Val
            20                  25                  30

Thr Leu Arg Val Asn Pro Lys Thr Ile Gly Lys Leu Gln Val Phe Pro
            35                  40                  45

Ala Gly Pro Gln Cys Ser Lys Val Glu Val Val Ala Ser Leu Lys Asn
50                  55                  60

Gly Lys Gln Val Cys Leu Asp Pro Glu Ala Pro Phe Leu Lys Lys Val
65                  70                  75                  80

Ile Gln Lys Ile Leu Asp Ser Gly Asn Lys Lys Asn Gly Gly Gly
                85                  90                  95

Ser Gly Gly Gly Ser Glu Ala His Lys Ser Glu Ile Ala His Arg
            100                 105                 110

Tyr Asn Asp Leu Gly Glu Gln His Phe Lys Gly Leu Val Leu Ile Ala
            115                 120                 125

Phe Ser Gln Tyr Leu Gln Lys Cys Ser Tyr Asp Glu His Ala Lys Leu
130                 135                 140

Val Gln Glu Val Thr Asp Phe Ala Lys Thr Cys Val Ala Asp Glu Ser
145                 150                 155                 160

Ala Ala Asn Cys Asp Lys Ser Leu His Thr Leu Phe Gly Asp Lys Leu
                165                 170                 175

Cys Ala Ile Pro Asn Leu Arg Glu Asn Tyr Gly Glu Leu Ala Asp Cys
            180                 185                 190

Cys Thr Lys Gln Glu Pro Glu Arg Asn Glu Cys Phe Leu Gln His Lys
            195                 200                 205

Asp Asp Asn Pro Ser Leu Pro Pro Phe Glu Arg Pro Glu Ala Glu Ala
210                 215                 220

Met Cys Thr Ser Phe Lys Glu Asn Pro Thr Thr Phe Met Gly His Tyr
225                 230                 235                 240

Leu His Glu Val Ala Arg Arg His Pro Tyr Phe Tyr Ala Pro Glu Leu
                245                 250                 255

Leu Tyr Tyr Ala Glu Gln Tyr Asn Glu Ile Leu Thr Gln Cys Cys Ala
            260                 265                 270

Glu Ala Asp Lys Glu Ser Cys Leu Thr Pro Lys Leu Asp Gly Val Lys
            275                 280                 285

Glu Lys Ala Leu Val Ser Ser Val Arg Gln Arg Met Lys Cys Ser Ser
290                 295                 300

Met Gln Lys Phe Gly Glu Arg Ala Phe Lys Ala Trp Ala Val Ala Arg
305                 310                 315                 320

Leu Ser Gln Thr Phe Pro Asn Ala Asp Phe Ala Glu Ile Thr Lys Leu
                325                 330                 335

Ala Thr Asp Leu Thr Lys Val Asn Lys Glu Cys Cys His Gly Asp Leu
            340                 345                 350

Leu Glu Cys Ala Asp Asp Arg Ala Glu Leu Ala Lys Tyr Met Cys Glu
            355                 360                 365

Asn Gln Ala Thr Ile Ser Ser Lys Leu Gln Thr Cys Cys Asp Lys Pro
```

```
                    370               375               380
Leu Leu Lys Lys Ala His Cys Leu Ser Glu Val Glu His Asp Thr Met
385                 390               395               400

Pro Ala Asp Leu Pro Ala Ile Ala Ala Asp Phe Val Glu Asp Gln Glu
                405               410               415

Val Cys Lys Asn Tyr Ala Glu Ala Lys Asp Val Phe Leu Gly Thr Phe
                420               425               430

Leu Tyr Glu Tyr Ser Arg Arg His Pro Asp Tyr Ser Val Ser Leu Leu
                435               440               445

Leu Arg Leu Ala Lys Lys Tyr Glu Ala Thr Leu Glu Lys Cys Cys Ala
450                 455               460

Glu Ala Asn Pro Pro Ala Cys Tyr Gly Thr Val Leu Ala Glu Phe Gln
465                 470               475               480

Pro Leu Val Glu Glu Pro Lys Asn Leu Val Lys Thr Asn Cys Asp Leu
                485               490               495

Tyr Glu Lys Leu Gly Glu Tyr Gly Phe Gln Asn Ala Ile Leu Val Arg
                500               505               510

Tyr Thr Gln Lys Ala Pro Gln Val Ser Thr Pro Thr Leu Val Glu Ala
                515               520               525

Ala Arg Asn Leu Gly Arg Val Gly Thr Lys Cys Cys Thr Leu Pro Glu
530                 535               540

Asp Gln Arg Leu Pro Cys Val Glu Asp Tyr Leu Ser Ala Ile Leu Asn
545                 550               555               560

Arg Val Cys Leu Leu His Glu Lys Thr Pro Val Ser Glu His Val Thr
                565               570               575

Lys Cys Cys Ser Gly Ser Leu Val Glu Arg Arg Pro Cys Phe Ser Ala
                580               585               590

Leu Thr Val Asp Glu Thr Tyr Val Pro Lys Glu Phe Lys Ala Glu Thr
                595               600               605

Phe Thr Phe His Ser Asp Ile Cys Thr Leu Pro Glu Lys Glu Lys Gln
                610               615               620

Ile Lys Lys Gln Thr Ala Leu Ala Glu Leu Val Lys His Lys Pro Lys
625                 630               635               640

Ala Thr Ala Glu Gln Leu Lys Thr Val Met Asp Asp Phe Ala Gln Phe
                645               650               655

Leu Asp Thr Cys Cys Lys Ala Ala Asp Lys Asp Thr Cys Phe Ser Thr
                660               665               670

Glu Gly Pro Asn Leu Val Thr Arg Cys Lys Asp Ala Leu Ala Gly Gly
                675               680               685

Gly Gly Ser His His His His His His
                690               695

<210> SEQ ID NO 69
<211> LENGTH: 688
<212> TYPE: PRT
<213> ORGANISM: Artificial Sequence
<220> FEATURE:
<223> OTHER INFORMATION: Synthetic: LS-hCXCL759-121-(Gly4Ser)2-mouse SA-
      (Gly4Ser)-His6

<400> SEQUENCE: 69

Met Arg Val Pro Ala Gln Leu Leu Gly Leu Leu Leu Leu Trp Leu Pro
1                   5                 10                15

Gly Ala Arg Cys Ala Glu Leu Arg Cys Met Cys Ile Lys Thr Thr Ser
                20                25                30
```

```
Gly Ile His Pro Lys Asn Ile Gln Ser Leu Glu Val Ile Gly Lys Gly
         35                  40                  45

Thr His Cys Asn Gln Val Glu Val Ile Ala Thr Leu Lys Asp Gly Arg
 50                  55                  60

Lys Ile Cys Leu Asp Pro Asp Ala Pro Arg Ile Lys Lys Ile Val Gln
 65                  70                  75                  80

Lys Lys Leu Gly Gly Gly Ser Gly Gly Gly Ser Glu Ala His
                 85                  90                  95

Lys Ser Glu Ile Ala His Arg Tyr Asn Asp Leu Gly Glu Gln His Phe
            100                 105                 110

Lys Gly Leu Val Leu Ile Ala Phe Ser Gln Tyr Leu Gln Lys Cys Ser
            115                 120                 125

Tyr Asp Glu His Ala Lys Leu Val Gln Glu Val Thr Asp Phe Ala Lys
130                 135                 140

Thr Cys Val Ala Asp Glu Ser Ala Ala Asn Cys Asp Lys Ser Leu His
145                 150                 155                 160

Thr Leu Phe Gly Asp Lys Leu Cys Ala Ile Pro Asn Leu Arg Glu Asn
                165                 170                 175

Tyr Gly Glu Leu Ala Asp Cys Cys Thr Lys Gln Glu Pro Glu Arg Asn
            180                 185                 190

Glu Cys Phe Leu Gln His Lys Asp Asp Asn Pro Ser Leu Pro Pro Phe
        195                 200                 205

Glu Arg Pro Glu Ala Glu Ala Met Cys Thr Ser Phe Lys Glu Asn Pro
    210                 215                 220

Thr Thr Phe Met Gly His Tyr Leu His Glu Val Ala Arg Arg His Pro
225                 230                 235                 240

Tyr Phe Tyr Ala Pro Glu Leu Leu Tyr Tyr Ala Glu Gln Tyr Asn Glu
                245                 250                 255

Ile Leu Thr Gln Cys Cys Ala Glu Ala Asp Lys Glu Ser Cys Leu Thr
            260                 265                 270

Pro Lys Leu Asp Gly Val Lys Glu Lys Ala Leu Val Ser Ser Val Arg
        275                 280                 285

Gln Arg Met Lys Cys Ser Ser Met Gln Lys Phe Gly Glu Arg Ala Phe
    290                 295                 300

Lys Ala Trp Ala Val Ala Arg Leu Ser Gln Thr Phe Pro Asn Ala Asp
305                 310                 315                 320

Phe Ala Glu Ile Thr Lys Leu Ala Thr Asp Leu Thr Lys Val Asn Lys
                325                 330                 335

Glu Cys Cys His Gly Asp Leu Leu Glu Cys Ala Asp Asp Arg Ala Glu
            340                 345                 350

Leu Ala Lys Tyr Met Cys Glu Asn Gln Ala Thr Ile Ser Ser Lys Leu
        355                 360                 365

Gln Thr Cys Cys Asp Lys Pro Leu Leu Lys Lys Ala His Cys Leu Ser
    370                 375                 380

Glu Val Glu His Asp Thr Met Pro Ala Asp Leu Pro Ala Ile Ala Ala
385                 390                 395                 400

Asp Phe Val Glu Asp Gln Glu Val Cys Lys Asn Tyr Ala Glu Ala Lys
                405                 410                 415

Asp Val Phe Leu Gly Thr Phe Leu Tyr Glu Tyr Ser Arg Arg His Pro
            420                 425                 430

Asp Tyr Ser Val Ser Leu Leu Leu Arg Leu Ala Lys Lys Tyr Glu Ala
        435                 440                 445

Thr Leu Glu Lys Cys Cys Ala Glu Ala Asn Pro Pro Ala Cys Tyr Gly
```

```
            450                 455                 460
Thr Val Leu Ala Glu Phe Gln Pro Leu Val Glu Pro Lys Asn Leu
465                 470                 475                 480

Val Lys Thr Asn Cys Asp Leu Tyr Glu Lys Leu Gly Glu Tyr Gly Phe
                485                 490                 495

Gln Asn Ala Ile Leu Val Arg Tyr Thr Gln Lys Ala Pro Gln Val Ser
                500                 505                 510

Thr Pro Thr Leu Val Glu Ala Ala Arg Asn Leu Gly Arg Val Gly Thr
            515                 520                 525

Lys Cys Cys Thr Leu Pro Glu Asp Gln Arg Leu Pro Cys Val Glu Asp
        530                 535                 540

Tyr Leu Ser Ala Ile Leu Asn Arg Val Cys Leu Leu His Glu Lys Thr
545                 550                 555                 560

Pro Val Ser Glu His Val Thr Lys Cys Cys Ser Gly Ser Leu Val Glu
                565                 570                 575

Arg Arg Pro Cys Phe Ser Ala Leu Thr Val Asp Glu Thr Tyr Val Pro
                580                 585                 590

Lys Glu Phe Lys Ala Glu Thr Phe Thr Phe His Ser Asp Ile Cys Thr
                595                 600                 605

Leu Pro Glu Lys Glu Lys Gln Ile Lys Lys Gln Thr Ala Leu Ala Glu
            610                 615                 620

Leu Val Lys His Lys Pro Lys Ala Thr Ala Glu Gln Leu Lys Thr Val
625                 630                 635                 640

Met Asp Asp Phe Ala Gln Phe Leu Asp Thr Cys Cys Lys Ala Ala Asp
                645                 650                 655

Lys Asp Thr Cys Phe Ser Thr Glu Gly Pro Asn Leu Val Thr Arg Cys
                660                 665                 670

Lys Asp Ala Leu Ala Gly Gly Gly Gly Ser His His His His His
            675                 680                 685

<210> SEQ ID NO 70
<211> LENGTH: 697
<212> TYPE: PRT
<213> ORGANISM: Artificial Sequence
<220> FEATURE:
<223> OTHER INFORMATION: Synthetic: LS-hCXCL828-99-(Gly4Ser)2-mouse SA-
      (Gly4Ser)-His6

<400> SEQUENCE: 70

Met Arg Val Pro Ala Gln Leu Leu Gly Leu Leu Leu Leu Trp Leu Pro
1               5                   10                  15

Gly Ala Arg Cys Ser Ala Lys Glu Leu Arg Cys Gln Cys Ile Lys Thr
            20                  25                  30

Tyr Ser Lys Pro Phe His Pro Lys Phe Ile Lys Glu Leu Arg Val Ile
        35                  40                  45

Glu Ser Gly Pro His Cys Ala Asn Thr Glu Ile Ile Val Lys Leu Ser
    50                  55                  60

Asp Gly Arg Glu Leu Cys Leu Asp Pro Lys Glu Asn Trp Val Gln Arg
65                  70                  75                  80

Val Val Glu Lys Phe Leu Lys Arg Ala Glu Asn Ser Gly Gly Gly Gly
                85                  90                  95

Ser Gly Gly Gly Gly Ser Glu Ala His Lys Ser Glu Ile Ala His Arg
            100                 105                 110

Tyr Asn Asp Leu Gly Glu Gln His Phe Lys Gly Leu Val Leu Ile Ala
        115                 120                 125
```

```
Phe Ser Gln Tyr Leu Gln Lys Cys Ser Tyr Asp Glu His Ala Lys Leu
    130                 135                 140
Val Gln Glu Val Thr Asp Phe Ala Lys Thr Cys Val Ala Asp Glu Ser
145                 150                 155                 160
Ala Ala Asn Cys Asp Lys Ser Leu His Thr Leu Phe Gly Asp Lys Leu
                165                 170                 175
Cys Ala Ile Pro Asn Leu Arg Glu Asn Tyr Gly Glu Leu Ala Asp Cys
            180                 185                 190
Cys Thr Lys Gln Glu Pro Glu Arg Asn Glu Cys Phe Leu Gln His Lys
        195                 200                 205
Asp Asp Asn Pro Ser Leu Pro Pro Phe Glu Arg Pro Glu Ala Glu Ala
210                 215                 220
Met Cys Thr Ser Phe Lys Glu Asn Pro Thr Thr Phe Met Gly His Tyr
225                 230                 235                 240
Leu His Glu Val Ala Arg Arg His Pro Tyr Phe Tyr Ala Pro Glu Leu
                245                 250                 255
Leu Tyr Tyr Ala Glu Gln Tyr Asn Glu Ile Leu Thr Gln Cys Cys Ala
            260                 265                 270
Glu Ala Asp Lys Glu Ser Cys Leu Thr Pro Lys Leu Asp Gly Val Lys
        275                 280                 285
Glu Lys Ala Leu Val Ser Ser Val Arg Gln Arg Met Lys Cys Ser Ser
290                 295                 300
Met Gln Lys Phe Gly Glu Arg Ala Phe Lys Ala Trp Ala Val Ala Arg
305                 310                 315                 320
Leu Ser Gln Thr Phe Pro Asn Ala Asp Phe Ala Glu Ile Thr Lys Leu
                325                 330                 335
Ala Thr Asp Leu Thr Lys Val Asn Lys Glu Cys Cys His Gly Asp Leu
            340                 345                 350
Leu Glu Cys Ala Asp Asp Arg Ala Glu Leu Ala Lys Tyr Met Cys Glu
        355                 360                 365
Asn Gln Ala Thr Ile Ser Ser Lys Leu Gln Thr Cys Cys Asp Lys Pro
370                 375                 380
Leu Leu Lys Lys Ala His Cys Leu Ser Glu Val Glu His Asp Thr Met
385                 390                 395                 400
Pro Ala Asp Leu Pro Ala Ile Ala Ala Asp Phe Val Glu Asp Gln Glu
                405                 410                 415
Val Cys Lys Asn Tyr Ala Glu Ala Lys Asp Val Phe Leu Gly Thr Phe
            420                 425                 430
Leu Tyr Glu Tyr Ser Arg Arg His Pro Asp Tyr Ser Val Ser Leu Leu
        435                 440                 445
Leu Arg Leu Ala Lys Lys Tyr Glu Ala Thr Leu Glu Lys Cys Cys Ala
450                 455                 460
Glu Ala Asn Pro Pro Ala Cys Tyr Gly Thr Val Leu Ala Glu Phe Gln
465                 470                 475                 480
Pro Leu Val Glu Glu Pro Lys Asn Leu Val Lys Thr Asn Cys Asp Leu
                485                 490                 495
Tyr Glu Lys Leu Gly Glu Tyr Gly Phe Gln Asn Ala Ile Leu Val Arg
            500                 505                 510
Tyr Thr Gln Lys Ala Pro Gln Val Ser Thr Pro Thr Leu Val Glu Ala
        515                 520                 525
Ala Arg Asn Leu Gly Arg Val Gly Thr Lys Cys Cys Thr Leu Pro Glu
530                 535                 540
Asp Gln Arg Leu Pro Cys Val Glu Asp Tyr Leu Ser Ala Ile Leu Asn
```

```
                       545                 550                 555                 560
Arg Val Cys Leu Leu His Glu Lys Thr Pro Val Ser Glu His Val Thr
                    565                 570                 575

Lys Cys Cys Ser Gly Ser Leu Val Glu Arg Pro Cys Phe Ser Ala
                580                 585                 590

Leu Thr Val Asp Glu Thr Tyr Val Pro Lys Glu Phe Lys Ala Glu Thr
            595                 600                 605

Phe Thr Phe His Ser Asp Ile Cys Thr Leu Pro Glu Lys Glu Lys Gln
        610                 615                 620

Ile Lys Lys Gln Thr Ala Leu Ala Glu Leu Val Lys His Lys Pro Lys
625                 630                 635                 640

Ala Thr Ala Glu Gln Leu Lys Thr Val Met Asp Asp Phe Ala Gln Phe
                645                 650                 655

Leu Asp Thr Cys Cys Lys Ala Ala Asp Lys Asp Thr Cys Phe Ser Thr
            660                 665                 670

Glu Gly Pro Asn Leu Val Thr Arg Cys Lys Asp Ala Leu Ala Gly Gly
        675                 680                 685

Gly Gly Ser His His His His His His
    690                 695

<210> SEQ ID NO 71
<211> LENGTH: 728
<212> TYPE: PRT
<213> ORGANISM: Artificial Sequence
<220> FEATURE:
<223> OTHER INFORMATION: Synthetic: LS-hCXCL923-115-(Gly4Ser)2-mouse SA-
      (Gly4Ser)-His6

<400> SEQUENCE: 71

Met Arg Val Pro Ala Gln Leu Leu Gly Leu Leu Leu Leu Trp Leu Pro
1               5                   10                  15

Gly Ala Arg Cys Thr Pro Val Val Arg Lys Gly Arg Cys Ser Cys Ile
                20                  25                  30

Ser Thr Asn Gln Gly Thr Ile His Leu Gln Ser Leu Lys Asp Leu Lys
            35                  40                  45

Gln Phe Ala Pro Ser Pro Ser Cys Glu Lys Ile Glu Ile Ile Ala Thr
        50                  55                  60

Leu Lys Asn Gly Val Gln Thr Cys Leu Asn Pro Asp Ser Ala Asp Val
65                  70                  75                  80

Lys Glu Leu Ile Lys Lys Trp Glu Lys Gln Val Ser Gln Lys Lys Lys
                85                  90                  95

Gln Lys Asn Gly Lys Lys His Gln Lys Lys Lys Val Leu Lys Val Arg
            100                 105                 110

Lys Ser Gln Arg Ser Arg Gln Lys Lys Thr Thr Gly Gly Gly Gly Ser
        115                 120                 125

Gly Gly Gly Gly Ser Glu Ala His Lys Ser Glu Ile Ala His Arg Tyr
    130                 135                 140

Asn Asp Leu Gly Glu Gln His Phe Lys Gly Leu Val Leu Ile Ala Phe
145                 150                 155                 160

Ser Gln Tyr Leu Gln Lys Cys Ser Tyr Asp Glu His Ala Lys Leu Val
                165                 170                 175

Gln Glu Val Thr Asp Phe Ala Lys Thr Cys Val Ala Asp Glu Ser Ala
            180                 185                 190

Ala Asn Cys Asp Lys Ser Leu His Thr Leu Phe Gly Asp Lys Leu Cys
        195                 200                 205
```

```
Ala Ile Pro Asn Leu Arg Glu Asn Tyr Gly Glu Leu Ala Asp Cys Cys
210                 215                 220
Thr Lys Gln Glu Pro Glu Arg Asn Glu Cys Phe Leu Gln His Lys Asp
225                 230                 235                 240
Asp Asn Pro Ser Leu Pro Pro Phe Glu Arg Pro Glu Ala Glu Ala Met
                245                 250                 255
Cys Thr Ser Phe Lys Glu Asn Pro Thr Thr Phe Met Gly His Tyr Leu
                260                 265                 270
His Glu Val Ala Arg Arg His Pro Tyr Phe Tyr Ala Pro Glu Leu Leu
            275                 280                 285
Tyr Tyr Ala Glu Gln Tyr Asn Glu Ile Leu Thr Gln Cys Cys Ala Glu
290                 295                 300
Ala Asp Lys Glu Ser Cys Leu Thr Pro Lys Leu Asp Gly Val Lys Glu
305                 310                 315                 320
Lys Ala Leu Val Ser Ser Val Arg Gln Arg Met Lys Cys Ser Ser Met
                325                 330                 335
Gln Lys Phe Gly Glu Arg Ala Phe Lys Ala Trp Ala Val Ala Arg Leu
                340                 345                 350
Ser Gln Thr Phe Pro Asn Ala Asp Phe Ala Glu Ile Thr Lys Leu Ala
            355                 360                 365
Thr Asp Leu Thr Lys Val Asn Lys Glu Cys Cys His Gly Asp Leu Leu
370                 375                 380
Glu Cys Ala Asp Asp Arg Ala Glu Leu Ala Lys Tyr Met Cys Glu Asn
385                 390                 395                 400
Gln Ala Thr Ile Ser Ser Lys Leu Gln Thr Cys Cys Asp Lys Pro Leu
                405                 410                 415
Leu Lys Lys Ala His Cys Leu Ser Glu Val Glu His Asp Thr Met Pro
                420                 425                 430
Ala Asp Leu Pro Ala Ile Ala Ala Asp Phe Val Glu Asp Gln Glu Val
            435                 440                 445
Cys Lys Asn Tyr Ala Glu Ala Lys Asp Val Phe Leu Gly Thr Phe Leu
450                 455                 460
Tyr Glu Tyr Ser Arg Arg His Pro Asp Tyr Ser Val Ser Leu Leu Leu
465                 470                 475                 480
Arg Leu Ala Lys Lys Tyr Glu Ala Thr Leu Glu Lys Cys Cys Ala Glu
                485                 490                 495
Ala Asn Pro Pro Ala Cys Tyr Gly Thr Val Leu Ala Glu Phe Gln Pro
                500                 505                 510
Leu Val Glu Glu Pro Lys Asn Leu Val Lys Thr Asn Cys Asp Leu Tyr
            515                 520                 525
Glu Lys Leu Gly Glu Tyr Gly Phe Gln Asn Ala Ile Leu Val Arg Tyr
530                 535                 540
Thr Gln Lys Ala Pro Gln Val Ser Thr Pro Thr Leu Val Glu Ala Ala
545                 550                 555                 560
Arg Asn Leu Gly Arg Val Gly Thr Lys Cys Cys Thr Leu Pro Glu Asp
                565                 570                 575
Gln Arg Leu Pro Cys Val Glu Asp Tyr Leu Ser Ala Ile Leu Asn Arg
                580                 585                 590
Val Cys Leu Leu His Glu Lys Thr Pro Val Ser Glu His Val Thr Lys
            595                 600                 605
Cys Cys Ser Gly Ser Leu Val Glu Arg Arg Pro Cys Phe Ser Ala Leu
610                 615                 620
Thr Val Asp Glu Thr Tyr Val Pro Lys Glu Phe Lys Ala Glu Thr Phe
```

```
              625                 630                 635                 640
Thr Phe His Ser Asp Ile Cys Thr Leu Pro Glu Lys Glu Lys Gln Ile
                    645                 650                 655

Lys Lys Gln Thr Ala Leu Ala Glu Leu Val Lys His Lys Pro Lys Ala
            660                 665                 670

Thr Ala Glu Gln Leu Lys Thr Val Met Asp Asp Phe Ala Gln Phe Leu
        675                 680                 685

Asp Thr Cys Cys Lys Ala Ala Asp Lys Asp Thr Cys Phe Ser Thr Glu
    690                 695                 700

Gly Pro Asn Leu Val Thr Arg Cys Lys Asp Ala Leu Ala Gly Gly Gly
705                 710                 715                 720

Gly Ser His His His His His His
                725

<210> SEQ ID NO 72
<211> LENGTH: 702
<212> TYPE: PRT
<213> ORGANISM: Artificial Sequence
<220> FEATURE:
<223> OTHER INFORMATION: Synthetic: LS-hCXCL1022-98-(Gly4Ser)2-mouse SA-
      (Gly4Ser)-His6

<400> SEQUENCE: 72

Met Arg Val Pro Ala Gln Leu Leu Gly Leu Leu Leu Leu Trp Leu Pro
1               5                   10                  15

Gly Ala Arg Cys Val Pro Leu Ser Arg Thr Val Arg Cys Thr Cys Ile
            20                  25                  30

Ser Ile Ser Asn Gln Pro Val Asn Pro Arg Ser Leu Glu Lys Leu Glu
        35                  40                  45

Ile Ile Pro Ala Ser Gln Phe Cys Pro Arg Val Glu Ile Ile Ala Thr
    50                  55                  60

Met Lys Lys Lys Gly Glu Lys Arg Cys Leu Asn Pro Glu Ser Lys Ala
65              70                  75                  80

Ile Lys Asn Leu Leu Lys Ala Val Ser Lys Glu Arg Ser Lys Arg Ser
                85                  90                  95

Pro Gly Gly Gly Gly Ser Gly Gly Gly Gly Ser Glu Ala His Lys Ser
            100                 105                 110

Glu Ile Ala His Arg Tyr Asn Asp Leu Gly Glu Gln His Phe Lys Gly
        115                 120                 125

Leu Val Leu Ile Ala Phe Ser Gln Tyr Leu Gln Lys Cys Ser Tyr Asp
    130                 135                 140

Glu His Ala Lys Leu Val Gln Glu Val Thr Asp Phe Ala Lys Thr Cys
145                 150                 155                 160

Val Ala Asp Glu Ser Ala Ala Asn Cys Asp Lys Ser Leu His Thr Leu
                165                 170                 175

Phe Gly Asp Lys Leu Cys Ala Ile Pro Asn Leu Arg Glu Asn Tyr Gly
            180                 185                 190

Glu Leu Ala Asp Cys Cys Thr Lys Gln Glu Pro Glu Arg Asn Glu Cys
        195                 200                 205

Phe Leu Gln His Lys Asp Asp Asn Pro Ser Leu Pro Pro Phe Glu Arg
    210                 215                 220

Pro Glu Ala Glu Ala Met Cys Thr Ser Phe Lys Glu Asn Pro Thr Thr
225                 230                 235                 240

Phe Met Gly His Tyr Leu His Glu Val Ala Arg Arg His Pro Tyr Phe
                245                 250                 255
```

-continued

```
Tyr Ala Pro Glu Leu Leu Tyr Ala Glu Gln Tyr Asn Glu Ile Leu
            260                 265                 270

Thr Gln Cys Cys Ala Glu Ala Asp Lys Glu Ser Cys Leu Thr Pro Lys
        275                 280                 285

Leu Asp Gly Val Lys Glu Lys Ala Leu Val Ser Ser Val Arg Gln Arg
    290                 295                 300

Met Lys Cys Ser Ser Met Gln Lys Phe Gly Glu Arg Ala Phe Lys Ala
305                 310                 315                 320

Trp Ala Val Ala Arg Leu Ser Gln Thr Phe Pro Asn Ala Asp Phe Ala
                325                 330                 335

Glu Ile Thr Lys Leu Ala Thr Asp Leu Thr Lys Val Asn Lys Glu Cys
            340                 345                 350

Cys His Gly Asp Leu Leu Glu Cys Ala Asp Asp Arg Ala Glu Leu Ala
        355                 360                 365

Lys Tyr Met Cys Glu Asn Gln Ala Thr Ile Ser Ser Lys Leu Gln Thr
    370                 375                 380

Cys Cys Asp Lys Pro Leu Leu Lys Lys Ala His Cys Leu Ser Glu Val
385                 390                 395                 400

Glu His Asp Thr Met Pro Ala Asp Leu Pro Ala Ile Ala Ala Asp Phe
                405                 410                 415

Val Glu Asp Gln Glu Val Cys Lys Asn Tyr Ala Glu Ala Lys Asp Val
            420                 425                 430

Phe Leu Gly Thr Phe Leu Tyr Glu Tyr Ser Arg Arg His Pro Asp Tyr
        435                 440                 445

Ser Val Ser Leu Leu Leu Arg Leu Ala Lys Lys Tyr Glu Ala Thr Leu
    450                 455                 460

Glu Lys Cys Cys Ala Glu Ala Asn Pro Pro Ala Cys Tyr Gly Thr Val
465                 470                 475                 480

Leu Ala Glu Phe Gln Pro Leu Val Glu Glu Pro Lys Asn Leu Val Lys
                485                 490                 495

Thr Asn Cys Asp Leu Tyr Glu Lys Leu Gly Glu Tyr Gly Phe Gln Asn
            500                 505                 510

Ala Ile Leu Val Arg Tyr Thr Gln Lys Ala Pro Gln Val Ser Thr Pro
        515                 520                 525

Thr Leu Val Glu Ala Ala Arg Asn Leu Gly Arg Val Gly Thr Lys Cys
    530                 535                 540

Cys Thr Leu Pro Glu Asp Gln Arg Leu Pro Cys Val Glu Asp Tyr Leu
545                 550                 555                 560

Ser Ala Ile Leu Asn Arg Val Cys Leu Leu His Glu Lys Thr Pro Val
                565                 570                 575

Ser Glu His Val Thr Lys Cys Cys Ser Gly Ser Leu Val Glu Arg Arg
            580                 585                 590

Pro Cys Phe Ser Ala Leu Thr Val Asp Glu Thr Tyr Val Pro Lys Glu
        595                 600                 605

Phe Lys Ala Glu Thr Phe Thr Phe His Ser Asp Ile Cys Thr Leu Pro
    610                 615                 620

Glu Lys Glu Lys Gln Ile Lys Lys Gln Thr Ala Leu Ala Glu Leu Val
625                 630                 635                 640

Lys His Lys Pro Lys Ala Thr Ala Glu Gln Leu Lys Thr Val Met Asp
                645                 650                 655

Asp Phe Ala Gln Phe Leu Asp Thr Cys Cys Lys Ala Ala Asp Lys Asp
            660                 665                 670

Thr Cys Phe Ser Thr Glu Gly Pro Asn Leu Val Thr Arg Cys Lys Asp
```

```
                    675                 680                 685
Ala Leu Ala Gly Gly Gly Ser His His His His His
                690                 695                 700

<210> SEQ ID NO 73
<211> LENGTH: 698
<212> TYPE: PRT
<213> ORGANISM: Artificial Sequence
<220> FEATURE:
<223> OTHER INFORMATION: Synthetic: LS-hCXCL1122-94-(Gly4Ser)2-mouse SA-
      (Gly4Ser)-His6

<400> SEQUENCE: 73

Met Arg Val Pro Ala Gln Leu Leu Gly Leu Leu Leu Leu Trp Leu Pro
1               5                   10                  15

Gly Ala Arg Cys Phe Pro Met Phe Lys Arg Gly Arg Cys Leu Cys Ile
                20                  25                  30

Gly Pro Gly Val Lys Ala Val Lys Val Ala Asp Ile Glu Lys Ala Ser
            35                  40                  45

Ile Met Tyr Pro Ser Asn Asn Cys Asp Lys Ile Glu Val Ile Ile Thr
        50                  55                  60

Leu Lys Glu Asn Lys Gly Gln Arg Cys Leu Asn Pro Lys Ser Lys Gln
65                  70                  75                  80

Ala Arg Leu Ile Ile Lys Lys Val Glu Arg Lys Asn Phe Gly Gly Gly
                85                  90                  95

Gly Ser Gly Gly Gly Gly Ser Glu Ala His Lys Ser Glu Ile Ala His
            100                 105                 110

Arg Tyr Asn Asp Leu Gly Glu Gln His Phe Lys Gly Leu Val Leu Ile
        115                 120                 125

Ala Phe Ser Gln Tyr Leu Gln Lys Cys Ser Tyr Asp Glu His Ala Lys
    130                 135                 140

Leu Val Gln Glu Val Thr Asp Phe Ala Lys Thr Cys Val Ala Asp Glu
145                 150                 155                 160

Ser Ala Ala Asn Cys Asp Lys Ser Leu His Thr Leu Phe Gly Asp Lys
                165                 170                 175

Leu Cys Ala Ile Pro Asn Leu Arg Glu Asn Tyr Gly Glu Leu Ala Asp
            180                 185                 190

Cys Cys Thr Lys Gln Glu Pro Glu Arg Asn Glu Cys Phe Leu Gln His
        195                 200                 205

Lys Asp Asp Asn Pro Ser Leu Pro Pro Phe Glu Arg Pro Glu Ala Glu
    210                 215                 220

Ala Met Cys Thr Ser Phe Lys Glu Asn Pro Thr Thr Phe Met Gly His
225                 230                 235                 240

Tyr Leu His Glu Val Ala Arg Arg His Pro Tyr Phe Tyr Ala Pro Glu
                245                 250                 255

Leu Leu Tyr Tyr Ala Glu Gln Tyr Asn Glu Ile Leu Thr Gln Cys Cys
            260                 265                 270

Ala Glu Ala Asp Lys Glu Ser Cys Leu Thr Pro Lys Leu Asp Gly Val
        275                 280                 285

Lys Glu Lys Ala Leu Val Ser Ser Val Arg Gln Arg Met Lys Cys Ser
    290                 295                 300

Ser Met Gln Lys Phe Gly Glu Arg Ala Phe Lys Ala Trp Ala Val Ala
305                 310                 315                 320

Arg Leu Ser Gln Thr Phe Pro Asn Ala Asp Phe Ala Glu Ile Thr Lys
                325                 330                 335
```

```
Leu Ala Thr Asp Leu Thr Lys Val Asn Lys Glu Cys Cys His Gly Asp
                340                 345                 350

Leu Leu Glu Cys Ala Asp Arg Ala Glu Leu Ala Lys Tyr Met Cys
            355                 360                 365

Glu Asn Gln Ala Thr Ile Ser Ser Lys Leu Gln Thr Cys Cys Asp Lys
370                 375                 380

Pro Leu Leu Lys Lys Ala His Cys Leu Ser Glu Val Glu His Asp Thr
385                 390                 395                 400

Met Pro Ala Asp Leu Pro Ala Ile Ala Ala Asp Phe Val Glu Asp Gln
                405                 410                 415

Glu Val Cys Lys Asn Tyr Ala Glu Ala Lys Asp Val Phe Leu Gly Thr
            420                 425                 430

Phe Leu Tyr Glu Tyr Ser Arg Arg His Pro Asp Tyr Ser Val Ser Leu
        435                 440                 445

Leu Leu Arg Leu Ala Lys Lys Tyr Glu Ala Thr Leu Glu Lys Cys Cys
450                 455                 460

Ala Glu Ala Asn Pro Pro Ala Cys Tyr Gly Thr Val Leu Ala Glu Phe
465                 470                 475                 480

Gln Pro Leu Val Glu Glu Pro Lys Asn Leu Val Lys Thr Asn Cys Asp
            485                 490                 495

Leu Tyr Glu Lys Leu Gly Glu Tyr Gly Phe Gln Asn Ala Ile Leu Val
        500                 505                 510

Arg Tyr Thr Gln Lys Ala Pro Gln Val Ser Thr Pro Thr Leu Val Glu
        515                 520                 525

Ala Ala Arg Asn Leu Gly Arg Val Gly Thr Lys Cys Cys Thr Leu Pro
530                 535                 540

Glu Asp Gln Arg Leu Pro Cys Val Glu Asp Tyr Leu Ser Ala Ile Leu
545                 550                 555                 560

Asn Arg Val Cys Leu Leu His Glu Lys Thr Pro Val Ser Glu His Val
            565                 570                 575

Thr Lys Cys Cys Ser Gly Ser Leu Val Glu Arg Arg Pro Cys Phe Ser
            580                 585                 590

Ala Leu Thr Val Asp Glu Thr Tyr Val Pro Lys Glu Phe Lys Ala Glu
        595                 600                 605

Thr Phe Thr Phe His Ser Asp Ile Cys Thr Leu Pro Glu Lys Glu Lys
        610                 615                 620

Gln Ile Lys Lys Gln Thr Ala Leu Ala Glu Leu Val Lys His Lys Pro
625                 630                 635                 640

Lys Ala Thr Ala Glu Gln Leu Lys Thr Val Met Asp Asp Phe Ala Gln
                645                 650                 655

Phe Leu Asp Thr Cys Cys Lys Ala Ala Asp Lys Asp Thr Cys Phe Ser
            660                 665                 670

Thr Glu Gly Pro Asn Leu Val Thr Arg Cys Lys Asp Ala Leu Ala Gly
        675                 680                 685

Gly Gly Gly Ser His His His His His His
    690                 695

<210> SEQ ID NO 74
<211> LENGTH: 697
<212> TYPE: PRT
<213> ORGANISM: Artificial Sequence
<220> FEATURE:
<223> OTHER INFORMATION: Synthetic: LS-mCXCL125-96-(Gly4Ser)2-mouse SA-
      (Gly4Ser)-His6

<400> SEQUENCE: 74
```

-continued

```
Met Arg Val Pro Ala Gln Leu Leu Gly Leu Leu Leu Trp Leu Pro
1               5                   10                  15

Gly Ala Arg Cys Ala Pro Ile Ala Asn Glu Leu Arg Cys Gln Cys Leu
                20                  25                  30

Gln Thr Met Ala Gly Ile His Leu Lys Asn Ile Gln Ser Leu Lys Val
            35                  40                  45

Leu Pro Ser Gly Pro His Cys Thr Gln Thr Glu Val Ile Ala Thr Leu
        50                  55                  60

Lys Asn Gly Arg Glu Ala Cys Leu Asp Pro Glu Ala Pro Leu Val Gln
65                  70                  75                  80

Lys Ile Val Gln Lys Met Leu Lys Gly Val Pro Lys Gly Gly Gly
                85                  90                  95

Ser Gly Gly Gly Gly Ser Glu Ala His Lys Ser Glu Ile Ala His Arg
                100                 105                 110

Tyr Asn Asp Leu Gly Glu Gln His Phe Lys Gly Leu Val Leu Ile Ala
            115                 120                 125

Phe Ser Gln Tyr Leu Gln Lys Cys Ser Tyr Asp Glu His Ala Lys Leu
        130                 135                 140

Val Gln Glu Val Thr Asp Phe Ala Lys Thr Cys Val Ala Asp Glu Ser
145                 150                 155                 160

Ala Ala Asn Cys Asp Lys Ser Leu His Thr Leu Phe Gly Asp Lys Leu
                165                 170                 175

Cys Ala Ile Pro Asn Leu Arg Glu Asn Tyr Gly Glu Leu Ala Asp Cys
            180                 185                 190

Cys Thr Lys Gln Glu Pro Glu Arg Asn Glu Cys Phe Leu Gln His Lys
        195                 200                 205

Asp Asp Asn Pro Ser Leu Pro Pro Phe Glu Arg Pro Glu Ala Glu Ala
210                 215                 220

Met Cys Thr Ser Phe Lys Glu Asn Pro Thr Thr Phe Met Gly His Tyr
225                 230                 235                 240

Leu His Glu Val Ala Arg Arg His Pro Tyr Phe Tyr Ala Pro Glu Leu
                245                 250                 255

Leu Tyr Tyr Ala Glu Gln Tyr Asn Glu Ile Leu Thr Gln Cys Cys Ala
            260                 265                 270

Glu Ala Asp Lys Glu Ser Cys Leu Thr Pro Lys Leu Asp Gly Val Lys
        275                 280                 285

Glu Lys Ala Leu Val Ser Ser Val Arg Gln Arg Met Lys Cys Ser Ser
290                 295                 300

Met Gln Lys Phe Gly Glu Arg Ala Phe Lys Ala Trp Ala Val Ala Arg
305                 310                 315                 320

Leu Ser Gln Thr Phe Pro Asn Ala Asp Phe Ala Glu Ile Thr Lys Leu
                325                 330                 335

Ala Thr Asp Leu Thr Lys Val Asn Lys Glu Cys Cys His Gly Asp Leu
            340                 345                 350

Leu Glu Cys Ala Asp Asp Arg Ala Glu Leu Ala Lys Tyr Met Cys Glu
        355                 360                 365

Asn Gln Ala Thr Ile Ser Ser Lys Leu Gln Thr Cys Cys Asp Lys Pro
370                 375                 380

Leu Leu Lys Lys Ala His Cys Leu Ser Glu Val Glu His Asp Thr Met
385                 390                 395                 400

Pro Ala Asp Leu Pro Ala Ile Ala Ala Asp Phe Val Glu Asp Gln Glu
                405                 410                 415
```

Val Cys Lys Asn Tyr Ala Glu Ala Lys Asp Val Phe Leu Gly Thr Phe
            420                 425                 430

Leu Tyr Glu Tyr Ser Arg Arg His Pro Asp Tyr Ser Val Ser Leu Leu
        435                 440                 445

Leu Arg Leu Ala Lys Lys Tyr Glu Ala Thr Leu Glu Lys Cys Cys Ala
    450                 455                 460

Glu Ala Asn Pro Pro Ala Cys Tyr Gly Thr Val Leu Ala Glu Phe Gln
465                 470                 475                 480

Pro Leu Val Glu Glu Pro Lys Asn Leu Val Lys Thr Asn Cys Asp Leu
                485                 490                 495

Tyr Glu Lys Leu Gly Glu Tyr Gly Phe Gln Asn Ala Ile Leu Val Arg
            500                 505                 510

Tyr Thr Gln Lys Ala Pro Gln Val Ser Thr Pro Thr Leu Val Glu Ala
        515                 520                 525

Ala Arg Asn Leu Gly Arg Val Gly Thr Lys Cys Cys Thr Leu Pro Glu
    530                 535                 540

Asp Gln Arg Leu Pro Cys Val Glu Asp Tyr Leu Ser Ala Ile Leu Asn
545                 550                 555                 560

Arg Val Cys Leu Leu His Glu Lys Thr Pro Val Ser Glu His Val Thr
                565                 570                 575

Lys Cys Cys Ser Gly Ser Leu Val Glu Arg Arg Pro Cys Phe Ser Ala
            580                 585                 590

Leu Thr Val Asp Glu Thr Tyr Val Pro Lys Glu Phe Lys Ala Glu Thr
        595                 600                 605

Phe Thr Phe His Ser Asp Ile Cys Thr Leu Pro Glu Lys Glu Lys Gln
    610                 615                 620

Ile Lys Lys Gln Thr Ala Leu Ala Glu Leu Val Lys His Lys Pro Lys
625                 630                 635                 640

Ala Thr Ala Glu Gln Leu Lys Thr Val Met Asp Asp Phe Ala Gln Phe
                645                 650                 655

Leu Asp Thr Cys Cys Lys Ala Ala Asp Lys Asp Thr Cys Phe Ser Thr
            660                 665                 670

Glu Gly Pro Asn Leu Val Thr Arg Cys Lys Asp Ala Leu Ala Gly Gly
        675                 680                 685

Gly Gly Ser His His His His His His
    690                 695

<210> SEQ ID NO 75
<211> LENGTH: 698
<212> TYPE: PRT
<213> ORGANISM: Artificial Sequence
<220> FEATURE:
<223> OTHER INFORMATION: Synthetic: LS-mCXCL228-100-(Gly4Ser)2-mouse SA-
      (Gly4Ser)-His6

<400> SEQUENCE: 75

Met Arg Val Pro Ala Gln Leu Leu Gly Leu Leu Leu Leu Trp Leu Pro
1               5                   10                  15

Gly Ala Arg Cys Ala Val Val Ala Ser Glu Leu Arg Cys Gln Cys Leu
            20                  25                  30

Lys Thr Leu Pro Arg Val Asp Phe Lys Asn Ile Gln Ser Leu Ser Val
        35                  40                  45

Thr Pro Pro Gly Pro His Cys Ala Gln Thr Glu Val Ile Ala Thr Leu
    50                  55                  60

Lys Gly Gly Gln Lys Val Cys Leu Asp Pro Glu Ala Pro Leu Val Gln
65                  70                  75                  80

-continued

```
Lys Ile Ile Gln Lys Ile Leu Asn Lys Gly Lys Ala Asn Gly Gly
                 85                  90                  95
Gly Ser Gly Gly Gly Ser Glu Ala His Lys Ser Glu Ile Ala His
                100                 105                 110
Arg Tyr Asn Asp Leu Gly Glu Gln His Phe Lys Gly Leu Val Leu Ile
                115                 120                 125
Ala Phe Ser Gln Tyr Leu Gln Lys Cys Ser Tyr Asp Glu His Ala Lys
        130                 135                 140
Leu Val Gln Glu Val Thr Asp Phe Ala Lys Thr Cys Val Ala Asp Glu
145                 150                 155                 160
Ser Ala Ala Asn Cys Asp Lys Ser Leu His Thr Leu Phe Gly Asp Lys
                165                 170                 175
Leu Cys Ala Ile Pro Asn Leu Arg Glu Asn Tyr Gly Glu Leu Ala Asp
                180                 185                 190
Cys Cys Thr Lys Gln Glu Pro Glu Arg Asn Glu Cys Phe Leu Gln His
        195                 200                 205
Lys Asp Asp Asn Pro Ser Leu Pro Pro Phe Glu Arg Pro Glu Ala Glu
        210                 215                 220
Ala Met Cys Thr Ser Phe Lys Glu Asn Pro Thr Thr Phe Met Gly His
225                 230                 235                 240
Tyr Leu His Glu Val Ala Arg Arg His Pro Tyr Phe Tyr Ala Pro Glu
                245                 250                 255
Leu Leu Tyr Tyr Ala Glu Gln Tyr Asn Glu Ile Leu Thr Gln Cys Cys
                260                 265                 270
Ala Glu Ala Asp Lys Glu Ser Cys Leu Thr Pro Lys Leu Asp Gly Val
        275                 280                 285
Lys Glu Lys Ala Leu Val Ser Ser Val Arg Gln Arg Met Lys Cys Ser
        290                 295                 300
Ser Met Gln Lys Phe Gly Glu Arg Ala Phe Lys Ala Trp Ala Val Ala
305                 310                 315                 320
Arg Leu Ser Gln Thr Phe Pro Asn Ala Asp Phe Ala Glu Ile Thr Lys
                325                 330                 335
Leu Ala Thr Asp Leu Thr Lys Val Asn Lys Glu Cys Cys His Gly Asp
                340                 345                 350
Leu Leu Glu Cys Ala Asp Asp Arg Ala Glu Leu Ala Lys Tyr Met Cys
        355                 360                 365
Glu Asn Gln Ala Thr Ile Ser Ser Lys Leu Gln Thr Cys Cys Asp Lys
        370                 375                 380
Pro Leu Leu Lys Lys Ala His Cys Leu Ser Glu Val Glu His Asp Thr
385                 390                 395                 400
Met Pro Ala Asp Leu Pro Ala Ile Ala Ala Asp Phe Val Glu Asp Gln
                405                 410                 415
Glu Val Cys Lys Asn Tyr Ala Glu Ala Lys Asp Val Phe Leu Gly Thr
                420                 425                 430
Phe Leu Tyr Glu Tyr Ser Arg Arg His Pro Asp Tyr Ser Val Ser Leu
        435                 440                 445
Leu Leu Arg Leu Ala Lys Lys Tyr Glu Ala Thr Leu Glu Lys Cys Cys
        450                 455                 460
Ala Glu Ala Asn Pro Pro Ala Cys Tyr Gly Thr Val Leu Ala Glu Phe
465                 470                 475                 480
Gln Pro Leu Val Glu Glu Pro Lys Asn Leu Val Lys Thr Asn Cys Asp
                485                 490                 495
```

```
Leu Tyr Glu Lys Leu Gly Glu Tyr Gly Phe Gln Asn Ala Ile Leu Val
            500                 505                 510

Arg Tyr Thr Gln Lys Ala Pro Gln Val Ser Thr Pro Thr Leu Val Glu
            515                 520                 525

Ala Ala Arg Asn Leu Gly Arg Val Gly Thr Lys Cys Cys Thr Leu Pro
            530                 535                 540

Glu Asp Gln Arg Leu Pro Cys Val Glu Asp Tyr Leu Ser Ala Ile Leu
545                 550                 555                 560

Asn Arg Val Cys Leu Leu His Glu Lys Thr Pro Val Ser Glu His Val
            565                 570                 575

Thr Lys Cys Cys Ser Gly Ser Leu Val Glu Arg Arg Pro Cys Phe Ser
            580                 585                 590

Ala Leu Thr Val Asp Glu Thr Tyr Val Pro Lys Glu Phe Lys Ala Glu
            595                 600                 605

Thr Phe Thr Phe His Ser Asp Ile Cys Thr Leu Pro Glu Lys Glu Lys
            610                 615                 620

Gln Ile Lys Lys Gln Thr Ala Leu Ala Glu Leu Val Lys His Lys Pro
625                 630                 635                 640

Lys Ala Thr Ala Glu Gln Leu Lys Thr Val Met Asp Asp Phe Ala Gln
            645                 650                 655

Phe Leu Asp Thr Cys Cys Lys Ala Ala Asp Lys Asp Thr Cys Phe Ser
            660                 665                 670

Thr Glu Gly Pro Asn Leu Val Thr Arg Cys Lys Asp Ala Leu Ala Gly
            675                 680                 685

Gly Gly Gly Ser His His His His His His
            690                 695
```

<210> SEQ ID NO 76
<211> LENGTH: 698
<212> TYPE: PRT
<213> ORGANISM: Artificial Sequence
<220> FEATURE:
<223> OTHER INFORMATION: Synthetic: LS-mCXCL328-100-(Gly4Ser)2-mouse SA-(Gly4Ser)-His6

<400> SEQUENCE: 76

```
Met Arg Val Pro Ala Gln Leu Leu Gly Leu Leu Leu Leu Trp Leu Pro
1               5                   10                  15

Gly Ala Arg Cys Ala Val Val Ala Ser Glu Leu Arg Cys Gln Cys Leu
            20                  25                  30

Asn Thr Leu Pro Arg Val Asp Phe Glu Thr Ile Gln Ser Leu Thr Val
            35                  40                  45

Thr Pro Pro Gly Pro His Cys Thr Gln Thr Glu Val Ile Ala Thr Leu
50                  55                  60

Lys Asp Gly Gln Glu Val Cys Leu Asn Pro Gln Gly Pro Arg Leu Gln
65                  70                  75                  80

Ile Ile Ile Lys Lys Ile Leu Lys Ser Gly Lys Ser Ser Gly Gly Gly
            85                  90                  95

Gly Ser Gly Gly Gly Gly Ser Glu Ala His Lys Ser Glu Ile Ala His
            100                 105                 110

Arg Tyr Asn Asp Leu Gly Glu Gln His Phe Lys Gly Leu Val Leu Ile
            115                 120                 125

Ala Phe Ser Gln Tyr Leu Gln Lys Cys Ser Tyr Asp Glu His Ala Lys
            130                 135                 140

Leu Val Gln Glu Val Thr Asp Phe Ala Lys Thr Cys Val Ala Asp Glu
145                 150                 155                 160
```

-continued

```
Ser Ala Ala Asn Cys Asp Lys Ser Leu His Thr Leu Phe Gly Asp Lys
                165                 170                 175
Leu Cys Ala Ile Pro Asn Leu Arg Glu Asn Tyr Gly Glu Leu Ala Asp
            180                 185                 190
Cys Cys Thr Lys Gln Glu Pro Glu Arg Asn Glu Cys Phe Leu Gln His
        195                 200                 205
Lys Asp Asp Asn Pro Ser Leu Pro Pro Phe Glu Arg Pro Glu Ala Glu
    210                 215                 220
Ala Met Cys Thr Ser Phe Lys Glu Asn Pro Thr Thr Phe Met Gly His
225                 230                 235                 240
Tyr Leu His Glu Val Ala Arg Arg His Pro Tyr Phe Tyr Ala Pro Glu
                245                 250                 255
Leu Leu Tyr Tyr Ala Glu Gln Tyr Asn Glu Ile Leu Thr Gln Cys Cys
            260                 265                 270
Ala Glu Ala Asp Lys Glu Ser Cys Leu Thr Pro Lys Leu Asp Gly Val
        275                 280                 285
Lys Glu Lys Ala Leu Val Ser Ser Val Arg Gln Arg Met Lys Cys Ser
    290                 295                 300
Ser Met Gln Lys Phe Gly Glu Arg Ala Phe Lys Ala Trp Ala Val Ala
305                 310                 315                 320
Arg Leu Ser Gln Thr Phe Pro Asn Ala Asp Phe Ala Glu Ile Thr Lys
                325                 330                 335
Leu Ala Thr Asp Leu Thr Lys Val Asn Lys Glu Cys Cys His Gly Asp
            340                 345                 350
Leu Leu Glu Cys Ala Asp Asp Arg Ala Glu Leu Ala Lys Tyr Met Cys
        355                 360                 365
Glu Asn Gln Ala Thr Ile Ser Ser Lys Leu Gln Thr Cys Cys Asp Lys
    370                 375                 380
Pro Leu Leu Lys Lys Ala His Cys Leu Ser Glu Val Glu His Asp Thr
385                 390                 395                 400
Met Pro Ala Asp Leu Pro Ala Ile Ala Ala Asp Phe Val Glu Asp Gln
                405                 410                 415
Glu Val Cys Lys Asn Tyr Ala Glu Ala Lys Asp Val Phe Leu Gly Thr
            420                 425                 430
Phe Leu Tyr Glu Tyr Ser Arg Arg His Pro Asp Tyr Ser Val Ser Leu
        435                 440                 445
Leu Leu Arg Leu Ala Lys Lys Tyr Glu Ala Thr Leu Glu Lys Cys Cys
    450                 455                 460
Ala Glu Ala Asn Pro Pro Ala Cys Tyr Gly Thr Val Leu Ala Glu Phe
465                 470                 475                 480
Gln Pro Leu Val Glu Glu Pro Lys Asn Leu Val Lys Thr Asn Cys Asp
                485                 490                 495
Leu Tyr Glu Lys Leu Gly Glu Tyr Gly Phe Gln Asn Ala Ile Leu Val
            500                 505                 510
Arg Tyr Thr Gln Lys Ala Pro Gln Val Ser Thr Pro Thr Leu Val Glu
        515                 520                 525
Ala Ala Arg Asn Leu Gly Arg Val Gly Thr Lys Cys Cys Thr Leu Pro
    530                 535                 540
Glu Asp Gln Arg Leu Pro Cys Val Glu Asp Tyr Leu Ser Ala Ile Leu
545                 550                 555                 560
Asn Arg Val Cys Leu Leu His Glu Lys Thr Pro Val Ser Glu His Val
                565                 570                 575
```

```
Thr Lys Cys Cys Ser Gly Ser Leu Val Glu Arg Arg Pro Cys Phe Ser
                580             585                 590

Ala Leu Thr Val Asp Glu Thr Tyr Val Pro Lys Glu Phe Lys Ala Glu
            595                 600                 605

Thr Phe Thr Phe His Ser Asp Ile Cys Thr Leu Pro Glu Lys Glu Lys
        610                 615                 620

Gln Ile Lys Lys Gln Thr Ala Leu Ala Glu Leu Val Lys His Lys Pro
625                 630                 635                 640

Lys Ala Thr Ala Glu Gln Leu Lys Thr Val Met Asp Asp Phe Ala Gln
                645                 650                 655

Phe Leu Asp Thr Cys Cys Lys Ala Ala Asp Lys Asp Thr Cys Phe Ser
            660                 665                 670

Thr Glu Gly Pro Asn Leu Val Thr Arg Cys Lys Asp Ala Leu Ala Gly
        675                 680                 685

Gly Gly Gly Ser His His His His His His
    690                 695

<210> SEQ ID NO 77
<211> LENGTH: 701
<212> TYPE: PRT
<213> ORGANISM: Artificial Sequence
<220> FEATURE:
<223> OTHER INFORMATION: Synthetic: LS-mCXCL430-105-(Gly4Ser)2-mouse SA-
      (Gly4Ser)-His6

<400> SEQUENCE: 77

Met Arg Val Pro Ala Gln Leu Leu Gly Leu Leu Leu Leu Trp Leu Pro
1               5                   10                  15

Gly Ala Arg Cys Val Thr Ser Ala Gly Pro Glu Glu Ser Asp Gly Asp
            20                  25                  30

Leu Ser Cys Val Cys Val Lys Thr Ile Ser Ser Gly Ile His Leu Lys
        35                  40                  45

His Ile Thr Ser Leu Glu Val Ile Lys Ala Gly Arg His Cys Ala Val
    50                  55                  60

Pro Gln Leu Ile Ala Thr Leu Lys Asn Gly Arg Lys Ile Cys Leu Asp
65                  70                  75                  80

Arg Gln Ala Pro Leu Tyr Lys Lys Val Ile Lys Lys Ile Leu Glu Ser
                85                  90                  95

Gly Gly Gly Gly Ser Gly Gly Gly Gly Ser Glu Ala His Lys Ser Glu
            100                 105                 110

Ile Ala His Arg Tyr Asn Asp Leu Gly Glu Gln His Phe Lys Gly Leu
        115                 120                 125

Val Leu Ile Ala Phe Ser Gln Tyr Leu Gln Lys Cys Ser Tyr Asp Glu
    130                 135                 140

His Ala Lys Leu Val Gln Glu Val Thr Asp Phe Ala Lys Thr Cys Val
145                 150                 155                 160

Ala Asp Glu Ser Ala Ala Asn Cys Asp Lys Ser Leu His Thr Leu Phe
                165                 170                 175

Gly Asp Lys Leu Cys Ala Ile Pro Asn Leu Arg Glu Asn Tyr Gly Glu
            180                 185                 190

Leu Ala Asp Cys Cys Thr Lys Gln Glu Pro Glu Arg Asn Glu Cys Phe
        195                 200                 205

Leu Gln His Lys Asp Asp Asn Pro Ser Leu Pro Pro Phe Glu Arg Pro
    210                 215                 220

Glu Ala Glu Ala Met Cys Thr Ser Phe Lys Glu Asn Pro Thr Thr Phe
225                 230                 235                 240
```

```
Met Gly His Tyr Leu His Glu Val Ala Arg Arg His Pro Tyr Phe Tyr
            245                 250                 255

Ala Pro Glu Leu Leu Tyr Tyr Ala Glu Gln Tyr Asn Glu Ile Leu Thr
            260                 265                 270

Gln Cys Cys Ala Glu Ala Asp Lys Glu Ser Cys Leu Thr Pro Lys Leu
            275                 280                 285

Asp Gly Val Lys Glu Lys Ala Leu Val Ser Ser Val Arg Gln Arg Met
            290                 295                 300

Lys Cys Ser Ser Met Gln Lys Phe Gly Glu Arg Ala Phe Lys Ala Trp
305                 310                 315                 320

Ala Val Ala Arg Leu Ser Gln Thr Phe Pro Asn Ala Asp Phe Ala Glu
            325                 330                 335

Ile Thr Lys Leu Ala Thr Asp Leu Thr Lys Val Asn Lys Glu Cys Cys
            340                 345                 350

His Gly Asp Leu Leu Glu Cys Ala Asp Asp Arg Ala Glu Leu Ala Lys
            355                 360                 365

Tyr Met Cys Glu Asn Gln Ala Thr Ile Ser Ser Lys Leu Gln Thr Cys
            370                 375                 380

Cys Asp Lys Pro Leu Leu Lys Lys Ala His Cys Leu Ser Glu Val Glu
385                 390                 395                 400

His Asp Thr Met Pro Ala Asp Leu Pro Ala Ile Ala Ala Asp Phe Val
            405                 410                 415

Glu Asp Gln Glu Val Cys Lys Asn Tyr Ala Glu Ala Lys Asp Val Phe
            420                 425                 430

Leu Gly Thr Phe Leu Tyr Glu Tyr Ser Arg Arg His Pro Asp Tyr Ser
            435                 440                 445

Val Ser Leu Leu Leu Arg Leu Ala Lys Lys Tyr Glu Ala Thr Leu Glu
            450                 455                 460

Lys Cys Cys Ala Glu Ala Asn Pro Pro Ala Cys Tyr Gly Thr Val Leu
465                 470                 475                 480

Ala Glu Phe Gln Pro Leu Val Glu Glu Pro Lys Asn Leu Val Lys Thr
            485                 490                 495

Asn Cys Asp Leu Tyr Glu Lys Leu Gly Glu Tyr Gly Phe Gln Asn Ala
            500                 505                 510

Ile Leu Val Arg Tyr Thr Gln Lys Ala Pro Gln Val Ser Thr Pro Thr
            515                 520                 525

Leu Val Glu Ala Ala Arg Asn Leu Gly Arg Val Gly Thr Lys Cys Cys
            530                 535                 540

Thr Leu Pro Glu Asp Gln Arg Leu Pro Cys Val Glu Asp Tyr Leu Ser
545                 550                 555                 560

Ala Ile Leu Asn Arg Val Cys Leu Leu His Glu Lys Thr Pro Val Ser
            565                 570                 575

Glu His Val Thr Lys Cys Cys Ser Gly Ser Leu Val Glu Arg Arg Pro
            580                 585                 590

Cys Phe Ser Ala Leu Thr Val Asp Glu Thr Tyr Val Pro Lys Glu Phe
            595                 600                 605

Lys Ala Glu Thr Phe Thr Phe His Ser Asp Ile Cys Thr Leu Pro Glu
            610                 615                 620

Lys Glu Lys Gln Ile Lys Lys Gln Thr Ala Leu Ala Glu Leu Val Lys
625                 630                 635                 640

His Lys Pro Lys Ala Thr Ala Glu Gln Leu Lys Thr Val Met Asp Asp
            645                 650                 655
```

```
Phe Ala Gln Phe Leu Asp Thr Cys Cys Lys Ala Ala Asp Lys Asp Thr
            660                 665                 670
Cys Phe Ser Thr Glu Gly Pro Asn Leu Val Thr Arg Cys Lys Asp Ala
        675                 680                 685
Leu Ala Gly Gly Gly Ser His His His His His His
    690                 695                 700
```

<210> SEQ ID NO 78
<211> LENGTH: 696
<212> TYPE: PRT
<213> ORGANISM: Artificial Sequence
<220> FEATURE:
<223> OTHER INFORMATION: Synthetic: LS-mCXCL548-118-(Gly4Ser)2-mouse SA-(Gly4Ser)-His6

<400> SEQUENCE: 78

```
Met Arg Val Pro Ala Gln Leu Leu Gly Leu Leu Leu Leu Trp Leu Pro
1               5                   10                  15
Gly Ala Arg Cys Ala Thr Glu Leu Arg Cys Val Cys Leu Thr Val Thr
            20                  25                  30
Pro Lys Ile Asn Pro Lys Leu Ile Ala Asn Leu Glu Val Ile Pro Ala
        35                  40                  45
Gly Pro Gln Cys Pro Thr Val Glu Val Ile Ala Lys Leu Lys Asn Gln
    50                  55                  60
Lys Glu Val Cys Leu Asp Pro Glu Ala Pro Val Ile Lys Lys Ile Ile
65                  70                  75                  80
Gln Lys Ile Leu Gly Ser Asp Lys Lys Ala Gly Gly Gly Gly Ser
                85                  90                  95
Gly Gly Gly Gly Ser Glu Ala His Lys Ser Glu Ile Ala His Arg Tyr
            100                 105                 110
Asn Asp Leu Gly Glu Gln His Phe Lys Gly Leu Val Leu Ile Ala Phe
        115                 120                 125
Ser Gln Tyr Leu Gln Lys Cys Ser Tyr Asp Glu His Ala Lys Leu Val
    130                 135                 140
Gln Glu Val Thr Asp Phe Ala Lys Thr Cys Val Ala Asp Glu Ser Ala
145                 150                 155                 160
Ala Asn Cys Asp Lys Ser Leu His Thr Leu Phe Gly Asp Lys Leu Cys
                165                 170                 175
Ala Ile Pro Asn Leu Arg Glu Asn Tyr Gly Glu Leu Ala Asp Cys Cys
            180                 185                 190
Thr Lys Gln Glu Pro Glu Arg Asn Glu Cys Phe Leu Gln His Lys Asp
        195                 200                 205
Asp Asn Pro Ser Leu Pro Pro Phe Glu Arg Pro Glu Ala Glu Ala Met
    210                 215                 220
Cys Thr Ser Phe Lys Glu Asn Pro Thr Thr Phe Met Gly His Tyr Leu
225                 230                 235                 240
His Glu Val Ala Arg Arg His Pro Tyr Phe Tyr Ala Pro Glu Leu Leu
                245                 250                 255
Tyr Tyr Ala Glu Gln Tyr Asn Glu Ile Leu Thr Gln Cys Cys Ala Glu
            260                 265                 270
Ala Asp Lys Glu Ser Cys Leu Thr Pro Lys Leu Asp Gly Val Lys Glu
        275                 280                 285
Lys Ala Leu Val Ser Ser Val Arg Gln Arg Met Lys Cys Ser Ser Met
    290                 295                 300
Gln Lys Phe Gly Glu Arg Ala Phe Lys Ala Trp Ala Val Ala Arg Leu
305                 310                 315                 320
```

Ser Gln Thr Phe Pro Asn Ala Asp Phe Ala Glu Ile Thr Lys Leu Ala
            325                 330                 335

Thr Asp Leu Thr Lys Val Asn Lys Glu Cys Cys His Gly Asp Leu Leu
        340                 345                 350

Glu Cys Ala Asp Asp Arg Ala Glu Leu Ala Lys Tyr Met Cys Glu Asn
    355                 360                 365

Gln Ala Thr Ile Ser Ser Lys Leu Gln Thr Cys Cys Asp Lys Pro Leu
370                 375                 380

Leu Lys Lys Ala His Cys Leu Ser Glu Val Glu His Asp Thr Met Pro
385                 390                 395                 400

Ala Asp Leu Pro Ala Ile Ala Ala Asp Phe Val Glu Asp Gln Glu Val
                405                 410                 415

Cys Lys Asn Tyr Ala Glu Ala Lys Asp Val Phe Leu Gly Thr Phe Leu
            420                 425                 430

Tyr Glu Tyr Ser Arg Arg His Pro Asp Tyr Ser Val Ser Leu Leu Leu
        435                 440                 445

Arg Leu Ala Lys Lys Tyr Glu Ala Thr Leu Glu Lys Cys Cys Ala Glu
    450                 455                 460

Ala Asn Pro Pro Ala Cys Tyr Gly Thr Val Leu Ala Glu Phe Gln Pro
465                 470                 475                 480

Leu Val Glu Glu Pro Lys Asn Leu Val Lys Thr Asn Cys Asp Leu Tyr
                485                 490                 495

Glu Lys Leu Gly Glu Tyr Gly Phe Gln Asn Ala Ile Leu Val Arg Tyr
            500                 505                 510

Thr Gln Lys Ala Pro Gln Val Ser Thr Pro Thr Leu Val Glu Ala Ala
        515                 520                 525

Arg Asn Leu Gly Arg Val Gly Thr Lys Cys Cys Thr Leu Pro Glu Asp
    530                 535                 540

Gln Arg Leu Pro Cys Val Glu Asp Tyr Leu Ser Ala Ile Leu Asn Arg
545                 550                 555                 560

Val Cys Leu Leu His Glu Lys Thr Pro Val Ser Glu His Val Thr Lys
                565                 570                 575

Cys Cys Ser Gly Ser Leu Val Glu Arg Arg Pro Cys Phe Ser Ala Leu
            580                 585                 590

Thr Val Asp Glu Thr Tyr Val Pro Lys Glu Phe Lys Ala Glu Thr Phe
        595                 600                 605

Thr Phe His Ser Asp Ile Cys Thr Leu Pro Glu Lys Glu Lys Gln Ile
    610                 615                 620

Lys Lys Gln Thr Ala Leu Ala Glu Leu Val Lys His Lys Pro Lys Ala
625                 630                 635                 640

Thr Ala Glu Gln Leu Lys Thr Val Met Asp Asp Phe Ala Gln Phe Leu
                645                 650                 655

Asp Thr Cys Cys Lys Ala Ala Asp Lys Asp Thr Cys Phe Ser Thr Glu
            660                 665                 670

Gly Pro Asn Leu Val Thr Arg Cys Lys Asp Ala Leu Ala Gly Gly Gly
        675                 680                 685

Gly Ser His His His His His His
    690                 695

<210> SEQ ID NO 79
<211> LENGTH: 691
<212> TYPE: PRT
<213> ORGANISM: Artificial Sequence
<220> FEATURE:

<223> OTHER INFORMATION: Synthetic: LS-mCXCL748-113-(Gly4Ser)2-mouse SA-(Gly4Ser)-His6

<400> SEQUENCE: 79

| | | | | | | | | | | | | | | |
|---|---|---|---|---|---|---|---|---|---|---|---|---|---|---|
| Met | Arg | Val | Pro | Ala | Gln | Leu | Leu | Gly | Leu | Leu | Leu | Trp | Leu | Pro |
| 1 | | | | 5 | | | | | 10 | | | | | 15 |
| Gly | Ala | Arg | Cys | Ile | Glu | Leu | Arg | Cys | Arg | Cys | Thr | Asn | Thr | Ile | Ser |
| | | | 20 | | | | | 25 | | | | | 30 | |
| Gly | Ile | Pro | Phe | Asn | Ser | Ile | Ser | Leu | Val | Asn | Val | Tyr | Arg | Pro | Gly |
| | | | 35 | | | | 40 | | | | | 45 | | |
| Val | His | Cys | Ala | Asp | Val | Glu | Val | Ile | Ala | Thr | Leu | Lys | Asn | Gly | Gln |
| | 50 | | | | | 55 | | | | | 60 | | | | |
| Lys | Thr | Cys | Leu | Asp | Pro | Asn | Ala | Pro | Gly | Val | Lys | Arg | Ile | Val | Met |
| 65 | | | | | 70 | | | | | 75 | | | | | 80 |
| Lys | Ile | Leu | Glu | Gly | Tyr | Gly | Gly | Gly | Ser | Gly | Gly | Gly | Gly | Ser |
| | | | | 85 | | | | | 90 | | | | | 95 |
| Glu | Ala | His | Lys | Ser | Glu | Ile | Ala | His | Arg | Tyr | Asn | Asp | Leu | Gly | Glu |
| | | | 100 | | | | | 105 | | | | | 110 | | |
| Gln | His | Phe | Lys | Gly | Leu | Val | Leu | Ile | Ala | Phe | Ser | Gln | Tyr | Leu | Gln |
| | | | 115 | | | | | 120 | | | | | 125 | | |
| Lys | Cys | Ser | Tyr | Asp | Glu | His | Ala | Lys | Leu | Val | Gln | Glu | Val | Thr | Asp |
| | 130 | | | | | 135 | | | | | 140 | | | | |
| Phe | Ala | Lys | Thr | Cys | Val | Ala | Asp | Glu | Ser | Ala | Ala | Asn | Cys | Asp | Lys |
| 145 | | | | | 150 | | | | | 155 | | | | | 160 |
| Ser | Leu | His | Thr | Leu | Phe | Gly | Asp | Lys | Leu | Cys | Ala | Ile | Pro | Asn | Leu |
| | | | | 165 | | | | | 170 | | | | | 175 | |
| Arg | Glu | Asn | Tyr | Gly | Glu | Leu | Ala | Asp | Cys | Cys | Thr | Lys | Gln | Glu | Pro |
| | | | 180 | | | | | 185 | | | | | 190 | | |
| Glu | Arg | Asn | Glu | Cys | Phe | Leu | Gln | His | Lys | Asp | Asp | Asn | Pro | Ser | Leu |
| | | | 195 | | | | | 200 | | | | | 205 | | |
| Pro | Pro | Phe | Glu | Arg | Pro | Glu | Ala | Glu | Ala | Met | Cys | Thr | Ser | Phe | Lys |
| | 210 | | | | | 215 | | | | | 220 | | | | |
| Glu | Asn | Pro | Thr | Thr | Phe | Met | Gly | His | Tyr | Leu | His | Glu | Val | Ala | Arg |
| 225 | | | | | 230 | | | | | 235 | | | | | 240 |
| Arg | His | Pro | Tyr | Phe | Tyr | Ala | Pro | Glu | Leu | Leu | Tyr | Tyr | Ala | Glu | Gln |
| | | | | 245 | | | | | 250 | | | | | 255 | |
| Tyr | Asn | Glu | Ile | Leu | Thr | Gln | Cys | Cys | Ala | Glu | Ala | Asp | Lys | Glu | Ser |
| | | | 260 | | | | | 265 | | | | | 270 | | |
| Cys | Leu | Thr | Pro | Lys | Leu | Asp | Gly | Val | Lys | Glu | Lys | Ala | Leu | Val | Ser |
| | | | 275 | | | | | 280 | | | | | 285 | | |
| Ser | Val | Arg | Gln | Arg | Met | Lys | Cys | Ser | Ser | Met | Gln | Lys | Phe | Gly | Glu |
| | 290 | | | | | 295 | | | | | 300 | | | | |
| Arg | Ala | Phe | Lys | Ala | Trp | Ala | Val | Ala | Arg | Leu | Ser | Gln | Thr | Phe | Pro |
| 305 | | | | | 310 | | | | | 315 | | | | | 320 |
| Asn | Ala | Asp | Phe | Ala | Glu | Ile | Thr | Lys | Leu | Ala | Thr | Asp | Leu | Thr | Lys |
| | | | | 325 | | | | | 330 | | | | | 335 | |
| Val | Asn | Lys | Glu | Cys | Cys | His | Gly | Asp | Leu | Leu | Glu | Cys | Ala | Asp | Asp |
| | | | 340 | | | | | 345 | | | | | 350 | | |
| Arg | Ala | Glu | Leu | Ala | Lys | Tyr | Met | Cys | Glu | Asn | Gln | Ala | Thr | Ile | Ser |
| | | | 355 | | | | | 360 | | | | | 365 | | |
| Ser | Lys | Leu | Gln | Thr | Cys | Cys | Asp | Lys | Pro | Leu | Leu | Lys | Lys | Ala | His |
| | 370 | | | | | 375 | | | | | 380 | | | | |
| Cys | Leu | Ser | Glu | Val | Glu | His | Asp | Thr | Met | Pro | Ala | Asp | Leu | Pro | Ala |
| 385 | | | | | 390 | | | | | 395 | | | | | 400 |

```
Ile Ala Ala Asp Phe Val Glu Asp Gln Glu Val Cys Lys Asn Tyr Ala
            405                 410                 415

Glu Ala Lys Asp Val Phe Leu Gly Thr Phe Leu Tyr Glu Tyr Ser Arg
            420                 425                 430

Arg His Pro Asp Tyr Ser Val Ser Leu Leu Leu Arg Leu Ala Lys Lys
            435                 440                 445

Tyr Glu Ala Thr Leu Glu Lys Cys Cys Ala Glu Ala Asn Pro Pro Ala
            450                 455                 460

Cys Tyr Gly Thr Val Leu Ala Glu Phe Gln Pro Leu Val Glu Glu Pro
465                 470                 475                 480

Lys Asn Leu Val Lys Thr Asn Cys Asp Leu Tyr Glu Lys Leu Gly Glu
            485                 490                 495

Tyr Gly Phe Gln Asn Ala Ile Leu Val Arg Tyr Thr Gln Lys Ala Pro
            500                 505                 510

Gln Val Ser Thr Pro Thr Leu Val Glu Ala Ala Arg Asn Leu Gly Arg
            515                 520                 525

Val Gly Thr Lys Cys Cys Thr Leu Pro Glu Asp Gln Arg Leu Pro Cys
            530                 535                 540

Val Glu Asp Tyr Leu Ser Ala Ile Leu Asn Arg Val Cys Leu Leu His
545                 550                 555                 560

Glu Lys Thr Pro Val Ser Glu His Val Thr Lys Cys Cys Ser Gly Ser
            565                 570                 575

Leu Val Glu Arg Arg Pro Cys Phe Ser Ala Leu Thr Val Asp Glu Thr
            580                 585                 590

Tyr Val Pro Lys Glu Phe Lys Ala Glu Thr Phe Thr Phe His Ser Asp
            595                 600                 605

Ile Cys Thr Leu Pro Glu Lys Glu Lys Gln Ile Lys Lys Gln Thr Ala
            610                 615                 620

Leu Ala Glu Leu Val Lys His Lys Pro Lys Ala Thr Ala Glu Gln Leu
625                 630                 635                 640

Lys Thr Val Met Asp Asp Phe Ala Gln Phe Leu Asp Thr Cys Cys Lys
            645                 650                 655

Ala Ala Asp Lys Asp Thr Cys Phe Ser Thr Glu Gly Pro Asn Leu Val
            660                 665                 670

Thr Arg Cys Lys Asp Ala Leu Ala Gly Gly Gly Ser His His His
            675                 680                 685

His His His
    690

<210> SEQ ID NO 80
<211> LENGTH: 730
<212> TYPE: PRT
<213> ORGANISM: Artificial Sequence
<220> FEATURE:
<223> OTHER INFORMATION: Synthetic: LS-mCXCL922-126-(Gly4Ser)2-mouse SA-
      (Gly4Ser)-His6

<400> SEQUENCE: 80

Met Arg Val Pro Ala Gln Leu Leu Gly Leu Leu Leu Leu Trp Leu Pro
1               5                   10                  15

Gly Ala Arg Cys Thr Leu Val Ile Arg Asn Ala Arg Cys Ser Cys Ile
            20                  25                  30

Ser Thr Ser Arg Gly Thr Ile His Tyr Lys Ser Leu Lys Asp Leu Lys
            35                  40                  45

Gln Phe Ala Pro Ser Pro Asn Cys Asn Lys Thr Glu Ile Ile Ala Thr
```

```
                  50                  55                  60

Leu Lys Asn Gly Asp Gln Thr Cys Leu Asp Pro Asp Ser Ala Asn Val
 65                  70                  75                  80

Lys Lys Leu Met Lys Glu Trp Glu Lys Lys Ile Ser Gln Lys Lys Lys
                     85                  90                  95

Gln Lys Arg Gly Lys Lys His Gln Lys Asn Met Lys Asn Arg Lys Pro
                100                 105                 110

Lys Thr Pro Gln Ser Arg Arg Ser Arg Lys Thr Thr Gly Gly Gly
            115                 120                 125

Gly Ser Gly Gly Gly Ser Glu Ala His Lys Ser Glu Ile Ala His
            130                 135                 140

Arg Tyr Asn Asp Leu Gly Glu Gln His Phe Lys Gly Leu Val Leu Ile
145                 150                 155                 160

Ala Phe Ser Gln Tyr Leu Gln Lys Cys Ser Tyr Asp Glu His Ala Lys
                165                 170                 175

Leu Val Gln Glu Val Thr Asp Phe Ala Lys Thr Cys Val Ala Asp Glu
                180                 185                 190

Ser Ala Ala Asn Cys Asp Lys Ser Leu His Thr Leu Phe Gly Asp Lys
                195                 200                 205

Leu Cys Ala Ile Pro Asn Leu Arg Glu Asn Tyr Gly Glu Leu Ala Asp
210                 215                 220

Cys Cys Thr Lys Gln Glu Pro Glu Arg Asn Glu Cys Phe Leu Gln His
225                 230                 235                 240

Lys Asp Asp Asn Pro Ser Leu Pro Pro Phe Glu Arg Pro Glu Ala Glu
                245                 250                 255

Ala Met Cys Thr Ser Phe Lys Glu Asn Pro Thr Thr Phe Met Gly His
                260                 265                 270

Tyr Leu His Glu Val Ala Arg Arg His Pro Tyr Phe Tyr Ala Pro Glu
                275                 280                 285

Leu Leu Tyr Tyr Ala Glu Gln Tyr Asn Glu Ile Leu Thr Gln Cys Cys
                290                 295                 300

Ala Glu Ala Asp Lys Glu Ser Cys Leu Thr Pro Lys Leu Asp Gly Val
305                 310                 315                 320

Lys Glu Lys Ala Leu Val Ser Ser Val Arg Gln Arg Met Lys Cys Ser
                325                 330                 335

Ser Met Gln Lys Phe Gly Glu Arg Ala Phe Lys Ala Trp Ala Val Ala
                340                 345                 350

Arg Leu Ser Gln Thr Phe Pro Asn Ala Asp Phe Ala Glu Ile Thr Lys
                355                 360                 365

Leu Ala Thr Asp Leu Thr Lys Val Asn Lys Glu Cys Cys His Gly Asp
                370                 375                 380

Leu Leu Glu Cys Ala Asp Asp Arg Ala Glu Leu Ala Lys Tyr Met Cys
385                 390                 395                 400

Glu Asn Gln Ala Thr Ile Ser Ser Lys Leu Gln Thr Cys Cys Asp Lys
                405                 410                 415

Pro Leu Leu Lys Lys Ala His Cys Leu Ser Glu Val Glu His Asp Thr
                420                 425                 430

Met Pro Ala Asp Leu Pro Ala Ile Ala Ala Asp Phe Val Glu Asp Gln
                435                 440                 445

Glu Val Cys Lys Asn Tyr Ala Glu Ala Lys Asp Val Phe Leu Gly Thr
                450                 455                 460

Phe Leu Tyr Glu Tyr Ser Arg Arg His Pro Asp Tyr Ser Val Ser Leu
465                 470                 475                 480
```

```
Leu Leu Arg Leu Ala Lys Lys Tyr Glu Ala Thr Leu Glu Lys Cys Cys
                485                 490                 495

Ala Glu Ala Asn Pro Pro Ala Cys Tyr Gly Thr Val Leu Ala Glu Phe
            500                 505                 510

Gln Pro Leu Val Glu Glu Pro Lys Asn Leu Val Lys Thr Asn Cys Asp
        515                 520                 525

Leu Tyr Glu Lys Leu Gly Glu Tyr Gly Phe Gln Asn Ala Ile Leu Val
    530                 535                 540

Arg Tyr Thr Gln Lys Ala Pro Gln Val Ser Thr Pro Thr Leu Val Glu
545                 550                 555                 560

Ala Ala Arg Asn Leu Gly Arg Val Gly Thr Lys Cys Cys Thr Leu Pro
                565                 570                 575

Glu Asp Gln Arg Leu Pro Cys Val Glu Asp Tyr Leu Ser Ala Ile Leu
            580                 585                 590

Asn Arg Val Cys Leu Leu His Glu Lys Thr Pro Val Ser Glu His Val
        595                 600                 605

Thr Lys Cys Cys Ser Gly Ser Leu Val Glu Arg Arg Pro Cys Phe Ser
    610                 615                 620

Ala Leu Thr Val Asp Glu Thr Tyr Val Pro Lys Glu Phe Lys Ala Glu
625                 630                 635                 640

Thr Phe Thr Phe His Ser Asp Ile Cys Thr Leu Pro Glu Lys Glu Lys
                645                 650                 655

Gln Ile Lys Lys Gln Thr Ala Leu Ala Glu Leu Val Lys His Lys Pro
            660                 665                 670

Lys Ala Thr Ala Glu Gln Leu Lys Thr Val Met Asp Asp Phe Ala Gln
        675                 680                 685

Phe Leu Asp Thr Cys Cys Lys Ala Ala Asp Lys Asp Thr Cys Phe Ser
    690                 695                 700

Thr Glu Gly Pro Asn Leu Val Thr Arg Cys Lys Asp Ala Leu Ala Gly
705                 710                 715                 720

Gly Gly Gly Ser His His His His His His
                725                 730

<210> SEQ ID NO 81
<211> LENGTH: 702
<212> TYPE: PRT
<213> ORGANISM: Artificial Sequence
<220> FEATURE:
<223> OTHER INFORMATION: Synthetic: LS-mCXCL1022-98-(Gly4Ser)2-mouse SA-
      (Gly4Ser)-His6

<400> SEQUENCE: 81

Met Arg Val Pro Ala Gln Leu Leu Gly Leu Leu Leu Leu Trp Leu Pro
1               5                   10                  15

Gly Ala Arg Cys Ile Pro Leu Ala Arg Thr Val Arg Cys Asn Cys Ile
            20                  25                  30

His Ile Asp Asp Gly Pro Val Arg Met Arg Ala Ile Gly Lys Leu Glu
        35                  40                  45

Ile Ile Pro Ala Ser Leu Ser Cys Pro Arg Val Glu Ile Ile Ala Thr
    50                  55                  60

Met Lys Lys Asn Asp Glu Gln Arg Cys Leu Asn Pro Glu Ser Lys Thr
65                  70                  75                  80

Ile Lys Asn Leu Met Lys Ala Phe Ser Gln Lys Arg Ser Lys Arg Ala
                85                  90                  95

Pro Gly Gly Gly Gly Ser Gly Gly Gly Gly Ser Glu Ala His Lys Ser
```

```
            100                 105                 110
Glu Ile Ala His Arg Tyr Asn Asp Leu Gly Glu Gln His Phe Lys Gly
            115                 120                 125
Leu Val Leu Ile Ala Phe Ser Gln Tyr Leu Gln Lys Cys Ser Tyr Asp
            130                 135                 140
Glu His Ala Lys Leu Val Gln Glu Val Thr Asp Phe Ala Lys Thr Cys
145                 150                 155                 160
Val Ala Asp Glu Ser Ala Ala Asn Cys Asp Lys Ser Leu His Thr Leu
                    165                 170                 175
Phe Gly Asp Lys Leu Cys Ala Ile Pro Asn Leu Arg Glu Asn Tyr Gly
                    180                 185                 190
Glu Leu Ala Asp Cys Cys Thr Lys Gln Glu Pro Glu Arg Asn Glu Cys
                    195                 200                 205
Phe Leu Gln His Lys Asp Asp Asn Pro Ser Leu Pro Pro Phe Glu Arg
                    210                 215                 220
Pro Glu Ala Glu Ala Met Cys Thr Ser Phe Lys Glu Asn Pro Thr Thr
225                 230                 235                 240
Phe Met Gly His Tyr Leu His Glu Val Ala Arg Arg His Pro Tyr Phe
                    245                 250                 255
Tyr Ala Pro Glu Leu Leu Tyr Tyr Ala Glu Gln Tyr Asn Glu Ile Leu
                    260                 265                 270
Thr Gln Cys Cys Ala Glu Ala Asp Lys Glu Ser Cys Leu Thr Pro Lys
                    275                 280                 285
Leu Asp Gly Val Lys Glu Lys Ala Leu Val Ser Ser Val Arg Gln Arg
            290                 295                 300
Met Lys Cys Ser Ser Met Gln Lys Phe Gly Glu Arg Ala Phe Lys Ala
305                 310                 315                 320
Trp Ala Val Ala Arg Leu Ser Gln Thr Phe Pro Asn Ala Asp Phe Ala
                    325                 330                 335
Glu Ile Thr Lys Leu Ala Thr Asp Leu Thr Lys Val Asn Lys Glu Cys
                    340                 345                 350
Cys His Gly Asp Leu Leu Glu Cys Ala Asp Asp Arg Ala Glu Leu Ala
                    355                 360                 365
Lys Tyr Met Cys Glu Asn Gln Ala Thr Ile Ser Ser Lys Leu Gln Thr
            370                 375                 380
Cys Cys Asp Lys Pro Leu Leu Lys Lys Ala His Cys Leu Ser Glu Val
385                 390                 395                 400
Glu His Asp Thr Met Pro Ala Asp Leu Pro Ala Ile Ala Ala Asp Phe
                    405                 410                 415
Val Glu Asp Gln Glu Val Cys Lys Asn Tyr Ala Glu Ala Lys Asp Val
                    420                 425                 430
Phe Leu Gly Thr Phe Leu Tyr Glu Tyr Ser Arg Arg His Pro Asp Tyr
                    435                 440                 445
Ser Val Ser Leu Leu Leu Arg Leu Ala Lys Lys Tyr Glu Ala Thr Leu
                    450                 455                 460
Glu Lys Cys Cys Ala Glu Ala Asn Pro Pro Ala Cys Tyr Gly Thr Val
465                 470                 475                 480
Leu Ala Glu Phe Gln Pro Leu Val Glu Glu Pro Lys Asn Leu Val Lys
                    485                 490                 495
Thr Asn Cys Asp Leu Tyr Glu Lys Leu Gly Glu Tyr Gly Phe Gln Asn
                    500                 505                 510
Ala Ile Leu Val Arg Tyr Thr Gln Lys Ala Pro Gln Val Ser Thr Pro
            515                 520                 525
```

-continued

```
Thr Leu Val Glu Ala Ala Arg Asn Leu Gly Arg Val Gly Thr Lys Cys
        530                 535                 540

Cys Thr Leu Pro Glu Asp Gln Arg Leu Pro Cys Val Glu Asp Tyr Leu
545                 550                 555                 560

Ser Ala Ile Leu Asn Arg Val Cys Leu Leu His Glu Lys Thr Pro Val
                565                 570                 575

Ser Glu His Val Thr Lys Cys Cys Ser Gly Ser Leu Val Glu Arg Arg
            580                 585                 590

Pro Cys Phe Ser Ala Leu Thr Val Asp Glu Thr Tyr Val Pro Lys Glu
        595                 600                 605

Phe Lys Ala Glu Thr Phe Thr Phe His Ser Asp Ile Cys Thr Leu Pro
    610                 615                 620

Glu Lys Glu Lys Gln Ile Lys Lys Gln Thr Ala Leu Ala Glu Leu Val
625                 630                 635                 640

Lys His Lys Pro Lys Ala Thr Ala Glu Gln Leu Lys Thr Val Met Asp
                645                 650                 655

Asp Phe Ala Gln Phe Leu Asp Thr Cys Cys Lys Ala Ala Asp Lys Asp
            660                 665                 670

Thr Cys Phe Ser Thr Glu Gly Pro Asn Leu Val Thr Arg Cys Lys Asp
        675                 680                 685

Ala Leu Ala Gly Gly Gly Gly Ser His His His His His
    690                 695                 700

<210> SEQ ID NO 82
<211> LENGTH: 704
<212> TYPE: PRT
<213> ORGANISM: Artificial Sequence
<220> FEATURE:
<223> OTHER INFORMATION: Synthetic: LS-mCXCL1122-100-(Gly4Ser)2-mouse
      SA-(Gly4Ser)-His6

<400> SEQUENCE: 82

Met Arg Val Pro Ala Gln Leu Leu Gly Leu Leu Leu Leu Trp Leu Pro
1               5                   10                  15

Gly Ala Arg Cys Phe Leu Met Phe Lys Gln Gly Arg Cys Leu Cys Ile
            20                  25                  30

Gly Pro Gly Met Lys Ala Val Lys Met Ala Glu Ile Glu Lys Ala Ser
        35                  40                  45

Val Ile Tyr Pro Ser Asn Gly Cys Asp Lys Val Glu Val Ile Val Thr
    50                  55                  60

Met Lys Ala His Lys Arg Gln Arg Cys Leu Asp Pro Arg Ser Lys Gln
65                  70                  75                  80

Ala Arg Leu Ile Met Gln Ala Ile Glu Lys Lys Asn Phe Leu Arg Arg
                85                  90                  95

Gln Asn Met Gly Gly Gly Gly Ser Gly Gly Gly Gly Ser Glu Ala His
            100                 105                 110

Lys Ser Glu Ile Ala His Arg Tyr Asn Asp Leu Gly Glu Gln His Phe
        115                 120                 125

Lys Gly Leu Val Leu Ile Ala Phe Ser Gln Tyr Leu Gln Lys Cys Ser
    130                 135                 140

Tyr Asp Glu His Ala Lys Leu Val Gln Glu Val Thr Asp Phe Ala Lys
145                 150                 155                 160

Thr Cys Val Ala Asp Glu Ser Ala Ala Asn Cys Asp Lys Ser Leu His
                165                 170                 175

Thr Leu Phe Gly Asp Lys Leu Cys Ala Ile Pro Asn Leu Arg Glu Asn
```

```
                180                 185                 190
Tyr Gly Glu Leu Ala Asp Cys Cys Thr Lys Gln Glu Pro Glu Arg Asn
            195                 200                 205
Glu Cys Phe Leu Gln His Lys Asp Asp Asn Pro Ser Leu Pro Pro Phe
            210                 215                 220
Glu Arg Pro Glu Ala Glu Ala Met Cys Thr Ser Phe Lys Glu Asn Pro
225                 230                 235                 240
Thr Thr Phe Met Gly His Tyr Leu His Glu Val Ala Arg Arg His Pro
                245                 250                 255
Tyr Phe Tyr Ala Pro Glu Leu Leu Tyr Tyr Ala Glu Gln Tyr Asn Glu
            260                 265                 270
Ile Leu Thr Gln Cys Cys Ala Glu Ala Asp Lys Glu Ser Cys Leu Thr
            275                 280                 285
Pro Lys Leu Asp Gly Val Lys Glu Lys Ala Leu Val Ser Ser Val Arg
            290                 295                 300
Gln Arg Met Lys Cys Ser Ser Met Gln Lys Phe Gly Glu Arg Ala Phe
305                 310                 315                 320
Lys Ala Trp Ala Val Ala Arg Leu Ser Gln Thr Phe Pro Asn Ala Asp
                325                 330                 335
Phe Ala Glu Ile Thr Lys Leu Ala Thr Asp Leu Thr Lys Val Asn Lys
                340                 345                 350
Glu Cys Cys His Gly Asp Leu Leu Glu Cys Ala Asp Asp Arg Ala Glu
            355                 360                 365
Leu Ala Lys Tyr Met Cys Glu Asn Gln Ala Thr Ile Ser Ser Lys Leu
            370                 375                 380
Gln Thr Cys Cys Asp Lys Pro Leu Leu Lys Lys Ala His Cys Leu Ser
385                 390                 395                 400
Glu Val Glu His Asp Thr Met Pro Ala Asp Leu Pro Ala Ile Ala Ala
                405                 410                 415
Asp Phe Val Glu Asp Gln Glu Val Cys Lys Asn Tyr Ala Glu Ala Lys
                420                 425                 430
Asp Val Phe Leu Gly Thr Phe Leu Tyr Glu Tyr Ser Arg Arg His Pro
            435                 440                 445
Asp Tyr Ser Val Ser Leu Leu Leu Arg Leu Ala Lys Lys Tyr Glu Ala
            450                 455                 460
Thr Leu Glu Lys Cys Cys Ala Glu Ala Asn Pro Pro Ala Cys Tyr Gly
465                 470                 475                 480
Thr Val Leu Ala Glu Phe Gln Pro Leu Val Glu Glu Pro Lys Asn Leu
                485                 490                 495
Val Lys Thr Asn Cys Asp Leu Tyr Glu Lys Leu Gly Glu Tyr Gly Phe
            500                 505                 510
Gln Asn Ala Ile Leu Val Arg Tyr Thr Gln Lys Ala Pro Gln Val Ser
            515                 520                 525
Thr Pro Thr Leu Val Glu Ala Ala Arg Asn Leu Gly Arg Val Gly Thr
            530                 535                 540
Lys Cys Cys Thr Leu Pro Glu Asp Gln Arg Leu Pro Cys Val Glu Asp
545                 550                 555                 560
Tyr Leu Ser Ala Ile Leu Asn Arg Val Cys Leu Leu His Glu Lys Thr
                565                 570                 575
Pro Val Ser Glu His Val Thr Lys Cys Cys Ser Gly Ser Leu Val Glu
            580                 585                 590
Arg Arg Pro Cys Phe Ser Ala Leu Thr Val Asp Glu Thr Tyr Val Pro
            595                 600                 605
```

```
Lys Glu Phe Lys Ala Glu Thr Phe Thr Phe His Ser Asp Ile Cys Thr
    610                 615                 620

Leu Pro Glu Lys Glu Lys Gln Ile Lys Lys Gln Thr Ala Leu Ala Glu
625                 630                 635                 640

Leu Val Lys His Lys Pro Lys Ala Thr Ala Glu Gln Leu Lys Thr Val
            645                 650                 655

Met Asp Asp Phe Ala Gln Phe Leu Asp Thr Cys Cys Lys Ala Ala Asp
            660                 665                 670

Lys Asp Thr Cys Phe Ser Thr Glu Gly Pro Asn Leu Val Thr Arg Cys
            675                 680                 685

Lys Asp Ala Leu Ala Gly Gly Gly Gly Ser His His His His His His
    690                 695                 700
```

<210> SEQ ID NO 83
<211> LENGTH: 2652
<212> TYPE: DNA
<213> ORGANISM: Artificial Sequence
<220> FEATURE:
<223> OTHER INFORMATION: Synthetic: gWiz-LS-mouse SA-(Gly4Ser)3-scFv
      (VL-VH) CK138-(Gly4Ser)-His6

<400> SEQUENCE: 83

```
atggacatga gagtgcctgc tcagctgctg ggcctgctgc tgctgtggct gcctggtgct    60
agatgcgaag cacacaagag tgagatcgcc catcggtata tgatttggg agaacaacat    120
ttcaaaggcc tagtcctgat tgccttttcc cagtatctcc agaaatgctc atacgatgag    180
catgccaaat tagtgcagga agtaacagac tttgcaaaga cgtgtgttgc cgatgagtct    240
gccgccaact gtgacaaatc ccttcacact cttttttggag ataagttgtg tgccattcca    300
aacctccgtg aaaactatgg tgaactggct gactgctgta caaaacaaga gcccgaaaga    360
aacgaatgtt tcctgcaaca caaagatgac aaccccagcc taccaccatt tgaaaggcca    420
gaggctgagg ccatgtgcac ctccttaag gaaaacccaa ccacctttat gggacactat    480
ttgcatgaag ttgccagaag acatccttat ttctatgccc cagaacttct ttactatgct    540
gagcagtaca atgagattct gacccagtgt tgtgcagagg ctgacaagga agctgcctg    600
accccgaagc ttgatggtgt gaaggagaaa gcattggtct catctgtccg tcagagaatg    660
aagtgctcca gtatgcagaa gtttggagag agagcttta agcatgggc agtagctcgt    720
ctgagccaga cattccccaa tgctgacttt gcagaaatca ccaaattggc aacagacctg    780
accaaagtca caaggagtg ctgccatggt gacctgctgg aatgcgcaga tgacagggcg    840
gaacttgcca gtacatgtg tgaaaaccag gcgactatct ccagcaaact gcagacttgc    900
tgcgataaac cactgttgaa gaaagcccac tgtcttagtg aggtggagca tgacaccatg    960
cctgctgatc tgcctgccat tgctgctgat tttgttgagg accaggaagt gtgcaagaac   1020
tatgctgagg ccaaggatgt cttcctgggc acgttcttgt atgaatattc aagaagacac   1080
cctgattact ctgtatccct gttgctgaga cttgctaaga atatgaagc cactctggaa   1140
aagtgctgcg ctgaagccaa tcctcccgca tgctacggca cagtgcttgc tgaatttcag   1200
cctcttgtag aagagcctaa gaacttggtc aaaaccaact gtgatcttta cgagaagctt   1260
ggagaatatg gattccaaaa tgccattcta gttcgctaca cccagaaagc acctcaggtg   1320
tcaaccccaa ctctcgtgga ggctgcaaga aacctaggaa gagtgggcac caagtgttgt   1380
acacttcctg aagatcagag actgcctgt gtggaagact atctgtctgc aatcctgaac   1440
cgtgtgtgtc tgctgcatga aagacccca gtgagtgagc atgttaccaa gtgctgtagt   1500
```

```
ggatccctgg tggaaaggcg gccatgcttc tctgctctga cagttgatga aacatatgtc    1560
cccaaagagt ttaaagctga gaccttcacc ttccactctg atatctgcac acttccagag    1620
aaggagaagc agattaagaa acaaacggct cttgctgagc tggtgaagca caagcccaag    1680
gctacagcgg agcaactgaa gactgtcatg gatgactttg cacagttcct ggatacatgt    1740
tgcaaggctg ctgacaagga cacctgcttc tcgactgagg tccaaacct tgtcactaga    1800 tgcaaagacg ccttagccgg tggaggaggc tctggtggag cggtagcgg aggcggaggg    1860 tcggctatcc agatgacccg gtccccgagc tccctgtccg cctctgtggg cgatagggtc    1920
accatcacct gccgtgccag tcagtaccac gacggttctg cagcctggta tcaacagaaa    1980
ccaggaaaag ctccgaagct tctgatttac ggtgcatcct acctctactc tggagtccct    2040
tcccgcttct ctggtagccg ttccgggacg gatttcactc tgaccatcag cagtctgcag    2100
ccggaagact tcgcaactta ttactgtcag caatcttctt attctctgat cacgttcgga    2160
cagggtacca aggtggagat caaaggtact actgccgcta gtggtagtag tggtggcagt    2220
agcagtggtg ccgaggttca gctggtggag tctgacggtg gcctggtgca gccaggggc    2280 tcactccgtt tgtcctgtgc agcttctggc ttcaacctct cttactacgg tatgcactgg    2340
gtgcgtcagg ccccgggtaa gggcctggaa tgggttgcat acattgcttc ttaccctggc    2400
tacacttctt atgccgatag cgtcaagggc cgtttcacta taagcgcaga cacatccaaa    2460
aacacagcct acctacaaat gaacagctta agagctgagg acactgccgt ctactattgt    2520
gctcgctctg gttacagtta ctctccgtat tattcttggt tctctgctgg tatgaactac    2580
tggggtcaag agccctggt caccgtctcc tcgggagggg gcggttccca ccatcaccac    2640
catcactgat ag    2652
```

<210> SEQ ID NO 84
<211> LENGTH: 2625
<212> TYPE: DNA
<213> ORGANISM: Artificial Sequence
<220> FEATURE:
<223> OTHER INFORMATION: Synthetic: gWiz-LS-mouse SA-(Gly4Ser)3-scFv
    (VL-VH) CK157-(Gly4Ser)-His6

<400> SEQUENCE: 84

```
atggacatga gagtgcctgc tcagctgctg ggcctgctgc tgctgtggct gcctggtgct     60
agatgcgaag cacacaagag tgagatcgcc catcggtata tgatttggg agaacaacat    120 ttcaaaggcc tagtcctgat tgcctttttcc cagtatctcc agaaatgctc atacgatgag    180
catgccaaat tagtgcagga agtaacagac tttgcaaaga cgtgtgttgc cgatgagtct    240
gccgccaact gtgacaaatc ccttcacact cttttggag ataagttgtg tgccattcca    300
aacctccgtg aaaactatgg tgaactggct gactgctgta caaaacaaga gcccgaaaga    360
aacgaatgtt tcctgcaaca caaagatgac aaccccagcc taccaccatt tgaaaggcca    420
gaggctgagg ccatgtgcac ctccttaag gaaaacccaa ccacctttat gggacactat    480
ttgcatgaag ttgccagaag acatccttat ttctatgccc cagaacttct ttactatgct    540
gagcagtaca atgagattct gacccagtgt tgtgcagagg ctgacaagga agctgcctg    600 accccgaagc ttgatggtgt gaaggagaaa gcattggtct catctgtccg tcagagaatg    660
aagtgctcca gtatgcagaa gtttggagag agagctttta agcatgggc agtagctcgt    720 ctgagccaga cattccccaa tgctgacttt gcagaaatca ccaaattggc aacagacctg    780
accaaagtca caaggagtg ctgccatggt gacctgctgg aatgcgcaga tgacagggcg    840
```

```
gaacttgcca agtacatgtg tgaaaaccag gcgactatct ccagcaaact gcagacttgc      900
tgcgataaac cactgttgaa gaaagcccac tgtcttagtg aggtggagca tgacaccatg      960
cctgctgatc tgcctgccat tgctgctgat tttgttgagg accaggaagt gtgcaagaac     1020
tatgctgagg ccaaggatgt cttcctgggc acgttcttgt atgaatattc aagaagacac     1080
cctgattact ctgtatccct gttgctgaga cttgctaaga aatatgaagc cactctggaa     1140
aagtgctgcg ctgaagccaa tcctcccgca tgctacggca cagtgcttgc tgaatttcag     1200
cctcttgtag aagagcctaa gaacttggtc aaaaccaact gtgatcttta cgagaagctt     1260
ggagaatatg gattccaaaa tgccattcta gttcgctaca cccagaaagc acctcaggtg     1320
tcaaccccaa ctctcgtgga ggctgcaaga aacctaggaa gagtgggcac caagtgttgt     1380
acacttcctg aagatcagag actgccttgt gtggaagact atctgtctgc aatcctgaac     1440
cgtgtgtgtc tgctgcatga aagaccccca gtgagtgagc atgttaccaa gtgctgtagt     1500
ggatccctgg tggaaaggcg gccatgcttc tctgctctga cagttgatga acatatgtc      1560
cccaaagagt ttaaagctga gccttcacc ttccactctg atatctgcac acttccagag     1620
aaggagaagc agattaagaa acaaacggct cttgctgagc tggtgaagca caagcccaag     1680
gctacagcgg agcaactgaa gactgtcatg gatgactttg cacagttcct ggatacatgt     1740
tgcaaggctg ctgacaagga cacctgcttc tcgactgagg gtccaaacct tgtcactaga     1800
tgcaaagacg ccttagccgg tggaggaggc tctggtggag gcggtagcgg aggcggaggg     1860
tcggatatcc agatgaccca gtccccgagc tccctgtccg cctctgtggg cgatagggtc     1920
accatcacct gccgtgccag tcagtcttac ggtggtgtag cctggtatca acagaaacca     1980
ggaaaagccc cgaagcttct gatttactct gcatcctacc tctactctgg agtcccttct     2040
cgcttctctg gtagccgttc cgggacggat ttcactctga ccatcagcag tctgcagccg     2100
gaagacttcg caacttatta ctgtcagcaa ccatctcatc tgatcacgtt cggacagggt     2160
accgaggtgg agatcaaagg tactactgcc gctagtggta gtagtggtgg cagtagcagt     2220
ggtgccgagg ttcagctggt ggagtctggc ggtggcctgg tgcagccagg gggctcactc     2280
cgtttgtcct gtgcagcttc tggctccaac ccctactact acgtggtac gcactgggtg      2340
cgtcaggccc cgggtgagga gctggaatgg gttgcatcta ttggttctta ccctggctac     2400
actgactatg ccgatagcgt caagggccgt tcactataa gcgcagacac atccaaaaac      2460
acagcctacc tacaaatgaa cagcttaaga gctgaggaca ctgccgtcta ttattgtgct     2520
cgccattact actggtacga tgctactgac tactggggtc aaggaaccct ggtcaccgtc     2580
tcctcgggag ggggcggttc caccatcac caccatcact gatag                      2625
```

<210> SEQ ID NO 85
<211> LENGTH: 2646
<212> TYPE: DNA
<213> ORGANISM: Artificial Sequence
<220> FEATURE:
<223> OTHER INFORMATION: Synthetic: gWiz-LS-mouse SA-(Gly4Ser)3-scFv
      (VL-VH) CK129-(Gly4Ser)-His6

<400> SEQUENCE: 85

```
atggacatga gagtgcctgc tcagctgctg ggcctgctgc tgctgtggct gcctggtgct       60
agatgcgaag cacacaagag tgagatcgcc catcggtata atgatttggg agaacaacat      120
ttcaaaggcc tagtcctgat tgccttttcc cagtatctcc agaaatgctc atacgatgag      180
catgccaaat tagtgcagga agtaacagac tttgcaaaga cgtgtgttgc cgatgagtct      240
```

```
gccgccaact gtgacaaatc ccttcacact cttttttggag ataagttgtg tgccattcca    300
aacctccgtg aaaactatgg tgaactggct gactgctgta caaaacaaga gcccgaaaga    360
aacgaatgtt tcctgcaaca caaagatgac aaccccagcc taccaccatt tgaaaggcca    420
gaggctgagg ccatgtgcac ctcctttaag gaaaacccaa ccacctttat gggacactat    480
ttgcatgaag ttgccagaag acatccttat ttctatgccc cagaacttct ttactatgct    540
gagcagtaca atgagattct gacccagtgt tgtgcagagg ctgacaagga aagctgcctg    600 acccccgaagc ttgatggtgt gaaggagaaa gcattggtct catctgtccg tcagagaatg    660
aagtgctcca gtatgcagaa gtttggagag agagcttttta agcatgggc agtagctcgt    720 ctgagccaga cattccccaa tgctgacttt gcagaaatca ccaaattggc aacagacctg    780
accaaagtca caaggagtg ctgccatggt gacctgctgg aatgcgcaga tgacagggcg    840
gaacttgcca agtacatgtg tgaaaaccag gcgactatct ccagcaaact gcagacttgc    900
tgcgataaac cactgttgaa gaaagcccac tgtcttagtg aggtggagca tgacaccatg    960
cctgctgatc tgcctgccat tgctgctgat tttgttgagg accaggaagt gtgcaagaac   1020
tatgctgagg ccaaggatgt cttcctgggc acgttcttgt atgaatattc aagaagacac   1080
cctgattact ctgtatccct gttgctgaga cttgctaaga aatatgaagc cactctggaa   1140
aagtgctgcg ctgaagccaa tcctcccgca tgctacggca cagtgcttgc tgaatttcag   1200
cctcttgtag aagagcctaa gaacttggtc aaaaccaact gtgatcttta cgagaagctt   1260
ggagaatatg gattccaaaa tgccattcta gttcgctaca cccagaaagc acctcaggtg   1320
tcaaccccaa ctctcgtgga ggctgcaaga aacctaggaa gagtgggcac caagtgttgt   1380
acacttcctg aagatcagag actgccttgt gtggaagact atctgtctgc aatcctgaac   1440
cgtgtgtgtc tgctgcatga aagaccccca gtgagtgagc atgttaccaa gtgctgtagt   1500
ggatccctgg tggaaaggcg gccatgcttc tctgctctga cagttgatga acatatgtc   1560 cccaaagagt ttaaagctga gaccttcacc ttccactctg atatctgcac acttccagag   1620
aaggagaagc agattaagaa acaaacggct cttgctgagc tggtgaagca caagcccaag   1680
gctacagcgg agcaactgaa gactgtcatg gatgactttg cacagttcct ggatacatgt   1740
tgcaaggctg ctgacaagga cacctgcttc tcgactgagg gtccaaacct tgtcactaga   1800
tgcaaagacg ccttagccgg tggaggaggc tctggtggag gcggtagcgg aggcggaggg   1860
tcggctagcg atatccagat gacccagtcc ccgagccccc tgtccgcctc tgtgggcgat   1920
agggtcacca tcacctgccg tgccagtcag tacggtggtt acgtagcctg gtatcaacag   1980
aaaccaggaa aagctccgaa gcttctgatt tacggtgcat cccttctcta ctctggagtc   2040
ccttctcgct tctctggtgg ccgttccggg acggatttca ctctgaccat cagcagtctg   2100
cagccggaag acttcgcaac ttattactgt cagcgaggtc atgctctgat cacgttcgga   2160
cagggtacca aggtggagat cgaaggtact actgccgcta gtggtagtag tggtggcagt   2220
agcagtggtg ccgaggttca gctggtggag tctggcggtg gcctggtgca gccagggggc   2280
tcactccgtt tatcctgtgc agcttctggc ttcaacatct cttcttacgg ttctatgcac   2340
tgggtgcgtc aggccccggg taagggcctg gaatgggttg catctattta cccttactct   2400
agctctactt actatgccga tagcgtcaag ggccgtttca ctataagcgc agacacatcc   2460
aaaaacacag cctacctaca aatgaacagc ttaagagctg aggacactgc cgtctattat   2520
tgtgctcgtg gttacggtcc gtggtacgct tactcttact tcgctttgga ctactgggt   2580
```

```
caaggaaccc tggtcaccgt ctcctcggga gggggcggtt cccaccatca ccaccatcac    2640
tgatag                                                               2646

<210> SEQ ID NO 86
<211> LENGTH: 2652
<212> TYPE: DNA
<213> ORGANISM: Artificial Sequence
<220> FEATURE:
<223> OTHER INFORMATION: Synthetic: gWiz-LS-mouse SA-(Gly4Ser)3-scFv
      (VL-VH) CK138-ds1 (VL100Q>C / VH44G>C)-(Gly4Ser)-His6

<400> SEQUENCE: 86
atggacatga gagtgcctgc tcagctgctg ggcctgctgc tgctgtggct gcctggtgct      60
agatgcgaag cacacaagag tgagatcgcc catcggtata tgatttggg agaacaacat     120 ttcaaaggcc tagtcctgat tgccttttcc cagtatctcc agaaatgctc atacgatgag     180
catgccaaat tagtgcagga agtaacagac tttgcaaaga cgtgtgttgc cgatgagtct     240
gccgccaact gtgacaaatc ccttcacact cttttggag ataagttgtg tgccattcca      300
aacctccgtg aaaactatgg tgaactggct gactgctgta caaaacaaga gcccgaaaga     360
aacgaatgtt tcctgcaaca caaagatgac aaccccagcc taccaccatt tgaaaggcca     420
gaggctgagg ccatgtgcac ctcctttaag gaaaacccaa ccacctttat gggacactat     480
ttgcatgaag ttgccagaag acatccttat ttctatgccc cagaacttct ttactatgct     540
gagcagtaca atgagattct gacccagtgt gtgtgcagagg ctgacaagga aagctgcctg     600 acccccgaagc ttgatggtgt gaaggagaaa gcattggtct catctgtccg tcagagaatg     660
aagtgctcca gtatgcagaa gtttggagag agagcttta aagcatgggc agtagctcgt      720
ctgagccaga cattccccaa tgctgacttt gcagaaatca ccaaattggc aacagacctg     780
accaaagtca acaaggagtg ctgccatggt gacctgctgg aatgcgcaga tgacagggcg     840
gaacttgcca gtacatgtg tgaaaaccag gcgactatct ccagcaaact gcagacttgc     900
tgcgataaac cactgttgaa gaaagcccac tgtcttagtg aggtggagca tgacaccatg     960
cctgctgatc tgcctgccat tgctgctgat tttgttgagg accaggaagt gtgcaagaac    1020
tatgctgagg ccaaggatgt cttcctgggc acgttcttgt atgaatattc aagaagacac    1080
cctgattact ctgtatccct gttgctgaga cttgctaaga aatatgaagc cactctggaa    1140
aagtgctgcg ctgaagccaa tcctcccgca tgctacggca cagtgcttgc tgaatttcag    1200
cctcttgtag aagagcctaa gaacttggtc aaaaccaact gtgatcttta cgagaagctt    1260
ggagaatatg gattccaaaa tgccattcta gttcgctaca cccagaaagc acctcaggtg    1320 tcaacccaa ctctcgtgga ggctgcaaga aacctaggaa gagtgggcac caagtgttgt    1380
acacttcctg aagatcagag actgccttgt gtggaagact atctgtctgc aatcctgaac    1440
cgtgtgtgtc tgctgcatga aagaccccca gtgagtgagc atgttaccaa gtgctgtagt    1500
ggatccctgg tggaaaggcg gccatgcttc tctgctctga cagttgatga acatatgtc    1560 cccaaagagt ttaaagctga gaccttcacc ttccactctg atatctgcac acttccagag    1620
aaggagaagc agattaagaa acaaacggct cttgctgagc tggtgaagca caagcccaag    1680
gctacagcgg agcaactgaa gactgtcatg gatgactttg cacagttcct ggatacatgt    1740
tgcaaggctg ctgacaagga cacctgcttc tcgactgagg gtccaaacct tgtcactaga    1800
tgcaaagacg cctagccgg tggaggaggc tctggtggag gcggtagcgg aggcggaggg    1860
tcggctatcc agatgacccg gtccccgagc tccctgtccg cctctgtggg cgatagggtc    1920
```

| | | |
|---|---|---|
| accatcacct gccgtgccag tcagtaccac gacggttctg cagcctggta tcaacagaaa | 1980 |
| ccaggaaaag ctccgaagct tctgatttac ggtgcatcct acctctactc tggagtccct | 2040 |
| tcccgcttct ctggtagccg ttccgggacg gatttcactc tgaccatcag cagtctgcag | 2100 |
| ccggaagact cgcaactta ttactgtcag caatcttctt attctctgat cacgttcgga | 2160 |
| tgcggtacca aggtggagat caaaggtact actgccgcta gtggtagtag tggtggcagt | 2220 |
| agcagtggtg ccgaggttca gctggtggag tctgacggtg gcctggtgca gccagggggc | 2280 |
| tcactccgtt tgtcctgtgc agcttctggc ttcaacctct cttactacgg tatgcactgg | 2340 |
| gtgcgtcagg ccccgggtaa gtgcctggaa tgggttgcat acattgcttc ttaccctggc | 2400 |
| tacacttctt atgccgatag cgtcaagggc cgtttcacta agcgcagac acatccaaa | 2460 |
| aacacagcct acctacaaat gaacagctta gagctgagg acactgccgt ctactattgt | 2520 |
| gctcgctctg gttacagtta ctctccgtat tattcttggt tctctgctgg tatgaactac | 2580 |
| tggggtcaag gagccctggt caccgtctcc tcgggagggg gcggttccca ccatcaccac | 2640 |
| catcactgat ag | 2652 |

<210> SEQ ID NO 87
<211> LENGTH: 2658
<212> TYPE: DNA
<213> ORGANISM: Artificial Sequence
<220> FEATURE:
<223> OTHER INFORMATION: Synthetic: gWiz-LS-mouse SA-(Gly4Ser)3-scFv
     (VL-VH) CK138-ds2 (VL43A>C / VH105Q>C)-(Gly4Ser)-His6

<400> SEQUENCE: 87

| | | |
|---|---|---|
| atggacatga gagtgcctgc tcagctgctg ggcctgctgc tgctgtggct gcctggtgct | 60 |
| agatgcgaag cacacaagag tgagatcgcc catcggtata atgatttggg agaacaacat | 120 |
| ttcaaaggcc tagtcctgat tgccttttcc cagtatctcc agaaatgctc atacgatgag | 180 |
| catgccaaat tagtgcagga agtaacagac tttgcaaaga cgtgtgttgc cgatgagtct | 240 |
| gccgccaact gtgacaaatc ccttcacact cttttttggag ataagttgtg tgccattcca | 300 |
| aacctccgtg aaaactatgg tgaactggct gactgctgta aaaacaaga gcccgaaaga | 360 |
| aacgaatgtt tcctgcaaca caaagatgac aaccccagcc taccaccatt tgaaaggcca | 420 |
| gaggctgagg ccatgtgcac ctcctttaag gaaaacccaa ccactttat gggacactat | 480 |
| ttgcatgaag ttgccagaag acatccttat ttctatgccc cagaacttct ttactatgct | 540 |
| gagcagtaca atgagattct gacccagtgt tgtgcagagg ctgacaagga agctgcctg | 600 |
| accccgaagc ttgatggtgt gaaggagaaa gcattggtct catctgtccg tcagagaatg | 660 |
| aagtgctcca gtatgcagaa gtttggagag agagctttta agcatgggc agtagctcgt | 720 |
| ctgagccaga cattccccaa tgctgacttt gcagaaatca ccaaattggc aacagacctg | 780 |
| accaaagtca caaggagtg ctgccatggt gacctgctgg aatgcgcaga tgacagggcg | 840 |
| gaacttgcca gtacatgtg tgaaaaccag gcgactatct ccagcaaact gcagacttgc | 900 |
| tgcgataaac cactgttgaa gaaagcccac tgtcttagtg aggtggagca tgacaccatg | 960 |
| cctgctgatc tgcctgccat tgctgctgat tttgttgagg accaggaagt gtgcaagaac | 1020 |
| tatgctgagg ccaaggatgt cttcctgggc acgttcttgt atgaatattc aagaagacac | 1080 |
| cctgattact ctgtatccct gttgctgaga cttgctaaga aatatgaagc cactctggaa | 1140 |
| aagtgctgcg ctgaagccaa tcctcccgca tgctacggca cagtgcttgc tgaatttcag | 1200 |
| cctcttgtag aagagcctaa gaacttggtc aaaaccaact gtgatctta cgagaagctt | 1260 |

-continued

```
ggagaatatg gattccaaaa tgccattcta gttcgctaca cccagaaagc acctcaggtg   1320
tcaaccccaa ctctcgtgga ggctgcaaga aacctaggaa gagtgggcac caagtgttgt   1380
acacttcctg aagatcagag actgccttgt gtggaagact atctgtctgc aatcctgaac   1440
cgtgtgtgtc tgctgcatga aagaccccca gtgagtgagc atgttaccaa gtgctgtagt   1500
ggatccctgg tggaaaggcg gccatgcttc tctgctctga cagttgatga acatatgtc    1560
cccaaagagt ttaaagctga gaccttcacc ttccactctg atatctgcac acttccagag   1620
aaggagaagc agattaagaa acaaacggct cttgctgagc tggtgaagca aagcccaag    1680
gctacagcgg agcaactgaa gactgtcatg gatgactttg cacagttcct ggatacatgt   1740
tgcaaggctg ctgacaagga cacctgcttc tcgactgagg gtccaaacct tgtcactaga   1800
tgcaaagacg ccttagccgg tggaggaggc tctggtggag cggtagcgg aggcggaggg    1860
tcggctagcg ctatccagat gacccggtcc ccgagctccc tgtccgcctc tgtgggcgat   1920
agggtcacca tcacctgccg tgccagtcag taccacgacg ttctgcagc ctggtatcaa    1980
cagaaaccag gaaaatgccc gaagcttctg atttacggtg catcctacct ctactctgga   2040
gtcccttccc gcttctctgg tagccgttcc gggacggatt tcactctgac catcagcagt   2100
ctgcagccga agacttcgc aacttattac tgtcagcaat cttcttattc tctgatcacg    2160
ttcggacagg gtaccaaggt ggagatcaaa ggtactactg ccgctagtgg tagtagtggt   2220
ggcagtagca gtggtgccga ggttcagctg gtggagtctg acggtggcct ggtgcagcca   2280
gggggctcac tccgtttgtc ctgtgcagct tctggcttca acctctctta ctacggtatg   2340
cactgggtgc gtcaggcccc gggtaagggc ctggaatggg ttgcatacat tgcttcttac   2400
cctggctaca cttcttatgc cgatagcgtc aagggccgtt tcactataag cgcagacaca   2460
tccaaaaaca cagcctacct acaaatgaac agcttaagag ctgaggacac tgccgtctac   2520
tattgtgctc gctctggtta cagttactct ccgtattatt cttggttctc tgctggtatg   2580
aactactggg gttgcggagc cctggtcacc gtctcctcgg aggggggcgg ttcccaccat   2640
caccaccatc actgatag                                                 2658
```

<210> SEQ ID NO 88
<211> LENGTH: 2625
<212> TYPE: DNA
<213> ORGANISM: Artificial Sequence
<220> FEATURE:
<223> OTHER INFORMATION: Synthetic: gWiz-LS-mouse SA-(Gly4Ser)3-scFv
      (VL-VH) CK157-ds1 (VL100Q>C / VH44E>C)-(Gly4Ser)-His6

<400> SEQUENCE: 88

```
atggacatga gagtgcctgc tcagctgctg ggcctgctgc tgctgtggct gcctggtgct    60
agatgcgaag cacacaagag tgagatcgcc catcggtata tgatttggg agaacaacat   120
ttcaaaggcc tagtcctgat tgccttttcc cagtatctcc agaaatgctc atacgatgag   180
catgccaaat tagtgcagga agtaacagac tttgcaaaga cgtgtgttgc cgatgagtct   240
gccgccaact gtgacaaatc ccttcacact ctttttggag ataagttgtg tgccattcca   300
aacctccgtg aaaactatgg tgaactggct gactgctgta caaaacaaga gcccgaaaga   360
aacgaatgtt tcctgcaaca caagatgac aaccccagcc taccaccatt tgaaaggcca    420
gaggctgagg ccatgtgcac ctccttaag gaaaacccaa ccacctttat gggacactat    480
ttgcatgaag ttgccagaag acatcctat ttctatgccc cagaacttct ttactatgct    540
gagcagtaca atgagattct gacccagtgt gtgtgcagagg ctgacaagga aagctgcctg   600
```

```
accccgaagc ttgatggtgt gaaggagaaa gcattggtct catctgtccg tcagagaatg    660
aagtgctcca gtatgcagaa gtttggagag agagctttta aagcatgggc agtagctcgt    720
ctgagccaga cattccccaa tgctgacttt gcagaaatca ccaaattggc aacagacctg    780
accaaagtca acaaggagtg ctgccatggt gacctgctgg aatgcgcaga tgacagggcg    840
gaacttgcca agtacatgtg tgaaaaccag gcgactatct ccagcaaact gcagacttgc    900
tgcgataaac cactgttgaa gaaagcccac tgtcttagtg aggtggagca tgacaccatg    960
cctgctgatc tgcctgccat tgctgctgat tttgttgagg accaggaagt gtgcaagaac   1020
tatgctgagg ccaaggatgt cttcctgggc acgttcttgt atgaatattc aagaagacac   1080
cctgattact ctgtatccct gttgctgaga cttgctaaga aatatgaagc cactctggaa   1140
aagtgctgcg ctgaagccaa tcctcccgca tgctacggca cagtgcttgc tgaatttcag   1200
cctcttgtag aagagcctaa gaacttggtc aaaaccaact gtgatcttta cgagaagctt   1260
ggagaatatg gattccaaaa tgccattcta gttcgctaca cccagaaagc acctcaggtg   1320
tcaaccccaa ctctcgtgga ggctgcaaga aacctaggaa gagtgggcac caagtgttgt   1380
acacttcctg aagatcagag actgccttgt gtggaagact atctgtctgc aatcctgaac   1440
cgtgtgtgtc tgctgcatga aagacccca gtgagtgagc atgttaccaa gtgctgtagt   1500
ggatccctgg tggaaaggcg gccatgcttc tctgctctga cagttgatga acatatgtc   1560 cccaaagagt ttaagctga gaccttcacc ttccactctg atatctgcac acttccagag   1620
aaggagaagc agattaagaa acaaacggct cttgctgagc tggtgaagca caagcccaag   1680
gctacagcgg agcaactgaa gactgtcatg gatgactttg cacagttcct ggatacatgt   1740
tgcaaggctg ctgacaagga cacctgcttc tcgactgagg gtccaaacct tgtcactaga   1800
tgcaaagacg ccttagccgg tggaggaggc tctggtggag cggtagcgg aggcggaggg   1860 tcggatatcc agatgaccca gtccccgagc tccctgtccg cctctgtggg cgatagggtc   1920
accatcacct gccgtgccag tcagtcttac ggtggtgtag cctggtatca acagaaacca   1980
ggaaaagccc cgaagcttct gatttactct gcatcctacc tctactctgg agtcccttct   2040
cgcttctctg gtagccgttc cgggacggat ttcactctga ccatcagcag tctgcagccg   2100
gaagacttcg caacttatta ctgtcagcaa ccatctcatc tgatcacgtt cggatgcggt   2160
accgaggtgg agatcaaagg tactactgcc gctagtggta gtagtggtgg cagtagcagt   2220
ggtgccgagg ttcagctggt ggagtctggc ggtggcctgg tgcagccagg ggctcactc    2280 cgtttgtcct gtgcagcttc tggctccaac ccctactact acggtggtac gcactgggtg   2340
cgtcaggccc cgggtgagtg cctggaatgg gttgcatcta ttggttctta ccctggctac   2400
actgactatg ccgatagcgt caagggccgt tcactataa gcgcagacac atccaaaaac   2460
acagcctacc tacaaatgaa cagcttaaga gctgaggaca ctgccgtcta ttattgtgct   2520
cgccattact actggtacga tgctactgac tactggggtc aaggaaccct ggtcaccgtc   2580
tcctcgggag ggggcggttc ccaccatcac caccatcact gatag               2625
```

<210> SEQ ID NO 89
<211> LENGTH: 2625
<212> TYPE: DNA
<213> ORGANISM: Artificial Sequence
<220> FEATURE:
<223> OTHER INFORMATION: Synthetic: gWiz-LS-mouse SA-(Gly4Ser)3-scFv
     (VL-VH) CK157-ds2 (VL43A>C / VH105Q>C)-(Gly4Ser)-His6

<400> SEQUENCE: 89

```
atggacatga gagtgcctgc tcagctgctg ggcctgctgc tgctgtggct gcctggtgct    60
agatgcgaag cacacaagag tgagatcgcc catcggtata atgatttggg agaacaacat   120
ttcaaaggcc tagtcctgat tgccttttcc cagtatctcc agaaatgctc atacgatgag   180
catgccaaat tagtgcagga agtaacagac tttgcaaaga cgtgtgttgc cgatgagtct   240
gccgccaact gtgacaaatc ccttcacact cttttggag ataagttgtg tgccattcca   300
aacctccgtg aaaactatgg tgaactggct gactgctgta caaaacaaga gcccgaaaga   360
aacgaatgtt tcctgcaaca caaagatgac aaccccagcc taccaccatt tgaaaggcca   420
gaggctgagg ccatgtgcac ctcctttaag gaaaacccaa ccacctttat gggacactat   480
ttgcatgaag ttgccagaag acatccttat ttctatgccc cagaacttct ttactatgct   540
gagcagtaca atgagattct gacccagtgt tgtgcagagg ctgacaagga aagctgcctg   600
accccgaagc ttgatggtgt gaaggagaaa gcattggtct catctgtccg tcagagaatg   660
aagtgctcca gtatgcagaa gtttggagag agagctttta agcatgggc agtagctcgt   720
ctgagccaga cattccccaa tgctgacttt gcagaaatca ccaaattggc aacagacctg   780
accaaagtca caaggagtg ctgccatggt gacctgctgg aatgcgcaga tgacagggcg   840
gaacttgcca agtacatgtg tgaaaaccag gcgactatct ccagcaaact gcagacttgc   900
tgcgataaac cactgttgaa gaaagcccac tgtcttagtg aggtggagca tgacaccatg   960
cctgctgatc tgcctgccat tgctgctgat tttgttgagg accaggaagt gtgcaagaac  1020
tatgctgagg ccaaggatgt cttcctgggc acgttcttgt atgaatattc aagaagacac  1080
cctgattact ctgtatccct gttgctgaga cttgctaaga aatatgaagc cactctggaa  1140
aagtgctgcg ctgaagccaa tcctcccgca tgctacggca cagtgcttgc tgaatttcag  1200
cctcttgtag aagagcctaa gaacttggtc aaaaccaact gtgatcttta cgagaagctt  1260
ggagaatatg gattccaaaa tgccattcta gttcgctaca cccagaaagc acctcaggtg  1320
tcaaccccaa ctctcgtgga ggctgcaaga aacctaggaa gagtgggcac caagtgttgt  1380
acacttcctg aagatcagag actgccttgt gtggaagact atctgtctgc aatcctgaac  1440
cgtgtgtgtc tgctgcatga aagaccccca gtgagtgagc atgttaccaa gtgctgtagt  1500
ggatccctgg tggaaaggcg gccatgcttc tctgctctga cagttgatga acatatgtc  1560
cccaaagagt ttaaagctga gaccttcacc ttccactctg atatctgcac acttccagag  1620
aaggagaagc agattaagaa acaaacggct cttgctgagc tggtgaagca caagcccaag  1680
gctacagcgg agcaactgaa gactgtcatg gatgactttg cacagttcct ggatacatgt  1740
tgcaaggctg ctgacaagga caccgcttc tcgactgagg gtccaaacct tgtcactaga  1800
tgcaaagacg ccttagccgg tggaggaggc tctggtggag gcggtagcgg aggcggaggg  1860
tcggatatcc agatgaccca gtccccgagc tccctgtccg cctctgtggg cgatagggtc  1920
accatcacct gccgtgccag tcagtcttac ggtggtgtag cctggtatca acagaaacca  1980
ggaaaatgcc cgaagcttct gatttactct gcatcctacc tctactctgg agtcccttct  2040
cgcttctctg gtagccgttc cgggacggat ttcactctga ccatcagcag tctgcagccg  2100
gaagacttcg caacttatta ctgtcagcaa ccatctcatc tgatcacgtt cggacagggt  2160
accgaggtgg agatcaaagg tactactgcc gctagtggta gtagtggtgg cagtagcagt  2220
ggtgccgagg ttcagctggt ggagtctggc ggtggcctgg tgcagccagg gggctcactc  2280
cgtttgtcct gtgcagcttc tggctccaac ccctactact acggtggtac gcactgggtg  2340
cgtcaggccc cgggtgagga gctggaatgg gttgcatcta ttggttctta ccctggctac  2400
```

```
actgactatg ccgatagcgt caagggccgt tcactataa gcgcagacac atccaaaaac    2460
acagcctacc tacaaatgaa cagcttaaga gctgaggaca ctgccgtcta ttattgtgct    2520
cgccattact actggtacga tgctactgac tactggggtt gcggaaccct ggtcaccgtc    2580
tcctcgggag ggggcggttc ccaccatcac caccatcact gatag                   2625

<210> SEQ ID NO 90
<211> LENGTH: 2217
<212> TYPE: DNA
<213> ORGANISM: Artificial Sequence
<220> FEATURE:
<223> OTHER INFORMATION: Synthetic: gWiz-LS-mouse SA-(Gly4Ser)-VL CK157-
      His6

<400> SEQUENCE: 90
atggacatga gagtgcctgc tcagctgctg ggcctgctgc tgctgtggct gcctggtgct      60
agatgcgaag cacacaagag tgagatcgcc catcggtata atgatttggg agaacaacat     120
ttcaaaggcc tagtcctgat tgcctttttcc cagtatctcc agaaatgctc atacgatgag    180
catgccaaat tagtgcagga agtaacagac tttgcaaaga cgtgtgttgc cgatgagtct    240
gccgccaact gtgacaaatc ccttcacact ctttttggag ataagttgtg tgccattcca    300
aacctccgtg aaaactatgg tgaactggct gactgctgta caaaacaaga gcccgaaaga    360
aacgaatgtt tcctgcaaca caaagatgac aaccccagcc taccaccatt tgaaaggcca    420
gaggctgagg ccatgtgcac ctcctttaag gaaaacccaa ccacctttat gggacactat    480
ttgcatgaag ttgccagaag acatccttat ttctatgccc cagaacttct ttactatgct    540
gagcagtaca atgagattct gacccagtgt tgtgcagagg ctgacaagga agctgcctg     600 accccgaagc ttgatggtgt gaaggagaaa gcattggtct catctgtccg tcagagaatg    660
aagtgctcca gtatgcagaa gtttggagag agagctttta agcatgggc agtagctcgt    720 ctgagccaga cattccccaa tgctgacttt gcagaaatca ccaaattggc aacagacctg    780
accaaagtca caaggagtg ctgccatggt gacctgctgg aatgcgcaga tgacagggcg     840
gaacttgcca gtacatgtg tgaaaaccag gcgactatct ccagcaaact gcagacttgc    900
tgcgataaac cactgttgaa gaaagcccac tgtcttagtg aggtggagca tgacaccatg    960
cctgctgatc tgcctgccat tgctgctgat tttgttgagg accaggaagt gtgcaagaac   1020
tatgctgagg ccaaggatgt cttcctgggc acgttcttgt atgaatattc aagaagacac   1080
cctgattact ctgtatccct gttgctgaga cttgctaaga atatgaagc cactctggaa   1140 aagtgctgcg ctgaagccaa tcctcccgca tgctacggca cagtgcttgc tgaatttcag    1200
cctcttgtag aagagcctaa gaacttggtc aaaaccaact gtgatcttta cgagaagctt    1260
ggagaatatg gattccaaaa tgccattcta gttcgctaca cccagaaagc acctcaggtg   1320
tcaaccccaa ctctcgtgga ggctgcaaga aacctaggaa gagtgggcac caagtgttgt    1380
acacttcctg aagatcagag actgcctgt gtggaagact atctgtctgc aatcctgaac    1440
cgtgtgtgtc tgctgcatga agaccccca gtgagtgagc atgttaccaa gtgctgtagt    1500
ggatccctgg tggaaaggcg gccatgcttc tctgctctga cagttgatga acatatgtc    1560 cccaaagagt ttaaagctga gaccttcacc ttccactctg atatctgcac acttccagag    1620
aaggagaagc agattaagaa acaaacggc cttgctgagc tggtgaagca caagcccaag    1680
gctacagcgg agcaactgaa gactgtcatg gatgactttg cacagttcct ggatacatgt    1740
tgcaaggctg ctgacaagga cacctgcttc tcgactgagg gtccaaacct tgtcactaga    1800
```

```
tgcaaagacg ccttagccgg tggaggaggc tctggtggag gcggtagcgg aggcggaggg    1860
tcggatatcc agatgaccca gtccccgagc tccctgtccg cctctgtggg cgatagggtc    1920
accatcacct gccgtgccag tcagtcttac ggtggtgtag cctggtatca acagaaacca    1980
ggaaaagccc cgaagcttct gatttactct gcatcctacc tctactctgg agtcccttct    2040
cgcttctctg gtagccgttc cgggacggat ttcactctga ccatcagcag tctgcagccg    2100
gaagacttcg caacttatta ctgtcagcaa ccatctcatc tgatcacgtt cggacagggg    2160
accgaggtgg agatcaaagg aggggggcggt tcccaccatc accaccatca ctgatag       2217
```

<210> SEQ ID NO 91
<211> LENGTH: 2265
<212> TYPE: DNA
<213> ORGANISM: Artificial Sequence
<220> FEATURE:
<223> OTHER INFORMATION: Synthetic: gWiz-LS-mouse SA-(Gly4Ser)-VH CK157-His6

<400> SEQUENCE: 91

```
atggacatga gagtgcctgc tcagctgctg ggcctgctgc tgctgtggct gcctggtgct     60
agatgcgaag cacacaagag tgagatcgcc catcggtata atgatttggg agaacaacat    120
ttcaaaggcc tagtcctgat tgccttttcc cagtatctcc agaaatgctc atacgatgag    180
catgccaaat tagtgcagga agtaacagac tttgcaaaga cgtgtgttgc cgatgagtct    240
gccgccaact gtgacaaatc ccttcacact ctttttggag ataagttgtg tgccattcca    300
aacctccgtg aaaactatgg tgaactggct gactgctgta caaaacaaga gcccgaaaga    360
aacgaatgtt tcctgcaaca caaagatgac aaccccagcc taccaccatt tgaaaggcca    420
gaggctgagc catgtgcac ctcctttaag gaaaacccaa ccacctttat gggacactat    480
ttgcatgaag ttgccagaag acatccttat ttctatgccc cagaacttct ttactatgct    540
gagcagtaca atgagattct gacccagtgt tgtgcagagg ctgacaagga agctgcctg     600 accccgaagc ttgatggtgt gaaggagaaa gcattggtct catctgtccg tcagagaatg    660
aagtgctcca gtatgcagaa gtttggagag agagctttta agcatgggc agtagctcgt    720 ctgagccaga cattccccaa tgctgacttt gcagaaatca ccaaattggc aacagacctg    780
accaaagtca caaggagtg ctgccatggt gacctgctgg aatgcgcaga tgacagggcg    840
gaacttgcca agtacatgtg tgaaaaccag gcgactatct ccagcaaact gcagacttgc    900
tgcgataaac cactgttgaa gaaagcccac tgtcttagtg aggtggagca tgacaccatg    960
cctgctgatc tgcctgccat tgctgctgat tttgttgagg accaggaagt gtgcaagaac    1020
tatgctgagg ccaaggatgt cttcctgggc acgttcttgt atgaatattc aagaagacac    1080
cctgattact ctgtatccct gttgctgaga cttgctaaga aatatgaagc cactctggaa    1140
aagtgctgcg ctgaagccaa tcctcccgca tgctacggca cagtgcttgc tgaatttcag    1200
cctcttgtag aagagcctaa gaacttggtc aaaaccaact gtgatcttta cgagaagctt    1260
ggagaatatg gattccaaaa tgccattcta gttcgctaca cccagaaagc acctcaggtg    1320 tcaacccccaa ctctcgtgga ggctgcaaga aacctaggaa gagtgggcac caagtgttgt    1380
acacttcctg aagatcagag actgccttgt gtggaagact atctgtctgc aatcctgaac    1440
cgtgtgtgtc tgctgcatga aagaccccca gtgagtgagc atgttaccaa gtgctgtagt    1500
ggatccctgg tggaaaggcg ccatgccttc tctgctctga cagttgatga acatatgtc     1560 cccaaagagt ttaaagctga gaccttcacc ttccactctg atatctgcac acttccagag    1620
```

```
aaggagaagc agattaagaa acaaacggct cttgctgagc tggtgaagca caagcccaag   1680
gctacagcgg agcaactgaa gactgtcatg gatgactttg cacagttcct ggatacatgt   1740
tgcaaggctg ctgacaagga cacctgcttc tcgactgagg gtccaaacct tgtcactaga   1800
tgcaaagacg ccttagccgg tggaggaggc tctggtggag cggtagcgg aggcggaggg   1860 tcggccgagg ttcagctggt ggagtctggc ggtggcctgg tgcagccagg gggctcactc   1920
cgtttgtcct gtgcagcttc tggctccaac ccctactact acggtggtac gcactgggtg   1980
cgtcaggccc cgggtgagga gctggaatgg gttgcatcta ttggttctta ccctggctac   2040
actgactatg ccgatagcgt caagggccgt tcactataa gcgcagacac atccaaaaac   2100
acagcctacc tacaaatgaa cagcttaaga gctgaggaca ctgccgtcta ttattgtgct   2160
cgccattact actggtacga tgctactgac tactggggtc aaggaaccct ggtcaccgtc   2220
tcctcgggag ggggcggttc ccaccatcac caccatcact gatag             2265
```

<210> SEQ ID NO 92
<211> LENGTH: 2640
<212> TYPE: DNA
<213> ORGANISM: Artificial Sequence
<220> FEATURE:
<223> OTHER INFORMATION: Synthetic: gWiz-LS-mouse SA-(Gly4Ser)3-scFv
      (VL-VH) CK129-ds1 (VL100Q>C / VH44G>C)-(Gly4Ser)-His6

<400> SEQUENCE: 92

```
atggacatga gagtgcctgc tcagctgctg ggcctgctgc tgctgtggct gcctggtgct     60
agatgcgaag cacacaagag tgagatcgcc catcggtata atgatttggg agaacaacat   120
ttcaaaggcc tagtcctgat tgcctttttcc cagtatctcc agaaatgctc atacgatgag   180
catgccaaat tagtgcagga agtaacagac tttgcaaaga cgtgtgttgc cgatgagtct   240
gccgccaact gtgacaaatc ccttcacact cttttttggag ataagttgtg tgccattcca   300
aacctccgtg aaaactatgg tgaactggct gactgctgta caaaacaaga gcccgaaaga   360
aacgaatgtt tcctgcaaca caaagatgac aaccccagcc taccaccatt tgaaaggcca   420
gaggctgagg ccatgtgcac ctcctttaag gaaaacccaa ccacctttat gggacactat   480
ttgcatgaag ttgccagaag acatccttat ttctatgccc cagaacttct ttactatgct   540
gagcagtaca atgagattct gacccagtgt tgtgcagagg ctgacaagga agctgcctg   600 accccgaagc ttgatggtgt gaaggagaaa gcattggtct catctgtccg tcagagaatg   660
aagtgctcca gtatgcagaa gtttggagag agagcttttaa agcatgggc agtagctcgt   720 ctgagccaga cattccccaa tgctgacttt gcagaaatca ccaaattggc aacagacctg   780
accaaagtca acaaggagtg ctgccatggt gacctgctgg aatgcgcaga tgacagggcg   840
gaacttgcca gtacatgtgt gaaaaccag gcgactatct ccagcaaact gcagacttgc   900
tgcgataaac cactgttgaa gaaagcccac tgtcttagtg aggtggagca tgacaccatg   960
cctgctgatc tgcctgccat tgctgctgat tttgttgagg accaggaagt gtgcaagaac  1020
tatgctgagg ccaaggatgt cttcctgggc acgttcttgt atgaatattc aagaagacac  1080
cctgattact ctgtatccct gttgctgaga cttgctaaga aatatgaagc cactctggaa  1140
aagtgctgcg ctgaagccaa tcctcccgca tgctacggca cagtgcttgc tgaatttcag  1200
cctcttgtag aagagcctaa gaacttggtc aaaaccaact gtgatcttta cgagaagctt  1260
ggagaatatg gattccaaaa tgccattcta gttcgctaca cccagaaagc acctcaggtg  1320 tcaacccccaa ctctcgtgga ggctgcaaga aacctaggaa gagtgggcac caagtgttgt  1380
```

```
acacttcctg aagatcagag actgccttgt gtggaagact atctgtctgc aatcctgaac    1440
cgtgtgtgtc tgctgcatga aagaccccca gtgagtgagc atgttaccaa gtgctgtagt    1500
ggatccctgg tggaaaggcg gccatgcttc tctgctctga cagttgatga acatatgtc     1560 cccaaagagt ttaaagctga gaccttcacc ttccactctg atatctgcac acttccagag    1620
aaggagaagc agattaagaa acaaacggct cttgctgagc tggtgaagca caagcccaag    1680
gctacagcgg agcaactgaa gactgtcatg gatgactttg cacagttcct ggatacatgt    1740
tgcaaggctg ctgacaagga cacctgcttc tcgactgagg gtccaaacct tgtcactaga    1800
tgcaaagacg ccttagccgg tggaggaggc tctggtggag cggtagcgg aggcggaggg     1860 tcggatatcc agatgaccca gtccccgagc ccctgtccg cctctgtggg cgatagggtc      1920
accatcacct gccgtgccag tcagtacggt ggttacgtag cctggtatca acagaaacca    1980
ggaaaagctc cgaagcttct gatttacggt gcatcccttc tctactctgg agtcccttct    2040
cgcttctctg gtggccgttc cgggacggat ttcactctga ccatcagcag tctgcagccg    2100
gaagacttcg caacttatta ctgtcagcga ggtcatgctc tgatcacgtt cggatgcggt    2160
accaaggtgg agatcgaagg tactactgcc gctagtggta gtagtggtgg cagtagcagt    2220
ggtgccgagg ttcagctggt ggagtctggc ggtggcctgg tgcagccagg gggctcactc    2280
cgtttatcct gtgcagcttc tggcttcaac atctcttctt acggttctat gcactgggtg    2340
cgtcaggccc cgggtaagtg cctggaatgg gttgcatcta tttacccta ctctagctct      2400 acttactatg ccgatagcgt caagggccgt tcactataa gcgcagacac atccaaaaac     2460
acagcctacc tacaaatgaa cagcttaaga gctgaggaca ctgccgtcta ttattgtgct    2520
cgtggttacg gtccgtggta cgcttactct tacttcgctt tggactactg gggtcaagga    2580
accctggtca ccgtctcctc ggggaggggc ggttcccacc atcaccacca tcactgatag    2640
```

<210> SEQ ID NO 93  
<211> LENGTH: 2640  
<212> TYPE: DNA  
<213> ORGANISM: Artificial Sequence  
<220> FEATURE:  
<223> OTHER INFORMATION: Synthetic: gWiz-LS-mouse SA-(Gly4Ser)3-scFv  
    (VL-VH) CK129-ds2 (VL43A>C / VH105Q>C)-(Gly4Ser)-His6

<400> SEQUENCE: 93

```
atggacatga gagtgcctgc tcagctgctg ggcctgctgc tgctgtggct gcctggtgct     60
agatgcgaag cacacaagag tgagatcgcc catcggtata atgatttggg agaacaacat    120
ttcaaaggcc tagtcctgat tgccttttcc cagtatctcc agaaatgctc atacgatgag    180
catgccaaat tagtgcagga agtaacagac tttgcaaaga cgtgtgttgc cgatgagtct    240
gccgccaact gtgacaaatc ccttcacact ctttttggag ataagttgtg tgccattcca    300
aacctccgtg aaaactatgg tgaactggct gactgctgta aaaacaaga gcccgaaaga    360 aacgaatgtt tcctgcaaca caagatgac aaccccagcc taccaccatt tgaaaggcca    420
gaggctgagg ccatgtgcac ctcctttaag gaaaacccaa ccacctttat gggacactat    480
ttgcatgaag ttgccagaag acatcctat ttctatgccc cagaacttct ttactatgct    540
gagcagtaca atgagattct gacccagtgt gtgcagagg ctgacaagga agctgcctg      600 accccgaagc ttgatggtgt gaaggagaaa gcattggtct catctgtccg tcagagaatg    660
aagtgctcca gtatgcagaa gtttggagag agagctttta agcatgggc agtagctcgt    720 ctgagccaga cattccccaa tgctgacttt gcagaaatca ccaaattggc aacagacctg    780
```

```
accaaagtca acaaggagtg ctgccatggt gacctgctgg aatgcgcaga tgacagggcg      840
gaacttgcca agtacatgtg tgaaaaccag gcgactatct ccagcaaact gcagacttgc      900
tgcgataaac cactgttgaa gaaagccac tgtcttagtg aggtggagca tgacaccatg       960
cctgctgatc tgcctgccat tgctgctgat tttgttgagg accaggaagt gtgcaagaac     1020
tatgctgagg ccaaggatgt cttcctgggc acgttcttgt atgaatattc aagaagacac     1080
cctgattact ctgtatccct gttgctgaga cttgctaaga aatatgaagc cactctggaa     1140
aagtgctgcg ctgaagccaa tcctcccgca tgctacggca cagtgcttgc tgaatttcag     1200
cctcttgtag aagagcctaa gaacttggtc aaaaccaact gtgatcttta cgagaagctt     1260
ggagaatatg gattccaaaa tgccattcta gttcgctaca cccagaaagc acctcaggtg     1320
tcaaccccaa ctctcgtgga ggctgcaaga aacctaggaa gagtgggcac caagtgttgt     1380
acacttcctg aagatcagag actgccttgt gtggaagact atctgtctgc aatcctgaac     1440
cgtgtgtgtc tgctgcatga gaagaccca gtgagtgagc atgttaccaa gtgctgtagt      1500
ggatccctgg tggaaaggcg gccatgcttc tctgctctga cagttgatga aacatatgtc     1560
cccaaagagt ttaaagctga gaccttcacc ttccactctg atatctgcac acttccagag     1620
aaggagaagc agattaagaa acaaacggct cttgctgagc tggtgaagca aagcccaag      1680
gctacagcgg agcaactgaa gactgtcatg gatgactttg cacagttcct ggatacatgt     1740
tgcaaggctg ctgacaagga cacctgcttc tcgactgagg tccaaacct tgtcactaga      1800
tgcaaagacg ccttagccgg tggaggaggc tctggtggag cggtagcgg aggcggaggg      1860
tcggatatcc agatgaccca gtccccgagc ccctgtccg cctctgtggg cgatagggtc      1920
accatcacct gccgtgccag tcagtacggt ggttacgtag cctggtatca acagaaacca     1980
ggaaaatgcc cgaagcttct gatttacggt gcatcccttc tctactctgg agtcccttct     2040
cgcttctctg gtggccgttc cgggacggat ttcactctga ccatcagcag tctgcagccg     2100
gaagacttcg caacttatta ctgtcagcga ggtcatgctc tgatcacgtt cggacagggt     2160
accaaggtgg agatcgaagg tactactgcc gctagtggta gtagtggtgg cagtagcagt     2220
ggtgccgagg ttcagctggt ggagtctggc ggtggcctgg tgcagccagg ggctcactc      2280
cgtttatcct gtgcagcttc tggcttcaac atctcttctt acggttctat gcactgggtg     2340
cgtcaggccc cgggtaaggg cctggaatgg gttgcatcta tttacccta ctctagctct      2400
acttactatg ccgatagcgt caagggccgt ttcactataa gcgcagacac atccaaaaac     2460
acagcctacc tacaaatgaa cagcttaaga gctgaggaca ctgccgtcta ttattgtgct     2520
cgtggttacg gtccgtggta cgcttactct tacttcgctt tggactactg gggttgcgga     2580
accctggtca ccgtctcctc gggagggggc ggttcccacc atcaccacca tcactgatag    2640
```

<210> SEQ ID NO 94
<211> LENGTH: 2625
<212> TYPE: DNA
<213> ORGANISM: Artificial Sequence
<220> FEATURE:
<223> OTHER INFORMATION: Synthetic: gWiz-LS-mouse SA-(Gly4Ser)3-scFv
      (VH-VL) sm3E-ds (VH44R>G / VL100G>C)-(Gly4Ser)-His6

<400> SEQUENCE: 94

```
atggacatga gagtgcctgc tcagctgctg ggcctgctgc tgctgtggct gcctggtgct       60
agatgcgaag cacacaagag tgagatcgcc catcggtata tgatttggg agaacaacat      120
ttcaaaggcc tagtcctgat tgccttttcc cagtatctcc agaaatgctc atacgatgag      180
```

-continued

```
catgccaaat tagtgcagga agtaacagac tttgcaaaga cgtgtgttgc cgatgagtct      240
gccgccaact gtgacaaatc ccttcacact cttttggag ataagttgtg tgccattcca       300
aacctccgtg aaaactatgg tgaactggct gactgctgta caaaacaaga gcccgaaaga     360
aacgaatgtt tcctgcaaca caaagatgac aacccccagcc taccaccatt tgaaaggcca    420
gaggctgagg ccatgtgcac ctcctttaag gaaaacccaa ccacctttat gggacactat    480
ttgcatgaag ttgccagaag acatccttat ttctatgccc cagaacttct ttactatgct    540
gagcagtaca atgagattct gacccagtgt tgtgcagagg ctgacaagga aagctgcctg     600
accccgaagc ttgatggtgt gaaggagaaa gcattggtct catctgtccg tcagagaatg    660
aagtgctcca gtatgcagaa gtttggagag agagctttta aagcatgggc agtagctcgt    720
ctgagccaga cattccccaa tgctgacttt gcagaaatca ccaaattggc aacagacctg    780
accaaagtca caaggagtg ctgccatggt gacctgctgg aatgcgcaga tgacagggcg     840
gaacttgcca gtacatgtg tgaaaaccag gcgactatct ccagcaaact gcagacttgc     900
tgcgataaac cactgttgaa gaaagcccac tgtcttagtg aggtggagca tgacaccatg    960
cctgctgatc tgcctgccat tgctgctgat tttgttgagg accaggaagt gtgcaagaac   1020
tatgctgagg ccaaggatgt cttcctgggc acgttcttgt atgaatattc aagaagacac   1080
cctgattact ctgtatccct gttgctgaga cttgctaaga aatatgaagc cactctggaa   1140
aagtgctgcg ctgaagccaa tcctcccgca tgctacggca cagtgcttgc tgaatttcag   1200
cctcttgtag aagagcctaa gaacttggtc aaaaccaact gtgatcttta cgagaagctt   1260
ggagaatatg gattccaaaa tgccattcta gttcgctaca cccagaaagc acctcaggtg   1320
tcaaccccaa ctctcgtgga ggctgcaaga aacctaggaa gagtgggcac caagtgttgt   1380
acacttcctg aagatcagag actgccttgt gtggaagact atctgtctgc aatcctgaac   1440
cgtgtgtgtc tgctgcatga gaagacccca gtgagtgagc atgttaccaa gtgctgtagt   1500
ggatccctgg tggaaaggcg gccatgcttc tctgctctga cagttgatga acatatgtc    1560 cccaaagagt ttaaagctga gaccttcacc ttccactctg atatctgcac acttccagag   1620
aaggagaagc agattaagaa acaaacggct cttgctgagc tggtgaagca caagcccaag   1680
gctacagcgg agcaactgaa gactgtcatg gatgactttg cacagttcct ggatacatgt   1740
tgcaaggctc tgacaagga cacctgcttc tcgactgagg tccaaacct tgtcactaga    1800 tgcaaagacg ccttagccgg tggaggaggc tctggtggag gcggtagcgg aggcggaggg   1860
tcgcaagtta aactggaaca gtccggtgct gaagttgtca aaccaggtgc ttccgtgaag   1920
ttgtcctgta aagcctctgg ttttaacatc aaggattcgt atatgcattg gttgagacaa   1980
gggccaggac aatgtttgga atggattggc tggattgatc cagagaatgg tgataccgag   2040
tacgctccta aatttcaggg aaaggctact tttactaccg acacttccgc taataccgca   2100
tacttgggct tatcttcctt gagaccagag gacactgccg tatactactg caacgaaggg   2160
acaccaactg gtccttacta tttcgactac tggggacaag gtaccttagt tactgtctct   2220
agcggtggcg gaggttcagg cggtggaggg tctggaggtg gcggtagtga aaatgtgctg   2280
acccaatctc caagctccat gtctgtttct gttggcgata gagtaaccat cgcttgtagc   2340
gcatcctcta gtgtcccata tatgcactgg cttcaacaga agccaggtaa aagcccaaag   2400
ttgttgattt atttgacatc caacttggct tctggagtgc cttcaaggtt ttctggttcc   2460
ggctcaggaa ccgattatag tttgactatt agctcagtgc agccagagga tgctgcaacc   2520
```
tactattgcc agcaaaggtc ctcatatcca ctgactttcg ggtgtggaac gaagttggaa    2580
atcaagggag ggggcggttc ccaccatcac caccatcact gatag    2625

<210> SEQ ID NO 95
<211> LENGTH: 884
<212> TYPE: PRT
<213> ORGANISM: Artificial Sequence
<220> FEATURE:
<223> OTHER INFORMATION: Synthetic: LS-mouse SA-(Gly4Ser)3-scFv (VL-VH)
      CK138-(Gly4Ser)-His6

<400> SEQUENCE: 95

```
Met Asp Met Arg Val Pro Ala Gln Leu Leu Gly Leu Leu Leu Leu Trp
1               5                   10                  15

Leu Pro Gly Ala Arg Cys Glu Ala His Lys Ser Glu Ile Ala His Arg
            20                  25                  30

Tyr Asn Asp Leu Gly Glu Gln His Phe Lys Gly Leu Val Leu Ile Ala
        35                  40                  45

Phe Ser Gln Tyr Leu Gln Lys Cys Ser Tyr Asp Glu His Ala Lys Leu
    50                  55                  60

Val Gln Glu Val Thr Asp Phe Ala Lys Thr Cys Val Ala Asp Glu Ser
65                  70                  75                  80

Ala Ala Asn Cys Asp Lys Ser Leu His Thr Leu Phe Gly Asp Lys Leu
                85                  90                  95

Cys Ala Ile Pro Asn Leu Arg Glu Asn Tyr Gly Glu Leu Ala Asp Cys
            100                 105                 110

Cys Thr Lys Gln Glu Pro Glu Arg Asn Glu Cys Phe Leu Gln His Lys
        115                 120                 125

Asp Asp Asn Pro Ser Leu Pro Pro Phe Glu Arg Pro Glu Ala Glu Ala
    130                 135                 140

Met Cys Thr Ser Phe Lys Glu Asn Pro Thr Thr Phe Met Gly His Tyr
145                 150                 155                 160

Leu His Glu Val Ala Arg Arg His Pro Tyr Phe Tyr Ala Pro Glu Leu
                165                 170                 175

Leu Tyr Tyr Ala Glu Gln Tyr Asn Glu Ile Leu Thr Gln Cys Cys Ala
            180                 185                 190

Glu Ala Asp Lys Glu Ser Cys Leu Thr Pro Lys Leu Asp Gly Val Lys
        195                 200                 205

Glu Lys Ala Leu Val Ser Ser Val Arg Gln Arg Met Lys Cys Ser Ser
    210                 215                 220

Met Gln Lys Phe Gly Glu Arg Ala Phe Lys Ala Trp Ala Val Ala Arg
225                 230                 235                 240

Leu Ser Gln Thr Phe Pro Asn Ala Asp Phe Ala Glu Ile Thr Lys Leu
                245                 250                 255

Ala Thr Asp Leu Thr Lys Val Asn Lys Glu Cys Cys His Gly Asp Leu
            260                 265                 270

Leu Glu Cys Ala Asp Asp Arg Ala Glu Leu Ala Lys Tyr Met Cys Glu
        275                 280                 285

Asn Gln Ala Thr Ile Ser Ser Lys Leu Gln Thr Cys Cys Asp Lys Pro
    290                 295                 300

Leu Leu Lys Lys Ala His Cys Leu Ser Glu Val Glu His Asp Thr Met
305                 310                 315                 320

Pro Ala Asp Leu Pro Ala Ile Ala Ala Asp Phe Val Glu Asp Gln Glu
                325                 330                 335

Val Cys Lys Asn Tyr Ala Glu Ala Lys Asp Val Phe Leu Gly Thr Phe
```

```
                340                 345                 350
Leu Tyr Glu Tyr Ser Arg Arg His Pro Asp Tyr Ser Val Ser Leu Leu
            355                 360                 365

Leu Arg Leu Ala Lys Lys Tyr Glu Ala Thr Leu Glu Lys Cys Cys Ala
        370                 375                 380

Glu Ala Asn Pro Pro Ala Cys Tyr Gly Thr Val Leu Ala Glu Phe Gln
385                 390                 395                 400

Pro Leu Glu Glu Pro Lys Asn Leu Val Lys Thr Asn Cys Asp Leu
                405                 410                 415

Tyr Glu Lys Leu Gly Glu Tyr Gly Phe Gln Asn Ala Ile Leu Val Arg
                420                 425                 430

Tyr Thr Gln Lys Ala Pro Gln Val Ser Thr Pro Thr Leu Val Glu Ala
            435                 440                 445

Ala Arg Asn Leu Gly Arg Val Gly Thr Lys Cys Cys Thr Leu Pro Glu
        450                 455                 460

Asp Gln Arg Leu Pro Cys Val Glu Asp Tyr Leu Ser Ala Ile Leu Asn
465                 470                 475                 480

Arg Val Cys Leu Leu His Glu Lys Thr Pro Val Ser Glu His Val Thr
                485                 490                 495

Lys Cys Cys Ser Gly Ser Leu Val Glu Arg Arg Pro Cys Phe Ser Ala
                500                 505                 510

Leu Thr Val Asp Glu Thr Tyr Val Pro Lys Glu Phe Lys Ala Glu Thr
            515                 520                 525

Phe Thr Phe His Ser Asp Ile Cys Thr Leu Pro Glu Lys Glu Lys Gln
        530                 535                 540

Ile Lys Lys Gln Thr Ala Leu Ala Glu Leu Val Lys His Lys Pro Lys
545                 550                 555                 560

Ala Thr Ala Glu Gln Leu Lys Thr Val Met Asp Asp Phe Ala Gln Phe
                565                 570                 575

Leu Asp Thr Cys Cys Lys Ala Ala Asp Lys Asp Thr Cys Phe Ser Thr
            580                 585                 590

Glu Gly Pro Asn Leu Val Thr Arg Cys Lys Asp Ala Leu Ala Gly Gly
        595                 600                 605

Gly Gly Ser Gly Gly Gly Ser Gly Gly Gly Ser Ala Ser Ala
        610                 615                 620

Ile Gln Met Thr Arg Ser Pro Ser Ser Leu Ser Ala Ser Val Gly Asp
625                 630                 635                 640

Arg Val Thr Ile Thr Cys Arg Ala Ser Gln Tyr His Asp Gly Ser Ala
                645                 650                 655

Ala Trp Tyr Gln Gln Lys Pro Gly Lys Ala Pro Lys Leu Leu Ile Tyr
            660                 665                 670

Gly Ala Ser Tyr Leu Tyr Ser Gly Val Pro Ser Arg Phe Ser Gly Ser
        675                 680                 685

Arg Ser Gly Thr Asp Phe Thr Leu Thr Ile Ser Ser Leu Gln Pro Glu
        690                 695                 700

Asp Phe Ala Thr Tyr Tyr Cys Gln Gln Ser Ser Tyr Ser Leu Ile Thr
705                 710                 715                 720

Phe Gly Gln Gly Thr Lys Val Glu Ile Lys Gly Thr Thr Ala Ala Ser
                725                 730                 735

Gly Ser Ser Gly Gly Ser Ser Ser Gly Ala Glu Val Gln Leu Val Glu
            740                 745                 750

Ser Asp Gly Gly Leu Val Gln Pro Gly Gly Ser Leu Arg Leu Ser Cys
        755                 760                 765
```

-continued

Ala Ala Ser Gly Phe Asn Leu Ser Tyr Tyr Gly Met His Trp Val Arg
        770                 775                 780

Gln Ala Pro Gly Lys Gly Leu Glu Trp Val Ala Tyr Ile Ala Ser Tyr
785                 790                 795                 800

Pro Gly Tyr Thr Ser Tyr Ala Asp Ser Val Lys Gly Arg Phe Thr Ile
        805                 810                 815

Ser Ala Asp Thr Ser Lys Asn Thr Ala Tyr Leu Gln Met Asn Ser Leu
        820                 825                 830

Arg Ala Glu Asp Thr Ala Val Tyr Tyr Cys Ala Arg Ser Gly Tyr Ser
        835                 840                 845

Tyr Ser Pro Tyr Tyr Ser Trp Phe Ser Ala Gly Met Asn Tyr Trp Gly
        850                 855                 860

Gln Gly Ala Leu Val Thr Val Ser Ser Gly Gly Gly Ser His His
865                 870                 875                 880

His His His His

<210> SEQ ID NO 96
<211> LENGTH: 875
<212> TYPE: PRT
<213> ORGANISM: Artificial Sequence
<220> FEATURE:
<223> OTHER INFORMATION: Synthetic: LS-mouse SA-(Gly4Ser)3-scFv (VL-VH)
      CK157-(Gly4Ser)-His6

<400> SEQUENCE: 96

Met Asp Met Arg Val Pro Ala Gln Leu Leu Gly Leu Leu Leu Leu Trp
1               5                   10                  15

Leu Pro Gly Ala Arg Cys Glu Ala His Lys Ser Glu Ile Ala His Arg
            20                  25                  30

Tyr Asn Asp Leu Gly Glu Gln His Phe Lys Gly Leu Val Leu Ile Ala
        35                  40                  45

Phe Ser Gln Tyr Leu Gln Lys Cys Ser Tyr Asp Glu His Ala Lys Leu
    50                  55                  60

Val Gln Glu Val Thr Asp Phe Ala Lys Thr Cys Val Ala Asp Glu Ser
65                  70                  75                  80

Ala Ala Asn Cys Asp Lys Ser Leu His Thr Leu Phe Gly Asp Lys Leu
                85                  90                  95

Cys Ala Ile Pro Asn Leu Arg Glu Asn Tyr Gly Glu Leu Ala Asp Cys
            100                 105                 110

Cys Thr Lys Gln Glu Pro Glu Arg Asn Glu Cys Phe Leu Gln His Lys
        115                 120                 125

Asp Asp Asn Pro Ser Leu Pro Pro Phe Glu Arg Pro Glu Ala Glu Ala
    130                 135                 140

Met Cys Thr Ser Phe Lys Glu Asn Pro Thr Thr Phe Met Gly His Tyr
145                 150                 155                 160

Leu His Glu Val Ala Arg Arg His Pro Tyr Phe Tyr Ala Pro Glu Leu
                165                 170                 175

Leu Tyr Tyr Ala Glu Gln Tyr Asn Glu Ile Leu Thr Gln Cys Cys Ala
            180                 185                 190

Glu Ala Asp Lys Glu Ser Cys Leu Thr Pro Lys Leu Asp Gly Val Lys
        195                 200                 205

Glu Lys Ala Leu Val Ser Ser Val Arg Gln Arg Met Lys Cys Ser Ser
    210                 215                 220

Met Gln Lys Phe Gly Glu Arg Ala Phe Lys Ala Trp Ala Val Ala Arg
225                 230                 235                 240

-continued

```
Leu Ser Gln Thr Phe Pro Asn Ala Asp Phe Ala Glu Ile Thr Lys Leu
                245                 250                 255
Ala Thr Asp Leu Thr Lys Val Asn Lys Glu Cys Cys His Gly Asp Leu
            260                 265                 270
Leu Glu Cys Ala Asp Asp Arg Ala Glu Leu Ala Lys Tyr Met Cys Glu
        275                 280                 285
Asn Gln Ala Thr Ile Ser Ser Lys Leu Gln Thr Cys Cys Asp Lys Pro
    290                 295                 300
Leu Leu Lys Lys Ala His Cys Leu Ser Glu Val Glu His Asp Thr Met
305                 310                 315                 320
Pro Ala Asp Leu Pro Ala Ile Ala Ala Asp Phe Val Glu Asp Gln Glu
                325                 330                 335
Val Cys Lys Asn Tyr Ala Glu Ala Lys Asp Val Phe Leu Gly Thr Phe
            340                 345                 350
Leu Tyr Glu Tyr Ser Arg Arg His Pro Asp Tyr Ser Val Ser Leu Leu
        355                 360                 365
Leu Arg Leu Ala Lys Lys Tyr Glu Ala Thr Leu Glu Lys Cys Cys Ala
    370                 375                 380
Glu Ala Asn Pro Pro Ala Cys Tyr Gly Thr Val Leu Ala Glu Phe Gln
385                 390                 395                 400
Pro Leu Val Glu Glu Pro Lys Asn Leu Val Lys Thr Asn Cys Asp Leu
                405                 410                 415
Tyr Glu Lys Leu Gly Glu Tyr Gly Phe Gln Asn Ala Ile Leu Val Arg
            420                 425                 430
Tyr Thr Gln Lys Ala Pro Gln Val Ser Thr Pro Thr Leu Val Glu Ala
        435                 440                 445
Ala Arg Asn Leu Gly Arg Val Gly Thr Lys Cys Cys Thr Leu Pro Glu
    450                 455                 460
Asp Gln Arg Leu Pro Cys Val Glu Asp Tyr Leu Ser Ala Ile Leu Asn
465                 470                 475                 480
Arg Val Cys Leu Leu His Glu Lys Thr Pro Val Ser Glu His Val Thr
                485                 490                 495
Lys Cys Cys Ser Gly Ser Leu Val Glu Arg Arg Pro Cys Phe Ser Ala
            500                 505                 510
Leu Thr Val Asp Glu Thr Tyr Val Pro Lys Glu Phe Lys Ala Glu Thr
        515                 520                 525
Phe Thr Phe His Ser Asp Ile Cys Thr Leu Pro Glu Lys Glu Lys Gln
    530                 535                 540
Ile Lys Lys Gln Thr Ala Leu Ala Glu Leu Val Lys His Lys Pro Lys
545                 550                 555                 560
Ala Thr Ala Glu Gln Leu Lys Thr Val Met Asp Asp Phe Ala Gln Phe
                565                 570                 575
Leu Asp Thr Cys Cys Lys Ala Ala Asp Lys Asp Thr Cys Phe Ser Thr
            580                 585                 590
Glu Gly Pro Asn Leu Val Thr Arg Cys Lys Asp Ala Leu Ala Gly Gly
        595                 600                 605
Gly Gly Ser Gly Gly Gly Gly Ser Gly Gly Gly Gly Ser Ala Ser Asp
    610                 615                 620
Ile Gln Met Thr Gln Ser Pro Ser Ser Leu Ser Ala Ser Val Gly Asp
625                 630                 635                 640
Arg Val Thr Ile Thr Cys Arg Ala Ser Gln Ser Tyr Gly Gly Val Ala
                645                 650                 655
```

```
Trp Tyr Gln Gln Lys Pro Gly Lys Ala Pro Lys Leu Leu Ile Tyr Ser
            660                 665                 670

Ala Ser Tyr Leu Tyr Ser Gly Val Pro Ser Arg Phe Ser Gly Ser Arg
        675                 680                 685

Ser Gly Thr Asp Phe Thr Leu Thr Ile Ser Ser Leu Gln Pro Glu Asp
    690                 695                 700

Phe Ala Thr Tyr Tyr Cys Gln Gln Pro Ser His Leu Ile Thr Phe Gly
705                 710                 715                 720

Gln Gly Thr Glu Val Glu Ile Lys Gly Thr Thr Ala Ala Ser Gly Ser
                725                 730                 735

Ser Gly Gly Ser Ser Ser Gly Ala Glu Val Gln Leu Val Glu Ser Gly
            740                 745                 750

Gly Gly Leu Val Gln Pro Gly Gly Ser Leu Arg Leu Ser Cys Ala Ala
        755                 760                 765

Ser Gly Ser Asn Pro Tyr Tyr Tyr Gly Gly Thr His Trp Val Arg Gln
    770                 775                 780

Ala Pro Gly Glu Glu Leu Glu Trp Val Ala Ser Ile Gly Ser Tyr Pro
785                 790                 795                 800

Gly Tyr Thr Asp Tyr Ala Asp Ser Val Lys Gly Arg Phe Thr Ile Ser
                805                 810                 815

Ala Asp Thr Ser Lys Asn Thr Ala Tyr Leu Gln Met Asn Ser Leu Arg
            820                 825                 830

Ala Glu Asp Thr Ala Val Tyr Tyr Cys Ala Arg His Tyr Tyr Trp Tyr
        835                 840                 845

Asp Ala Thr Asp Tyr Trp Gly Gln Gly Thr Leu Val Thr Val Ser Ser
850                 855                 860

Gly Gly Gly Gly Ser His His His His His
865                 870                 875

<210> SEQ ID NO 97
<211> LENGTH: 880
<212> TYPE: PRT
<213> ORGANISM: Artificial Sequence
<220> FEATURE:
<223> OTHER INFORMATION: Synthetic: LS-mouse SA-(Gly4Ser)3-scFv (VL-VH)
      CK129-(Gly4Ser)-His6

<400> SEQUENCE: 97

Met Asp Met Arg Val Pro Ala Gln Leu Leu Gly Leu Leu Leu Leu Trp
1               5                   10                  15

Leu Pro Gly Ala Arg Cys Glu Ala His Lys Ser Glu Ile Ala His Arg
            20                  25                  30

Tyr Asn Asp Leu Gly Glu Gln His Phe Lys Gly Leu Val Leu Ile Ala
        35                  40                  45

Phe Ser Gln Tyr Leu Gln Lys Cys Ser Tyr Asp Glu His Ala Lys Leu
    50                  55                  60

Val Gln Glu Val Thr Asp Phe Ala Lys Thr Cys Val Ala Asp Glu Ser
65                  70                  75                  80

Ala Ala Asn Cys Asp Lys Ser Leu His Thr Leu Phe Gly Asp Lys Leu
                85                  90                  95

Cys Ala Ile Pro Asn Leu Arg Glu Asn Tyr Gly Glu Leu Ala Asp Cys
            100                 105                 110

Cys Thr Lys Gln Glu Pro Glu Arg Asn Glu Cys Phe Leu Gln His Lys
        115                 120                 125

Asp Asp Asn Pro Ser Leu Pro Pro Phe Glu Arg Pro Glu Ala Glu Ala
    130                 135                 140
```

```
Met Cys Thr Ser Phe Lys Glu Asn Pro Thr Thr Phe Met Gly His Tyr
145                 150                 155                 160

Leu His Glu Val Ala Arg Arg His Pro Tyr Phe Tyr Ala Pro Glu Leu
            165                 170                 175

Leu Tyr Tyr Ala Glu Gln Tyr Asn Glu Ile Leu Thr Gln Cys Cys Ala
        180                 185                 190

Glu Ala Asp Lys Glu Ser Cys Leu Thr Pro Lys Leu Asp Gly Val Lys
    195                 200                 205

Glu Lys Ala Leu Val Ser Ser Val Arg Gln Arg Met Lys Cys Ser Ser
210                 215                 220

Met Gln Lys Phe Gly Glu Arg Ala Phe Lys Ala Trp Ala Val Ala Arg
225                 230                 235                 240

Leu Ser Gln Thr Phe Pro Asn Ala Asp Phe Ala Glu Ile Thr Lys Leu
                245                 250                 255

Ala Thr Asp Leu Thr Lys Val Asn Lys Glu Cys Cys His Gly Asp Leu
            260                 265                 270

Leu Glu Cys Ala Asp Asp Arg Ala Glu Leu Ala Lys Tyr Met Cys Glu
        275                 280                 285

Asn Gln Ala Thr Ile Ser Ser Lys Leu Gln Thr Cys Cys Asp Lys Pro
290                 295                 300

Leu Leu Lys Lys Ala His Cys Leu Ser Glu Val Glu His Asp Thr Met
305                 310                 315                 320

Pro Ala Asp Leu Pro Ala Ile Ala Ala Asp Phe Val Glu Asp Gln Glu
                325                 330                 335

Val Cys Lys Asn Tyr Ala Glu Ala Lys Asp Val Phe Leu Gly Thr Phe
            340                 345                 350

Leu Tyr Glu Tyr Ser Arg Arg His Pro Asp Tyr Ser Val Ser Leu Leu
        355                 360                 365

Leu Arg Leu Ala Lys Lys Tyr Glu Ala Thr Leu Glu Lys Cys Cys Ala
    370                 375                 380

Glu Ala Asn Pro Pro Ala Cys Tyr Gly Thr Val Leu Ala Glu Phe Gln
385                 390                 395                 400

Pro Leu Val Glu Glu Pro Lys Asn Leu Val Lys Thr Asn Cys Asp Leu
                405                 410                 415

Tyr Glu Lys Leu Gly Glu Tyr Gly Phe Gln Asn Ala Ile Leu Val Arg
            420                 425                 430

Tyr Thr Gln Lys Ala Pro Gln Val Ser Thr Pro Thr Leu Val Glu Ala
        435                 440                 445

Ala Arg Asn Leu Gly Arg Val Gly Thr Lys Cys Cys Thr Leu Pro Glu
    450                 455                 460

Asp Gln Arg Leu Pro Cys Val Glu Asp Tyr Leu Ser Ala Ile Leu Asn
465                 470                 475                 480

Arg Val Cys Leu Leu His Glu Lys Thr Pro Val Ser Glu His Val Thr
                485                 490                 495

Lys Cys Cys Ser Gly Ser Leu Val Glu Arg Arg Pro Cys Phe Ser Ala
            500                 505                 510

Leu Thr Val Asp Glu Thr Tyr Val Pro Lys Glu Phe Lys Ala Glu Thr
        515                 520                 525

Phe Thr Phe His Ser Asp Ile Cys Thr Leu Pro Glu Lys Glu Lys Gln
    530                 535                 540

Ile Lys Lys Gln Thr Ala Leu Ala Glu Leu Val Lys His Lys Pro Lys
545                 550                 555                 560
```

Ala Thr Ala Glu Gln Leu Lys Thr Val Met Asp Asp Phe Ala Gln Phe
            565                 570                 575

Leu Asp Thr Cys Cys Lys Ala Ala Asp Lys Thr Cys Phe Ser Thr
        580                 585                 590

Glu Gly Pro Asn Leu Val Thr Arg Cys Lys Asp Ala Leu Ala Gly Gly
        595                 600                 605

Gly Gly Ser Gly Gly Gly Ser Gly Gly Gly Ser Ala Ser Asp
    610                 615                 620

Ile Gln Met Thr Gln Ser Pro Ser Leu Ser Ala Ser Val Gly Asp
625                 630                 635                 640

Arg Val Thr Ile Thr Cys Arg Ala Ser Gln Tyr Gly Gly Tyr Val Ala
                645                 650                 655

Trp Tyr Gln Gln Lys Pro Gly Lys Ala Pro Lys Leu Leu Ile Tyr Gly
                660                 665                 670

Ala Ser Leu Leu Tyr Ser Gly Val Pro Ser Arg Phe Ser Gly Gly Arg
            675                 680                 685

Ser Gly Thr Asp Phe Thr Leu Thr Ile Ser Ser Leu Gln Pro Glu Asp
        690                 695                 700

Phe Ala Thr Tyr Tyr Cys Gln Arg Gly His Ala Leu Ile Thr Phe Gly
705                 710                 715                 720

Gln Gly Thr Lys Val Glu Ile Glu Gly Thr Thr Ala Ala Ser Gly Ser
                725                 730                 735

Ser Gly Gly Ser Ser Ser Gly Ala Glu Val Gln Leu Val Glu Ser Gly
            740                 745                 750

Gly Gly Leu Val Gln Pro Gly Gly Ser Leu Arg Leu Ser Cys Ala Ala
        755                 760                 765

Ser Gly Phe Asn Ile Ser Ser Tyr Gly Ser Met His Trp Val Arg Gln
    770                 775                 780

Ala Pro Gly Lys Gly Leu Glu Trp Val Ala Ser Ile Tyr Pro Tyr Ser
785                 790                 795                 800

Ser Ser Thr Tyr Tyr Ala Asp Ser Val Lys Gly Arg Phe Thr Ile Ser
                805                 810                 815

Ala Asp Thr Ser Lys Asn Thr Ala Tyr Leu Gln Met Asn Ser Leu Arg
            820                 825                 830

Ala Glu Asp Thr Ala Val Tyr Tyr Cys Ala Arg Gly Tyr Gly Pro Trp
        835                 840                 845

Tyr Ala Tyr Ser Tyr Phe Ala Leu Asp Tyr Trp Gly Gln Gly Thr Leu
    850                 855                 860

Val Thr Val Ser Ser Gly Gly Gly Ser His His His His His His
865                 870                 875                 880

<210> SEQ ID NO 98
<211> LENGTH: 884
<212> TYPE: PRT
<213> ORGANISM: Artificial Sequence
<220> FEATURE:
<223> OTHER INFORMATION: Synthetic: LS-mouse SA-(Gly4Ser)3-scFv (VL-VH)
      CK138-ds1 (VL100Q>C / VH44G>C)-(Gly4Ser)-His6

<400> SEQUENCE: 98

Met Asp Met Arg Val Pro Ala Gln Leu Leu Gly Leu Leu Leu Leu Trp
1               5                   10                  15

Leu Pro Gly Ala Arg Cys Glu Ala His Lys Ser Glu Ile Ala His Arg
            20                  25                  30

Tyr Asn Asp Leu Gly Glu Gln His Phe Lys Gly Leu Val Leu Ile Ala
        35                  40                  45

Phe Ser Gln Tyr Leu Gln Lys Cys Ser Tyr Asp Glu His Ala Lys Leu
50                  55                  60

Val Gln Glu Val Thr Asp Phe Ala Lys Thr Cys Val Ala Asp Glu Ser
65                  70                  75                  80

Ala Ala Asn Cys Asp Lys Ser Leu His Thr Leu Phe Gly Asp Lys Leu
                85                  90                  95

Cys Ala Ile Pro Asn Leu Arg Glu Asn Tyr Gly Glu Leu Ala Asp Cys
            100                 105                 110

Cys Thr Lys Gln Glu Pro Glu Arg Asn Glu Cys Phe Leu Gln His Lys
            115                 120                 125

Asp Asp Asn Pro Ser Leu Pro Pro Phe Glu Arg Pro Glu Ala Glu Ala
130                 135                 140

Met Cys Thr Ser Phe Lys Glu Asn Pro Thr Thr Phe Met Gly His Tyr
145                 150                 155                 160

Leu His Glu Val Ala Arg Arg His Pro Tyr Phe Tyr Ala Pro Glu Leu
                165                 170                 175

Leu Tyr Tyr Ala Glu Gln Tyr Asn Glu Ile Leu Thr Gln Cys Cys Ala
            180                 185                 190

Glu Ala Asp Lys Glu Ser Cys Leu Thr Pro Lys Leu Asp Gly Val Lys
            195                 200                 205

Glu Lys Ala Leu Val Ser Ser Val Arg Gln Arg Met Lys Cys Ser Ser
210                 215                 220

Met Gln Lys Phe Gly Glu Arg Ala Phe Lys Ala Trp Ala Val Ala Arg
225                 230                 235                 240

Leu Ser Gln Thr Phe Pro Asn Ala Asp Phe Ala Glu Ile Thr Lys Leu
            245                 250                 255

Ala Thr Asp Leu Thr Lys Val Asn Lys Glu Cys Cys His Gly Asp Leu
            260                 265                 270

Leu Glu Cys Ala Asp Asp Arg Ala Glu Leu Ala Lys Tyr Met Cys Glu
            275                 280                 285

Asn Gln Ala Thr Ile Ser Ser Lys Leu Gln Thr Cys Cys Asp Lys Pro
            290                 295                 300

Leu Leu Lys Lys Ala His Cys Leu Ser Glu Val Glu His Asp Thr Met
305                 310                 315                 320

Pro Ala Asp Leu Pro Ala Ile Ala Ala Asp Phe Val Glu Asp Gln Glu
            325                 330                 335

Val Cys Lys Asn Tyr Ala Glu Ala Lys Asp Val Phe Leu Gly Thr Phe
            340                 345                 350

Leu Tyr Glu Tyr Ser Arg Arg His Pro Asp Tyr Ser Val Ser Leu Leu
            355                 360                 365

Leu Arg Leu Ala Lys Lys Tyr Glu Ala Thr Leu Glu Lys Cys Cys Ala
            370                 375                 380

Glu Ala Asn Pro Pro Ala Cys Tyr Gly Thr Val Leu Ala Glu Phe Gln
385                 390                 395                 400

Pro Leu Val Glu Glu Pro Lys Asn Leu Val Lys Thr Asn Cys Asp Leu
            405                 410                 415

Tyr Glu Lys Leu Gly Glu Tyr Gly Phe Gln Asn Ala Ile Leu Val Arg
            420                 425                 430

Tyr Thr Gln Lys Ala Pro Gln Val Ser Thr Pro Thr Leu Val Glu Ala
            435                 440                 445

Ala Arg Asn Leu Gly Arg Val Gly Thr Lys Cys Cys Thr Leu Pro Glu
450                 455                 460

-continued

Asp Gln Arg Leu Pro Cys Val Glu Asp Tyr Leu Ser Ala Ile Leu Asn
465                 470                 475                 480

Arg Val Cys Leu Leu His Glu Lys Thr Pro Val Ser Glu His Val Thr
                485                 490                 495

Lys Cys Cys Ser Gly Ser Leu Val Glu Arg Pro Cys Phe Ser Ala
            500                 505                 510

Leu Thr Val Asp Glu Thr Tyr Val Pro Lys Glu Phe Lys Ala Glu Thr
            515                 520                 525

Phe Thr Phe His Ser Asp Ile Cys Thr Leu Pro Glu Lys Glu Lys Gln
            530                 535                 540

Ile Lys Lys Gln Thr Ala Leu Ala Glu Leu Val Lys His Lys Pro Lys
545                 550                 555                 560

Ala Thr Ala Glu Gln Leu Lys Thr Val Met Asp Asp Phe Ala Gln Phe
                565                 570                 575

Leu Asp Thr Cys Cys Lys Ala Ala Asp Lys Asp Thr Cys Phe Ser Thr
            580                 585                 590

Glu Gly Pro Asn Leu Val Thr Arg Cys Lys Asp Ala Leu Ala Gly Gly
            595                 600                 605

Gly Gly Ser Gly Gly Gly Ser Gly Gly Gly Ser Ala Ser Ala
            610                 615                 620

Ile Gln Met Thr Arg Ser Pro Ser Ser Leu Ser Ala Ser Val Gly Asp
625                 630                 635                 640

Arg Val Thr Ile Thr Cys Arg Ala Ser Gln Tyr His Asp Gly Ser Ala
                645                 650                 655

Ala Trp Tyr Gln Gln Lys Pro Gly Lys Ala Pro Lys Leu Leu Ile Tyr
                660                 665                 670

Gly Ala Ser Tyr Leu Tyr Ser Gly Val Pro Ser Arg Phe Ser Gly Ser
            675                 680                 685

Arg Ser Gly Thr Asp Phe Thr Leu Thr Ile Ser Ser Leu Gln Pro Glu
            690                 695                 700

Asp Phe Ala Thr Tyr Tyr Cys Gln Gln Ser Ser Tyr Ser Leu Ile Thr
705                 710                 715                 720

Phe Gly Cys Gly Thr Lys Val Glu Ile Lys Gly Thr Thr Ala Ala Ser
                725                 730                 735

Gly Ser Ser Gly Gly Ser Ser Ser Gly Ala Glu Val Gln Leu Val Glu
            740                 745                 750

Ser Asp Gly Gly Leu Val Gln Pro Gly Gly Ser Leu Arg Leu Ser Cys
            755                 760                 765

Ala Ala Ser Gly Phe Asn Leu Ser Tyr Tyr Gly Met His Trp Val Arg
            770                 775                 780

Gln Ala Pro Gly Lys Cys Leu Glu Trp Val Ala Tyr Ile Ala Ser Tyr
785                 790                 795                 800

Pro Gly Tyr Thr Ser Tyr Ala Asp Ser Val Lys Gly Arg Phe Thr Ile
                805                 810                 815

Ser Ala Asp Thr Ser Lys Asn Thr Ala Tyr Leu Gln Met Asn Ser Leu
                820                 825                 830

Arg Ala Glu Asp Thr Ala Val Tyr Tyr Cys Ala Arg Ser Gly Tyr Ser
            835                 840                 845

Tyr Ser Pro Tyr Tyr Ser Trp Phe Ser Ala Gly Met Asn Tyr Trp Gly
            850                 855                 860

Gln Gly Ala Leu Val Thr Val Ser Ser Gly Gly Gly Ser His His
865                 870                 875                 880

His His His His

<210> SEQ ID NO 99
<211> LENGTH: 884
<212> TYPE: PRT
<213> ORGANISM: Artificial Sequence
<220> FEATURE:
<223> OTHER INFORMATION: Synthetic: LS-mouse SA-(Gly4Ser)3-scFv (VL-VH)
    CK138-ds2 (VL43A>C / VH105Q>C)-(Gly4Ser)-His6

<400> SEQUENCE: 99

```
Met Asp Met Arg Val Pro Ala Gln Leu Leu Gly Leu Leu Leu Leu Trp
1               5                   10                  15

Leu Pro Gly Ala Arg Cys Glu Ala His Lys Ser Glu Ile Ala His Arg
            20                  25                  30

Tyr Asn Asp Leu Gly Glu Gln His Phe Lys Gly Leu Val Leu Ile Ala
        35                  40                  45

Phe Ser Gln Tyr Leu Gln Lys Cys Ser Tyr Asp Glu His Ala Lys Leu
    50                  55                  60

Val Gln Glu Val Thr Asp Phe Ala Lys Thr Cys Val Ala Asp Glu Ser
65                  70                  75                  80

Ala Ala Asn Cys Asp Lys Ser Leu His Thr Leu Phe Gly Asp Lys Leu
                85                  90                  95

Cys Ala Ile Pro Asn Leu Arg Glu Asn Tyr Gly Glu Leu Ala Asp Cys
            100                 105                 110

Cys Thr Lys Gln Glu Pro Glu Arg Asn Glu Cys Phe Leu Gln His Lys
        115                 120                 125

Asp Asp Asn Pro Ser Leu Pro Pro Phe Glu Arg Pro Glu Ala Glu Ala
    130                 135                 140

Met Cys Thr Ser Phe Lys Glu Asn Pro Thr Thr Phe Met Gly His Tyr
145                 150                 155                 160

Leu His Glu Val Ala Arg Arg His Pro Tyr Phe Tyr Ala Pro Glu Leu
                165                 170                 175

Leu Tyr Tyr Ala Glu Gln Tyr Asn Glu Ile Leu Thr Gln Cys Cys Ala
            180                 185                 190

Glu Ala Asp Lys Glu Ser Cys Leu Thr Pro Lys Leu Asp Gly Val Lys
        195                 200                 205

Glu Lys Ala Leu Val Ser Ser Val Arg Gln Arg Met Lys Cys Ser Ser
    210                 215                 220

Met Gln Lys Phe Gly Glu Arg Ala Phe Lys Ala Trp Ala Val Ala Arg
225                 230                 235                 240

Leu Ser Gln Thr Phe Pro Asn Ala Asp Phe Ala Glu Ile Thr Lys Leu
                245                 250                 255

Ala Thr Asp Leu Thr Lys Val Asn Lys Glu Cys Cys His Gly Asp Leu
            260                 265                 270

Leu Glu Cys Ala Asp Asp Arg Ala Glu Leu Ala Lys Tyr Met Cys Glu
        275                 280                 285

Asn Gln Ala Thr Ile Ser Ser Lys Leu Gln Thr Cys Cys Asp Lys Pro
    290                 295                 300

Leu Leu Lys Lys Ala His Cys Leu Ser Glu Val Glu His Asp Thr Met
305                 310                 315                 320

Pro Ala Asp Leu Pro Ala Ile Ala Ala Asp Phe Val Glu Asp Gln Glu
                325                 330                 335

Val Cys Lys Asn Tyr Ala Glu Ala Lys Asp Val Phe Leu Gly Thr Phe
            340                 345                 350

Leu Tyr Glu Tyr Ser Arg Arg His Pro Asp Tyr Ser Val Ser Leu Leu
```

```
              355                 360                 365
Leu Arg Leu Ala Lys Lys Tyr Glu Ala Thr Leu Glu Lys Cys Cys Ala
    370                 375                 380
Glu Ala Asn Pro Pro Ala Cys Tyr Gly Thr Val Leu Ala Glu Phe Gln
385                 390                 395                 400
Pro Leu Val Glu Glu Pro Lys Asn Leu Val Lys Thr Asn Cys Asp Leu
                405                 410                 415
Tyr Glu Lys Leu Gly Glu Tyr Gly Phe Gln Asn Ala Ile Leu Val Arg
            420                 425                 430
Tyr Thr Gln Lys Ala Pro Gln Val Ser Thr Pro Thr Leu Val Glu Ala
        435                 440                 445
Ala Arg Asn Leu Gly Arg Val Gly Thr Lys Cys Cys Thr Leu Pro Glu
    450                 455                 460
Asp Gln Arg Leu Pro Cys Val Glu Asp Tyr Leu Ser Ala Ile Leu Asn
465                 470                 475                 480
Arg Val Cys Leu Leu His Glu Lys Thr Pro Val Ser Glu His Val Thr
                485                 490                 495
Lys Cys Cys Ser Gly Ser Leu Val Glu Arg Arg Pro Cys Phe Ser Ala
            500                 505                 510
Leu Thr Val Asp Glu Thr Tyr Val Pro Lys Glu Phe Lys Ala Glu Thr
        515                 520                 525
Phe Thr Phe His Ser Asp Ile Cys Thr Leu Pro Glu Lys Glu Lys Gln
    530                 535                 540
Ile Lys Lys Gln Thr Ala Leu Ala Glu Leu Val Lys His Lys Pro Lys
545                 550                 555                 560
Ala Thr Ala Glu Gln Leu Lys Thr Val Met Asp Asp Phe Ala Gln Phe
                565                 570                 575
Leu Asp Thr Cys Cys Lys Ala Ala Asp Lys Asp Thr Cys Phe Ser Thr
            580                 585                 590
Glu Gly Pro Asn Leu Val Thr Arg Cys Lys Asp Ala Leu Ala Gly Gly
        595                 600                 605
Gly Gly Ser Gly Gly Gly Ser Gly Gly Gly Ser Ala Ser Ala
    610                 615                 620
Ile Gln Met Thr Arg Ser Pro Ser Ser Leu Ser Ala Ser Val Gly Asp
625                 630                 635                 640
Arg Val Thr Ile Thr Cys Arg Ala Ser Gln Tyr His Asp Gly Ser Ala
                645                 650                 655
Ala Trp Tyr Gln Gln Lys Pro Gly Lys Cys Pro Lys Leu Leu Ile Tyr
            660                 665                 670
Gly Ala Ser Tyr Leu Tyr Ser Gly Val Pro Ser Arg Phe Ser Gly Ser
        675                 680                 685
Arg Ser Gly Thr Asp Phe Leu Thr Ile Ser Ser Leu Gln Pro Glu
    690                 695                 700
Asp Phe Ala Thr Tyr Tyr Cys Gln Gln Ser Ser Tyr Ser Leu Ile Thr
705                 710                 715                 720
Phe Gly Gln Gly Thr Lys Val Glu Ile Lys Gly Thr Thr Ala Ala Ser
                725                 730                 735
Gly Ser Ser Gly Gly Ser Ser Gly Ala Glu Val Gln Leu Val Glu
            740                 745                 750
Ser Asp Gly Gly Leu Val Gln Pro Gly Gly Ser Leu Arg Leu Ser Cys
        755                 760                 765
Ala Ala Ser Gly Phe Asn Leu Ser Tyr Tyr Gly Met His Trp Val Arg
    770                 775                 780
```

-continued

```
Gln Ala Pro Gly Lys Gly Leu Glu Trp Val Ala Tyr Ile Ala Ser Tyr
785                 790                 795                 800

Pro Gly Tyr Thr Ser Tyr Ala Asp Ser Val Lys Gly Arg Phe Thr Ile
            805                 810                 815

Ser Ala Asp Thr Ser Lys Asn Thr Ala Tyr Leu Gln Met Asn Ser Leu
        820                 825                 830

Arg Ala Glu Asp Thr Ala Val Tyr Tyr Cys Ala Arg Ser Gly Tyr Ser
        835                 840                 845

Tyr Ser Pro Tyr Tyr Ser Trp Phe Ser Ala Gly Met Asn Tyr Trp Gly
    850                 855                 860

Cys Gly Ala Leu Val Thr Val Ser Ser Gly Gly Gly Ser His His
865                 870                 875                 880

His His His His

<210> SEQ ID NO 100
<211> LENGTH: 875
<212> TYPE: PRT
<213> ORGANISM: Artificial Sequence
<220> FEATURE:
<223> OTHER INFORMATION: Synthetic: LS-mouse SA-(Gly4Ser)3-scFv (VL-VH)
      CK157-ds1 (VL100Q>C / VH44E>C)-(Gly4Ser)-His6

<400> SEQUENCE: 100

Met Asp Met Arg Val Pro Ala Gln Leu Leu Gly Leu Leu Leu Leu Trp
1               5                   10                  15

Leu Pro Gly Ala Arg Cys Glu Ala His Lys Ser Glu Ile Ala His Arg
            20                  25                  30

Tyr Asn Asp Leu Gly Glu Gln His Phe Lys Gly Leu Val Leu Ile Ala
        35                  40                  45

Phe Ser Gln Tyr Leu Gln Lys Cys Ser Tyr Asp Glu His Ala Lys Leu
    50                  55                  60

Val Gln Glu Val Thr Asp Phe Ala Lys Thr Cys Val Ala Asp Glu Ser
65                  70                  75                  80

Ala Ala Asn Cys Asp Lys Ser Leu His Thr Leu Phe Gly Asp Lys Leu
                85                  90                  95

Cys Ala Ile Pro Asn Leu Arg Glu Asn Tyr Gly Glu Leu Ala Asp Cys
            100                 105                 110

Cys Thr Lys Gln Glu Pro Glu Arg Asn Glu Cys Phe Leu Gln His Lys
        115                 120                 125

Asp Asp Asn Pro Ser Leu Pro Pro Phe Glu Arg Pro Glu Ala Glu Ala
    130                 135                 140

Met Cys Thr Ser Phe Lys Glu Asn Pro Thr Thr Phe Met Gly His Tyr
145                 150                 155                 160

Leu His Glu Val Ala Arg Arg His Pro Tyr Phe Tyr Ala Pro Glu Leu
                165                 170                 175

Leu Tyr Tyr Ala Glu Gln Tyr Asn Glu Ile Leu Thr Gln Cys Cys Ala
            180                 185                 190

Glu Ala Asp Lys Glu Ser Cys Leu Thr Pro Lys Leu Asp Gly Val Lys
        195                 200                 205

Glu Lys Ala Leu Val Ser Ser Val Arg Gln Arg Met Lys Cys Ser Ser
    210                 215                 220

Met Gln Lys Phe Gly Glu Arg Ala Phe Lys Ala Trp Ala Val Ala Arg
225                 230                 235                 240

Leu Ser Gln Thr Phe Pro Asn Ala Asp Phe Ala Glu Ile Thr Lys Leu
                245                 250                 255
```

```
Ala Thr Asp Leu Thr Lys Val Asn Lys Glu Cys Cys His Gly Asp Leu
            260                 265                 270

Leu Glu Cys Ala Asp Asp Arg Ala Glu Leu Ala Lys Tyr Met Cys Glu
        275                 280                 285

Asn Gln Ala Thr Ile Ser Ser Lys Leu Gln Thr Cys Cys Asp Lys Pro
    290                 295                 300

Leu Leu Lys Lys Ala His Cys Leu Ser Glu Val Glu His Asp Thr Met
305                 310                 315                 320

Pro Ala Asp Leu Pro Ala Ile Ala Ala Asp Phe Val Glu Asp Gln Glu
                325                 330                 335

Val Cys Lys Asn Tyr Ala Glu Ala Lys Asp Val Phe Leu Gly Thr Phe
                340                 345                 350

Leu Tyr Glu Tyr Ser Arg Arg His Pro Asp Tyr Ser Val Ser Leu Leu
            355                 360                 365

Leu Arg Leu Ala Lys Lys Tyr Glu Ala Thr Leu Glu Lys Cys Cys Ala
    370                 375                 380

Glu Ala Asn Pro Pro Ala Cys Tyr Gly Thr Val Leu Ala Glu Phe Gln
385                 390                 395                 400

Pro Leu Val Glu Glu Pro Lys Asn Leu Val Lys Thr Asn Cys Asp Leu
                405                 410                 415

Tyr Glu Lys Leu Gly Glu Tyr Gly Phe Gln Asn Ala Ile Leu Val Arg
            420                 425                 430

Tyr Thr Gln Lys Ala Pro Gln Val Ser Thr Pro Thr Leu Val Glu Ala
        435                 440                 445

Ala Arg Asn Leu Gly Arg Val Gly Thr Lys Cys Cys Thr Leu Pro Glu
    450                 455                 460

Asp Gln Arg Leu Pro Cys Val Glu Asp Tyr Leu Ser Ala Ile Leu Asn
465                 470                 475                 480

Arg Val Cys Leu Leu His Glu Lys Thr Pro Val Ser Glu His Val Thr
                485                 490                 495

Lys Cys Cys Ser Gly Ser Leu Val Glu Arg Arg Pro Cys Phe Ser Ala
            500                 505                 510

Leu Thr Val Asp Glu Thr Tyr Val Pro Lys Glu Phe Lys Ala Glu Thr
        515                 520                 525

Phe Thr Phe His Ser Asp Ile Cys Thr Leu Pro Glu Lys Glu Lys Gln
    530                 535                 540

Ile Lys Lys Gln Thr Ala Leu Ala Glu Leu Val Lys His Lys Pro Lys
545                 550                 555                 560

Ala Thr Ala Glu Gln Leu Lys Thr Val Met Asp Asp Phe Ala Gln Phe
                565                 570                 575

Leu Asp Thr Cys Cys Lys Ala Ala Asp Lys Asp Thr Cys Phe Ser Thr
            580                 585                 590

Glu Gly Pro Asn Leu Val Thr Arg Cys Lys Asp Ala Leu Ala Gly Gly
        595                 600                 605

Gly Gly Ser Gly Gly Gly Gly Ser Gly Gly Gly Gly Ser Ala Ser Asp
    610                 615                 620

Ile Gln Met Thr Gln Ser Pro Ser Ser Leu Ser Ala Ser Val Gly Asp
625                 630                 635                 640

Arg Val Thr Ile Thr Cys Arg Ala Ser Gln Ser Tyr Gly Gly Val Ala
                645                 650                 655

Trp Tyr Gln Gln Lys Pro Gly Lys Ala Pro Lys Leu Leu Ile Tyr Ser
            660                 665                 670
```

Ala Ser Tyr Leu Tyr Ser Gly Val Pro Ser Arg Phe Ser Gly Ser Arg
            675                 680                 685
Ser Gly Thr Asp Phe Thr Leu Thr Ile Ser Ser Leu Gln Pro Glu Asp
    690                 695                 700
Phe Ala Thr Tyr Tyr Cys Gln Gln Pro Ser His Leu Ile Thr Phe Gly
705                 710                 715                 720
Cys Gly Thr Glu Val Glu Ile Lys Gly Thr Thr Ala Ala Ser Gly Ser
                725                 730                 735
Ser Gly Gly Ser Ser Gly Ala Glu Val Gln Leu Val Glu Ser Gly
            740                 745                 750
Gly Gly Leu Val Gln Pro Gly Gly Ser Leu Arg Leu Ser Cys Ala Ala
        755                 760                 765
Ser Gly Ser Asn Pro Tyr Tyr Tyr Gly Gly Thr His Trp Val Arg Gln
    770                 775                 780
Ala Pro Gly Glu Cys Leu Glu Trp Val Ala Ser Ile Gly Ser Tyr Pro
785                 790                 795                 800
Gly Tyr Thr Asp Tyr Ala Asp Ser Val Lys Gly Arg Phe Thr Ile Ser
                805                 810                 815
Ala Asp Thr Ser Lys Asn Thr Ala Tyr Leu Gln Met Asn Ser Leu Arg
            820                 825                 830
Ala Glu Asp Thr Ala Val Tyr Tyr Cys Ala Arg His Tyr Tyr Trp Tyr
        835                 840                 845
Asp Ala Thr Asp Tyr Trp Gly Gln Gly Thr Leu Val Thr Val Ser Ser
    850                 855                 860
Gly Gly Gly Gly Ser His His His His His
865                 870                 875

<210> SEQ ID NO 101
<211> LENGTH: 875
<212> TYPE: PRT
<213> ORGANISM: Artificial Sequence
<220> FEATURE:
<223> OTHER INFORMATION: Synthetic: LS-mouse SA-(Gly4Ser)3-scFv (VL-VH)
    CK157-ds2 (VL43A>C / VH105Q>C)-(Gly4Ser)-His6

<400> SEQUENCE: 101

Met Asp Met Arg Val Pro Ala Gln Leu Leu Gly Leu Leu Leu Leu Trp
1               5                   10                  15
Leu Pro Gly Ala Arg Cys Glu Ala His Lys Ser Glu Ile Ala His Arg
            20                  25                  30
Tyr Asn Asp Leu Gly Glu Gln His Phe Lys Gly Leu Val Leu Ile Ala
        35                  40                  45
Phe Ser Gln Tyr Leu Gln Lys Cys Ser Tyr Asp Glu His Ala Lys Leu
    50                  55                  60
Val Gln Glu Val Thr Asp Phe Ala Lys Thr Cys Val Ala Asp Glu Ser
65                  70                  75                  80
Ala Ala Asn Cys Asp Lys Ser Leu His Thr Leu Phe Gly Asp Lys Leu
                85                  90                  95
Cys Ala Ile Pro Asn Leu Arg Glu Asn Tyr Gly Glu Leu Ala Asp Cys
            100                 105                 110
Cys Thr Lys Gln Glu Pro Glu Arg Asn Glu Cys Phe Leu Gln His Lys
        115                 120                 125
Asp Asp Asn Pro Ser Leu Pro Pro Phe Glu Arg Pro Glu Ala Glu Ala
    130                 135                 140
Met Cys Thr Ser Phe Lys Glu Asn Pro Thr Thr Phe Met Gly His Tyr
145                 150                 155                 160

```
Leu His Glu Val Ala Arg Arg His Pro Tyr Phe Tyr Ala Pro Glu Leu
                165                 170                 175

Leu Tyr Tyr Ala Glu Gln Tyr Asn Glu Ile Leu Thr Gln Cys Cys Ala
            180                 185                 190

Glu Ala Asp Lys Glu Ser Cys Leu Thr Pro Lys Leu Asp Gly Val Lys
        195                 200                 205

Glu Lys Ala Leu Val Ser Ser Val Arg Gln Arg Met Lys Cys Ser Ser
    210                 215                 220

Met Gln Lys Phe Gly Glu Arg Ala Phe Lys Ala Trp Ala Val Ala Arg
225                 230                 235                 240

Leu Ser Gln Thr Phe Pro Asn Ala Asp Phe Ala Glu Ile Thr Lys Leu
                245                 250                 255

Ala Thr Asp Leu Thr Lys Val Asn Lys Glu Cys Cys His Gly Asp Leu
            260                 265                 270

Leu Glu Cys Ala Asp Asp Arg Ala Glu Leu Ala Lys Tyr Met Cys Glu
        275                 280                 285

Asn Gln Ala Thr Ile Ser Ser Lys Leu Gln Thr Cys Cys Asp Lys Pro
    290                 295                 300

Leu Leu Lys Lys Ala His Cys Leu Ser Glu Val Glu His Asp Thr Met
305                 310                 315                 320

Pro Ala Asp Leu Pro Ala Ile Ala Ala Asp Phe Val Glu Asp Gln Glu
                325                 330                 335

Val Cys Lys Asn Tyr Ala Glu Ala Lys Asp Val Phe Leu Gly Thr Phe
            340                 345                 350

Leu Tyr Glu Tyr Ser Arg Arg His Pro Asp Tyr Ser Val Ser Leu Leu
        355                 360                 365

Leu Arg Leu Ala Lys Lys Tyr Glu Ala Thr Leu Glu Lys Cys Cys Ala
    370                 375                 380

Glu Ala Asn Pro Pro Ala Cys Tyr Gly Thr Val Leu Ala Glu Phe Gln
385                 390                 395                 400

Pro Leu Val Glu Glu Pro Lys Asn Leu Val Lys Thr Asn Cys Asp Leu
                405                 410                 415

Tyr Glu Lys Leu Gly Glu Tyr Gly Phe Gln Asn Ala Ile Leu Val Arg
            420                 425                 430

Tyr Thr Gln Lys Ala Pro Gln Val Ser Thr Pro Thr Leu Val Glu Ala
        435                 440                 445

Ala Arg Asn Leu Gly Arg Val Gly Thr Lys Cys Cys Thr Leu Pro Glu
    450                 455                 460

Asp Gln Arg Leu Pro Cys Val Glu Asp Tyr Leu Ser Ala Ile Leu Asn
465                 470                 475                 480

Arg Val Cys Leu Leu His Glu Lys Thr Pro Val Ser Glu His Val Thr
                485                 490                 495

Lys Cys Cys Ser Gly Ser Leu Val Glu Arg Arg Pro Cys Phe Ser Ala
            500                 505                 510

Leu Thr Val Asp Glu Thr Tyr Val Pro Lys Glu Phe Lys Ala Glu Thr
        515                 520                 525

Phe Thr Phe His Ser Asp Ile Cys Thr Leu Pro Glu Lys Glu Lys Gln
    530                 535                 540

Ile Lys Lys Gln Thr Ala Leu Ala Glu Leu Val Lys His Lys Pro Lys
545                 550                 555                 560

Ala Thr Ala Glu Gln Leu Lys Thr Val Met Asp Asp Phe Ala Gln Phe
                565                 570                 575
```

```
Leu Asp Thr Cys Cys Lys Ala Ala Asp Lys Asp Thr Cys Phe Ser Thr
            580                 585                 590

Glu Gly Pro Asn Leu Val Thr Arg Cys Lys Asp Ala Leu Ala Gly Gly
        595                 600                 605

Gly Gly Ser Gly Gly Gly Ser Gly Gly Gly Ser Ala Ser Asp
    610                 615                 620

Ile Gln Met Thr Gln Ser Pro Ser Ser Leu Ser Ala Ser Val Gly Asp
625                 630                 635                 640

Arg Val Thr Ile Thr Cys Arg Ala Ser Gln Ser Tyr Gly Gly Val Ala
                645                 650                 655

Trp Tyr Gln Gln Lys Pro Gly Lys Cys Pro Lys Leu Leu Ile Tyr Ser
            660                 665                 670

Ala Ser Tyr Leu Tyr Ser Gly Val Pro Ser Arg Phe Ser Gly Ser Arg
        675                 680                 685

Ser Gly Thr Asp Phe Thr Leu Thr Ile Ser Ser Leu Gln Pro Glu Asp
    690                 695                 700

Phe Ala Thr Tyr Tyr Cys Gln Gln Pro Ser His Leu Ile Thr Phe Gly
705                 710                 715                 720

Gln Gly Thr Glu Val Glu Ile Lys Gly Thr Thr Ala Ala Ser Gly Ser
                725                 730                 735

Ser Gly Gly Ser Ser Gly Ala Glu Val Gln Leu Val Glu Ser Gly
            740                 745                 750

Gly Gly Leu Val Gln Pro Gly Gly Ser Leu Arg Leu Ser Cys Ala Ala
        755                 760                 765

Ser Gly Ser Asn Pro Tyr Tyr Tyr Gly Gly Thr His Trp Val Arg Gln
    770                 775                 780

Ala Pro Gly Glu Glu Leu Glu Trp Val Ala Ser Ile Gly Ser Tyr Pro
785                 790                 795                 800

Gly Tyr Thr Asp Tyr Ala Asp Ser Val Lys Gly Arg Phe Thr Ile Ser
                805                 810                 815

Ala Asp Thr Ser Lys Asn Thr Ala Tyr Leu Gln Met Asn Ser Leu Arg
            820                 825                 830

Ala Glu Asp Thr Ala Val Tyr Tyr Cys Ala Arg His Tyr Tyr Trp Tyr
        835                 840                 845

Asp Ala Thr Asp Tyr Trp Gly Cys Gly Thr Leu Val Thr Val Ser Ser
850                 855                 860

Gly Gly Gly Gly Ser His His His His
865                 870                 875

<210> SEQ ID NO 102
<211> LENGTH: 739
<212> TYPE: PRT
<213> ORGANISM: Artificial Sequence
<220> FEATURE:
<223> OTHER INFORMATION: Synthetic: LS-mouse SA-(Gly4Ser)-VL CK157-His6

<400> SEQUENCE: 102

Met Asp Met Arg Val Pro Ala Gln Leu Leu Gly Leu Leu Leu Leu Trp
1               5                   10                  15

Leu Pro Gly Ala Arg Cys Glu Ala His Lys Ser Glu Ile Ala His Arg
            20                  25                  30

Tyr Asn Asp Leu Gly Glu Gln His Phe Lys Gly Leu Val Leu Ile Ala
        35                  40                  45

Phe Ser Gln Tyr Leu Gln Lys Cys Ser Tyr Asp Glu His Ala Lys Leu
    50                  55                  60
```

```
Val Gln Glu Val Thr Asp Phe Ala Lys Thr Cys Val Ala Asp Glu Ser
 65                  70                  75                  80

Ala Ala Asn Cys Asp Lys Ser Leu His Thr Leu Phe Gly Asp Lys Leu
             85                  90                  95

Cys Ala Ile Pro Asn Leu Arg Glu Asn Tyr Gly Glu Leu Ala Asp Cys
            100                 105                 110

Cys Thr Lys Gln Glu Pro Glu Arg Asn Glu Cys Phe Leu Gln His Lys
            115                 120                 125

Asp Asp Asn Pro Ser Leu Pro Pro Phe Glu Arg Pro Glu Ala Glu Ala
130                 135                 140

Met Cys Thr Ser Phe Lys Glu Asn Pro Thr Thr Phe Met Gly His Tyr
145                 150                 155                 160

Leu His Glu Val Ala Arg Arg His Pro Tyr Phe Tyr Ala Pro Glu Leu
                165                 170                 175

Leu Tyr Tyr Ala Glu Gln Tyr Asn Glu Ile Leu Thr Gln Cys Cys Ala
            180                 185                 190

Glu Ala Asp Lys Glu Ser Cys Leu Thr Pro Lys Leu Asp Gly Val Lys
            195                 200                 205

Glu Lys Ala Leu Val Ser Ser Val Arg Gln Arg Met Lys Cys Ser Ser
210                 215                 220

Met Gln Lys Phe Gly Glu Arg Ala Phe Lys Ala Trp Ala Val Ala Arg
225                 230                 235                 240

Leu Ser Gln Thr Phe Pro Asn Ala Asp Phe Ala Glu Ile Thr Lys Leu
                245                 250                 255

Ala Thr Asp Leu Thr Lys Val Asn Lys Glu Cys Cys His Gly Asp Leu
            260                 265                 270

Leu Glu Cys Ala Asp Asp Arg Ala Glu Leu Ala Lys Tyr Met Cys Glu
            275                 280                 285

Asn Gln Ala Thr Ile Ser Ser Lys Leu Gln Thr Cys Cys Asp Lys Pro
290                 295                 300

Leu Leu Lys Lys Ala His Cys Leu Ser Glu Val Glu His Asp Thr Met
305                 310                 315                 320

Pro Ala Asp Leu Pro Ala Ile Ala Ala Asp Phe Val Glu Asp Gln Glu
                325                 330                 335

Val Cys Lys Asn Tyr Ala Glu Ala Lys Asp Val Phe Leu Gly Thr Phe
            340                 345                 350

Leu Tyr Glu Tyr Ser Arg Arg His Pro Asp Tyr Ser Val Ser Leu Leu
            355                 360                 365

Leu Arg Leu Ala Lys Lys Tyr Glu Ala Thr Leu Glu Lys Cys Cys Ala
370                 375                 380

Glu Ala Asn Pro Pro Ala Cys Tyr Gly Thr Val Leu Ala Glu Phe Gln
385                 390                 395                 400

Pro Leu Val Glu Glu Pro Lys Asn Leu Val Lys Thr Asn Cys Asp Leu
                405                 410                 415

Tyr Glu Lys Leu Gly Glu Tyr Gly Phe Gln Asn Ala Ile Leu Val Arg
            420                 425                 430

Tyr Thr Gln Lys Ala Pro Gln Val Ser Thr Pro Thr Leu Val Glu Ala
            435                 440                 445

Ala Arg Asn Leu Gly Arg Val Gly Thr Lys Cys Cys Thr Leu Pro Glu
450                 455                 460

Asp Gln Arg Leu Pro Cys Val Glu Asp Tyr Leu Ser Ala Ile Leu Asn
465                 470                 475                 480

Arg Val Cys Leu Leu His Glu Lys Thr Pro Val Ser Glu His Val Thr
```

```
            485                 490                 495
Lys Cys Cys Ser Gly Ser Leu Val Glu Arg Pro Cys Phe Ser Ala
            500                 505                 510

Leu Thr Val Asp Glu Thr Tyr Val Pro Lys Glu Phe Lys Ala Glu Thr
            515                 520                 525

Phe Thr Phe His Ser Asp Ile Cys Thr Leu Pro Glu Lys Glu Lys Gln
            530                 535                 540

Ile Lys Lys Gln Thr Ala Leu Ala Glu Leu Val Lys His Lys Pro Lys
545                 550                 555                 560

Ala Thr Ala Glu Gln Leu Lys Thr Val Met Asp Asp Phe Ala Gln Phe
                565                 570                 575

Leu Asp Thr Cys Cys Lys Ala Ala Asp Lys Asp Thr Cys Phe Ser Thr
            580                 585                 590

Glu Gly Pro Asn Leu Val Thr Arg Cys Lys Asp Ala Leu Ala Gly Gly
            595                 600                 605

Gly Gly Ser Gly Gly Gly Ser Gly Gly Gly Ser Ala Ser Asp
            610                 615                 620

Ile Gln Met Thr Gln Ser Pro Ser Ser Leu Ser Ala Ser Val Gly Asp
625                 630                 635                 640

Arg Val Thr Ile Thr Cys Arg Ala Ser Gln Ser Tyr Gly Gly Val Ala
                645                 650                 655

Trp Tyr Gln Gln Lys Pro Gly Lys Ala Pro Lys Leu Leu Ile Tyr Ser
                660                 665                 670

Ala Ser Tyr Leu Tyr Ser Gly Val Pro Ser Arg Phe Ser Gly Ser Arg
            675                 680                 685

Ser Gly Thr Asp Phe Thr Leu Thr Ile Ser Ser Leu Gln Pro Glu Asp
690                 695                 700

Phe Ala Thr Tyr Tyr Cys Gln Gln Pro Ser His Leu Ile Thr Phe Gly
705                 710                 715                 720

Gln Gly Thr Glu Val Glu Ile Lys Gly Gly Gly Ser His His His
                725                 730                 735

His His His
```

<210> SEQ ID NO 103
<211> LENGTH: 755
<212> TYPE: PRT
<213> ORGANISM: Artificial Sequence
<220> FEATURE:
<223> OTHER INFORMATION: Synthetic: LS-mouse SA-(Gly4Ser)-VH CK157-His6

<400> SEQUENCE: 103

```
Met Asp Met Arg Val Pro Ala Gln Leu Leu Gly Leu Leu Leu Leu Trp
1               5                   10                  15

Leu Pro Gly Ala Arg Cys Glu Ala His Lys Ser Glu Ile Ala His Arg
                20                  25                  30

Tyr Asn Asp Leu Gly Glu Gln His Phe Lys Gly Leu Val Leu Ile Ala
            35                  40                  45

Phe Ser Gln Tyr Leu Gln Lys Cys Ser Tyr Asp Glu His Ala Lys Leu
        50                  55                  60

Val Gln Glu Val Thr Asp Phe Ala Lys Thr Cys Val Ala Asp Glu Ser
65                  70                  75                  80

Ala Ala Asn Cys Asp Lys Ser Leu His Thr Leu Phe Gly Asp Lys Leu
                85                  90                  95

Cys Ala Ile Pro Asn Leu Arg Glu Asn Tyr Gly Glu Leu Ala Asp Cys
            100                 105                 110
```

-continued

```
Cys Thr Lys Gln Glu Pro Glu Arg Asn Glu Cys Phe Leu Gln His Lys
        115                 120                 125

Asp Asp Asn Pro Ser Leu Pro Pro Phe Glu Arg Pro Glu Ala Glu Ala
130                 135                 140

Met Cys Thr Ser Phe Lys Glu Asn Pro Thr Thr Phe Met Gly His Tyr
145                 150                 155                 160

Leu His Glu Val Ala Arg Arg His Pro Tyr Phe Tyr Ala Pro Glu Leu
                165                 170                 175

Leu Tyr Tyr Ala Glu Gln Tyr Asn Glu Ile Leu Thr Gln Cys Cys Ala
            180                 185                 190

Glu Ala Asp Lys Glu Ser Cys Leu Thr Pro Lys Leu Asp Gly Val Lys
        195                 200                 205

Glu Lys Ala Leu Val Ser Ser Val Arg Gln Arg Met Lys Cys Ser Ser
210                 215                 220

Met Gln Lys Phe Gly Glu Arg Ala Phe Lys Ala Trp Ala Val Ala Arg
225                 230                 235                 240

Leu Ser Gln Thr Phe Pro Asn Ala Asp Phe Ala Glu Ile Thr Lys Leu
                245                 250                 255

Ala Thr Asp Leu Thr Lys Val Asn Lys Glu Cys Cys His Gly Asp Leu
            260                 265                 270

Leu Glu Cys Ala Asp Asp Arg Ala Glu Leu Ala Lys Tyr Met Cys Glu
        275                 280                 285

Asn Gln Ala Thr Ile Ser Ser Lys Leu Gln Thr Cys Cys Asp Lys Pro
290                 295                 300

Leu Leu Lys Lys Ala His Cys Leu Ser Glu Val Glu His Asp Thr Met
305                 310                 315                 320

Pro Ala Asp Leu Pro Ala Ile Ala Ala Asp Phe Val Glu Asp Gln Glu
                325                 330                 335

Val Cys Lys Asn Tyr Ala Glu Ala Lys Asp Val Phe Leu Gly Thr Phe
            340                 345                 350

Leu Tyr Glu Tyr Ser Arg Arg His Pro Asp Tyr Ser Val Ser Leu Leu
        355                 360                 365

Leu Arg Leu Ala Lys Lys Tyr Glu Ala Thr Leu Glu Lys Cys Cys Ala
370                 375                 380

Glu Ala Asn Pro Pro Ala Cys Tyr Gly Thr Val Leu Ala Glu Phe Gln
385                 390                 395                 400

Pro Leu Val Glu Glu Pro Lys Asn Leu Val Lys Thr Asn Cys Asp Leu
                405                 410                 415

Tyr Glu Lys Leu Gly Glu Tyr Gly Phe Gln Asn Ala Ile Leu Val Arg
            420                 425                 430

Tyr Thr Gln Lys Ala Pro Gln Val Ser Thr Pro Thr Leu Val Glu Ala
        435                 440                 445

Ala Arg Asn Leu Gly Arg Val Gly Thr Lys Cys Cys Thr Leu Pro Glu
450                 455                 460

Asp Gln Arg Leu Pro Cys Val Glu Asp Tyr Leu Ser Ala Ile Leu Asn
465                 470                 475                 480

Arg Val Cys Leu Leu His Glu Lys Thr Pro Val Ser Glu His Val Thr
                485                 490                 495

Lys Cys Cys Ser Gly Ser Leu Val Glu Arg Arg Pro Cys Phe Ser Ala
            500                 505                 510

Leu Thr Val Asp Glu Thr Tyr Val Pro Lys Glu Phe Lys Ala Glu Thr
        515                 520                 525
```

Phe Thr Phe His Ser Asp Ile Cys Thr Leu Pro Glu Lys Glu Lys Gln
                530                 535                 540

Ile Lys Lys Gln Thr Ala Leu Ala Glu Leu Val Lys His Lys Pro Lys
545                 550                 555                 560

Ala Thr Ala Glu Gln Leu Lys Thr Val Met Asp Asp Phe Ala Gln Phe
                565                 570                 575

Leu Asp Thr Cys Cys Lys Ala Ala Asp Lys Asp Thr Cys Phe Ser Thr
                580                 585                 590

Glu Gly Pro Asn Leu Val Thr Arg Cys Lys Asp Ala Leu Ala Gly Gly
                595                 600                 605

Gly Gly Ser Gly Gly Gly Ser Gly Gly Gly Ser Ala Ser Ala
                610                 615                 620

Glu Val Gln Leu Val Glu Ser Gly Gly Gly Leu Val Gln Pro Gly Gly
625                 630                 635                 640

Ser Leu Arg Leu Ser Cys Ala Ala Ser Gly Ser Asn Pro Tyr Tyr Tyr
                645                 650                 655

Gly Gly Thr His Trp Val Arg Gln Ala Pro Gly Glu Glu Leu Glu Trp
                660                 665                 670

Val Ala Ser Ile Gly Ser Tyr Pro Gly Tyr Thr Asp Tyr Ala Asp Ser
                675                 680                 685

Val Lys Gly Arg Phe Thr Ile Ser Ala Asp Thr Ser Lys Asn Thr Ala
690                 695                 700

Tyr Leu Gln Met Asn Ser Leu Arg Ala Glu Asp Thr Ala Val Tyr Tyr
705                 710                 715                 720

Cys Ala Arg His Tyr Tyr Trp Tyr Asp Ala Thr Asp Tyr Trp Gly Gln
                725                 730                 735

Gly Thr Leu Val Thr Val Ser Ser Gly Gly Gly Gly Ser His His His
                740                 745                 750

His His His
        755

<210> SEQ ID NO 104
<211> LENGTH: 880
<212> TYPE: PRT
<213> ORGANISM: Artificial Sequence
<220> FEATURE:
<223> OTHER INFORMATION: Synthetic: LS-mouse SA-(Gly4Ser)3-scFv (VL-VH)
      CK129-ds1 (VL100Q>C / VH44G>C)-(Gly4Ser)-His6

<400> SEQUENCE: 104

Met Asp Met Arg Val Pro Ala Gln Leu Leu Gly Leu Leu Leu Leu Trp
1               5                   10                  15

Leu Pro Gly Ala Arg Cys Glu Ala His Lys Ser Glu Ile Ala His Arg
                20                  25                  30

Tyr Asn Asp Leu Gly Glu Gln His Phe Lys Gly Leu Val Leu Ile Ala
                35                  40                  45

Phe Ser Gln Tyr Leu Gln Lys Cys Ser Tyr Asp Glu His Ala Lys Leu
                50                  55                  60

Val Gln Glu Val Thr Asp Phe Ala Lys Thr Cys Val Ala Asp Glu Ser
65                  70                  75                  80

Ala Ala Asn Cys Asp Lys Ser Leu His Thr Leu Phe Gly Asp Lys Leu
                85                  90                  95

Cys Ala Ile Pro Asn Leu Arg Glu Asn Tyr Gly Glu Leu Ala Asp Cys
                100                 105                 110

Cys Thr Lys Gln Glu Pro Glu Arg Asn Glu Cys Phe Leu Gln His Lys
                115                 120                 125

-continued

Asp Asp Asn Pro Ser Leu Pro Pro Phe Glu Arg Pro Glu Ala Glu Ala
130                 135                 140

Met Cys Thr Ser Phe Lys Glu Asn Pro Thr Thr Phe Met Gly His Tyr
145                 150                 155                 160

Leu His Glu Val Ala Arg Arg His Pro Tyr Phe Tyr Ala Pro Glu Leu
                165                 170                 175

Leu Tyr Tyr Ala Glu Gln Tyr Asn Glu Ile Leu Thr Gln Cys Cys Ala
                180                 185                 190

Glu Ala Asp Lys Glu Ser Cys Leu Thr Pro Lys Leu Asp Gly Val Lys
                195                 200                 205

Glu Lys Ala Leu Val Ser Ser Val Arg Gln Arg Met Lys Cys Ser Ser
210                 215                 220

Met Gln Lys Phe Gly Glu Arg Ala Phe Lys Ala Trp Ala Val Ala Arg
225                 230                 235                 240

Leu Ser Gln Thr Phe Pro Asn Ala Asp Phe Ala Glu Ile Thr Lys Leu
                245                 250                 255

Ala Thr Asp Leu Thr Lys Val Asn Lys Glu Cys Cys His Gly Asp Leu
                260                 265                 270

Leu Glu Cys Ala Asp Asp Arg Ala Glu Leu Ala Lys Tyr Met Cys Glu
                275                 280                 285

Asn Gln Ala Thr Ile Ser Ser Lys Leu Gln Thr Cys Cys Asp Lys Pro
290                 295                 300

Leu Leu Lys Lys Ala His Cys Leu Ser Glu Val Glu His Asp Thr Met
305                 310                 315                 320

Pro Ala Asp Leu Pro Ala Ile Ala Ala Asp Phe Val Glu Asp Gln Glu
                325                 330                 335

Val Cys Lys Asn Tyr Ala Glu Ala Lys Asp Val Phe Leu Gly Thr Phe
                340                 345                 350

Leu Tyr Glu Tyr Ser Arg Arg His Pro Asp Tyr Ser Val Ser Leu Leu
                355                 360                 365

Leu Arg Leu Ala Lys Lys Tyr Glu Ala Thr Leu Glu Lys Cys Cys Ala
                370                 375                 380

Glu Ala Asn Pro Pro Ala Cys Tyr Gly Thr Val Leu Ala Glu Phe Gln
385                 390                 395                 400

Pro Leu Val Glu Glu Pro Lys Asn Leu Val Lys Thr Asn Cys Asp Leu
                405                 410                 415

Tyr Glu Lys Leu Gly Glu Tyr Gly Phe Gln Asn Ala Ile Leu Val Arg
                420                 425                 430

Tyr Thr Gln Lys Ala Pro Gln Val Ser Thr Pro Thr Leu Val Glu Ala
                435                 440                 445

Ala Arg Asn Leu Gly Arg Val Gly Thr Lys Cys Cys Thr Leu Pro Glu
450                 455                 460

Asp Gln Arg Leu Pro Cys Val Glu Asp Tyr Leu Ser Ala Ile Leu Asn
465                 470                 475                 480

Arg Val Cys Leu Leu His Glu Lys Thr Pro Val Ser Glu His Val Thr
                485                 490                 495

Lys Cys Cys Ser Gly Ser Leu Val Glu Arg Arg Pro Cys Phe Ser Ala
                500                 505                 510

Leu Thr Val Asp Glu Thr Tyr Val Pro Lys Glu Phe Lys Ala Glu Thr
                515                 520                 525

Phe Thr Phe His Ser Asp Ile Cys Thr Leu Pro Glu Lys Glu Lys Gln
530                 535                 540

Ile Lys Lys Gln Thr Ala Leu Ala Glu Leu Val His Lys Pro Lys
545                 550                 555                 560

Ala Thr Ala Glu Gln Leu Lys Thr Val Met Asp Asp Phe Ala Gln Phe
            565                 570                 575

Leu Asp Thr Cys Cys Lys Ala Ala Asp Lys Asp Thr Cys Phe Ser Thr
                580                 585                 590

Glu Gly Pro Asn Leu Val Thr Arg Cys Lys Asp Ala Leu Ala Gly Gly
            595                 600                 605

Gly Gly Ser Gly Gly Gly Ser Gly Gly Gly Ser Ala Ser Asp
610                 615                 620

Ile Gln Met Thr Gln Ser Pro Ser Leu Ser Ala Ser Val Gly Asp
625                 630                 635                 640

Arg Val Thr Ile Thr Cys Arg Ala Ser Gln Tyr Gly Gly Tyr Val Ala
                645                 650                 655

Trp Tyr Gln Gln Lys Pro Gly Lys Ala Pro Lys Leu Leu Ile Tyr Gly
            660                 665                 670

Ala Ser Leu Leu Tyr Ser Gly Val Pro Ser Arg Phe Ser Gly Gly Arg
            675                 680                 685

Ser Gly Thr Asp Phe Thr Leu Thr Ile Ser Ser Leu Gln Pro Glu Asp
            690                 695                 700

Phe Ala Thr Tyr Tyr Cys Gln Arg Gly His Ala Leu Ile Thr Phe Gly
705                 710                 715                 720

Cys Gly Thr Lys Val Glu Ile Glu Gly Thr Thr Ala Ala Ser Gly Ser
                725                 730                 735

Ser Gly Gly Ser Ser Gly Ala Glu Val Gln Leu Val Glu Ser Gly
            740                 745                 750

Gly Gly Leu Val Gln Pro Gly Gly Ser Leu Arg Leu Ser Cys Ala Ala
            755                 760                 765

Ser Gly Phe Asn Ile Ser Ser Tyr Gly Ser Met His Trp Val Arg Gln
            770                 775                 780

Ala Pro Gly Lys Cys Leu Glu Trp Val Ala Ser Ile Tyr Pro Tyr Ser
785                 790                 795                 800

Ser Ser Thr Tyr Tyr Ala Asp Ser Val Lys Gly Arg Phe Thr Ile Ser
                805                 810                 815

Ala Asp Thr Ser Lys Asn Thr Ala Tyr Leu Gln Met Asn Ser Leu Arg
            820                 825                 830

Ala Glu Asp Thr Ala Val Tyr Tyr Cys Ala Arg Gly Tyr Gly Pro Trp
            835                 840                 845

Tyr Ala Tyr Ser Tyr Phe Ala Leu Asp Tyr Trp Gly Gln Gly Thr Leu
850                 855                 860

Val Thr Val Ser Ser Gly Gly Gly Gly Ser His His His His His
865                 870                 875                 880

<210> SEQ ID NO 105
<211> LENGTH: 880
<212> TYPE: PRT
<213> ORGANISM: Artificial Sequence
<220> FEATURE:
<223> OTHER INFORMATION: Synthetic: LS-mouse SA-(Gly4Ser)3-scFv (VL-VH)
      CK129-ds2 (VL43A>C / VH105Q>C)-(Gly4Ser)-His6

<400> SEQUENCE: 105

Met Asp Met Arg Val Pro Ala Gln Leu Leu Gly Leu Leu Leu Leu Trp
1               5                   10                  15

Leu Pro Gly Ala Arg Cys Glu Ala His Lys Ser Glu Ile Ala His Arg
            20                  25                  30

```
Tyr Asn Asp Leu Gly Glu Gln His Phe Lys Gly Leu Val Leu Ile Ala
        35                  40                  45

Phe Ser Gln Tyr Leu Gln Lys Cys Ser Tyr Asp Glu His Ala Lys Leu
    50                  55                  60

Val Gln Glu Val Thr Asp Phe Ala Lys Thr Cys Val Ala Asp Glu Ser
65              70                  75                  80

Ala Ala Asn Cys Asp Lys Ser Leu His Thr Leu Phe Gly Asp Lys Leu
                85                  90                  95

Cys Ala Ile Pro Asn Leu Arg Glu Asn Tyr Gly Glu Leu Ala Asp Cys
            100                 105                 110

Cys Thr Lys Gln Glu Pro Glu Arg Asn Glu Cys Phe Leu Gln His Lys
            115                 120                 125

Asp Asp Asn Pro Ser Leu Pro Pro Phe Glu Arg Pro Glu Ala Glu Ala
130                 135                 140

Met Cys Thr Ser Phe Lys Glu Asn Pro Thr Thr Phe Met Gly His Tyr
145                 150                 155                 160

Leu His Glu Val Ala Arg Arg His Pro Tyr Phe Tyr Ala Pro Glu Leu
                165                 170                 175

Leu Tyr Tyr Ala Glu Gln Tyr Asn Glu Ile Leu Thr Gln Cys Cys Ala
            180                 185                 190

Glu Ala Asp Lys Glu Ser Cys Leu Thr Pro Lys Leu Asp Gly Val Lys
            195                 200                 205

Glu Lys Ala Leu Val Ser Ser Val Arg Gln Arg Met Lys Cys Ser Ser
            210                 215                 220

Met Gln Lys Phe Gly Glu Arg Ala Phe Lys Ala Trp Ala Val Ala Arg
225                 230                 235                 240

Leu Ser Gln Thr Phe Pro Asn Ala Asp Phe Ala Glu Ile Thr Lys Leu
                245                 250                 255

Ala Thr Asp Leu Thr Lys Val Asn Lys Glu Cys Cys His Gly Asp Leu
            260                 265                 270

Leu Glu Cys Ala Asp Asp Arg Ala Glu Leu Ala Lys Tyr Met Cys Glu
        275                 280                 285

Asn Gln Ala Thr Ile Ser Ser Lys Leu Gln Thr Cys Cys Asp Lys Pro
290                 295                 300

Leu Leu Lys Lys Ala His Cys Leu Ser Glu Val Glu His Asp Thr Met
305                 310                 315                 320

Pro Ala Asp Leu Pro Ala Ile Ala Ala Asp Phe Val Glu Asp Gln Glu
            325                 330                 335

Val Cys Lys Asn Tyr Ala Glu Ala Lys Asp Val Phe Leu Gly Thr Phe
                340                 345                 350

Leu Tyr Glu Tyr Ser Arg Arg His Pro Asp Tyr Ser Val Ser Leu Leu
        355                 360                 365

Leu Arg Leu Ala Lys Lys Tyr Glu Ala Thr Leu Glu Lys Cys Cys Ala
        370                 375                 380

Glu Ala Asn Pro Pro Ala Cys Tyr Gly Thr Val Leu Ala Glu Phe Gln
385                 390                 395                 400

Pro Leu Val Glu Glu Pro Lys Asn Leu Val Lys Thr Asn Cys Asp Leu
                405                 410                 415

Tyr Glu Lys Leu Gly Glu Tyr Gly Phe Gln Asn Ala Ile Leu Val Arg
            420                 425                 430

Tyr Thr Gln Lys Ala Pro Gln Val Ser Thr Pro Thr Leu Val Glu Ala
            435                 440                 445
```

```
Ala Arg Asn Leu Gly Arg Val Gly Thr Lys Cys Cys Thr Leu Pro Glu
    450                 455                 460
Asp Gln Arg Leu Pro Cys Val Glu Asp Tyr Leu Ser Ala Ile Leu Asn
465                 470                 475                 480
Arg Val Cys Leu Leu His Glu Lys Thr Pro Val Ser Glu His Val Thr
                485                 490                 495
Lys Cys Cys Ser Gly Ser Leu Val Glu Arg Arg Pro Cys Phe Ser Ala
            500                 505                 510
Leu Thr Val Asp Glu Thr Tyr Val Pro Lys Glu Phe Lys Ala Glu Thr
                515                 520                 525
Phe Thr Phe His Ser Asp Ile Cys Thr Leu Pro Glu Lys Glu Lys Gln
    530                 535                 540
Ile Lys Lys Gln Thr Ala Leu Ala Glu Leu Val Lys His Lys Pro Lys
545                 550                 555                 560
Ala Thr Ala Glu Gln Leu Lys Thr Val Met Asp Asp Phe Ala Gln Phe
                565                 570                 575
Leu Asp Thr Cys Cys Lys Ala Ala Asp Lys Asp Thr Cys Phe Ser Thr
                580                 585                 590
Glu Gly Pro Asn Leu Val Thr Arg Cys Lys Asp Ala Leu Ala Gly Gly
            595                 600                 605
Gly Gly Ser Gly Gly Gly Ser Gly Gly Gly Ser Ala Ser Asp
            610                 615                 620
Ile Gln Met Thr Gln Ser Pro Ser Leu Ser Ala Ser Val Gly Asp
625                 630                 635                 640
Arg Val Thr Ile Thr Cys Arg Ala Ser Gln Tyr Gly Gly Tyr Val Ala
                645                 650                 655
Trp Tyr Gln Gln Lys Pro Gly Lys Cys Pro Lys Leu Leu Ile Tyr Gly
            660                 665                 670
Ala Ser Leu Leu Tyr Ser Gly Val Pro Ser Arg Phe Ser Gly Gly Arg
                675                 680                 685
Ser Gly Thr Asp Phe Thr Leu Thr Ile Ser Ser Leu Gln Pro Glu Asp
            690                 695                 700
Phe Ala Thr Tyr Tyr Cys Gln Arg Gly His Ala Leu Ile Thr Phe Gly
705                 710                 715                 720
Gln Gly Thr Lys Val Glu Ile Glu Gly Thr Thr Ala Ala Ser Gly Ser
                725                 730                 735
Ser Gly Gly Ser Ser Gly Ala Glu Val Gln Leu Val Glu Ser Gly
            740                 745                 750
Gly Gly Leu Val Gln Pro Gly Gly Ser Leu Arg Leu Ser Cys Ala Ala
                755                 760                 765
Ser Gly Phe Asn Ile Ser Ser Tyr Gly Ser Met His Trp Val Arg Gln
            770                 775                 780
Ala Pro Gly Lys Gly Leu Glu Trp Val Ala Ser Ile Tyr Pro Tyr Ser
785                 790                 795                 800
Ser Ser Thr Tyr Tyr Ala Asp Ser Val Lys Gly Arg Phe Thr Ile Ser
                805                 810                 815
Ala Asp Thr Ser Lys Asn Thr Ala Tyr Leu Gln Met Asn Ser Leu Arg
            820                 825                 830
Ala Glu Asp Thr Ala Val Tyr Tyr Cys Ala Arg Gly Tyr Gly Pro Trp
                835                 840                 845
Tyr Ala Tyr Ser Tyr Phe Ala Leu Asp Tyr Trp Gly Cys Gly Thr Leu
850                 855                 860
Val Thr Val Ser Ser Gly Gly Gly Gly Ser His His His His His His
```

```
865                 870                 875                 880
```

<210> SEQ ID NO 106
<211> LENGTH: 875
<212> TYPE: PRT
<213> ORGANISM: Artificial Sequence
<220> FEATURE:
<223> OTHER INFORMATION: Synthetic: LS-mouse SA-(Gly4Ser)3-scFv (VH-VL)
      sm3E-ds (VH44R>C / VL100G>C)-(Gly4Ser)-His6

<400> SEQUENCE: 106

```
Met Asp Met Arg Val Pro Ala Gln Leu Leu Gly Leu Leu Leu Leu Trp
1               5                   10                  15

Leu Pro Gly Ala Arg Cys Glu Ala His Lys Ser Glu Ile Ala His Arg
            20                  25                  30

Tyr Asn Asp Leu Gly Glu Gln His Phe Lys Gly Leu Val Leu Ile Ala
        35                  40                  45

Phe Ser Gln Tyr Leu Gln Lys Cys Ser Tyr Asp Glu His Ala Lys Leu
    50                  55                  60

Val Gln Glu Val Thr Asp Phe Ala Lys Thr Cys Val Ala Asp Glu Ser
65                  70                  75                  80

Ala Ala Asn Cys Asp Lys Ser Leu His Thr Leu Phe Gly Asp Lys Leu
                85                  90                  95

Cys Ala Ile Pro Asn Leu Arg Glu Asn Tyr Gly Glu Leu Ala Asp Cys
            100                 105                 110

Cys Thr Lys Gln Glu Pro Glu Arg Asn Glu Cys Phe Leu Gln His Lys
        115                 120                 125

Asp Asp Asn Pro Ser Leu Pro Pro Phe Glu Arg Pro Glu Ala Glu Ala
    130                 135                 140

Met Cys Thr Ser Phe Lys Glu Asn Pro Thr Thr Phe Met Gly His Tyr
145                 150                 155                 160

Leu His Glu Val Ala Arg Arg His Pro Tyr Phe Tyr Ala Pro Glu Leu
                165                 170                 175

Leu Tyr Tyr Ala Glu Gln Tyr Asn Glu Ile Leu Thr Gln Cys Cys Ala
            180                 185                 190

Glu Ala Asp Lys Glu Ser Cys Leu Thr Pro Lys Leu Asp Gly Val Lys
        195                 200                 205

Glu Lys Ala Leu Val Ser Ser Val Arg Gln Arg Met Lys Cys Ser Ser
    210                 215                 220

Met Gln Lys Phe Gly Glu Arg Ala Phe Lys Ala Trp Ala Val Ala Arg
225                 230                 235                 240

Leu Ser Gln Thr Phe Pro Asn Ala Asp Phe Ala Glu Ile Thr Lys Leu
                245                 250                 255

Ala Thr Asp Leu Thr Lys Val Asn Lys Glu Cys Cys His Gly Asp Leu
            260                 265                 270

Leu Glu Cys Ala Asp Asp Arg Ala Glu Leu Ala Lys Tyr Met Cys Glu
        275                 280                 285

Asn Gln Ala Thr Ile Ser Ser Lys Leu Gln Thr Cys Cys Asp Lys Pro
    290                 295                 300

Leu Leu Lys Lys Ala His Cys Leu Ser Glu Val Glu His Asp Thr Met
305                 310                 315                 320

Pro Ala Asp Leu Pro Ala Ile Ala Ala Asp Phe Val Glu Asp Gln Glu
                325                 330                 335

Val Cys Lys Asn Tyr Ala Glu Ala Lys Asp Val Phe Leu Gly Thr Phe
            340                 345                 350
```

-continued

```
Leu Tyr Glu Tyr Ser Arg Arg His Pro Asp Tyr Ser Val Ser Leu Leu
            355                 360                 365

Leu Arg Leu Ala Lys Lys Tyr Glu Ala Thr Leu Glu Lys Cys Cys Ala
    370                 375                 380

Glu Ala Asn Pro Pro Ala Cys Tyr Gly Thr Val Leu Ala Glu Phe Gln
385                 390                 395                 400

Pro Leu Val Glu Glu Pro Lys Asn Leu Val Lys Thr Asn Cys Asp Leu
                405                 410                 415

Tyr Glu Lys Leu Gly Glu Tyr Gly Phe Gln Asn Ala Ile Leu Val Arg
            420                 425                 430

Tyr Thr Gln Lys Ala Pro Gln Val Ser Thr Pro Thr Leu Val Glu Ala
    435                 440                 445

Ala Arg Asn Leu Gly Arg Val Gly Thr Lys Cys Cys Thr Leu Pro Glu
450                 455                 460

Asp Gln Arg Leu Pro Cys Val Glu Asp Tyr Leu Ser Ala Ile Leu Asn
465                 470                 475                 480

Arg Val Cys Leu Leu His Glu Lys Thr Pro Val Ser Glu His Val Thr
                485                 490                 495

Lys Cys Cys Ser Gly Ser Leu Val Glu Arg Arg Pro Cys Phe Ser Ala
            500                 505                 510

Leu Thr Val Asp Glu Thr Tyr Val Pro Lys Glu Phe Lys Ala Glu Thr
    515                 520                 525

Phe Thr Phe His Ser Asp Ile Cys Thr Leu Pro Glu Lys Glu Lys Gln
530                 535                 540

Ile Lys Lys Gln Thr Ala Leu Ala Glu Leu Val Lys His Lys Pro Lys
545                 550                 555                 560

Ala Thr Ala Glu Gln Leu Lys Thr Val Met Asp Asp Phe Ala Gln Phe
                565                 570                 575

Leu Asp Thr Cys Cys Lys Ala Ala Asp Lys Asp Thr Cys Phe Ser Thr
            580                 585                 590

Glu Gly Pro Asn Leu Val Thr Arg Cys Lys Asp Ala Leu Ala Gly Gly
    595                 600                 605

Gly Gly Ser Gly Gly Gly Gly Ser Gly Gly Gly Gly Ser Ala Ser Gln
610                 615                 620

Val Lys Leu Glu Gln Ser Gly Ala Glu Val Val Lys Pro Gly Ala Ser
625                 630                 635                 640

Val Lys Leu Ser Cys Lys Ala Ser Gly Phe Asn Ile Lys Asp Ser Tyr
                645                 650                 655

Met His Trp Leu Arg Gln Gly Pro Gly Gln Cys Leu Glu Trp Ile Gly
            660                 665                 670

Trp Ile Asp Pro Glu Asn Gly Asp Thr Glu Tyr Ala Pro Lys Phe Gln
    675                 680                 685

Gly Lys Ala Thr Phe Thr Thr Asp Thr Ser Ala Asn Thr Ala Tyr Leu
690                 695                 700

Gly Leu Ser Ser Leu Arg Pro Glu Asp Thr Ala Val Tyr Tyr Cys Asn
705                 710                 715                 720

Glu Gly Thr Pro Thr Gly Pro Tyr Tyr Phe Asp Tyr Trp Gly Gln Gly
                725                 730                 735

Thr Leu Val Thr Val Ser Ser Gly Gly Gly Ser Gly Gly Gly Gly
            740                 745                 750

Ser Gly Gly Gly Gly Ser Glu Asn Val Leu Thr Gln Ser Pro Ser Ser
    755                 760                 765

Met Ser Val Ser Val Gly Asp Arg Val Thr Ile Ala Cys Ser Ala Ser
```

Ser Ser Val Pro Tyr Met His Trp Leu Gln Gln Lys Pro Gly Lys Ser
785                 790                 795                 800

Pro Lys Leu Leu Ile Tyr Leu Thr Ser Asn Leu Ala Ser Gly Val Pro
                805                 810                 815

Ser Arg Phe Ser Gly Ser Gly Ser Gly Thr Asp Tyr Ser Leu Thr Ile
            820                 825                 830

Ser Ser Val Gln Pro Glu Asp Ala Ala Thr Tyr Tyr Cys Gln Gln Arg
        835                 840                 845

Ser Ser Tyr Pro Leu Thr Phe Gly Cys Gly Thr Lys Leu Glu Ile Lys
    850                 855                 860

Gly Gly Gly Gly Ser His His His His His
865                 870                 875

<210> SEQ ID NO 107
<211> LENGTH: 573
<212> TYPE: DNA
<213> ORGANISM: Artificial Sequence
<220> FEATURE:
<223> OTHER INFORMATION: Synthetic: pCHA-LS-hCXCL138-107-G3-c-myc-Aga2

<400> SEQUENCE: 107
atgaaggttt tgattgtctt gttggctatc ttcgctgctt tgccattggc cttagctcaa      60
ccggttattt ctactaccgt cggttccgct gcagaaggct ctttggacaa gagagccacc     120
gagctgagat gccagtgcct gcagaccctg cagggcatcc accccaagaa catccagagc     180
gtgaacgtga agtcccctgg cccccactgc gcccagaccg aagtgatcgc caccctgaag     240
aacggccgga aggcctgcct gaaccccgcc agccccatcg tgaagaaaat catcgagaag     300
atgctgaaca cgacaagag caacggcgga ggcgaacaaa agcttatctc gaagaagac      360 ttgcaggaac tgacaactat atgcgagcaa atcccctcac caactttaga atcgacgccg     420
tactctttgt caacgactac tattttggcc aacgggaagg caatgcaagg agtttttgaa     480
tattacaaat cagtaacgtt tgtcagtaat tgcggttctc acccctcaac aactagcaaa     540
ggcagcccca taaacacaca gtatgttttt taa                                 573

<210> SEQ ID NO 108
<211> LENGTH: 573
<212> TYPE: DNA
<213> ORGANISM: Artificial Sequence
<220> FEATURE:
<223> OTHER INFORMATION: Synthetic: pCHA-LS-hCXCL238-107-G3-c-myc-Aga2

<400> SEQUENCE: 108
atgaaggttt tgattgtctt gttggctatc ttcgctgctt tgccattggc cttagctcaa      60
ccggttattt ctactaccgt cggttccgct gcagaaggct ctttggacaa gagagccaca     120
gagctgagat gccagtgcct ccagacactc cagggcatcc acctgaagaa catccagagc     180
gtgaaagtga agtcccctgg cccccactgc gcccagacag aagtgatcgc caccctgaag     240
aatggccaga aggcctgcct gaaccccgcc agccctatgg tcaagaaaat catcgagaag     300
atgctgaaga acggcaagag caacggcgga ggcgaacaaa agcttatctc gaagaagac      360 ttgcaggaac tgacaactat atgcgagcaa atcccctcac caactttaga atcgacgccg     420
tactctttgt caacgactac tattttggcc aacgggaagg caatgcaagg agtttttgaa     480
tattacaaat cagtaacgtt tgtcagtaat tgcggttctc acccctcaac aactagcaaa     540
ggcagcccca taaacacaca gtatgttttt taa                                 573

<210> SEQ ID NO 109
<211> LENGTH: 573
<212> TYPE: DNA
<213> ORGANISM: Artificial Sequence
<220> FEATURE:
<223> OTHER INFORMATION: Synthetic: pCHA-LS-hCXCL338-107-G3-c-myc-Aga2

<400> SEQUENCE: 109

```
atgaaggttt tgattgtctt gttggctatc ttcgctgctt tgccattggc cttagctcaa      60
ccggttattt ctactaccgt cggttccgct gcagaaggct ctttggacaa gagagtgacc     120
gagctgagat gccagtgcct ccagacactc cagggcatcc acctgaagaa catccagagc     180
gtgaacgtgc ggagccctgg ccctcattgt gcccagacag aagtgatcgc caccctgaag     240
aatggcaaga aggcctgcct gaaccccgcc agccctatgg tgcagaagat catcgagaag     300
atcctgaaca agggcagcac caacggcgga ggcgaacaaa agcttatctc gaagaagac     360
ttgcaggaac tgacaactat atgcgagcaa atcccctcac caactttaga atcgacgccg     420
tactctttgt caacgactac tattttggcc aacgggaagg caatgcaagg agttttgaa     480
tattacaaat cagtaacgtt tgtcagtaat tgcggttctc acccctcaac aactagcaaa     540
ggcagcccca taaacacaca gtatgttttt taa                                  573
```

<210> SEQ ID NO 110
<211> LENGTH: 573
<212> TYPE: DNA
<213> ORGANISM: Artificial Sequence
<220> FEATURE:
<223> OTHER INFORMATION: Synthetic: pCHA-LS-hCXCL432-101-G3-c-myc-Aga2

<400> SEQUENCE: 110

```
atgaaggttt tgattgtctt gttggctatc ttcgctgctt tgccattggc cttagctcaa      60
ccggttattt ctactaccgt cggttccgct gcagaaggct ctttggacaa gagagaggct     120
gaagaggacg gcgatctcca gtgcctgtgc gtgaaaacca ccagccaagt gcggcccaga     180
cacatcacca gcctggaagt gatcaaggcc ggaccccact gtcctaccgc ccagctgatt     240
gccaccctga gaacggccg aagatctgc ctggacctcc aggcccccct gtacaagaag        300
atcatcaaga agctgctgga aagcggcgga ggcgaacaaa agcttatctc gaagaagac      360
ttgcaggaac tgacaactat atgcgagcaa atcccctcac caactttaga atcgacgccg     420
tactctttgt caacgactac tattttggcc aacgggaagg caatgcaagg agttttgaa     480
tattacaaat cagtaacgtt tgtcagtaat tgcggttctc acccctcaac aactagcaaa     540
ggcagcccca taaacacaca gtatgttttt taa                                  573
```

<210> SEQ ID NO 111
<211> LENGTH: 576
<212> TYPE: DNA
<213> ORGANISM: Artificial Sequence
<220> FEATURE:
<223> OTHER INFORMATION: Synthetic: pCHA-LS-hCXCL544-114-G3-c-myc-Aga2

<400> SEQUENCE: 111

```
atgaaggttt tgattgtctt gttggctatc ttcgctgctt tgccattggc cttagctcaa      60
ccggttattt ctactaccgt cggttccgct gcagaaggct ctttggacaa gagactgcgc     120
gagctgagat gcgtgtgcct gcagaccacc cagggcgtgc accccaagat gatcagcaac     180
ctccaggtgt tcgccatcgg ccccagtgc agcaaggtgg aagtggtggc cagcctgaag     240
```

-continued

```
aacggcaaag agatctgcct ggaccccgag gccccattcc tgaagaaagt gatccagaag    300
atcctggacg gcggcaacaa agagaacggc ggaggcgaac aaaagcttat ctccgaagaa    360
gacttgcagg aactgacaac tatatgcgag caaatcccct caccaacttt agaatcgacg    420
ccgtactctt tgtcaacgac tactattttg gccaacggga aggcaatgca aggagttttt    480
gaatattaca aatcagtaac gtttgtcagt aattgcggtt ctcaccccctc aacaactagc   540 aaaggcagcc ccataaacac acagtatgtt ttttaa                              576
```

<210> SEQ ID NO 112
<211> LENGTH: 576
<212> TYPE: DNA
<213> ORGANISM: Artificial Sequence
<220> FEATURE:
<223> OTHER INFORMATION: Synthetic: pCHA-LS-hCXCL644-114-G3-c-myc-Aga2

<400> SEQUENCE: 112

```
atgaaggttt tgattgtctt gttggctatc ttcgctgctt tgccattggc cttagctcaa     60
ccggttattt ctactaccgt cggttccgct gcagaaggct ctttggacaa gagactgacc    120
gagctgcggt gcacctgtct gagagtgacc ctgcgcgtga accccaagac catcggcaag    180
ctccaggtgt ccctgccgg ccctcagtgc agcaaggtgg aagtggtggc cagcctgaaa     240
aacggaaaac aagtgtgcct ggaccccgag gccccattcc tgaagaaagt gatccagaag    300
atcctggaca gcggcaacaa gaagaacggc ggaggcgaac aaaagcttat ctccgaagaa    360
gacttgcagg aactgacaac tatatgcgag caaatcccct caccaacttt agaatcgacg    420
ccgtactctt tgtcaacgac tactattttg gccaacggga aggcaatgca aggagttttt    480
gaatattaca aatcagtaac gtttgtcagt aattgcggtt ctcacccctc aacaactagc    540
aaaggcagcc ccataaacac acagtatgtt ttttaa                              576
```

<210> SEQ ID NO 113
<211> LENGTH: 552
<212> TYPE: DNA
<213> ORGANISM: Artificial Sequence
<220> FEATURE:
<223> OTHER INFORMATION: Synthetic: pCHA-LS-hCXCL759-121-G3-c-myc-Aga2

<400> SEQUENCE: 113

```
atgaaggttt tgattgtctt gttggctatc ttcgctgctt tgccattggc cttagctcaa     60
ccggttattt ctactaccgt cggttccgct gcagaaggct ctttggacaa gagagccgag    120
ctgcggtgca tgtgcatcaa gaccaccagc ggaatccacc caagaatat ccagtccctg     180 gaagtgattg gcaagggcac ccactgcaac caggtggaag tgattgccac actgaaagac    240
ggccggaaga tctgcctgga ccctgacgcc ccagaatca agaaaatcgt gcagaaaaag    300
ctgggcggag gcgaacaaaa gcttatctcc gaagaagact tgcaggaact gacaactata    360
tgcgagcaaa tcccctcacc aactttagaa tcgacgccgt actctttgtc aacgactact    420
attttggcca acgggaaggc aatgcaagga gttttgaat attacaaatc agtaacgttt     480
gtcagtaatt gcggttctca cccctcaaca actagcaaag gcagccccat aaacacacag    540 tatgttttt aa                                                         552
```

<210> SEQ ID NO 114
<211> LENGTH: 576
<212> TYPE: DNA
<213> ORGANISM: Artificial Sequence
<220> FEATURE:
<223> OTHER INFORMATION: Synthetic: pCHA-LS-hCXCL829-99-G3-c-myc-Aga2

<400> SEQUENCE: 114

```
atgaaggttt tgattgtctt gttggctatc ttcgctgctt tgccattggc cttagctcaa      60
ccggttattt ctactaccgt cggttccgct gcagaaggct ctttggacaa gagagccaaa     120
gaactgcggt gccagtgcat caagacctac agcaagccct ccacccccaa gttcatcaaa     180
gaactgagag tgatcgagag cggccctcac tgcgccaaca ccgagatcat cgtgaagctg     240
agcgacggca gagagctgtg cctggacccc aaagaaaact gggtgcagcg ggtggtggaa     300
aagttcctga gcgggccgga acagcggcg ggaggcgaac aaaagcttat ctccgaagaa      360
gacttgcagg aactgacaac tatatgcgag caaatcccct caccaacttt agaatcgacg     420
ccgtactctt tgtcaacgac tactattttg ccaacgggaa aggcaatgca aggagttttt     480
gaatattaca atcagtaac gtttgtcagt aattgcggtt ctcaccccctc aacaactagc     540
aaaggcagcc ccataaacac acagtatgtt tttaa                                576
```

<210> SEQ ID NO 115
<211> LENGTH: 672
<212> TYPE: DNA
<213> ORGANISM: Artificial Sequence
<220> FEATURE:
<223> OTHER INFORMATION: Synthetic: pCHA-LS-hCXCL923-115-G3-c-myc-Aga2

<400> SEQUENCE: 115

```
atgaaggttt tgattgtctt gttggctatc ttcgctgctt tgccattggc cttagctcaa      60
ccggttattt ctactaccgt cggttccgct gcagaaggct ctttggacaa gagaaccccc     120
gtcgtgcgga agggcagatg cagctgtatc agcaccaacc agggcaccat ccatctccag     180
tctctgaagg acctgaagca gttcgccccc agccccagct cgagaagat cgagattatc      240
gccacactga aaaacggggt gcagacctgc ctgaaccccg acagcgccga cgtgaaagaa     300
ctgatcaaga atgggagaa acaggtgtcc cagaagaaga gcagaagaa cggaaagaag      360
caccagaaaa agaaagtgct gaaagtgcgg aagtcccagc ggagccggca agagaaaacc     420
acaggcggag cgaacaaaa gcttatctcc gaagaagact gcaggaact gacaactata      480
tgcgagcaaa tcccctcacc aactttagaa tcgacgccgt actctttgtc aacgactact     540
attttggcca acgggaaggc aatgcaagga gtttttgaat attacaaatc agtaacgttt     600
gtcagtaatt gcggttctca ccccctcaaca actagcaaag gcagccccat aaacacacag     660
tatgtttttt aa                                                          672
```

<210> SEQ ID NO 116
<211> LENGTH: 594
<212> TYPE: DNA
<213> ORGANISM: Artificial Sequence
<220> FEATURE:
<223> OTHER INFORMATION: Synthetic: pCHA-LS-hCXCL1022-98-G3-c-myc-Aga2

<400> SEQUENCE: 116

```
atgaaggttt tgattgtctt gttggctatc ttcgctgctt tgccattggc cttagctcaa      60
ccggttattt ctactaccgt cggttccgct gcagaaggct ctttggacaa gagagtgcct     120
ctgagcagaa ccgtgcggtg cacctgtatc agcatcagca accagccgt gaaccccaga      180
agcctggaaa agctggaaat catccccgcc agccagttct gccccagagt ggaaattatc     240
gccaccatga gaagaaagg cgagaagcgg tgcctgaacc ccgagagcaa ggccatcaag     300
aacctgctga aggccgtgtc caaagagcgg agcaagcgga gcccaggcgg aggcgaacaa     360
```

```
aagcttatct ccgaagaaga cttgcaggaa ctgacaacta tatgcgagca atcccctca    420 ccaactttag aatcgacgcc gtactctttg tcaacgacta ctattttggc caacgggaag    480
gcaatgcaag gagtttttga atattacaaa tcagtaacgt tgtcagtaa ttgcggttct    540 caccccctcaa caactagcaa aggcagcccc ataaacacac agtatgtttt ttaa         594

<210> SEQ ID NO 117
<211> LENGTH: 582
<212> TYPE: DNA
<213> ORGANISM: Artificial Sequence
<220> FEATURE:
<223> OTHER INFORMATION: Synthetic: pCHA-LS-hCXCL1122-94-G3-c-myc-Aga2

<400> SEQUENCE: 117
atgaaggttt tgattgtctt gttggctatc ttcgctgctt tgccattggc cttagctcaa    60
ccggttattt ctactaccgt cggttccgct gcagaaggct ctttggacaa gagattcccc   120
atgttcaagc ggggcagatg cctgtgcatc ggccctggcg tgaaagccgt gaaggtggcc   180
gatatcgaga aggccagcat catgtacccc agcaacaact cgacaagat cgaagtgatc    240 atcaccctga agagaacaa gggccagaga tgcctgaatc ccaagtccaa gcaggcccgg   300
ctgatcatca gaaggtgga acggaagaac ttcggcggag cgaacaaaa gcttatctcc    360 gaagaagact tgcaggaact gacaactata tgcgagcaaa tcccctcacc aactttagaa   420
tcgacgccgt actctttgtc aacgactact attttggcca acgggaaggc aatgcaagga   480 gttttttgaat attacaaatc agtaacgttt gtcagtaatt gcggttctca ccctcaaca    540 actagcaaag gcagcccat aaacacacag tatgttttt aa                        582

<210> SEQ ID NO 118
<211> LENGTH: 570
<212> TYPE: DNA
<213> ORGANISM: Artificial Sequence
<220> FEATURE:
<223> OTHER INFORMATION: Synthetic: pCHA-LS-mCXCL128-96-G3-c-myc-Aga2

<400> SEQUENCE: 118
atgaaggttt tgattgtctt gttggctatc ttcgctgctt tgccattggc cttagctcaa    60
ccggttattt ctactaccgt cggttccgct gcagaaggct ctttggacaa gagagccaac   120
gagctgcggt gccagtgcct gcagaccatg gccggcatcc acctgaagaa catccagagc   180
ctgaaggtgc tgcccagcgg ccctcactgc acccagaccg aagtgatcgc caccctgaag   240
aacggcagag aggcctgcct ggatcccgag gcccccctgg tgcagaaaat cgtgcagaaa   300
atgctgaagg gcgtgcccaa gggcggaggc gaacaaaagc ttatctccga agaagacttg   360
caggaactga caactatatg cgagcaaatc ccctcaccaa ctttagaatc gacgccgtac   420
tctttgtcaa cgactactat tttggccaac gggaaggcaa tgcaaggagt ttttgaatat   480
tacaaatcag taacgtttgt cagtaattgc ggttctcacc cctcaacaac tagcaaaggc   540
agccccataa acacacagta tgttttttaa                                    570

<210> SEQ ID NO 119
<211> LENGTH: 573
<212> TYPE: DNA
<213> ORGANISM: Artificial Sequence
<220> FEATURE:
<223> OTHER INFORMATION: Synthetic: pCHA-LS-mCXCL231-100-G3-c-myc-Aga2

<400> SEQUENCE: 119
atgaaggttt tgattgtctt gttggctatc ttcgctgctt tgccattggc cttagctcaa    60
```

```
ccggttattt ctactaccgt cggttccgct gcagaaggct ctttggacaa gagagccagc    120
gagctgcggt gccagtgcct gaaaaccctg ccccgggtgg acttcaagaa catccagagc    180
ctgagcgtga ccccccctgg ccctcactgt gcccagaccg aagtgatcgc caccctgaag    240
ggcggccaga aagtgtgcct ggaccccgag gccccctgg tgcagaagat catccagaag     300
atcctgaaca agggcaaggc caacggcgga ggcgaacaaa agcttatctc gaagaagac     360 ttgcaggaac tgacaactat atgcgagcaa atcccctcac caactttaga atcgacgccg    420
tactctttgt caacgactac tattttggcc aacgggaagg caatgcaagg agttttgaa     480 tattacaaat cagtaacgtt tgtcagtaat tgcggttctc accctcaac aactagcaaa     540 ggcagcccca taaacacaca gtatgttttt taa                                 573

<210> SEQ ID NO 120
<211> LENGTH: 573
<212> TYPE: DNA
<213> ORGANISM: Artificial Sequence
<220> FEATURE:
<223> OTHER INFORMATION: Synthetic: pCHA-LS-mCXCL331-100-G3-c-myc-Aga2

<400> SEQUENCE: 120
atgaaggttt tgattgtctt gttggctatc ttcgctgctt tgccattggc cttagctcaa     60
ccggttattt ctactaccgt cggttccgct gcagaaggct ctttggacaa gagagcctct    120
gagctgagat gccagtgcct gaacaccctg ccccgggtgg acttcgagac aatccagagc    180
ctgaccgtga ccccccctgg ccctcactgt gcccagacag aagtgatcgc caccctgaag    240
gacggccagg aagtgtgcct gaatccccag ggccccagac tccagatcat catcaagaag    300
atcctgaagt ccggcaagag cagcggcgga ggcgaacaaa agcttatctc gaagaagac     360 ttgcaggaac tgacaactat atgcgagcaa atcccctcac caactttaga atcgacgccg    420
tactctttgt caacgactac tattttggcc aacgggaagg caatgcaagg agttttgaa     480 tattacaaat cagtaacgtt tgtcagtaat tgcggttctc accctcaac aactagcaaa     540 ggcagcccca taaacacaca gtatgttttt taa                                 573

<210> SEQ ID NO 121
<211> LENGTH: 591
<212> TYPE: DNA
<213> ORGANISM: Artificial Sequence
<220> FEATURE:
<223> OTHER INFORMATION: Synthetic: pCHA-LS-mCXCL430-105-G3-c-myc-Aga2

<400> SEQUENCE: 121
atgaaggttt tgattgtctt gttggctatc ttcgctgctt tgccattggc cttagctcaa     60
ccggttattt ctactaccgt cggttccgct gcagaaggct ctttggacaa gagagtgaca    120
tctgccggcc ctgaggaaag cgacggcgat ctgtcttgcg tgtgcgtgaa aaccatcagc    180
agcggcatcc acctgaagca catcaccagc ctggaagtga tcaaggccgg caggcactgt    240
gccgtgcctc agctgattgc caccctgaag aacggccgga agatctgcct ggacagacag    300 gccccctgt acaagaaagt gattaagaag atcctggaaa gcggcggagg cgaacaaaag    360
cttatctccg aagaagactt gcaggaactg acaactatat gcgagcaaat cccctcacca    420
actttagaat cgacgccgta ctctttgtca acgactacta ttttggccaa cgggaaggca    480
atgcaaggag ttttgaata ttacaaatca gtaacgtttg tcagtaattg cggttctcac     540
ccctcaacaa ctagcaaagg cagccccata aacacacagt atgttttta a              591
```

<210> SEQ ID NO 122
<211> LENGTH: 576
<212> TYPE: DNA
<213> ORGANISM: Artificial Sequence
<220> FEATURE:
<223> OTHER INFORMATION: Synthetic: pCHA-LS-mCXCL548-118-G3-c-myc-Aga2

<400> SEQUENCE: 122

```
atgaaggttt tgattgtctt gttggctatc ttcgctgctt tgccattggc cttagctcaa      60
ccggttattt ctactaccgt cggttccgct gcagaaggct ctttggacaa gagagccacc     120
gagctgagat gcgtgtgcct gaccgtgacc cccaagatca accccaagct gatcgccaac     180
ctggaagtga tccctgccgg ccctcagtgc ccaccgtgg aagtgattgc caagctgaag      240
aaccagaaag aagtgtgcct ggaccccgag gcccccgtga tcaagaagat catccagaag     300
atcctgggca gcgacaagaa gaaagccggc ggaggcgaac aaaagcttat ctccgaagaa     360
gacttgcagg aactgacaac tatatgcgag caaatcccct caccaacttt agaatcgacg     420
ccgtactctt tgtcaacgac tactattttg gccaacggga aggcaatgca aggagttttt     480
gaatattaca atcagtaac gtttgtcagt aattgcggtt ctcacccctc aacaactagc     540
aaaggcagcc ccataaacac acagtatgtt ttttaa                                576
```

<210> SEQ ID NO 123
<211> LENGTH: 561
<212> TYPE: DNA
<213> ORGANISM: Artificial Sequence
<220> FEATURE:
<223> OTHER INFORMATION: Synthetic: pCHA-LS-mCXCL748-113-G3-c-myc-Aga2

<400> SEQUENCE: 123

```
atgaaggttt tgattgtctt gttggctatc ttcgctgctt tgccattggc cttagctcaa      60
ccggttattt ctactaccgt cggttccgct gcagaaggct ctttggacaa gagaatcgag     120
ctgcggtgcc ggtgcaccaa caccatcagc ggcatccctt caacagcat cagcctcgtg      180
aacgtgtaca gacccggcgt gcactgcgcc gacgtggaag tgattgctac actgaagaat     240
gggcagaaaa cctgcctgga ccccaacgcc cctggcgtga gcggatcgt gatgaagatt     300
ctggaaggct acggcggagg cgaacaaaag cttatctccg aagaagactt gcaggaactg     360
acaactatat gcgagcaaat cccctcacca actttagaat cgacgccgta ctctttgtca     420
acgactacta ttttggccaa cgggaaggca atgcaaggag ttttgaata ttacaaatca      480
gtaacgtttg tcagtaattg cggttctcac ccctcaacaa ctagcaaagg cagccccata     540
aacacacagt atgtttttta a                                                561
```

<210> SEQ ID NO 124
<211> LENGTH: 678
<212> TYPE: DNA
<213> ORGANISM: Artificial Sequence
<220> FEATURE:
<223> OTHER INFORMATION: Synthetic: pCHA-LS-mCXCL922-126-G3-c-myc-Aga2

<400> SEQUENCE: 124

```
atgaaggttt tgattgtctt gttggctatc ttcgctgctt tgccattggc cttagctcaa      60
ccggttattt ctactaccgt cggttccgct gcagaaggct ctttggacaa gagaaccctc     120
gtgatccgga cgcccggtg cagctgtatc agcaccagca gcaggcacca tccactacaag      180
agcctgaagg atctgaagca gttcgccccc agccccaact gcaacaagac cgagattatc     240
gccacactga aaaacgggga ccagacctgt ctggaccccg acagcgccaa cgtgaagaaa     300
```

```
ctgatgaagg aatgggagaa gaagatcagc cagaagaaga agcagaagcg gggcaagaaa      360
caccagaaaa acatgaagaa ccggaagccc aagaccccccc agagccggcg gagatccaga     420
aagaccacag gcggaggcga acaaaagctt atctccgaag aagacttgca ggaactgaca      480
actatatgcg agcaaatccc ctcaccaact ttagaatcga cgccgtactc tttgtcaacg      540
actactattt tggccaacgg gaaggcaatg caaggagttt ttgaatatta caaatcagta      600
acgtttgtca gtaattgcgg ttctcacccc tcaacaacta gcaaaggcag ccccataaac      660
acacagtatg tttttttaa                                                   678
```

\<210\> SEQ ID NO 125
\<211\> LENGTH: 594
\<212\> TYPE: DNA
\<213\> ORGANISM: Artificial Sequence
\<220\> FEATURE:
\<223\> OTHER INFORMATION: Synthetic: pCHA-LS-mCXCL1022-98-G3-c-myc-Aga2

\<400\> SEQUENCE: 125

```
atgaaggttt tgattgtctt gttggctatc ttcgctgctt tgccattggc cttagctcaa      60
ccggttattt ctactaccgt cggttccgct gcagaaggc ctttggacaa gagaatccca      120
ctggccagaa ccgtgcggtg caactgcatc cacatcgacg atggcccgt gcggatgaga      180 gccatcggca agctggaaat catccccgcc agcctgagct gccccagagt ggaaattatc      240
gccaccatga agaagaacga cgagcagcgg tgcctgaacc ccgagagcaa gaccatcaag      300
aacctgatga aggcctttag ccagaagcgg agcaagaggg ccccaggcgg aggcgaacaa      360
aagcttatct ccgaagaaga cttgcaggaa ctgacaacta tatgcgagca aatcccctca      420 ccaacttttag aatcgacgcc gtactctttg tcaacgacta ctattttggc caacgggaag      480
gcaatgcaag gagtttttga atattacaaa tcagtaacgt ttgtcagtaa ttgcggttct      540
cacccctcaa caactagcaa aggcagcccc ataaacacac agtatgttt ttaa             594
```

\<210\> SEQ ID NO 126
\<211\> LENGTH: 600
\<212\> TYPE: DNA
\<213\> ORGANISM: Artificial Sequence
\<220\> FEATURE:
\<223\> OTHER INFORMATION: Synthetic: pCHA-LS-mCXCL1122-100-G3-c-myc-Aga2

\<400\> SEQUENCE: 126

```
atgaaggttt tgattgtctt gttggctatc ttcgctgctt tgccattggc cttagctcaa      60
ccggttattt ctactaccgt cggttccgct gcagaaaggc ctttggacaa gagattcctg     120
atgttcaagc agggccggtg cctgtgcatc ggccctggaa tgaaggccgt gaagatggcc     180
gagatcgaga aggccagcgt gatctacccc agcaacggct cgacaaggt ggaagtgatc      240 gtgaccatga aggcccacaa gcggcagaga tgcctggacc ccagatccaa gcaggcccgg     300
ctgatcatgc aggctatcga agaagaaat tcctgcggc ggcagaacat gggcggaggc      360
gaacaaaagc ttatctccga agaagacttg caggaactga caactatatg cgagcaaatc      420
ccctcaccaa ctttagaatc gacgccgtac tctttgtcaa cgactactat tttggccaac     480
gggaaggcaa tgcaaggagt ttttgaatat tacaaatcag taacgtttgt cagtaattgc      540
ggttctcacc cctcaacaac tagcaaaggc agccccataa acacacagta tgtttttaa      600
```

\<210\> SEQ ID NO 127
\<211\> LENGTH: 190
\<212\> TYPE: PRT

<213> ORGANISM: Artificial Sequence
<220> FEATURE:
<223> OTHER INFORMATION: Synthetic: LS-hCXCL138-107-G3-c-myc-Aga2

<400> SEQUENCE: 127

```
Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
            20                  25                  30

Gly Ser Leu Asp Lys Arg Ala Thr Glu Leu Arg Cys Gln Cys Leu Gln
        35                  40                  45

Thr Leu Gln Gly Ile His Pro Lys Asn Ile Gln Ser Val Asn Val Lys
    50                  55                  60

Ser Pro Gly Pro His Cys Ala Gln Thr Glu Val Ile Ala Thr Leu Lys
65                  70                  75                  80

Asn Gly Arg Lys Ala Cys Leu Asn Pro Ala Ser Pro Ile Val Lys Lys
                85                  90                  95

Ile Ile Glu Lys Met Leu Asn Ser Asp Lys Ser Asn Gly Gly Gly Glu
            100                 105                 110

Gln Lys Leu Ile Ser Glu Glu Asp Leu Gln Glu Leu Thr Thr Ile Cys
        115                 120                 125

Glu Gln Ile Pro Ser Pro Thr Leu Glu Ser Thr Pro Tyr Ser Leu Ser
    130                 135                 140

Thr Thr Thr Ile Leu Ala Asn Gly Lys Ala Met Gln Gly Val Phe Glu
145                 150                 155                 160

Tyr Tyr Lys Ser Val Thr Phe Val Ser Asn Cys Gly Ser His Pro Ser
                165                 170                 175

Thr Thr Ser Lys Gly Ser Pro Ile Asn Thr Gln Tyr Val Phe
            180                 185                 190
```

<210> SEQ ID NO 128
<211> LENGTH: 190
<212> TYPE: PRT
<213> ORGANISM: Artificial Sequence
<220> FEATURE:
<223> OTHER INFORMATION: Synthetic: LS-hCXCL238-107-G3-c-myc-Aga2

<400> SEQUENCE: 128

```
Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
            20                  25                  30

Gly Ser Leu Asp Lys Arg Ala Thr Glu Leu Arg Cys Gln Cys Leu Gln
        35                  40                  45

Thr Leu Gln Gly Ile His Leu Lys Asn Ile Gln Ser Val Lys Val Lys
    50                  55                  60

Ser Pro Gly Pro His Cys Ala Gln Thr Glu Val Ile Ala Thr Leu Lys
65                  70                  75                  80

Asn Gly Gln Lys Ala Cys Leu Asn Pro Ala Ser Pro Met Val Lys Lys
                85                  90                  95

Ile Ile Glu Lys Met Leu Lys Asn Gly Lys Ser Asn Gly Gly Gly Glu
            100                 105                 110

Gln Lys Leu Ile Ser Glu Glu Asp Leu Gln Glu Leu Thr Thr Ile Cys
        115                 120                 125

Glu Gln Ile Pro Ser Pro Thr Leu Glu Ser Thr Pro Tyr Ser Leu Ser
    130                 135                 140
```

```
Thr Thr Thr Ile Leu Ala Asn Gly Lys Ala Met Gln Gly Val Phe Glu
145                 150                 155                 160

Tyr Tyr Lys Ser Val Thr Phe Val Ser Asn Cys Gly Ser His Pro Ser
                165                 170                 175

Thr Thr Ser Lys Gly Ser Pro Ile Asn Thr Gln Tyr Val Phe
            180                 185                 190

<210> SEQ ID NO 129
<211> LENGTH: 190
<212> TYPE: PRT
<213> ORGANISM: Artificial Sequence
<220> FEATURE:
<223> OTHER INFORMATION: Synthetic: LS-hCXCL338-107-G3-c-myc-Aga2

<400> SEQUENCE: 129

Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
            20                  25                  30

Gly Ser Leu Asp Lys Arg Val Thr Glu Leu Arg Cys Gln Cys Leu Gln
        35                  40                  45

Thr Leu Gln Gly Ile His Leu Lys Asn Ile Gln Ser Val Asn Val Arg
    50                  55                  60

Ser Pro Gly Pro His Cys Ala Gln Thr Glu Val Ile Ala Thr Leu Lys
65                  70                  75                  80

Asn Gly Lys Lys Ala Cys Leu Asn Pro Ala Ser Pro Met Val Gln Lys
                85                  90                  95

Ile Ile Glu Lys Ile Leu Asn Lys Gly Ser Thr Asn Gly Gly Gly Glu
            100                 105                 110

Gln Lys Leu Ile Ser Glu Glu Asp Leu Gln Glu Leu Thr Thr Ile Cys
        115                 120                 125

Glu Gln Ile Pro Ser Pro Thr Leu Glu Ser Thr Pro Tyr Ser Leu Ser
    130                 135                 140

Thr Thr Thr Ile Leu Ala Asn Gly Lys Ala Met Gln Gly Val Phe Glu
145                 150                 155                 160

Tyr Tyr Lys Ser Val Thr Phe Val Ser Asn Cys Gly Ser His Pro Ser
                165                 170                 175

Thr Thr Ser Lys Gly Ser Pro Ile Asn Thr Gln Tyr Val Phe
            180                 185                 190

<210> SEQ ID NO 130
<211> LENGTH: 190
<212> TYPE: PRT
<213> ORGANISM: Artificial Sequence
<220> FEATURE:
<223> OTHER INFORMATION: Synthetic: LS-hCXCL432-101-G3-c-myc-Aga2

<400> SEQUENCE: 130

Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
            20                  25                  30

Gly Ser Leu Asp Lys Arg Glu Ala Glu Asp Gly Asp Leu Gln Cys
        35                  40                  45

Leu Cys Val Lys Thr Thr Ser Gln Val Arg Pro Arg His Ile Thr Ser
    50                  55                  60

Leu Glu Val Ile Lys Ala Gly Pro His Cys Pro Thr Ala Gln Leu Ile
65                  70                  75                  80
```

```
Ala Thr Leu Lys Asn Gly Arg Lys Ile Cys Leu Asp Leu Gln Ala Pro
            85                  90                  95

Leu Tyr Lys Lys Ile Ile Lys Lys Leu Leu Glu Ser Gly Gly Gly Glu
            100                 105                 110

Gln Lys Leu Ile Ser Glu Glu Asp Leu Gln Glu Leu Thr Thr Ile Cys
            115                 120                 125

Glu Gln Ile Pro Ser Pro Thr Leu Glu Ser Thr Pro Tyr Ser Leu Ser
130                 135                 140

Thr Thr Thr Ile Leu Ala Asn Gly Lys Ala Met Gln Gly Val Phe Glu
145                 150                 155                 160

Tyr Tyr Lys Ser Val Thr Phe Val Ser Asn Cys Gly Ser His Pro Ser
            165                 170                 175

Thr Thr Ser Lys Gly Ser Pro Ile Asn Thr Gln Tyr Val Phe
            180                 185                 190

<210> SEQ ID NO 131
<211> LENGTH: 191
<212> TYPE: PRT
<213> ORGANISM: Artificial Sequence
<220> FEATURE:
<223> OTHER INFORMATION: Synthetic: LS-hCXCL544-114-G3-c-myc-Aga2

<400> SEQUENCE: 131

Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
            20                  25                  30

Gly Ser Leu Asp Lys Arg Leu Arg Glu Leu Arg Cys Val Cys Leu Gln
            35                  40                  45

Thr Thr Gln Gly Val His Pro Lys Met Ile Ser Asn Leu Gln Val Phe
50                  55                  60

Ala Ile Gly Pro Gln Cys Ser Lys Val Glu Val Val Ala Ser Leu Lys
65                  70                  75                  80

Asn Gly Lys Glu Ile Cys Leu Asp Pro Glu Ala Pro Phe Leu Lys Lys
            85                  90                  95

Val Ile Gln Lys Ile Leu Asp Gly Gly Asn Lys Glu Asn Gly Gly Gly
            100                 105                 110

Glu Gln Lys Leu Ile Ser Glu Glu Asp Leu Gln Glu Leu Thr Thr Ile
            115                 120                 125

Cys Glu Gln Ile Pro Ser Pro Thr Leu Glu Ser Thr Pro Tyr Ser Leu
130                 135                 140

Ser Thr Thr Thr Ile Leu Ala Asn Gly Lys Ala Met Gln Gly Val Phe
145                 150                 155                 160

Glu Tyr Tyr Lys Ser Val Thr Phe Val Ser Asn Cys Gly Ser His Pro
            165                 170                 175

Ser Thr Thr Ser Lys Gly Ser Pro Ile Asn Thr Gln Tyr Val Phe
            180                 185                 190

<210> SEQ ID NO 132
<211> LENGTH: 191
<212> TYPE: PRT
<213> ORGANISM: Artificial Sequence
<220> FEATURE:
<223> OTHER INFORMATION: Synthetic: LS-hCXCL644-114-G3-c-myc-Aga2

<400> SEQUENCE: 132

Met Lys Val Leu Ile Val Leu Leu Ala Ile Phe Ala Ala Leu Pro Leu
```

```
            1               5                  10                 15
Ala Leu Ala Gln Pro Val Ile Ser Thr Thr Val Gly Ser Ala Ala Glu
            20                 25                 30

Gly Ser Leu Asp Lys Arg Leu Thr Glu Leu Arg Cys Thr Cys Leu Arg
            35                 40                 45

Val Thr Leu Arg Val Asn Pro Lys Thr Ile Gly Lys Leu Gln Val Phe
 50                 55                 60

Pro Ala Gly Pro Gln Cys Ser Lys Val Glu Val Val Ala Ser Leu Lys
 65                 70                 75                 80

Asn Gly Lys Gln Val Cys Leu Asp Pro Glu Ala Pro Phe Leu Lys Lys
                    85                 90                 95

Val Ile Gln Lys Ile Leu Asp Ser Gly Asn Lys Lys Asn Gly Gly Gly
                    100                105                110

Glu Gln Lys Leu Ile Ser Glu Glu Asp Leu Gln Glu Leu Thr Thr Ile
                    115                120                125

Cys Glu Gln Ile Pro Ser Pro Thr Leu Glu Ser Thr Pro Tyr Ser Leu
130                 135                140

Ser Thr Thr Thr Ile Leu Ala Asn Gly Lys Ala Met Gln Gly Val Phe
145                 150                155                160

Glu Tyr Tyr Lys Ser Val Thr Phe Val Ser Asn Cys Gly Ser His Pro
                    165                170                175

Ser Thr Ser Lys Gly Ser Pro Ile Asn Thr Gln Tyr Val Phe
                    180                185                190

<210> SEQ ID NO 133
<211> LENGTH: 183
<212> TYPE: PRT
<213> ORGANISM: Artificial Sequence
<220> FEATURE:
<223> OTHER INFORMATION: Synthetic: LS-hCXCL759-121-G3-c-myc-Aga2

<400> SEQUENCE: 133

Met Lys Val Leu Ile Val Leu Leu Ala Ile Phe Ala Ala Leu Pro Leu
 1               5                  10                 15

Ala Leu Ala Gln Pro Val Ile Ser Thr Thr Val Gly Ser Ala Ala Glu
                    20                 25                 30

Gly Ser Leu Asp Lys Arg Ala Glu Leu Arg Cys Met Cys Ile Lys Thr
                    35                 40                 45

Thr Ser Gly Ile His Pro Lys Asn Ile Gln Ser Leu Glu Val Ile Gly
 50                 55                 60

Lys Gly Thr His Cys Asn Gln Val Glu Val Ile Ala Thr Leu Lys Asp
 65                 70                 75                 80

Gly Arg Lys Ile Cys Leu Asp Pro Asp Ala Pro Arg Ile Lys Lys Ile
                    85                 90                 95

Val Gln Lys Lys Leu Gly Gly Gly Glu Gln Lys Leu Ile Ser Glu Glu
                    100                105                110

Asp Leu Gln Glu Leu Thr Thr Ile Cys Glu Gln Ile Pro Ser Pro Thr
                    115                120                125

Leu Glu Ser Thr Pro Tyr Ser Leu Ser Thr Thr Thr Ile Leu Ala Asn
                    130                135                140

Gly Lys Ala Met Gln Gly Val Phe Glu Tyr Tyr Lys Ser Val Thr Phe
145                 150                155                160

Val Ser Asn Cys Gly Ser His Pro Ser Thr Thr Ser Lys Gly Ser Pro
                    165                170                175

Ile Asn Thr Gln Tyr Val Phe
```

-continued

180

<210> SEQ ID NO 134
<211> LENGTH: 191
<212> TYPE: PRT
<213> ORGANISM: Artificial Sequence
<220> FEATURE:
<223> OTHER INFORMATION: Synthetic: LS-hCXCL829-99-G3-c-myc-Aga2

<400> SEQUENCE: 134

Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
            20                  25                  30

Gly Ser Leu Asp Lys Arg Ala Lys Glu Leu Arg Cys Gln Cys Ile Lys
        35                  40                  45

Thr Tyr Ser Lys Pro Phe His Pro Lys Phe Ile Lys Glu Leu Arg Val
    50                  55                  60

Ile Glu Ser Gly Pro His Cys Ala Asn Thr Glu Ile Ile Val Lys Leu
65                  70                  75                  80

Ser Asp Gly Arg Glu Leu Cys Leu Asp Pro Lys Glu Asn Trp Val Gln
                85                  90                  95

Arg Val Val Glu Lys Phe Leu Lys Arg Ala Glu Asn Ser Gly Gly Gly
            100                 105                 110

Glu Gln Lys Leu Ile Ser Glu Asp Leu Gln Glu Leu Thr Thr Ile
        115                 120                 125

Cys Glu Gln Ile Pro Ser Pro Thr Leu Glu Ser Thr Pro Tyr Ser Leu
130                 135                 140

Ser Thr Thr Thr Ile Leu Ala Asn Gly Lys Ala Met Gln Gly Val Phe
145                 150                 155                 160

Glu Tyr Tyr Lys Ser Val Thr Phe Val Ser Asn Cys Gly Ser His Pro
                165                 170                 175

Ser Thr Thr Ser Lys Gly Ser Pro Ile Asn Thr Gln Tyr Val Phe
            180                 185                 190

<210> SEQ ID NO 135
<211> LENGTH: 223
<212> TYPE: PRT
<213> ORGANISM: Artificial Sequence
<220> FEATURE:
<223> OTHER INFORMATION: Synthetic: LS-hCXCL923-115-G3-c-myc-Aga2

<400> SEQUENCE: 135

Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
            20                  25                  30

Gly Ser Leu Asp Lys Arg Thr Pro Val Val Arg Lys Gly Arg Cys Ser
        35                  40                  45

Cys Ile Ser Thr Asn Gln Gly Thr Ile His Leu Gln Ser Leu Lys Asp
    50                  55                  60

Leu Lys Gln Phe Ala Pro Ser Pro Ser Cys Glu Lys Ile Glu Ile Ile
65                  70                  75                  80

Ala Thr Leu Lys Asn Gly Val Gln Thr Cys Leu Asn Pro Asp Ser Ala
                85                  90                  95

Asp Val Lys Glu Leu Ile Lys Lys Trp Glu Lys Gln Val Ser Gln Lys
            100                 105                 110

Lys Lys Gln Lys Asn Gly Lys Lys His Gln Lys Lys Val Leu Lys
            115                 120                 125

Val Arg Lys Ser Gln Arg Ser Arg Gln Lys Lys Thr Thr Gly Gly Gly
130                 135                 140

Glu Gln Lys Leu Ile Ser Glu Glu Asp Leu Gln Glu Leu Thr Thr Ile
145                 150                 155                 160

Cys Glu Gln Ile Pro Ser Pro Thr Leu Glu Ser Thr Pro Tyr Ser Leu
                165                 170                 175

Ser Thr Thr Thr Ile Leu Ala Asn Gly Lys Ala Met Gln Gly Val Phe
            180                 185                 190

Glu Tyr Tyr Lys Ser Val Thr Phe Val Ser Asn Cys Gly Ser His Pro
        195                 200                 205

Ser Thr Thr Ser Lys Gly Ser Pro Ile Asn Thr Gln Tyr Val Phe
    210                 215                 220

<210> SEQ ID NO 136
<211> LENGTH: 197
<212> TYPE: PRT
<213> ORGANISM: Artificial Sequence
<220> FEATURE:
<223> OTHER INFORMATION: Synthetic: LS-hCXCL1022-98-G3-c-myc-Aga2

<400> SEQUENCE: 136

Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
            20                  25                  30

Gly Ser Leu Asp Lys Arg Val Pro Leu Ser Arg Thr Val Arg Cys Thr
        35                  40                  45

Cys Ile Ser Ile Ser Asn Gln Pro Val Asn Pro Arg Ser Leu Glu Lys
    50                  55                  60

Leu Glu Ile Ile Pro Ala Ser Gln Phe Cys Pro Arg Val Glu Ile Ile
65                  70                  75                  80

Ala Thr Met Lys Lys Lys Gly Glu Lys Arg Cys Leu Asn Pro Glu Ser
                85                  90                  95

Lys Ala Ile Lys Asn Leu Leu Lys Ala Val Ser Lys Glu Arg Ser Lys
            100                 105                 110

Arg Ser Pro Gly Gly Gly Glu Gln Lys Leu Ile Ser Glu Glu Asp Leu
        115                 120                 125

Gln Glu Leu Thr Thr Ile Cys Glu Gln Ile Pro Ser Pro Thr Leu Glu
    130                 135                 140

Ser Thr Pro Tyr Ser Leu Ser Thr Thr Thr Ile Leu Ala Asn Gly Lys
145                 150                 155                 160

Ala Met Gln Gly Val Phe Glu Tyr Tyr Lys Ser Val Thr Phe Val Ser
                165                 170                 175

Asn Cys Gly Ser His Pro Ser Thr Thr Ser Lys Gly Ser Pro Ile Asn
            180                 185                 190

Thr Gln Tyr Val Phe
        195

<210> SEQ ID NO 137
<211> LENGTH: 193
<212> TYPE: PRT
<213> ORGANISM: Artificial Sequence
<220> FEATURE:
<223> OTHER INFORMATION: Synthetic: LS-hCXCL1122-94-G3-c-myc-Aga2

<400> SEQUENCE: 137

Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
            20                  25                  30

Gly Ser Leu Asp Lys Arg Phe Pro Met Phe Lys Arg Gly Arg Cys Leu
        35                  40                  45

Cys Ile Gly Pro Gly Val Lys Ala Val Lys Val Ala Asp Ile Glu Lys
50                  55                  60

Ala Ser Ile Met Tyr Pro Ser Asn Asn Cys Asp Lys Ile Glu Val Ile
65                  70                  75                  80

Ile Thr Leu Lys Glu Asn Lys Gly Gln Arg Cys Leu Asn Pro Lys Ser
            85                  90                  95

Lys Gln Ala Arg Leu Ile Ile Lys Lys Val Glu Arg Lys Asn Phe Gly
        100                 105                 110

Gly Gly Glu Gln Lys Leu Ile Ser Glu Glu Asp Leu Gln Glu Leu Thr
    115                 120                 125

Thr Ile Cys Glu Gln Ile Pro Ser Pro Thr Leu Glu Ser Thr Pro Tyr
130                 135                 140

Ser Leu Ser Thr Thr Ile Leu Ala Asn Gly Lys Ala Met Gln Gly
145                 150                 155                 160

Val Phe Glu Tyr Tyr Lys Ser Val Thr Phe Val Ser Asn Cys Gly Ser
            165                 170                 175

His Pro Ser Thr Thr Ser Lys Gly Ser Pro Ile Asn Thr Gln Tyr Val
        180                 185                 190

Phe

<210> SEQ ID NO 138
<211> LENGTH: 189
<212> TYPE: PRT
<213> ORGANISM: Artificial Sequence
<220> FEATURE:
<223> OTHER INFORMATION: Synthetic: LS-mCXCL128-96-G3-c-myc-Aga2

<400> SEQUENCE: 138

Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
            20                  25                  30

Gly Ser Leu Asp Lys Arg Ala Asn Glu Leu Arg Cys Gln Cys Leu Gln
        35                  40                  45

Thr Met Ala Gly Ile His Leu Lys Asn Ile Gln Ser Leu Lys Val Leu
50                  55                  60

Pro Ser Gly Pro His Cys Thr Gln Thr Glu Val Ile Ala Thr Leu Lys
65                  70                  75                  80

Asn Gly Arg Glu Ala Cys Leu Asp Pro Glu Ala Pro Leu Val Gln Lys
            85                  90                  95

Ile Val Gln Lys Met Leu Lys Gly Val Pro Lys Gly Gly Gly Glu Gln
        100                 105                 110

Lys Leu Ile Ser Glu Glu Asp Leu Gln Glu Leu Thr Thr Ile Cys Glu
    115                 120                 125

Gln Ile Pro Ser Pro Thr Leu Glu Ser Thr Pro Tyr Ser Leu Ser Thr
    130                 135                 140

Thr Thr Ile Leu Ala Asn Gly Lys Ala Met Gln Gly Val Phe Glu Tyr
145                 150                 155                 160

Tyr Lys Ser Val Thr Phe Val Ser Asn Cys Gly Ser His Pro Ser Thr
                165                 170                 175

Thr Ser Lys Gly Ser Pro Ile Asn Thr Gln Tyr Val Phe
        180                 185

<210> SEQ ID NO 139
<211> LENGTH: 190
<212> TYPE: PRT
<213> ORGANISM: Artificial Sequence
<220> FEATURE:
<223> OTHER INFORMATION: Synthetic: LS-mCXCL231-100-G3-c-myc-Aga2

<400> SEQUENCE: 139

Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
            20                  25                  30

Gly Ser Leu Asp Lys Arg Ala Ser Glu Leu Arg Cys Gln Cys Leu Lys
        35                  40                  45

Thr Leu Pro Arg Val Asp Phe Lys Asn Ile Gln Ser Leu Ser Val Thr
    50                  55                  60

Pro Pro Gly Pro His Cys Ala Gln Thr Glu Val Ile Ala Thr Leu Lys
65                  70                  75                  80

Gly Gly Gln Lys Val Cys Leu Asp Pro Glu Ala Pro Leu Val Gln Lys
                85                  90                  95

Ile Ile Gln Lys Ile Leu Asn Lys Gly Lys Ala Asn Gly Gly Gly Glu
            100                 105                 110

Gln Lys Leu Ile Ser Glu Glu Asp Leu Gln Glu Leu Thr Thr Ile Cys
        115                 120                 125

Glu Gln Ile Pro Ser Pro Thr Leu Glu Ser Thr Pro Tyr Ser Leu Ser
    130                 135                 140

Thr Thr Thr Ile Leu Ala Asn Gly Lys Ala Met Gln Gly Val Phe Glu
145                 150                 155                 160

Tyr Tyr Lys Ser Val Thr Phe Val Ser Asn Cys Gly Ser His Pro Ser
                165                 170                 175

Thr Thr Ser Lys Gly Ser Pro Ile Asn Thr Gln Tyr Val Phe
            180                 185                 190

<210> SEQ ID NO 140
<211> LENGTH: 190
<212> TYPE: PRT
<213> ORGANISM: Artificial Sequence
<220> FEATURE:
<223> OTHER INFORMATION: Synthetic: LS-mCXCL331-100-G3-c-myc-Aga2

<400> SEQUENCE: 140

Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
            20                  25                  30

Gly Ser Leu Asp Lys Arg Ala Ser Glu Leu Arg Cys Gln Cys Leu Asn
        35                  40                  45

Thr Leu Pro Arg Val Asp Phe Glu Thr Ile Gln Ser Leu Thr Val Thr
    50                  55                  60

Pro Pro Gly Pro His Cys Thr Gln Thr Glu Val Ile Ala Thr Leu Lys
65                  70                  75                  80

Asp Gly Gln Glu Val Cys Leu Asn Pro Gln Gly Pro Arg Leu Gln Ile
                85                  90                  95

```
Ile Ile Lys Lys Ile Leu Lys Ser Gly Lys Ser Ser Gly Gly Gly Glu
            100                 105                 110

Gln Lys Leu Ile Ser Glu Glu Asp Leu Gln Glu Leu Thr Thr Ile Cys
            115                 120                 125

Glu Gln Ile Pro Ser Pro Thr Leu Glu Ser Thr Pro Tyr Ser Leu Ser
            130                 135                 140

Thr Thr Thr Ile Leu Ala Asn Gly Lys Ala Met Gln Gly Val Phe Glu
145                 150                 155                 160

Tyr Tyr Lys Ser Val Thr Phe Val Ser Asn Cys Gly Ser His Pro Ser
                165                 170                 175

Thr Thr Ser Lys Gly Ser Pro Ile Asn Thr Gln Tyr Val Phe
            180                 185                 190

<210> SEQ ID NO 141
<211> LENGTH: 196
<212> TYPE: PRT
<213> ORGANISM: Artificial Sequence
<220> FEATURE:
<223> OTHER INFORMATION: Synthetic: LS-mCXCL430-105-G3-c-myc-Aga2

<400> SEQUENCE: 141

Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
            20                  25                  30

Gly Ser Leu Asp Lys Arg Val Thr Ser Ala Gly Pro Glu Glu Ser Asp
        35                  40                  45

Gly Asp Leu Ser Cys Val Cys Val Lys Thr Ile Ser Ser Gly Ile His
50                  55                  60

Leu Lys His Ile Thr Ser Leu Glu Val Ile Lys Ala Gly Arg His Cys
65                  70                  75                  80

Ala Val Pro Gln Leu Ile Ala Thr Leu Lys Asn Gly Arg Lys Ile Cys
                85                  90                  95

Leu Asp Arg Gln Ala Pro Leu Tyr Lys Lys Val Ile Lys Lys Ile Leu
            100                 105                 110

Glu Ser Gly Gly Gly Glu Gln Lys Leu Ile Ser Glu Glu Asp Leu Gln
        115                 120                 125

Glu Leu Thr Thr Ile Cys Glu Gln Ile Pro Ser Pro Thr Leu Glu Ser
    130                 135                 140

Thr Pro Tyr Ser Leu Ser Thr Thr Thr Ile Leu Ala Asn Gly Lys Ala
145                 150                 155                 160

Met Gln Gly Val Phe Glu Tyr Tyr Lys Ser Val Thr Phe Val Ser Asn
                165                 170                 175

Cys Gly Ser His Pro Ser Thr Thr Ser Lys Gly Ser Pro Ile Asn Thr
            180                 185                 190

Gln Tyr Val Phe
        195

<210> SEQ ID NO 142
<211> LENGTH: 191
<212> TYPE: PRT
<213> ORGANISM: Artificial Sequence
<220> FEATURE:
<223> OTHER INFORMATION: Synthetic: LS-mCXCL548-118-G3-c-myc-Aga2

<400> SEQUENCE: 142

Met Lys Val Leu Ile Val Leu Leu Ala Ile Phe Ala Ala Leu Pro Leu
```

```
                1               5                  10                 15
            Ala Leu Ala Gln Pro Val Ile Ser Thr Thr Val Gly Ser Ala Ala Glu
                            20                  25                 30

Gly Ser Leu Asp Lys Arg Ala Thr Glu Leu Arg Cys Val Cys Leu Thr
                            35                  40                 45

Val Thr Pro Lys Ile Asn Pro Lys Leu Ile Ala Asn Leu Glu Val Ile
             50                  55                  60

Pro Ala Gly Pro Gln Cys Pro Thr Val Glu Val Ile Ala Lys Leu Lys
             65                  70                  75                 80

Asn Gln Lys Glu Val Cys Leu Asp Pro Glu Ala Pro Val Ile Lys Lys
                            85                  90                 95

Ile Ile Gln Lys Ile Leu Gly Ser Asp Lys Lys Ala Gly Gly
                            100                 105                110

Glu Gln Lys Leu Ile Ser Glu Glu Asp Leu Gln Glu Leu Thr Thr Ile
                            115                 120                125

Cys Glu Gln Ile Pro Ser Pro Thr Leu Glu Ser Thr Pro Tyr Ser Leu
             130                 135                 140

Ser Thr Thr Thr Ile Leu Ala Asn Gly Lys Ala Met Gln Gly Val Phe
             145                 150                 155                160

Glu Tyr Tyr Lys Ser Val Thr Phe Val Ser Asn Cys Gly Ser His Pro
                            165                 170                175

Ser Thr Thr Ser Lys Gly Ser Pro Ile Asn Thr Gln Tyr Val Phe
                            180                 185                 190

<210> SEQ ID NO 143
            <211> LENGTH: 186
            <212> TYPE: PRT
            <213> ORGANISM: Artificial Sequence
            <220> FEATURE:
            <223> OTHER INFORMATION: Synthetic: LS-mCXCL748-113-G3-c-myc-Aga2

<400> SEQUENCE: 143

Met Lys Val Leu Ile Val Leu Leu Ala Ile Phe Ala Ala Leu Pro Leu
             1               5                  10                 15

Ala Leu Ala Gln Pro Val Ile Ser Thr Thr Val Gly Ser Ala Ala Glu
                            20                  25                 30

Gly Ser Leu Asp Lys Arg Ile Glu Leu Arg Cys Arg Cys Thr Asn Thr
                            35                  40                 45

Ile Ser Gly Ile Pro Phe Asn Ser Ile Ser Leu Val Asn Val Tyr Arg
             50                  55                  60

Pro Gly Val His Cys Ala Asp Val Glu Val Ile Ala Thr Leu Lys Asn
             65                  70                  75                 80

Gly Gln Lys Thr Cys Leu Asp Pro Asn Ala Pro Gly Val Lys Arg Ile
                            85                  90                 95

Val Met Lys Ile Leu Glu Gly Tyr Gly Gly Glu Gln Lys Leu Ile
                            100                 105                110

Ser Glu Glu Asp Leu Gln Glu Leu Thr Thr Ile Cys Glu Gln Ile Pro
                            115                 120                125

Ser Pro Thr Leu Glu Ser Thr Pro Tyr Ser Leu Ser Thr Thr Thr Ile
             130                 135                 140

Leu Ala Asn Gly Lys Ala Met Gln Gly Val Phe Glu Tyr Tyr Lys Ser
             145                 150                 155                160

Val Thr Phe Val Ser Asn Cys Gly Ser His Pro Ser Thr Thr Ser Lys
                            165                 170                175

Gly Ser Pro Ile Asn Thr Gln Tyr Val Phe
```

-continued

```
                180                 185

<210> SEQ ID NO 144
<211> LENGTH: 225
<212> TYPE: PRT
<213> ORGANISM: Artificial Sequence
<220> FEATURE:
<223> OTHER INFORMATION: Synthetic: LS-mCXCL922-126-G3-c-myc-Aga2

<400> SEQUENCE: 144

Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
                20                  25                  30

Gly Ser Leu Asp Lys Arg Thr Leu Val Ile Arg Asn Ala Arg Cys Ser
            35                  40                  45

Cys Ile Ser Thr Ser Arg Gly Thr Ile His Tyr Lys Ser Leu Lys Asp
        50                  55                  60

Leu Lys Gln Phe Ala Pro Ser Pro Asn Cys Asn Lys Thr Glu Ile Ile
65                  70                  75                  80

Ala Thr Leu Lys Asn Gly Asp Gln Thr Cys Leu Asp Pro Asp Ser Ala
                85                  90                  95

Asn Val Lys Lys Leu Met Lys Glu Trp Glu Lys Lys Ile Ser Gln Lys
            100                 105                 110

Lys Lys Gln Lys Arg Gly Lys Lys His Gln Lys Asn Met Lys Asn Arg
        115                 120                 125

Lys Pro Lys Thr Pro Gln Ser Arg Arg Arg Ser Arg Lys Thr Thr Gly
    130                 135                 140

Gly Gly Glu Gln Lys Leu Ile Ser Glu Glu Asp Leu Gln Glu Leu Thr
145                 150                 155                 160

Thr Ile Cys Glu Gln Ile Pro Ser Pro Thr Leu Glu Ser Thr Pro Tyr
                165                 170                 175

Ser Leu Ser Thr Thr Thr Ile Leu Ala Asn Gly Lys Ala Met Gln Gly
            180                 185                 190

Val Phe Glu Tyr Tyr Lys Ser Val Thr Phe Val Ser Asn Cys Gly Ser
        195                 200                 205

His Pro Ser Thr Thr Ser Lys Gly Ser Pro Ile Asn Thr Gln Tyr Val
    210                 215                 220

Phe
225

<210> SEQ ID NO 145
<211> LENGTH: 197
<212> TYPE: PRT
<213> ORGANISM: Artificial Sequence
<220> FEATURE:
<223> OTHER INFORMATION: Synthetic: LS-mCXCL1022-98-G3-c-myc-Aga2

<400> SEQUENCE: 145

Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
                20                  25                  30

Gly Ser Leu Asp Lys Arg Ile Pro Leu Ala Arg Thr Val Arg Cys Asn
            35                  40                  45

Cys Ile His Ile Asp Asp Gly Pro Val Arg Met Arg Ala Ile Gly Lys
        50                  55                  60
```

Leu Glu Ile Ile Pro Ala Ser Leu Ser Cys Pro Arg Val Glu Ile Ile
65                  70                  75                  80

Ala Thr Met Lys Lys Asn Asp Glu Gln Arg Cys Leu Asn Pro Glu Ser
                85                  90                  95

Lys Thr Ile Lys Asn Leu Met Lys Ala Phe Ser Gln Lys Arg Ser Lys
            100                 105                 110

Arg Ala Pro Gly Gly Gly Glu Gln Lys Leu Ile Ser Glu Glu Asp Leu
        115                 120                 125

Gln Glu Leu Thr Thr Ile Cys Glu Gln Ile Pro Ser Pro Thr Leu Glu
    130                 135                 140

Ser Thr Pro Tyr Ser Leu Ser Thr Thr Thr Ile Leu Ala Asn Gly Lys
145                 150                 155                 160

Ala Met Gln Gly Val Phe Glu Tyr Tyr Lys Ser Val Thr Phe Val Ser
                165                 170                 175

Asn Cys Gly Ser His Pro Ser Thr Thr Ser Lys Gly Ser Pro Ile Asn
            180                 185                 190

Thr Gln Tyr Val Phe
        195

<210> SEQ ID NO 146
<211> LENGTH: 199
<212> TYPE: PRT
<213> ORGANISM: Artificial Sequence
<220> FEATURE:
<223> OTHER INFORMATION: Synthetic: LS-mCXCL1122-100-G3-c-myc-Aga2

<400> SEQUENCE: 146

Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
            20                  25                  30

Gly Ser Leu Asp Lys Arg Phe Leu Met Phe Lys Gln Gly Arg Cys Leu
        35                  40                  45

Cys Ile Gly Pro Gly Met Lys Ala Val Lys Met Ala Glu Ile Glu Lys
    50                  55                  60

Ala Ser Val Ile Tyr Pro Ser Asn Gly Cys Asp Lys Val Glu Val Ile
65                  70                  75                  80

Val Thr Met Lys Ala His Lys Arg Gln Arg Cys Leu Asp Pro Arg Ser
                85                  90                  95

Lys Gln Ala Arg Leu Ile Met Gln Ala Ile Glu Lys Lys Asn Phe Leu
            100                 105                 110

Arg Arg Gln Asn Met Gly Gly Gly Glu Gln Lys Leu Ile Ser Glu Glu
        115                 120                 125

Asp Leu Gln Glu Leu Thr Thr Ile Cys Glu Gln Ile Pro Ser Pro Thr
    130                 135                 140

Leu Glu Ser Thr Pro Tyr Ser Leu Ser Thr Thr Thr Ile Leu Ala Asn
145                 150                 155                 160

Gly Lys Ala Met Gln Gly Val Phe Glu Tyr Tyr Lys Ser Val Thr Phe
                165                 170                 175

Val Ser Asn Cys Gly Ser His Pro Ser Thr Thr Ser Lys Gly Ser Pro
            180                 185                 190

Ile Asn Thr Gln Tyr Val Phe
        195

<210> SEQ ID NO 147
<211> LENGTH: 573

<212> TYPE: DNA
<213> ORGANISM: Artificial Sequence
<220> FEATURE:
<223> OTHER INFORMATION: Synthetic: pCHA-LS-hCXCL1-G3-c-myc-Aga2

<400> SEQUENCE: 147

```
atgaaggttt tgattgtctt gttggctatc ttcgctgctt tgccattggc cttagctcaa      60
ccggttattt ctactaccgt cggttccgct gcagaaggct ctttggacaa gagagccacc     120
gagctgagat gccagtgcct gcagaccctg cagggcatcc accccaagaa catccagagc     180
gtgaacgtga agtcccctgg ccccactgc gcccagaccg aagtgatcgc caccctgaag      240
aacggccgga aggcctgcct gaaccccgcc agccccatcg tgaagaaaat catcgagaag     300
atgctgaaca gcgacaagag caacggcgga ggcgaacaaa agcttatctc cgaagaagac     360
ttgcaggaac tgacaactat atgcgagcaa atcccctcac caactttaga atcgacgccg     420
tactctttgt caacgactac tattttggcc aacgggaagg caatgcaagg agttttttgaa     480
tattacaaat cagtaacgtt tgtcagtaat tgcggttctc accctcaac aactagcaaa      540
ggcagcccca taaacacaca gtatgttttt taa                                  573
```

<210> SEQ ID NO 148
<211> LENGTH: 190
<212> TYPE: PRT
<213> ORGANISM: Artificial Sequence
<220> FEATURE:
<223> OTHER INFORMATION: Synthetic: LS-hCXCL1-G3-c-myc-Aga2

<400> SEQUENCE: 148

```
Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
            20                  25                  30

Gly Ser Leu Asp Lys Arg Ala Thr Glu Leu Arg Cys Gln Cys Leu Gln
        35                  40                  45

Thr Leu Gln Gly Ile His Pro Lys Asn Ile Gln Ser Val Asn Val Lys
    50                  55                  60

Ser Pro Gly Pro His Cys Ala Gln Thr Glu Val Ile Ala Thr Leu Lys
65                  70                  75                  80

Asn Gly Arg Lys Ala Cys Leu Asn Pro Ala Ser Pro Ile Val Lys Lys
                85                  90                  95

Ile Ile Glu Lys Met Leu Asn Ser Asp Lys Ser Asn Gly Gly Gly Glu
            100                 105                 110

Gln Lys Leu Ile Ser Glu Glu Asp Leu Gln Glu Leu Thr Thr Ile Cys
        115                 120                 125

Glu Gln Ile Pro Ser Pro Thr Leu Glu Ser Thr Pro Tyr Ser Leu Ser
    130                 135                 140

Thr Thr Thr Ile Leu Ala Asn Gly Lys Ala Met Gln Gly Val Phe Glu
145                 150                 155                 160

Tyr Tyr Lys Ser Val Thr Phe Val Ser Asn Cys Gly Ser His Pro Ser
                165                 170                 175

Thr Thr Ser Lys Gly Ser Pro Ile Asn Thr Gln Tyr Val Phe
            180                 185                 190
```

<210> SEQ ID NO 149
<211> LENGTH: 2556
<212> TYPE: DNA
<213> ORGANISM: Artificial Sequence
<220> FEATURE:

<223> OTHER INFORMATION: Synthetic: mouse SA-(Gly4Ser)3-scFv (VL-VH) CK138

<400> SEQUENCE: 149

| | | | | | |
|---|---|---|---|---|---|
| atggaagcac | acaagagtga | gatcgcccat | cggtataatg | atttgggaga | acaacatttc | 60 |
| aaaggcctag | tcctgattgc | cttttcccag | tatctccaga | aatgctcata | cgatgagcat | 120 |
| gccaaattag | tgcaggaagt | aacagacttt | gcaaagacgt | gtgttgccga | tgagtctgcc | 180 |
| gccaactgtg | acaaatccct | tcacactctt | tttggagata | agttgtgtgc | cattccaaac | 240 |
| ctccgtgaaa | actatggtga | actggctgac | tgctgtacaa | acaagagcc | cgaaagaaac | 300 |
| gaatgtttcc | tgcaacacaa | agatgacaac | cccagcctac | caccatttga | aaggccagag | 360 |
| gctgaggcca | tgtgcacctc | ctttaaggaa | aacccaacca | cctttatggg | acactatttg | 420 |
| catgaagttg | ccagaagaca | tccttatttc | tatgccccag | aacttcttta | ctatgctgag | 480 |
| cagtacaatg | agattctgac | ccagtgttgt | gcagaggctg | acaaggaaag | ctgcctgacc | 540 |
| ccgaagcttg | atggtgtgaa | ggagaaagca | ttggtctcat | ctgtccgtca | gagaatgaag | 600 |
| tgctccagta | tgcagaagtt | tggagagaga | gcttttaaag | catgggcagt | agctcgtctg | 660 |
| agccagacat | tccccaatgc | tgactttgca | gaaatcacca | aattggcaac | agacctgacc | 720 |
| aaagtcaaca | aggagtgctg | ccatggtgac | ctgctggaat | gcgcagatga | cagggcggaa | 780 |
| cttgccaagt | acatgtgtga | aaaccaggcg | actatctcca | gcaaactgca | gacttgctgc | 840 |
| gataaaccac | tgttgaagaa | agcccactgt | cttagtgagg | tggagcatga | caccatgcct | 900 |
| gctgatctgc | ctgccattgc | tgctgatttt | gttgaggacc | aggaagtgtg | caagaactat | 960 |
| gctgaggcca | aggatgtctt | cctgggcacg | ttcttgtatg | aatattcaag | aagacaccct | 1020 |
| gattactctg | tatccctgtt | gctgagactt | gctaagaaat | atgaagccac | tctggaaaag | 1080 |
| tgctgcgctg | aagccaatcc | tcccgcatgc | tacggcacag | tgcttgctga | atttcagcct | 1140 |
| cttgtagaag | agcctaagaa | cttggtcaaa | accaactgtg | atcttacga | aagcttgga | 1200 |
| gaatatggat | tccaaaatgc | cattctagtt | cgctacaccc | agaaagcacc | tcaggtgtca | 1260 |
| accccaactc | tcgtggaggc | tgcaagaaac | ctaggaagag | tgggcaccaa | gtgttgtaca | 1320 |
| cttcctgaag | atcagagact | gccttgtgtg | gaagactatc | tgtctgcaat | cctgaaccgt | 1380 |
| gtgtgtctgc | tgcatgagaa | gaccccagtg | agtgagcatg | ttaccaagtg | ctgtagtgga | 1440 |
| tccctggtgg | aaaggcggcc | atgcttctct | gctctgacag | ttgatgaaac | atatgtcccc | 1500 |
| aaagagttta | agctgagac | cttcaccttc | cactctgata | tctgcacact | tccagagaag | 1560 |
| gagaagcaga | ttaagaaaca | aacggctctt | gctgagctgg | tgaagcacaa | gcccaaggct | 1620 |
| acagcggagc | aactgaagac | tgtcatggat | gactttgcac | agttcctgga | tacatgttgc | 1680 |
| aaggctgctg | acaaggacac | ctgcttctcg | actgagggtc | caaaccttgt | cactagatgc | 1740 |
| aaagacgcct | tagccggtgg | aggaggctct | ggtggaggcg | gtagcggagg | cggagggtcg | 1800 |
| gctatccaga | tgacccggtc | cccgagctcc | ctgtccgcct | ctgtgggcga | tagggtcacc | 1860 |
| atcacctgcc | gtgccagtca | gtaccacgac | ggttctgcag | cctggtatca | acagaaacca | 1920 |
| ggaaaagctc | cgaagcttct | gatttacggt | gcatcctacc | tctactctgg | agtcccttcc | 1980 |
| cgcttctctg | gtagccgttc | cggacggat | ttcactctga | ccatcagcag | tctgcagccg | 2040 |
| gaagacttcg | caacttatta | ctgtcagcaa | tcttcttatt | ctctgatcac | gttcggacag | 2100 |
| ggtaccaagg | tggagatcaa | aggtactact | gccgctagtg | gtagtagtgg | tggcagtagc | 2160 |
| agtggtgccg | aggttcagct | ggtggagtct | gacggtggcc | tggtgcagcc | aggggctca | 2220 |

```
ctccgtttgt cctgtgcagc ttctggcttc aacctctctt actacggtat gcactgggtg    2280
cgtcaggccc cgggtaaggg cctggaatgg gttgcataca ttgcttctta ccctggctac    2340
acttcttatg ccgatagcgt caagggccgt ttcactataa gcgcagacac atccaaaaac    2400
acagcctacc tacaaatgaa cagcttaaga gctgaggaca ctgccgtcta ctattgtgct    2460
cgctctggtt acagttactc tccgtattat tcttggttct ctgctggtat gaactactgg    2520
ggtcaaggag ccctggtcac cgtctcctcg tgatag                              2556
```

<210> SEQ ID NO 150
<211> LENGTH: 2530
<212> TYPE: DNA
<213> ORGANISM: Artificial Sequence
<220> FEATURE:
<223> OTHER INFORMATION: Synthetic: mouse SA-(Gly4Ser)3-scFv (VL-VH)
      CK157

<400> SEQUENCE: 150

```
atgcgaagca cacaagagtg agatcgccca tcggtataat gatttgggag aacaacattt      60
caaaggccta gtcctgattg ccttttccca gtatctccag aaatgctcat acgatgagca     120
tgccaaatta gtgcaggaag taacagactt tgcaaagacg tgtgttgccg atgagtctgc     180
cgccaactgt gacaaatccc ttcacactct ttttggagat aagttgtgtg ccattccaaa     240
cctccgtgaa aactatggtg aactggctga ctgctgtaca aaacaagagc ccgaaagaaa     300
cgaatgtttc ctgcaacaca agatgacaaa ccccagccta ccaccatttg aaaggccaga     360
ggctgaggcc atgtgcacct cctttaagga aaacccaacc accttttatgg gacactattt     420 gcatgaagtt gccagaagac atccttattt ctatgcccca gaacttcttt actatgctga     480
gcagtacaat gagattctga cccagtgttg tgcagaggct gacaaggaaa gctgcctgac     540
cccgaagctt gatggtgtga aggagaaagc attggtctca tctgtccgtc agagaatgaa     600
gtgctccagt atgcagaagt ttggagagag agcttttaaa gcatgggcag tagctcgtct     660
gagccagaca ttccccaatg ctgactttgc agaaatcacc aaattggcaa cagacctgac     720
caaagtcaac aaggagtgct gccatggtga cctgctggaa tgcgcagatg acagggcgga     780
acttgccaag tacatgtgtg aaaaccaggc gactatctcc agcaaactgc agacttgctg     840
cgataaacca ctgttgaaga agcccactg tcttagtgag gtggagcatg acaccatgcc     900
tgctgatctg cctgccattg ctgctgattt tgttgaggac aggaagtgt gcaagaacta     960 tgctgaggcc aaggatgtct tcctgggcac gttcttgtat gaatattcaa gaagacaccc    1020
tgattactct gtatccctgt tgctgagact tgctaagaaa tatgaagcca ctctggaaaa    1080
gtgctgcgct gaagccaatc ctcccgcatg ctacggcaca gtgcttgctg aatttcagcc    1140
tcttgtagaa gagcctaaga acttggtcaa aaccaactgt gatctttacg agaagcttgg    1200
agaatatgga ttccaaaatg ccattctagt tcgctacacc cagaaagcac ctcaggtgtc    1260 aacccccaact ctcgtggagg ctgcaagaaa cctaggaaga gtgggcacca agtgttgtac    1320
acttcctgaa gatcagagac tgccttgtgt ggaagactat ctgtctgcaa tcctgaaccg    1380
tgtgtgtctg ctgcatgaga gaccccagt gagtgagcat gttaccaagt gctgtagtgg    1440
atccctggtg gaaaggcggc catgcttctc tgctctgaca gttgatgaaa catatgtccc    1500
caaagagttt aaagctgaga ccttcacctt ccactctgat atctgcacac ttccagagaa    1560
ggagaagcag attaagaaac aaacggctct gctgagctg gtgaagcaca gcccaaggc     1620 tacagcggag caactgaaga ctgtcatgga tgactttgca cagttcctgg atacatgttg    1680
```

| | |
|---|---|
| caaggctgct gacaaggaca cctgcttctc gactgagggt ccaaaccttg tcactagatg | 1740 |
| caaagacgcc ttagccggtg gaggaggctc tggtggaggc ggtagcggag gcggagggtc | 1800 |
| ggatatccag atgacccagt ccccgagctc cctgtccgcc tctgtgggcg atagggtcac | 1860 |
| catcacctgc cgtgccagtc agtcttacgg tggtgtagcc tggtatcaac agaaaccagg | 1920 |
| aaaagccccg aagcttctga tttactctgc atcctacctc tactctggag tcccttctcg | 1980 |
| cttctctggt agccgttccg ggacggattt cactctgacc atcagcagtc tgcagccgga | 2040 |
| agacttcgca acttattact gtcagcaacc atctcatctg atcacgttcg gacagggtac | 2100 |
| cgaggtggag atcaaggta ctactgccgc tagtggtagt agtggtggca gtagcagtgg | 2160 |
| tgccgaggtt cagctggtgg agtctggcgg tggcctggtg cagccagggg gctcactccg | 2220 |
| tttgtcctgt gcagcttctg gctccaaccc ctactactac ggtggtacgc actgggtgcg | 2280 |
| tcaggccccg ggtgaggagc tggaatgggt tgcatctatt ggttcttacc ctggctacac | 2340 |
| tgactatgcc gatagcgtca agggccgttt cactataagc gcagacacat ccaaaaacac | 2400 |
| agcctaccta caaatgaaca gcttaagagc tgaggacact gccgtctatt attgtgctcg | 2460 |
| ccattactac tggtacgatg ctactgacta ctggggtcaa ggaaccctgg tcaccgtctc | 2520 |
| ctcgtgatag | 2530 |

<210> SEQ ID NO 151
<211> LENGTH: 2550
<212> TYPE: DNA
<213> ORGANISM: Artificial Sequence
<220> FEATURE:
<223> OTHER INFORMATION: Synthetic: mouse SA-(Gly4Ser)3-scFv (VL-VH) CK129

<400> SEQUENCE: 151

| | |
|---|---|
| atggaagcac acaagagtga gatcgcccat cggtataatg atttgggaga caacatttc | 60 |
| aaaggcctag tcctgattgc cttttcccag tatctccaga aatgctcata cgatgagcat | 120 |
| gccaaattag tgcaggaagt aacagacttt gcaaagacgt gtgttgccga tgagtctgcc | 180 |
| gccaactgtg acaaatccct tcacactctt tttggagata agttgtgtgc cattccaaac | 240 |
| ctccgtgaaa actatggtga actggctgac tgctgtacaa acaagagcc cgaaagaaac | 300 |
| gaatgtttcc tgcaacacaa agatgacaac cccagcctac caccatttga aaggccagag | 360 |
| gctgaaggcca tgtgcacctc ctttaaggaa aacccaacca cctttatggg acactatttg | 420 |
| catgaagttg ccagaagaca tccttatttc tatgccccag aacttcttta ctatgctgag | 480 |
| cagtacaatg agattctgac ccagtgttgt gcagaggctg acaaggaaag ctgcctgacc | 540 |
| ccgaagcttg atggtgtgaa ggagaaagca ttggtctcat ctgtccgtca gagaatgaag | 600 |
| tgctccagta tgcagaagtt tggagagaga gcttttaaag catgggcagt agctcgtctg | 660 |
| agccagacat tccccaatgc tgactttgca gaaatcacca attggcaac agacctgacc | 720 |
| aaagtcaaca ggagtgctg ccatggtgac ctgctggaat cgcagatga cagggcggaa | 780 |
| cttgccaagt acatgtgtga aaaccaggcg actatctcca gcaaactgca gacttgctgc | 840 |
| gataaaccac tgttgaagaa agcccactgt cttagtgagg tggagcatga caccatgcct | 900 |
| gctgatctgc ctgccattgc tgctgatttt gttgaggacc aggaagtgtg caagaactat | 960 |
| gctgaggcca aggatgtctt cctgggcacg ttcttgtatg aatattcaag aagacaccct | 1020 |
| gattactctg tatccctgtt gctgagactt gctaagaaat atgaagccac tctggaaaag | 1080 |
| tgctgcgctg aagccaatcc tcccgcatgc tacggcacag tgcttgctga atttcagcct | 1140 |

```
cttgtagaag agcctaagaa cttggtcaaa accaactgtg atctttacga gaagcttgga    1200
gaatatggat tccaaaatgc cattctagtt cgctacaccc agaaagcacc tcaggtgtca    1260
accccaactc tcgtggaggc tgcaagaaac ctaggaagag tgggcaccaa gtgttgtaca    1320
cttcctgaag atcagagact gccttgtgtg aagactatc tgtctgcaat cctgaaccgt     1380
gtgtgtctgc tgcatgagaa gaccccagtg agtgagcatg ttaccaagtg ctgtagtgga    1440
tccctggtgg aaaggcggcc atgcttctct gctctgacag ttgatgaaac atatgtcccc    1500
aaagagttta agctgagac cttcaccttc cactctgata tctgcacact tccagagaag     1560
gagaagcaga ttaagaaaca aacggctctt gctgagctgg tgaagcacaa gcccaaggct    1620
acagcggagc aactgaagac tgtcatggat gactttgcac agttcctgga tacatgttgc    1680
aaggctgctg acaaggacac ctgcttctcg actgagggtc aaaccttgt cactagatgc     1740
aaagacgcct tagccggtgg aggaggctct ggtggaggcg tagcggagg cggagggtcg     1800
gctagcgata tccagatgac ccagtccccg agcccctgt ccgcctctgt gggcgatagg     1860
gtcaccatca cctgccgtgc cagtcagtac ggtggttacg tagcctggta tcaacagaaa    1920
ccaggaaaag ctccgaagct tctgatttac ggtgcatccc ttctctactc tggagtccct    1980
tctcgcttct ctggtggccg ttccgggacg gatttcactc tgaccatcag cagtctgcag    2040
ccggaagact tcgcaactta ttactgtcag cgaggtcatg ctctgatcac gttcggacag    2100
ggtaccaagg tggagatcga aggtactact gccgctagtg gtagtagtgg tggcagtagc    2160
agtggtgccg aggttcagct ggtggagtct ggcggtggcc tggtgcagcc agggggctca    2220
ctccgtttat cctgtgcagc ttctggcttc aacatctctt cttacggttc tatgcactgg    2280
gtgcgtcagg ccccgggtaa gggcctggaa tgggttgcat ctatttaccc ttactctagc    2340
tctacttact atgccgatag cgtcaagggc cgtttcacta taagcgcaga cacatccaaa    2400
aacacagcct acctacaaat gaacagctta agagctgagg acactgccgt ctattattgt    2460
gctcgtggtt acggtccgtg gtacgcttac tcttacttcg cttttggacta ctgggggtcaa    2520
ggaaccctgg tcaccgtctc ctcgtgatag                                     2550
```

<210> SEQ ID NO 152
<211> LENGTH: 2556
<212> TYPE: DNA
<213> ORGANISM: Artificial Sequence
<220> FEATURE:
<223> OTHER INFORMATION: Synthetic: mouse SA-(Gly4Ser)3-scFv (VL-VH)
      CK138-ds1 (VL100Q>C / VH44G>C)

<400> SEQUENCE: 152

```
atggaagcac acaagagtga gatcgcccat cggtataatg atttgggaga caacatttc     60
aaaggcctag tcctgattgc ttttccccag tatctccaga aatgctcata cgatgagcat    120
gccaaattag tgcaggaagt aacagacttt gcaaagacgt gtgttgccga tgagtctgcc    180
gccaactgtg acaaatccct tcacactctt tttggagata gttgtgtgc cattccaaac    240
ctccgtgaaa actatggtga actggctgac tgctgtacaa acaagagcc cgaaagaaac     300
gaatgtttcc tgcaacacaa agatgacaac cccagcctac caccatttga aaggccagag    360
gctgaggcca tgtgcacctc cttaaggaa acccaacca cctttatggg acactatttg      420
catgaagttg ccagaagaca tccttatttc tatgccccag aacttcttta ctatgctgag    480
cagtacaatg agattctgac ccagtgttgt gcagaggctg acaaggaaag ctgcctgacc    540
ccgaagcttg atggtgtgaa ggagaaagca ttggtctcat ctgtccgtca gagaatgaag    600
```

| | |
|---|---|
| tgctccagta tgcagaagtt tggagagaga gcttttaaag catgggcagt agctcgtctg | 660 |
| agccagacat tccccaatgc tgactttgca gaaatcacca aattggcaac agacctgacc | 720 |
| aaagtcaaca aggagtgctg ccatggtgac ctgctggaat gcgcagatga cagggcggaa | 780 |
| cttgccaagt acatgtgtga aaaccaggcg actatctcca gcaaactgca gacttgctgc | 840 |
| gataaaccac tgttgaagaa agcccactgt cttagtgagg tggagcatga caccatgcct | 900 |
| gctgatctgc ctgccattgc tgctgatttt gttgaggacc aggaagtgtg caagaactat | 960 |
| gctgaggcca aggatgtctt cctgggcacg ttcttgtatg aatattcaag aagacaccct | 1020 |
| gattactctg tatccctgtt gctgagactt gctaagaaat atgaagccac tctggaaaag | 1080 |
| tgctgcgctg aagccaatcc tcccgcatgc tacggcacag tgcttgctga atttcagcct | 1140 |
| cttgtagaag agcctaagaa cttggtcaaa accaactgtg atctttacga agcttgga | 1200 |
| gaatatggat ccaaaatgc cattctagtt cgctacaccc agaaagcacc tcaggtgtca | 1260 |
| accccaactc tcgtggaggc tgcaagaaac ctaggaagag tgggcaccaa gtgttgtaca | 1320 |
| cttcctgaag atcagagact gccttgtgtg aagactatc tgtctgcaat cctgaaccgt | 1380 |
| gtgtgtctgc tgcatgagaa dacccccagtg agtgagcatg ttaccaagtg ctgtagtgga | 1440 |
| tccctggtgg aaaggcggcc atgcttctct gctctgacag ttgatgaaac atatgtcccc | 1500 |
| aaagagttta agctgagac cttcaccttc cactctgata tctgcacact tccagagaag | 1560 |
| gagaagcaga ttaagaaaca aacggctctt gctgagctgg tgaagcacaa gcccaaggct | 1620 |
| acagcggagc aactgaagac tgtcatggat gactttgcac agttcctgga tacatgttgc | 1680 |
| aaggctgctg acaaggacac ctgcttctcg actgagggtc aaaccttgt cactagatgc | 1740 |
| aaagacgcct tagccggtgg aggaggctct ggtggaggcg gtagcggagg cggagggtcg | 1800 |
| gctatccaga tgacccggtc cccgagctcc ctgtccgcct ctgtgggcga tagggtcacc | 1860 |
| atcacctgcc gtgccagtca gtaccacgac ggttctgcag cctggtatca acagaaacca | 1920 |
| ggaaaagctc cgaagcttct gatttacggt gcatcctacc tctactctgg agtcccttcc | 1980 |
| cgcttctctg gtagccgttc cgggacggat ttcactctga ccatcagcag tctgcagccg | 2040 |
| gaagacttcg caacttatta ctgtcagcaa tcttcttatt ctctgatcac gttcggatgc | 2100 |
| ggtaccaagg tggagatcaa aggtactact gccgctagtg gtagtagtgg tggcagtagc | 2160 |
| agtggtgccg aggttcagct ggtggagtct gacggtggcc tggtgcagcc aggggggctca | 2220 |
| ctccgtttgt cctgtgcagc ttctggcttc aacctctctt actacggtat gcactgggtg | 2280 |
| cgtcaggccc cgggtaagtg cctggaatgg gttgcataca ttgcttctta ccctggctac | 2340 |
| acttcttatg ccgatagcgt caagggccgt ttcactataa gcgcagacac atccaaaaac | 2400 |
| acagcctacc tacaaatgaa cagcttaaga gctgaggaca ctgccgtcta ctattgtgct | 2460 |
| cgctctggtt acagttactc tccgtattat tcttggttct ctgctggtat gaactactgg | 2520 |
| ggtcaaggag ccctggtcac cgtctcctcg tgatag | 2556 |

<210> SEQ ID NO 153
<211> LENGTH: 2562
<212> TYPE: DNA
<213> ORGANISM: Artificial Sequence
<220> FEATURE:
<223> OTHER INFORMATION: Synthetic: mouse SA-(Gly4Ser)3-scFv (VL-VH) CK138-ds2 (VL43A>C / VH105Q>C)

<400> SEQUENCE: 153
atggaagcac acaagagtga gatcgcccat cggtataatg atttgggaga acaacatttc      60

```
aaaggcctag tcctgattgc cttttcccag tatctccaga aatgctcata cgatgagcat    120
gccaaattag tgcaggaagt aacagacttt gcaaagacgt gtgttgccga tgagtctgcc    180
gccaactgtg acaaatccct tcacactctt tttggagata agttgtgtgc cattccaaac    240
ctccgtgaaa actatggtga actggctgac tgctgtacaa aacaagagcc cgaaagaaac    300
gaatgtttcc tgcaacacaa agatgacaac cccagcctac caccatttga aaggccagag    360
gctgaggcca tgtgcacctc ctttaaggaa aacccaacca cctttatggg acactatttg    420
catgaagttg ccagaagaca tccttatttc tatgccccag aacttcttta ctatgctgag    480
cagtacaatg agattctgac ccagtgttgt gcagaggctg acaaggaaag ctgcctgacc    540
ccgaagcttg atggtgtgaa ggagaaagca ttggtctcat ctgtccgtca gagaatgaag    600
tgctccagta tgcagaagtt tggagagaga gcttttaaag catgggcagt agctcgtctg    660
agccagacat tccccaatgc tgactttgca gaaatcacca aattggcaac agacctgacc    720
aaagtcaaca aggagtgctg ccatggtgac ctgctggaat gcgcagatga cagggcggaa    780
cttgccaagt acatgtgtga aaaccaggcg actatctcca gcaaactgca gacttgctgc    840
gataaaccac tgttgaagaa agcccactgt cttagtgagg tggagcatga caccatgcct    900
gctgatctgc ctgccattgc tgctgatttt gttgaggacc aggaagtgtg caagaactat    960
gctgaggcca aggatgtctt cctgggcacg ttcttgtatg aatattcaag aagacaccct   1020
gattactctg tatccctgtt gctgagactt gctaagaaat atgaagccac tctggaaaag   1080
tgctgcgctg aagccaatcc tcccgcatgc tacggcacag tgcttgctga atttcagcct   1140
cttgtagaag agcctaagaa cttggtcaaa accaactgtg atctttacga gaagcttgga   1200
gaatatggat tccaaaatgc cattctagtt cgctacaccc agaaagcacc tcaggtgtca   1260
accccaactc tcgtgggagc tgcaagaaac ctaggaagag tgggcaccaa gtgttgtaca   1320
cttcctgaag atcagagact gccttgtgtg gaagactatc tgtctgcaat cctgaaccgt   1380
gtgtgtctgc tgcatgagaa gacccccagtg agtgagcatg ttaccaagtg ctgtagtgga   1440
tccctggtgg aaaggcggcc atgcttctct gctctgacag ttgatgaaac atatgtcccc   1500
aaagagttta agctgagac cttcaccttc cactctgata tctgcacact tccagagaag   1560
gagaagcaga ttaagaaaca aacggctctt gctgagctgg tgaagcacaa gcccaaggct   1620
acagcggagc aactgaagac tgtcatggat gactttgcac agttcctgga tacatgttgc   1680
aaggctgctg acaaggacac ctgcttctcg actgagggtc caaaccttgt cactagatgc   1740
aaagacgcct tagccggtgg aggaggctct ggtggaggcg gtagcggagg cggagggtcg   1800
gctagcgcta tccagatgac ccggtccccg agctccctgt ccgcctctgt gggcgatagg   1860
gtcaccatca cctgccgtgc cagtcagtac cacgacggtt ctgcagcctg gtatcaacag   1920
aaaccaggaa aatgcccgaa gcttctgatt tacggtgcat cctacctcta ctctggagtc   1980
ccttcccgct tctctggtag ccgttccggg acggatttca ctctgaccat cagcagtctg   2040
cagccggaag acttcgcaac ttattactgt cagcaatctt cttattctct gatcacgttc   2100
ggacagggta ccaaggtgga gatcaaaggt actactgccg ctagtggtag tagtggtggc   2160
agtagcagtg tgccgaggt tcagctggtg gagtctgacg gtggcctggt gcagccaggg   2220
ggctcactcc gtttgtcctg tgcagcttct ggcttcaacc tctcttacta cggtatgcac   2280
tgggtgcgtc aggcccgggg taagggcctg gaatggggttg catacattgc ttcttaccct   2340
ggctacactt cttatgccga tagcgtcaag ggccgtttca ctataagcgc agacacatcc   2400
aaaaacacag cctacctaca aatgaacagc ttaagagctg aggacactgc cgtctactat   2460
```

```
tgtgctcgct ctggttacag ttactctccg tattattctt ggttctctgc tggtatgaac    2520
tactggggtt gcggagccct ggtcaccgtc tcctcgtgat ag                       2562

<210> SEQ ID NO 154
<211> LENGTH: 2529
<212> TYPE: DNA
<213> ORGANISM: Artificial Sequence
<220> FEATURE:
<223> OTHER INFORMATION: Synthetic: mouse SA-(Gly4Ser)3-scFv (VL-VH)
      CK157-ds1 (VL100Q>C / VH44E>C)

<400> SEQUENCE: 154
atggaagcac acaagagtga gatcgcccat cggtataatg atttgggaga caacatttc      60 aaaggcctag tcctgattgc ctttttccag tatctccaga aatgctcata cgatgagcat    120
gccaaattag tgcaggaagt aacagacttt gcaaagacgt gtgttgccga tgagtctgcc    180
gccaactgtg acaaatccct tcacactctt tttggagata agttgtgtgc cattccaaac    240
ctccgtgaaa actatggtga actggctgac tgctgtacaa acaagagcc cgaaagaaac    300 gaatgttttcc tgcaacacaa agatgacaac cccagcctac caccatttga aggccagag    360 gctgaggcca tgtgcacctc ctttaaggaa aacccaacca cctttatggg acactatttg    420
catgaagttg ccagaagaca tccttatttc tatgccccag aacttcttta ctatgctgag    480
cagtacaatg agattctgac ccagtgttgt gcagaggctg acaaggaaag ctgcctgacc    540
ccgaagcttg atggtgtgaa ggagaaagca ttggtctcat ctgtccgtca gagaatgaag    600
tgctccagta tgcagaagtt tggagagaga gcttttaaag catgggcagt agctcgtctg    660
agccagacat tccccaatgc tgactttgca gaaatcacca attggcaaca gacctgacc    720 aaagtcaaca aggagtgctg ccatggtgac ctgctggaat gcgcagatga cagggcggaa    780
cttgccaagt acatgtgtga aaaccaggcg actatctcca gcaaactgca gacttgctgc    840
gataaaccac tgttgaagaa agcccactgt cttagtgagg tggagcatga caccatgcct    900
gctgatctgc ctgccattgc tgctgatttt gttgaggacc aggaagtgtg caagaactat    960
gctgaggcca aggatgtctt cctgggcacg ttcttgtatg aatattcaag aagacaccct   1020
gattactctg tatccctgtt gctgagactt gctaagaaat atgaagccac tctggaaaag   1080
tgctgcgctg aagccaatcc tcccgcatgc tacggcacag tgcttgctga atttcagcct   1140
cttgtagaag agcctaagaa cttggtcaaa accaactgtg atctttacga agcttgga     1200 gaatatggat ccaaaatgc cattctagtt cgctacaccc agaaagcacc tcaggtgtca   1260
accccaactc tcgtggaggc tgcaagaaac ctaggaagag tgggcaccaa gtgttgtaca   1320
cttcctgaag atcagagact gccttgtgtg aagactatc tgtctgcaat cctgaaccgt   1380
gtgtgtctgc tgcatgagaa gacccagtg agtgagcatg ttaccaagtg ctgtagtgga   1440
tccctggtgg aaaggcggcc atgcttctct gctctgacag ttgatgaaac atatgtcccc   1500
aaagagttta agctgagac cttcaccttc cactctgata tctgcacact tccagagaag   1560
gagaagcaga ttaagaaaca aacggctctt gctgagctgg tgaagcacaa gcccaaggct   1620
acagcggagc aactgaagac tgtcatggat gactttgcac agttcctgga tacatgttgc   1680
aaggctgctg acaaggacac ctgcttctcg actgagggtc caaaccttgt cactagatgc   1740
aaagacgcct tagccggtgg aggaggctct ggtggaggcg gtagcggagg cggagggtcg   1800
gatatccaga tgacccagtc cccgagctcc ctgtccgcct ctgtgggcga tagggtcacc   1860
atcacctgcc gtgccagtca gcttacggt ggtgtagcct ggtatcaaca gaaaccagga   1920
```

-continued

```
aaagccccga agcttctgat ttactctgca tcctacctct actctggagt cccttctcgc    1980
ttctctggta gccgttccgg gacggatttc actctgacca tcagcagtct gcagccggaa    2040
gacttcgcaa cttattactg tcagcaacca tctcatctga tcacgttcgg atgcggtacc    2100
gaggtggaga tcaaaggtac tactgccgct agtggtagta gtggtggcag tagcagtggt    2160
gccgaggttc agctggtgga gtctggcggt ggcctggtgc agccaggggg ctcactccgt    2220
ttgtcctgtg cagcttctgg ctccaacccc tactactacg tggtacgca ctgggtgcgt     2280
caggccccgg gtgagtgcct ggaatgggtt gcatctattg gttcttaccc tggctacact    2340
gactatgccg atagcgtcaa gggccgtttc actataagcg cagacacatc caaaaacaca    2400
gcctacctac aaatgaacag cttaagagct gaggacactg ccgtctatta ttgtgctcgc    2460
cattactact ggtacgatgc tactgactac tggggtcaag aaccctggt caccgtctcc     2520
tcgtgatag                                                             2529
```

<210> SEQ ID NO 155
<211> LENGTH: 2529
<212> TYPE: DNA
<213> ORGANISM: Artificial Sequence
<220> FEATURE:
<223> OTHER INFORMATION: Synthetic: mouse SA-(Gly4Ser)3-scFv (VL-VH) CK157-ds2 (VL43A>C / VH105Q>C)

<400> SEQUENCE: 155

```
atggaagcac acaagagtga gatcgcccat cggtataatg atttgggaga caacatttc     60
aaaggcctag tcctgattgc cttttcccag tatctccaga aatgctcata cgatgagcat    120
gccaaattag tgcaggaagt aacagacttt gcaagacgt gtgttgccga tgagtctgcc    180
gccaactgtg acaaatccct tcacactctt tttggagata agttgtgtgc cattccaaac    240
ctccgtgaaa actatggtga actggctgac tgctgtacaa acaagagcc gaaagaaac     300
gaatgttttcc tgcaacacaa agatgacaac cccagcctac caccattga aaggccagag    360
gctgaggcca tgtgcacctc ctttaaggaa acccaacca cctttatggg acactatttg    420
catgaagttg ccagaagaca tccttatttc tatgccccag aacttcttta ctatgctgag    480
cagtacaatg agattctgac ccagtgttgt gcagaggctg acaaggaaag ctgcctgacc    540
ccgaagcttg atggtgtgaa ggagaaagca ttggtctcat ctgtccgtca gagaatgaag    600
tgctccagta tgcagaagtt tggagagaga gcttttaaag catgggcagt agctcgtctg    660
agccagacat tccccaatgc tgactttgca gaaatcacca aattggcaac agacctgacc    720
aaagtcaaca aggagtgctg ccatggtgac ctgctggaat gcgcagatga cagggcggaa    780
cttgccaagt acatgtgtga aaaccaggcg actatctcca gcaaactgca gacttgctgc    840
gataaaccac tgttgaagaa agcccactgt cttagtgagg tggagcatga caccatgcct    900
gctgatctgc ctgccattgc tgctgatttt gttgaggacc aggaagtgtg caagaactat    960
gctgaggcca aggatgtctt cctgggcacg ttcttgtatg aatattcaag aagacaccct   1020
gattactctg tatccctgtt gctgagactt gctaagaaat atgaagccac tctggaaaag   1080
tgctgcgctg aagccaatcc tcccgcatgc tacggcacag tgcttgctga atttcagcct   1140
cttgtagaag agcctaagaa cttggtcaaa accaactgtg atcttacga gaagcttgga    1200
gaatatggat ccaaaatgc cattctagtt cgctacaccc agaaagcacc tcaggtgtca    1260
accccaactc tcgtgaggc tgcaagaaac ctaggaagag tgggcaccaa gtgttgtaca    1320
cttcctgaag atcagagact gccttgtgtg gaagactatc tgtctgcaat cctgaaccgt    1380
```

| | |
|---|---|
| gtgtgtctgc tgcatgagaa gacccagtg agtgagcatg ttaccaagtg ctgtagtgga | 1440 |
| tccctggtgg aaaggcggcc atgcttctct gctctgacag ttgatgaaac atatgtcccc | 1500 |
| aaagagttta agctgagac cttcaccttc cactctgata tctgcacact tccagagaag | 1560 |
| gagaagcaga ttaagaaaca aacggctctt gctgagctgg tgaagcacaa gcccaaggct | 1620 |
| acagcggagc aactgaagac tgtcatggat gactttgcac agttcctgga tacatgttgc | 1680 |
| aaggctgctg acaaggacac ctgcttctcg actgagggtc caaaccttgt cactagatgc | 1740 |
| aaagacgcct tagccggtgg aggaggctct ggtggaggcg gtagcggagg cggagggtcg | 1800 |
| gatatccaga tgacccagtc cccgagctcc ctgtccgcct ctgtgggcga tagggtcacc | 1860 |
| atcacctgcc gtgccagtca gtcttacggt ggtgtagcct ggtatcaaca gaaaccagga | 1920 |
| aaatgcccga agcttctgat ttactctgca tcctacctct actctggagt cccttctcgc | 1980 |
| ttctctggta gccgttccgg gacggatttc actctgacca tcagcagtct gcagccggaa | 2040 |
| gacttcgcaa cttattactg tcagcaacca tctcatctga tcacgttcgg acagggtacc | 2100 |
| gaggtggaga tcaaaggtac tactgccgct agtggtagta gtggtggcag tagcagtggt | 2160 |
| gccgaggttc agctggtgga gtctggcggt ggcctggtgc agccagggg ctcactccgt | 2220 |
| ttgtcctgtg cagcttctgg ctccaaccc tactactacg gtggtacgca ctgggtgcgt | 2280 |
| caggccccgg gtgaggagct ggaatgggtt gcatctattg gttcttaccc tggctacact | 2340 |
| gactatgccg atagcgtcaa gggccgtttc actataagcg cagacacatc caaaaacaca | 2400 |
| gcctacctac aaatgaacag cttaagagct gaggacactg ccgtctatta ttgtgctcgc | 2460 |
| cattactact ggtacgatgc tactgactac tggggttgcg aaccctggt caccgtctcc | 2520 |
| tcgtgatag | 2529 |

<210> SEQ ID NO 156
<211> LENGTH: 2121
<212> TYPE: DNA
<213> ORGANISM: Artificial Sequence
<220> FEATURE:
<223> OTHER INFORMATION: Synthetic: mouse SA-(Gly4Ser)-VL CK157

<400> SEQUENCE: 156

| | |
|---|---|
| atggaagcac acaagagtga gatcgcccat cggtataatg atttgggaga caacatttc | 60 |
| aaaggcctag tcctgattgc ctttttccag tatctccaga aatgctcata cgatgagcat | 120 |
| gccaaattag tgcaggaagt aacagacttt gcaaagacgt gtgttgccga tgagtctgcc | 180 |
| gccaactgtg acaaatccct tcacactctt tttggagata agttgtgtgc cattccaaac | 240 |
| ctccgtgaaa actatggtga actggctgac tgctgtacaa acaagagcc gaaagaaac | 300 |
| gaatgtttcc tgcaacacaa agatgacaac cccagcctac caccatttga aaggccagag | 360 |
| gctgaggcca tgtgcacctc ctttaaggaa aacccaacca cctttatggg acactatttg | 420 |
| catgaagttg ccagaagaca tccttatttc tatgccccag aacttcttta ctatgctgag | 480 |
| cagtacaatg agattctgac ccagtgttgt gcagaggctg acaaggaaag ctgcctgacc | 540 |
| ccgaagcttg atggtgtgaa ggagaaagca ttggtctcat ctgtccgtca gagaatgaag | 600 |
| tgctccagta tgcagaagtt tggagagaga gcttttaaag catgggcagt agctcgtctg | 660 |
| agccagacat tccccaatgc tgactttgca gaaatcacca aattggcaac agacctgacc | 720 |
| aaagtcaaca aggagtgctg ccatggtgac ctgctggaat gcgcagatga cagggcggaa | 780 |
| cttgccaagt acatgtgtga aaaccaggcg actatctcca gcaaactgca gacttgctgc | 840 |

| | |
|---|---:|
| gataaaccac tgttgaagaa agcccactgt cttagtgagg tggagcatga caccatgcct | 900 |
| gctgatctgc ctgccattgc tgctgatttt gttgaggacc aggaagtgtg caagaactat | 960 |
| gctgaggcca aggatgtctt cctgggcacg ttcttgtatg aatattcaag aagacaccct | 1020 |
| gattactctg tatccctgtt gctgagactt gctaagaaat atgaagccac tctggaaaag | 1080 |
| tgctgcgctg aagccaatcc tcccgcatgc tacggacag tgcttgctga atttcagcct | 1140 |
| cttgtagaag agcctaagaa cttggtcaaa accaactgtg atctttacga aagcttgga | 1200 |
| gaatatggat tccaaaatgc cattctagtt cgctacaccc agaaagcacc tcaggtgtca | 1260 |
| accccaactc tcgtggaggc tgcaagaaac ctaggaagag tgggcaccaa gtgttgtaca | 1320 |
| cttcctgaag atcagagact gccttgtgtg aagactatc tgtctgcaat cctgaaccgt | 1380 |
| gtgtgtctgc tgcatgagaa gaccccagtg agtgagcatg ttaccaagtg ctgtagtgga | 1440 |
| tccctggtgg aaaggcggcc atgcttctct gctctgacag ttgatgaaac atatgtcccc | 1500 |
| aaagagttta agctgagac cttcaccttc cactctgata tctgcacact tccagagaag | 1560 |
| gagaagcaga ttaagaaaca aacggctctt gctgagctgg tgaagcacaa gcccaaggct | 1620 |
| acagcggagc aactgaagac tgtcatggat gactttgcac agttcctgga tacatgttgc | 1680 |
| aaggctgctg acaaggacac ctgcttctcg actgagggtc caaaccttgt cactagatgc | 1740 |
| aaagacgcct tagccggtgg aggaggctct ggtggaggcg gtagcggagg cggagggtcg | 1800 |
| gatatccaga tgacccagtc cccgagctcc ctgtccgcct ctgtgggcga tagggtcacc | 1860 |
| atcacctgcc gtgccagtca gtcttacggt ggtgtagcct ggtatcaaca gaaaccagga | 1920 |
| aaagcccga agcttctgat ttactctgca tcctacctct actctggagt cccttctcgc | 1980 |
| ttctctggta gccgttccgg gacggatttc actctgacca tcagcagtct gcagccggaa | 2040 |
| gacttcgcaa cttattactg tcagcaacca tctcatctga tcacgttcgg acagggtacc | 2100 |
| gaggtggaga tcaaatgata g | 2121 |

<210> SEQ ID NO 157
<211> LENGTH: 2169
<212> TYPE: DNA
<213> ORGANISM: Artificial Sequence
<220> FEATURE:
<223> OTHER INFORMATION: Synthetic: mouse SA-(Gly4Ser)-VH CK157

<400> SEQUENCE: 157

| | |
|---|---:|
| atggaagcac acaagagtga gatcgcccat cggtataatg atttgggaga caacatttc | 60 |
| aaaggcctag tcctgattgc cttttcccag tatctccaga aatgctcata cgatgagcat | 120 |
| gccaaattag tgcaggaagt aacagacttt gcaaagacgt gtgttgccga tgagtctgcc | 180 |
| gccaactgtg acaaatccct tcacactctt tttggagata agttgtgtgc cattccaaac | 240 |
| ctccgtgaaa actatggtga actggctgac tgctgtacaa acaagagcc cgaaagaaac | 300 |
| gaatgtttcc tgcaacacaa agatgacaac cccagcctac caccatttga aaggccagag | 360 |
| gctgaggcca tgtgcacctc ctttaaggaa aacccaacca ctttatggg acactatttg | 420 |
| catgaagttg ccagaagaca tccttatttc tatgccccag aacttcttta ctatgctgag | 480 |
| cagtacaatg agattctgac ccagtgttgt gcagaggctg acaaggaaag ctgcctgacc | 540 |
| ccgaagcttg atggtgtgaa ggagaaagca ttggtctcat ctgtccgtca gagaatgaag | 600 |
| tgctccagta tgcagaagtt tggagagaga gctttaaag catgggcagt agctcgtctg | 660 |
| agccagacat tccccaatgc tgactttgca gaaatcacca aattggcaac agacctgacc | 720 |
| aaagtcaaca aggagtgctg ccatggtgac ctgctggaat gcgcagatga cagggcggaa | 780 |

```
cttgccaagt acatgtgtga aaaccaggcg actatctcca gcaaactgca gacttgctgc    840
gataaaccac tgttgaagaa agcccactgt cttagtgagg tggagcatga caccatgcct    900
gctgatctgc ctgccattgc tgctgatttt gttgaggacc aggaagtgtg caagaactat    960
gctgaggcca aggatgtctt cctgggcacg ttccttgtatg aatattcaag aagacaccct   1020
gattactctg tatccctgtt gctgagactt gctaagaaat atgaagccac tctggaaaag   1080
tgctgcgctg aagccaatcc tcccgcatgc tacggcacag tgcttgctga atttcagcct   1140
cttgtagaag agcctaagaa cttggtcaaa accaactgtg atctttacga agcttgga     1200
gaatatggat ccaaaatgc cattctagtt cgctacaccc agaaagcacc tcaggtgtca    1260
accccaactc tcgtggaggc tgcaagaaac ctaggaagag tgggcaccaa gtgttgtaca   1320
cttcctgaag atcagagact gccttgtgtg aagactatc tgtctgcaat cctgaaccgt    1380
gtgtgtctgc tgcatgagaa gaccccagtg agtgagcatg ttaccaagtg ctgtagtgga   1440
tccctggtgg aaaggcggcc atgcttctct gctctgacag ttgatgaaac atatgtcccc   1500
aaagagttta agctgagac cttcaccttc cactctgata tctgcacact tccagagaag    1560
gagaagcaga ttaagaaaca aacggctctt gctgagctgg tgaagcacaa gcccaaggct   1620
acagcggagc aactgaagac tgtcatggat gactttgcac agttcctgga tacatgttgc   1680
aaggctgctg acaaggacac ctgcttctcg actgagggtc aaaccttgt cactagatgc    1740
aaagacgcct tagccggtgg aggaggctct ggtggaggcg gtagcggagg cggagggtcg   1800
gccgaggttc agctggtgga gtctggcggt ggcctggtgc agccgggggg ctcactccgt   1860
ttgtcctgtg cagcttctgg ctccaacccc tactactacg gtggtacgca ctgggtgcgt   1920
caggccccgg gtgaggagct ggaatgggtt gcatctattg ttcttaccc tggctacact    1980
gactatgccg atagcgtcaa gggccgtttc actataagcg cagacacatc caaaaacaca   2040
gcctacctac aaatgaacag cttaagagct gaggacactg ccgtctatta ttgtgctcgc   2100
cattactact ggtacgatgc tactgactac tggggtcaag gaaccctggt caccgtctcc   2160
tcgtgatag                                                           2169
```

<210> SEQ ID NO 158
<211> LENGTH: 2544
<212> TYPE: DNA
<213> ORGANISM: Artificial Sequence
<220> FEATURE:
<223> OTHER INFORMATION: Synthetic: mouse SA-(Gly4Ser)3-scFv (VL-VH)
      CK129-ds1 (VL100Q>C / VH44G>C)

<400> SEQUENCE: 158

```
atggaagcac acaagagtga gatcgcccat cggtataatg atttgggaga caacatttc     60
aaaggcctag tcctgattgc cttttcccag tatctccaga aatgctcata cgatgagcat   120
gccaaattag tgcaggaagt aacagacttt gcaaagacgt gtgttgccga tgagtctgcc   180
gccaactgtg acaaatccct tcacactctt tttggagata agttgtgtgc cattccaaac   240
ctccgtgaaa actatggtga actggctgac tgctgtacaa acaagagcc cgaaagaaac    300
gaatgtttcc tgcaacacaa agatgacaac cccagcctac caccatttga aaggccagag   360
gctgaggcca tgtgcacctc cttttaaggaa aacccaacca cctttatggg acactatttg   420
catgaagttg ccagaagaca tccttatttc tatgccccag aacttcttta ctatgctgag   480
cagtacaatg agattctgac ccagtgttgt gcagaggctg acaaggaaag ctgcctgacc   540
ccgaagcttg atggtgtgaa ggagaaagca ttggtctcat ctgtccgtca gagaatgaag   600
```

```
tgctccagta tgcagaagtt tggagagaga gcttttaaag catgggcagt agctcgtctg      660
agccagacat tccccaatgc tgactttgca gaaatcacca aattggcaac agacctgacc      720
aaagtcaaca aggagtgctg ccatggtgac ctgctggaat gcgcagatga cagggcggaa      780
cttgccaagt acatgtgtga aaaccaggcg actatctcca gcaaactgca gacttgctgc      840
gataaaccac tgttgaagaa agcccactgt cttagtgagg tggagcatga caccatgcct      900
gctgatctgc ctgccattgc tgctgatttt gttgaggacc aggaagtgtg caagaactat      960
gctgaggcca aggatgtctt cctgggcacg ttcttgtatg aatattcaag aagacaccct     1020
gattactctg tatccctgtt gctgagactt gctaagaaat atgaagccac tctggaaaag     1080
tgctgcgctg aagccaatcc tcccgcatgc tacggcacag tgcttgctga atttcagcct     1140
cttgtagaag agcctaagaa cttggtcaaa accaactgtg atctttacga agacttggaa     1200
gaatatggat ccaaaatgca cattctagtt cgctacaccc agaaagcacc tcaggtgtca     1260
accccaactc tcgtggaggc tgcaagaaac ctaggaagag tgggcaccaa gtgttgtaca     1320
cttcctgaag atcagagact gccttgtgtg aagactatc tgtctgcaat cctgaaccgt     1380
gtgtgtctgc tgcatgagaa gacccccagtg agtgagcatg ttaccaagtg ctgtagtgga     1440
tccctggtgg aaaggcggcc atgcttctct gctctgacag ttgatgaaac atatgtcccc     1500
aaagagttta agctgagac cttcaccttc cactctgata tctgcacact tccagagaag     1560
gagaagcaga ttaagaaaca acggctctt gctgagctgg tgaagcacaa gcccaaggct     1620
acagcggagc aactgaagac tgtcatggat gactttgcac agttcctgga tacatgttgc     1680
aaggctgctg acaaggacac ctgcttctcg actgagggtc aaaccttgt cactagatgc     1740 aaagacgcct tagccggtgg aggaggctct ggtggaggcg gtagcggagg cggagggtcg     1800
gatatccaga tgacccagtc cccgagcccc ctgtccgcct ctgtgggcga tagggtcacc     1860
atcacctgcc gtgccagtca gtacggtggt tacgtagcct ggtatcaaca gaaaccagga     1920
aaagctccga agcttctgat ttacggtgca tcccttctct actctggagt cccttctcgc     1980
ttctctggtg gccgttccgg gacggatttc actctgacca tcagcagtct gcagccggaa     2040
gacttcgcaa cttattactg tcagcgaggt catgctctga tcacgttcgg atgcggtacc     2100
aaggtggaga tcgaaggtac tactgccgct agtggtagta gtggtggcag tagcagtggt     2160
gccgaggttc agctggtgga gtctggcggt ggcctggtgc agccaggggg ctcactccgt     2220
ttatcctgtg cagcttctgg cttcaacatc tcttcttacg gttctatgca ctgggtgcgt     2280
caggccccgg gtaagtgcct ggaatgggtt gcatctattt accccttactc tagctctact     2340 tactatgccg atagcgtcaa gggccgtttc actataagcg cagacacatc caaaaacaca     2400
gcctacctac aaatgaacag cttaagagct gaggacactg ccgtctatta ttgtgctcgt     2460
ggttacggtc cgtggtacgc ttactcttac ttcgctttgg actactgggg tcaaggaacc     2520
ctggtcaccg tctcctcgtg atag                                           2544
```

<210> SEQ ID NO 159
<211> LENGTH: 2544
<212> TYPE: DNA
<213> ORGANISM: Artificial Sequence
<220> FEATURE:
<223> OTHER INFORMATION: Synthetic: mouse SA-(Gly4Ser)3-scFv (VL-VH) CK129-ds2 (VL43A>C / VH105Q>C)

<400> SEQUENCE: 159

```
atggaagcac acaagagtga gatcgcccat cggtataatg atttgggaga acaacatttc      60
```

```
aaaggcctag tcctgattgc cttttcccag tatctccaga aatgctcata cgatgagcat    120
gccaaattag tgcaggaagt aacagacttt gcaaagacgt gtgttgccga tgagtctgcc    180
gccaactgtg acaaatccct tcacactctt tttggagata agttgtgtgc cattccaaac    240
ctccgtgaaa actatggtga actggctgac tgctgtacaa aacaagagcc cgaaagaaac    300
gaatgtttcc tgcaacacaa agatgacaac cccagcctac caccatttga aaggccagag    360
gctgaggcca tgtgcacctc ctttaaggaa aacccaacca cctttatggg acactatttg    420
catgaagttg ccagaagaca tccttatttc tatgccccag aacttcttta ctatgctgag    480
cagtacaatg agattctgac ccagtgttgt gcagaggctg acaaggaaag ctgcctgacc    540
ccgaagcttg atggtgtgaa ggagaaagca ttggtctcat ctgtccgtca gagaatgaag    600
tgctccagta tgcagaagtt tggagagaga gcttttaaag catgggcagt agctcgtctg    660
agccagacat tccccaatgc tgactttgca gaaatcacca aattggcaac agacctgacc    720
aaagtcaaca aggagtgctg ccatggtgac ctgctggaat cgcagatgca gggcggaa     780 cttgccaagt acatgtgtga aaaccaggcg actatctcca gcaaactgca gacttgctgc    840
gataaaccac tgttgaagaa agcccactgt cttagtgagg tggagcatga caccatgcct    900
gctgatctgc ctgccattgc tgctgatttt gttgaggacc aggaagtgtg caagaactat    960
gctgaggcca aggatgtctt cctgggcacg ttcttgtatg aatattcaag aagacaccct   1020
gattactctg tatccctgtt gctgagactt gctaagaaat atgaagccac tctggaaaag   1080
tgctgcgctg aagccaatcc tcccgcatgc tacggcacag tgcttgctga atttcagcct   1140
cttgtagaag agcctaagaa cttggtcaaa accaactgtg atctttacga aagcttgga    1200 gaatatggat tccaaaatgc cattctagtt cgctacaccc agaaagcacc tcaggtgtca   1260 acccccaactc tcgtggaggc tgcaagaaac ctaggaagag tgggcaccaa gtgttgtaca   1320
cttcctgaag atcagagact gccttgtgtg gaagactatc tgtctgcaat cctgaaccgt   1380
gtgtgtctgc tgcatgagaa gacccccagtg agtgagcatg ttaccaagtg ctgtagtgga   1440
tccctggtgg aaaggcggcc atgcttctct gctctgacag ttgatgaaac atatgtcccc   1500
aaagagttta agctgagac cttcaccttc cactctgata tctgcacact tccagagaag   1560
gagaagcaga ttaagaaaca aacggctctt gctgagctgg tgaagcacaa gcccaaggct   1620
acagcggagc aactgaagac tgtcatggat gactttgcac agttcctgga tacatgttgc   1680
aaggctgctg acaaggacac ctgcttctcg actgagggtc aaaccttgt cactagatgc   1740 aaagacgcct tagccggtgg aggaggctct ggtggaggcg gtagcggagg cggagggtcg   1800
gatatccaga tgacccagtc cccgagcccc ctgtccgcct ctgtgggcga tagggtcacc   1860
atcacctgcc gtgccagtca gtacggtggt tacgtagcct ggtatcaaca gaaaccagga   1920
aaatgcccga agcttctgat ttacggtgca tcccttctct actctggagt cccttctcgc   1980
ttctctggtg gccgttccgg gacggatttc actctgacca tcagcagtct gcagccggaa   2040
gacttcgcaa cttattactg tcagcgaggt catgctctga tcacgttcgg acagggtacc   2100
aaggtggaga tcgaaggtac tactgccgct agtggtagta gtggtggcag tagcagtggt   2160
gccgaggttc agctggtgga gtctggcggt ggcctggtgc agccaggggg ctcactccgt   2220
ttatcctgtg cagcttctgg cttcaacatc tcttcttacg gttctatgca ctgggtgcgt   2280 caggcccgg gtaagggcct ggaatggggt gcatctattt acccttactc tagctctact   2340
tactatgccg atagcgtcaa gggccgtttc actataagcg cagacacatc caaaaacaca   2400
```

-continued

```
gcctacctac aaatgaacag cttaagagct gaggacactg ccgtctatta ttgtgctcgt      2460
ggttacggtc cgtggtacgc ttactcttac ttcgctttgg actactgggg ttgcggaacc      2520
ctggtcaccg tctcctcgtg atag                                             2544
```

<210> SEQ ID NO 160
<211> LENGTH: 851
<212> TYPE: PRT
<213> ORGANISM: Artificial Sequence
<220> FEATURE:
<223> OTHER INFORMATION: Synthetic: mouse SA-(Gly4Ser)3-scFv (VL-VH)
      CK138

<400> SEQUENCE: 160

```
Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
            20                  25                  30

Lys Cys Ser Tyr Asp Glu His Ala Lys Leu Val Gln Glu Val Thr Asp
        35                  40                  45

Phe Ala Lys Thr Cys Val Ala Asp Glu Ser Ala Ala Asn Cys Asp Lys
    50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
    130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
    210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
            260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
    290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335
```

```
Arg His Pro Asp Tyr Ser Val Ser Leu Leu Arg Leu Ala Lys Lys
            340                 345                 350

Tyr Glu Ala Thr Leu Glu Lys Cys Cys Ala Glu Ala Asn Pro Pro Ala
            355                 360                 365

Cys Tyr Gly Thr Val Leu Ala Glu Phe Gln Pro Leu Val Glu Glu Pro
            370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
            405                 410                 415

Gln Val Ser Thr Pro Thr Leu Val Glu Ala Ala Arg Asn Leu Gly Arg
            420                 425                 430

Val Gly Thr Lys Cys Cys Thr Leu Pro Glu Asp Gln Arg Leu Pro Cys
            435                 440                 445

Val Glu Asp Tyr Leu Ser Ala Ile Leu Asn Arg Val Cys Leu Leu His
            450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
            485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
            515                 520                 525

Leu Ala Glu Leu Val Lys His Lys Pro Lys Ala Thr Ala Glu Gln Leu
            530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
            565                 570                 575

Thr Arg Cys Lys Asp Ala Leu Ala Gly Gly Gly Ser Gly Gly Gly
            580                 585                 590

Gly Ser Gly Gly Gly Ser Ala Ser Ala Ile Gln Met Thr Arg Ser
            595                 600                 605

Pro Ser Ser Leu Ser Ala Ser Val Gly Asp Arg Val Thr Ile Thr Cys
            610                 615                 620

Arg Ala Ser Gln Tyr His Asp Gly Ser Ala Ala Trp Tyr Gln Gln Lys
625                 630                 635                 640

Pro Gly Lys Ala Pro Lys Leu Leu Ile Tyr Gly Ala Ser Tyr Leu Tyr
            645                 650                 655

Ser Gly Val Pro Ser Arg Phe Ser Gly Ser Arg Ser Gly Thr Asp Phe
            660                 665                 670

Thr Leu Thr Ile Ser Ser Leu Gln Pro Glu Asp Phe Ala Thr Tyr Tyr
            675                 680                 685

Cys Gln Gln Ser Ser Tyr Ser Leu Ile Thr Phe Gly Gln Gly Thr Lys
            690                 695                 700

Val Glu Ile Lys Gly Thr Thr Ala Ala Ser Gly Ser Ser Gly Gly Ser
705                 710                 715                 720

Ser Ser Gly Ala Glu Val Gln Leu Val Glu Ser Asp Gly Gly Leu Val
            725                 730                 735

Gln Pro Gly Gly Ser Leu Arg Leu Ser Cys Ala Ala Ser Gly Phe Asn
            740                 745                 750
```

Leu Ser Tyr Tyr Gly Met His Trp Val Arg Gln Ala Pro Gly Lys Gly
            755                 760                 765

Leu Glu Trp Val Ala Tyr Ile Ala Ser Tyr Pro Gly Tyr Thr Ser Tyr
    770                 775                 780

Ala Asp Ser Val Lys Gly Arg Phe Thr Ile Ser Ala Asp Thr Ser Lys
785                 790                 795                 800

Asn Thr Ala Tyr Leu Gln Met Asn Ser Leu Arg Ala Glu Asp Thr Ala
                805                 810                 815

Val Tyr Tyr Cys Ala Arg Ser Gly Tyr Ser Tyr Ser Pro Tyr Tyr Ser
            820                 825                 830

Trp Phe Ser Ala Gly Met Asn Tyr Trp Gly Gln Gly Ala Leu Val Thr
        835                 840                 845

Val Ser Ser
    850

<210> SEQ ID NO 161
<211> LENGTH: 842
<212> TYPE: PRT
<213> ORGANISM: Artificial Sequence
<220> FEATURE:
<223> OTHER INFORMATION: Synthetic: mouse SA-(Gly4Ser)3-scFv (VL-VH)
      CK157

<400> SEQUENCE: 161

Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
                20                  25                  30

Lys Cys Ser Tyr Asp Glu His Ala Lys Leu Val Gln Glu Val Thr Asp
            35                  40                  45

Phe Ala Lys Thr Cys Val Ala Asp Glu Ser Ala Ala Asn Cys Asp Lys
    50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
    115                 120                 125

Glu Asn Pro Thr Thr Phe Met Gly His Tyr Leu His Glu Val Ala Arg
130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
    195                 200                 205

Arg Ala Phe Lys Ala Trp Ala Val Ala Arg Leu Ser Gln Thr Phe Pro
210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

-continued

Arg Ala Glu Leu Ala Lys Tyr Met Cys Glu Asn Gln Ala Thr Ile Ser
        260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
        290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

Arg His Pro Asp Tyr Ser Val Ser Leu Leu Arg Leu Ala Lys Lys
        340                 345                 350

Tyr Glu Ala Thr Leu Glu Lys Cys Cys Ala Glu Ala Asn Pro Pro Ala
        355                 360                 365

Cys Tyr Gly Thr Val Leu Ala Glu Phe Gln Pro Leu Val Glu Glu Pro
        370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
                405                 410                 415

Gln Val Ser Thr Pro Thr Leu Val Glu Ala Ala Arg Asn Leu Gly Arg
        420                 425                 430

Val Gly Thr Lys Cys Cys Thr Leu Pro Glu Asp Gln Arg Leu Pro Cys
        435                 440                 445

Val Glu Asp Tyr Leu Ser Ala Ile Leu Asn Arg Val Cys Leu Leu His
        450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495

Tyr Val Pro Lys Glu Phe Lys Ala Glu Thr Phe Thr Phe His Ser Asp
        500                 505                 510

Ile Cys Thr Leu Pro Glu Lys Glu Lys Gln Ile Lys Lys Gln Thr Ala
        515                 520                 525

Leu Ala Glu Leu Val Lys His Lys Pro Lys Ala Thr Ala Glu Gln Leu
        530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
                565                 570                 575

Thr Arg Cys Lys Asp Ala Leu Ala Gly Gly Gly Ser Gly Gly Gly
        580                 585                 590

Gly Ser Gly Gly Gly Ser Ala Ser Asp Ile Gln Met Thr Gln Ser
        595                 600                 605

Pro Ser Ser Leu Ser Ala Ser Val Gly Asp Arg Val Thr Ile Thr Cys
        610                 615                 620

Arg Ala Ser Gln Ser Tyr Gly Val Ala Trp Tyr Gln Gln Lys Pro
625                 630                 635                 640

Gly Lys Ala Pro Lys Leu Leu Ile Tyr Ser Ala Ser Tyr Leu Tyr Ser
                645                 650                 655

Gly Val Pro Ser Arg Phe Ser Gly Ser Arg Ser Gly Thr Asp Phe Thr
        660                 665                 670

```
Leu Thr Ile Ser Ser Leu Gln Pro Glu Asp Phe Ala Thr Tyr Tyr Cys
            675                 680                 685

Gln Gln Pro Ser His Leu Ile Thr Phe Gly Gln Gly Thr Glu Val Glu
        690                 695                 700

Ile Lys Gly Thr Thr Ala Ala Ser Gly Ser Ser Gly Ser Ser Ser
705                 710                 715                 720

Gly Ala Glu Val Gln Leu Val Glu Ser Gly Gly Leu Val Gln Pro
                725                 730                 735

Gly Gly Ser Leu Arg Leu Ser Cys Ala Ala Ser Gly Ser Asn Pro Tyr
                740                 745                 750

Tyr Tyr Gly Gly Thr His Trp Val Arg Gln Ala Pro Gly Glu Glu Leu
            755                 760                 765

Glu Trp Val Ala Ser Ile Gly Ser Tyr Pro Gly Tyr Thr Asp Tyr Ala
770                 775                 780

Asp Ser Val Lys Gly Arg Phe Thr Ile Ser Ala Asp Thr Ser Lys Asn
785                 790                 795                 800

Thr Ala Tyr Leu Gln Met Asn Ser Leu Arg Ala Glu Asp Thr Ala Val
                805                 810                 815

Tyr Tyr Cys Ala Arg His Tyr Tyr Trp Tyr Asp Ala Thr Asp Tyr Trp
            820                 825                 830

Gly Gln Gly Thr Leu Val Thr Val Ser Ser
        835                 840
```

<210> SEQ ID NO 162
<211> LENGTH: 847
<212> TYPE: PRT
<213> ORGANISM: Artificial Sequence
<220> FEATURE:
<223> OTHER INFORMATION: Synthetic: mouse SA-(Gly4Ser)3-scFv (VL-VH) CK129

<400> SEQUENCE: 162

```
Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
                20                  25                  30

Lys Cys Ser Tyr Asp Glu His Ala Lys Leu Val Gln Glu Val Thr Asp
            35                  40                  45

Phe Ala Lys Thr Cys Val Ala Asp Glu Ser Ala Ala Asn Cys Asp Lys
        50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190
```

```
Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
            245                 250                 255

Arg Ala Glu Leu Ala Lys Tyr Met Cys Glu Asn Gln Ala Thr Ile Ser
                260                 265                 270

Ser Lys Leu Gln Thr Cys Cys Asp Lys Pro Leu Leu Lys Lys Ala His
            275                 280                 285

Cys Leu Ser Glu Val Glu His Asp Thr Met Pro Ala Asp Leu Pro Ala
            290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

Arg His Pro Asp Tyr Ser Val Ser Leu Leu Arg Leu Ala Lys Lys
                340                 345                 350

Tyr Glu Ala Thr Leu Glu Lys Cys Cys Ala Glu Ala Asn Pro Pro Ala
                355                 360                 365

Cys Tyr Gly Thr Val Leu Ala Glu Phe Gln Pro Leu Val Glu Glu Pro
            370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
                405                 410                 415

Gln Val Ser Thr Pro Thr Leu Val Glu Ala Ala Arg Asn Leu Gly Arg
            420                 425                 430

Val Gly Thr Lys Cys Cys Thr Leu Pro Glu Asp Gln Arg Leu Pro Cys
            435                 440                 445

Val Glu Asp Tyr Leu Ser Ala Ile Leu Asn Arg Val Cys Leu Leu His
            450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
            515                 520                 525

Leu Ala Glu Leu Val Lys His Lys Pro Lys Ala Thr Ala Glu Gln Leu
530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
                565                 570                 575

Thr Arg Cys Lys Asp Ala Leu Ala Gly Gly Gly Ser Gly Gly
            580                 585                 590

Gly Ser Gly Gly Gly Ser Ala Ser Asp Ile Gln Met Thr Gln Ser
            595                 600                 605
```

-continued

Pro Ser Pro Leu Ser Ala Ser Val Gly Asp Arg Val Thr Ile Thr Cys
    610             615             620

Arg Ala Ser Gln Tyr Gly Gly Tyr Val Ala Trp Tyr Gln Gln Lys Pro
625             630             635             640

Gly Lys Ala Pro Lys Leu Leu Ile Tyr Gly Ala Ser Leu Leu Tyr Ser
            645             650             655

Gly Val Pro Ser Arg Phe Ser Gly Arg Ser Gly Thr Asp Phe Thr
        660             665             670

Leu Thr Ile Ser Ser Leu Gln Pro Glu Asp Phe Ala Thr Tyr Tyr Cys
        675             680             685

Gln Arg Gly His Ala Leu Ile Thr Phe Gly Gln Gly Thr Lys Val Glu
    690             695             700

Ile Glu Gly Thr Thr Ala Ala Ser Gly Ser Ser Gly Ser Ser Ser
705             710             715             720

Gly Ala Glu Val Gln Leu Val Glu Ser Gly Gly Leu Val Gln Pro
            725             730             735

Gly Gly Ser Leu Arg Leu Ser Cys Ala Ala Ser Gly Phe Asn Ile Ser
        740             745             750

Ser Tyr Gly Ser Met His Trp Val Arg Gln Ala Pro Gly Lys Gly Leu
    755             760             765

Glu Trp Val Ala Ser Ile Tyr Pro Tyr Ser Ser Ser Thr Tyr Tyr Ala
770             775             780

Asp Ser Val Lys Gly Arg Phe Thr Ile Ser Ala Asp Thr Ser Lys Asn
785             790             795             800

Thr Ala Tyr Leu Gln Met Asn Ser Leu Arg Ala Glu Asp Thr Ala Val
            805             810             815

Tyr Tyr Cys Ala Arg Gly Tyr Gly Pro Trp Tyr Ala Tyr Ser Tyr Phe
        820             825             830

Ala Leu Asp Tyr Trp Gly Gln Gly Thr Leu Val Thr Val Ser Ser
    835             840             845

<210> SEQ ID NO 163
<211> LENGTH: 851
<212> TYPE: PRT
<213> ORGANISM: Artificial Sequence
<220> FEATURE:
<223> OTHER INFORMATION: Synthetic: mouse SA-(Gly4Ser)3-scFv (VL-VH)
      CK138-ds1 (VL100Q>C / VH44G>C)

<400> SEQUENCE: 163

Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
            20                  25                  30

Lys Cys Ser Tyr Asp Glu His Ala Lys Leu Val Gln Glu Val Thr Asp
        35                  40                  45

Phe Ala Lys Thr Cys Val Ala Asp Glu Ser Ala Ala Asn Cys Asp Lys
    50                  55                  60

Ser Leu His Thr Leu Phe Gly Asp Lys Leu Cys Ala Ile Pro Asn Leu
65              70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

```
Glu Asn Pro Thr Thr Phe Met Gly His Tyr Leu His Glu Val Ala Arg
    130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
            260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

Arg His Pro Asp Tyr Ser Val Ser Leu Leu Leu Arg Leu Ala Lys Lys
            340                 345                 350

Tyr Glu Ala Thr Leu Glu Lys Cys Cys Ala Glu Ala Asn Pro Pro Ala
        355                 360                 365

Cys Tyr Gly Thr Val Leu Ala Glu Phe Gln Pro Leu Val Glu Glu Pro
370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
                405                 410                 415

Gln Val Ser Thr Pro Thr Leu Val Glu Ala Ala Arg Asn Leu Gly Arg
            420                 425                 430

Val Gly Thr Lys Cys Cys Thr Leu Pro Glu Asp Gln Arg Leu Pro Cys
        435                 440                 445

Val Glu Asp Tyr Leu Ser Ala Ile Leu Asn Arg Val Cys Leu Leu His
450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
        515                 520                 525

Leu Ala Glu Leu Val Lys His Lys Pro Lys Ala Thr Ala Glu Gln Leu
530                 535                 540
```

```
Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
                565                 570                 575

Thr Arg Cys Lys Asp Ala Leu Ala Gly Gly Gly Ser Gly Gly Gly Gly
            580                 585                 590

Gly Ser Gly Gly Gly Ser Ala Ser Ala Ile Gln Met Thr Arg Ser
    595                 600                 605

Pro Ser Ser Leu Ser Ala Ser Val Gly Asp Arg Val Thr Ile Thr Cys
        610                 615                 620

Arg Ala Ser Gln Tyr His Asp Gly Ser Ala Ala Trp Tyr Gln Gln Lys
625                 630                 635                 640

Pro Gly Lys Ala Pro Lys Leu Leu Ile Tyr Gly Ala Ser Tyr Leu Tyr
                645                 650                 655

Ser Gly Val Pro Ser Arg Phe Ser Gly Ser Arg Ser Gly Thr Asp Phe
                660                 665                 670

Thr Leu Thr Ile Ser Ser Leu Gln Pro Glu Asp Phe Ala Thr Tyr Tyr
            675                 680                 685

Cys Gln Gln Ser Ser Tyr Ser Leu Ile Thr Phe Gly Cys Gly Thr Lys
    690                 695                 700

Val Glu Ile Lys Gly Thr Thr Ala Ala Ser Gly Ser Ser Gly Gly Ser
705                 710                 715                 720

Ser Ser Gly Ala Glu Val Gln Leu Val Glu Ser Asp Gly Gly Leu Val
                725                 730                 735

Gln Pro Gly Gly Ser Leu Arg Leu Ser Cys Ala Ala Ser Gly Phe Asn
            740                 745                 750

Leu Ser Tyr Tyr Gly Met His Trp Val Arg Gln Ala Pro Gly Lys Cys
    755                 760                 765

Leu Glu Trp Val Ala Tyr Ile Ala Ser Tyr Pro Gly Tyr Thr Ser Tyr
770                 775                 780

Ala Asp Ser Val Lys Gly Arg Phe Thr Ile Ser Ala Asp Thr Ser Lys
785                 790                 795                 800

Asn Thr Ala Tyr Leu Gln Met Asn Ser Leu Arg Ala Glu Asp Thr Ala
                805                 810                 815

Val Tyr Tyr Cys Ala Arg Ser Gly Tyr Ser Tyr Ser Pro Tyr Tyr Ser
            820                 825                 830

Trp Phe Ser Ala Gly Met Asn Tyr Trp Gly Gln Gly Ala Leu Val Thr
    835                 840                 845

Val Ser Ser
    850

<210> SEQ ID NO 164
<211> LENGTH: 851
<212> TYPE: PRT
<213> ORGANISM: Artificial Sequence
<220> FEATURE:
<223> OTHER INFORMATION: Synthetic: mouse SA-(Gly4Ser)3-scFv (VL-VH)
      CK138-ds2 (VL43A>C / VH105Q>C)

<400> SEQUENCE: 164

Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
                20                  25                  30

Lys Cys Ser Tyr Asp Glu His Ala Lys Leu Val Gln Glu Val Thr Asp
            35                  40                  45
```

-continued

```
Phe Ala Lys Thr Cys Val Ala Asp Glu Ser Ala Ala Asn Cys Asp Lys
    50                  55                  60
Ser Leu His Thr Leu Phe Gly Asp Lys Leu Cys Ala Ile Pro Asn Leu
65                  70                  75                  80
Arg Glu Asn Tyr Gly Glu Leu Ala Asp Cys Cys Thr Lys Gln Glu Pro
                85                  90                  95
Glu Arg Asn Glu Cys Phe Leu Gln His Lys Asp Asp Asn Pro Ser Leu
            100                 105                 110
Pro Pro Phe Glu Arg Pro Glu Ala Glu Ala Met Cys Thr Ser Phe Lys
        115                 120                 125
Glu Asn Pro Thr Thr Phe Met Gly His Tyr Leu His Glu Val Ala Arg
    130                 135                 140
Arg His Pro Tyr Phe Tyr Ala Pro Glu Leu Leu Tyr Tyr Ala Glu Gln
145                 150                 155                 160
Tyr Asn Glu Ile Leu Thr Gln Cys Cys Ala Glu Ala Asp Lys Glu Ser
                165                 170                 175
Cys Leu Thr Pro Lys Leu Asp Gly Val Lys Glu Lys Ala Leu Val Ser
            180                 185                 190
Ser Val Arg Gln Arg Met Lys Cys Ser Ser Met Gln Lys Phe Gly Glu
        195                 200                 205
Arg Ala Phe Lys Ala Trp Ala Val Ala Arg Leu Ser Gln Thr Phe Pro
    210                 215                 220
Asn Ala Asp Phe Ala Glu Ile Thr Lys Leu Ala Thr Asp Leu Thr Lys
225                 230                 235                 240
Val Asn Lys Glu Cys Cys His Gly Asp Leu Leu Glu Cys Ala Asp Asp
                245                 250                 255
Arg Ala Glu Leu Ala Lys Tyr Met Cys Glu Asn Gln Ala Thr Ile Ser
            260                 265                 270
Ser Lys Leu Gln Thr Cys Cys Asp Lys Pro Leu Leu Lys Lys Ala His
        275                 280                 285
Cys Leu Ser Glu Val Glu His Asp Thr Met Pro Ala Asp Leu Pro Ala
    290                 295                 300
Ile Ala Ala Asp Phe Val Glu Asp Gln Glu Val Cys Lys Asn Tyr Ala
305                 310                 315                 320
Glu Ala Lys Asp Val Phe Leu Gly Thr Phe Leu Tyr Glu Tyr Ser Arg
                325                 330                 335
Arg His Pro Asp Tyr Ser Val Ser Leu Leu Leu Arg Leu Ala Lys Lys
            340                 345                 350
Tyr Glu Ala Thr Leu Glu Lys Cys Cys Ala Glu Ala Asn Pro Pro Ala
        355                 360                 365
Cys Tyr Gly Thr Val Leu Ala Glu Phe Gln Pro Leu Val Glu Glu Pro
    370                 375                 380
Lys Asn Leu Val Lys Thr Asn Cys Asp Leu Tyr Glu Lys Leu Gly Glu
385                 390                 395                 400
Tyr Gly Phe Gln Asn Ala Ile Leu Val Arg Tyr Thr Gln Lys Ala Pro
                405                 410                 415
Gln Val Ser Thr Pro Thr Leu Val Glu Ala Ala Arg Asn Leu Gly Arg
            420                 425                 430
Val Gly Thr Lys Cys Cys Thr Leu Pro Glu Asp Gln Arg Leu Pro Cys
        435                 440                 445
Val Glu Asp Tyr Leu Ser Ala Ile Leu Asn Arg Val Cys Leu Leu His
    450                 455                 460
```

```
Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
        515                 520                 525

Leu Ala Glu Leu Val Lys His Lys Pro Lys Ala Thr Ala Glu Gln Leu
    530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
                565                 570                 575

Thr Arg Cys Lys Asp Ala Leu Ala Gly Gly Gly Ser Gly Gly Gly
            580                 585                 590

Gly Ser Gly Gly Gly Ser Ala Ser Ile Gln Met Thr Arg Ser
        595                 600                 605

Pro Ser Ser Leu Ser Ala Ser Val Gly Asp Arg Val Thr Ile Thr Cys
610                 615                 620

Arg Ala Ser Gln Tyr His Asp Gly Ser Ala Ala Trp Tyr Gln Gln Lys
625                 630                 635                 640

Pro Gly Lys Cys Pro Lys Leu Leu Ile Tyr Gly Ala Ser Tyr Leu Tyr
            645                 650                 655

Ser Gly Val Pro Ser Arg Phe Ser Gly Ser Arg Ser Gly Thr Asp Phe
            660                 665                 670

Thr Leu Thr Ile Ser Ser Leu Gln Pro Glu Asp Phe Ala Thr Tyr Tyr
        675                 680                 685

Cys Gln Gln Ser Ser Tyr Ser Leu Ile Thr Phe Gly Gln Gly Thr Lys
    690                 695                 700

Val Glu Ile Lys Gly Thr Thr Ala Ala Ser Gly Ser Ser Gly Gly Ser
705                 710                 715                 720

Ser Ser Gly Ala Glu Val Gln Leu Val Glu Ser Asp Gly Gly Leu Val
                725                 730                 735

Gln Pro Gly Gly Ser Leu Arg Leu Ser Cys Ala Ala Ser Gly Phe Asn
            740                 745                 750

Leu Ser Tyr Tyr Gly Met His Trp Val Arg Gln Ala Pro Gly Lys Gly
        755                 760                 765

Leu Glu Trp Val Ala Tyr Ile Ala Ser Tyr Pro Gly Tyr Thr Ser Tyr
    770                 775                 780

Ala Asp Ser Val Lys Gly Arg Phe Thr Ile Ser Ala Asp Thr Ser Lys
785                 790                 795                 800

Asn Thr Ala Tyr Leu Gln Met Asn Ser Leu Arg Ala Glu Asp Thr Ala
                805                 810                 815

Val Tyr Tyr Cys Ala Arg Ser Gly Tyr Ser Tyr Ser Pro Tyr Tyr Ser
            820                 825                 830

Trp Phe Ser Ala Gly Met Asn Tyr Trp Gly Cys Gly Ala Leu Val Thr
        835                 840                 845

Val Ser Ser
    850

<210> SEQ ID NO 165
<211> LENGTH: 842
<212> TYPE: PRT
```

<213> ORGANISM: Artificial Sequence
<220> FEATURE:
<223> OTHER INFORMATION: Synthetic: mouse SA-(Gly4Ser)3-scFv (VL-VH)
      CK157-ds1 (VL100Q>C / VH44E>C)

<400> SEQUENCE: 165

```
Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
            20                  25                  30

Lys Cys Ser Tyr Asp Glu His Ala Lys Leu Val Gln Glu Val Thr Asp
        35                  40                  45

Phe Ala Lys Thr Cys Val Ala Asp Glu Ser Ala Ala Asn Cys Asp Lys
    50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
    130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
    210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
            260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
    290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

Arg His Pro Asp Tyr Ser Val Ser Leu Leu Leu Arg Leu Ala Lys Lys
            340                 345                 350

Tyr Glu Ala Thr Leu Glu Lys Cys Cys Ala Glu Ala Asn Pro Pro Ala
        355                 360                 365

Cys Tyr Gly Thr Val Leu Ala Glu Phe Gln Pro Leu Val Glu Glu Pro
    370                 375                 380
```

```
Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
            405                 410                 415

Gln Val Ser Thr Pro Thr Leu Val Glu Ala Ala Arg Asn Leu Gly Arg
        420                 425                 430

Val Gly Thr Lys Cys Cys Thr Leu Pro Glu Asp Gln Arg Leu Pro Cys
        435                 440                 445

Val Glu Asp Tyr Leu Ser Ala Ile Leu Asn Arg Val Cys Leu Leu His
    450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
            485                 490                 495

Tyr Val Pro Lys Glu Phe Lys Ala Glu Thr Phe Thr Phe His Ser Asp
        500                 505                 510

Ile Cys Thr Leu Pro Glu Lys Glu Lys Gln Ile Lys Lys Gln Thr Ala
        515                 520                 525

Leu Ala Glu Leu Val Lys His Lys Pro Lys Ala Thr Ala Glu Gln Leu
530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
            565                 570                 575

Thr Arg Cys Lys Asp Ala Leu Ala Gly Gly Gly Ser Gly Gly Gly
            580                 585                 590

Gly Ser Gly Gly Gly Gly Ser Ala Ser Asp Ile Gln Met Thr Gln Ser
        595                 600                 605

Pro Ser Ser Leu Ser Ala Ser Val Gly Asp Arg Val Thr Ile Thr Cys
        610                 615                 620

Arg Ala Ser Gln Ser Tyr Gly Gly Val Ala Trp Tyr Gln Gln Lys Pro
625                 630                 635                 640

Gly Lys Ala Pro Lys Leu Leu Ile Tyr Ser Ala Ser Tyr Leu Tyr Ser
            645                 650                 655

Gly Val Pro Ser Arg Phe Ser Gly Ser Arg Ser Gly Thr Asp Phe Thr
        660                 665                 670

Leu Thr Ile Ser Ser Leu Gln Pro Glu Asp Phe Ala Thr Tyr Tyr Cys
        675                 680                 685

Gln Gln Pro Ser His Leu Ile Thr Phe Gly Cys Gly Thr Glu Val Glu
        690                 695                 700

Ile Lys Gly Thr Thr Ala Ala Ser Gly Ser Ser Gly Gly Ser Ser Ser
705                 710                 715                 720

Gly Ala Glu Val Gln Leu Val Glu Ser Gly Gly Leu Val Gln Pro
            725                 730                 735

Gly Gly Ser Leu Arg Leu Ser Cys Ala Ala Ser Gly Ser Asn Pro Tyr
            740                 745                 750

Tyr Tyr Gly Gly Thr His Trp Val Arg Gln Ala Pro Gly Glu Cys Leu
        755                 760                 765

Glu Trp Val Ala Ser Ile Gly Ser Tyr Pro Gly Tyr Thr Asp Tyr Ala
        770                 775                 780

Asp Ser Val Lys Gly Arg Phe Thr Ile Ser Ala Asp Thr Ser Lys Asn
785                 790                 795                 800

Thr Ala Tyr Leu Gln Met Asn Ser Leu Arg Ala Glu Asp Thr Ala Val
```

-continued

```
                    805                 810                 815
Tyr Tyr Cys Ala Arg His Tyr Tyr Trp Tyr Asp Ala Thr Asp Tyr Trp
                820                 825                 830

Gly Gln Gly Thr Leu Val Thr Val Ser Ser
            835                 840

<210> SEQ ID NO 166
<211> LENGTH: 842
<212> TYPE: PRT
<213> ORGANISM: Artificial Sequence
<220> FEATURE:
<223> OTHER INFORMATION: Synthetic: mouse SA-(Gly4Ser)3-scFv (VL-VH)
      CK157-ds2 (VL43A>C / VH105Q>C)

<400> SEQUENCE: 166

Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
            20                  25                  30

Lys Cys Ser Tyr Asp Glu His Ala Lys Leu Val Gln Glu Val Thr Asp
        35                  40                  45

Phe Ala Lys Thr Cys Val Ala Asp Glu Ser Ala Ala Asn Cys Asp Lys
50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
            260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
290                 295                 300

Ile Ala Ala Asp Phe Val Glu Asp Gln Glu Val Cys Lys Asn Tyr Ala
305                 310                 315                 320
```

-continued

Glu Ala Lys Asp Val Phe Leu Gly Thr Phe Leu Tyr Glu Tyr Ser Arg
                325                 330                 335

Arg His Pro Asp Tyr Ser Val Ser Leu Leu Arg Leu Ala Lys Lys
            340                 345                 350

Tyr Glu Ala Thr Leu Glu Lys Cys Cys Ala Glu Ala Asn Pro Pro Ala
        355                 360                 365

Cys Tyr Gly Thr Val Leu Ala Glu Phe Gln Pro Leu Val Glu Glu Pro
    370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
                405                 410                 415

Gln Val Ser Thr Pro Thr Leu Val Glu Ala Ala Arg Asn Leu Gly Arg
            420                 425                 430

Val Gly Thr Lys Cys Cys Thr Leu Pro Glu Asp Gln Arg Leu Pro Cys
        435                 440                 445

Val Glu Asp Tyr Leu Ser Ala Ile Leu Asn Arg Val Cys Leu Leu His
    450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
        515                 520                 525

Leu Ala Glu Leu Val Lys His Lys Pro Lys Ala Thr Ala Glu Gln Leu
    530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
                565                 570                 575

Thr Arg Cys Lys Asp Ala Leu Ala Gly Gly Gly Ser Gly Gly Gly
            580                 585                 590

Gly Ser Gly Gly Gly Gly Ser Ala Ser Asp Ile Gln Met Thr Gln Ser
    595                 600                 605

Pro Ser Ser Leu Ser Ala Ser Val Gly Asp Arg Val Thr Ile Thr Cys
    610                 615                 620

Arg Ala Ser Gln Ser Tyr Gly Gly Val Ala Trp Tyr Gln Gln Lys Pro
625                 630                 635                 640

Gly Lys Cys Pro Lys Leu Leu Ile Tyr Ser Ala Ser Tyr Leu Tyr Ser
                645                 650                 655

Gly Val Pro Ser Arg Phe Ser Gly Ser Arg Ser Gly Thr Asp Phe Thr
            660                 665                 670

Leu Thr Ile Ser Ser Leu Gln Pro Glu Asp Phe Ala Thr Tyr Tyr Cys
        675                 680                 685

Gln Gln Pro Ser His Leu Ile Thr Phe Gly Gln Gly Thr Glu Val Glu
    690                 695                 700

Ile Lys Gly Thr Thr Ala Ala Ser Gly Ser Gly Gly Ser Ser Ser
705                 710                 715                 720

Gly Ala Glu Val Gln Leu Val Glu Ser Gly Gly Leu Val Gln Pro
                725                 730                 735

Gly Gly Ser Leu Arg Leu Ser Cys Ala Ala Ser Gly Ser Asn Pro Tyr

```
                    740                 745                 750
Tyr Tyr Gly Gly Thr His Trp Val Arg Gln Ala Pro Gly Glu Glu Leu
            755                 760                 765

Glu Trp Val Ala Ser Ile Gly Ser Tyr Pro Gly Tyr Thr Asp Tyr Ala
        770                 775                 780

Asp Ser Val Lys Gly Arg Phe Thr Ile Ser Ala Asp Thr Ser Lys Asn
785                 790                 795                 800

Thr Ala Tyr Leu Gln Met Asn Ser Leu Arg Ala Glu Asp Thr Ala Val
                805                 810                 815

Tyr Tyr Cys Ala Arg His Tyr Tyr Trp Tyr Asp Ala Thr Asp Tyr Trp
            820                 825                 830

Gly Cys Gly Thr Leu Val Thr Val Ser Ser
            835                 840

<210> SEQ ID NO 167
<211> LENGTH: 706
<212> TYPE: PRT
<213> ORGANISM: Artificial Sequence
<220> FEATURE:
<223> OTHER INFORMATION: Synthetic: mouse SA-(Gly4Ser)-VL CK157

<400> SEQUENCE: 167

Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
                20                  25                  30

Lys Cys Ser Tyr Asp Glu His Ala Lys Leu Val Gln Glu Val Thr Asp
            35                  40                  45

Phe Ala Lys Thr Cys Val Ala Asp Glu Ser Ala Ala Asn Cys Asp Lys
        50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
    210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
```

```
              260                 265                 270
Ser Lys Leu Gln Thr Cys Cys Asp Lys Pro Leu Leu Lys Lys Ala His
        275                 280                 285
Cys Leu Ser Glu Val Glu His Asp Thr Met Pro Ala Asp Leu Pro Ala
290                 295                 300
Ile Ala Ala Asp Phe Val Glu Asp Gln Glu Val Cys Lys Asn Tyr Ala
305                 310                 315                 320
Glu Ala Lys Asp Val Phe Leu Gly Thr Phe Leu Tyr Glu Tyr Ser Arg
                325                 330                 335
Arg His Pro Asp Tyr Ser Val Ser Leu Leu Leu Arg Leu Ala Lys Lys
                340                 345                 350
Tyr Glu Ala Thr Leu Glu Lys Cys Cys Ala Glu Ala Asn Pro Pro Ala
                355                 360                 365
Cys Tyr Gly Thr Val Leu Ala Glu Phe Gln Pro Leu Val Glu Glu Pro
        370                 375                 380
Lys Asn Leu Val Lys Thr Asn Cys Asp Leu Tyr Glu Lys Leu Gly Glu
385                 390                 395                 400
Tyr Gly Phe Gln Asn Ala Ile Leu Val Arg Tyr Thr Gln Lys Ala Pro
                405                 410                 415
Gln Val Ser Thr Pro Thr Leu Val Glu Ala Ala Arg Asn Leu Gly Arg
                420                 425                 430
Val Gly Thr Lys Cys Cys Thr Leu Pro Glu Asp Gln Arg Leu Pro Cys
                435                 440                 445
Val Glu Asp Tyr Leu Ser Ala Ile Leu Asn Arg Val Cys Leu Leu His
                450                 455                 460
Glu Lys Thr Pro Val Ser Glu His Val Thr Lys Cys Cys Ser Gly Ser
465                 470                 475                 480
Leu Val Glu Arg Arg Pro Cys Phe Ser Ala Leu Thr Val Asp Glu Thr
                485                 490                 495
Tyr Val Pro Lys Glu Phe Lys Ala Glu Thr Phe Thr Phe His Ser Asp
                500                 505                 510
Ile Cys Thr Leu Pro Glu Lys Glu Lys Gln Ile Lys Lys Gln Thr Ala
                515                 520                 525
Leu Ala Glu Leu Val Lys His Lys Pro Lys Ala Thr Ala Glu Gln Leu
                530                 535                 540
Lys Thr Val Met Asp Asp Phe Ala Gln Phe Leu Asp Thr Cys Cys Lys
545                 550                 555                 560
Ala Ala Asp Lys Asp Thr Cys Phe Ser Thr Glu Gly Pro Asn Leu Val
                565                 570                 575
Thr Arg Cys Lys Asp Ala Leu Ala Gly Gly Gly Ser Gly Gly Gly
                580                 585                 590
Gly Ser Gly Gly Gly Ser Ala Ser Asp Ile Gln Met Thr Gln Ser
                595                 600                 605
Pro Ser Ser Leu Ser Ala Ser Val Gly Asp Arg Val Thr Ile Thr Cys
                610                 615                 620
Arg Ala Ser Gln Ser Tyr Gly Gly Val Ala Trp Tyr Gln Gln Lys Pro
625                 630                 635                 640
Gly Lys Ala Pro Lys Leu Leu Ile Tyr Ser Ala Ser Tyr Leu Tyr Ser
                645                 650                 655
Gly Val Pro Ser Arg Phe Ser Gly Ser Arg Ser Gly Thr Asp Phe Thr
                660                 665                 670
Leu Thr Ile Ser Ser Leu Gln Pro Glu Asp Phe Ala Thr Tyr Tyr Cys
                675                 680                 685
```

Gln Gln Pro Ser His Leu Ile Thr Phe Gly Gln Gly Thr Glu Val Glu
            690                 695                 700

Ile Lys
705

<210> SEQ ID NO 168
<211> LENGTH: 722
<212> TYPE: PRT
<213> ORGANISM: Artificial Sequence
<220> FEATURE:
<223> OTHER INFORMATION: Synthetic: mouse SA-(Gly4Ser)-VH CK157

<400> SEQUENCE: 168

Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
            20                  25                  30

Lys Cys Ser Tyr Asp Glu His Ala Lys Leu Val Gln Glu Val Thr Asp
        35                  40                  45

Phe Ala Lys Thr Cys Val Ala Asp Glu Ser Ala Ala Asn Cys Asp Lys
    50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
    130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
    210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
            260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
    290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

```
Arg His Pro Asp Tyr Ser Val Ser Leu Leu Arg Leu Ala Lys Lys
            340                 345                 350

Tyr Glu Ala Thr Leu Glu Lys Cys Cys Ala Glu Ala Asn Pro Pro Ala
            355                 360                 365

Cys Tyr Gly Thr Val Leu Ala Glu Phe Gln Pro Leu Val Glu Glu Pro
            370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
                405                 410                 415

Gln Val Ser Thr Pro Thr Leu Val Glu Ala Ala Arg Asn Leu Gly Arg
            420                 425                 430

Val Gly Thr Lys Cys Cys Thr Leu Pro Glu Asp Gln Arg Leu Pro Cys
            435                 440                 445

Val Glu Asp Tyr Leu Ser Ala Ile Leu Asn Arg Val Cys Leu Leu His
            450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
            515                 520                 525

Leu Ala Glu Leu Val Lys His Lys Pro Lys Ala Thr Ala Glu Gln Leu
            530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
                565                 570                 575

Thr Arg Cys Lys Asp Ala Leu Ala Gly Gly Gly Ser Gly Gly Gly
            580                 585                 590

Gly Ser Gly Gly Gly Ser Ala Ser Ala Glu Val Gln Leu Val Glu
            595                 600                 605

Ser Gly Gly Gly Leu Val Gln Pro Gly Gly Ser Leu Arg Leu Ser Cys
610                 615                 620

Ala Ala Ser Gly Ser Asn Pro Tyr Tyr Gly Gly Thr His Trp Val
625                 630                 635                 640

Arg Gln Ala Pro Gly Glu Glu Leu Glu Trp Val Ala Ser Ile Gly Ser
                645                 650                 655

Tyr Pro Gly Tyr Thr Asp Tyr Ala Asp Ser Val Lys Gly Arg Phe Thr
            660                 665                 670

Ile Ser Ala Asp Thr Ser Lys Asn Thr Ala Tyr Leu Gln Met Asn Ser
            675                 680                 685

Leu Arg Ala Glu Asp Thr Ala Val Tyr Tyr Cys Ala Arg His Tyr Tyr
            690                 695                 700

Trp Tyr Asp Ala Thr Asp Tyr Trp Gly Gln Gly Thr Leu Val Thr Val
705                 710                 715                 720

Ser Ser
```

<210> SEQ ID NO 169
<211> LENGTH: 847
<212> TYPE: PRT

<213> ORGANISM: Artificial Sequence
<220> FEATURE:
<223> OTHER INFORMATION: Synthetic: mouse SA-(Gly4Ser)3-scFv (VL-VH)
    CK129-ds1 (VL100Q>C / VH44G>C)

<400> SEQUENCE: 169

```
Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
            20                  25                  30

Lys Cys Ser Tyr Asp Glu His Ala Lys Leu Val Gln Glu Val Thr Asp
        35                  40                  45

Phe Ala Lys Thr Cys Val Ala Asp Glu Ser Ala Ala Asn Cys Asp Lys
50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
            260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

Arg His Pro Asp Tyr Ser Val Ser Leu Leu Leu Arg Leu Ala Lys Lys
            340                 345                 350

Tyr Glu Ala Thr Leu Glu Lys Cys Cys Ala Glu Ala Asn Pro Pro Ala
        355                 360                 365

Cys Tyr Gly Thr Val Leu Ala Glu Phe Gln Pro Leu Val Glu Glu Pro
370                 375                 380
```

```
Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
            405                 410                 415

Gln Val Ser Thr Pro Thr Leu Val Glu Ala Ala Arg Asn Leu Gly Arg
        420                 425                 430

Val Gly Thr Lys Cys Cys Thr Leu Pro Glu Asp Gln Arg Leu Pro Cys
        435                 440                 445

Val Glu Asp Tyr Leu Ser Ala Ile Leu Asn Arg Val Cys Leu Leu His
        450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
            485                 490                 495

Tyr Val Pro Lys Glu Phe Lys Ala Glu Thr Phe Thr Phe His Ser Asp
        500                 505                 510

Ile Cys Thr Leu Pro Glu Lys Glu Lys Gln Ile Lys Lys Gln Thr Ala
        515                 520                 525

Leu Ala Glu Leu Val Lys His Lys Pro Lys Ala Thr Ala Glu Gln Leu
530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
            565                 570                 575

Thr Arg Cys Lys Asp Ala Leu Ala Gly Gly Gly Ser Gly Gly Gly
            580                 585                 590

Gly Ser Gly Gly Gly Gly Ser Ala Ser Asp Ile Gln Met Thr Gln Ser
        595                 600                 605

Pro Ser Pro Leu Ser Ala Ser Val Gly Asp Arg Val Thr Ile Thr Cys
        610                 615                 620

Arg Ala Ser Gln Tyr Gly Gly Tyr Val Ala Trp Tyr Gln Gln Lys Pro
625                 630                 635                 640

Gly Lys Ala Pro Lys Leu Leu Ile Tyr Gly Ala Ser Leu Leu Tyr Ser
            645                 650                 655

Gly Val Pro Ser Arg Phe Ser Gly Arg Ser Gly Thr Asp Phe Thr
        660                 665                 670

Leu Thr Ile Ser Ser Leu Gln Pro Glu Asp Phe Ala Thr Tyr Tyr Cys
        675                 680                 685

Gln Arg Gly His Ala Leu Ile Thr Phe Gly Cys Gly Thr Lys Val Glu
        690                 695                 700

Ile Glu Gly Thr Thr Ala Ala Ser Gly Ser Ser Gly Ser Ser Ser
705                 710                 715                 720

Gly Ala Glu Val Gln Leu Val Glu Ser Gly Gly Leu Val Gln Pro
            725                 730                 735

Gly Gly Ser Leu Arg Leu Ser Cys Ala Ala Ser Gly Phe Asn Ile Ser
            740                 745                 750

Ser Tyr Gly Ser Met His Trp Val Arg Gln Ala Pro Gly Lys Cys Leu
        755                 760                 765

Glu Trp Val Ala Ser Ile Tyr Pro Tyr Ser Ser Ser Thr Tyr Tyr Ala
        770                 775                 780

Asp Ser Val Lys Gly Arg Phe Thr Ile Ser Ala Asp Thr Ser Lys Asn
785                 790                 795                 800

Thr Ala Tyr Leu Gln Met Asn Ser Leu Arg Ala Glu Asp Thr Ala Val
```

```
                    805                 810                 815
Tyr Tyr Cys Ala Arg Gly Tyr Gly Pro Trp Tyr Ala Tyr Ser Tyr Phe
            820                 825                 830

Ala Leu Asp Tyr Trp Gly Gln Gly Thr Leu Val Thr Val Ser Ser
            835                 840                 845

<210> SEQ ID NO 170
<211> LENGTH: 847
<212> TYPE: PRT
<213> ORGANISM: Artificial Sequence
<220> FEATURE:
<223> OTHER INFORMATION: Synthetic: mouse SA-(Gly4Ser)3-scFv (VL-VH)
      CK129-ds2 (VL43A>C / VH105Q>C)

<400> SEQUENCE: 170

Glu Ala His Lys Ser Glu Ile Ala His Arg Tyr Asn Asp Leu Gly Glu
1               5                   10                  15

Gln His Phe Lys Gly Leu Val Leu Ile Ala Phe Ser Gln Tyr Leu Gln
            20                  25                  30

Lys Cys Ser Tyr Asp Glu His Ala Lys Leu Val Gln Glu Val Thr Asp
        35                  40                  45

Phe Ala Lys Thr Cys Val Ala Asp Glu Ser Ala Ala Asn Cys Asp Lys
    50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
            100                 105                 110

Pro Pro Phe Glu Arg Pro Glu Ala Glu Ala Met Cys Thr Ser Phe Lys
        115                 120                 125

Glu Asn Pro Thr Thr Phe Met Gly His Tyr Leu His Glu Val Ala Arg
130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
    210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
            260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
    290                 295                 300

Ile Ala Ala Asp Phe Val Glu Asp Gln Glu Val Cys Lys Asn Tyr Ala
305                 310                 315                 320
```

```
Glu Ala Lys Asp Val Phe Leu Gly Thr Phe Leu Tyr Glu Tyr Ser Arg
                325                 330                 335

Arg His Pro Asp Tyr Ser Val Ser Leu Leu Arg Leu Ala Lys Lys
        340                 345                 350

Tyr Glu Ala Thr Leu Glu Lys Cys Cys Ala Glu Ala Asn Pro Pro Ala
        355                 360                 365

Cys Tyr Gly Thr Val Leu Ala Glu Phe Gln Pro Leu Val Glu Glu Pro
    370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
                405                 410                 415

Gln Val Ser Thr Pro Thr Leu Val Glu Ala Ala Arg Asn Leu Gly Arg
        420                 425                 430

Val Gly Thr Lys Cys Cys Thr Leu Pro Glu Asp Gln Arg Leu Pro Cys
        435                 440                 445

Val Glu Asp Tyr Leu Ser Ala Ile Leu Asn Arg Val Cys Leu Leu His
    450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
        515                 520                 525

Leu Ala Glu Leu Val Lys His Lys Pro Lys Ala Thr Ala Glu Gln Leu
    530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
                565                 570                 575

Thr Arg Cys Lys Asp Ala Leu Ala Gly Gly Gly Gly Ser Gly Gly Gly
            580                 585                 590

Gly Ser Gly Gly Gly Gly Ser Ala Ser Asp Ile Gln Met Thr Gln Ser
        595                 600                 605

Pro Ser Pro Leu Ser Ala Ser Val Gly Asp Arg Val Thr Ile Thr Cys
    610                 615                 620

Arg Ala Ser Gln Tyr Gly Gly Tyr Val Ala Trp Tyr Gln Gln Lys Pro
625                 630                 635                 640

Gly Lys Cys Pro Lys Leu Leu Ile Tyr Gly Ala Ser Leu Leu Tyr Ser
                645                 650                 655

Gly Val Pro Ser Arg Phe Ser Gly Gly Arg Ser Gly Thr Asp Phe Thr
            660                 665                 670

Leu Thr Ile Ser Ser Leu Gln Pro Glu Asp Phe Ala Thr Tyr Tyr Cys
        675                 680                 685

Gln Arg Gly His Ala Leu Ile Thr Phe Gly Gln Gly Thr Lys Val Glu
    690                 695                 700

Ile Glu Gly Thr Thr Ala Ser Gly Ser Gly Gly Ser Ser Ser
705                 710                 715                 720

Gly Ala Glu Val Gln Leu Val Glu Ser Gly Gly Leu Val Gln Pro
                725                 730                 735

Gly Gly Ser Leu Arg Leu Ser Cys Ala Ala Ser Gly Phe Asn Ile Ser
```

```
                    740                 745                 750
Ser Tyr Gly Ser Met His Trp Val Arg Gln Ala Pro Gly Lys Gly Leu
                755                 760                 765

Glu Trp Val Ala Ser Ile Tyr Pro Tyr Ser Ser Thr Tyr Tyr Ala
            770                 775                 780

Asp Ser Val Lys Gly Arg Phe Thr Ile Ser Ala Asp Thr Ser Lys Asn
785                 790                 795                 800

Thr Ala Tyr Leu Gln Met Asn Ser Leu Arg Ala Glu Asp Thr Ala Val
                805                 810                 815

Tyr Tyr Cys Ala Arg Gly Tyr Gly Pro Trp Tyr Ala Tyr Ser Tyr Phe
                820                 825                 830

Ala Leu Asp Tyr Trp Gly Cys Gly Thr Leu Val Thr Val Ser Ser
                835                 840                 845

<210> SEQ ID NO 171
<211> LENGTH: 585
<212> TYPE: PRT
<213> ORGANISM: Homo sapiens

<400> SEQUENCE: 171

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270
```

```
Ser Lys Leu Lys Glu Cys Cys Glu Lys Pro Leu Leu Glu Lys Ser His
            275                 280                 285
Cys Ile Ala Glu Val Glu Asn Asp Glu Met Pro Ala Asp Leu Pro Ser
        290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Arg Leu Ala Lys Thr
            340                 345                 350
Tyr Glu Thr Thr Leu Glu Lys Cys Cys Ala Ala Ala Asp Pro His Glu
            355                 360                 365
Cys Tyr Ala Lys Val Phe Asp Glu Phe Lys Pro Leu Val Glu Glu Pro
        370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
        450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
            580                 585

<210> SEQ ID NO 172
<211> LENGTH: 330
<212> TYPE: PRT
<213> ORGANISM: Homo sapiens

<400> SEQUENCE: 172

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
```

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 173
<211> LENGTH: 584
<212> TYPE: PRT
<213> ORGANISM: Homo sapiens

<400> SEQUENCE: 173

Glu Ala His Lys Ser Glu Ile Ala His Arg Tyr Asn Asp Leu Gly Glu
 1               5                  10                  15

Gln His Phe Lys Gly Leu Val Leu Ile Ala Phe Ser Gln Tyr Leu Gln
            20                  25                  30

Lys Cys Ser Tyr Asp Glu His Ala Lys Leu Val Gln Glu Val Thr Asp
        35                  40                  45

Phe Ala Lys Thr Cys Val Ala Asp Glu Ser Ala Ala Asn Cys Asp Lys
    50                  55                  60

Ser Leu His Thr Leu Phe Gly Asp Lys Leu Cys Ala Ile Pro Asn Leu
65                  70                  75                  80

Arg Glu Asn Tyr Gly Glu Leu Ala Asp Cys Cys Thr Lys Gln Glu Pro
                85                  90                  95

Glu Arg Asn Glu Cys Phe Leu Gln His Lys Asp Asp Asn Pro Ser Leu
```

```
                100                 105                 110
Pro Pro Phe Glu Arg Pro Glu Ala Glu Ala Met Cys Thr Ser Phe Lys
            115                 120                 125

Glu Asn Pro Thr Thr Phe Met Gly His Tyr Leu His Glu Val Ala Arg
130                 135                 140

Arg His Pro Tyr Phe Tyr Ala Pro Glu Leu Leu Tyr Tyr Ala Glu Gln
145                 150                 155                 160

Tyr Asn Glu Ile Leu Thr Gln Cys Cys Ala Glu Ala Asp Lys Glu Ser
                165                 170                 175

Cys Leu Thr Pro Lys Leu Asp Gly Val Lys Glu Lys Ala Leu Val Ser
            180                 185                 190

Ser Val Arg Gln Arg Met Lys Cys Ser Ser Met Gln Lys Phe Gly Glu
        195                 200                 205

Arg Ala Phe Lys Ala Trp Ala Val Ala Arg Leu Ser Gln Thr Phe Pro
    210                 215                 220

Asn Ala Asp Phe Ala Glu Ile Thr Lys Leu Ala Thr Asp Leu Thr Lys
225                 230                 235                 240

Val Asn Lys Glu Cys Cys His Gly Asp Leu Leu Glu Cys Ala Asp Asp
                245                 250                 255

Arg Ala Glu Leu Ala Lys Tyr Met Cys Glu Asn Gln Ala Thr Ile Ser
            260                 265                 270

Ser Lys Leu Gln Thr Cys Cys Asp Lys Pro Leu Leu Lys Lys Ala His
        275                 280                 285

Cys Leu Ser Glu Val Glu His Asp Thr Met Pro Ala Asp Leu Pro Ala
    290                 295                 300

Ile Ala Ala Asp Phe Val Glu Asp Gln Glu Val Cys Lys Asn Tyr Ala
305                 310                 315                 320

Glu Ala Lys Asp Val Phe Leu Gly Thr Phe Leu Tyr Glu Tyr Ser Arg
                325                 330                 335

Arg His Pro Asp Tyr Ser Val Ser Leu Leu Leu Arg Leu Ala Lys Lys
            340                 345                 350

Tyr Glu Ala Thr Leu Glu Lys Cys Cys Ala Glu Ala Asn Pro Pro Ala
        355                 360                 365

Cys Tyr Gly Thr Val Leu Ala Glu Phe Gln Pro Leu Val Glu Glu Pro
    370                 375                 380

Lys Asn Leu Val Lys Thr Asn Cys Asp Leu Tyr Glu Lys Leu Gly Glu
385                 390                 395                 400

Tyr Gly Phe Gln Asn Ala Ile Leu Val Arg Tyr Thr Gln Lys Ala Pro
                405                 410                 415

Gln Val Ser Thr Pro Thr Leu Val Glu Ala Ala Arg Asn Leu Gly Arg
            420                 425                 430

Val Gly Thr Lys Cys Cys Thr Leu Pro Glu Asp Gln Arg Leu Pro Cys
        435                 440                 445

Val Glu Asp Tyr Leu Ser Ala Ile Leu Asn Arg Val Cys Leu Leu His
    450                 455                 460

Glu Lys Thr Pro Val Ser Glu His Val Thr Lys Cys Cys Ser Gly Ser
465                 470                 475                 480

Leu Val Glu Arg Arg Pro Cys Phe Ser Ala Leu Thr Val Asp Glu Thr
                485                 490                 495

Tyr Val Pro Lys Glu Phe Lys Ala Glu Thr Phe Thr Phe His Ser Asp
            500                 505                 510

Ile Cys Thr Leu Pro Glu Lys Glu Lys Gln Ile Lys Lys Gln Thr Ala
        515                 520                 525
```

```
Leu Ala Glu Leu Val Lys His Lys Pro Lys Ala Thr Ala Glu Gln Leu
            530                 535                 540

Lys Thr Val Met Asp Asp Phe Ala Gln Phe Leu Asp Thr Cys Cys Lys
545                 550                 555                 560

Ala Ala Asp Lys Asp Thr Cys Phe Ser Thr Glu Gly Pro Asn Leu Val
                565                 570                 575

Thr Arg Cys Lys Asp Ala Leu Ala
            580
```

<210> SEQ ID NO 174
<211> LENGTH: 232
<212> TYPE: PRT
<213> ORGANISM: Homo sapiens

<400> SEQUENCE: 174

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 175
<211> LENGTH: 197
<212> TYPE: PRT
<213> ORGANISM: Artificial Sequence
<220> FEATURE:
<223> OTHER INFORMATION: Synthetic: HSA domain I

<400> SEQUENCE: 175

```
Asp Ala His Lys Ser Glu Val Ala His Arg Phe Lys Asp Leu Gly Glu
1               5                   10                  15
```

```
Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg
            195

<210> SEQ ID NO 176
<211> LENGTH: 197
<212> TYPE: PRT
<213> ORGANISM: Artificial Sequence
<220> FEATURE:
<223> OTHER INFORMATION: Synthetic: HSA domain II

<400> SEQUENCE: 176

Gly Lys Ala Ser Ser Ala Lys Gln Arg Leu Lys Cys Ala Ser Leu Gln
1                5                  10                  15

Lys Phe Gly Glu Arg Ala Phe Lys Ala Trp Ala Val Ala Arg Leu Ser
                20                  25                  30

Gln Arg Phe Pro Lys Ala Glu Phe Ala Glu Val Ser Lys Leu Val Thr
            35                  40                  45

Asp Leu Thr Lys Val His Thr Glu Cys Cys His Gly Asp Leu Leu Glu
 50                  55                  60

Cys Ala Asp Asp Arg Ala Asp Leu Ala Lys Tyr Ile Cys Glu Asn Gln
 65                  70                  75                  80

Asp Ser Ile Ser Ser Lys Leu Lys Glu Cys Cys Glu Lys Pro Leu Leu
                 85                  90                  95

Glu Lys Ser His Cys Ile Ala Glu Val Glu Asn Asp Glu Met Pro Ala
            100                 105                 110

Asp Leu Pro Ser Leu Ala Ala Asp Phe Val Glu Ser Lys Asp Val Cys
            115                 120                 125

Lys Asn Tyr Ala Glu Ala Lys Asp Val Phe Leu Gly Met Phe Leu Tyr
130                 135                 140

Glu Tyr Ala Arg Arg His Pro Asp Tyr Ser Val Val Leu Leu Leu Arg
145                 150                 155                 160

Leu Ala Lys Thr Tyr Glu Thr Thr Leu Glu Lys Cys Cys Ala Ala Ala
                165                 170                 175
```

```
Asp Pro His Glu Cys Tyr Ala Lys Val Phe Asp Glu Phe Lys Pro Leu
            180                 185                 190

Val Glu Glu Pro Gln
        195
```

<210> SEQ ID NO 177
<211> LENGTH: 200
<212> TYPE: PRT
<213> ORGANISM: Artificial Sequence
<220> FEATURE:
<223> OTHER INFORMATION: Synthetic: HSA domain III

<400> SEQUENCE: 177

```
Asn Leu Ile Lys Gln Asn Cys Glu Leu Phe Glu Gln Leu Gly Glu Tyr
1               5                   10                  15

Lys Phe Gln Asn Ala Leu Leu Val Arg Tyr Thr Lys Lys Val Pro Gln
            20                  25                  30

Val Ser Thr Pro Thr Leu Val Glu Val Ser Arg Asn Leu Gly Lys Val
        35                  40                  45

Gly Ser Lys Cys Cys Lys His Pro Glu Ala Lys Arg Met Pro Cys Ala
    50                  55                  60

Glu Asp Tyr Leu Ser Val Val Leu Asn Gln Leu Cys Val Leu His Glu
65                  70                  75                  80

Lys Thr Pro Val Ser Asp Arg Val Thr Lys Cys Cys Thr Glu Ser Leu
                85                  90                  95

Val Asn Arg Arg Pro Cys Phe Ser Ala Leu Glu Val Asp Glu Thr Tyr
            100                 105                 110

Val Pro Lys Glu Phe Asn Ala Glu Thr Phe Thr Phe His Ala Asp Ile
        115                 120                 125

Cys Thr Leu Ser Glu Lys Glu Arg Gln Ile Lys Lys Gln Thr Ala Leu
    130                 135                 140

Val Glu Leu Val Lys His Lys Pro Lys Ala Thr Lys Glu Gln Leu Lys
145                 150                 155                 160

Ala Val Met Asp Asp Phe Ala Ala Phe Val Glu Lys Cys Cys Lys Ala
                165                 170                 175

Asp Asp Lys Glu Thr Cys Phe Ala Glu Glu Gly Lys Lys Leu Val Ala
            180                 185                 190

Ala Ser Gln Ala Ala Leu Gly Leu
        195                 200
```

<210> SEQ ID NO 178
<211> LENGTH: 15
<212> TYPE: PRT
<213> ORGANISM: Artificial Sequence
<220> FEATURE:
<223> OTHER INFORMATION: Synthetic: linker domain

<400> SEQUENCE: 178

```
Gly Gly Gly Gly Ser Gly Gly Gly Gly Ser Gly Gly Gly Gly Ser
1               5                   10                  15
```

<210> SEQ ID NO 179
<211> LENGTH: 22
<212> TYPE: PRT
<213> ORGANISM: Artificial Sequence
<220> FEATURE:
<223> OTHER INFORMATION: Synthetic: Secretory leader sequence

<400> SEQUENCE: 179

```
Met Asp Met Arg Val Pro Ala Gln Leu Leu Gly Leu Leu Leu Leu Trp
```

```
1               5                  10                 15
Leu Pro Gly Ala Arg Cys
            20

<210> SEQ ID NO 180
<211> LENGTH: 8
<212> TYPE: PRT
<213> ORGANISM: Artificial Sequence
<220> FEATURE:
<223> OTHER INFORMATION: Synthetic: FLAG tag

<400> SEQUENCE: 180

Asp Tyr Lys Asp Asp Asp Asp Lys
1               5

<210> SEQ ID NO 181
<211> LENGTH: 6
<212> TYPE: PRT
<213> ORGANISM: Artificial Sequence
<220> FEATURE:
<223> OTHER INFORMATION: Synthetic: Polyhistidine (6-His)

<400> SEQUENCE: 181

His His His His His His
1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic: Hemagglutinin

<400> SEQUENCE: 182

Tyr Pro Tyr Asp Val Pro Asp Tyr Ala
1               5

<210> SEQ ID NO 183
<211> LENGTH: 51
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (2)..(51)
<223> OTHER INFORMATION: "Gly Gly Gly Gly Ser" is present at least once
      and may or may not repeat up to 10 times.

<400> SEQUENCE: 183

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser Gly Gly Gly Gly Ser Gly Gly
        35                  40                  45

Gly Gly Ser
        50

<210> SEQ ID NO 184
<211> LENGTH: 16
<212> TYPE: PRT
<213> ORGANISM: Artificial Sequence
<220> FEATURE:
<223> OTHER INFORMATION: Synthetic: linker
```

```
<400> SEQUENCE: 184

Ser Gly Gly Gly Gly Ser Gly Gly Gly Ser Gly Gly Gly Gly Ser
1               5                   10                  15

<210> SEQ ID NO 185
<211> LENGTH: 21
<212> TYPE: PRT
<213> ORGANISM: Artificial Sequence
<220> FEATURE:
<223> OTHER INFORMATION: Synthetic: linker

<400> SEQUENCE: 185

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 186
<211> LENGTH: 31
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (2)..(31)
<223> OTHER INFORMATION: "Gly Gly Gly Gly Ser" is present at least once
      and may or may not repeat up to 6 times.

<400> SEQUENCE: 186

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser
            20                  25                  30

<210> SEQ ID NO 187
<211> LENGTH: 24
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (1)..(24)
<223> OTHER INFORMATION: "Gly Gly Gly Ser" is present at least once and
      may or may not repeat up to 6 times.

<400> SEQUENCE: 187

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 188
<211> LENGTH: 26
<212> TYPE: PRT
<213> ORGANISM: Artificial Sequence
<220> FEATURE:
<223> OTHER INFORMATION: Synthetic: Fc interlinker from human IgG1 CH2
      residues 297-322

<400> SEQUENCE: 188

Asn Ser Thr Tyr Arg Val Val Ser Val Leu Thr Val Leu His Gln Asp
1               5                   10                  15

Trp Leu Asn Gly Lys Glu Tyr Lys Cys Lys
            20                  25
```

```
<210> SEQ ID NO 189
<211> LENGTH: 25
<212> TYPE: PRT
<213> ORGANISM: Artificial Sequence
<220> FEATURE:
<223> OTHER INFORMATION: Synthetic: HSA interlinker from the D3 domain
      of human serum albumin

<400> SEQUENCE: 189

Phe Gln Asn Ala Leu Leu Val Arg Tyr Thr Lys Lys Val Pro Gln Val
1               5                   10                  15

Ser Thr Pro Thr Leu Val Glu Val Ser
            20                  25

<210> SEQ ID NO 190
<211> LENGTH: 27
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (2)..(26)
<223> OTHER INFORMATION: "Glu Ala Ala Ala Lys" is present at least twice
      and may or may not repeat up to 5 times

<400> SEQUENCE: 190

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 191
<211> LENGTH: 50
<212> TYPE: PRT
<213> ORGANISM: Artificial Sequence
<220> FEATURE:
<223> OTHER INFORMATION: Synthetic: alpha-helix forming linker

<400> SEQUENCE: 191

Leu Glu Ala Glu Ala Ala Ala Lys Glu Ala Ala Lys Glu Ala Ala
1               5                   10                  15

Ala Lys Glu Ala Ala Ala Lys Ala Leu Glu Ala Glu Ala Ala Ala Lys
            20                  25                  30

Glu Ala Ala Ala Lys Glu Ala Ala Lys Glu Ala Ala Ala Lys Ala
        35                  40                  45

Leu Glu
    50

<210> SEQ ID NO 192
<211> LENGTH: 4
<212> TYPE: PRT
<213> ORGANISM: Artificial Sequence
<220> FEATURE:
<223> OTHER INFORMATION: Synthetic: linker

<400> SEQUENCE: 192

Gly Gly Ser Gly
1

<210> SEQ ID NO 193
<211> LENGTH: 20
<212> TYPE: PRT
<213> ORGANISM: Artificial Sequence
```

```
<220> FEATURE:
<223> OTHER INFORMATION: Synthetic: linker
<220> FEATURE:
<221> NAME/KEY: misc_feature
<222> LOCATION: (1)..(20)
<223> OTHER INFORMATION: "Gly Gly Ser Gly" is present at least once and
      may or may not repeat up to 5 times

<400> SEQUENCE: 193

Gly Gly Ser Gly Gly Gly Ser Gly Gly Gly Ser Gly Gly Gly Ser Gly
1               5                   10                  15

Gly Gly Ser Gly
            20

<210> SEQ ID NO 194
<211> LENGTH: 4
<212> TYPE: PRT
<213> ORGANISM: Artificial Sequence
<220> FEATURE:
<223> OTHER INFORMATION: Synthetic: linker

<400> SEQUENCE: 194

Gly Ser Ala Thr
1

<210> SEQ ID NO 195
<211> LENGTH: 30
<212> TYPE: PRT
<213> ORGANISM: Artificial Sequence
<220> FEATURE:
<223> OTHER INFORMATION: Synthetic: linker
<220> FEATURE:
<221> NAME/KEY: misc_feature
<222> LOCATION: (1)..(30)
<223> OTHER INFORMATION: "Gly Gly Ser Gly Gly Ser" is present at least
      once and may or may not repeat up to 5 times

<400> SEQUENCE: 195

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

<210> SEQ ID NO 196
<211> LENGTH: 15
<212> TYPE: PRT
<213> ORGANISM: Artificial Sequence
<220> FEATURE:
<223> OTHER INFORMATION: Synthetic: linker

<400> SEQUENCE: 196

Gly Leu Asn Asp Ile Phe Glu Ala Gln Lys Ile Glu Trp His Glu
1               5                   10                  15

<210> SEQ ID NO 197
<211> LENGTH: 20
<212> TYPE: PRT
<213> ORGANISM: Artificial Sequence
<220> FEATURE:
<223> OTHER INFORMATION: Synthetic: secretory leader peptide sequence

<400> SEQUENCE: 197

Met Arg Val Pro Ala Gln Leu Leu Gly Leu Leu Leu Trp Leu Pro
1               5                   10                  15

Gly Ala Arg Cys
            20
```

```
<210> SEQ ID NO 198
<211> LENGTH: 8
<212> TYPE: PRT
<213> ORGANISM: Artificial Sequence
<220> FEATURE:
<223> OTHER INFORMATION: Synthetic: acid flexible linker

<400> SEQUENCE: 198

Ser Ser Gly Val Asp Leu Gly Thr
1               5

<210> SEQ ID NO 199
<211> LENGTH: 7
<212> TYPE: PRT
<213> ORGANISM: Artificial Sequence
<220> FEATURE:
<223> OTHER INFORMATION: Synthetic: Tobacco Etch Virus proteolytic
      cleavage site
<220> FEATURE:
<221> NAME/KEY: misc_feature
<222> LOCATION: (7)..(7)
<223> OTHER INFORMATION: Xaa is Ala or Val

<400> SEQUENCE: 199

Glu Asn Leu Tyr Phe Gln Xaa
1               5

<210> SEQ ID NO 200
<211> LENGTH: 10
<212> TYPE: PRT
<213> ORGANISM: Artificial Sequence
<220> FEATURE:
<223> OTHER INFORMATION: Synthetic: linker

<400> SEQUENCE: 200

Gly Gly Gly Gly Ser Gly Gly Gly Gly Ser
1               5                   10

<210> SEQ ID NO 201
<211> LENGTH: 5
<212> TYPE: PRT
<213> ORGANISM: Artificial Sequence
<220> FEATURE:
<223> OTHER INFORMATION: Synthetic: five amino-acid flexible spacer

<400> SEQUENCE: 201

Gly Gly Gly Gly Ser
1               5

<210> SEQ ID NO 202
<211> LENGTH: 18
<212> TYPE: PRT
<213> ORGANISM: Artificial Sequence
<220> FEATURE:
<223> OTHER INFORMATION: Synthetic: secretory leader sequence

<400> SEQUENCE: 202

Met Gln Leu Leu Arg Cys Phe Ser Ile Phe Ser Val Ile Ala Ser Val
1               5                   10                  15

Leu Ala

<210> SEQ ID NO 203
<211> LENGTH: 15
<212> TYPE: PRT
<213> ORGANISM: Artificial Sequence
<220> FEATURE:
<223> OTHER INFORMATION: Synthetic: flexible linker
```

-continued

<400> SEQUENCE: 203

Gly Gly Gly Gly Ser Gly Gly Gly Gly Ser Gly Gly Gly Gly Ser
1               5                   10                  15

<210> SEQ ID NO 204
<211> LENGTH: 16
<212> TYPE: PRT
<213> ORGANISM: Artificial Sequence
<220> FEATURE:
<223> OTHER INFORMATION: Synthetic: flexible linker

<400> SEQUENCE: 204

Gly Thr Thr Ala Ala Ser Gly Ser Ser Gly Gly Ser Ser Ser Gly Ala
1               5                   10                  15

<210> SEQ ID NO 205
<211> LENGTH: 11
<212> TYPE: PRT
<213> ORGANISM: Artificial Sequence
<220> FEATURE:
<223> OTHER INFORMATION: Synthetic: c-myc epitope tag

<400> SEQUENCE: 205

Glu Gln Lys Leu Ile Ser Glu Glu Asp Leu Gln
1               5                   10

<210> SEQ ID NO 206
<211> LENGTH: 33
<212> TYPE: DNA
<213> ORGANISM: Artificial Sequence
<220> FEATURE:
<223> OTHER INFORMATION: Synthetic: primer

<400> SEQUENCE: 206
ggaggcggta gcggaggcgg agggtcggct agc                                 33

<210> SEQ ID NO 207
<211> LENGTH: 31
<212> TYPE: DNA
<213> ORGANISM: Artificial Sequence
<220> FEATURE:
<223> OTHER INFORMATION: Synthetic: primer

<400> SEQUENCE: 207
gtcctcttca gaaataagct tttgttcgga t                                   31

<210> SEQ ID NO 208
<211> LENGTH: 22
<212> TYPE: PRT
<213> ORGANISM: Artificial Sequence
<220> FEATURE:
<223> OTHER INFORMATION: Synthetic: secretory leader peptide sequence

<400> SEQUENCE: 208

Met Asp Met Arg Val Pro Ala Gln Leu Leu Gly Leu Leu Leu Leu Trp
1               5                   10                  15

Leu Pro Gly Ala Arg Cys
            20

<210> SEQ ID NO 209
<211> LENGTH: 38
<212> TYPE: PRT
<213> ORGANISM: Artificial Sequence
<220> FEATURE:
<223> OTHER INFORMATION: Synthetic: secretory leader sequence

```
<400> SEQUENCE: 209

Met Lys Val Leu Ile Val Leu Leu Ala Ile Phe Ala Ala Leu Pro Leu
1               5                   10                  15

Ala Leu Ala Gln Pro Val Ile Ser Thr Thr Val Gly Ser Ala Ala Glu
                20                  25                  30

Gly Ser Leu Asp Lys Arg
            35
```